US012673938B2

(12) United States Patent
Lefever

(10) Patent No.: US 12,673,938 B2
(45) Date of Patent: Jul. 7, 2026

(54) CONJUGATES INCLUDING A DETECTABLE MOIETY

(71) Applicant: Ventana Medical Systems, Inc., Tucson, AZ (US)

(72) Inventor: Mark Lefever, Quepos (CR)

(73) Assignee: Ventana Medical Systems, Inc., Tucson, AZ (US)

( * ) Notice: Subject to any disclaimer, the term of this patent is extended or adjusted under 35 U.S.C. 154(b) by 548 days.

(21) Appl. No.: 18/113,549

(22) Filed: Feb. 23, 2023

(65) Prior Publication Data

US 2023/0192658 A1 Jun. 22, 2023

Related U.S. Application Data

(63) Continuation of application No. PCT/EP2021/073731, filed on Aug. 27, 2021.

(60) Provisional application No. 63/071,518, filed on Aug. 28, 2020.

(51) Int. Cl.

| | |
|---|---|
| ***C07D 403/06*** | (2006.01) |
| ***C07D 401/10*** | (2006.01) |
| ***C07F 9/572*** | (2006.01) |
| ***C07F 9/6547*** | (2006.01) |
| ***C07F 9/655*** | (2006.01) |
| ***C07F 9/6561*** | (2006.01) |
| *C12Q 1/6818* | (2018.01) |

(52) U.S. Cl.

CPC ......... *C07D 403/06* (2013.01); *C07D 401/10* (2013.01); *C07F 9/5728* (2013.01); *C07F 9/6547* (2013.01); *C07F 9/65522* (2013.01); *C07F 9/6561* (2013.01); *C12Q 1/6818* (2013.01)

(58) Field of Classification Search

CPC ... C07D 403/06; C07D 401/10; C07F 9/5728; C07F 9/6547; C07F 9/65522; C07F 9/6561; C12Q 1/6818

USPC ............................................................ 514/81

See application file for complete search history.

(56) References Cited

U.S. PATENT DOCUMENTS

| | | | |
|---|---|---|---|
| 5,977,351 | A | 11/1999 | Chu |
| 2005/0026082 | A1 | 2/2005 | Shimada |
| 2009/0293956 | A1 | 12/2009 | Kitamura |
| 2013/0109019 | A1 | 5/2013 | Murillo et al. |
| 2017/0299482 | A1 | 10/2017 | Gupta et al. |
| 2021/0299285 | A1 | 9/2021 | Furdui et al. |

FOREIGN PATENT DOCUMENTS

| | | | |
|---|---|---|---|
| CN | 109641922 | A | 4/2019 |
| CN | 109642898 | A | 4/2019 |
| CN | 110790812 | | 2/2025 |
| EP | 1507170 | A2 | 2/2005 |
| EP | 3293230 | A1 | 3/2018 |
| JP | 2008185884 | A | 8/2008 |
| JP | 2013531801 | A | 8/2013 |
| WO | 1997041856 | A1 | 11/1997 |
| WO | 2012003476 | A2 | 1/2012 |
| WO | 2012003478 | A2 | 1/2012 |
| WO | 2013148189 | A1 | 10/2013 |
| WO | 2014144898 | A1 | 9/2014 |
| WO | 2015134969 | A1 | 9/2015 |
| WO | 2018002016 | A1 | 1/2018 |
| WO | 2020018613 | | 1/2020 |
| WO | 2020058339 | A1 | 3/2020 |
| WO | 2020132607 | A1 | 6/2020 |
| WO | 2022043491 | A2 | 3/2022 |

OTHER PUBLICATIONS

Anton H N Hopman et al, "Rapid Synthesis of Biotin-, Digoxigenin-, Trinitrophenyl-, and Fluorochrome-labeled Tyramides and Their Application for In Situ Hybridization Using CARD Amplification", The Journal of Histochemistry & Cytochemistry, vol. 46, Jan. 1, 1998 (Jan. 1, 1998).

Jonathan B Grimm et al, "A general method to improve fluorophores for live-cell and single-molecule microscopy", Nature Methods, vol. 12, No. 3, Jan. 19, 2015 (Jan. 19, 2015).

Féau Clémentine et al, "Synthesis and characterization of coumarin-based europium complexes and luminescence measurements in aqueous media", Organic & Biomolecular Chemistry, vol. 7, No. 24, Jan. 1, 2009 (Jan. 1, 2009).

Marianna Dakanali et al, "Self-calibrating viscosity probes: Design and subcellular localization", May 12, 2012 (May 12, 2012), vol. 20, No. 14.

Mohamed-Anis Alouini? et al, "Interaction of Fluorescently Labeled Triethyleneglycol and Peptide Derivatives with ?-Cyclodextrin", Chemphyschem, vol. 15, No. 3, Jan. 8, 2014 (Jan. 8, 2014).

Murray James et al, "Solid phase synthesis of functionalised SAM-forming alkanethiol-oligoethyleneglycols", Journal of Materials Chemistry. B, vol. 2, No. 24, Jan. 1, 2014 (Jan. 1, 2014).

Dauphin-Ducharme Philippe et al, "Simulation-Based Approach to Determining Electron Transfer Rates Using Square-Wave Voltammetry", Langmuir,vol. 33, No. 18, Apr. 26, 2017 (Apr. 26, 2017).

Kurnik Martin et al, "Quantitative measurements of protein-surface interaction thermodynamics", Proceedings of the National Academy of Sciences,vol. 115, No. 33, Jul. 30, 2018 (Jul. 30, 2018).

Giller Gerald et al, "Incorporation of reporter molecule-labeled nucleotides by DNA polymerases. I. Chemical synthesis of various reporter group-labeled 2'-deoxyribonucleoside-5'-triphosphates", Nucleic Acids Research, Oxford University Press, GB,vol. 31, No. 10, May 15, 2003 (May 15, 2003).

(Continued)

*Primary Examiner* — Kristin A Vajda

(74) *Attorney, Agent, or Firm* — Charney IP Law LLC; Thomas M. Finetti

(57) ABSTRACT

Disclosed herein are detectable moieties and detectable conjugates comprising one or more detectable moieties. In some embodiments, the disclosed detectable moieties have a narrow wavelength and are suitable for multiplexing. Also disclosed are methods of labeling one or more targets within a biological specimen using any of the detectable conjugates and/or detectable moieties described herein.

19 Claims, 28 Drawing Sheets

(56) References Cited

OTHER PUBLICATIONS

John T Ngo et al, “Click-EM for imaging metabolically tagged nonprotein biomolecules”, Nature Chemical Biology,vol. 12, No. 6, Jun. 1, 2016 (Jun. 1, 2016).
Wei Tao et al, “Black Phosphorus Nanosheets as a Robust Delivery Platform for Cancer Theranostics”, Advanced Materials,vol. 29, No. 1, Jan. 1, 2017 (Jan. 1, 2017).
International Search Report and Written Opinion for PCT/EP2021/073731, mailed on Jul. 4, 2022.

10 11 12 13 14 15

CONJUGATES INCLUDING A DETECTABLE MOIETY

CROSS REFERENCE TO RELATED APPLICATIONS

The present application is a continuation of International Application No. PCT/EP2021/073731 filed on Aug. 27, 2021, which application claims the benefit of the filing date of U.S. Provisional Patent Application No. 63/071,518 filed on Aug. 28, 2020, the disclosures of which are hereby incorporated by reference herein in their entireties.

FIELD OF THE DISCLOSURE

The present disclosure pertains to conjugates including a detectable moiety, such as conjugates for use in detecting one or more targets within a biological sample.

BACKGROUND OF THE DISCLOSURE

Immunohistochemistry (IHC) refers to the processes of detecting, localizing, and/or quantifying antigens, such as a protein, in a biological sample using antibodies specific to the particular antigens. IHC provides the substantial advantage of identifying exactly where a particular protein is located within the tissue sample. It is also an effective way to examine the tissues themselves. In situ hybridization (ISH) refers to the process of detecting, localizing, and quantifying nucleic acids. Both IHC and ISH can be performed on various biological samples, such as tissue (e.g., fresh frozen, formalin fixed, paraffin embedded) and cytological samples. Recognition of the targets can be detected using various labels (e.g., chromogenic, fluorescent, luminescent, radiometric), irrespective of whether the target is a nucleic acid or an antigen. To robustly detect, locate, and quantify targets in a clinical setting, amplification of the recognition event is desirable as the ability to confidently detect cellular markers of low abundance becomes increasingly important for diagnostic purposes. For example, depositing at the marker's site hundreds or thousands of label molecules in response to a single antigen detection event enhances, through amplification, the ability to detect that recognition event.

Adverse events often accompany amplification, such as non-specific signals that are apparent as an increased background signal. An increased background signal interferes with the clinical analysis by obscuring faint signals that may be associated with low, but clinically significant, expressions. Accordingly, while amplification of recognition events is desirable, amplification methods that do not increase background signal are highly desirable. One such method is Tyramide Signal Amplification (TSA), which has also been referred to as catalyzed reporter deposition (CARD). U.S. Pat. No. 5,583,001 discloses a method for detecting and/or quantitating an analyte using an analyte-dependent enzyme activation system that relies on catalyzed reporter deposition to amplify the detectable label signal. Catalysis of an enzyme in a CARD or TSA method is enhanced by reacting a labeled phenol molecule with an enzyme. Modern methods utilizing TSA effectively increase the signals obtained from IHC and ISH assays while not producing significant background signal amplification (see, for example, U.S. application publication No. 2012/0171668 which is hereby incorporated by reference in its entirety for disclosure related to tyramide amplification reagents). Reagents for these amplification approaches are being applied to clinically important targets to provide robust diagnostic capabilities previously unattainable (VENTANA OptiView Amplification Kit, Ventana Medical Systems, Tucson Ariz., Catalog No. 760-099).

TSA takes advantage of the reaction between horseradish peroxidase (HRP) and tyramide. In the presence of $H_2O_2$, tyramide is converted to a highly reactive and short-lived radical intermediate that reacts preferentially with electron-rich amino acid residues on proteins. Covalently bound detectable labels can then be detected by variety of chromogenic visualization techniques and/or by fluorescence microscopy. In solid-phase immunoassays, such as IHC and ISH, where spatial and morphological context is highly valued, the short lifetime of the radical intermediate results in covalent binding of the tyramide to proteins on tissue in close proximity to the site of generation, giving discrete and specific signal.

Co-pending application PCT/EP2015/053556 entitled "Quinone Methide Analog Signal Amplification," having an international filing date of Feb. 20, 2015, describes an alternative technique ("QMSA") that, like TSA, may be used to increase signal amplification without increasing background signals. Indeed, PCT/EP2015/053556 describes novel quinone methide analog precursors and methods of using the quinone methide analog precursors in detecting one or more targets in a biological sample. There, the method of detection is described as comprising the steps of contacting the sample with a detection probe, then contacting the sample with a labeling conjugate that comprises an enzyme. The enzyme interacts with a quinone methide analog precursor comprising a detectable label, forming a reactive quinone methide analog, which binds to the biological sample proximally to or directly on the target. The detectable label is then detected.

BRIEF SUMMARY OF THE DISCLOSURE

A first aspect of the present disclosure is a compound having Formula (I):

$$[Z]\text{-}[Q]_m\text{-}[W] \quad (I),$$

where Q is a branched or unbranched, linear or cyclic, substituted or unsubstituted group having between 2 and 40 carbon atoms, and optionally having one or more heteroatoms selected from O, N, or S m is 0, 1, or 2; W is a detectable moiety, and Z is a "tissue reactive moiety" or a moiety capable of participating in a "click chemistry" reaction. In some embodiments, W is moiety having any one of Formulas (IIA), (IIB), (IIC), (IIIA), (IIIB), (IVA), (IVB), (IVC), (IVD), (IVE), (IVF), (IVG), (IVH), (VA), (VB), (VI), (VIIA), (VIIB), and (VIIC) (each described herein).

In some embodiments, W is a moiety having Formula (IIA):

(IIA)

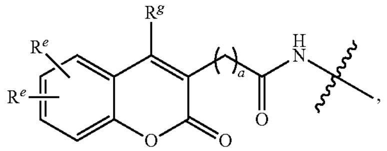

wherein each $R^e$ is independently —OH, —O-alkyl, or —$N(R^x)(R^y)$, where $R^x$ and $R^y$ are independently H or a branched or unbranched $C_1$-$C_4$ alkyl group optionally substituted with one or more halogen atoms, or where $R^x$ and $R^y$ together form a 3-, 4-, or 5-membered cyclic ring which may be optionally substituted with one or more halogen atoms or one or more $C_1$-$C_2$ alkyl groups;

$R^g$ is —H, —$CH_3$ or —$CH_2$—$CH_3$; and a is 0 or an integer ranging from 1 to 4.

In some embodiments, a is 0.

In some embodiments, when $R^e$ is —N($R^x$)($R^y$), then at least one of $R^x$ and $R^y$ comprise a $C_1$-$C_4$ alkyl group including a halogen, e.g., a fluorine atom.

In some embodiments, if $R^e$ is —N($R^x$)($R^y$) and each of $R^x$ and $R^y$ are —$CH_2$—$CH_2$—, then the compound of Formula (IIA) further includes either (i) a second $R^e$ group that is other than H; or a (ii) $R^g$ group that is other than H.

In some embodiments, when $R^e$ is —N($R^x$)($R^y$) and of $R^x$ and $R^y$ form a heterocyclic ring including nitrogen, then the heterocyclic ring further comprises a substitution, such as a halogen substitution. In some embodiments, when $R^e$ is —N($R^x$)($R^y$) and of $R^x$ and $R^y$ form a heterocyclic ring including nitrogen, then the compound of Formula (IIA) further includes either (i) a second $R^e$ group that is other than H; or (ii) a $R^g$ group that is other than H.

In some embodiments, W is a moiety having Formula (IIIA):

(IIIA)

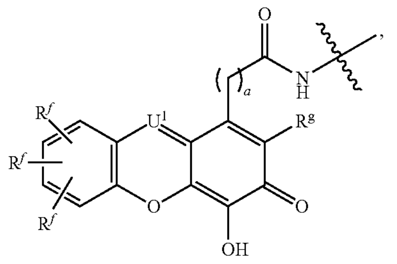

wherein each $R^f$ is independently —N($R^x$)($R^y$), where $R^x$ and $R^y$ are independently H or a branched or unbranched $C_1$-$C_4$ alkyl group optionally substituted with one or more halogen atoms; or where any two $R^f$ groups may together form a substituted or unsubstituted, saturated or unsaturated ring;

$R^g$ is —H, —$CH_3$ or —$CH_2$—$CH_3$;

$U^1$ is O, N, or S; and a is 0 or an integer ranging from 1 to 6.

In some embodiments, W is selected from Formula (IVA):

(IVA)

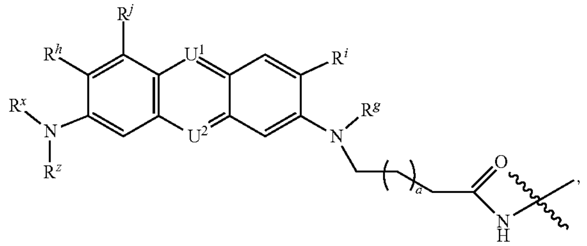

wherein $U^1$ is O, N, or S;

$U^2$ is O or S;

$R^g$ is —$CH_3$ or —$CH_2$—$CH_3$;

$R^i$ is H or a branched or unbranched $C_1$-$C_6$ alkyl group; or where $R^g$ and $R^i$ together form a 5-, 6-, or 7-membered cyclic or aromatic ring which may be optionally substituted with a halogen, a $C_1$-$C_4$ alkyl group;

$R^h$ is H or a branched or unbranched $C_1$-$C_4$ alkyl group;

$R^x$ is H or a branched or unbranched $C_1$-$C_4$ alkyl group optionally substituted with one or more halogen atoms;

$R^z$ is H, or a branched or unbranched $C_1$-$C_4$ alkyl group optionally substituted with one or more halogen atoms or with a —S(O)(O)—$O^-$ group;

or where $R^h$ and one of $R^x$ or $R^z$ together form a 5-, 6-, or 7-membered cyclic or aromatic ring which may be optionally substituted with one or more halogen atoms or one or more $C_1$-$C_2$ alkyl groups;

$R^j$ is H or a branched or unbranched $C_1$-$C_6$ alkyl group; or where $R^j$ and $R^h$ form a 5- or 6-membered ring, optionally substituted with one or more $C_1$-$C_4$ alkyl groups; and a is 0 or an integer ranging from 1 to 6.

In some embodiments, W is selected from any one of Formulas (VA) or (VB):

(VA)

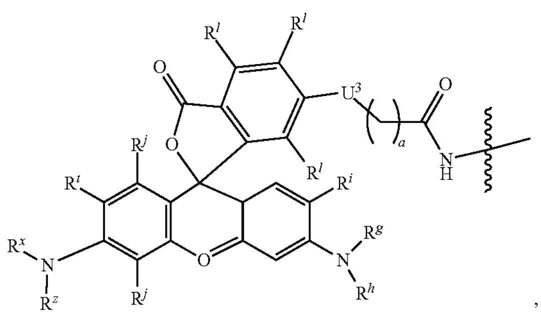

, (VB)

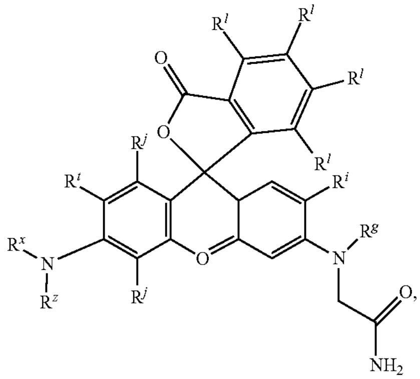

wherein $R^g$ is —$CH_3$ or —$CH_2$—$CH_3$;

$R^i$ is H or a branched or unbranched $C_1$-$C_6$ alkyl group; or where $R^g$ and $R^i$ together form a 5-, 6-, or 7-membered ring which may be optionally substituted with a halogen, a $C_1$-$C_4$ alkyl group;

$R^h$ is H or a branched or unbranched $C_1$-$C_4$ alkyl group;

$R^x$ is H or a branched or unbranched $C_1$-$C_4$ alkyl group optionally substituted with one or more halogen atoms;

$R^z$ is H, or a $C_1$-$C_4$ alkyl group optionally substituted with one or more halogen atoms or with a —S(O)(O)—$O^-$ group;

$R^t$ is H or a branched or unbranched $C_1$-$C_4$ alkyl group; or where $R^t$ and one of $R^x$ or $R^z$ together form a 5-, 6-, or 7-membered cyclic or aromatic ring which may be optionally substituted with one or more halogen atoms or one or more $C_1$-$C_2$ alkyl groups;

each $R^j$ is independently H or a branched or unbranched $C_1$-$C_6$ alkyl group;

or where $R^j$ and $R^t$ form a 5- or 6-membered ring, optionally substituted with one or one or more $C_1$-$C_2$ alkyl groups; or where $R^j$ and one of $R^x$ or $R^z$ form a 5- or 6-membered ring, optionally substituted with one or more $C_1$-$C_2$ alkyl groups; or where $R^x$, $R^t$, and $R^j$ together form a bicyclic ring which may be saturated or unsaturated and which may be optionally substituted with one or more halogen atoms or one or more $C_1$-$C_2$ alkyl groups;

each $R^l$ is independently H or a halogen atom; and a is 0 or an integer ranging from 1 to 6.

In some embodiments, W is selected from Formula (VI):

(VI)

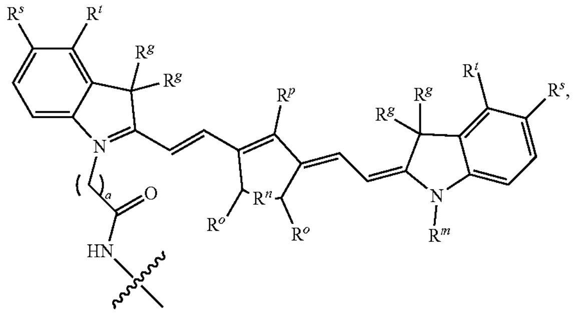

wherein a is 0 or an integer ranging from 1 to 6;

$R^p$ is a halogen atom;

$R^n$ is a bond or —$CH_2$—;

each $R_o$ is independently a branched or unbranched $C_1$-$C_4$ alkyl group, or when $R_n$ is a bond, then both $R^o$ groups together may form a 6-member cyclic or aromatic ring, optionally substituted with one or more halogen groups or one or more $C_1$-$C_2$ alkyl groups;

each $R^g$ is independently-$CH_3$ or —$CH_2$—$CH_3$;

$R^m$ is H, a branched or unbranched $C_1$-$C_4$ alkyl group which is optionally substituted with one or more halogen atoms and or one or more —S(O)(O)(OH) group, or a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction; and each $R^s$ or $R^t$ group is independently selected from a branched or unbranched $C_1$-$C_6$ alkyl group;

or wherein any two adjacent $R^s$ and $R^t$ groups and/or any two adjacent $R_g$ and $R^t$ groups may together form a 5- or 6-membered cyclic or aromatic group, optionally substituted with one or more $C_1$-$C_2$ alkyl groups.

In some embodiments, W is selected from Formula (VIIA):

(VIIA)

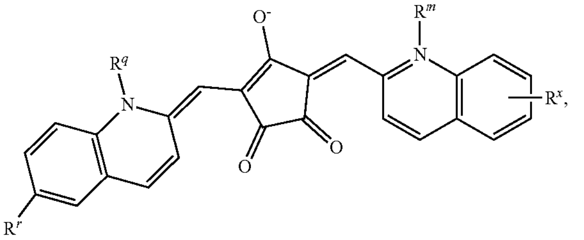

wherein $R^x$ is H or a branched or unbranched $C_1$-$C_4$ alkyl group optionally substituted with one or more halogen atoms;

$R^m$ is H, a branched or unbranched $C_1$-$C_4$ alkyl group which is optionally substituted with one or more halogen atoms and or one or more —S(O)(O)(OH) group, or a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction; and $R^q$ and $R^r$ are each independently H, a branched or unbranched $C_1$-$C_4$ alkyl group optionally substituted with one or more halogen atoms, or a group $R^s$, where $R^s$ is a saturated or unsaturated $C_1$-$C_{20}$ alkyl group comprising at least one amide group, and which is optionally substituted with one or more heteroatoms, provided that the group $R^s$ terminates in a moiety capable of participating in a click chemistry reaction, provided that at least one of $R^q$ or $R^r$ comprises a group $R^s$, and further provided that $R^q$ and $R^r$ are both not $R^s$.

A second aspect of the present disclosure is a compound having Formula (VIII):

$$[X]\text{-}[Q]_m\text{-}[W] \quad \text{(VIII)},$$

where Q is a branched or unbranched, linear or cyclic, substituted or unsubstituted group having between 2 and 40 carbon atoms, and optionally having one or more heteroatoms selected from O, N, or S; m is 0, 1, or 2; W is a "detectable moiety," and X is a "tissue reactive moiety" selected from a quinone methide precursor, a derivative or analog of a quinone methide precursor, a tyramide, or a tyramide derivative. In some embodiments, W is moiety having any one of Formulas (IIA), (IIB), (IIC), (IIIA), (IIIB), (IVA), (IVB), (IVC), (IVD), (IVE), (IVF), (IVG), (IVH), (VA), (VB), (VI), (VIIA), (VIIB), and (VIIC).

In some embodiments, the quinone methide precursor or the derivative or analog of the quinone methide precursor has the structure of any one of Formulas (IXA) or (IXE):

(IXA)

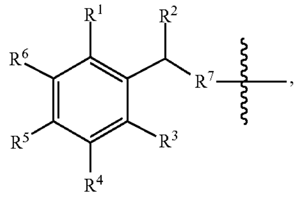

-continued (IXE)

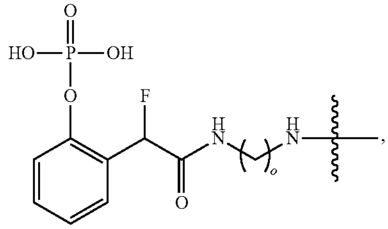
, where $R^1$ is selected from the group consisting of phosphate, amide, nitro, urea, sulfate, methyl, ester, beta-lactam, and a sugar; $R^2$ is a halide; $R^3$, $R^4$, $R^5$, and $R^6$ are independently selected from hydrogen or an aliphatic group having between 1 and 4 carbon atoms; and $R^7$ is $—(CH_2)_wNH—$, $—O(CH_2)_wNH—$, $—N(H)C(O)(CH_2)_wNH—$, $—C(O)N(H)(CH_2)_wNH—$, $—(CH_2)_wO—$, $—O(CH_2)_wO—$, $—O(CH_2CH_2O)_w—$, $—N(H)C(O)(CH_2)_wO—$, $—C(O)N(H)(CH_2)_wO—$, $—C(o)N(H)(CH_2CH_2O)_w—$, $—(CH_2)_wS—$, $—O(CH_2)_wS—$, $—N(H)C(O)(CH_2)_wS—$, $—C(O)N(H)(CH_2)_wS—$, $—(CH_2)_wNH—$, $—C(O)N(H)(CH_2CH_2O)_wCH_2CH_2NH$, $—C(O)(CH_2CH_2O)_wCH_2CH_2NH—$, $—C(O)N(H)(CH_2)NHC(O)CH(CH_3)(CH_2)_wNH—$, or $—N(H)(CH_2)_wNH—$, where w is an integer ranging from 1 to 12;

In some embodiments, w ranges from 2 to 6.

In some embodiments, the tyramide or the tyramide derivative has the structure of any one of Formulas (XA) or (XB):

(XA)

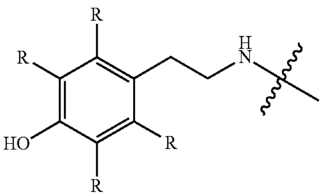

or (XB)

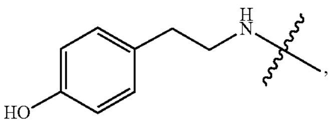
, wherein each R group is independently selected from hydrogen or lower alkyl group having between 1 and 4 carbon atoms; or In some embodiments, Q has the structure of Formula (XIA)

(XIA)

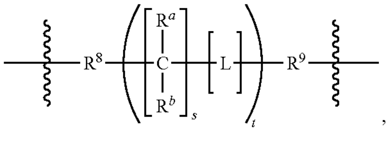
, wherein s is 0, 1, or 2; L is a bond, O, S, or $N(R^c)(R^d)$; $R^a$ and $R^b$ are independently H, a $C_1$-$C_4$ alkyl group, F, Cl, or $—N(R^c)(R^d)$; $R^c$ and $R^d$ are independently selected from $CH_3$ or H; $R^8$ and $R^9$ are independently a bond or a group selected from carbonyl, amide, imide, ester, ether, amine, thione, thiol; and t is an integer ranging from 1 to 8.

In some embodiments, Q has the structure of Formula (XIB):

(XIB)

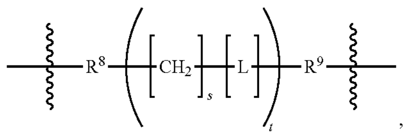
, wherein s is 0, 1, or 2; L is a bond, O, S, or $N(R^c)(R^d)$; $R^c$ and $R^d$ are independently $CH_3$ or H; $R^8$ and $R^9$ are independently a bond, or a group selected from carbonyl, amide, imide, ester, ether, amine, or thiol; and t is an integer ranging from 1 to 8.

A third aspect of the present disclosure is a compound having Formula (XII):

$$[Y]\text{-}[Q]_m\text{-}[W] \qquad (XII),$$

where Q is a branched or unbranched, linear or cyclic, substituted or unsubstituted group having between 2 and 40 carbon atoms, and optionally having one or more heteroatoms selected from O, N, or S; m is 0, 1, or 2; W is a detectable moiety; and Y is a moiety capable of participating in a click chemistry reaction. In some embodiments, W is moiety having any one of Formulas (IIA), (IIB), (IIC), (IIIA), (IIIB), (IVA), (IVB), (IVC), (IVD), (IVE), (IVF), (IVG), (IVH), (VA), (VB), (VI), (VIIA), (VIIB), and (VIIC).

In some embodiments, Y is selected from the group consisting of dibenzocyclooctyne, trans-cyclooctene, azide, tetrazine, maleimide, thiol, 1,3-nitrone, aldehyde, ketone, hydrazine, and hydroxylamine.

In some embodiments, Q has the structure of Formula (XIA)

(XIA)

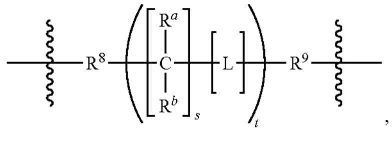
, wherein f is 0, 1, or 2; L is a bond, O, S, or $N(R^c)(R^d)$; $R^a$ and $R^b$ are independently H, a $C_1$-$C_4$ alkyl group, F, Cl, or $—N(R^c)(R^d)$; $R^c$ and $R^d$ are independently selected from $CH_3$ or H; $R^8$ and $R^9$ are independently a bond or a group selected from carbonyl, amide, imide, ester, ether, amine, thione, thiol; and j is an integer ranging from 1 to 8.

In some embodiments, Q has the structure of Formula (XIB):

(XIB)

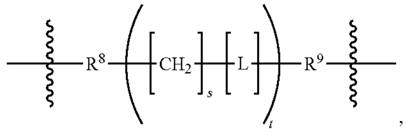
, wherein f is 0, 1, or 2; L is a bond, O, S, or $N(R^c)(R^d)$; $R^c$ and $R^d$ are independently $CH_3$ or H; $R^8$ and $R^9$ are independently a bond, or a group selected from carbonyl, amide, imide, ester, ether, amine, or thiol; and j is an integer ranging from 1 to 8.

In a fourth aspect of the present disclosure is a kit comprising: (a) a compound having Formula (XIII):

$$[Y']-[Q]_m-[W] \quad \text{(XIII)},$$

where Q is a branched or unbranched, linear or cyclic, substituted or unsubstituted group having between 2 and 40 carbon atoms, and optionally having one or more heteroatoms selected from O, N, or S; m is 0, 1, or 2; W is a detectable moiety; and $Y^1$ comprises a moiety including a first member of a pair of reactive functional groups capable of participating in a click chemistry reaction; and (b) a compound having Formula (XIV):

$$[X]-[M]_n-[Y^2] \quad \text{(XIV)},$$

wherein X is a "tissue reactive moiety;" M is a substituted or unsubstituted, linear or cyclic, aliphatic group having between 1 and 12 carbon atoms, and optionally substituted one or more heteroatoms selected from O, N, or S, and optionally including one or more carbonyl groups; and $Y^2$ comprises a moiety including a second member of the pair of reactive functional groups capable of participating in a click chemistry reaction. In some embodiments, W is moiety having any one of Formulas (IIA), (IIB), (IIC), (IIIA), (IIIB), (IVA), (IVB), (IVC), (IVD), (IVE), (IVF), (IVG), (IVH), (VA), (VB), (VI), (VIIA), (VIIB), and (VIIC).

A fifth aspect of the present disclosure is a compound having Formula (I):

$$[Z]-[Q]_m-[W] \quad \text{(I)},$$

wherein

Z is (i) a "tissue reactive moiety," or (ii) a functional group or a moiety including a functional group capable of participating in a "click chemistry" reaction;

Q is a branched or unbranched, linear or cyclic, substituted or unsubstituted group having between 2 and 40 carbon atoms, and optionally having one or more heteroatoms selected from O, N, or S;

m is 0, 1, or 2; and

W has Formula (IIA):

(IIA)

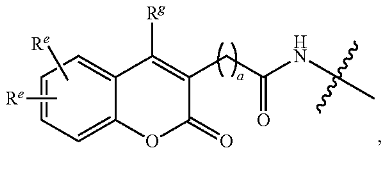

, wherein each $R^e$ is independently —OH, —O-alkyl, or —$N(R^x)(R^y)$, where $R^x$ and $R^y$ are independently H or a branched or unbranched $C_1$-$C_4$ alkyl group optionally substituted with one or more halogen atoms, or where $R^x$ and $R^y$ together form a 3-, 4-, or 5-membered cyclic ring which may be optionally substituted with one or more halogen atoms or one or more $C_1$-$C_2$ alkyl groups; $R^g$ is —H, —$CH_3$ or —$CH_2$—$CH_3$; and a is 0 or an integer ranging from 1 to 4.

In some embodiments, W has Formula (IIB):

(IIB)

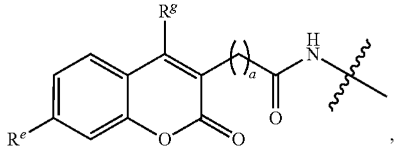

, wherein $R^e$ is —OH, —O-alkyl, or —$N(R^x)(R^y)$, where $R^x$ and $R^y$ are independently H or a branched or unbranched $C_1$-$C_4$ alkyl group optionally substituted with one or more halogen atoms, or where $R^x$ and $R^y$ together form a 3-, 4-, or 5-membered cyclic ring which may be optionally substituted with one or more halogen atoms or one or more $C_1$-$C_2$ alkyl groups; $R^g$ is —H, —$CH_3$ or —$CH_2$—$CH_3$; and a is 0 or an integer ranging from 1 to 4.

In some embodiments is —N(H)(Me). In some embodiments, $R^e$ is —$N(H)CF_3$. In some embodiments, $R^e$ is —$N(R^x)(R^y)$, and where $R^x$ and $R^y$ together form a 3-, 4-, or 5-membered cyclic ring which may be optionally substituted with one or more halogen atoms or one or more $C_1$-$C_2$ alkyl groups. In some embodiments, $R^e$ is —$N(R^x)(R^y)$, and where $R^x$ and $R^y$ together form a 4-membered cyclic ring which is unsubstituted. In some embodiments, $R^e$ is —$N(R^x)(R^y)$, and where $R^x$ and $R^y$ together form a 4-membered cyclic ring which is substituted with a halogen.

In some embodiments, W has Formula (IIC):

(IIC)

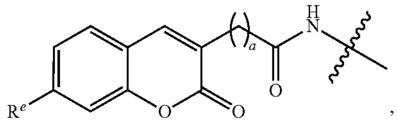

, wherein $R^e$ is —OH, —O-alkyl, or —$N(R^x)(R^y)$, where $R^x$ and $R^y$ are independently H or a branched or unbranched $C_1$-$C_4$ alkyl group optionally substituted with one or more halogen atoms, or where $R^x$ and $R^y$ together form a 3-, 4-, or 5-membered cyclic ring which may be optionally substituted with one or more halogen atoms or one or more $C_1$-$C_2$ alkyl groups; and a is 0 or an integer ranging from 1 to 6.

In some embodiments, a is 0.

In some embodiments, W is selected from the group consisting of:

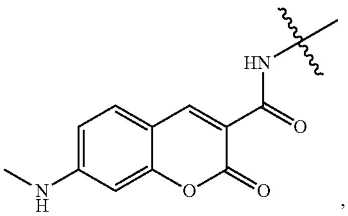

,

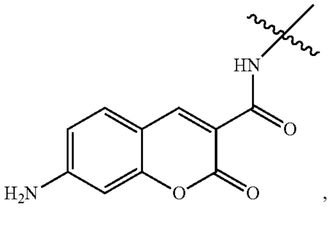

,

-continued

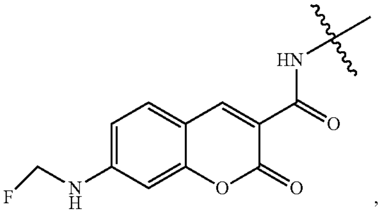

,

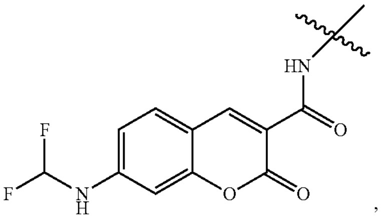

,

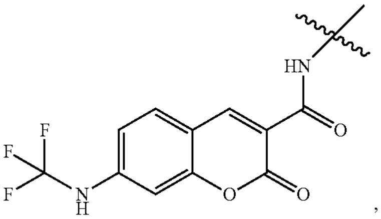

,

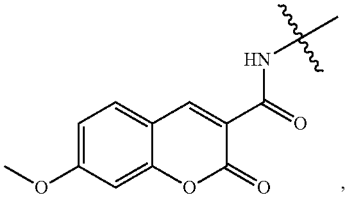

,

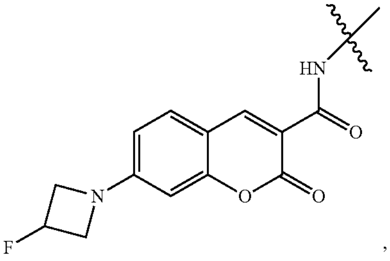

,

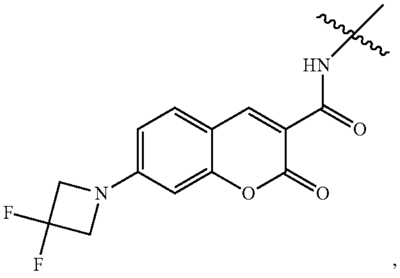

,

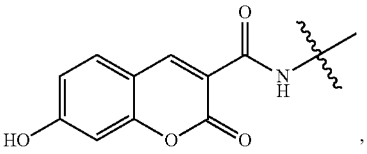

,

-continued

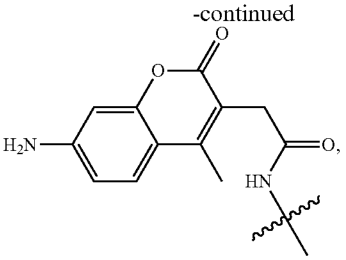

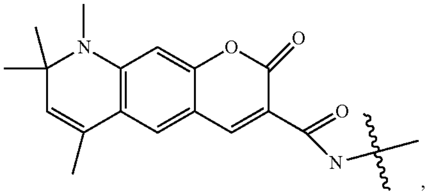

, and

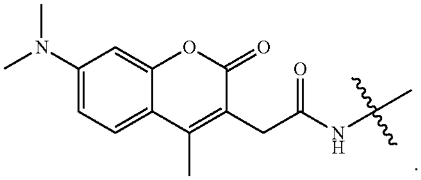

.

A sixth aspect of the present disclosure is a compound having Formula (I):

$$[Z]\text{-}[Q]_m\text{-}[W] \quad \text{(I)},$$

wherein

Z is (i) a "tissue reactive moiety," or (ii) a functional group or a moiety including a functional group capable of participating in a "click chemistry" reaction;

Q is a branched or unbranched, linear or cyclic, substituted or unsubstituted group having between 2 and 40 carbon atoms, and optionally having one or more heteroatoms selected from O, N, or S;

m is 0, 1, or 2; and

W has Formula (IIIA):

(IIIa)

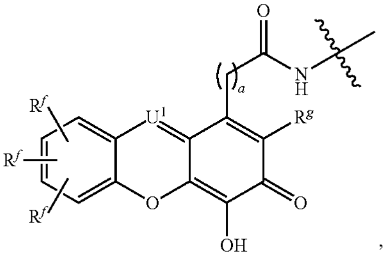

, wherein each $R^f$ is independently —$N(R^x)(R^y)$, where $R^x$ and $R^y$ are independently H or a branched or unbranched $C_1$-$C_4$ alkyl group optionally substituted with one or more halogen atoms; or where any two $R^f$ groups may together form a substituted or unsubstituted, saturated or unsaturated ring; $R^g$ is —H, —$CH_3$ or —$CH_2$—$CH_3$; $U^1$ is O, N, or S; and a is 0 or an integer ranging from 1 to 6.

In some embodiments, $R^e$ is —N(H)(Me). In some embodiments, $R^e$ is —N(H)$CF_3$. In some embodiments, $U^1$ is N; and $R^f$ is —N(H)(Me), —$NH_2$, —N(H)$CF_3$, —N(H)—$CH_2$—F, —N(H)—$CH_2$—$CH_2$—F, —N(H)—CH(F)(F), —N(Me)$CF_3$, —N(Et)$CF_3$, or —N(H)(Ipr). In some embodiments, a is 0. In some embodiments, $U^1$ is N.

In some embodiments, W has Formula (IIIB):

(IIIB)

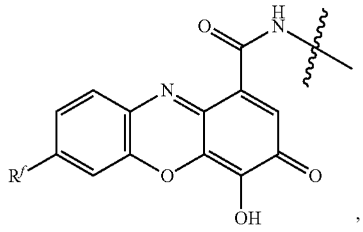

, wherein $R^f$ is —$N(R^x)(R^y)$, where $R^x$ and $R^y$ are independently H or a branched or unbranched $C_1$-$C_4$ alkyl group optionally substituted with one or more halogen atoms;

$R^g$ is —H, —$CH_3$ or —$CH_2$—$CH_3$; $U^1$ is O, N, or S; and a is 0 or an integer ranging from 1 to 6.

In some embodiments, at least one of $R^x$ and $R^y$ is H. In some embodiments, a is 0.

In some embodiments, W is:

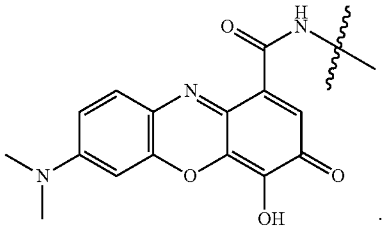 [SMILES: *NC(=O)c1cc(=O)c(O)c2oc3cc(N(C)C)ccc3nc1-2]

.

A seventh aspect of the present disclosure is a compound having Formula (I):

$$[Z]-[Q]_m-[W] \quad (I),$$

wherein

Z is (i) a "tissue reactive moiety," or (ii) a functional group or a moiety including a functional group capable of participating in a "click chemistry" reaction;

Q is a branched or unbranched, linear or cyclic, substituted or unsubstituted group having between 2 and 40 carbon atoms, and optionally having one or more heteroatoms selected from O, N, or S;

m is 0, 1, or 2; and

W has Formula (IVA):

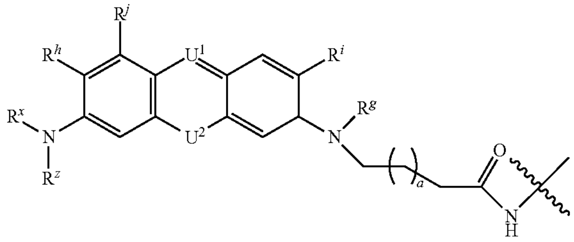

wherein $U^1$ is O, N, or S; $U^2$ is O or S; $R^g$ is —$CH_3$ or —$CH_2$—$CH_3$; $R^i$ is H or a branched or unbranched $C_1$-$C_6$ alkyl group; or where $R^g$ and $R^i$ together form a 5-, 6-, or 7-membered cyclic or aromatic ring which may be optionally substituted with a halogen, a $C_1$-$C_4$ alkyl group; $R^h$ is H or a branched or unbranched $C_1$-$C_4$ alkyl group; $R^x$ is H or a branched or unbranched $C_1$-$C_4$ alkyl group optionally substituted with one or more halogen atoms; $R^z$ is H, or a branched or unbranched $C_1$-$C_4$ alkyl group optionally substituted with one or more halogen atoms or with a —S(O)(O)—$O^-$ group; or where $R^x$ and $R^z$ together form a 3-, 4-, or 5-membered ring which may be optionally be substituted; or where $R^h$ and one of $R^x$ or $R^z$ together form a 5-, 6-, or 7-membered cyclic or aromatic ring which may be optionally substituted with one or more halogen atoms or one or more $C_1$-$C_2$ alkyl groups; $R^j$ is H or a branched or unbranched $C_1$-$C_6$ alkyl group; or where $R^j$ and $R^h$ form a 5- or 6-membered ring, optionally substituted with one or more $C_1$-$C_4$ alkyl groups; and a is 0 or an integer ranging from 1 to 6.

In some embodiments, a is 0. In some embodiments, $R^x$ is a $C_1$-$C_2$ alkyl group. In some embodiments, $U^2$ is S. In some embodiments, $U^1$ is N.

In some embodiments, $U^2$ is O and $R^z$ is an unbranched $C_1$-$C_4$ alkyl group substituted with a —S(O)(O)—$O^-$ group. In some embodiments, $U^1$ is N, $U^2$ is O and $R^z$ is an unbranched $C_1$-$C_4$ alkyl group substituted with a —S(O)(O)—$O^-$ group. In some embodiments, $U^2$ is S and $R^z$ is an unbranched $C_1$-$C_4$ alkyl group substituted with one or more halogen atoms. In some embodiments, $U^1$ is N, $U^2$ is O and $R^z$ is an unbranched $C_1$-$C_4$ alkyl group substituted with one or more halogen atoms. In some embodiments, $U^1$ is N, $U^2$ is S and $R^z$ is an unbranched $C_1$-$C_4$ alkyl group substituted with one or more halogen atoms.

In some embodiments, W has any one of Formulas (IVC) or (IVD):

(IVC)

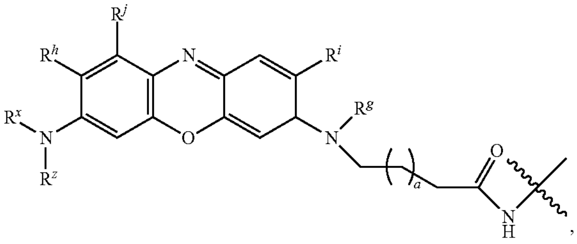

, (IVD)

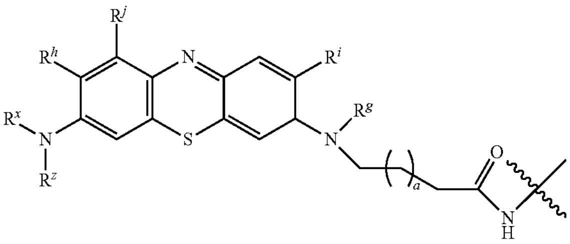

, $R^g$ is —$CH_3$ or —$CH_2$—$CH_3$; $R^i$ is H or a branched or unbranched $C_1$-$C_6$ alkyl group;

or where $R^g$ and $R^i$ together form a 5-, 6-, or 7-membered ring which may be optionally substituted with a halogen, a $C_1$-$C_4$ alkyl group; $R^h$ is H or a branched or unbranched $C_1$-$C_4$ alkyl group; R is H or a branched or unbranched $C_1$-$C_4$ alkyl group optionally substituted with one or more halogen atoms; $R^z$ is H, or a branched or unbranched $C_1$-$C_4$ alkyl group optionally substituted with one or more halogen atoms or with a —S(O)(O)—$O^-$ group; or where $R^h$ and one of $R^x$ or $R^z$ together form a 5-, 6-, or 7-membered cyclic or aromatic ring which may be optionally substituted with one or more halogen atoms or one or more $C_1$-$C_2$ alkyl groups; $R^j$ is H or a branched or unbranched $C_1$-$C_6$ alkyl group; or where $R^j$ and $R^h$ form a 5- or 6-membered ring, optionally substituted with one or more $C_1$-$C_4$ alkyl groups; and a is 0 or an integer ranging from 1 to 6.

In some embodiments, W has Formula (IVE):

(IVE)

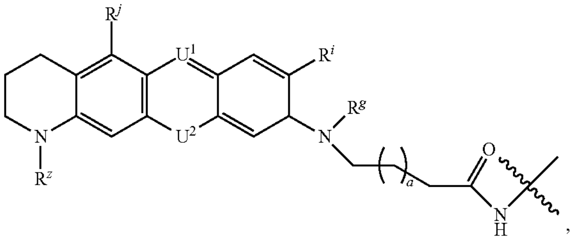

, wherein $U^1$ is O, N, or S; $U^2$ is O or S; $R^g$ is-$CH_3$ or —$CH_2$—$CH_3$; $R^i$ is H or a branched or unbranched $C_1$-$C_6$ alkyl group; or where $R^g$ and $R^i$ together form a 5-, 6-, or 7-membered ring which may be optionally substituted with a halogen, a $C_1$-$C_4$ alkyl group; $R^z$ is H, or a branched or unbranched $C_1$-$C_4$ alkyl group optionally substituted with one or more halogen atoms or with a —S(O)(O)—$O^-$ group; $R^j$ is H or a branched or unbranched $C_1$-$C_6$ alkyl group; a is 0 or an integer ranging from 1 to 6.

In some embodiments, $R^i$ and $R^g$ together form a 6-membered cyclic ring and $R^z$ is a $C_1$-$C_4$ alkyl group. In some embodiments, $U^2$ is O, $R^i$ and $R^g$ together form a 6-membered cyclic ring and $R^z$ is a $C_1$-$C_4$ alkyl group. In some embodiments, $U^2$ is S, $R^i$ and $R^g$ together form a 6-membered cyclic ring, and $R^z$ is a $C_1$-$C_4$ alkyl group. 35. In some embodiments, $R^i$ and $R^g$ together form a 6-membered cyclic ring, $U^2$ is O, and $R^z$ is an unbranched $C_1$-$C_4$ alkyl group substituted with a —S(O)(O)—$O^-$ group.

In some embodiments, W has any one of Formulas (IVG) and (IVH):

(IVG)

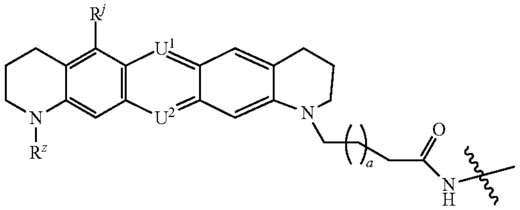

, (IVH)

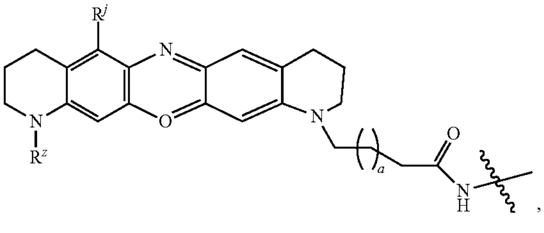

, wherein $U^1$ is O, N, or S; $U^2$ is O or S; $R^z$ is H, or a branched or unbranched $C_1$-$C_4$ alkyl group optionally substituted with one or more halogen atoms or with a —S(O)(O)—$O^-$ group; $R^j$ is H or a branched or unbranched $C_1$-$C_6$ alkyl group; a is 0 or an integer ranging from 1 to 6.

In some embodiments, $R^z$ is a $C_1$-$C_4$ alkyl group. In some embodiments, $R^z$ is an unbranched $C_1$-$C_4$ alkyl group. In some embodiments, $R^z$ is an unbranched $C_1$-$C_3$ alkyl group substituted with a —S(O)(O)—$O^-$ group.

In some embodiments, W is selected from the group consisting of:

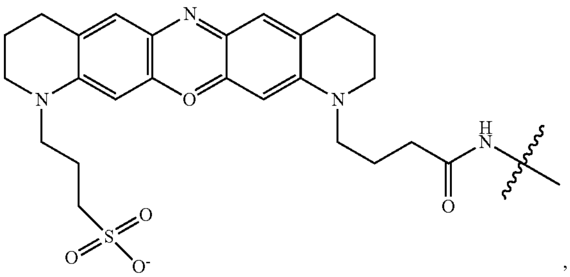

,

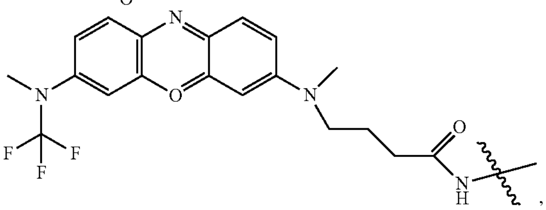

,

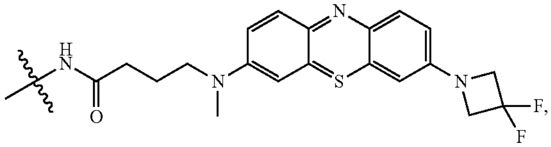

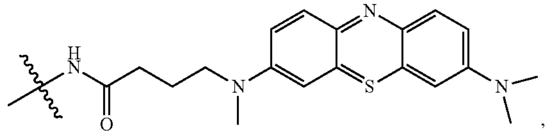

,

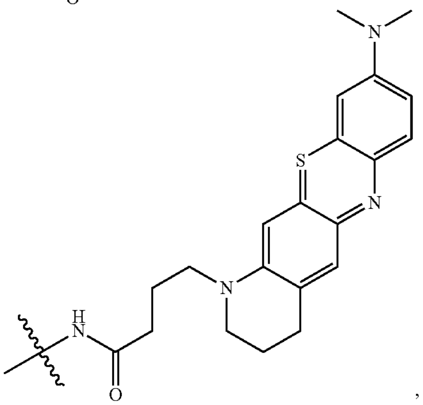

,

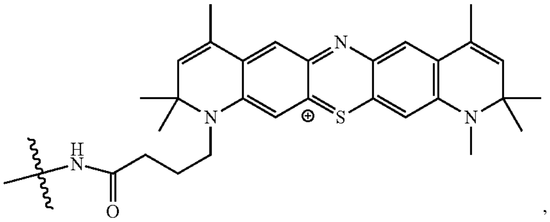

,

-continued

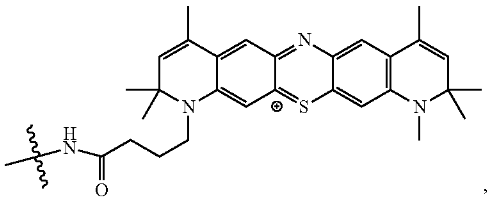

, and

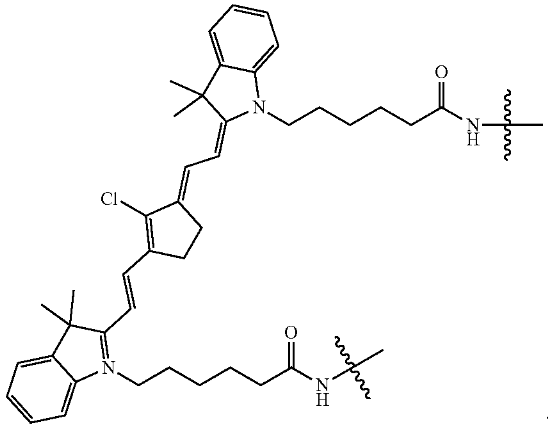

.

An eighth aspect of the present disclosure is a compound having Formula (I):

$$[Z]\text{-}[Q]_m\text{-}[W] \quad (I),$$

wherein

Z is (i) a "tissue reactive moiety," or (ii) a functional group or a moiety including a functional group capable of participating in a "click chemistry" reaction;

Q is a branched or unbranched, linear or cyclic, substituted or unsubstituted group having between 2 and 40 carbon atoms, and optionally having one or more heteroatoms selected from O, N, or S;

m is 0, 1, or 2; and

W has any one of Formulas (VA) and (VB):

(VA)

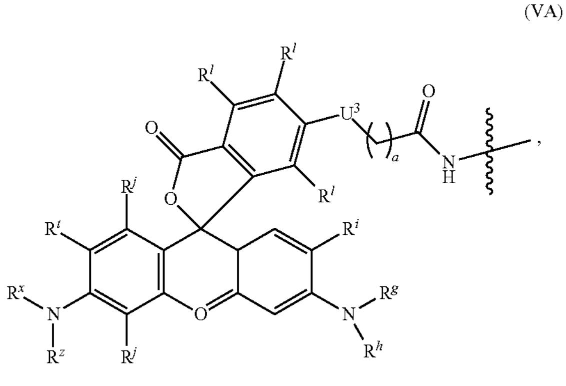

,

-continued (VB)

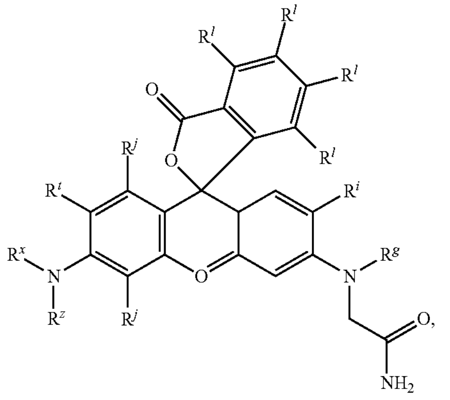

wherein $R^g$ is —$CH_3$ or —$CH_2$—$CH_3$; $R^i$ is H or a branched or unbranched $C_1$-$C_6$ alkyl group;

or where $R^g$ and $R^i$ together form a 5-, 6-, or 7-membered ring which may be optionally substituted with a halogen, a $C_1$-$C_4$ alkyl group; $R^h$ is H or a branched or unbranched $C_1$-$C_4$ alkyl group; R is H or a branched or unbranched $C_1$-$C_4$ alkyl group optionally substituted with one or more halogen atoms; $R^z$ is H, or a $C_1$-$C_4$ alkyl group optionally substituted with one or more halogen atoms or with a —S(O)(O)—$O^-$ group; $R^t$ is H or a branched or unbranched $C_1$-$C_4$ alkyl group; or where $R^t$ and one of $R^x$ or $R^z$ together form a 5-, 6-, or 7-membered cyclic or aromatic ring which may be optionally substituted with one or more halogen atoms or one or more $C_1$-$C_2$ alkyl groups; each $R^j$ is independently H or a branched or unbranched $C_1$-$C_6$ alkyl group; or where $R^j$ and $R^t$ form a 5- or 6-membered ring, optionally substituted with one or one or more $C_1$-$C_2$ alkyl groups; or where $R^j$ and one of $R^x$ or $R^z$ form a 5- or 6-membered ring, optionally substituted with one or more $C_1$-$C_2$ alkyl groups; or where $R^x$, $R^t$, and $R^j$ together form a bicyclic ring which may be saturated or unsaturated and which may be optionally substituted with one or more halogen atoms or one or more $C_1$-$C_2$ alkyl groups; each $R^l$ is independently H or a halogen atom; and a is 0 or an integer ranging from 1 to 6.

In some embodiments, $R^t$ and $R^x$ together form a 6-membered ring. In some embodiments, $R^t$ and $R^x$ together form a 6-membered ring substituted with one or more methyl or ethyl groups, one or more —$CH_2$—S(O)(O)(OH) groups, one or more —$CH_2$—$CH_2$—S(O)(O)(OH) groups, —$CH_2$—$CH_2$—$CH_2$—S(O)(O)(OH) groups, or —$CH_2$—$CH_2$—$CH_2$—$CH_2$—S(O)(O)(OH) groups. In some embodiments, $R^i$ and $R^g$ together form a 6-membered substituted ring. In some embodiments, $R^t$ and $R^x$ together form a 6-membered ring, and $R^i$ and $R^g$ together form a 6-membered ring. In some embodiments, $R^x$, $R^t$, and $R^j$ together form a bicyclic ring. In some embodiments, $R^x$, $R^t$, and $R^j$ together form a bicyclic ring, and $R^i$ and $R^g$ together form a 6-membered ring. In some embodiments, $R^i$ and $R^g$ together form a 6-membered ring substituted with one or more methyl or ethyl groups, one or more —$CH_2$—S(O)(O)(OH) groups, one or more —$CH_2$—$CH_2$—S(O)(O)(OH) groups, —$CH_2$—$CH_2$—$CH_2$—S(O)(O)(OH) groups, or —$CH_2$—$CH_2$—$CH_2$—$CH_2$—S(O)(O)(OH) groups. In some embodiments, a is 0.

In some embodiments, W is selected from the group consisting of:
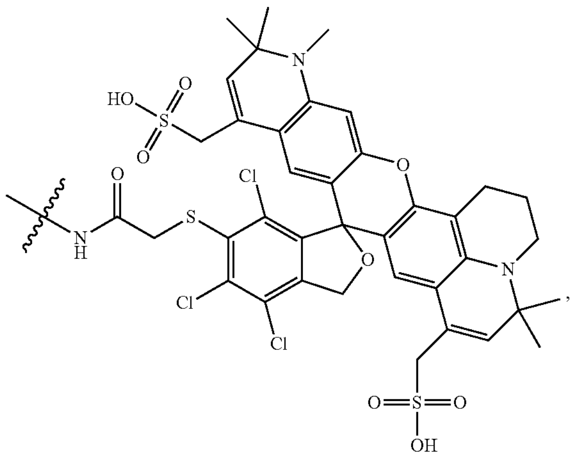
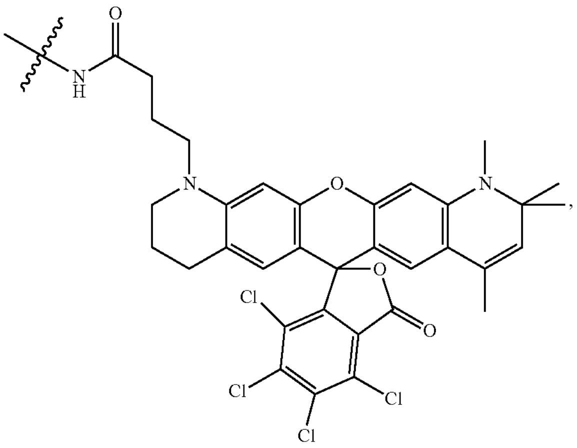
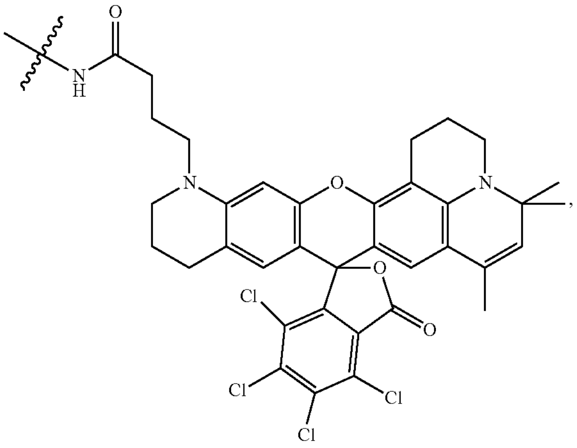
-continued
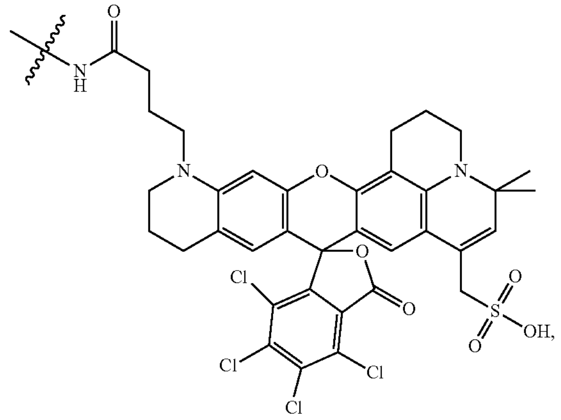
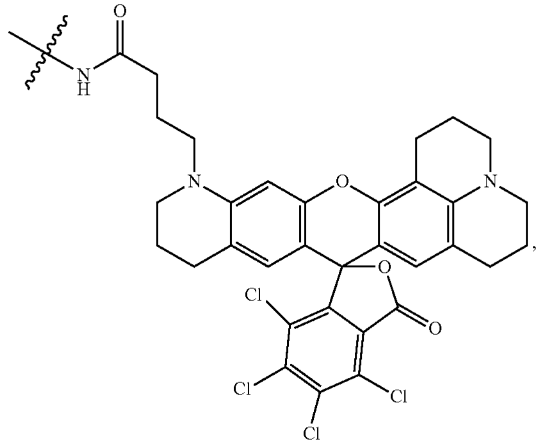
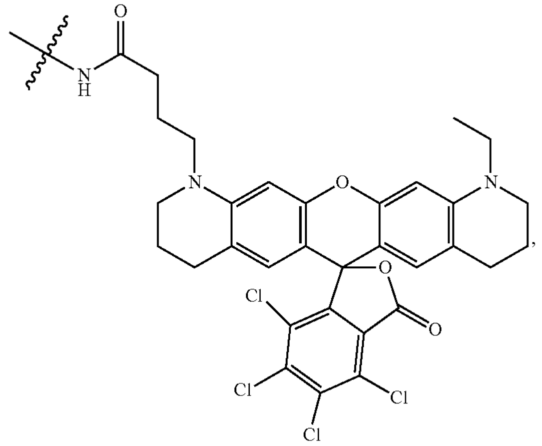
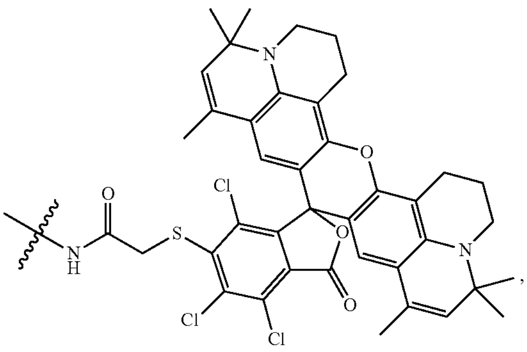
and -continued

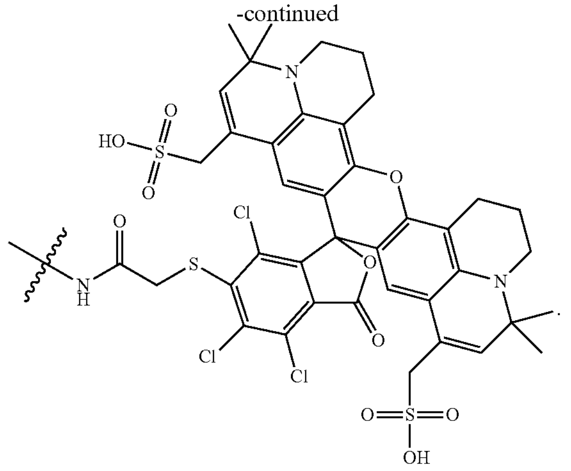

A ninth aspect of the present disclosure is a compound having Formula (I):

[Z]-[Q]$_m$-[W] (I), wherein

Z is (i) a "tissue reactive moiety," or (ii) a functional group or a moiety including a functional group capable of participating in a "click chemistry" reaction;

Q is a branched or unbranched, linear or cyclic, substituted or unsubstituted group having between 2 and 40 carbon atoms, and optionally having one or more heteroatoms selected from O, N, or S;

m is 0, 1, or 2; and

W has Formula (VI):

(VI)

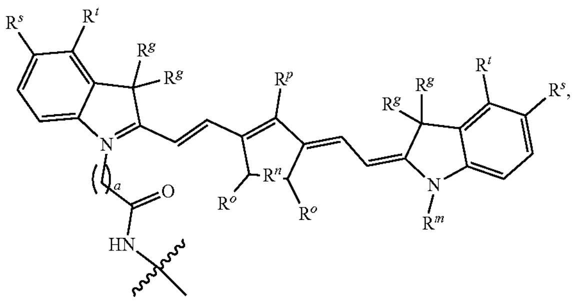

wherein a is 0 or an integer ranging from 1 to 6; $R^p$ is a halogen atom; $R''$ is a bond or —$CH_2$—; each $R^o$ is independently a branched or unbranched $C_1$-$C_4$ alkyl group, or when $R''$ is —$CH_2$— then both $R^o$ groups together may form a 6-member cyclic or aromatic ring, optionally substituted with one or more halogen groups or one or more $C_1$-$C_2$ alkyl groups; each $R^g$ is independently-$CH_3$ or —$CH_2$—$CH_3$; $R'''$ is H, a branched or unbranched $C_1$-$C_4$ alkyl group which is optionally substituted with one or more halogen atoms and or one or more —S(O)(O)(OH) groups, or a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction; each $R^s$ or $R^t$ group is independently selected from a branched or unbranched $C_1$-$C_6$ alkyl group; or wherein any two adjacent $R^s$ and $R^t$ groups and/or any two adjacent $R_g$ and $R^t$ groups may together form a 5- or 6-membered cyclic or aromatic group, optionally substituted with one or more $C_1$-$C_2$ alkyl groups.

In some embodiments, $R''$ is —$CH_2$—. In some embodiments, $R''$ is a bond and wherein at least one $R^g$ is methyl. In some embodiments, $R''$ is —$CH_2$— and each $R^o$ together forms a 6-membered ring. In some embodiments, one set of adjacent $R^t$ and $R^s$ groups forms a 6-membered ring. In some embodiments, both sets of adjacent $R^t$ and $R^s$ groups form a 6-membered ring. In some embodiments, one set of adjacent $R^t$ and $R^s$ groups forms a 6-membered ring, and where $R''$ is —$CH_2$— and each $R^o$ together forms a 6-membered ring. In some embodiments, at least one set of adjacent $R^t$, $R^s$, and $R^g$ groups forms a bicyclic ring. In some embodiments, $R''$ is —$CH_2$—, and wherein $R'''$ is a branched or unbranched $C_1$-$C_4$ alkyl group which is optionally substituted with one or more halogen atoms and or one or more —S(O)(O)(OH) groups. In some embodiments, one set of adjacent $R^t$ and $R^s$ groups forms a 6-membered ring, and wherein $R'''$ is a branched or unbranched $C_1$-$C_4$ alkyl group which is optionally substituted with one or more halogen atoms and or one or more —S(O)(O)(OH) groups.

In some embodiments, one set of adjacent $R^t$, $R^s$, and $R^g$ groups forms a bicyclic ring, another set of adjacent $R^t$ and $R^s$ groups forms a 6-membered ring, and wherein $R'''$ is a branched or unbranched $C_1$-$C_4$ alkyl group which is optionally substituted with one or more halogen atoms and or one or more —S(O)(O)(OH) groups. In some embodiments, $R''$ is a bond, at least one $R^g$ is methyl, and wherein $R'''$ is a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction. In some embodiments, $R''$ is —$CH_2$—, and wherein $R'''$ is a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction. In some embodiments, set of adjacent $R^t$, $R^s$, and $R^g$ groups forms a bicyclic ring, and wherein $R'''$ is a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction.

In some embodiments, W is selected from the group consisting of:

-continued
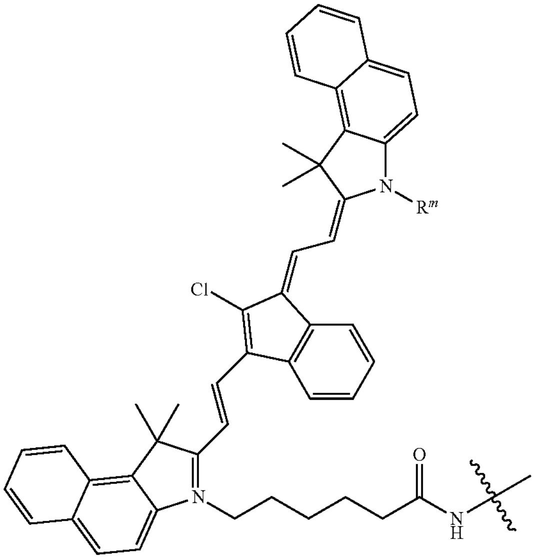
,
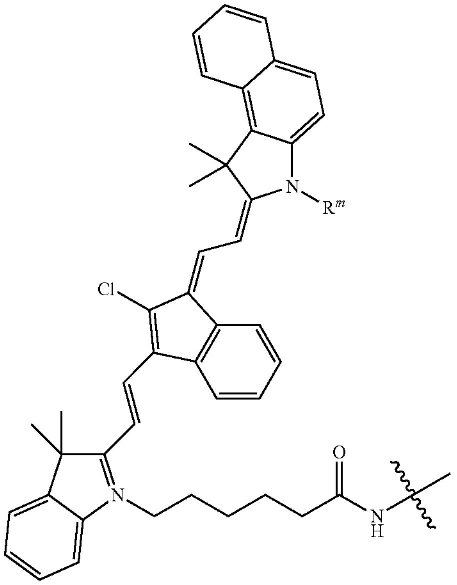
,
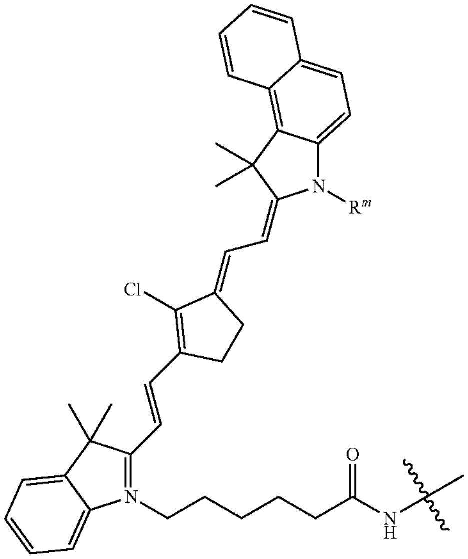
,
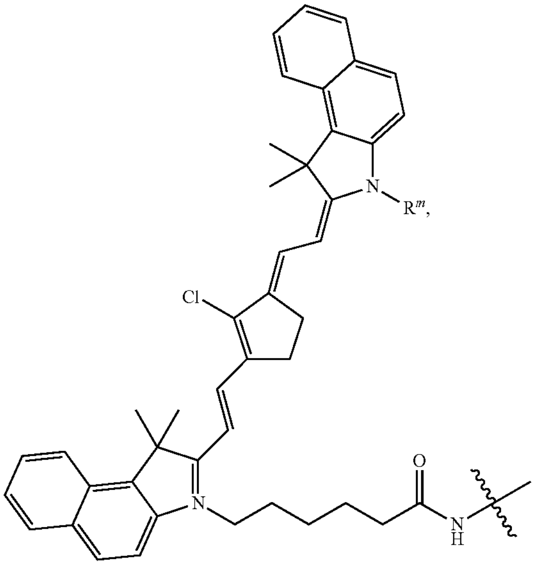
,
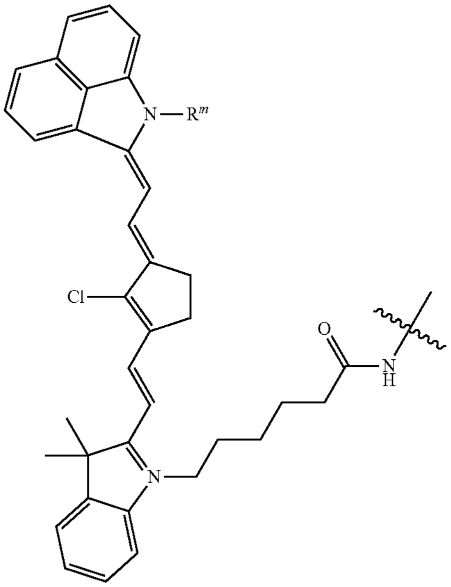
,
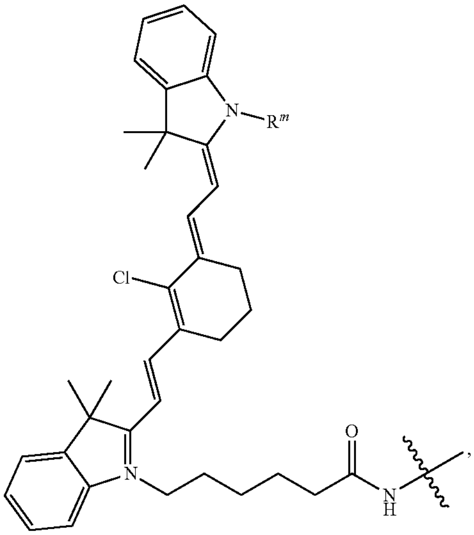
, and -continued

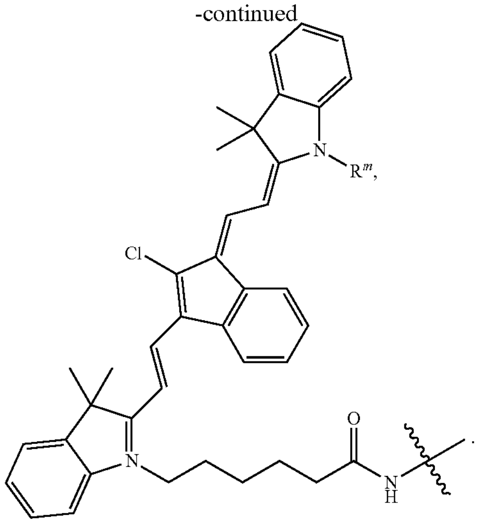

A tenth aspect of the present disclosure is a compound having Formula (I):

$[Z]-[Q]_m-[W]$ (I), wherein

Z is (i) a "tissue reactive moiety," or (ii) a functional group or a moiety including a functional group capable of participating in a "click chemistry" reaction;

Q is a branched or unbranched, linear or cyclic, substituted or unsubstituted group having between 2 and 40 carbon atoms, and optionally having one or more heteroatoms selected from O, N, or S;

m is 0, 1, or 2; and

W has Formula (VIIA):

(VIIA)

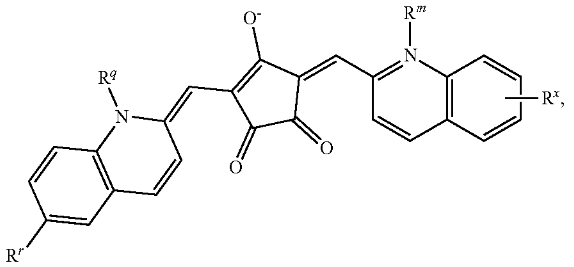

wherein $R^x$ is H or a branched or unbranched $C_1$-$C_4$ alkyl group optionally substituted with one or more halogen atoms; $R^m$ is H, a branched or unbranched $C_1$-$C_4$ alkyl group which is optionally substituted with one or more halogen atoms and or one or more —S(O)(O)(OH) group, or a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction; $R^q$ and $R^r$ are each independently H, a branched or unbranched $C_1$-$C_4$ alkyl group optionally substituted with one or more halogen atoms, or a group $R^s$, where $R^s$ is a saturated or unsaturated $C_1$-$C_{20}$ alkyl group comprising at least one amide group, and which is optionally substituted with one or more heteroatoms, provided that the group $R^s$ terminates in a moiety capable of participating in a click chemistry reaction, provided that at least one of $R^q$ or $R^r$ comprises a group $R^s$, and further provided that $R^q$ and $R^r$ are both not $R^s$.

In some embodiments, $R^f$ and $R^x$ are both H. In some embodiments, $R^m$ is a branched or unbranched $C_1$-$C_4$ alkyl group which is optionally substituted with one or more halogen atoms and or one or more —S(O)(O)(OH) group. In some embodiments, one of $R^f$ or $R^m$ is a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction.

In some embodiments, W has any one of Formulas (VIIB) and (VIIC):

(VIIB)

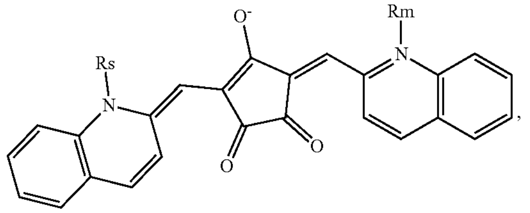

(VIIC)

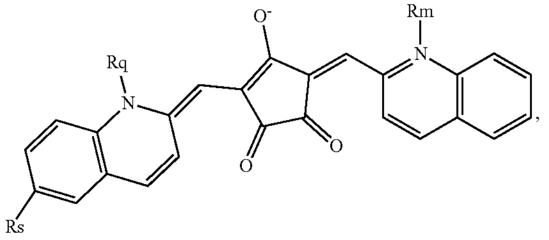

wherein $R^x$ is H or a branched or unbranched $C_1$-$C_4$ alkyl group optionally substituted with one or more halogen atoms; $R^m$ is H, a branched or unbranched $C_1$-$C_4$ alkyl group which is optionally substituted with one or more halogen atoms and or one or more —S(O)(O)(OH) group, or a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction; $R^q$ is H or a branched or unbranched $C_1$-$C_4$ alkyl group optionally substituted with one or more halogen atoms; and $R^s$ is a saturated or unsaturated $C_1$-$C_{20}$ alkyl group comprising at least one amide group, and which is optionally substituted with one or more heteroatoms, provided that the group $R^s$ terminates in a moiety capable of participating in a click chemistry reaction.

In some embodiments, W is selected from the group consisting of:

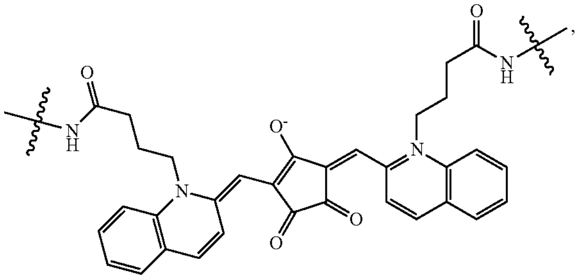
,
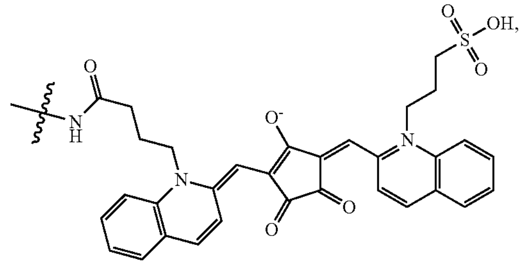
, and
-continued
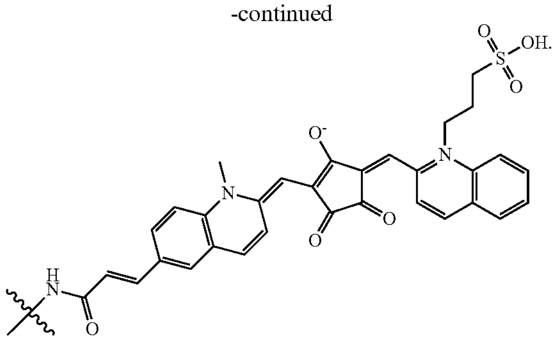
.
An eleventh aspect of the present disclosure is a conjugate selected from the group consisting of:
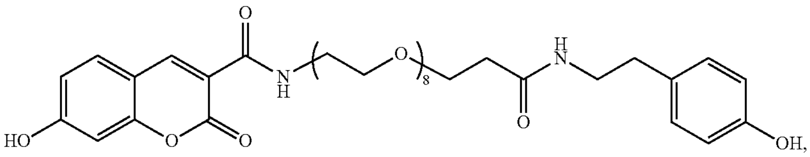
,
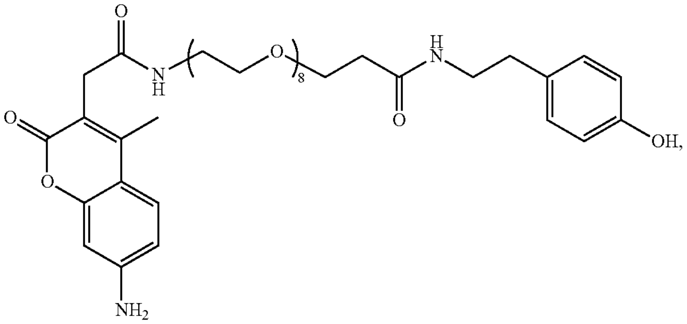
,
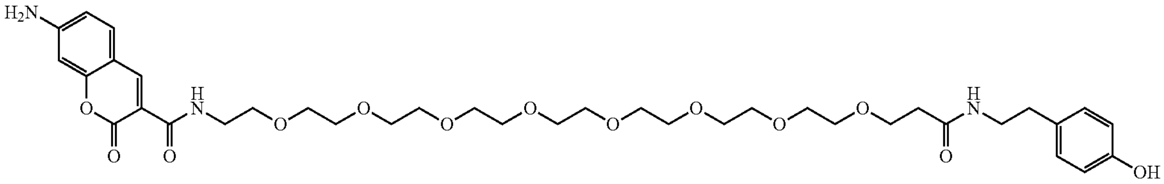
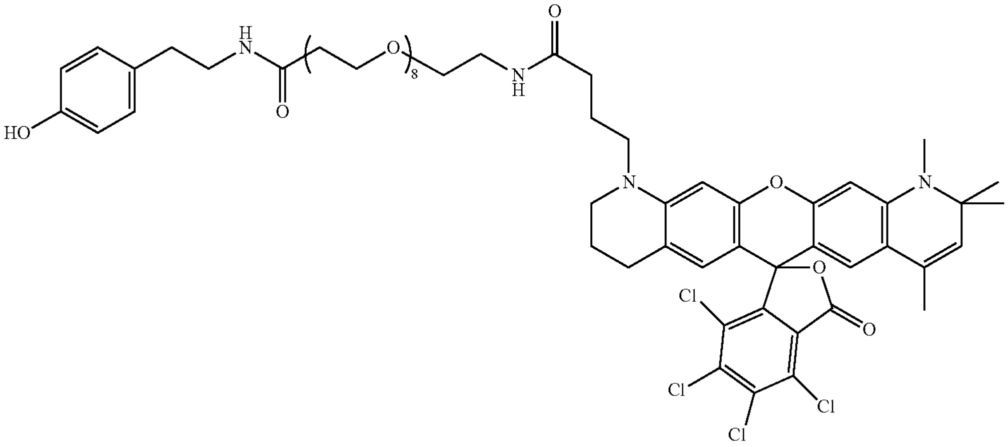

-continued
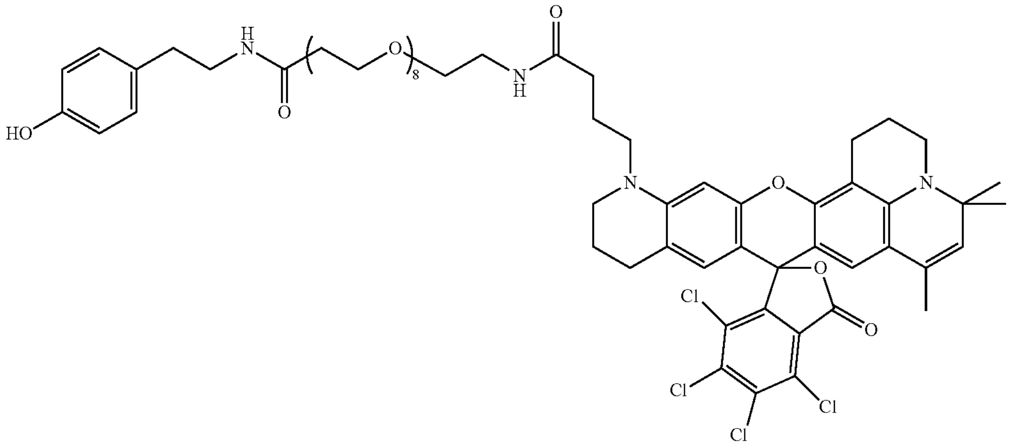
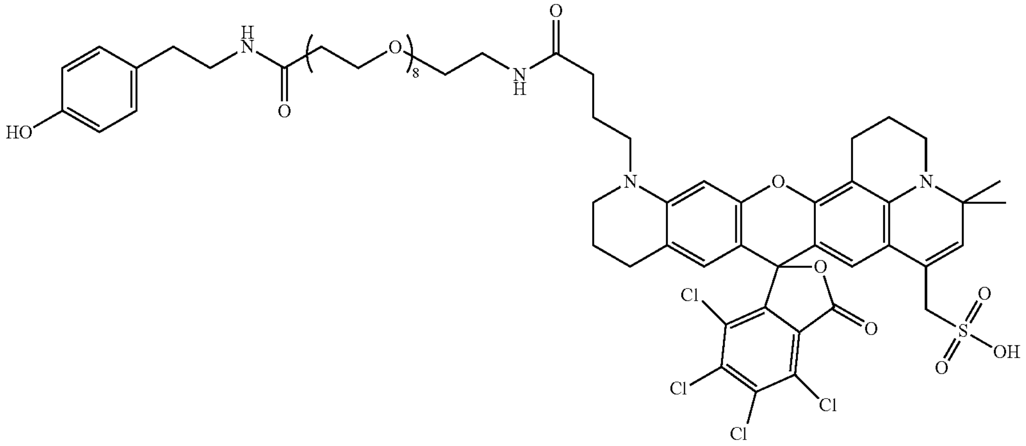
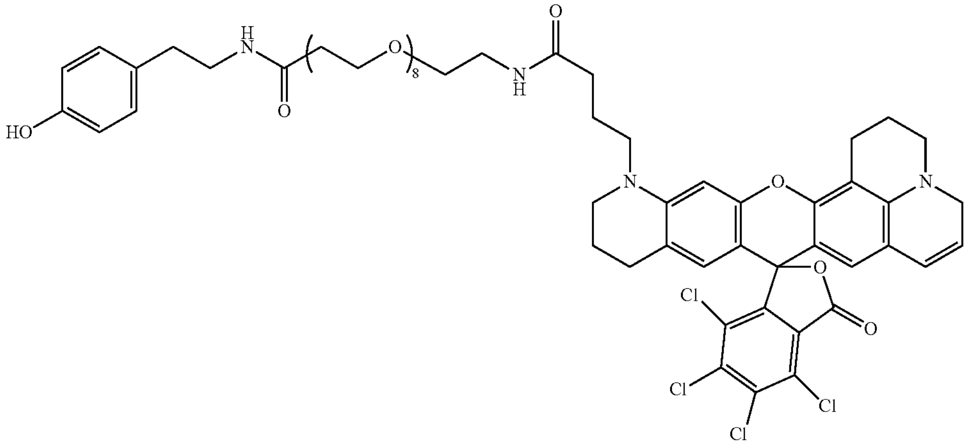

-continued
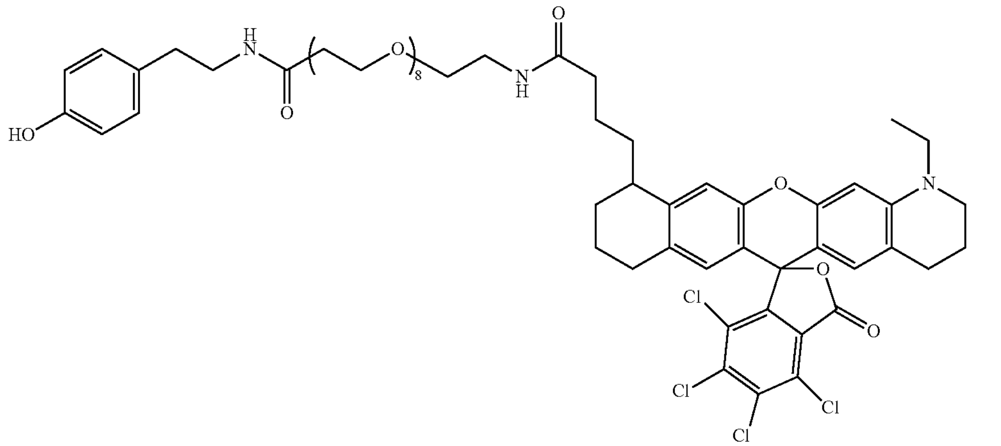
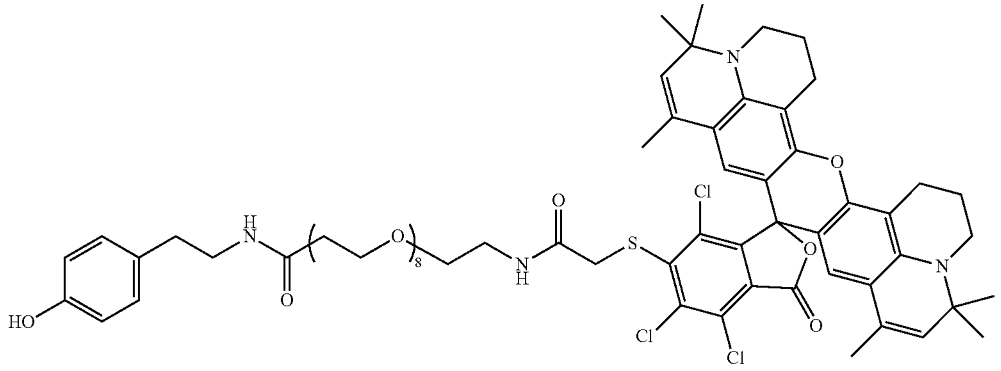
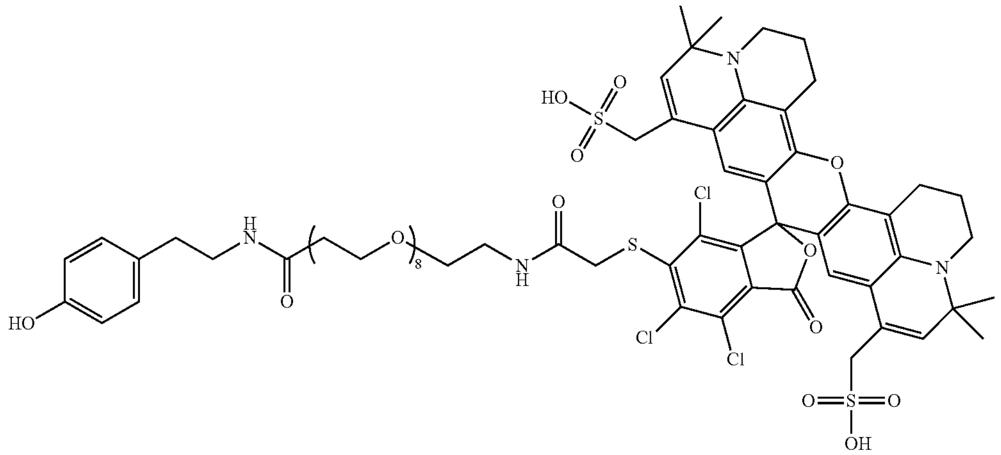
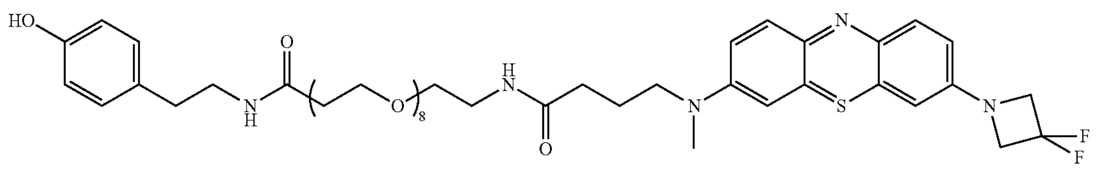

-continued
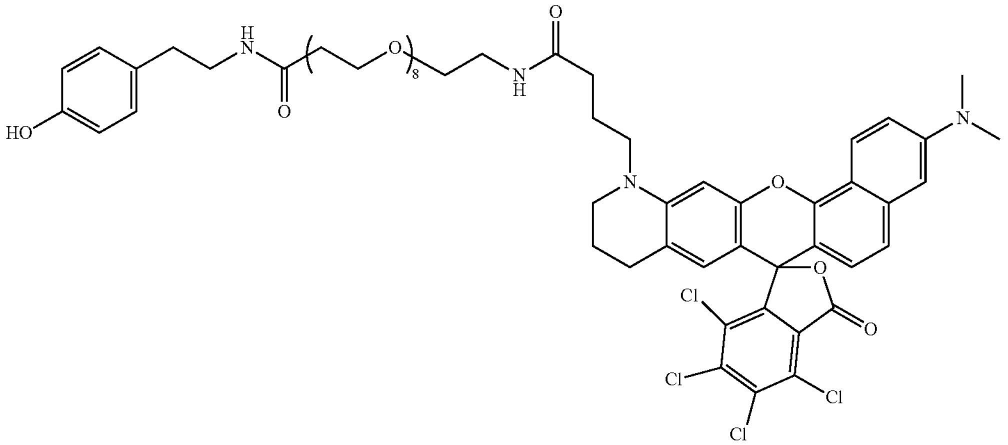
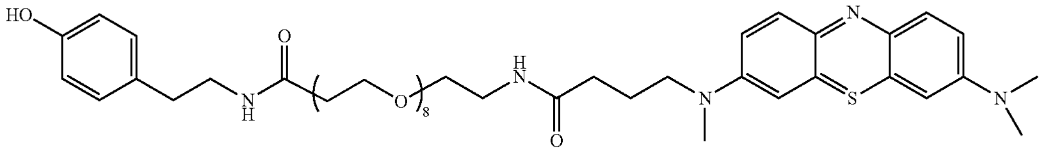
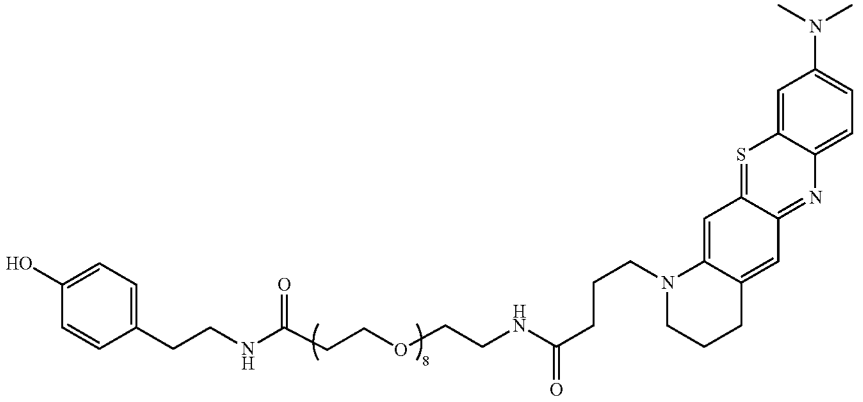
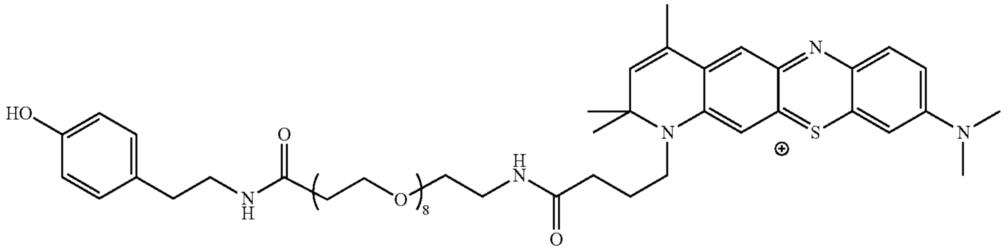
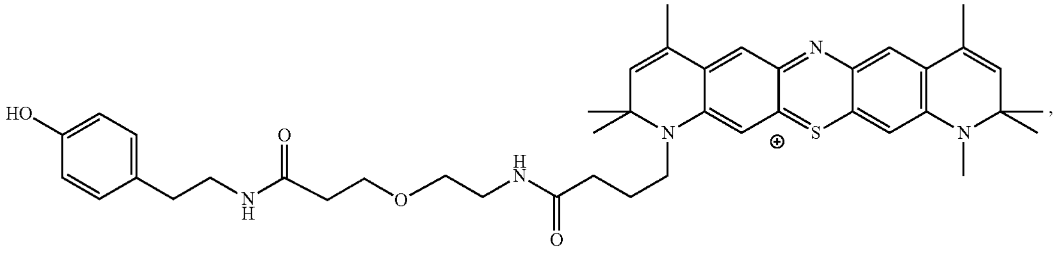
,

-continued
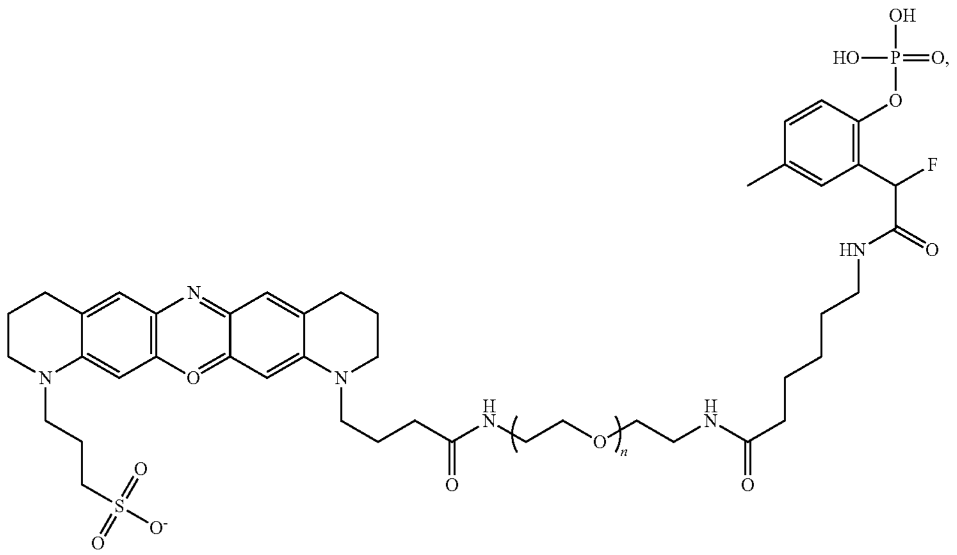
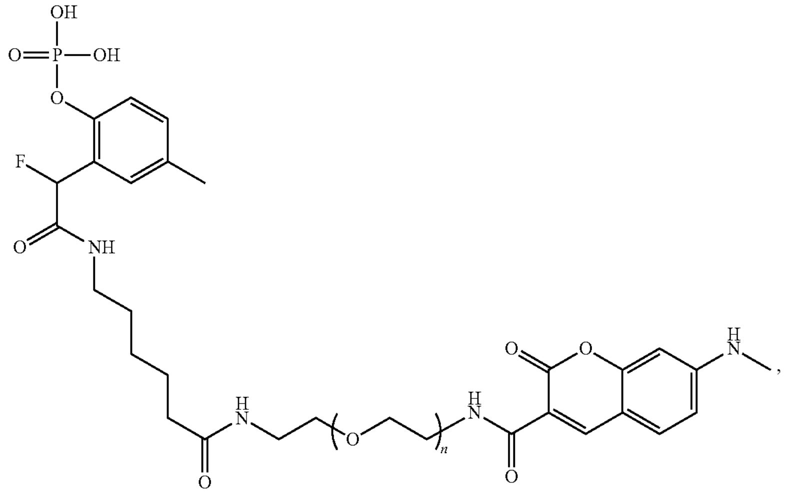
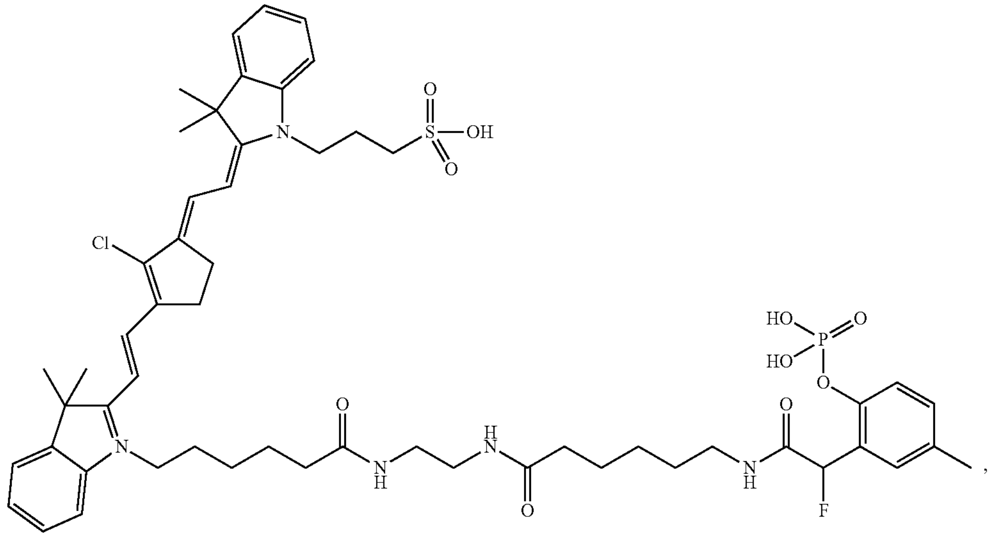

-continued
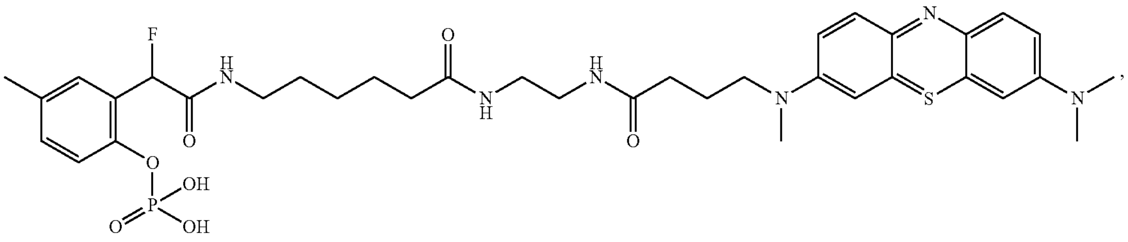
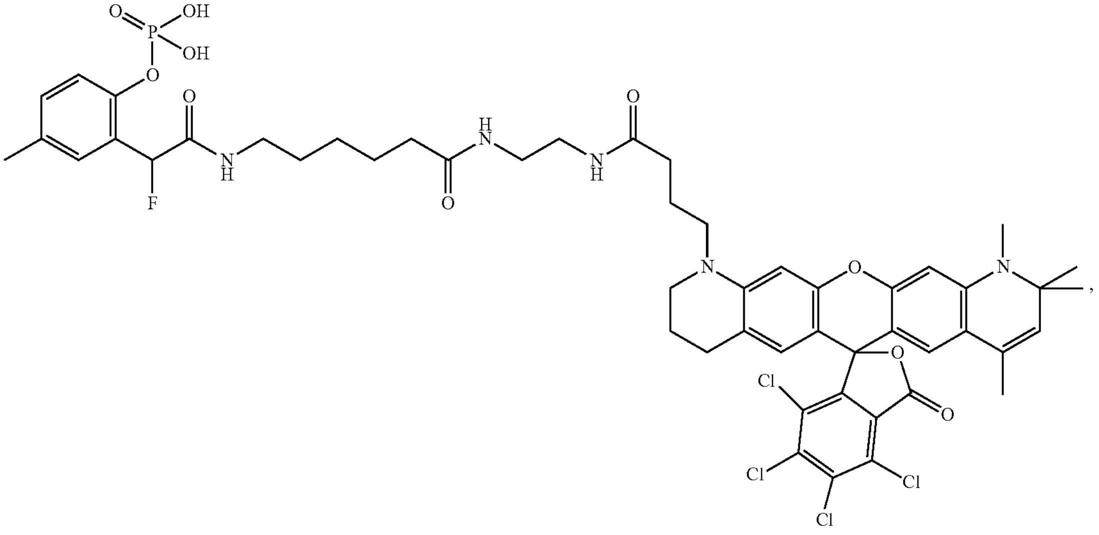
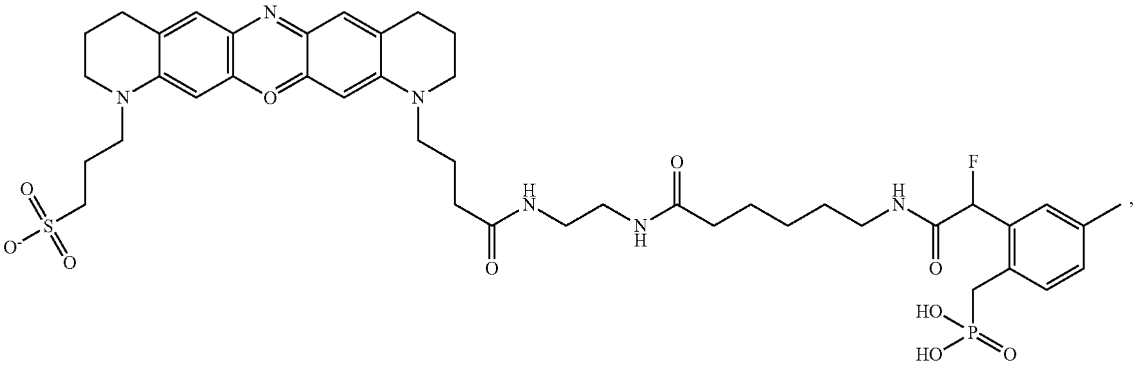
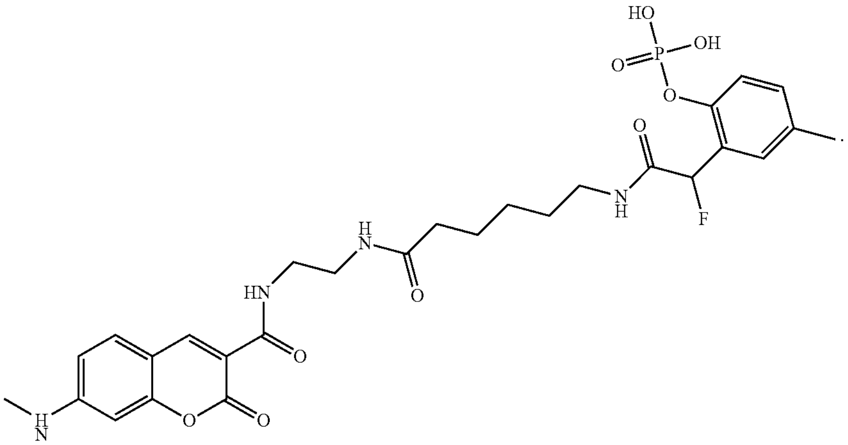

A twelfth aspect of the present disclosure is a conjugate selected from the group consisting of:
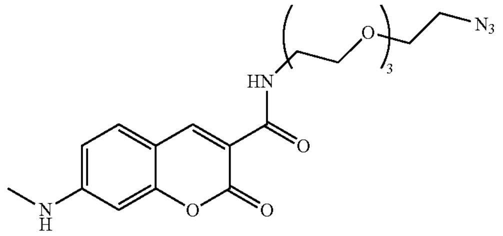
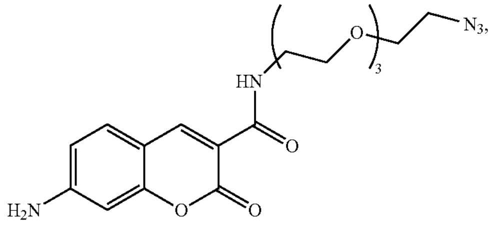,
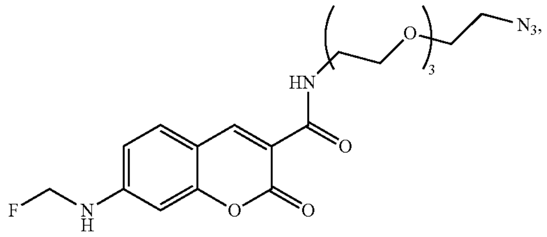,
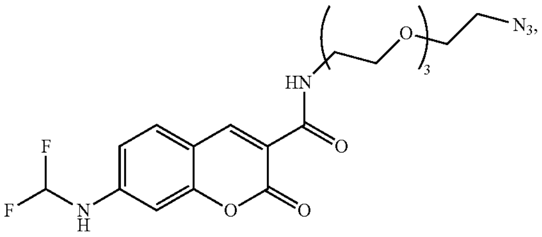,
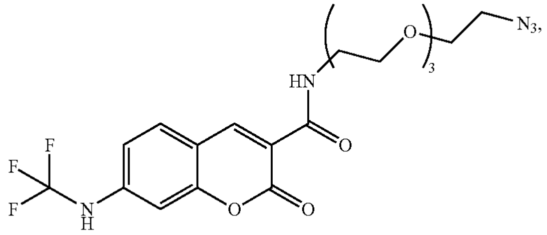,
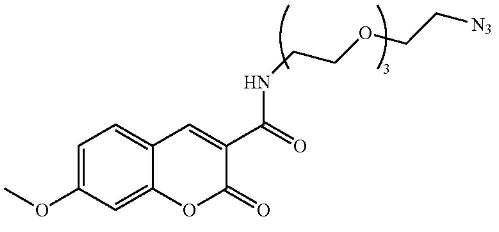
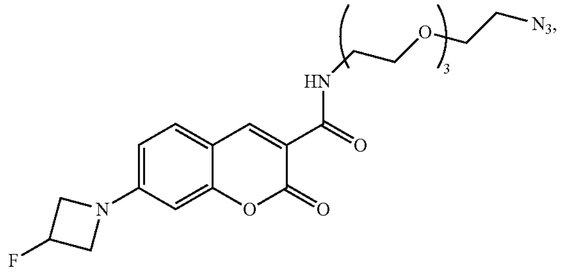,
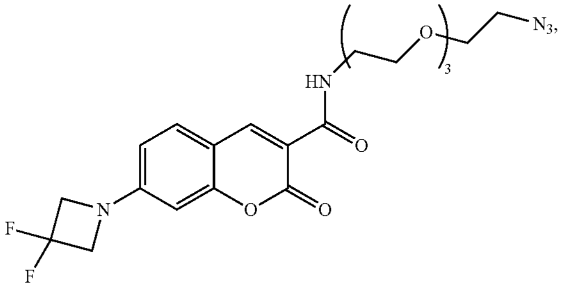,
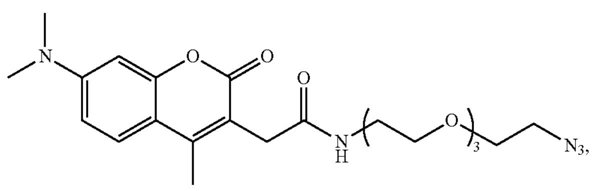,
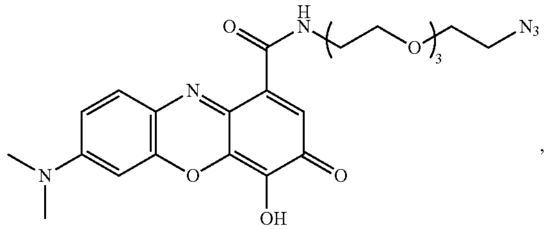,
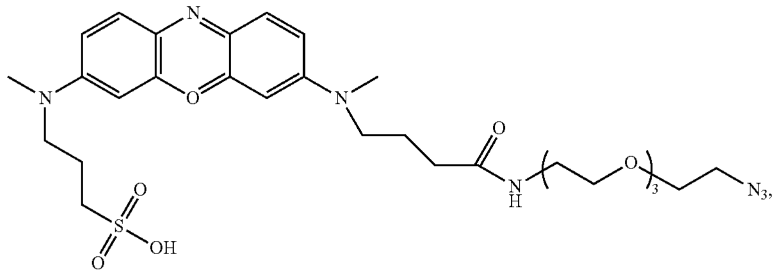, -continued
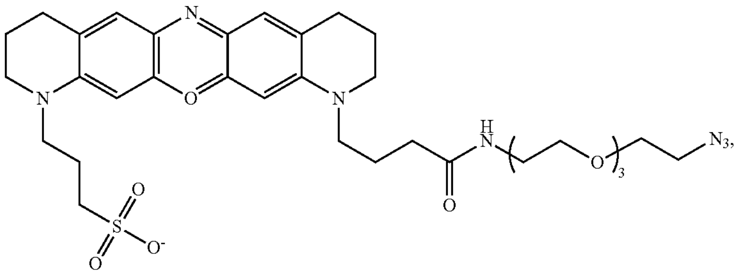
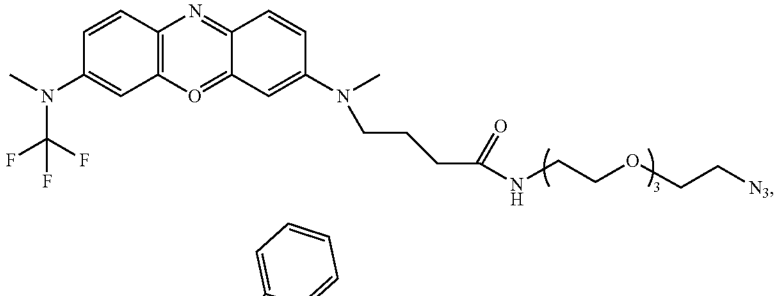
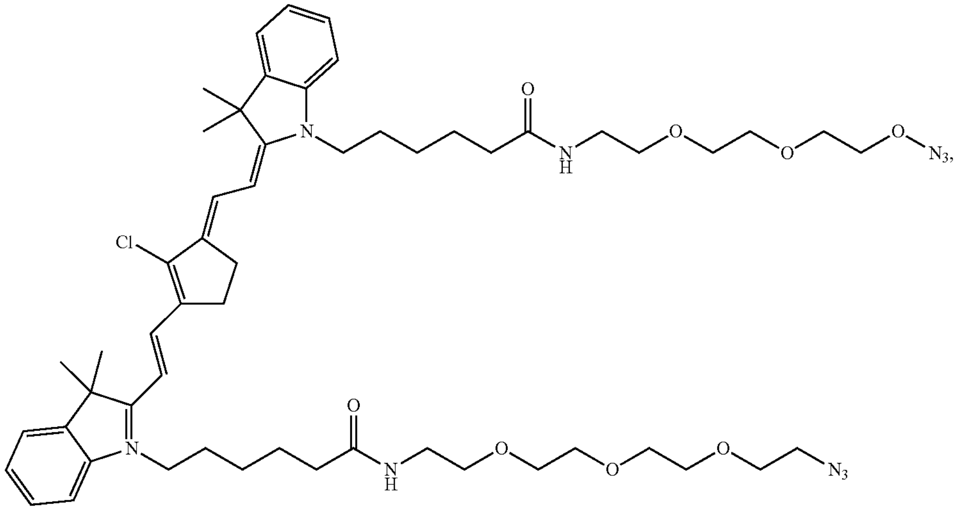
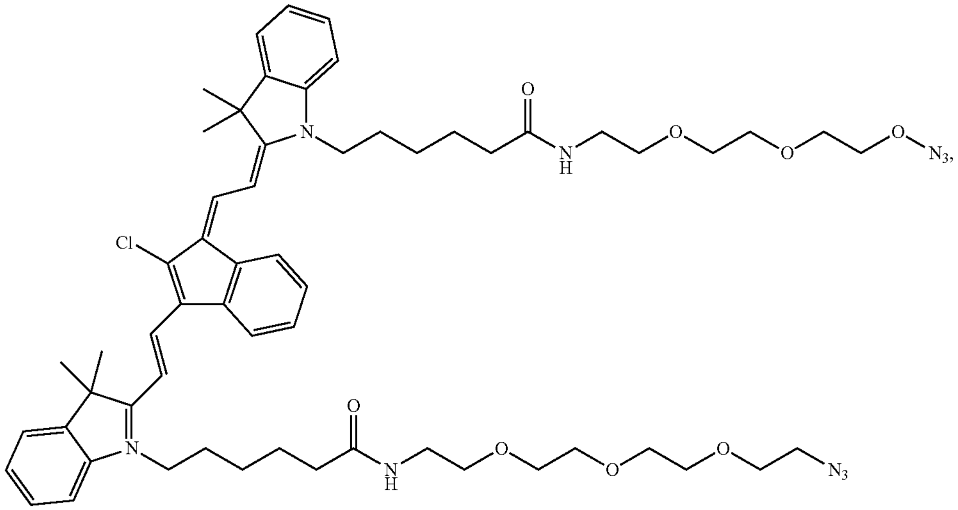

-continued
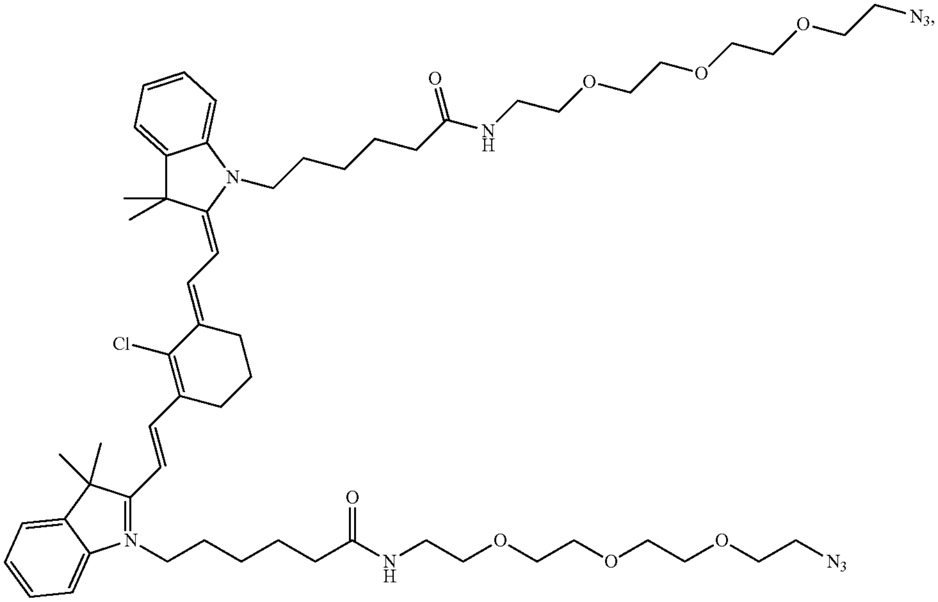
,
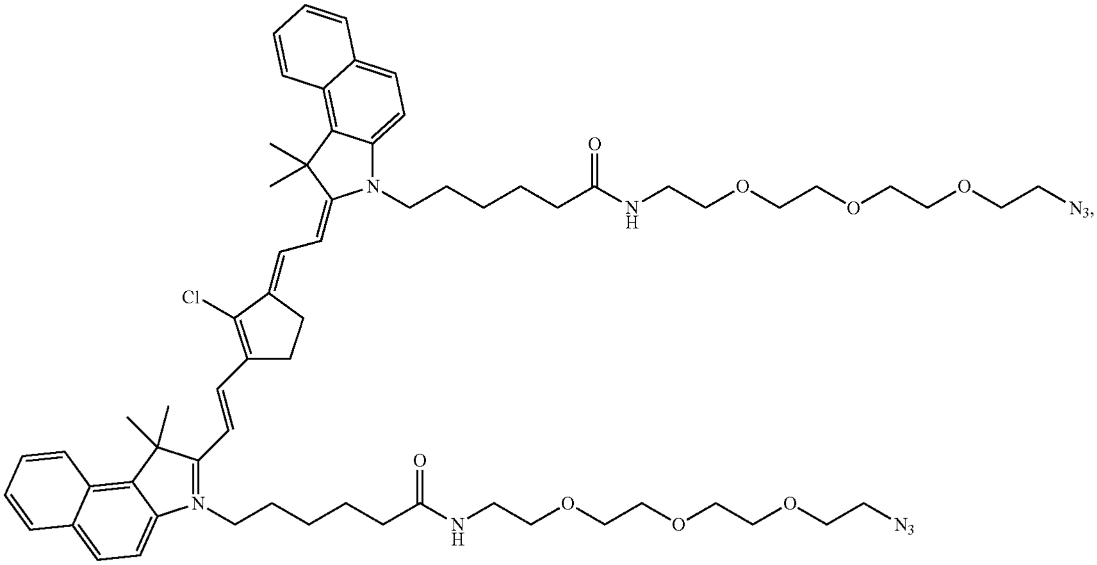
,
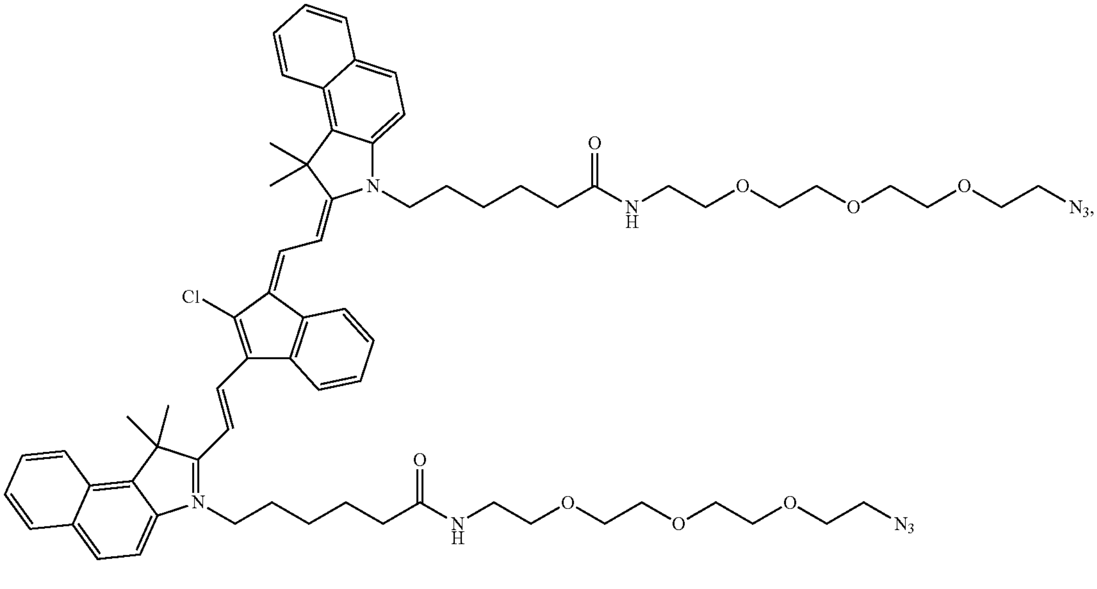
,

-continued
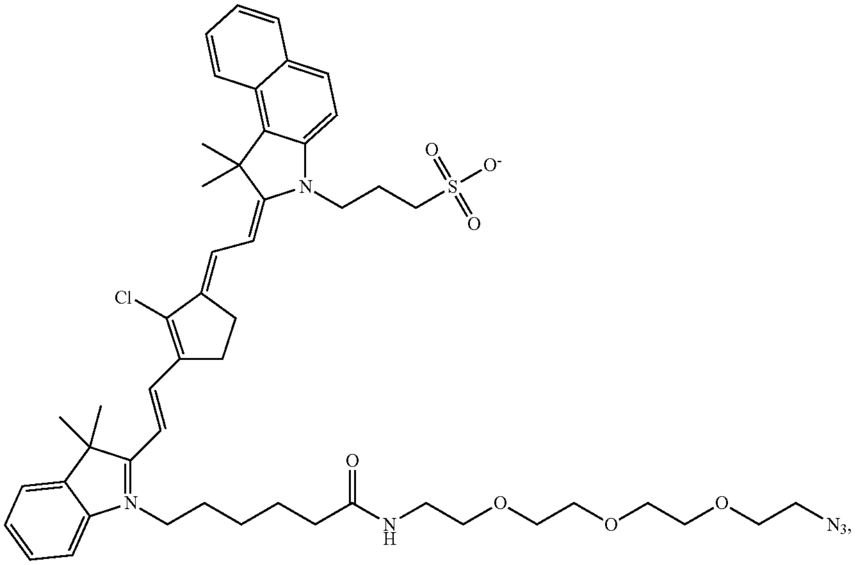
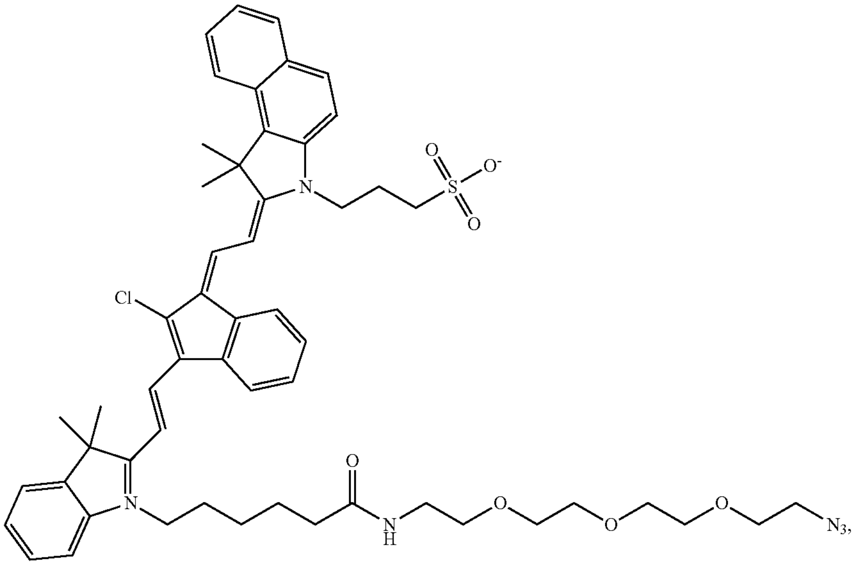
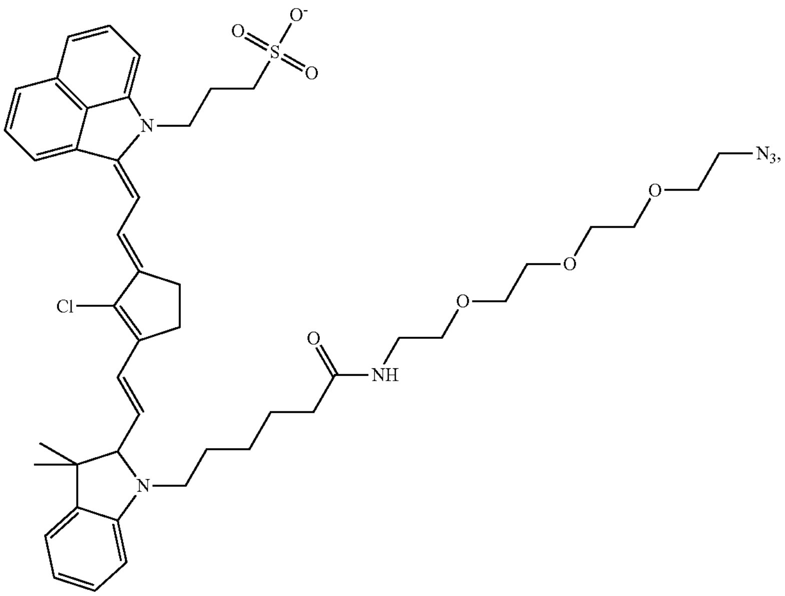

-continued
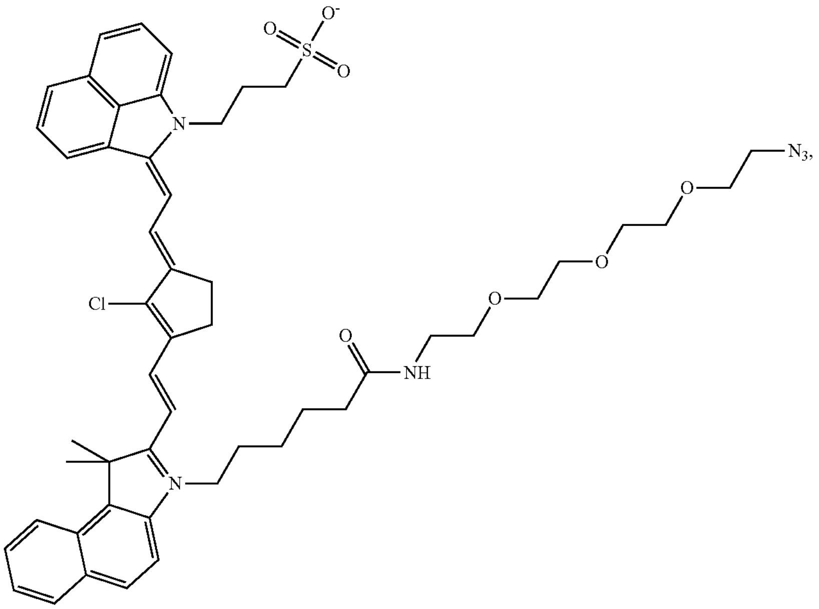
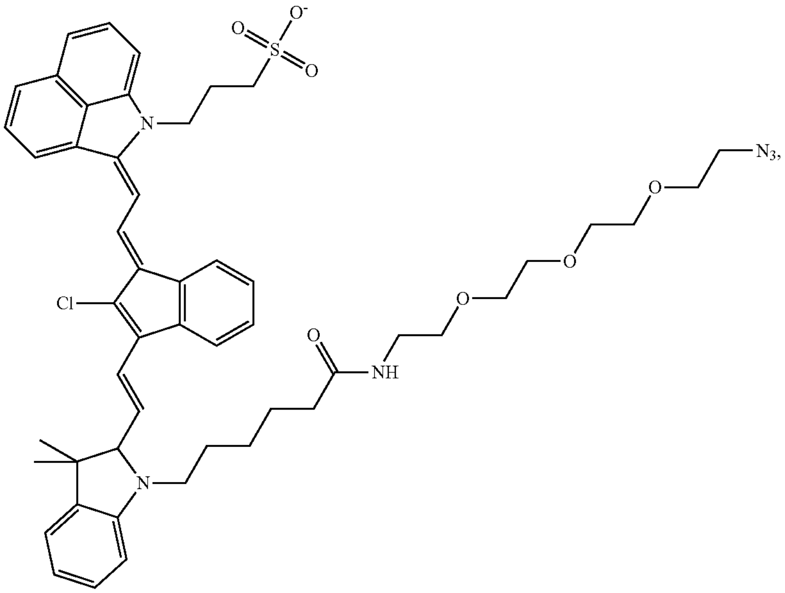

-continued
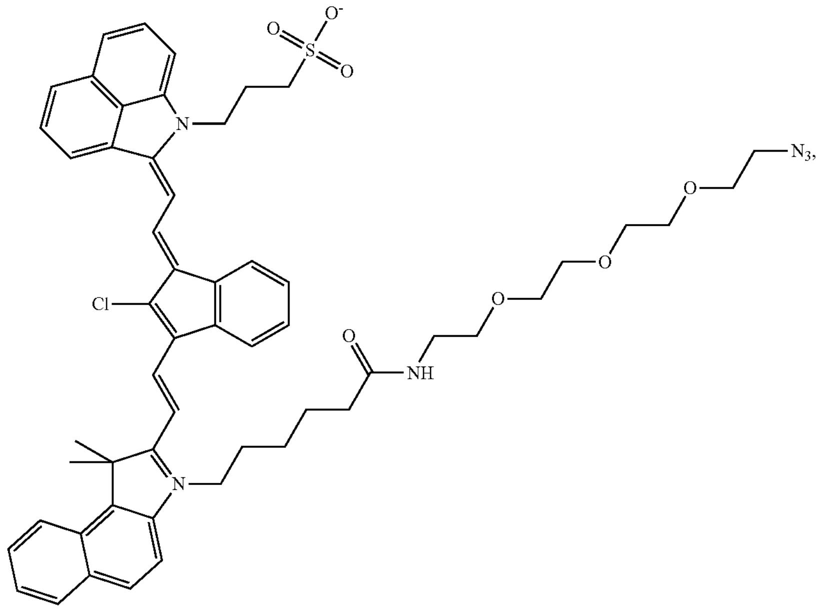
,
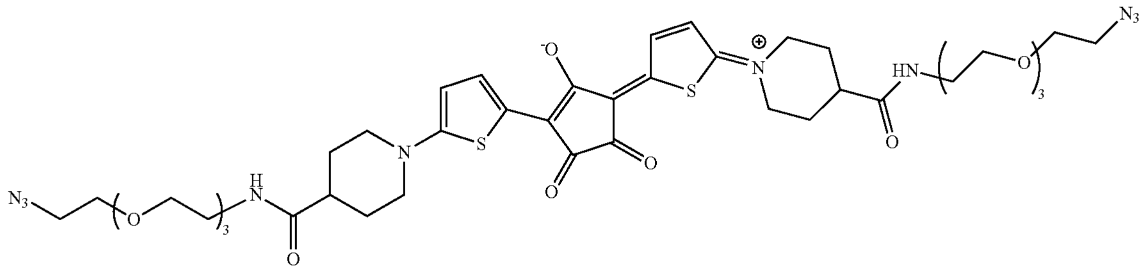
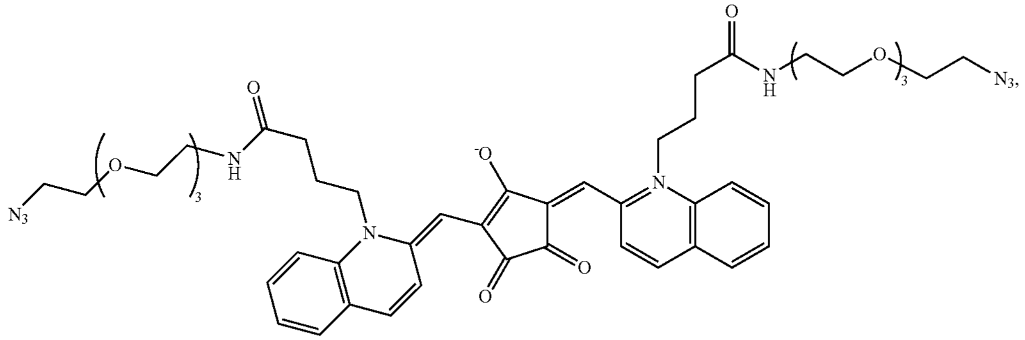
,
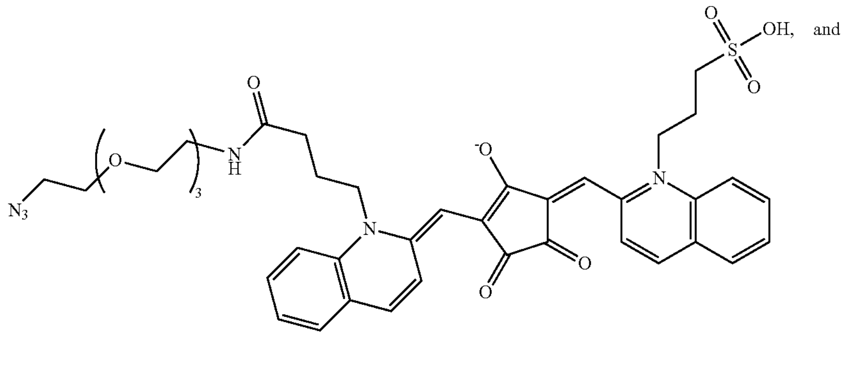
and

-continued

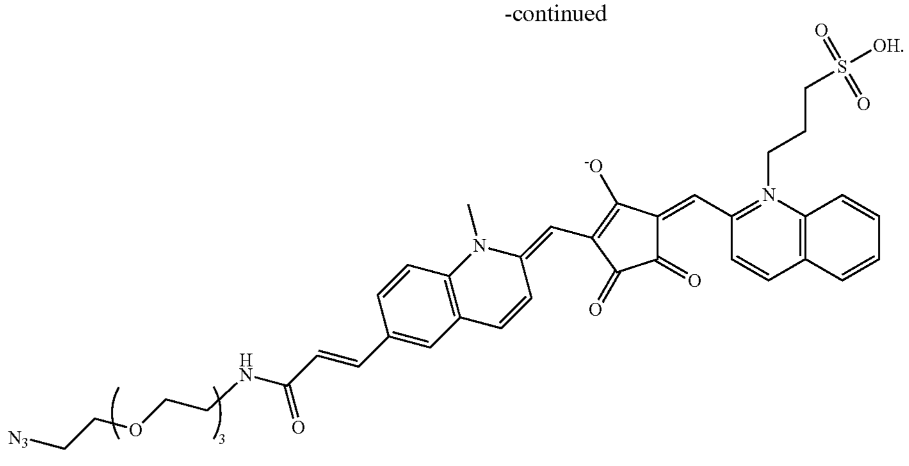

DETAILED DESCRIPTION

Figure 1A:
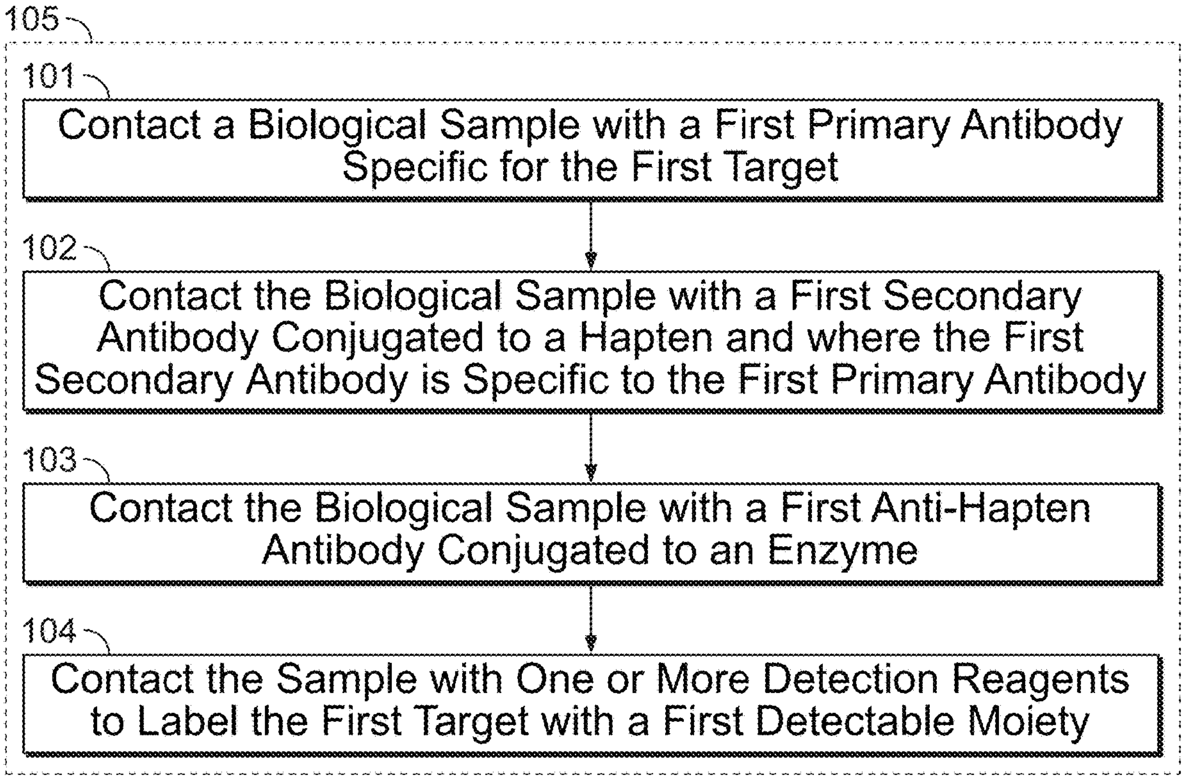
FIG. 1A illustrates methods of labeling a target with detectable moiety in accordance with one embodiment of the present disclosure.

Disclosed herein are detectable moieties and detectable conjugates comprising one or more detectable moieties. In some embodiments, the disclosed detectable moieties have a narrow wavelength and are suitable for multiplexing.

Definitions

As used herein, the singular terms "a," "an," and "the" include plural referents unless context clearly indicates otherwise. Similarly, the word "or" is intended to include "and" unless the context clearly indicates otherwise. The term "includes" is defined inclusively, such that "includes A or B" means including A, B, or A and B.

The terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein, the terms "alkyl," "aromatic," "heteroalkyl," "cycloalkyl," etc. include both substituted and unsubstituted forms of the indicated radical. In that regard, whenever a group or moiety is described as being "substituted" or "optionally substituted" (or "optionally having" or "optionally comprising") that group may be unsubstituted or substituted with one or more of the indicated substituents. Likewise, when a group is described as being "substituted or unsubstituted" if substituted, the substituent(s) may be selected from one or more of the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, cyanate, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an ether, amino (e.g. a mono-substituted amino group or a di-substituted amino group), and protected derivatives thereof. Any of the above groups may include one or more heteroatoms, including O, N, or S. For example, where a moiety is substituted with an alkyl group, that alkyl group may comprise a heteroatom selected from O, N, or S (e.g. $-(CH_2-CH_2-O-CH_2-CH_3)$).

As used herein, alkaline phosphatase (AP) is an enzyme that removes (by hydrolysis) and transfers phosphate group organic esters by breaking the phosphate-oxygen bond, and temporarily forming an intermediate enzyme-substrate bond. For example, AP hydrolyzes naphthol phosphate esters (a substrate) to phenolic compounds and phosphates. The phenols couple to colorless diazonium salts (chromogen) to produce insoluble, colored azo dyes.

As used herein, the term "antibody," occasionally abbreviated "Ab," refers to immunoglobulins or immunoglobulin-like molecules, including by way of example and without limitation, IgA, IgD, IgE, IgG and IgM, combinations thereof, and similar molecules produced during an immune response in any vertebrate, (e.g., in mammals such as humans, goats, rabbits and mice) and antibody fragments that specifically bind to a molecule of interest (or a group of highly similar molecules of interest) to the substantial exclusion of binding to other molecules. Antibody further refers to a polypeptide ligand comprising at least a light chain or heavy chain immunoglobulin variable region which specifically recognizes and binds an epitope of an antigen. Antibodies may be composed of a heavy and a light chain, each of which has a variable region, termed the variable heavy (VH) region and the variable light (VL) region. Together, the VH region and the VL region are responsible for binding the antigen recognized by the antibody. The term antibody also includes intact immunoglobulins and the variants and portions of them well known in the art.

As used herein, the term "antigen" refers to a compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, nucleic acids and proteins.

As used herein, the term "aryl" means an aromatic carbocyclic radical or a substituted carbocyclic radical containing preferably from 6 to 10 carbon atoms, such as phenyl or naphtyl or phenyl or naphtyl, optionally substituted by at least one of the substituents selected in the group constituted by alkyl, alkenyl, alkynyl, aryl, aralkyl, hydroxy, alkoxy, aryloxy, aralkoxy, carboxy, aroyl, halo, nitro, trihalomethyl, cyano, alkoxycarbonyl, aryloxycarbonyl, aralkoxycarbonyl, acylamino, aroylamino, carbamoyl, alkylcarbamoyl, dialkylcarbamoyl, alkylthio, arylthio, alkylene or —NYY' where Y and Y' are independently hydrogen, alkyl, aryl, or aralkyl.

As used herein, the term a "biological sample" can be any solid or fluid sample obtained from, excreted by or secreted by any living organism, including without limitation, single celled organisms, such as bacteria, yeast, protozoans, and amoebas among others, multicellular organisms (such as plants or animals, including samples from a healthy or apparently healthy human subject or a human patient affected by a condition or disease to be diagnosed or investigated, such as cancer). For example, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease). A biological sample can also be a sample obtained from any organ or tissue (including a biopsy or autopsy specimen, such as a tumor biopsy) or can include a cell (whether a primary cell or cultured cell) or medium conditioned by any cell, tissue or organ. In some examples, a biological sample is a nuclear extract. In certain examples, a sample is a quality control sample, such as one of the disclosed cell pellet section samples. In other examples, a sample is a test sample. Samples can be prepared using any method known in the art by of one of ordinary skill. The samples can be obtained from a subject for routine screening or from a subject that is suspected of having a disorder, such as a genetic abnormality, infection, or a neoplasia. The described embodiments of the disclosed method can also be applied to samples that do not have genetic abnormalities, diseases, disorders, etc., referred to as "normal" samples. Samples can include multiple targets that can be specifically bound by one or more detection probes.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl or aryl group, or the total number of carbon atoms and heteroatoms in a heteroalkyl, heterocyclyl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$, $CH_3CH_2CH(CH_3)$— and $(CH_3)_3C$—. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

As used herein, the term "conjugate" refers to two or more molecules or moieties (including macromolecules or supramolecular molecules) that are covalently linked into a larger construct. In some embodiments, a conjugate includes one or more biomolecules (such as peptides, proteins, enzymes, sugars, polysaccharides, lipids, glycoproteins, and lipoproteins) covalently linked to one or more other molecules moieties.

As used herein, the terms "couple" or "coupling" refers to the joining, bonding (e.g. covalent bonding), or linking of one molecule or atom to another molecule or atom.

As used herein, "cycloalkyl" of like terms (e.g. a cyclic alkyl group) refer to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, the term "detectable moiety" refers to a molecule or material that can produce a detectable (such as visually, electronically or otherwise) signal that indicates the presence (i.e. qualitative analysis) and/or concentration (i.e. quantitative analysis) of the label in a sample.

As used herein, the terms "halogen atom" or "halogen" mean any one of the radio-stable atoms of column 7 of the Periodic Table of the Elements, such as, fluorine, chlorine, bromine and iodine.

As used herein, the term "heteroatom" is meant to include boron (B), oxygen (O), nitrogen (N), sulfur (S), phosphorus (P), and silicon (Si). In some embodiments, a "heterocyclic ring" may comprise one or more heteroatoms. In other embodiments, an aliphatic group may comprise or be substituted by one or more heteroatoms.

As used herein, horseradish peroxidase (HRP) is an enzyme that can be conjugated to a labeled molecule. It produces a colored, fluorimetric, or luminescent derivative of the labeled molecule when incubated with a proper substrate, allowing it to be detected and quantified. HRP acts in the presence of an electron donor to first form an enzyme substrate complex and then subsequently acts to oxidize an electronic donor. For example, HRP may act on 3,3'-diaminobenzidinetrahydrochloride (DAB) to produce a detectable color. HRP may also act upon a labeled tyramide conjugate, or tyramide like reactive conjugates (i.e. ferulate, coumaric, caffeic, cinnamate, dopamine, etc.), to deposit a colored or fluorescent or colorless reporter moiety for tyramide signal amplification (TSA).

As used herein, the term "label" refers to a detectable moiety that may be atoms or molecules, or a collection of atoms or molecules. A label may provide an optical, electrochemical, magnetic, or electrostatic (e.g., inductive, capacitive) signature which may be detected.

As used herein, the terms "multiplex," "multiplexed," or "multiplexing" refer to detecting multiple targets in a sample concurrently, substantially simultaneously, or sequentially. Multiplexing can include identifying and/or quantifying multiple distinct nucleic acids (e.g., DNA, RNA, mRNA, miRNA) and polypeptides (e.g., proteins) both individually and in any and all combinations.

As used herein, a "quinone methide precursor" is a quinone analog where one of the carbonyl oxygens on the corresponding quinone is replaced by a methylene group (—$CH_2$—) to form an alkene.

As used herein, the terms "reactive group" or "reactive functional group" refer to a functional group that are capable of chemically associating with, interacting with, hybridizing with, hydrogen bonding with, or coupling with a functional group of a different moiety. In some embodiments, a "reaction" between two reactive groups or two reactive functional groups may mean that a covalent linkage is formed between two reactive groups or two reactive functional groups; or may mean that the two reactive groups or two reactive functional groups associate with each other, interact with each other, hybridize to each other, hydrogen bond with each other, etc. In some embodiments, the "reaction" thus includes binding events, such as the binding of a hapten with an anti-hapten antibody, or a guest molecule associating with a supramolecular host molecule.

As used herein, the term "specific binding entity" refers to a member of a specific-binding pair. Specific binding pairs are pairs of molecules that are characterized in that they bind each other to the substantial exclusion of binding to other molecules (for example, specific binding pairs can have a binding constant that is at least 10-3 M greater, 10-4 M greater or 10-5 M greater than a binding constant for either of the two members of the binding pair with other molecules in a biological sample). Particular examples of specific binding moieties include specific binding proteins (for example, antibodies, lectins, avidins such as streptavidins, and protein A). Specific binding moieties can also include the molecules (or portions thereof) that are specifically bound by such specific binding proteins.

Whenever a group or moiety is described as being "substituted" or "optionally substituted" (or "optionally having" or "optionally comprising") that group may be unsubstituted or substituted with one or more of the indicated substituents. Likewise, when a group is described as being "substituted or unsubstituted" if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, cyanate, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, ether, amino (e.g. a mono-substituted amino group or a di-substituted amino group), and protected derivatives thereof. Any of the above groups may include one or more heteroatoms, including O, N, or S. For example, where a moiety is substituted with an alkyl group, that alkyl group may comprise a heteroatom selected from O, N, or S (e.g. $-(CH_2-CH_2-O-CH_2-CH_2)-$).

As used herein, the term "target" refers to any molecule for which the presence, location and/or concentration is or can be determined. Examples of target molecules include proteins, nucleic acid sequences, and haptens, such as haptens covalently bonded to proteins. Target molecules are typically detected using one or more conjugates of a specific binding molecule and a detectable label.

As used herein, the symbol "" refers to a location a moiety is bonded to another moiety.

Overview

The present disclosure provides compounds including a detectable moiety. In some embodiments, the compounds are conjugates of a detectable moiety and either (i) a tissue reactive moiety, or (ii) a functional group capable of participating in a "click chemistry" reaction (referred to herein as a "detectable conjugate"). In some embodiments, the detectable moieties have a narrow wavelength, as described herein.

In some embodiments, the detectable conjugates are suitable for use in labeling target molecules, such as target molecules present within a biological sample (e.g. a cytological specimen or a histological specimen). In some embodiments, the detectable conjugates of the present disclosure are suitable for use in immunohistochemistry assays and/or in situ hybridization assays. In some embodiments, the detectable conjugates of the present disclosure are suitable for use in multiplex immunohistochemistry assays and/or in multiplex in situ hybridization assays.

Detectable Conjugates

In some embodiments of the present disclosure is a compound having Formula (I):

$$[Z]-[Q]_m-[W] \quad (I),$$

wherein

Z is (i) a "tissue reactive moiety," or (ii) a functional group or a moiety including a functional group capable of participating in a "click chemistry" reaction;

Q is a branched or unbranched, linear or cyclic, substituted or unsubstituted group having between 2 and 40 carbon atoms, and optionally having one or more heteroatoms selected from O, N, or S;

W is a "detectable moiety;" and m is 0, 1, or 2.

In some embodiments, m is 0. In other embodiments, m is 1. In yet other embodiments, m is 2.

Each of the moieties Z, Q, and W are described further herein.

Detectable Moieties

As noted above, the compounds of Formula (I) include a detectable moiety. In some embodiments, the detectable moiety has a wavelength that is outside the visible spectrum. In other embodiments, the detectable moiety has a wavelength that is outside the visible spectrum and where the detectable moiety is does not absorb light leading to electronic excitation (i.e. photoexcitation). In other embodiments, the detectable moiety has a wavelength that is outside the visible spectrum and where the detectable moiety is not a luminescent moiety. In other embodiments, the detectable moiety has a wavelength that is outside the visible spectrum and where the detectable moiety is not a photoluminescent moiety. In other embodiments, the detectable moiety has a wavelength that is outside the visible spectrum and where the detectable moiety is not a chemiluminescent moiety. In other embodiments, the detectable moiety has a wavelength that is outside the visible spectrum and where the detectable moiety is not a fluorescent moiety.

Properties of Detectable Moieties

In some embodiments, the detectable moieties of any of the detectable conjugates of the present disclosure may be characterized according to a full width of an absorbance peak at the half maximum absorbance, referred to herein as FWHM. FWHM is an expression of the extent of function given by the difference between the two extreme values of the independent variable at which the dependent variable is equal to half of its maximum value. In other words, it is the width of a spectrum curve measured between those points on the y-axis which are half the maximum amplitude. It is given by the distance between points on the curve at which the function reaches half its maximum value. Essentially, FWHM is a parameter commonly used to describe the width of a "bump" on a curve or function. In some embodiments, while an absorbance maximum ($\lambda_{max}$) may describe the wavelength of maximum absorption of a detectable moiety, the FWHM describes the breadth of the spectral absorbance.

In some embodiments, the detectable moieties have a narrow FWHM. In some embodiments, the detectable moiety has a first absorbance peak having a full width at half maximum which is less than the FWHM of a traditional dye or chromogen (e.g., one typically deposited by precipitation). For example, a traditional chromogen (e.g., DAB, Fast Red, Fast Blue, or a nanoparticulate silver stain as used in SISH techniques) may have a FWHM of about 200 nm or more; while the detectable moieties of the present disclosure may have a FWHM of less than about 200 nm, for example, less than about 150 nm, less than about 130 nm, less than about 100 nm, less than about 80 nm, or less than about 60 nm.

In some embodiments, the FWHM of the detectable moieties have a FWHM which is 40% less than a FWHM of a conventional dye or chromogen (e.g. hematoxylin, eosin or a special stain); 50% less than a FWHM of a conventional dye or chromogen; 55% less than a FWHM of a conventional dye or chromogen; 65% less than a FWHM of a conventional dye or chromogen; 70% less than a FWHM of a conventional dye or chromogen; 75% less than a FWHM of a conventional dye or chromogen; 80% less than the FWHM of a conventional dye or chromogen; 85% less than a FWHM of a conventional dye or chromogen; 90% less than a FWHM of a conventional dye or chromogen; or 95% less than a FWHM of a conventional dye or chromogen.

In some embodiments, the detectable moieties have a first absorbance peak with FWHM of less than about 200 nm. In some embodiments, the detectable moieties have a first absorbance peak with FWHM of less than about 190 nm. In some embodiments, the detectable moieties have a first absorbance peak with FWHM of less than about 180 nm. In some embodiments, the detectable moieties have a first absorbance peak with FWHM of less than about 170 nm. In some embodiments, the detectable moieties have a first absorbance peak with FWHM of less than about 160 nm. In some embodiments, the detectable moieties have a first absorbance peak with FWHM of less than about 150 nm. In some embodiments, the detectable moieties have a first absorbance peak with FWHM of less than about 140 nm. In some embodiments, the detectable moieties have a first absorbance peak with FWHM of less than about 130 nm. In some embodiments, the detectable moieties have a first absorbance peak with FWHM of less than about 120 nm. In some embodiments, the detectable moieties have a first absorbance peak with FWHM of less than about 110 nm. In some embodiments, the detectable moieties have a first absorbance peak with FWHM of less than about 100 nm. In some embodiments, the detectable moieties have a first absorbance peak with FWHM of less than about 90 nm. In some embodiments, the detectable moieties have a first absorbance peak with FWHM of less than about 80 nm. In some embodiments, the detectable moieties have a first absorbance peak with FWHM of less than about 70 nm. In some embodiments, the detectable moieties have a first absorbance peak with FWHM of less than about 60 nm. In some embodiments, the detectable moieties have a first absorbance peak with FWHM of less than about 50 nm.

In some embodiments, the detectable moieties of the present disclosure have an absorbance peak with FWHM of between 15 nm and 150 nm. In some embodiments, the detectable moieties have an absorbance peak with FWHM of between 15 nm and 145 nm. In some embodiments, the detectable moieties have an absorbance peak with FWHM of between 15 nm and 140 nm. In some embodiments, the detectable moieties have an absorbance peak with FWHM of between 15 nm and 135 nm. In some embodiments the detectable moieties have has an absorbance peak with FWHM of between 15 nm and 130 nm. In some embodiments the detectable moieties have an absorbance peak with FWHM of between 15 nm and 125 nm. In some embodiments, the detectable moieties have an absorbance peak with FWHM of between 15 nm and 120 nm. In some embodiments, the detectable moieties have an absorbance peak with FWHM of between 15 nm and 110 nm. In some embodiments, the detectable moieties have an absorbance peak with FWHM of between 15 nm and 100 nm. In some embodiments, the detectable moieties have an absorbance peak with FWHM of between 15 nm and 90 nm.

In some embodiments, the detectable moieties of the present disclosure have an absorbance peak with FWHM of between 20 nm and 150 nm. In some embodiments, the detectable moieties have an absorbance peak with FWHM of between 20 nm and 145 nm. In some embodiments, the detectable moieties have an absorbance peak with FWHM of between 20 nm and 140 nm. In some embodiments, the detectable moieties have an absorbance peak with FWHM of between 20 nm and 135 nm. In some embodiments the detectable moieties have has an absorbance peak with FWHM of between 20 nm and 130 nm. In some embodiments the detectable moieties have an absorbance peak with FWHM of between 20 nm and 125 nm. In some embodiments, the detectable moieties have an absorbance peak with FWHM of between 20 nm and 120 nm. In some embodiments, the detectable moieties have an absorbance peak with FWHM of between 20 nm and 110 nm. In some embodiments, the detectable moieties have an absorbance peak with FWHM of between 20 nm and 100 nm. In some embodiments, the detectable moieties have an absorbance peak with FWHM of between 20 nm and 90 nm.

In some embodiments, the detectable moieties of the present disclosure have an absorbance peak with FWHM of between 25 nm and 150 nm. In some embodiments, the detectable moieties have an absorbance peak with FWHM of between 25 nm and 145 nm. In some embodiments, the detectable moieties have an absorbance peak with FWHM of between 25 nm and 140 nm. In some embodiments, the detectable moieties have an absorbance peak with FWHM of between 25 nm and 135 nm. In some embodiments the detectable moieties have has an absorbance peak with FWHM of between 25 nm and 130 nm. In some embodiments the detectable moieties have an absorbance peak with FWHM of between 25 nm and 125 nm. In some embodiments, the detectable moieties have an absorbance peak with FWHM of between 25 nm and 120 nm. In some embodiments, the detectable moieties have an absorbance peak with FWHM of between 25 nm and 110 nm. In some embodiments, the detectable moieties have an absorbance peak with FWHM of between 25 nm and 100 nm. In some embodiments, the detectable moieties have an absorbance peak with FWHM of between 25 nm and 90 nm.

In some embodiments, the detectable moieties of the present disclosure have an absorbance peak with FWHM of between 30 nm and 150 nm. In some embodiments, the detectable moieties have an absorbance peak with FWHM of between 30 nm and 145 nm. In some embodiments, the detectable moieties have an absorbance peak with FWHM of between 30 nm and 140 nm. In some embodiments, the detectable moieties have an absorbance peak with FWHM of between 30 nm and 135 nm. In some embodiments the detectable moieties have has an absorbance peak with FWHM of between 30 nm and 130 nm. In some embodiments the detectable moieties have an absorbance peak with FWHM of between 30 nm and 125 nm. In some embodiments, the detectable moieties have an absorbance peak with FWHM of between 30 nm and 120 nm. In some embodiments, the detectable moieties have an absorbance peak with FWHM of between 30 nm and 110 nm. In some embodiments, the detectable moieties have an absorbance peak with FWHM of between 30 nm and 100 nm. In some embodiments, the detectable moieties have an absorbance peak with FWHM of between 30 nm and 90 nm.

Detectable Moieties within the Ultraviolet Spectrum

In some embodiments, the detectable moieties have a peak absorbance wavelength within the ultraviolet spectrum. In some embodiments, the detectable moieties have a peak absorbance peak absorbance wavelength of less than about 420 nm. In some embodiments, the detectable moieties have a peak absorbance wavelength of less than about 415 nm. In some embodiments, the detectable moieties have a peak absorbance wavelength of less than about 410 nm. In some embodiments, the detectable moieties have a peak absorbance wavelength of less than about 400 nm. In some embodiments, the detectable moieties have a peak absorbance wavelength of less than about 405 nm. In some embodiments, the detectable moiety of the disclosed compounds has a peak absorbance wavelength of less than about 395 nm. In some embodiments, the detectable moieties have a peak absorbance wavelength of less than about 390 nm. In some embodiments, the detectable moieties have a peak absorbance wavelength of less than about 385 nm. In some embodiments, the detectable moieties have a peak absorbance wavelength of less than about 380 nm. In some embodiments, the detectable moieties have a peak absorbance wavelength of less than about 375 nm. In some embodiments, the detectable moiety of the disclosed compounds has a peak absorbance wavelength of less than about 370 nm. In some embodiments, the detectable moieties have a peak absorbance wavelength ranging from between about 100 nm to about 400 nm, from about 100 nm to about 390 nm, from about 100 nm to about 380 nm, or from about 100 nm to about 370 nm.

In some embodiments, the detectable moieties have a peak absorbance wavelength of less than about 420 nm and a first absorbance peak with FWHM of less than 160 nm. In some embodiments, the detectable moieties have a peak absorbance wavelength of less than about 415 nm and a first absorbance peak with FWHM of less than 160 nm. In some embodiments, the detectable moieties have a peak absorbance wavelength of less than about 410 nm and a first absorbance peak with FWHM of less than 160 nm. In some embodiments, the detectable moieties have a peak absorbance wavelength of less than about 400 nm and a first absorbance peak with FWHM of less than 160 nm. In some embodiments, the detectable moieties have a peak absorbance wavelength of less than about 405 nm and a first absorbance peak with FWHM of less than 160 nm. In some embodiments, the detectable moiety of the disclosed compounds has a peak absorbance wavelength of less than about 395 nm and a first absorbance peak with FWHM of less than 160 nm. In some embodiments, the detectable moieties have a peak absorbance wavelength of less than about 390 nm and a first absorbance peak with FWHM of less than 160 nm. In some embodiments, the detectable moieties have a peak absorbance wavelength of less than about 385 nm and a first absorbance peak with FWHM of less than 160 nm. In some embodiments, the detectable moieties have a peak absorbance wavelength of less than about 380 nm and a first absorbance peak with FWHM of less than 160 nm. In some embodiments, the detectable moieties have a peak absorbance wavelength of less than about 375 nm and a first absorbance peak with FWHM of less than 160 nm. In some embodiments, the detectable moiety of the disclosed compounds has a peak absorbance wavelength of less than about 370 nm and a first absorbance peak with FWHM of less than 160 nm.

In some embodiments, the detectable moieties have a peak absorbance wavelength of less than about 420 nm and a first absorbance peak with FWHM of less than 130 nm. In some embodiments, the detectable moieties have a peak absorbance wavelength of less than about 415 nm and a first absorbance peak with FWHM of less than 130 nm. In some embodiments, the detectable moieties have a peak absorbance wavelength of less than about 410 nm and a first absorbance peak with FWHM of less than 130 nm. In some embodiments, the detectable moieties have a peak absorbance wavelength of less than about 400 nm and a first absorbance peak with FWHM of less than 130 nm. In some embodiments, the detectable moieties have a peak absorbance wavelength of less than about 405 nm and a first absorbance peak with FWHM of less than 130 nm. In some embodiments, the detectable moiety of the disclosed compounds has a peak absorbance wavelength of less than about 395 nm and a first absorbance peak with FWHM of less than 130 nm. In some embodiments, the detectable moieties have a peak absorbance wavelength of less than about 390 nm and a first absorbance peak with FWHM of less than 130 nm. In some embodiments, the detectable moieties have a peak absorbance wavelength of less than about 385 nm and a first absorbance peak with FWHM of less than 130 nm. In some embodiments, the detectable moieties have a peak absorbance wavelength of less than about 380 nm and a first absorbance peak with FWHM of less than 130 nm. In some embodiments, the detectable moieties have a peak absorbance wavelength of less than about 375 nm and a first absorbance peak with FWHM of less than 130 nm. In some embodiments, the detectable moiety of the disclosed compounds has a peak absorbance wavelength of less than about 370 nm and a first absorbance peak with FWHM of less than 130 nm.

In some embodiments, the detectable moieties have a peak absorbance wavelength of less than about 420 nm and a first absorbance peak with FWHM of less than 100 nm. In some embodiments, the detectable moieties have a peak absorbance wavelength of less than about 415 nm and a first absorbance peak with FWHM of less than 100 nm. In some embodiments, the detectable moieties have a peak absorbance wavelength of less than about 410 nm and a first absorbance peak with FWHM of less than 100 nm. In some embodiments, the detectable moieties have a peak absorbance wavelength of less than about 400 nm and a first absorbance peak with FWHM of less than 100 nm. In some embodiments, the detectable moieties have a peak absorbance wavelength of less than about 405 nm and a first absorbance peak with FWHM of less than 100 nm. In some embodiments, the detectable moiety of the disclosed compounds has a peak absorbance wavelength of less than about 395 nm and a first absorbance peak with FWHM of less than 100 nm. In some embodiments, the detectable moieties have a peak absorbance wavelength of less than about 390 nm and a first absorbance peak with FWHM of less than 100 nm. In some embodiments, the detectable moieties have a peak absorbance wavelength of less than about 385 nm and a first absorbance peak with FWHM of less than 100 nm. In some embodiments, the detectable moieties have a peak absorbance wavelength of less than about 380 nm and a first absorbance peak with FWHM of less than 100 nm. In some embodiments, the detectable moieties have a peak absorbance wavelength of less than about 375 nm and a first absorbance peak with FWHM of less than 100 nm. In some embodiments, the detectable moiety of the disclosed compounds has a peak absorbance wavelength of less than about 370 nm and a first absorbance peak with FWHM of less than 100 nm.

In some embodiments, the detectable moieties have a peak absorbance wavelength of less than about 420 nm and a first absorbance peak with FWHM of less than 80 nm. In some embodiments, the detectable moieties have a peak absorbance wavelength of less than about 415 nm and a first absorbance peak with FWHM of less than 80 nm. In some embodiments, the detectable moieties have a peak absorbance wavelength of less than about 410 nm and a first absorbance peak with FWHM of less than 80 nm. In some embodiments, the detectable moieties have a peak absorbance wavelength of less than about 400 nm and a first absorbance peak with FWHM of less than 80 nm. In some embodiments, the detectable moieties have a peak absorbance wavelength of less than about 405 nm and a first absorbance peak with FWHM of less than 80 nm. In some embodiments, the detectable moiety of the disclosed compounds has a peak absorbance wavelength of less than about 395 nm and a first absorbance peak with FWHM of less than 80 nm. In some embodiments, the detectable moieties have a peak absorbance wavelength of less than about 390 nm and a first absorbance peak with FWHM of less than 80 nm. In some embodiments, the detectable moieties have a peak absorbance wavelength of less than about 385 nm and a first absorbance peak with FWHM of less than 80 nm. In some embodiments, the detectable moieties have a peak absorbance wavelength of less than about 380 nm and a first absorbance peak with FWHM of less than 80 nm. In some embodiments, the detectable moieties have a peak absorbance wavelength of less than about 375 nm and a first absorbance peak with FWHM of less than 80 nm. In some embodiments, the detectable moiety of the disclosed compounds has a peak absorbance wavelength of less than about 370 nm and a first absorbance peak with FWHM of less than 80 nm.

In some embodiments, the detectable moieties have a peak absorbance wavelength of less than about 420 nm and a first absorbance peak with FWHM of less than 60 nm. In some embodiments, the detectable moieties have a peak absorbance wavelength of less than about 415 nm and a first absorbance peak with FWHM of less than 60 nm. In some embodiments, the detectable moieties have a peak absorbance wavelength of less than about 410 nm and a first absorbance peak with FWHM of less than 60 nm. In some embodiments, the detectable moieties have a peak absorbance wavelength of less than about 400 nm and a first absorbance peak with FWHM of less than 60 nm. In some embodiments, the detectable moieties have a peak absorbance wavelength of less than about 405 nm and a first absorbance peak with FWHM of less than 60 nm. In some embodiments, the detectable moiety of the disclosed compounds has a peak absorbance wavelength of less than about 395 nm and a first absorbance peak with FWHM of less than 60 nm. In some embodiments, the detectable moieties have a peak absorbance wavelength of less than about 390 nm and a first absorbance peak with FWHM of less than 60 nm. In some embodiments, the detectable moieties have a peak absorbance wavelength of less than about 385 nm and a first absorbance peak with FWHM of less than 60 nm. In some embodiments, the detectable moieties have a peak absorbance wavelength of less than about 380 nm and a first absorbance peak with FWHM of less than 60 nm. In some embodiments, the detectable moieties have a peak absorbance wavelength of less than about 375 nm and a first absorbance peak with FWHM of less than 60 nm. In some embodiments, the detectable moiety of the disclosed compounds has a peak absorbance wavelength of less than about 370 nm and a first absorbance peak with FWHM of less than 60 nm.

In some embodiments, the detectable moieties have a peak absorbance wavelength of less than about 420 nm and a first absorbance peak with FWHM of less than 50 nm. In some embodiments, the detectable moieties have a peak absorbance wavelength of less than about 415 nm and a first absorbance peak with FWHM of less than 50 nm. In some embodiments, the detectable moieties have a peak absorbance wavelength of less than about 410 nm and a first absorbance peak with FWHM of less than 50 nm. In some embodiments, the detectable moieties have a peak absorbance wavelength of less than about 400 nm and a first absorbance peak with FWHM of less than 50 nm. In some embodiments, the detectable moieties have a peak absorbance wavelength of less than about 405 nm and a first absorbance peak with FWHM of less than 50 nm. In some embodiments, the detectable moiety of the disclosed compounds has a peak absorbance wavelength of less than about 395 nm and a first absorbance peak with FWHM of less than 50 nm. In some embodiments, the detectable moieties have a peak absorbance wavelength of less than about 390 nm and a first absorbance peak with FWHM of less than 50 nm. In some embodiments, the detectable moieties have a peak absorbance wavelength of less than about 385 nm and a first absorbance peak with FWHM of less than 50 nm. In some embodiments, the detectable moieties have a peak absorbance wavelength of less than about 380 nm and a first absorbance peak with FWHM of less than 50 nm. In some embodiments, the detectable moieties have a peak absorbance wavelength of less than about 375 nm and a first absorbance peak with FWHM of less than 50 nm. In some embodiments, the detectable moiety of the disclosed compounds has a peak absorbance wavelength of less than about 370 nm and a first absorbance peak with FWHM of less than 50 nm.

In some embodiments, the detectable moieties have a peak absorbance wavelength of less than about 420 nm and a first absorbance peak with FWHM of less than 40 nm. In some embodiments, the detectable moieties have a peak absorbance wavelength of less than about 415 nm and a first absorbance peak with FWHM of less than 40 nm. In some embodiments, the detectable moieties have a peak absorbance wavelength of less than about 410 nm and a first absorbance peak with FWHM of less than 40 nm. In some embodiments, the detectable moieties have a peak absorbance wavelength of less than about 400 nm and a first absorbance peak with FWHM of less than 40 nm. In some embodiments, the detectable moieties have a peak absorbance wavelength of less than about 405 nm and a first absorbance peak with FWHM of less than 40 nm. In some embodiments, the detectable moiety of the disclosed compounds has a peak absorbance wavelength of less than about 395 nm and a first absorbance peak with FWHM of less than 40 nm. In some embodiments, the detectable moieties have a peak absorbance wavelength of less than about 390 nm and a first absorbance peak with FWHM of less than 40 nm. In some embodiments, the detectable moieties have a peak absorbance wavelength of less than about 385 nm and a first absorbance peak with FWHM of less than 40 nm. In some embodiments, the detectable moieties have a peak absorbance wavelength of less than about 380 nm and a first absorbance peak with FWHM of less than 40 nm. In some embodiments, the detectable moieties have a peak absorbance wavelength of less than about 375 nm and a first absorbance peak with FWHM of less than 40 nm. In some embodiments, the detectable moiety of the disclosed compounds has a peak absorbance wavelength of less than about 370 nm and a first absorbance peak with FWHM of less than 40 nm.

In some embodiments, the detectable moiety includes or is derived from a coumarin (i.e. the detectable moiety includes a coumarin core). In some embodiments, the coumarin core is a coumarinamine core. In some embodiments, the coumarin core is a 7-coumarinamine core. In some embodiments, the coumarin core is a coumarinol core. In some embodiments, the coumarin core is a 7-coumarinol core. Non-limiting examples of detectable moieties having a coumarin core have Formula (IIA) as described herein.

In some embodiments, the coumarin core includes (or is modified to include) one or more electron withdrawing groups (where each electron withdrawing group may be the same or different). In some embodiments, the coumarin core includes (or is modified to include) one electron withdrawing group. In some embodiments, the coumarin core includes (or is modified to include) two electron withdrawing groups. In some embodiments, the coumarin core includes (or is modifying to include) three electron withdrawing groups. In some embodiments, the coumarin core includes (or is modifying to include) three different electron withdrawing groups. In some embodiments, the coumarin core includes (or is modified to include) four electron withdrawing groups. In some embodiments, the one or more electron withdrawing groups have an electronegatively ranging from between about 1.5 to about 3.5 each.

In some embodiments, the coumarin core includes (or is modified to include) one or more electron donating groups (where each electron donating group may be the same or different). In some embodiments, the coumarin core includes (or is modified to include) one electron donating group. In some embodiments, the coumarin core includes (or is modified to include) two electron donating groups. In some embodiments, the coumarin core includes (or is modifying to include) three electron donating groups. In some embodiments, the coumarin core includes (or is modifying to include) three different electron donating groups. In some embodiments, the coumarin core includes (or is modified to include) four electron donating groups. In some embodiments, the one or more electron donating groups have an electronegatively ranging from between about 1.5 to about 3.5 each. In some embodiments, one or more electronic withdrawing and/or donating groups are incorporated to facilitate a shift towards the "red" spectrum or the "blue" spectrum.

In some embodiments, the detectable moieties having the coumarin core have a wavelength ranging from about 300 nm to about 460 nm. In some embodiments, the detectable moieties having the coumarin core have a wavelength ranging from about 320 nm to about 440 nm. In some embodiments, the detectable moieties having the coumarin core have a wavelength ranging from about 340 nm to about 430 nm. These ranges may be altered or shift as more or less electronegative is introduced to the coumarin core.

In some embodiments, the detectable moieties having the coumarin core have a peak absorbance wavelength of about 460 nm+/−10 nm. In some embodiments, the detectable moieties having the coumarin core have a peak absorbance wavelength of about 455+/−10 nm. In some embodiments, the detectable moieties having the coumarin core have a peak absorbance wavelength of about 450 nm+/−10 nm. In some embodiments, the detectable moieties having the coumarin core have a peak absorbance wavelength of about 445 nm+/−10 nm. In some embodiments, the detectable moieties having the coumarin core have a peak absorbance wavelength of about 440 nm+/−10 nm. In some embodiments, the detectable moieties having the coumarin core have a peak absorbance wavelength of about 435 nm+/−10 nm. In some embodiments, the detectable moieties having the coumarin core have a peak absorbance wavelength of about 430 nm+/−10 nm. In some embodiments, the detectable moieties having the coumarin core have a peak absorbance wavelength of about 425 nm+/−10 nm. In some embodiments, the detectable moieties having the coumarin core have a peak absorbance wavelength of about 420 nm+/−10 nm. In some embodiments, the detectable moieties having the coumarin core have a peak absorbance wavelength of about 415 nm+/−10 nm. In some embodiments, the detectable moieties having the coumarin core have a peak absorbance wavelength of about 410 nm+/−10 nm. In some embodiments, the detectable moieties having the coumarin core have a peak absorbance wavelength of about 405 nm+/−10 nm. In some embodiments, the detectable moieties having the coumarin core have a peak absorbance wavelength of about 400 nm+/−10 nm. In some embodiments, the detectable moieties having the coumarin core have a peak absorbance wavelength of about 395 nm+/−10 nm. In some embodiments, the detectable moieties having the coumarin core have a peak absorbance wavelength of about 390 nm+/−10 nm. In some embodiments, the detectable moieties having the coumarin core have a peak absorbance wavelength of about 385 nm+/−10 nm. In some embodiments, the detectable moieties having the coumarin core have a peak absorbance wavelength of about 380 nm+/−10 nm. In some embodiments, the detectable moieties having the coumarin core have a peak absorbance wavelength of about 375 nm+/−10 nm. In some embodiments, the detectable moieties having the coumarin core have a peak absorbance wavelength of about 370 nm+/−10 nm. In some embodiments, the detectable moieties having the coumarin core have a peak absorbance wavelength of about 365 nm+/−10 nm. In some embodiments, the detectable moieties having the coumarin core have a peak absorbance wavelength of about 360 nm+/−10 nm. In some embodiments, the detectable moieties having the coumarin core have a peak absorbance wavelength of about 355 nm+/−10 nm. In some embodiments, the detectable moieties having the coumarin core have a peak absorbance wavelength of about 350 nm+/−10 nm. In some embodiments, the detectable moieties having the coumarin core have a peak absorbance wavelength of about 345 nm+/−10 nm. In some embodiments, the detectable moieties having the coumarin core have a peak absorbance wavelength of about 340 nm+/−10 nm. In some embodiments, the detectable moieties having the coumarin core have a peak absorbance wavelength of about 335 nm+/−10 nm. In some embodiments, the detectable moieties having the coumarin core have a peak absorbance wavelength of about 330 nm+/−10 nm.

In some embodiments, the detectable moieties having the coumarin core have a peak absorbance wavelength of about 460 nm+/−10 nm and a first absorbance peak with FWHM of less than 160 nm. In some embodiments, the detectable moieties having the coumarin core have a peak absorbance wavelength of about 455+/−10 nm and a first absorbance peak with FWHM of less than 160 nm. In some embodiments, the detectable moieties having the coumarin core have a peak absorbance wavelength of about 450 nm+/−10 nm and a first absorbance peak with FWHM of less than 160 nm. In some embodiments, the detectable moieties having the coumarin core have a peak absorbance wavelength of about 445 nm+/−10 nm and a first absorbance peak with FWHM of less than 160 nm. In some embodiments, the detectable moieties having the coumarin core have a peak absorbance wavelength of about 440 nm+/−10 nm and a first absorbance peak with FWHM of less than 160 nm. In some embodiments, the detectable moieties having the coumarin core have a peak absorbance wavelength of about 435 nm+/−10 nm and a first absorbance peak with FWHM of less than 160 nm. In some embodiments, the detectable moieties having the coumarin core have a peak absorbance wavelength of about 430 nm+/−10 nm and a first absorbance peak with FWHM of less than 160 nm. In some embodiments, the detectable moieties having the coumarin core have a peak absorbance wavelength of about 425 nm+/−10 nm and a first absorbance peak with FWHM of less than 160 nm. In some embodiments, the detectable moieties having the coumarin core have a peak absorbance wavelength of about 420 nm+/−10 nm and a first absorbance peak with FWHM of less than 160 nm. In some embodiments, the detectable moieties having the coumarin core have a peak absorbance wavelength of about 415 nm+/−10 nm and a first absorbance peak with FWHM of less than 160 nm. In some embodiments, the detectable moieties having the coumarin core have a peak absorbance wavelength of about 410 nm and a first absorbance peak with FWHM of less than 160 nm. In some embodiments, the detectable moieties having the coumarin core have a peak absorbance wavelength of about 405 nm+/−10 nm and a first absorbance peak with FWHM of less than 160 nm. In some embodiments, the detectable moieties having the coumarin core have a peak absorbance wavelength of about 400 nm+/−10 nm and a first absorbance peak with FWHM of less than 160 nm. In some embodiments, the detectable moieties having the coumarin core have a peak absorbance wavelength of about 395 nm+/−10 nm and a first absorbance peak with FWHM of less than 160 nm. In some embodiments, the detectable moieties having the coumarin core have a peak absorbance wavelength of about 390 nm+/−10 nm and a first absorbance peak with FWHM of less than 160 nm. In some embodiments, the detectable moieties having the coumarin core have a peak absorbance wavelength of about 385 nm+/−10 nm and a first absorbance peak with FWHM of less than 160 nm. In some embodiments, the detectable moieties having the coumarin core have a peak absorbance wavelength of about 380 nm+/−10 nm and a first absorbance peak with FWHM of less than 160 nm. In some embodiments, the detectable moieties having the coumarin core have a peak absorbance wavelength of about 375 nm+/−10 nm and a first absorbance peak with FWHM of less than 160 nm. In some embodiments, the detectable moieties having the coumarin core have a peak absorbance wavelength of about 370 nm+/−10 nm and a first absorbance peak with FWHM of less than 160 nm. In some embodiments, the detectable moieties having the coumarin core have a peak absorbance wavelength of about 365 nm+/−10 nm and a first absorbance peak with FWHM of less than 160 nm. In some embodiments, the detectable moieties having the coumarin core have a peak absorbance wavelength of about 3160 nm+/−10 nm and a first absorbance peak with FWHM of less than 160 nm. In some embodiments, the detectable moieties having the coumarin core have a peak absorbance wavelength of about 355 nm+/−10 nm and a first absorbance peak with FWHM of less than 160 nm. In some embodiments, the detectable moieties having the coumarin core have a peak absorbance wavelength of about 350 nm+/−10 nm and a first absorbance peak with FWHM of less than 160 nm. In some embodiments, the detectable moieties having the coumarin core have a peak absorbance wavelength of about 345 nm+/−10 nm and a first absorbance peak with FWHM of less than 160 nm. In some embodiments, the detectable moieties having the coumarin core have a peak absorbance wavelength of about 340 nm+/−10 nm and a first absorbance peak with FWHM of less than 160 nm. In some embodiments, the detectable moieties having the coumarin core have a peak absorbance wavelength of about 335 nm+/−10 nm and a first absorbance peak with FWHM of less than 160 nm. In some embodiments, the detectable moieties having the coumarin core have a peak absorbance wavelength of about 330 nm+/−10 nm and a first absorbance peak with FWHM of less than 160 nm.

In some embodiments, the detectable moieties having the coumarin core have a peak absorbance wavelength of about 460 nm+/−10 nm and a first absorbance peak with FWHM of less than 130 nm. In some embodiments, the detectable moieties having the coumarin core have a peak absorbance wavelength of about 455+/−10 nm and a first absorbance peak with FWHM of less than 130 nm. In some embodiments, the detectable moieties having the coumarin core have a peak absorbance wavelength of about 450 nm+/−10 nm and a first absorbance peak with FWHM of less than 130 nm. In some embodiments, the detectable moieties having the coumarin core have a peak absorbance wavelength of about 445 nm+/−10 nm and a first absorbance peak with FWHM of less than 130 nm. In some embodiments, the detectable moieties having the coumarin core have a peak absorbance wavelength of about 440 nm+/−10 nm and a first absorbance peak with FWHM of less than 130 nm. In some embodiments, the detectable moieties having the coumarin core have a peak absorbance wavelength of about 435 nm+/−10 nm and a first absorbance peak with FWHM of less than 130 nm. In some embodiments, the detectable moieties having the coumarin core have a peak absorbance wavelength of about 430 nm+/−10 nm and a first absorbance peak with FWHM of less than 130 nm. In some embodiments, the detectable moieties having the coumarin core have a peak absorbance wavelength of about 425 nm+/−10 nm and a first absorbance peak with FWHM of less than 130 nm. In some embodiments, the detectable moieties having the coumarin core have a peak absorbance wavelength of about 420 nm+/−10 nm and a first absorbance peak with FWHM of less than 130 nm. In some embodiments, the detectable moieties having the coumarin core have a peak absorbance wavelength of about 415 nm+/−10 nm and a first absorbance peak with FWHM of less than 130 nm. In some embodiments, the detectable moieties having the coumarin core have a peak absorbance wavelength of about 410 nm and a first absorbance peak with FWHM of less than 130 nm. In some embodiments, the detectable moieties having the coumarin core have a peak absorbance wavelength of about 405 nm+/−10 nm and a first absorbance peak with FWHM of less than 130 nm. In some embodiments, the detectable moieties having the coumarin core have a peak absorbance wavelength of about 400 nm+/−10 nm and a first absorbance peak with FWHM of less than 130 nm. In some embodiments, the detectable moieties having the coumarin core have a peak absorbance wavelength of about 395 nm+/−10 nm and a first absorbance peak with FWHM of less than 130 nm. In some embodiments, the detectable moieties having the coumarin core have a peak absorbance wavelength of about 390 nm+/−10 nm and a first absorbance peak with FWHM of less than 130 nm. In some embodiments, the detectable moieties having the coumarin core have a peak absorbance wavelength of about 385 nm+/−10 nm and a first absorbance peak with FWHM of less than 130 nm. In some embodiments, the detectable moieties having the coumarin core have a peak absorbance wavelength of about 380 nm+/−10 nm and a first absorbance peak with FWHM of less than 130 nm. In some embodiments, the detectable moieties having the coumarin core have a peak absorbance wavelength of about 375 nm+/−10 nm and a first absorbance peak with FWHM of less than 130 nm. In some embodiments, the detectable moieties having the coumarin core have a peak absorbance wavelength of about 370 nm+/−10 nm and a first absorbance peak with FWHM of less than 130 nm. In some embodiments, the detectable moieties having the coumarin core have a peak absorbance wavelength of about 365 nm+/−10 nm and a first absorbance peak with FWHM of less than 130 nm. In some embodiments, the detectable moieties having the coumarin core have a peak absorbance wavelength of about 3130 nm+/−10 nm and a first absorbance peak with FWHM of less than 130 nm. In some embodiments, the detectable moieties having the coumarin core have a peak absorbance wavelength of about 355 nm+/−10 nm and a first absorbance peak with FWHM of less than 130 nm. In some embodiments, the detectable moieties having the coumarin core have a peak absorbance wavelength of about 350 nm+/−10 nm and a first absorbance peak with FWHM of less than 130 nm. In some embodiments, the detectable moieties having the coumarin core have a peak absorbance wavelength of about 345 nm+/−10 nm and a first absorbance peak with FWHM of less than 130 nm. In some embodiments, the detectable moieties having the coumarin core have a peak absorbance wavelength of about 340 nm+/−10 nm and a first absorbance peak with FWHM of less than 130 nm. In some embodiments, the detectable moieties having the coumarin core have a peak absorbance wavelength of about 335 nm+/−10 nm and a first absorbance peak with FWHM of less than 130 nm. In some embodiments, the detectable moieties having the coumarin core have a peak absorbance wavelength of about 330 nm+/−10 nm and a first absorbance peak with FWHM of less than 130 nm.

In some embodiments, the detectable moieties having the coumarin core have a peak absorbance wavelength of about 460 nm+/−10 nm and a first absorbance peak with FWHM of less than 100 nm. In some embodiments, the detectable moieties having the coumarin core have a peak absorbance wavelength of about 455+/−10 nm and a first absorbance peak with FWHM of less than 100 nm. In some embodiments, the detectable moieties having the coumarin core have a peak absorbance wavelength of about 450 nm+/−10 nm and a first absorbance peak with FWHM of less than 100 nm. In some embodiments, the detectable moieties having the coumarin core have a peak absorbance wavelength of about 445 nm+/−10 nm and a first absorbance peak with FWHM of less than 100 nm. In some embodiments, the detectable moieties having the coumarin core have a peak absorbance wavelength of about 440 nm+/−10 nm and a first absorbance peak with FWHM of less than 100 nm. In some embodiments, the detectable moieties having the coumarin core have a peak absorbance wavelength of about 435 nm+/−10 nm and a first absorbance peak with FWHM of less than 100 nm. In some embodiments, the detectable moieties having the coumarin core have a peak absorbance wavelength of about 430 nm+/−10 nm and a first absorbance peak with FWHM of less than 100 nm. In some embodiments, the detectable moieties having the coumarin core have a peak absorbance wavelength of about 425 nm+/−10 nm and a first absorbance peak with FWHM of less than 100 nm. In some embodiments, the detectable moieties having the coumarin core have a peak absorbance wavelength of about 420 nm+/−10 nm and a first absorbance peak with FWHM of less than 100 nm. In some embodiments, the detectable moieties having the coumarin core have a peak absorbance wavelength of about 415 nm+/−10 nm and a first absorbance peak with FWHM of less than 100 nm. In some embodiments, the detectable moieties having the coumarin core have a peak absorbance wavelength of about 410 nm and a first absorbance peak with FWHM of less than 100 nm. In some embodiments, the detectable moieties having the coumarin core have a peak absorbance wavelength of about 405 nm+/−10 nm and a first absorbance peak with FWHM of less than 100 nm. In some embodiments, the detectable moieties having the coumarin core have a peak absorbance wavelength of about 400 nm+/−10 nm and a first absorbance peak with FWHM of less than 100 nm. In some embodiments, the detectable moieties having the coumarin core have a peak absorbance wavelength of about 395 nm+/−10 nm and a first absorbance peak with FWHM of less than 100 nm. In some embodiments, the detectable moieties having the coumarin core have a peak absorbance wavelength of about 390 nm+/−10 nm and a first absorbance peak with FWHM of less than 100 nm. In some embodiments, the detectable moieties having the coumarin core have a peak absorbance wavelength of about 385 nm+/−10 nm and a first absorbance peak with FWHM of less than 100 nm. In some embodiments, the detectable moieties having the coumarin core have a peak absorbance wavelength of about 380 nm+/−10 nm and a first absorbance peak with FWHM of less than 100 nm. In some embodiments, the detectable moieties having the coumarin core have a peak absorbance wavelength of about 375 nm+/−10 nm and a first absorbance peak with FWHM of less than 100 nm. In some embodiments, the detectable moieties having the coumarin core have a peak absorbance wavelength of about 370 nm+/−10 nm and a first absorbance peak with FWHM of less than 100 nm. In some embodiments, the detectable moieties having the coumarin core have a peak absorbance wavelength of about 365 nm+/−10 nm and a first absorbance peak with FWHM of less than 100 nm. In some embodiments, the detectable moieties having the coumarin core have a peak absorbance wavelength of about 360 nm+/−10 nm and a first absorbance peak with FWHM of less than 100 nm. In some embodiments, the detectable moieties having the coumarin core have a peak absorbance wavelength of about 355 nm+/−10 nm and a first absorbance peak with FWHM of less than 100 nm. In some embodiments, the detectable moieties having the coumarin core have a peak absorbance wavelength of about 350 nm+/−10 nm and a first absorbance peak with FWHM of less than 100 nm. In some embodiments, the detectable moieties having the coumarin core have a peak absorbance wavelength of about 345 nm+/−10 nm and a first absorbance peak with FWHM of less than 100 nm. In some embodiments, the detectable moieties having the coumarin core have a peak absorbance wavelength of about 340 nm+/−10 nm and a first absorbance peak with FWHM of less than 100 nm. In some embodiments, the detectable moieties having the coumarin core have a peak absorbance wavelength of about 335 nm+/−10 nm and a first absorbance peak with FWHM of less than 100 nm. In some embodiments, the detectable moieties having the coumarin core have a peak absorbance wavelength of about 330 nm+/−10 nm and a first absorbance peak with FWHM of less than 100 nm.

In some embodiments, the detectable moieties having the coumarin core have a peak absorbance wavelength of about 460 nm+/−10 nm and a first absorbance peak with FWHM of less than 80 nm. In some embodiments, the detectable moieties having the coumarin core have a peak absorbance wavelength of about 455+/−10 nm and a first absorbance peak with FWHM of less than 80 nm. In some embodiments, the detectable moieties having the coumarin core have a peak absorbance wavelength of about 450 nm+/−10 nm and a first absorbance peak with FWHM of less than 80 nm. In some embodiments, the detectable moieties having the coumarin core have a peak absorbance wavelength of about 445 nm+/−10 nm and a first absorbance peak with FWHM of less than 80 nm. In some embodiments, the detectable moieties having the coumarin core have a peak absorbance wavelength of about 440 nm+/−10 nm and a first absorbance peak with FWHM of less than 80 nm. In some embodiments, the detectable moieties having the coumarin core have a peak absorbance wavelength of about 435 nm+/−10 nm and a first absorbance peak with FWHM of less than 80 nm. In some embodiments, the detectable moieties having the coumarin core have a peak absorbance wavelength of about 430 nm+/−10 nm and a first absorbance peak with FWHM of less than 80 nm. In some embodiments, the detectable moieties having the coumarin core have a peak absorbance wavelength of about 425 nm+/−10 nm and a first absorbance peak with FWHM of less than 80 nm. In some embodiments, the detectable moieties having the coumarin core have a peak absorbance wavelength of about 420 nm+/−10 nm and a first absorbance peak with FWHM of less than 80 nm. In some embodiments, the detectable moieties having the coumarin core have a peak absorbance wavelength of about 415 nm+/−10 nm and a first absorbance peak with FWHM of less than 80 nm. In some embodiments, the detectable moieties having the coumarin core have a peak absorbance wavelength of about 410 nm and a first absorbance peak with FWHM of less than 80 nm. In some embodiments, the detectable moieties having the coumarin core have a peak absorbance wavelength of about 405 nm+/−10 nm and a first absorbance peak with FWHM of less than 80 nm. In some embodiments, the detectable moieties having the coumarin core have a peak absorbance wavelength of about 400 nm+/−10 nm and a first absorbance peak with FWHM of less than 80 nm. In some embodiments, the detectable moieties having the coumarin core have a peak absorbance wavelength of about 395 nm+/−10 nm and a first absorbance peak with FWHM of less than 80 nm. In some embodiments, the detectable moieties having the coumarin core have a peak absorbance wavelength of about 390 nm+/−10 nm and a first absorbance peak with FWHM of less than 80 nm. In some embodiments, the detectable moieties having the coumarin core have a peak absorbance wavelength of about 385 nm+/−10 nm and a first absorbance peak with FWHM of less than 80 nm. In some embodiments, the detectable moieties having the coumarin core have a peak absorbance wavelength of about 380 nm+/−10 nm and a first absorbance peak with FWHM of less than 80 nm. In some embodiments, the detectable moieties having the coumarin core have a peak absorbance wavelength of about 375 nm+/−10 nm and a first absorbance peak with FWHM of less than 80 nm. In some embodiments, the detectable moieties having the coumarin core have a peak absorbance wavelength of about 370 nm+/−10 nm and a first absorbance peak with FWHM of less than 80 nm. In some embodiments, the detectable moieties having the coumarin core have a peak absorbance wavelength of about 365 nm+/−10 nm and a first absorbance peak with FWHM of less than 80 nm. In some embodiments, the detectable moieties having the coumarin core have a peak absorbance wavelength of about 360 nm+/−10 nm and a first absorbance peak with FWHM of less than 80 nm. In some embodiments, the detectable moieties having the coumarin core have a peak absorbance wavelength of about 355 nm+/−10 nm and a first absorbance peak with FWHM of less than 80 nm. In some embodiments, the detectable moieties having the coumarin core have a peak absorbance wavelength of about 350 nm+/−10 nm and a first absorbance peak with FWHM of less than 80 nm. In some embodiments, the detectable moieties having the coumarin core have a peak absorbance wavelength of about 345 nm+/−10 nm and a first absorbance peak with FWHM of less than 80 nm. In some embodiments, the detectable moieties having the coumarin core have a peak absorbance wavelength of about 340 nm+/−10 nm and a first absorbance peak with FWHM of less than 80 nm. In some embodiments, the detectable moieties having the coumarin core have a peak absorbance wavelength of about 335 nm+/−10 nm and a first absorbance peak with FWHM of less than 80 nm. In some embodiments, the detectable moieties having the coumarin core have a peak absorbance wavelength of about 330 nm+/−10 nm and a first absorbance peak with FWHM of less than 80 nm.

In some embodiments, the detectable moieties having the coumarin core have a peak absorbance wavelength of about 460 nm+/−10 nm and a first absorbance peak with FWHM of less than 60 nm. In some embodiments, the detectable moieties having the coumarin core have a peak absorbance wavelength of about 455+/−10 nm and a first absorbance peak with FWHM of less than 60 nm. In some embodiments, the detectable moieties having the coumarin core have a peak absorbance wavelength of about 450 nm+/−10 nm and a first absorbance peak with FWHM of less than 60 nm. In some embodiments, the detectable moieties having the coumarin core have a peak absorbance wavelength of about 445 nm+/−10 nm and a first absorbance peak with FWHM of less than 60 nm. In some embodiments, the detectable moieties having the coumarin core have a peak absorbance wavelength of about 440 nm+/−10 nm and a first absorbance peak with FWHM of less than 60 nm. In some embodiments, the detectable moieties having the coumarin core have a peak absorbance wavelength of about 435 nm+/−10 nm and a first absorbance peak with FWHM of less than 60 nm. In some embodiments, the detectable moieties having the coumarin core have a peak absorbance wavelength of about 430 nm+/−10 nm and a first absorbance peak with FWHM of less than 60 nm. In some embodiments, the detectable moieties having the coumarin core have a peak absorbance wavelength of about 425 nm+/−10 nm and a first absorbance peak with FWHM of less than 60 nm. In some embodiments, the detectable moieties having the coumarin core have a peak absorbance wavelength of about 420 nm+/−10 nm and a first absorbance peak with FWHM of less than 60 nm. In some embodiments, the detectable moieties having the coumarin core have a peak absorbance wavelength of about 415 nm+/−10 nm and a first absorbance peak with FWHM of less than 60 nm. In some embodiments, the detectable moieties having the coumarin core have a peak absorbance wavelength of about 410 nm and a first absorbance peak with FWHM of less than 60 nm. In some embodiments, the detectable moieties having the coumarin core have a peak absorbance wavelength of about 405 nm+/−10 nm and a first absorbance peak with FWHM of less than 60 nm. In some embodiments, the detectable moieties having the coumarin core have a peak absorbance wavelength of about 400 nm+/−10 nm and a first absorbance peak with FWHM of less than 60 nm. In some embodiments, the detectable moieties having the coumarin core have a peak absorbance wavelength of about 395 nm+/−10 nm and a first absorbance peak with FWHM of less than 60 nm. In some embodiments, the detectable moieties having the coumarin core have a peak absorbance wavelength of about 390 nm+/−10 nm and a first absorbance peak with FWHM of less than 60 nm. In some embodiments, the detectable moieties having the coumarin core have a peak absorbance wavelength of about 385 nm+/−10 nm and a first absorbance peak with FWHM of less than 60 nm. In some embodiments, the detectable moieties having the coumarin core have a peak absorbance wavelength of about 380 nm+/−10 nm and a first absorbance peak with FWHM of less than 60 nm. In some embodiments, the detectable moieties having the coumarin core have a peak absorbance wavelength of about 375 nm+/−10 nm and a first absorbance peak with FWHM of less than 60 nm. In some embodiments, the detectable moieties having the coumarin core have a peak absorbance wavelength of about 370 nm+/−10 nm and a first absorbance peak with FWHM of less than 60 nm. In some embodiments, the detectable moieties having the coumarin core have a peak absorbance wavelength of about 365 nm+/−10 nm and a first absorbance peak with FWHM of less than 60 nm. In some embodiments, the detectable moieties having the coumarin core have a peak absorbance wavelength of about 360 nm+/−10 nm and a first absorbance peak with FWHM of less than 60 nm. In some embodiments, the detectable moieties having the coumarin core have a peak absorbance wavelength of about 355 nm+/−10 nm and a first absorbance peak with FWHM of less than 60 nm. In some embodiments, the detectable moieties having the coumarin core have a peak absorbance wavelength of about 350 nm+/−10 nm and a first absorbance peak with FWHM of less than 60 nm. In some embodiments, the detectable moieties having the coumarin core have a peak absorbance wavelength of about 345 nm+/−10 nm and a first absorbance peak with FWHM of less than 60 nm. In some embodiments, the detectable moieties having the coumarin core have a peak absorbance wavelength of about 340 nm+/−10 nm and a first absorbance peak with FWHM of less than 60 nm. In some embodiments, the detectable moieties having the coumarin core have a peak absorbance wavelength of about 335 nm+/−10 nm and a first absorbance peak with FWHM of less than 60 nm. In some embodiments, the detectable moieties having the coumarin core have a peak absorbance wavelength of about 330 nm+/−10 nm and a first absorbance peak with FWHM of less than 60 nm.

Examples of suitable coumarin moieties are described herein, and where any of the coumarin moieties may have the peak absorbance wavelength values and/or FWHM values described above.

Detectable Moieties within the Visible Spectrum

In some embodiments, the detectable moieties have a peak absorbance wavelength within the visible spectrum. In some embodiments, the detectable moieties have a peak absorbance peak absorbance wavelength of between about 400 nm to about 760 nm. In some embodiments, the detectable moieties have a peak absorbance wavelength of between about 440 nm to about 720 nm. In some embodiments, the detectable moieties have a peak absorbance wavelength of between about 460 nm to about 680 nm. In some embodiments, the detectable moieties have a peak absorbance wavelength of between about 500 nm to about 640 nm. In some embodiments, the detectable moieties have a peak absorbance wavelength of between about 540 nm to about 600 nm.

In some embodiments, the detectable moieties have a peak absorbance wavelength within the visible spectrum. In some embodiments, the detectable moieties have a peak absorbance peak absorbance wavelength of between about 400 nm to about 760 nm and a first absorbance peak with FWHM a first absorbance peak with FWHM of less than 160 nm. In some embodiments, the detectable moieties have a peak absorbance wavelength of between about 440 nm to about 720 nm and a first absorbance peak with FWHM of less than 160 nm. In some embodiments, the detectable moieties have a peak absorbance wavelength of between about 460 nm to about 680 nm and a first absorbance peak with FWHM of less than 160 nm. In some embodiments, the detectable moieties have a peak absorbance wavelength of between about 500 nm to about 640 nm and a first absorbance peak with FWHM of less than 160 nm. In some embodiments, the detectable moieties have a peak absorbance wavelength of between about 540 nm to about 600 nm and a first absorbance peak with FWHM of less than 160 nm.

In some embodiments, the detectable moieties have a peak absorbance peak absorbance wavelength of between about 400 nm to about 760 nm and a first absorbance peak with FWHM of less than 130 nm. In some embodiments, the detectable moieties have a peak absorbance wavelength of between about 440 nm to about 720 nm and a first absorbance peak with FWHM of less than 130 nm. In some embodiments, the detectable moieties have a peak absorbance wavelength of between about 460 nm to about 680 nm and a first absorbance peak with FWHM of less than 130 nm. In some embodiments, the detectable moieties have a peak absorbance wavelength of between about 500 nm to about 640 nm and a first absorbance peak with FWHM of less than 130 nm. In some embodiments, the detectable moieties have a peak absorbance wavelength of between about 540 nm to about 600 nm and a first absorbance peak with FWHM of less than 130 nm.

In some embodiments, the detectable moieties have a peak absorbance peak absorbance wavelength of between about 400 nm to about 760 nm and a first absorbance peak with FWHM of less than 100 nm. In some embodiments, the detectable moieties have a peak absorbance wavelength of between about 440 nm to about 720 nm and a first absorbance peak with FWHM of less than 100 nm. In some embodiments, the detectable moieties have a peak absorbance wavelength of between about 460 nm to about 680 nm and a first absorbance peak with FWHM of less than 100 nm. In some embodiments, the detectable moieties have a peak absorbance wavelength of between about 500 nm to about 640 nm and a first absorbance peak with FWHM of less than 100 nm. In some embodiments, the detectable moieties have a peak absorbance wavelength of between about 540 nm to about 600 nm and a first absorbance peak with FWHM of less than 100 nm.

In some embodiments, the detectable moieties have a peak absorbance peak absorbance wavelength of between about 400 nm to about 760 nm and a first absorbance peak with FWHM of less than 80 nm. In some embodiments, the detectable moieties have a peak absorbance wavelength of between about 440 nm to about 720 nm and a first absorbance peak with FWHM of less than 80 nm. In some embodiments, the detectable moieties have a peak absorbance wavelength of between about 460 nm to about 680 nm and a first absorbance peak with FWHM of less than 80 nm. In some embodiments, the detectable moieties have a peak absorbance wavelength of between about 500 nm to about 640 nm and a first absorbance peak with FWHM of less than 80 nm. In some embodiments, the detectable moieties have a peak absorbance wavelength of between about 540 nm to about 600 nm and a first absorbance peak with FWHM of less than 80 nm.

In some embodiments, the detectable moieties have a peak absorbance wavelength within the visible spectrum. In some embodiments, the detectable moieties have a peak absorbance peak absorbance wavelength of between about 400 nm to about 760 nm and a first absorbance peak with FWHM of less than 60 nm. In some embodiments, the detectable moieties have a peak absorbance wavelength of between about 440 nm to about 720 nm and a first absorbance peak with FWHM of less than 60 nm. In some embodiments, the detectable moieties have a peak absorbance wavelength of between about 460 nm to about 680 nm and a first absorbance peak with FWHM of less than 60 nm. In some embodiments, the detectable moieties have a peak absorbance wavelength of between about 500 nm to about 640 nm and a first absorbance peak with FWHM of less than 60 nm. In some embodiments, the detectable moieties have a peak absorbance wavelength of between about 540 nm to about 600 nm and a first absorbance peak with FWHM of less than 60 nm.

In some embodiments, the detectable moieties have a peak absorbance peak absorbance wavelength of between about 400 nm to about 760 nm and a first absorbance peak with FWHM of less than 50 nm. In some embodiments, the detectable moieties have a peak absorbance wavelength of between about 440 nm to about 720 nm and a first absorbance peak with FWHM of less than 50 nm. In some embodiments, the detectable moieties have a peak absorbance wavelength of between about 450 nm to about 680 nm and a first absorbance peak with FWHM of less than 50 nm. In some embodiments, the detectable moieties have a peak absorbance wavelength of between about 500 nm to about 640 nm and a first absorbance peak with FWHM of less than 50 nm. In some embodiments, the detectable moieties have a peak absorbance wavelength of between about 540 nm to about 600 nm and a first absorbance peak with FWHM of less than 50 nm.

In some embodiments, the detectable moieties have a peak absorbance peak absorbance wavelength of between about 400 nm to about 760 nm and a first absorbance peak with FWHM of less than 40 nm. In some embodiments, the detectable moieties have a peak absorbance wavelength of between about 440 nm to about 720 nm and a first absorbance peak with FWHM of less than 40 nm. In some embodiments, the detectable moieties have a peak absorbance wavelength of between about 450 nm to about 680 nm and a first absorbance peak with FWHM of less than 40 nm. In some embodiments, the detectable moieties have a peak absorbance wavelength of between about 500 nm to about 640 nm and a first absorbance peak with FWHM of less than 40 nm. In some embodiments, the detectable moieties have a peak absorbance wavelength of between about 540 nm to about 600 nm and a first absorbance peak with FWHM of less than 40 nm.

In some embodiments, the detectable moiety includes or is derived from a phenoxazine or a phenoxazinone (i.e., the detectable moiety includes a phenoxazine or a phenoxazinone core). In some embodiments, the detectable moiety derived from a phenoxazine or a phenoxazinone is a 4-Hydroxy-3-phenoxazinone or is a 7-amino-4-Hydroxy-3-phenoxazinone. Non-limiting examples of detectable moieties having a phenoxazine or a phenoxazinone core have Formula (IIIA) as described herein.

In some embodiments, the phenoxazine or a phenoxazinone core includes (or is modified to include) one or more electron withdrawing groups (where each electron withdrawing group may be the same or different). In some embodiments, the phenoxazine or a phenoxazinone core includes (or is modified to include) one electron withdrawing group. In some embodiments, the phenoxazine or a phenoxazinone core includes (or is modified to include) two electron withdrawing groups. In some embodiments, the phenoxazine or a phenoxazinone core includes (or is modifying to include) three electron withdrawing groups. In some embodiments, the phenoxazine or a phenoxazinone core includes (or is modifying to include) three different electron withdrawing groups. In some embodiments, the phenoxazine or a phenoxazinone core includes (or is modified to include) four electron withdrawing groups.

In some embodiments, the phenoxazine or a phenoxazinone core includes (or is modified to include) one or more electron donating groups (where each electron withdrawing group may be the same or different). In some embodiments, the phenoxazine or a phenoxazinone core includes (or is modified to include) one electron donating group. In some embodiments, the phenoxazine or a phenoxazinone core includes (or is modified to include) two electron donating groups. In some embodiments, the phenoxazine or a phenoxazinone core includes (or is modifying to include) three electron donating groups. In some embodiments, the phenoxazine or a phenoxazinone core includes (or is modifying to include) three different electron donating groups. In some embodiments, the phenoxazine or a phenoxazinone core includes (or is modified to include) four electron donating groups.

In some embodiments, the detectable moieties having the phenoxazine or a phenoxazinone core have a peak absorbance wavelength ranging from about 580 nm to about 700 nm. In some embodiments, the detectable moieties having the phenoxazine or a phenoxazinone core have a peak absorbance wavelength ranging from about 600 nm to about 680 nm. In some embodiments, the detectable moieties having the phenoxazine or a phenoxazinone core have a peak absorbance wavelength ranging from about 620 nm to about 660 nm.

In some embodiments, the detectable moieties having the phenoxazine or a phenoxazinone core have a peak absorbance wavelength of about 700+/−10 nm. In some embodiments, the detectable moieties having the phenoxazine or a phenoxazinone core have a peak absorbance wavelength of about 695+/−10 nm. In some embodiments, the detectable moieties having the phenoxazine or a phenoxazinone core have a peak absorbance wavelength of about 690+/−10 nm. In some embodiments, the detectable moieties having the phenoxazine or a phenoxazinone core have a peak absorbance wavelength of about 685+/−10 nm. In some embodiments, the detectable moieties having the phenoxazine or a phenoxazinone core have a peak absorbance wavelength of about 680+/−10 nm. In some embodiments, the detectable moieties having the phenoxazine or a phenoxazinone core have a peak absorbance wavelength of about 675+/−10 nm. In some embodiments, the detectable moieties having the phenoxazine or a phenoxazinone core have a peak absorbance wavelength of about 670+/−10 nm. In some embodiments, the detectable moieties having the phenoxazine or a phenoxazinone core have a peak absorbance wavelength of about 665+/−10 nm. In some embodiments, the detectable moieties having the phenoxazine or a phenoxazinone core have a peak absorbance wavelength of about 660+/−10 nm. In some embodiments, the detectable moieties having the phenoxazine or a phenoxazinone core have a peak absorbance wavelength of about 655+/−10 nm. In some embodiments, the detectable moieties having the phenoxazine or a phenoxazinone core have a peak absorbance wavelength of about 650+/−10 nm. In some embodiments, the detectable moieties having the phenoxazine or a phenoxazinone core have a peak absorbance wavelength of about 645+/−10 nm. In some embodiments, the detectable moieties having the phenoxazine or a phenoxazinone core have a peak absorbance wavelength of about 640+/−10 nm. In some embodiments, the detectable moieties having the phenoxazine or a phenoxazinone core have a peak absorbance wavelength of about 635+/−10 nm. In some embodiments, the detectable moieties having the phenoxazine or a phenoxazinone core have a peak absorbance wavelength of about 630+/−10 nm. In some embodiments, the detectable moieties having the phenoxazine or a phenoxazinone core have a peak absorbance wavelength of about 625+/−10 nm. In some embodiments, the detectable moieties having the phenoxazine or a phenoxazinone core have a peak absorbance wavelength of about 620+/−10 nm. In some embodiments, the detectable moieties having the phenoxazine or a phenoxazinone core have a peak absorbance wavelength of about 615+/−10 nm. In some embodiments, the detectable moieties having the phenoxazine or a phenoxazinone core have a peak absorbance wavelength of about 610+/−10 nm. In some embodiments, the detectable moieties having the phenoxazine or a phenoxazinone core have a peak absorbance wavelength of about 605+/−10 nm. In some embodiments, the detectable moieties having the phenoxazine or a phenoxazinone core have a peak absorbance wavelength of about 600+/−10 nm. In some embodiments, the detectable moieties having the phenoxazine or a phenoxazinone core have a peak absorbance wavelength of about 595+/−10 nm. In some embodiments, the detectable moieties having the phenoxazine or a phenoxazinone core have a peak absorbance wavelength of about 590+/−10 nm. In some embodiments, the detectable moieties having the phenoxazine or a phenoxazinone core have a peak absorbance wavelength of about 585+/−10 nm. In some embodiments, the detectable moieties having the phenoxazine or a phenoxazinone core have a peak absorbance wavelength of about 580+/−10 nm.

In some embodiments, the detectable moieties having the phenoxazine or a phenoxazinone core have a peak absorbance wavelength of about 700+/−10 nm and a first absorbance peak with FWHM of less than 160 nm. In some embodiments, the detectable moieties having the phenoxazine or a phenoxazinone core have a peak absorbance wavelength of about 695+/−10 nm and a first absorbance peak with FWHM of less than 160 nm. In some embodiments, the detectable moieties having the phenoxazine or a phenoxazinone core have a peak absorbance wavelength of about 690+/−10 nm and a first absorbance peak with FWHM of less than 160 nm. In some embodiments, the detectable moieties having the phenoxazine or a phenoxazinone core have a peak absorbance wavelength of about 685+/−10 nm and a first absorbance peak with FWHM of less than 160 nm. In some embodiments, the detectable moieties having the phenoxazine or a phenoxazinone core have a peak absorbance wavelength of about 680+/−10 nm and a first absorbance peak with FWHM of less than 160 nm. In some embodiments, the detectable moieties having the phenoxazine or a phenoxazinone core have a peak absorbance wavelength of about 675+/−10 nm and a first absorbance peak with FWHM of less than 160 nm. In some embodiments, the detectable moieties having the phenoxazine or a phenoxazinone core have a peak absorbance wavelength of about 670+/−10 nm and a first absorbance peak with FWHM of less than 160 nm. In some embodiments, the detectable moieties having the phenoxazine or a phenoxazinone core have a peak absorbance wavelength of about 665+/−10 nm and a first absorbance peak with FWHM of less than 160 nm. In some embodiments, the detectable moieties having the phenoxazine or a phenoxazinone core have a peak absorbance wavelength of about 660+/−10 nm and a first absorbance peak with FWHM of less than 160 nm. In some embodiments, the detectable moieties having the phenoxazine or a phenoxazinone core have a peak absorbance wavelength of about 655+/−10 nm and a first absorbance peak with FWHM of less than 160 nm. In some embodiments, the detectable moieties having the phenoxazine or a phenoxazinone core have a peak absorbance wavelength of about 650+/−10 nm and a first absorbance peak with FWHM of less than 160 nm. In some embodiments, the detectable moieties having the phenoxazine or a phenoxazinone core have a peak absorbance wavelength of about 645+/−10 nm and a first absorbance peak with FWHM of less than 160 nm. In some embodiments, the detectable moieties having the phenoxazine or a phenoxazinone core have a peak absorbance wavelength of about 640+/−10 nm and a first absorbance peak with FWHM of less than 160 nm. In some embodiments, the detectable moieties having the phenoxazine or a phenoxazinone core have a peak absorbance wavelength of about 635+/−10 nm and a first absorbance peak with FWHM of less than 160 nm. In some embodiments, the detectable moieties having the phenoxazine or a phenoxazinone core have a peak absorbance wavelength of about 630+/−10 nm and a first absorbance peak with FWHM of less than 160 nm. In some embodiments, the detectable moieties having the phenoxazine or a phenoxazinone core have a peak absorbance wavelength of about 625+/−10 nm and a first absorbance peak with FWHM of less than 160 nm. In some embodiments, the detectable moieties having the phenoxazine or a phenoxazinone core have a peak absorbance wavelength of about 620+/−10 nm and a first absorbance peak with FWHM of less than 160 nm. In some embodiments, the detectable moieties having the phenoxazine or a phenoxazinone core have a peak absorbance wavelength of about 615+/−10 nm and a first absorbance peak with FWHM of less than 160 nm. In some embodiments, the detectable moieties having the phenoxazine or a phenoxazinone core have a peak absorbance wavelength of about 610+/−10 nm and a first absorbance peak with FWHM of less than 160 nm. In some embodiments, the detectable moieties having the phenoxazine or a phenoxazinone core have a peak absorbance wavelength of about 605+/−10 nm and a first absorbance peak with FWHM of less than 160 nm. In some embodiments, the detectable moieties having the phenoxazine or a phenoxazinone core have a peak absorbance wavelength of about 600+/−10 nm and a first absorbance peak with FWHM of less than 160 nm. In some embodiments, the detectable moieties having the phenoxazine or a phenoxazinone core have a peak absorbance wavelength of about 595+/−10 nm and a first absorbance peak with FWHM of less than 160 nm. In some embodiments, the detectable moieties having the phenoxazine or a phenoxazinone core have a peak absorbance wavelength of about 590+/−10 nm and a first absorbance peak with FWHM of less than 160 nm. In some embodiments, the detectable moieties having the phenoxazine or a phenoxazinone core have a peak absorbance wavelength of about 585+/−10 nm and a first absorbance peak with FWHM of less than 160 nm. In some embodiments, the detectable moieties having the phenoxazine or a phenoxazinone core have a peak absorbance wavelength of about 580+/−10 nm and a first absorbance peak with FWHM of less than 160 nm.

In some embodiments, the detectable moieties having the phenoxazine or a phenoxazinone core have a peak absorbance wavelength of about 700+/−10 nm and a first absorbance peak with FWHM of less than 130 nm. In some embodiments, the detectable moieties having the phenoxazine or a phenoxazinone core have a peak absorbance wavelength of about 695+/−10 nm and a first absorbance peak with FWHM of less than 130 nm. In some embodiments, the detectable moieties having the phenoxazine or a phenoxazinone core have a peak absorbance wavelength of about 690+/−10 nm and a first absorbance peak with FWHM of less than 130 nm. In some embodiments, the detectable moieties having the phenoxazine or a phenoxazinone core have a peak absorbance wavelength of about 685+/−10 nm and a first absorbance peak with FWHM of less than 130 nm. In some embodiments, the detectable moieties having the phenoxazine or a phenoxazinone core have a peak absorbance wavelength of about 680+/−10 nm and a first absorbance peak with FWHM of less than 130 nm. In some embodiments, the detectable moieties having the phenoxazine or a phenoxazinone core have a peak absorbance wavelength of about 675+/−10 nm and a first absorbance peak with FWHM of less than 130 nm. In some embodiments, the detectable moieties having the phenoxazine or a phenoxazinone core have a peak absorbance wavelength of about 670+/−10 nm and a first absorbance peak with FWHM of less than 130 nm. In some embodiments, the detectable moieties having the phenoxazine or a phenoxazinone core have a peak absorbance wavelength of about 665+/−10 nm and a first absorbance peak with FWHM of less than 130 nm. In some embodiments, the detectable moieties having the phenoxazine or a phenoxazinone core have a peak absorbance wavelength of about 660+/−10 nm and a first absorbance peak with FWHM of less than 130 nm. In some embodiments, the detectable moieties having the phenoxazine or a phenoxazinone core have a peak absorbance wavelength of about 655+/−10 nm and a first absorbance peak with FWHM of less than 130 nm. In some embodiments, the detectable moieties having the phenoxazine or a phenoxazinone core have a peak absorbance wavelength of about 650+/−10 nm and a first absorbance peak with FWHM of less than 130 nm. In some embodiments, the detectable moieties having the phenoxazine or a phenoxazinone core have a peak absorbance wavelength of about 645+/−10 nm and a first absorbance peak with FWHM of less than 130 nm. In some embodiments, the detectable moieties having the phenoxazine or a phenoxazinone core have a peak absorbance wavelength of about 640+/−10 nm and a first absorbance peak with FWHM of less than 130 nm. In some embodiments, the detectable moieties having the phenoxazine or a phenoxazinone core have a peak absorbance wavelength of about 635+/−10 nm and a first absorbance peak with FWHM of less than 130 nm. In some embodiments, the detectable moieties having the phenoxazine or a phenoxazinone core have a peak absorbance wavelength of about 630+/−10 nm and a first absorbance peak with FWHM of less than 130 nm. In some embodiments, the detectable moieties having the phenoxazine or a phenoxazinone core have a peak absorbance wavelength of about 625+/−10 nm and a first absorbance peak with FWHM of less than 130 nm. In some embodiments, the detectable moieties having the phenoxazine or a phenoxazinone core have a peak absorbance wavelength of about 620+/−10 nm and a first absorbance peak with FWHM of less than 130 nm. In some embodiments, the detectable moieties having the phenoxazine or a phenoxazinone core have a peak absorbance wavelength of about 615+/−10 nm and a first absorbance peak with FWHM of less than 130 nm. In some embodiments, the detectable moieties having the phenoxazine or a phenoxazinone core have a peak absorbance wavelength of about 610+/−10 nm and a first absorbance peak with FWHM of less than 130 nm. In some embodiments, the detectable moieties having the phenoxazine or a phenoxazinone core have a peak absorbance wavelength of about 605+/−10 nm and a first absorbance peak with FWHM of less than 130 nm. In some embodiments, the detectable moieties having the phenoxazine or a phenoxazinone core have a peak absorbance wavelength of about 600+/−10 nm and a first absorbance peak with FWHM of less than 130 nm. In some embodiments, the detectable moieties having the phenoxazine or a phenoxazinone core have a peak absorbance wavelength of about 595+/−10 nm and a first absorbance peak with FWHM of less than 130 nm. In some embodiments, the detectable moieties having the phenoxazine or a phenoxazinone core have a peak absorbance wavelength of about 590+/−10 nm and a first absorbance peak with FWHM of less than 130 nm. In some embodiments, the detectable moieties having the phenoxazine or a phenoxazinone core have a peak absorbance wavelength of about 585+/−10 nm and a first absorbance peak with FWHM of less than 130 nm. In some embodiments, the detectable moieties having the phenoxazine or a phenoxazinone core have a peak absorbance wavelength of about 580+/−10 nm and a first absorbance peak with FWHM of less than 130 nm.

In some embodiments, the detectable moieties having the phenoxazine or a phenoxazinone core have a peak absorbance wavelength of about 700+/−10 nm and a first absorbance peak with FWHM of less than 100 nm. In some embodiments, the detectable moieties having the phenoxazine or a phenoxazinone core have a peak absorbance wavelength of about 695+/−10 nm and a first absorbance peak with FWHM of less than 100 nm. In some embodiments, the detectable moieties having the phenoxazine or a phenoxazinone core have a peak absorbance wavelength of about 690+/−10 nm and a first absorbance peak with FWHM of less than 100 nm. In some embodiments, the detectable moieties having the phenoxazine or a phenoxazinone core have a peak absorbance wavelength of about 685+/−10 nm and a first absorbance peak with FWHM of less than 100 nm. In some embodiments, the detectable moieties having the phenoxazine or a phenoxazinone core have a peak absorbance wavelength of about 680+/−10 nm and a first absorbance peak with FWHM of less than 100 nm. In some embodiments, the detectable moieties having the phenoxazine or a phenoxazinone core have a peak absorbance wavelength of about 675+/−10 nm and a first absorbance peak with FWHM of less than 100 nm. In some embodiments, the detectable moieties having the phenoxazine or a phenoxazinone core have a peak absorbance wavelength of about 670+/−10 nm and a first absorbance peak with FWHM of less than 100 nm. In some embodiments, the detectable moieties having the phenoxazine or a phenoxazinone core have a peak absorbance wavelength of about 665+/−10 nm and a first absorbance peak with FWHM of less than 100 nm. In some embodiments, the detectable moieties having the phenoxazine or a phenoxazinone core have a peak absorbance wavelength of about 660+/−10 nm and a first absorbance peak with FWHM of less than 100 nm. In some embodiments, the detectable moieties having the phenoxazine or a phenoxazinone core have a peak absorbance wavelength of about 655+/−10 nm and a first absorbance peak with FWHM of less than 100 nm. In some embodiments, the detectable moieties having the phenoxazine or a phenoxazinone core have a peak absorbance wavelength of about 650+/−10 nm and a first absorbance peak with FWHM of less than 100 nm. In some embodiments, the detectable moieties having the phenoxazine or a phenoxazinone core have a peak absorbance wavelength of about 645+/−10 nm and a first absorbance peak with FWHM of less than 100 nm. In some embodiments, the detectable moieties having the phenoxazine or a phenoxazinone core have a peak absorbance wavelength of about 640+/−10 nm and a first absorbance peak with FWHM of less than 100 nm. In some embodiments, the detectable moieties having the phenoxazine or a phenoxazinone core have a peak absorbance wavelength of about 635+/−10 nm and a first absorbance peak with FWHM of less than 100 nm. In some embodiments, the detectable moieties having the phenoxazine or a phenoxazinone core have a peak absorbance wavelength of about 630+/−10 nm and a first absorbance peak with FWHM of less than 100 nm. In some embodiments, the detectable moieties having the phenoxazine or a phenoxazinone core have a peak absorbance wavelength of about 625+/−10 nm and a first absorbance peak with FWHM of less than 100 nm. In some embodiments, the detectable moieties having the phenoxazine or a phenoxazinone core have a peak absorbance wavelength of about 620+/−10 nm and a first absorbance peak with FWHM of less than 100 nm. In some embodiments, the detectable moieties having the phenoxazine or a phenoxazinone core have a peak absorbance wavelength of about 615+/−10 nm and a first absorbance peak with FWHM of less than 100 nm. In some embodiments, the detectable moieties having the phenoxazine or a phenoxazinone core have a peak absorbance wavelength of about 610+/−10 nm and a first absorbance peak with FWHM of less than 100 nm. In some embodiments, the detectable moieties having the phenoxazine or a phenoxazinone core have a peak absorbance wavelength of about 605+/−10 nm and a first absorbance peak with FWHM of less than 100 nm. In some embodiments, the detectable moieties having the phenoxazine or a phenoxazinone core have a peak absorbance wavelength of about 600+/−10 nm and a first absorbance peak with FWHM of less than 100 nm. In some embodiments, the detectable moieties having the phenoxazine or a phenoxazinone core have a peak absorbance wavelength of about 595+/−10 nm and a first absorbance peak with FWHM of less than 100 nm. In some embodiments, the detectable moieties having the phenoxazine or a phenoxazinone core have a peak absorbance wavelength of about 590+/−10 nm and a first absorbance peak with FWHM of less than 100 nm. In some embodiments, the detectable moieties having the phenoxazine or a phenoxazinone core have a peak absorbance wavelength of about 585+/−10 nm and a first absorbance peak with FWHM of less than 100 nm. In some embodiments, the detectable moieties having the phenoxazine or a phenoxazinone core have a peak absorbance wavelength of about 580+/−10 nm and a first absorbance peak with FWHM of less than 100 nm.

In some embodiments, the detectable moieties having the phenoxazine or a phenoxazinone core have a peak absorbance wavelength of about 700+/−10 nm and a first absorbance peak with FWHM of less than 60 nm. In some embodiments, the detectable moieties having the phenoxazine or a phenoxazinone core have a peak absorbance wavelength of about 695+/−10 nm and a first absorbance peak with FWHM of less than 60 nm. In some embodiments, the detectable moieties having the phenoxazine or a phenoxazinone core have a peak absorbance wavelength of about 690+/−10 nm and a first absorbance peak with FWHM of less than 60 nm. In some embodiments, the detectable moieties having the phenoxazine or a phenoxazinone core have a peak absorbance wavelength of about 685+/−10 nm and a first absorbance peak with FWHM of less than 60 nm. In some embodiments, the detectable moieties having the phenoxazine or a phenoxazinone core have a peak absorbance wavelength of about 680+/−10 nm and a first absorbance peak with FWHM of less than 60 nm. In some embodiments, the detectable moieties having the phenoxazine or a phenoxazinone core have a peak absorbance wavelength of about 675+/−10 nm and a first absorbance peak with FWHM of less than 60 nm. In some embodiments, the detectable moieties having the phenoxazine or a phenoxazinone core have a peak absorbance wavelength of about 670+/−10 nm and a first absorbance peak with FWHM of less than 60 nm. In some embodiments, the detectable moieties having the phenoxazine or a phenoxazinone core have a peak absorbance wavelength of about 665+/−10 nm and a first absorbance peak with FWHM of less than 60 nm. In some embodiments, the detectable moieties having the phenoxazine or a phenoxazinone core have a peak absorbance wavelength of about 660+/−10 nm and a first absorbance peak with FWHM of less than 60 nm. In some embodiments, the detectable moieties having the phenoxazine or a phenoxazinone core have a peak absorbance wavelength of about 655+/−10 nm and a first absorbance peak with FWHM of less than 60 nm. In some embodiments, the detectable moieties having the phenoxazine or a phenoxazinone core have a peak absorbance wavelength of about 650+/−10 nm and a first absorbance peak with FWHM of less than 60 nm. In some embodiments, the detectable moieties having the phenoxazine or a phenoxazinone core have a peak absorbance wavelength of about 645+/−10 nm and a first absorbance peak with FWHM of less than 60 nm. In some embodiments, the detectable moieties having the phenoxazine or a phenoxazinone core have a peak absorbance wavelength of about 640+/−10 nm and a first absorbance peak with FWHM of less than 60 nm. In some embodiments, the detectable moieties having the phenoxazine or a phenoxazinone core have a peak absorbance wavelength of about 635+/−10 nm and a first absorbance peak with FWHM of less than 60 nm. In some embodiments, the detectable moieties having the phenoxazine or a phenoxazinone core have a peak absorbance wavelength of about 630+/−10 nm and a first absorbance peak with FWHM of less than 60 nm. In some embodiments, the detectable moieties having the phenoxazine or a phenoxazinone core have a peak absorbance wavelength of about 625+/−10 nm and a first absorbance peak with FWHM of less than 60 nm. In some embodiments, the detectable moieties having the phenoxazine or a phenoxazinone core have a peak absorbance wavelength of about 620+/−10 nm and a first absorbance peak with FWHM of less than 60 nm. In some embodiments, the detectable moieties having the phenoxazine or a phenoxazinone core have a peak absorbance wavelength of about 615+/−10 nm and a first absorbance peak with FWHM of less than 60 nm. In some embodiments, the detectable moieties having the phenoxazine or a phenoxazinone core have a peak absorbance wavelength of about 610+/−10 nm and a first absorbance peak with FWHM of less than 60 nm. In some embodiments, the detectable moieties having the phenoxazine or a phenoxazinone core have a peak absorbance wavelength of about 605+/−10 nm and a first absorbance peak with FWHM of less than 60 nm. In some embodiments, the detectable moieties having the phenoxazine or a phenoxazinone core have a peak absorbance wavelength of about 600+/−10 nm and a first absorbance peak with FWHM of less than 60 nm. In some embodiments, the detectable moieties having the phenoxazine or a phenoxazinone core have a peak absorbance wavelength of about 595+/−10 nm and a first absorbance peak with FWHM of less than 60 nm. In some embodiments, the detectable moieties having the phenoxazine or a phenoxazinone core have a peak absorbance wavelength of about 590+/−10 nm and a first absorbance peak with FWHM of less than 60 nm. In some embodiments, the detectable moieties having the phenoxazine or a phenoxazinone core have a peak absorbance wavelength of about 585+/−10 nm and a first absorbance peak with FWHM of less than 60 nm. In some embodiments, the detectable moieties having the phenoxazine or a phenoxazinone core have a peak absorbance wavelength of about 580+/−10 nm and a first absorbance peak with FWHM of less than 60 nm.

In some embodiments, the detectable moiety includes or is derived from a thioninium, phenoxazine, or phenoxathiin-3-one core (i.e., the detectable moiety includes a thioninium or phenoxathiin-3-one core). Non-limiting examples of detectable moieties having a thioninium, phenoxazine, or phenoxathiin-3-one core have Formula (IIIA), or Formula (IVA) as described herein.

In some embodiments, the thioninium, phenoxazine, or phenoxathiin-3-one core includes (or is modified to include) one or more electron withdrawing groups (where each electron withdrawing group may be the same or different). In some embodiments, the thioninium, phenoxazine, or phenoxathiin-3-one core includes (or is modified to include) one electron withdrawing group. In some embodiments, the thioninium, phenoxazine, or phenoxathiin-3-one core includes (or is modified to include) two electron withdrawing groups. In some embodiments, the thioninium, phenoxazine, or phenoxathiin-3-one core includes (or is modifying to include) three electron withdrawing groups. In some embodiments, the thioninium, phenoxazine, or phenoxathiin-3-one core includes (or is modifying to include) three different electron withdrawing groups. In some embodiments, the thioninium, phenoxazine, or phenoxathiin-3-one core includes (or is modified to include) four electron withdrawing groups.

In some embodiments, the thioninium, phenoxazine, or phenoxathiin-3-one core includes (or is modified to include) one or more electron donating groups (where each electron withdrawing group may be the same or different). In some embodiments, the thioninium, phenoxazine, or phenoxathiin-3-one core includes (or is modified to include) one electron donating group. In some embodiments, the thioninium, phenoxazine, or phenoxathiin-3-one core includes (or is modified to include) two electron donating groups. In some embodiments, the thioninium, phenoxazine, or phenoxathiin-3-one core includes (or is modifying to include) three electron donating groups. In some embodiments, the thioninium, phenoxazine, or phenoxathiin-3-one core includes (or is modifying to include) three different electron donating groups. In some embodiments, the thioninium, phenoxazine, or phenoxathiin-3-one core includes (or is modified to include) four electron donating groups.

In some embodiments, the detectable moieties having the thioninium, phenoxazine, or phenoxathiin-3-one core have a peak absorbance wavelength ranging from about 580 nm to about 720 nm. In some embodiments, the detectable moieties having the thioninium, phenoxazine, or phenoxathiin-3-one core have a peak absorbance wavelength ranging from about 600 nm to about 720 nm. In some embodiments, the detectable moieties having the thioninium, phenoxazine, or phenoxathiin-3-one core have a peak absorbance wavelength ranging from about 630 nm to about 720 nm. In some embodiments, the detectable moieties having the thioninium, phenoxazine, or phenoxathiin-3-one core have a peak absorbance wavelength ranging from about 645 nm to about 700 nm. In some embodiments, the detectable moieties having the thioninium, phenoxazine, or phenoxathiin-3-one core have a peak absorbance wavelength ranging from about 665 nm to about 690 nm.

In some embodiments, the detectable moieties having the thioninium, phenoxazine, or phenoxathiin-3-one core have a wavelength ranging from about 580 nm to about 720 nm and a first absorbance peak with FWHM of less than 160 nm. In some embodiments, the detectable moieties having the thioninium, phenoxazine, or phenoxathiin-3-one core have a wavelength ranging from about 600 nm to about 720 nm and a first absorbance peak with FWHM of less than 160 nm. In some embodiments, the detectable moieties having the thioninium, phenoxazine, or phenoxathiin-3-one core have a wavelength ranging from about 630 nm to about 720 nm and a first absorbance peak with FWHM of less than 160 nm. In some embodiments, the detectable moieties having the thioninium, phenoxazine, or phenoxathiin-3-one core have a wavelength ranging from about 645 nm to about 700 nm and a first absorbance peak with FWHM of less than 160 nm. In some embodiments, the detectable moieties having the thioninium, phenoxazine, or phenoxathiin-3-one core have a wavelength ranging from about 665 nm to about 690 nm and a first absorbance peak with FWHM of less than 160 nm.

In some embodiments, the detectable moieties having the thioninium, phenoxazine, or phenoxathiin-3-one core have a wavelength ranging from about 580 nm to about 720 nm and a first absorbance peak with FWHM of less than 130 nm. In some embodiments, the detectable moieties having the thioninium, phenoxazine, or phenoxathiin-3-one core have a wavelength ranging from about 600 nm to about 720 nm and a first absorbance peak with FWHM of less than 130 nm. In some embodiments, the detectable moieties having the thioninium, phenoxazine, or phenoxathiin-3-one core have a wavelength ranging from about 630 nm to about 720 nm and a first absorbance peak with FWHM of less than 130 nm. In some embodiments, the detectable moieties having the thioninium, phenoxazine, or phenoxathiin-3-one core have a wavelength ranging from about 645 nm to about 700 nm and a first absorbance peak with FWHM of less than 130 nm. In some embodiments, the detectable moieties having the thioninium, phenoxazine, or phenoxathiin-3-one core have a wavelength ranging from about 665 nm to about 690 nm and a first absorbance peak with FWHM of less than 130 nm.

In some embodiments, the detectable moieties having the thioninium, phenoxazine, or phenoxathiin-3-one core have a wavelength ranging from about 580 nm to about 720 nm and a first absorbance peak with FWHM of less than 100 nm. In some embodiments, the detectable moieties having the thioninium, phenoxazine, or phenoxathiin-3-one core have a wavelength ranging from about 600 nm to about 720 nm and a first absorbance peak with FWHM of less than 100 nm. In some embodiments, the detectable moieties having the thioninium, phenoxazine, or phenoxathiin-3-one core have a wavelength ranging from about 630 nm to about 720 nm and a first absorbance peak with FWHM of less than 100 nm. In some embodiments, the detectable moieties having the thioninium, phenoxazine, or phenoxathiin-3-one core have a wavelength ranging from about 645 nm to about 700 nm and a first absorbance peak with FWHM of less than 100 nm. In some embodiments, the detectable moieties having the thioninium, phenoxazine, or phenoxathiin-3-one core have a wavelength ranging from about 665 nm to about 690 nm and a first absorbance peak with FWHM of less than 100 nm.

In some embodiments, the detectable moieties having the thioninium, phenoxazine, or phenoxathiin-3-one core have a wavelength ranging from about 580 nm to about 720 nm and a first absorbance peak with FWHM of less than 60 nm. In some embodiments, the detectable moieties having the thioninium, phenoxazine, or phenoxathiin-3-one core have a wavelength ranging from about 600 nm to about 720 nm and a first absorbance peak with FWHM of less than 60 nm. In some embodiments, the detectable moieties having the thioninium, phenoxazine, or phenoxathiin-3-one core have a wavelength ranging from about 630 nm to about 720 nm and a first absorbance peak with FWHM of less than 60 nm. In some embodiments, the detectable moieties having the thioninium, phenoxazine, or phenoxathiin-3-one core have a wavelength ranging from about 645 nm to about 700 nm and a first absorbance peak with FWHM of less than 60 nm. In some embodiments, the detectable moieties having the thioninium, phenoxazine, or phenoxathiin-3-one core have a wavelength ranging from about 665 nm to about 690 nm and a first absorbance peak with FWHM of less than 60 nm.

In some embodiments, the detectable moieties having the thioninium, phenoxazine, or phenoxathiin-3-one core have a peak absorbance wavelength of about 720+/−10 nm. In some embodiments, the detectable moieties having thioninium, phenoxazine, or phenoxathiin-3-one core have a peak absorbance wavelength of about 715+/−10 nm. In some embodiments, the detectable moieties having the thioninium, phenoxazine, or phenoxathiin-3-one core have a peak absorbance wavelength of about 710+/−10 nm. In some embodiments, the detectable moieties having the thioninium, phenoxazine, or phenoxathiin-3-one core have a peak absorbance wavelength of about 705+/−10 nm. In some embodiments, the detectable moieties having the thioninium, phenoxazine, or phenoxathiin-3-one core have a peak absorbance wavelength of about 700+/−10 nm. In some embodiments, the detectable moieties having the thioninium, phenoxazine, or phenoxathiin-3-one core have a peak absorbance wavelength of about 695+/−10 nm. In some embodiments, the detectable moieties having the thioninium, phenoxazine, or phenoxathiin-3-one core have a peak absorbance wavelength of about 690+/−10 nm. In some embodiments, the detectable moieties having the thioninium, phenoxazine, or phenoxathiin-3-one core have a peak absorbance wavelength of about 685+/−10 nm. In some embodiments, the detectable moieties having the thioninium, phenoxazine, or phenoxathiin-3-one core have a peak absorbance wavelength of about 680+/−10 nm. In some embodiments, the detectable moieties having the thioninium, phenoxazine, or phenoxathiin-3-one core have a peak absorbance wavelength of about 675+/−10 nm. In some embodiments, the detectable moieties having the thioninium, phenoxazine, or phenoxathiin-3-one core have a peak absorbance wavelength of about 670+/−10 nm. In some embodiments, the detectable moieties having the thioninium, phenoxazine, or phenoxathiin-3-one core have a peak absorbance wavelength of about 665+/−10 nm. In some embodiments, the detectable moieties having the thioninium, phenoxazine, or phenoxathiin-3-one core have a peak absorbance wavelength of about 660+/−10 nm. In some embodiments, the detectable moieties having the thioninium, phenoxazine, or phenoxathiin-3-one core have a peak absorbance wavelength of about 655+/−10 nm. In some embodiments, the detectable moieties having the thioninium, phenoxazine, or phenoxathiin-3-one core have a peak absorbance wavelength of about 650+/−10 nm. In some embodiments, the detectable moieties having the thioninium, phenoxazine, or phenoxathiin-3-one core have a peak absorbance wavelength of about 645+/−10 nm. In some embodiments, the detectable moieties having the thioninium, phenoxazine, or phenoxathiin-3-one core have a peak absorbance wavelength of about 640+/−10 nm. In some embodiments, the detectable moieties having the thioninium, phenoxazine, or phenoxathiin-3-one core have a peak absorbance wavelength of about 635+/−10 nm. In some embodiments, the detectable moieties having the thioninium, phenoxazine, or phenoxathiin-3-one core have a peak absorbance wavelength of about 630+/−10 nm. In some embodiments, the detectable moieties having the thioninium, phenoxazine, or phenoxathiin-3-one core have a peak absorbance wavelength of about 625+/−10 nm. In some embodiments, the detectable moieties having the thioninium, phenoxazine, or phenoxathiin-3-one core have a peak absorbance wavelength of about 620+/−10 nm. In some embodiments, the detectable moieties having the thioninium, phenoxazine, or phenoxathiin-3-one core have a peak absorbance wavelength of about 615+/−10 nm. In some embodiments, the detectable moieties having the thioninium, phenoxazine, or phenoxathiin-3-one core have a peak absorbance wavelength of about 610+/−10 nm. In some embodiments, the detectable moieties having the thioninium, phenoxazine, or phenoxathiin-3-one core have a peak absorbance wavelength of about 605+/−10 nm. In some embodiments, the detectable moieties having the thioninium, phenoxazine, or phenoxathiin-3-one core have a peak absorbance wavelength of about 600+/−10 nm. In some embodiments, the detectable moieties having the thioninium, phenoxazine, or phenoxathiin-3-one core have a peak absorbance wavelength of about 595+/−10 nm. In some embodiments, the detectable moieties having the thioninium, phenoxazine, or phenoxathiin-3-one core have a peak absorbance wavelength of about 590+/−10 nm. In some embodiments, the detectable moieties having the thioninium, phenoxazine, or phenoxathiin-3-one core have a peak absorbance wavelength of about 585+/−10 nm. In some embodiments, the detectable moieties having the thioninium, phenoxazine, or phenoxathiin-3-one core have a peak absorbance wavelength of about 580+/−10 nm.

In some embodiments, the detectable moieties having the thioninium, phenoxazine, or phenoxathiin-3-one core have a peak absorbance wavelength of about 720+/−10 nm and a first absorbance peak with FWHM of less than 160 nm. In some embodiments, the detectable moieties having thioninium, phenoxazine, or phenoxathiin-3-one core have a peak absorbance wavelength of about 715+/−10 nm and a first absorbance peak with FWHM of less than 160 nm. In some embodiments, the detectable moieties having the thioninium, phenoxazine, or phenoxathiin-3-one core have a peak absorbance wavelength of about 710+/−10 nm and a first absorbance peak with FWHM of less than 160 nm. In some embodiments, the detectable moieties having the thioninium, phenoxazine, or phenoxathiin-3-one core have a peak absorbance wavelength of about 705+/−10 nm and a first absorbance peak with FWHM of less than 160 nm. In some embodiments, the detectable moieties having the thioninium, phenoxazine, or phenoxathiin-3-one core have a peak absorbance wavelength of about 700+/−10 nm and a first absorbance peak with FWHM of less than 160 nm. In some embodiments, the detectable moieties having the thioninium, phenoxazine, or phenoxathiin-3-one core have a peak absorbance wavelength of about 695+/−10 nm and a first absorbance peak with FWHM of less than 160 nm. In some embodiments, the detectable moieties having the thioninium, phenoxazine, or phenoxathiin-3-one core have a peak absorbance wavelength of about 690+/−10 nm and a first absorbance peak with FWHM of less than 160 nm. In some embodiments, the detectable moieties having the thioninium, phenoxazine, or phenoxathiin-3-one core have a peak absorbance wavelength of about 685+/−10 nm and a first absorbance peak with FWHM of less than 160 nm. In some embodiments, the detectable moieties having the thioninium, phenoxazine, or phenoxathiin-3-one core have a peak absorbance wavelength of about 680+/−10 nm and a first absorbance peak with FWHM of less than 160 nm. In some embodiments, the detectable moieties having the thioninium, phenoxazine, or phenoxathiin-3-one core have a peak absorbance wavelength of about 675+/−10 nm and a first absorbance peak with FWHM of less than 160 nm. In some embodiments, the detectable moieties having the thioninium, phenoxazine, or phenoxathiin-3-one core have a peak absorbance wavelength of about 670+/−10 nm and a first absorbance peak with FWHM of less than 160 nm. In some embodiments, the detectable moieties having the thioninium, phenoxazine, or phenoxathiin-3-one core have a peak absorbance wavelength of about 665+/−10 nm and a first absorbance peak with FWHM of less than 160 nm. In some embodiments, the detectable moieties having the thioninium, phenoxazine, or phenoxathiin-3-one core have a peak absorbance wavelength of about 660+/−10 nm and a first absorbance peak with FWHM of less than 160 nm. In some embodiments, the detectable moieties having the thioninium, phenoxazine, or phenoxathiin-3-one core have a peak absorbance wavelength of about 655+/−10 nm and a first absorbance peak with FWHM of less than 160 nm. In some embodiments, the detectable moieties having the thioninium, phenoxazine, or phenoxathiin-3-one core have a peak absorbance wavelength of about 650+/−10 nm and a first absorbance peak with FWHM of less than 160 nm. In some embodiments, the detectable moieties having the thioninium, phenoxazine, or phenoxathiin-3-one core have a peak absorbance wavelength of about 645+/−10 nm and a first absorbance peak with FWHM of less than 160 nm. In some embodiments, the detectable moieties having the thioninium, phenoxazine, or phenoxathiin-3-one core have a peak absorbance wavelength of about 640+/−10 nm and a first absorbance peak with FWHM of less than 160 nm. In some embodiments, the detectable moieties having the thioninium, phenoxazine, or phenoxathiin-3-one core have a peak absorbance wavelength of about 635+/−10 nm and a first absorbance peak with FWHM of less than 160 nm. In some embodiments, the detectable moieties having the thioninium, phenoxazine, or phenoxathiin-3-one core have a peak absorbance wavelength of about 630+/−10 nm and a first absorbance peak with FWHM of less than 160 nm. In some embodiments, the detectable moieties having the thioninium, phenoxazine, or phenoxathiin-3-one core have a peak absorbance wavelength of about 625+/−10 nm and a first absorbance peak with FWHM of less than 160 nm. In some embodiments, the detectable moieties having the thioninium, phenoxazine, or phenoxathiin-3-one core have a peak absorbance wavelength of about 620+/−10 nm and a first absorbance peak with FWHM of less than 160 nm. In some embodiments, the detectable moieties having the thioninium, phenoxazine, or phenoxathiin-3-one core have a peak absorbance wavelength of about 615+/−10 nm and a first absorbance peak with FWHM of less than 160 nm. In some embodiments, the detectable moieties having the thioninium, phenoxazine, or phenoxathiin-3-one core have a peak absorbance wavelength of about 610+/−10 nm and a first absorbance peak with FWHM of less than 160 nm. In some embodiments, the detectable moieties having the thioninium, phenoxazine, or phenoxathiin-3-one core have a peak absorbance wavelength of about 605+/−10 nm and a first absorbance peak with FWHM of less than 160 nm. In some embodiments, the detectable moieties having the thioninium, phenoxazine, or phenoxathiin-3-one core have a peak absorbance wavelength of about 600+/−10 nm and a first absorbance peak with FWHM of less than 160 nm. In some embodiments, the detectable moieties having the thioninium, phenoxazine, or phenoxathiin-3-one core have a peak absorbance wavelength of about 595+/−10 nm and a first absorbance peak with FWHM of less than 160 nm. In some embodiments, the detectable moieties having the thioninium, phenoxazine, or phenoxathiin-3-one core have a peak absorbance wavelength of about 590+/−10 nm and a first absorbance peak with FWHM of less than 160 nm. In some embodiments, the detectable moieties having the thioninium, phenoxazine, or phenoxathiin-3-one core have a peak absorbance wavelength of about 585+/−10 nm and a first absorbance peak with FWHM of less than 160 nm. In some embodiments, the detectable moieties having the thioninium, phenoxazine, or phenoxathiin-3-one core have a peak absorbance wavelength of about 580+/−10 nm and a first absorbance peak with FWHM of less than 160 nm.

In some embodiments, the detectable moieties having the thioninium, phenoxazine, or phenoxathiin-3-one core have a peak absorbance wavelength of about 720+/−10 nm and a first absorbance peak with FWHM of less than 130 nm. In some embodiments, the detectable moieties having thioninium, phenoxazine, or phenoxathiin-3-one core have a peak absorbance wavelength of about 715+/−10 nm and a first absorbance peak with FWHM of less than 130 nm. In some embodiments, the detectable moieties having the thioninium, phenoxazine, or phenoxathiin-3-one core have a peak absorbance wavelength of about 710+/−10 nm and a first absorbance peak with FWHM of less than 130 nm. In some embodiments, the detectable moieties having the thioninium, phenoxazine, or phenoxathiin-3-one core have a peak absorbance wavelength of about 705+/−10 nm and a first absorbance peak with FWHM of less than 130 nm. In some embodiments, the detectable moieties having the thioninium, phenoxazine, or phenoxathiin-3-one core have a peak absorbance wavelength of about 700+/−10 nm and a first absorbance peak with FWHM of less than 130 nm. In some embodiments, the detectable moieties having the thioninium, phenoxazine, or phenoxathiin-3-one core have a peak absorbance wavelength of about 695+/−10 nm and a first absorbance peak with FWHM of less than 130 nm. In some embodiments, the detectable moieties having the thioninium, phenoxazine, or phenoxathiin-3-one core have a peak absorbance wavelength of about 690+/−10 nm and a first absorbance peak with FWHM of less than 130 nm. In some embodiments, the detectable moieties having the thioninium, phenoxazine, or phenoxathiin-3-one core have a peak absorbance wavelength of about 685+/−10 nm and a first absorbance peak with FWHM of less than 130 nm. In some embodiments, the detectable moieties having the thioninium, phenoxazine, or phenoxathiin-3-one core have a peak absorbance wavelength of about 680+/−10 nm and a first absorbance peak with FWHM of less than 130 nm. In some embodiments, the detectable moieties having the thioninium, phenoxazine, or phenoxathiin-3-one core have a peak absorbance wavelength of about 675+/−10 nm and a first absorbance peak with FWHM of less than 130 nm. In some embodiments, the detectable moieties having the thioninium, phenoxazine, or phenoxathiin-3-one core have a peak absorbance wavelength of about 670+/−10 nm and a first absorbance peak with FWHM of less than 130 nm. In some embodiments, the detectable moieties having the thioninium, phenoxazine, or phenoxathiin-3-one core have a peak absorbance wavelength of about 665+/−10 nm and a first absorbance peak with FWHM of less than 130 nm. In some embodiments, the detectable moieties having the thioninium, phenoxazine, or phenoxathiin-3-one core have a peak absorbance wavelength of about 660+/−10 nm and a first absorbance peak with FWHM of less than 130 nm. In some embodiments, the detectable moieties having the thioninium, phenoxazine, or phenoxathiin-3-one core have a peak absorbance wavelength of about 655+/−10 nm and a first absorbance peak with FWHM of less than 130 nm. In some embodiments, the detectable moieties having the thioninium, phenoxazine, or phenoxathiin-3-one core have a peak absorbance wavelength of about 650+/−10 nm and a first absorbance peak with FWHM of less than 130 nm. In some embodiments, the detectable moieties having the thioninium, phenoxazine, or phenoxathiin-3-one core have a peak absorbance wavelength of about 645+/−10 nm and a first absorbance peak with FWHM of less than 130 nm. In some embodiments, the detectable moieties having the thioninium, phenoxazine, or phenoxathiin-3-one core have a peak absorbance wavelength of about 640+/−10 nm and a first absorbance peak with FWHM of less than 130 nm. In some embodiments, the detectable moieties having the thioninium, phenoxazine, or phenoxathiin-3-one core have a peak absorbance wavelength of about 635+/−10 nm and a first absorbance peak with FWHM of less than 130 nm. In some embodiments, the detectable moieties having the thioninium, phenoxazine, or phenoxathiin-3-one core have a peak absorbance wavelength of about 630+/−10 nm and a first absorbance peak with FWHM of less than 130 nm. In some embodiments, the detectable moieties having the thioninium, phenoxazine, or phenoxathiin-3-one core have a peak absorbance wavelength of about 625+/−10 nm and a first absorbance peak with FWHM of less than 130 nm. In some embodiments, the detectable moieties having the thioninium, phenoxazine, or phenoxathiin-3-one core have a peak absorbance wavelength of about 620+/−10 nm and a first absorbance peak with FWHM of less than 130 nm. In some embodiments, the detectable moieties having the thioninium, phenoxazine, or phenoxathiin-3-one core have a peak absorbance wavelength of about 615+/−10 nm and a first absorbance peak with FWHM of less than 130 nm. In some embodiments, the detectable moieties having the thioninium, phenoxazine, or phenoxathiin-3-one core have a peak absorbance wavelength of about 610+/−10 nm and a first absorbance peak with FWHM of less than 130 nm. In some embodiments, the detectable moieties having the thioninium, phenoxazine, or phenoxathiin-3-one core have a peak absorbance wavelength of about 605+/−10 nm and a first absorbance peak with FWHM of less than 130 nm. In some embodiments, the detectable moieties having the thioninium, phenoxazine, or phenoxathiin-3-one core have a peak absorbance wavelength of about 600+/−10 nm and a first absorbance peak with FWHM of less than 130 nm. In some embodiments, the detectable moieties having the thioninium, phenoxazine, or phenoxathiin-3-one core have a peak absorbance wavelength of about 595+/−10 nm and a first absorbance peak with FWHM of less than 130 nm. In some embodiments, the detectable moieties having the thioninium, phenoxazine, or phenoxathiin-3-one core have a peak absorbance wavelength of about 590+/−10 nm and a first absorbance peak with FWHM of less than 130 nm. In some embodiments, the detectable moieties having the thioninium, phenoxazine, or phenoxathiin-3-one core have a peak absorbance wavelength of about 585+/−10 nm and a first absorbance peak with FWHM of less than 130 nm. In some embodiments, the detectable moieties having the thioninium, phenoxazine, or phenoxathiin-3-one core have a peak absorbance wavelength of about 580+/−10 nm and a first absorbance peak with FWHM of less than 130 nm.

In some embodiments, the detectable moieties having the thioninium, phenoxazine, or phenoxathiin-3-one core have a peak absorbance wavelength of about 720+/−10 nm and a first absorbance peak with FWHM of less than 100 nm. In some embodiments, the detectable moieties having thioninium, phenoxazine, or phenoxathiin-3-one core have a peak absorbance wavelength of about 715+/−10 nm and a first absorbance peak with FWHM of less than 100 nm. In some embodiments, the detectable moieties having the thioninium, phenoxazine, or phenoxathiin-3-one core have a peak absorbance wavelength of about 710+/−10 nm and a first absorbance peak with FWHM of less than 100 nm. In some embodiments, the detectable moieties having the thioninium, phenoxazine, or phenoxathiin-3-one core have a peak absorbance wavelength of about 705+/−10 nm and a first absorbance peak with FWHM of less than 100 nm. In some embodiments, the detectable moieties having the thioninium, phenoxazine, or phenoxathiin-3-one core have a peak absorbance wavelength of about 700+/−10 nm and a first absorbance peak with FWHM of less than 100 nm. In some embodiments, the detectable moieties having the thioninium, phenoxazine, or phenoxathiin-3-one core have a peak absorbance wavelength of about 695+/−10 nm and a first absorbance peak with FWHM of less than 100 nm. In some embodiments, the detectable moieties having the thioninium, phenoxazine, or phenoxathiin-3-one core have a peak absorbance wavelength of about 690+/−10 nm and a first absorbance peak with FWHM of less than 100 nm. In some embodiments, the detectable moieties having the thioninium, phenoxazine, or phenoxathiin-3-one core have a peak absorbance wavelength of about 685+/−10 nm and a first absorbance peak with FWHM of less than 100 nm. In some embodiments, the detectable moieties having the thioninium, phenoxazine, or phenoxathiin-3-one core have a peak absorbance wavelength of about 680+/−10 nm and a first absorbance peak with FWHM of less than 100 nm. In some embodiments, the detectable moieties having the thioninium, phenoxazine, or phenoxathiin-3-one core have a peak absorbance wavelength of about 675+/−10 nm and a first absorbance peak with FWHM of less than 100 nm. In some embodiments, the detectable moieties having the thioninium, phenoxazine, or phenoxathiin-3-one core have a peak absorbance wavelength of about 670+/−10 nm and a first absorbance peak with FWHM of less than 100 nm. In some embodiments, the detectable moieties having the thioninium, phenoxazine, or phenoxathiin-3-one core have a peak absorbance wavelength of about 665+/−10 nm and a first absorbance peak with FWHM of less than 100 nm. In some embodiments, the detectable moieties having the thioninium, phenoxazine, or phenoxathiin-3-one core have a peak absorbance wavelength of about 660+/−10 nm and a first absorbance peak with FWHM of less than 100 nm. In some embodiments, the detectable moieties having the thioninium, phenoxazine, or phenoxathiin-3-one core have a peak absorbance wavelength of about 655+/−10 nm and a first absorbance peak with FWHM of less than 100 nm. In some embodiments, the detectable moieties having the thioninium, phenoxazine, or phenoxathiin-3-one core have a peak absorbance wavelength of about 650+/−10 nm and a first absorbance peak with FWHM of less than 100 nm. In some embodiments, the detectable moieties having the thioninium, phenoxazine, or phenoxathiin-3-one core have a peak absorbance wavelength of about 645+/−10 nm and a first absorbance peak with FWHM of less than 100 nm. In some embodiments, the detectable moieties having the thioninium, phenoxazine, or phenoxathiin-3-one core have a peak absorbance wavelength of about 640+/−10 nm and a first absorbance peak with FWHM of less than 100 nm. In some embodiments, the detectable moieties having the thioninium, phenoxazine, or phenoxathiin-3-one core have a peak absorbance wavelength of about 635+/−10 nm and a first absorbance peak with FWHM of less than 100 nm. In some embodiments, the detectable moieties having the thioninium, phenoxazine, or phenoxathiin-3-one core have a peak absorbance wavelength of about 630+/−10 nm and a first absorbance peak with FWHM of less than 100 nm. In some embodiments, the detectable moieties having the thioninium, phenoxazine, or phenoxathiin-3-one core have a peak absorbance wavelength of about 625+/−10 nm and a first absorbance peak with FWHM of less than 100 nm. In some embodiments, the detectable moieties having the thioninium, phenoxazine, or phenoxathiin-3-one core have a peak absorbance wavelength of about 620+/−10 nm and a first absorbance peak with FWHM of less than 100 nm. In some embodiments, the detectable moieties having the thioninium, phenoxazine, or phenoxathiin-3-one core have a peak absorbance wavelength of about 615+/−10 nm and a first absorbance peak with FWHM of less than 100 nm. In some embodiments, the detectable moieties having the thioninium, phenoxazine, or phenoxathiin-3-one core have a peak absorbance wavelength of about 610+/−10 nm and a first absorbance peak with FWHM of less than 100 nm. In some embodiments, the detectable moieties having the thioninium, phenoxazine, or phenoxathiin-3-one core have a peak absorbance wavelength of about 605+/−10 nm and a first absorbance peak with FWHM of less than 100 nm. In some embodiments, the detectable moieties having the thioninium, phenoxazine, or phenoxathiin-3-one core have a peak absorbance wavelength of about 600+/−10 nm and a first absorbance peak with FWHM of less than 100 nm. In some embodiments, the detectable moieties having the thioninium, phenoxazine, or phenoxathiin-3-one core have a peak absorbance wavelength of about 595+/−10 nm and a first absorbance peak with FWHM of less than 100 nm. In some embodiments, the detectable moieties having the thioninium, phenoxazine, or phenoxathiin-3-one core have a peak absorbance wavelength of about 590+/−10 nm and a first absorbance peak with FWHM of less than 100 nm. In some embodiments, the detectable moieties having the thioninium, phenoxazine, or phenoxathiin-3-one core have a peak absorbance wavelength of about 585+/−10 nm and a first absorbance peak with FWHM of less than 100 nm. In some embodiments, the detectable moieties having the thioninium, phenoxazine, or phenoxathiin-3-one core have a peak absorbance wavelength of about 580+/−10 nm and a first absorbance peak with FWHM of less than 100 nm.

In some embodiments, the detectable moieties having the thioninium, phenoxazine, or phenoxathiin-3-one core have a peak absorbance wavelength of about 720+/−10 nm and a first absorbance peak with FWHM of less than 60 nm. In some embodiments, the detectable moieties having thioninium, phenoxazine, or phenoxathiin-3-one core have a peak absorbance wavelength of about 715+/−10 nm and a first absorbance peak with FWHM of less than 60 nm. In some embodiments, the detectable moieties having the thioninium, phenoxazine, or phenoxathiin-3-one core have a peak absorbance wavelength of about 710+/−10 nm and a first absorbance peak with FWHM of less than 60 nm. In some embodiments, the detectable moieties having the thioninium, phenoxazine, or phenoxathiin-3-one core have a peak absorbance wavelength of about 705+/−10 nm and a first absorbance peak with FWHM of less than 60 nm. In some embodiments, the detectable moieties having the thioninium, phenoxazine, or phenoxathiin-3-one core have a peak absorbance wavelength of about 700+/−10 nm and a first absorbance peak with FWHM of less than 60 nm. In some embodiments, the detectable moieties having the thioninium, phenoxazine, or phenoxathiin-3-one core have a peak absorbance wavelength of about 695+/−10 nm and a first absorbance peak with FWHM of less than 60 nm. In some embodiments, the detectable moieties having the thioninium, phenoxazine, or phenoxathiin-3-one core have a peak absorbance wavelength of about 690+/−10 nm and a first absorbance peak with FWHM of less than 60 nm. In some embodiments, the detectable moieties having the thioninium, phenoxazine, or phenoxathiin-3-one core have a peak absorbance wavelength of about 685+/−10 nm and a first absorbance peak with FWHM of less than 60 nm. In some embodiments, the detectable moieties having the thioninium, phenoxazine, or phenoxathiin-3-one core have a peak absorbance wavelength of about 680+/−10 nm and a first absorbance peak with FWHM of less than 60 nm. In some embodiments, the detectable moieties having the thioninium, phenoxazine, or phenoxathiin-3-one core have a peak absorbance wavelength of about 675+/−10 nm and a first absorbance peak with FWHM of less than 60 nm. In some embodiments, the detectable moieties having the thioninium, phenoxazine, or phenoxathiin-3-one core have a peak absorbance wavelength of about 670+/−10 nm and a first absorbance peak with FWHM of less than 60 nm. In some embodiments, the detectable moieties having the thioninium, phenoxazine, or phenoxathiin-3-one core have a peak absorbance wavelength of about 665+/−10 nm and a first absorbance peak with FWHM of less than 60 nm. In some embodiments, the detectable moieties having the thioninium, phenoxazine, or phenoxathiin-3-one core have a peak absorbance wavelength of about 660+/−10 nm and a first absorbance peak with FWHM of less than 60 nm. In some embodiments, the detectable moieties having the thioninium, phenoxazine, or phenoxathiin-3-one core have a peak absorbance wavelength of about 655+/−10 nm and a first absorbance peak with FWHM of less than 60 nm. In some embodiments, the detectable moieties having the thioninium, phenoxazine, or phenoxathiin-3-one core have a peak absorbance wavelength of about 650+/−10 nm and a first absorbance peak with FWHM of less than 60 nm. In some embodiments, the detectable moieties having the thioninium, phenoxazine, or phenoxathiin-3-one core have a peak absorbance wavelength of about 645+/−10 nm and a first absorbance peak with FWHM of less than 60 nm. In some embodiments, the detectable moieties having the thioninium, phenoxazine, or phenoxathiin-3-one core have a peak absorbance wavelength of about 640+/−10 nm and a first absorbance peak with FWHM of less than 60 nm. In some embodiments, the detectable moieties having the thioninium, phenoxazine, or phenoxathiin-3-one core have a peak absorbance wavelength of about 635+/−10 nm and a first absorbance peak with FWHM of less than 60 nm. In some embodiments, the detectable moieties having the thioninium, phenoxazine, or phenoxathiin-3-one core have a peak absorbance wavelength of about 630+/−10 nm and a first absorbance peak with FWHM of less than 60 nm. In some embodiments, the detectable moieties having the thioninium, phenoxazine, or phenoxathiin-3-one core have a peak absorbance wavelength of about 625+/−10 nm and a first absorbance peak with FWHM of less than 60 nm. In some embodiments, the detectable moieties having the thioninium, phenoxazine, or phenoxathiin-3-one core have a peak absorbance wavelength of about 620+/−10 nm and a first absorbance peak with FWHM of less than 60 nm. In some embodiments, the detectable moieties having the thioninium, phenoxazine, or phenoxathiin-3-one core have a peak absorbance wavelength of about 615+/−10 nm and a first absorbance peak with FWHM of less than 60 nm. In some embodiments, the detectable moieties having the thioninium, phenoxazine, or phenoxathiin-3-one core have a peak absorbance wavelength of about 610+/−10 nm and a first absorbance peak with FWHM of less than 60 nm. In some embodiments, the detectable moieties having the thioninium, phenoxazine, or phenoxathiin-3-one core have a peak absorbance wavelength of about 605+/−10 nm and a first absorbance peak with FWHM of less than 60 nm. In some embodiments, the detectable moieties having the thioninium, phenoxazine, or phenoxathiin-3-one core have a peak absorbance wavelength of about 600+/−10 nm and a first absorbance peak with FWHM of less than 60 nm. In some embodiments, the detectable moieties having the thioninium, phenoxazine, or phenoxathiin-3-one core have a peak absorbance wavelength of about 595+/−10 nm and a first absorbance peak with FWHM of less than 60 nm. In some embodiments, the detectable moieties having the thioninium, phenoxazine, or phenoxathiin-3-one core have a peak absorbance wavelength of about 590+/−10 nm and a first absorbance peak with FWHM of less than 60 nm. In some embodiments, the detectable moieties having the thioninium, phenoxazine, or phenoxathiin-3-one core have a peak absorbance wavelength of about 585+/−10 nm and a first absorbance peak with FWHM of less than 60 nm. In some embodiments, the detectable moieties having the thioninium, phenoxazine, or phenoxathiin-3-one core have a peak absorbance wavelength of about 580+/−10 nm and a first absorbance peak with FWHM of less than 60 nm.

In some embodiments, the detectable moiety includes or is derived from a xanthene core (i.e., the detectable moiety includes a xanthene core). Non-limiting examples of detectable moieties having the xanthene core have Formulas (VA) or (VB) as described herein.

In some embodiments, the xanthene core includes (or is modified to include) one or more electron withdrawing groups (where each electron withdrawing group may be the same or different). In some embodiments, the xanthene core includes (or is modified to include) one electron withdrawing group. In some embodiments, the xanthene core includes (or is modified to include) two electron withdrawing groups. In some embodiments, the xanthene core includes (or is modifying to include) three electron withdrawing groups. In some embodiments, the xanthene core includes (or is modifying to include) three different electron withdrawing groups. In some embodiments, the xanthene core includes (or is modified to include) four electron withdrawing groups.

In some embodiments, the xanthene core includes (or is modified to include) one or more electron donating groups (where each electron donating group may be the same or different). In some embodiments, the xanthene core includes (or is modified to include) one electron donating group. In some embodiments, the xanthene core includes (or is modified to include) two electron donating groups. In some embodiments, the xanthene core includes (or is modifying to include) three electron donating groups. In some embodiments, the xanthene core includes (or is modifying to include) three different electron donating groups. In some embodiments, the xanthene core includes (or is modified to include) four electron donating groups.

In some embodiments, the detectable moieties having the xanthene core have a peak absorbance wavelength ranging from about 580 nm to about 650 nm. In some embodiments, the detectable moieties having the xanthene core have a wavelength ranging from about 590 nm to about 640 nm. In some embodiments, the detectable moieties having the xanthene core have a wavelength ranging from about 600 nm to about 630 nm. In some embodiments, the aforementioned absorbances may be shifted by between about 5 to about 10 nm to the red spectrum when a conjugate including a detectable moiety including a xanthene core is applied to issue.

In some embodiments, the detectable moieties having the xanthene core have a peak absorbance wavelength ranging from about 580 nm to about 650 nm and a first absorbance peak with FWHM of less than 160 nm. In some embodiments, the detectable moieties having the xanthene core have a wavelength ranging from about 590 nm to about 640 nm and a first absorbance peak with FWHM of less than 160 nm. In some embodiments, the detectable moieties having the xanthene core have a wavelength ranging from about 600 nm to about 630 nm and a first absorbance peak with FWHM of less than 160 nm. In some embodiments, the aforementioned absorbances may be shifted by between about 5 to about 10 nm to the red spectrum when a conjugate including a detectable moiety including a xanthene core is applied to issue.

In some embodiments, the detectable moieties having the xanthene core have a peak absorbance wavelength ranging from about 580 nm to about 650 nm and a first absorbance peak with FWHM of less than 130 nm. In some embodiments, the detectable moieties having the xanthene core have a wavelength ranging from about 590 nm to about 640 nm and a first absorbance peak with FWHM of less than 130 nm. In some embodiments, the detectable moieties having the xanthene core have a wavelength ranging from about 600 nm to about 630 nm and a first absorbance peak with FWHM of less than 130 nm. In some embodiments, the aforementioned absorbances may be shifted by between about 5 to about 10 nm to the red spectrum when a conjugate including a detectable moiety including a xanthene core is applied to issue.

In some embodiments, the detectable moieties having the xanthene core have a peak absorbance wavelength ranging from about 580 nm to about 650 nm and a first absorbance peak with FWHM of less than 100 nm. In some embodiments, the detectable moieties having the xanthene core have a wavelength ranging from about 590 nm to about 640 nm and a first absorbance peak with FWHM of less than 100 nm. In some embodiments, the detectable moieties having the xanthene core have a wavelength ranging from about 600 nm to about 630 nm and a first absorbance peak with FWHM of less than 100 nm. In some embodiments, the aforementioned absorbances may be shifted by between about 5 to about 10 nm to the red spectrum when a conjugate including a detectable moiety including a xanthene core is applied to issue.

In some embodiments, the detectable moieties having the xanthene core have a peak absorbance wavelength ranging from about 580 nm to about 650 nm and a first absorbance peak with FWHM of less than 80 nm. In some embodiments, the detectable moieties having the xanthene core have a wavelength ranging from about 590 nm to about 640 nm and a first absorbance peak with FWHM of less than 80 nm. In some embodiments, the detectable moieties having the xanthene core have a wavelength ranging from about 600 nm to about 630 nm and a first absorbance peak with FWHM of less than 80 nm. In some embodiments, the aforementioned absorbances may be shifted by between about 5 to about 10 nm to the red spectrum when a conjugate including a detectable moiety including a xanthene core is applied to issue.

In some embodiments, the detectable moieties having the xanthene core have a peak absorbance wavelength ranging from about 580 nm to about 650 nm and a first absorbance peak with FWHM of less than 60 nm. In some embodiments, the detectable moieties having the xanthene core have a wavelength ranging from about 590 nm to about 640 nm and a first absorbance peak with FWHM of less than 60 nm. In some embodiments, the detectable moieties having the xanthene core have a wavelength ranging from about 600 nm to about 630 nm and a first absorbance peak with FWHM of less than 60 nm. In some embodiments, the aforementioned absorbances may be shifted by between about 5 to about 10 nm to the red spectrum when a conjugate including a detectable moiety including a xanthene core is applied to issue.

In some embodiments, the detectable moieties having the xanthene core have a peak absorbance wavelength of about 650+/−10 nm. In some embodiments, the detectable moieties having the xanthene core have a peak absorbance wavelength of about 645+/−10 nm. In some embodiments, the detectable moieties having the xanthene core have a peak absorbance wavelength of about 640+/−10 nm. In some embodiments, the detectable moieties having the xanthene core have a peak absorbance wavelength of about 635+/−10 nm. In some embodiments, the detectable moieties having the xanthene core have a peak absorbance wavelength of about 630+/−10 nm. In some embodiments, the detectable moieties having the xanthene core have a peak absorbance wavelength of about 625+/−10 nm. In some embodiments, the detectable moieties having the xanthene core have a peak absorbance wavelength of about 620+/−10 nm. In some embodiments, the detectable moieties having the xanthene core have a peak absorbance wavelength of about 615+/−10 nm. In some embodiments, the detectable moieties having the xanthene core have a peak absorbance wavelength of about 610+/−10 nm. In some embodiments, the detectable moieties having the xanthene core have a peak absorbance wavelength of about 605+/−10 nm. In some embodiments, the detectable moieties having the xanthene core have a peak absorbance wavelength of about 600+/−10 nm. In some embodiments, the detectable moieties having the xanthene core have a peak absorbance wavelength of about 595+/−10 nm. In some embodiments, the detectable moieties having the xanthene core have a peak absorbance wavelength of about 590+/−10 nm. In some embodiments, the detectable moieties having the xanthene core have a peak absorbance wavelength of about 585+/−10 nm. In some embodiments, the detectable moieties having the xanthene core have a peak absorbance wavelength of about 580+/−10 nm.

In some embodiments, the detectable moieties having the xanthene core have a peak absorbance wavelength of about 650+/−10 nm and a first absorbance peak with FWHM of less than 160 nm. In some embodiments, the detectable moieties having the xanthene core have a peak absorbance wavelength of about 645+/−10 nm and a first absorbance peak with FWHM of less than 160 nm. In some embodiments, the detectable moieties having the xanthene core have a peak absorbance wavelength of about 640+/−10 nm and a first absorbance peak with FWHM of less than 160 nm. In some embodiments, the detectable moieties having the xanthene core have a peak absorbance wavelength of about 635+/−10 nm and a first absorbance peak with FWHM of less than 160 nm. In some embodiments, the detectable moieties having the xanthene core have a peak absorbance wavelength of about 630+/−10 nm and a first absorbance peak with FWHM of less than 160 nm. In some embodiments, the detectable moieties having the xanthene core have a peak absorbance wavelength of about 625+/−10 nm and a first absorbance peak with FWHM of less than 160 nm. In some embodiments, the detectable moieties having the xanthene core have a peak absorbance wavelength of about 620+/−10 nm and a first absorbance peak with FWHM of less than 160 nm. In some embodiments, the detectable moieties having the xanthene core have a peak absorbance wavelength of about 615+/−10 nm and a first absorbance peak with FWHM of less than 160 nm. In some embodiments, the detectable moieties having the xanthene core have a peak absorbance wavelength of about 610+/−10 nm and a first absorbance peak with FWHM of less than 160 nm. In some embodiments, the detectable moieties having the xanthene core have a peak absorbance wavelength of about 605+/−10 nm and a first absorbance peak with FWHM of less than 160 nm. In some embodiments, the detectable moieties having the xanthene core have a peak absorbance wavelength of about 600+/−10 nm and a first absorbance peak with FWHM of less than 160 nm. In some embodiments, the detectable moieties having the xanthene core have a peak absorbance wavelength of about 595+/−10 nm and a first absorbance peak with FWHM of less than 160 nm. In some embodiments, the detectable moieties having the xanthene core have a peak absorbance wavelength of about 590+/−10 nm and a first absorbance peak with FWHM of less than 160 nm. In some embodiments, the detectable moieties having the xanthene core have a peak absorbance wavelength of about 585+/−10 nm and a first absorbance peak with FWHM of less than 160 nm. In some embodiments, the detectable moieties having the xanthene core have a peak absorbance wavelength of about 580+/−10 nm and a first absorbance peak with FWHM of less than 160 nm.

In some embodiments, the detectable moieties having the xanthene core have a peak absorbance wavelength of about 650+/−10 nm and a first absorbance peak with FWHM of less than 130 nm. In some embodiments, the detectable moieties having the xanthene core have a peak absorbance wavelength of about 645+/−10 nm and a first absorbance peak with FWHM of less than 130 nm. In some embodiments, the detectable moieties having the xanthene core have a peak absorbance wavelength of about 640+/−10 nm and a first absorbance peak with FWHM of less than 130 nm. In some embodiments, the detectable moieties having the xanthene core have a peak absorbance wavelength of about 635+/−10 nm and a first absorbance peak with FWHM of less than 130 nm. In some embodiments, the detectable moieties having the xanthene core have a peak absorbance wavelength of about 630+/−10 nm and a first absorbance peak with FWHM of less than 130 nm. In some embodiments, the detectable moieties having the xanthene core have a peak absorbance wavelength of about 625+/−10 nm and a first absorbance peak with FWHM of less than 130 nm. In some embodiments, the detectable moieties having the xanthene core have a peak absorbance wavelength of about 620+/−10 nm and a first absorbance peak with FWHM of less than 130 nm. In some embodiments, the detectable moieties having the xanthene core have a peak absorbance wavelength of about 615+/−10 nm and a first absorbance peak with FWHM of less than 130 nm. In some embodiments, the detectable moieties having the xanthene core have a peak absorbance wavelength of about 610+/−10 nm and a first absorbance peak with FWHM of less than 130 nm. In some embodiments, the detectable moieties having the xanthene core have a peak absorbance wavelength of about 605+/−10 nm and a first absorbance peak with FWHM of less than 130 nm. In some embodiments, the detectable moieties having the xanthene core have a peak absorbance wavelength of about 600+/−10 nm and a first absorbance peak with FWHM of less than 130 nm. In some embodiments, the detectable moieties having the xanthene core have a peak absorbance wavelength of about 595+/−10 nm and a first absorbance peak with FWHM of less than 130 nm. In some embodiments, the detectable moieties having the xanthene core have a peak absorbance wavelength of about 590+/−10 nm and a first absorbance peak with FWHM of less than 130 nm. In some embodiments, the detectable moieties having the xanthene core have a peak absorbance wavelength of about 585+/−10 nm and a first absorbance peak with FWHM of less than 130 nm. In some embodiments, the detectable moieties having the xanthene core have a peak absorbance wavelength of about 580+/−10 nm and a first absorbance peak with FWHM of less than 130 nm.

In some embodiments, the detectable moieties having the xanthene core have a peak absorbance wavelength of about 650+/−10 nm and a first absorbance peak with FWHM of less than 100 nm. In some embodiments, the detectable moieties having the xanthene core have a peak absorbance wavelength of about 645+/−10 nm and a first absorbance peak with FWHM of less than 100 nm. In some embodiments, the detectable moieties having the xanthene core have a peak absorbance wavelength of about 640+/−10 nm and a first absorbance peak with FWHM of less than 100 nm. In some embodiments, the detectable moieties having the xanthene core have a peak absorbance wavelength of about 635+/−10 nm and a first absorbance peak with FWHM of less than 100 nm. In some embodiments, the detectable moieties having the xanthene core have a peak absorbance wavelength of about 630+/−10 nm and a first absorbance peak with FWHM of less than 100 nm. In some embodiments, the detectable moieties having the xanthene core have a peak absorbance wavelength of about 625+/−10 nm and a first absorbance peak with FWHM of less than 100 nm. In some embodiments, the detectable moieties having the xanthene core have a peak absorbance wavelength of about 620+/−10 nm and a first absorbance peak with FWHM of less than 100 nm. In some embodiments, the detectable moieties having the xanthene core have a peak absorbance wavelength of about 615+/−10 nm and a first absorbance peak with FWHM of less than 100 nm. In some embodiments, the detectable moieties having the xanthene core have a peak absorbance wavelength of about 610+/−10 nm and a first absorbance peak with FWHM of less than 100 nm. In some embodiments, the detectable moieties having the xanthene core have a peak absorbance wavelength of about 605+/−10 nm and a first absorbance peak with FWHM of less than 100 nm. In some embodiments, the detectable moieties having the xanthene core have a peak absorbance wavelength of about 600+/−10 nm and a first absorbance peak with FWHM of less than 100 nm. In some embodiments, the detectable moieties having the xanthene core have a peak absorbance wavelength of about 595+/−10 nm and a first absorbance peak with FWHM of less than 100 nm. In some embodiments, the detectable moieties having the xanthene core have a peak absorbance wavelength of about 590+/−10 nm and a first absorbance peak with FWHM of less than 100 nm. In some embodiments, the detectable moieties having the xanthene core have a peak absorbance wavelength of about 585+/−10 nm and a first absorbance peak with FWHM of less than 100 nm. In some embodiments, the detectable moieties having the xanthene core have a peak absorbance wavelength of about 580+/−10 nm and a first absorbance peak with FWHM of less than 100 nm.

In some embodiments, the detectable moieties having the xanthene core have a peak absorbance wavelength of about 650+/−10 nm and a first absorbance peak with FWHM of less than 60 nm. In some embodiments, the detectable moieties having the xanthene core have a peak absorbance wavelength of about 645+/−10 nm and a first absorbance peak with FWHM of less than 60 nm. In some embodiments, the detectable moieties having the xanthene core have a peak absorbance wavelength of about 640+/−10 nm and a first absorbance peak with FWHM of less than 60 nm. In some embodiments, the detectable moieties having the xanthene core have a peak absorbance wavelength of about 635+/−10 nm and a first absorbance peak with FWHM of less than 60 nm. In some embodiments, the detectable moieties having the xanthene core have a peak absorbance wavelength of about 630+/−10 nm and a first absorbance peak with FWHM of less than 60 nm. In some embodiments, the detectable moieties having the xanthene core have a peak absorbance wavelength of about 625+/−10 nm and a first absorbance peak with FWHM of less than 60 nm. In some embodiments, the detectable moieties having the xanthene core have a peak absorbance wavelength of about 620+/−10 nm and a first absorbance peak with FWHM of less than 60 nm. In some embodiments, the detectable moieties having the xanthene core have a peak absorbance wavelength of about 615+/−10 nm and a first absorbance peak with FWHM of less than 60 nm. In some embodiments, the detectable moieties having the xanthene core have a peak absorbance wavelength of about 610+/−10 nm and a first absorbance peak with FWHM of less than 60 nm. In some embodiments, the detectable moieties having the xanthene core have a peak absorbance wavelength of about 605+/−10 nm and a first absorbance peak with FWHM of less than 60 nm. In some embodiments, the detectable moieties having the xanthene core have a peak absorbance wavelength of about 600+/−10 nm and a first absorbance peak with FWHM of less than 60 nm. In some embodiments, the detectable moieties having the xanthene core have a peak absorbance wavelength of about 595+/−10 nm and a first absorbance peak with FWHM of less than 60 nm. In some embodiments, the detectable moieties having the xanthene core have a peak absorbance wavelength of about 590+/−10 nm and a first absorbance peak with FWHM of less than 60 nm. In some embodiments, the detectable moieties having the xanthene core have a peak absorbance wavelength of about 585+/−10 nm and a first absorbance peak with FWHM of less than 60 nm. In some embodiments, the detectable moieties having the xanthene core have a peak absorbance wavelength of about 580+/−10 nm and a first absorbance peak with FWHM of less than 60 nm.

Detectable Moieties within the Infrared Spectrum

In some embodiments, the detectable moieties have a wavelength within the infrared spectrum. In some embodiments, the detectable moieties have a wavelength of greater than about 740 nm. In some embodiments, the detectable moieties have a wavelength of greater than about 750 nm. In some embodiments, the detectable moieties have a wavelength of greater than about 760 nm. In some embodiments, the detectable moieties have a wavelength of greater than about 765 nm. In some embodiments, the detectable moieties have a wavelength of greater than about 770 nm. In some embodiments, the detectable moieties have a wavelength of greater than about 775 nm. In some embodiments, the detectable moieties have a wavelength of greater than about 780 nm. In some embodiments, the detectable moieties have a wavelength of greater than about 785 nm. In some embodiments, the detectable moieties have a wavelength of greater than about 790 nm. In some embodiments the detectable moieties have a wavelength ranging from between about 760 nm to about 1 mm, from about 770 nm to about 1 mm, or from about 780 nm to about 1 mm.

In some embodiments, the detectable moieties have a wavelength of greater than about 740 nm and a first absorbance peak with FWHM of less than 160 nm. In some embodiments, the detectable moieties have a wavelength of greater than about 750 nm and a first absorbance peak with FWHM of less than 160 nm. In some embodiments, the detectable moieties have a wavelength of greater than about 760 nm and a first absorbance peak with FWHM of less than 160 nm. In some embodiments, the detectable moieties have a wavelength of greater than about 765 nm and a first absorbance peak with FWHM of less than 160 nm. In some embodiments, the detectable moieties have a wavelength of greater than about 770 nm and a first absorbance peak with FWHM of less than 160 nm. In some embodiments, the detectable moieties have a wavelength of greater than about 775 nm and a first absorbance peak with FWHM of less than 160 nm. In some embodiments, the detectable moieties have a wavelength of greater than about 780 nm and a first absorbance peak with FWHM of less than 160 nm. In some embodiments, the detectable moieties have a wavelength of greater than about 785 nm and a first absorbance peak with FWHM of less than 160 nm. In some embodiments, the detectable moieties have a wavelength of greater than about 790 nm and a first absorbance peak with FWHM of less than 160 nm.

In some embodiments, the detectable moieties have a wavelength of greater than about 740 nm and a first absorbance peak with FWHM of less than 130 nm. In some embodiments, the detectable moieties have a wavelength of greater than about 750 nm and a first absorbance peak with FWHM of less than 130 nm. In some embodiments, the detectable moieties have a wavelength of greater than about 760 nm and a first absorbance peak with FWHM of less than 130 nm. In some embodiments, the detectable moieties have a wavelength of greater than about 765 nm and a first absorbance peak with FWHM of less than 130 nm. In some embodiments, the detectable moieties have a wavelength of greater than about 770 nm and a first absorbance peak with FWHM of less than 130 nm. In some embodiments, the detectable moieties have a wavelength of greater than about 775 nm and a first absorbance peak with FWHM of less than 130 nm. In some embodiments, the detectable moieties have a wavelength of greater than about 780 nm and a first absorbance peak with FWHM of less than 130 nm. In some embodiments, the detectable moieties have a wavelength of greater than about 785 nm and a first absorbance peak with FWHM of less than 130 nm. In some embodiments, the detectable moieties have a wavelength of greater than about 790 nm and a first absorbance peak with FWHM of less than 130 nm.

In some embodiments, the detectable moieties have a wavelength of greater than about 740 nm and a first absorbance peak with FWHM of less than 100 nm. In some embodiments, the detectable moieties have a wavelength of greater than about 750 nm and a first absorbance peak with FWHM of less than 100 nm. In some embodiments, the detectable moieties have a wavelength of greater than about 760 nm and a first absorbance peak with FWHM of less than 100 nm. In some embodiments, the detectable moieties have a wavelength of greater than about 765 nm and a first absorbance peak with FWHM of less than 100 nm. In some embodiments, the detectable moieties have a wavelength of greater than about 770 nm and a first absorbance peak with FWHM of less than 100 nm. In some embodiments, the detectable moieties have a wavelength of greater than about 775 nm and a first absorbance peak with FWHM of less than 100 nm. In some embodiments, the detectable moieties have a wavelength of greater than about 780 nm and a first absorbance peak with FWHM of less than 100 nm. In some embodiments, the detectable moieties have a wavelength of greater than about 785 nm and a first absorbance peak with FWHM of less than 100 nm. In some embodiments, the detectable moieties have a wavelength of greater than about 790 nm and a first absorbance peak with FWHM of less than 100 nm.

In some embodiments, the detectable moieties have a wavelength of greater than about 740 nm and a first absorbance peak with FWHM of less than 80 nm. In some embodiments, the detectable moieties have a wavelength of greater than about 750 nm and a first absorbance peak with FWHM of less than 80 nm. In some embodiments, the detectable moieties have a wavelength of greater than about 760 nm and a first absorbance peak with FWHM of less than 80 nm. In some embodiments, the detectable moieties have a wavelength of greater than about 765 nm and a first absorbance peak with FWHM of less than 80 nm. In some embodiments, the detectable moieties have a wavelength of greater than about 770 nm and a first absorbance peak with FWHM of less than 80 nm. In some embodiments, the detectable moieties have a wavelength of greater than about 775 nm and a first absorbance peak with FWHM of less than 80 nm. In some embodiments, the detectable moieties have a wavelength of greater than about 780 nm and a first absorbance peak with FWHM of less than 80 nm. In some embodiments, the detectable moieties have a wavelength of greater than about 785 nm and a first absorbance peak with FWHM of less than 80 nm. In some embodiments, the detectable moieties have a wavelength of greater than about 790 nm and a first absorbance peak with FWHM of less than 80 nm.

In some embodiments, the detectable moieties have a wavelength of greater than about 740 nm and a first absorbance peak with FWHM of less than 60 nm. In some embodiments, the detectable moieties have a wavelength of greater than about 750 nm and a first absorbance peak with FWHM of less than 60 nm. In some embodiments, the detectable moieties have a wavelength of greater than about 760 nm and a first absorbance peak with FWHM of less than 60 nm. In some embodiments, the detectable moieties have a wavelength of greater than about 765 nm and a first absorbance peak with FWHM of less than 60 nm. In some embodiments, the detectable moieties have a wavelength of greater than about 770 nm and a first absorbance peak with FWHM of less than 60 nm. In some embodiments, the detectable moieties have a wavelength of greater than about 775 nm and a first absorbance peak with FWHM of less than 60 nm. In some embodiments, the detectable moieties have a wavelength of greater than about 780 nm and a first absorbance peak with FWHM of less than 60 nm. In some embodiments, the detectable moieties have a wavelength of greater than about 785 nm and a first absorbance peak with FWHM of less than 60 nm. In some embodiments, the detectable moieties have a wavelength of greater than about 790 nm and a first absorbance peak with FWHM of less than 60 nm.

In some embodiments, the detectable moieties have a wavelength of greater than about 740 nm and a first absorbance peak with FWHM of less than 50 nm. In some embodiments, the detectable moieties have a wavelength of greater than about 750 nm and a first absorbance peak with FWHM of less than 50 nm. In some embodiments, the detectable moieties have a wavelength of greater than about 760 nm and a first absorbance peak with FWHM of less than 50 nm. In some embodiments, the detectable moieties have a wavelength of greater than about 765 nm and a first absorbance peak with FWHM of less than 50 nm. In some embodiments, the detectable moieties have a wavelength of greater than about 770 nm and a first absorbance peak with FWHM of less than 50 nm. In some embodiments, the detectable moieties have a wavelength of greater than about 775 nm and a first absorbance peak with FWHM of less than 50 nm. In some embodiments, the detectable moieties have a wavelength of greater than about 780 nm and a first absorbance peak with FWHM of less than 50 nm. In some embodiments, the detectable moieties have a wavelength of greater than about 785 nm and a first absorbance peak with FWHM of less than 50 nm. In some embodiments, the detectable moieties have a wavelength of greater than about 790 nm and a first absorbance peak with FWHM of less than 50 nm.

In some embodiments, the detectable moiety includes or is derived from a heptamethine cyanine core (i.e., the detectable moiety includes a heptamethine cyanine core). Non-limiting examples of detectable moieties having the heptamethine cyanine core have Formula (VI) as described herein.

In some embodiments, the heptamethine cyanine core (includes (or is modified to include) one or more electron withdrawing groups (where each electron withdrawing group may be the same or different). In some embodiments, the heptamethine cyanine core includes (or is modified to include) one electron withdrawing group. In some embodiments, the heptamethine cyanine core includes (or is modified to include) two electron withdrawing groups. In some embodiments, the heptamethine cyanine core includes (or is modifying to include) three electron withdrawing groups. In some embodiments, the heptamethine cyanine core includes (or is modifying to include) three different electron withdrawing groups. In some embodiments, the heptamethine cyanine core includes (or is modified to include) four electron withdrawing groups.

In some embodiments, the heptamethine cyanine core (includes (or is modified to include) one or more electron donating groups (where each electron withdrawing group may be the same or different). In some embodiments, the heptamethine cyanine core includes (or is modified to include) one electron donating group. In some embodiments, the heptamethine cyanine core includes (or is modified to include) two electron donating groups. In some embodiments, the heptamethine cyanine core includes (or is modifying to include) three electron donating groups. In some embodiments, the heptamethine cyanine core includes (or is modifying to include) three different electron donating groups. In some embodiments, the heptamethine cyanine core includes (or is modified to include) four electron donating groups.

In some embodiments, the detectable moieties having the heptamethine cyanine core have a wavelength ranging from about 780 nm to about 950 nm. In some embodiments, the detectable moieties having the heptamethine cyanine core have a wavelength ranging from about 810 nm to about 920 nm. In some embodiments, the detectable moieties having the heptamethine cyanine have a wavelength ranging from about 840 nm to about 880 nm.

In some embodiments, the detectable moieties having the heptamethine cyanine core have a wavelength ranging from about 780 nm to about 950 nm and a first absorbance peak with FWHM of less than 160 nm. In some embodiments, the detectable moieties having the heptamethine cyanine core have a wavelength ranging from about 810 nm to about 920 nm and a first absorbance peak with FWHM of less than 160 nm. In some embodiments, the detectable moieties having the heptamethine cyanine have a wavelength ranging from about 840 nm to about 880 nm and a first absorbance peak with FWHM of less than 160 nm.

In some embodiments, the detectable moieties having the heptamethine cyanine core have a wavelength ranging from about 780 nm to about 950 nm and a first absorbance peak with FWHM of less than 130 nm. In some embodiments, the detectable moieties having the heptamethine cyanine core have a wavelength ranging from about 810 nm to about 920 nm and a first absorbance peak with FWHM of less than 130 nm. In some embodiments, the detectable moieties having the heptamethine cyanine have a wavelength ranging from about 840 nm to about 880 nm and a first absorbance peak with FWHM of less than 130 nm.

In some embodiments, the detectable moieties having the heptamethine cyanine core have a wavelength ranging from about 780 nm to about 950 nm and a first absorbance peak with FWHM of less than 100 nm. In some embodiments, the detectable moieties having the heptamethine cyanine core have a wavelength ranging from about 810 nm to about 920 nm and a first absorbance peak with FWHM of less than 100 nm. In some embodiments, the detectable moieties having the heptamethine cyanine have a wavelength ranging from about 840 nm to about 880 nm and a first absorbance peak with FWHM of less than 100 nm.

In some embodiments, the detectable moieties having the heptamethine cyanine core have a wavelength ranging from about 780 nm to about 950 nm and a first absorbance peak with FWHM of less than 80 nm. In some embodiments, the detectable moieties having the heptamethine cyanine core have a wavelength ranging from about 810 nm to about 920 nm and a FWHM of less than 80 nm. In some embodiments, the detectable moieties having the heptamethine cyanine have a wavelength ranging from about 840 nm to about 880 nm and a first absorbance peak with FWHM of less than 80 nm.

In some embodiments, the detectable moieties having the heptamethine cyanine core have a wavelength ranging from about 780 nm to about 950 nm and a first absorbance peak with FWHM of less than 60 nm. In some embodiments, the detectable moieties having the heptamethine cyanine core have a wavelength ranging from about 810 nm to about 920 nm and a FWHM of less than 60 nm. In some embodiments, the detectable moieties having the heptamethine cyanine have a wavelength ranging from about 840 nm to about 880 nm and a first absorbance peak with FWHM of less than 60 nm.

In some embodiments, the detectable moieties having the heptamethine cyanine core have a peak absorbance wavelength of about 950+/−10 nm. In some embodiments, the detectable moieties having the heptamethine cyanine core have a peak absorbance wavelength of about 945+/−10 nm. In some embodiments, the detectable moieties having the heptamethine cyanine core have a peak absorbance wavelength of about 940+/−10 nm. In some embodiments, the detectable moieties having the heptamethine cyanine core have a peak absorbance wavelength of about 935+/−10 nm. In some embodiments, the detectable moieties having the heptamethine cyanine core have a peak absorbance wavelength of about 930+/−10 nm. In some embodiments, the detectable moieties having the heptamethine cyanine core have a peak absorbance wavelength of about 925+/−10 nm. In some embodiments, the detectable moieties having the heptamethine cyanine core have a peak absorbance wavelength of about 920+/−10 nm. In some embodiments, the detectable moieties having the heptamethine cyanine core have a peak absorbance wavelength of about 915+/−10 nm. In some embodiments, the detectable moieties having the heptamethine cyanine core have a peak absorbance wavelength of about 910+/−10 nm. In some embodiments, the detectable moieties having the heptamethine cyanine core have a peak absorbance wavelength of about 905+/−10 nm. In some embodiments, the detectable moieties having the heptamethine cyanine core have a peak absorbance wavelength of about 900+/−10 nm. In some embodiments, the detectable moieties having the heptamethine cyanine core have a peak absorbance wavelength of about 895+/−10 nm. In some embodiments, the detectable moieties having the heptamethine cyanine core have a peak absorbance wavelength of about 890+/−10 nm. In some embodiments, the detectable moieties having the heptamethine cyanine core have a peak absorbance wavelength of about 885+/−10 nm. In some embodiments, the detectable moieties having the heptamethine cyanine core have a peak absorbance wavelength of about 880+/−10 nm. In some embodiments, the detectable moieties having the heptamethine cyanine core have a peak absorbance wavelength of about 870+/−10 nm. In some embodiments, the detectable moieties having the heptamethine cyanine core have a peak absorbance wavelength of about 865+/−10 nm. In some embodiments, the detectable moieties having the heptamethine cyanine core have a peak absorbance wavelength of about 860+/−10 nm. In some embodiments, the detectable moieties having the heptamethine cyanine core have a peak absorbance wavelength of about 855+/−10 nm. In some embodiments, the detectable moieties having the heptamethine cyanine core have a peak absorbance wavelength of about 850+/−10 nm. In some embodiments, the detectable moieties having the heptamethine cyanine core have a peak absorbance wavelength of about 845+/−10 nm. In some embodiments, the detectable moieties having the heptamethine cyanine core have a peak absorbance wavelength of about 840+/−10 nm. In some embodiments, the detectable moieties having the heptamethine cyanine core have a peak absorbance wavelength of about 835+/−10 nm. In some embodiments, the detectable moieties having the heptamethine cyanine core have a peak absorbance wavelength of about 830+/−10 nm. In some embodiments, the detectable moieties having the heptamethine cyanine core have a peak absorbance wavelength of about 825+/−10 nm. In some embodiments, the detectable moieties having the heptamethine cyanine core have a peak absorbance wavelength of about 820+/−10 nm. In some embodiments, the detectable moieties having the heptamethine cyanine core have a peak absorbance wavelength of about 815+/−10 nm. In some embodiments, the detectable moieties having the heptamethine cyanine core have a peak absorbance wavelength of about 800+/−10 nm. In some embodiments, the detectable moieties having the heptamethine cyanine core have a peak absorbance wavelength of about 795+/−10 nm. In some embodiments, the detectable moieties having the heptamethine cyanine core have a peak absorbance wavelength of about 790+/−10 nm. In some embodiments, the detectable moieties having the heptamethine cyanine core have a peak absorbance wavelength of about 785+/−10 nm. In some embodiments, the detectable moieties having the heptamethine cyanine core have a peak absorbance wavelength of about 780+/−10 nm.

In some embodiments, the detectable moieties having the heptamethine cyanine core have a peak absorbance wavelength of about 950+/−10 nm and a first absorbance peak with FWHM of less than 160 nm. In some embodiments, the detectable moieties having the heptamethine cyanine core have a peak absorbance wavelength of about 945+/−10 nm and a first absorbance peak with FWHM of less than 160 nm. In some embodiments, the detectable moieties having the heptamethine cyanine core have a peak absorbance wavelength of about 940+/−10 nm and a first absorbance peak with FWHM of less than 160 nm. In some embodiments, the detectable moieties having the heptamethine cyanine core have a peak absorbance wavelength of about 935+/−10 nm and a first absorbance peak with FWHM of less than 160 nm. In some embodiments, the detectable moieties having the heptamethine cyanine core have a peak absorbance wavelength of about 930+/−10 nm and a first absorbance peak with FWHM of less than 160 nm. In some embodiments, the detectable moieties having the heptamethine cyanine core have a peak absorbance wavelength of about 925+/−10 nm and a first absorbance peak with FWHM of less than 160 nm. In some embodiments, the detectable moieties having the heptamethine cyanine core have a peak absorbance wavelength of about 920+/−10 nm and a first absorbance peak with FWHM of less than 160 nm. In some embodiments, the detectable moieties having the heptamethine cyanine core have a peak absorbance wavelength of about 915+/−10 nm and a first absorbance peak with FWHM of less than 160 nm. In some embodiments, the detectable moieties having the heptamethine cyanine core have a peak absorbance wavelength of about 910+/−10 nm and a first absorbance peak with FWHM of less than 160 nm. In some embodiments, the detectable moieties having the heptamethine cyanine core have a peak absorbance wavelength of about 905+/−10 nm and a first absorbance peak with FWHM of less than 160 nm. In some embodiments, the detectable moieties having the heptamethine cyanine core have a peak absorbance wavelength of about 900+/−10 nm and a first absorbance peak with FWHM of less than 160 nm. In some embodiments, the detectable moieties having the heptamethine cyanine core have a peak absorbance wavelength of about 895+/−10 nm and a first absorbance peak with FWHM of less than 160 nm. In some embodiments, the detectable moieties having the heptamethine cyanine core have a peak absorbance wavelength of about 890+/−10 nm and a first absorbance peak with FWHM of less than 160 nm. In some embodiments, the detectable moieties having the heptamethine cyanine core have a peak absorbance wavelength of about 885+/−10 nm and a first absorbance peak with FWHM of less than 160 nm. In some embodiments, the detectable moieties having the heptamethine cyanine core have a peak absorbance wavelength of about 880+/−10 nm and a first absorbance peak with FWHM of less than 160 nm. In some embodiments, the detectable moieties having the heptamethine cyanine core have a peak absorbance wavelength of about 870+/−10 nm and a first absorbance peak with FWHM of less than 160 nm. In some embodiments, the detectable moieties having the heptamethine cyanine core have a peak absorbance wavelength of about 865+/−10 nm and a first absorbance peak with FWHM of less than 160 nm. In some embodiments, the detectable moieties having the heptamethine cyanine core have a peak absorbance wavelength of about 860+/−10 nm and a first absorbance peak with FWHM of less than 160 nm. In some embodiments, the detectable moieties having the heptamethine cyanine core have a peak absorbance wavelength of about 855+/−10 nm and a first absorbance peak with FWHM of less than 160 nm. In some embodiments, the detectable moieties having the heptamethine cyanine core have a peak absorbance wavelength of about 850+/−10 nm and a first absorbance peak with FWHM of less than 160 nm. In some embodiments, the detectable moieties having the heptamethine cyanine core have a peak absorbance wavelength of about 845+/−10 nm and a first absorbance peak with FWHM of less than 160 nm. In some embodiments, the detectable moieties having the heptamethine cyanine core have a peak absorbance wavelength of about 840+/−10 nm and a first absorbance peak with FWHM of less than 160 nm. In some embodiments, the detectable moieties having the heptamethine cyanine core have a peak absorbance wavelength of about 835+/−10 nm and a first absorbance peak with FWHM of less than 160 nm. In some embodiments, the detectable moieties having the heptamethine cyanine core have a peak absorbance wavelength of about 830+/−10 nm and a first absorbance peak with FWHM of less than 160 nm. In some embodiments, the detectable moieties having the heptamethine cyanine core have a peak absorbance wavelength of about 825+/−10 nm and a first absorbance peak with FWHM of less than 160 nm. In some embodiments, the detectable moieties having the heptamethine cyanine core have a peak absorbance wavelength of about 820+/−10 nm and a first absorbance peak with FWHM of less than 160 nm. In some embodiments, the detectable moieties having the heptamethine cyanine core have a peak absorbance wavelength of about 815+/−10 nm and a first absorbance peak with FWHM of less than 160 nm. In some embodiments, the detectable moieties having the heptamethine cyanine core have a peak absorbance wavelength of about 800+/−10 nm and a first absorbance peak with FWHM of less than 160 nm. In some embodiments, the detectable moieties having the heptamethine cyanine core have a peak absorbance wavelength of about 795+/−10 nm and a first absorbance peak with FWHM of less than 160 nm. In some embodiments, the detectable moieties having the heptamethine cyanine core have a peak absorbance wavelength of about 790+/−10 nm and a first absorbance peak with FWHM of less than 160 nm. In some embodiments, the detectable moieties having the heptamethine cyanine core have a peak absorbance wavelength of about 785+/−10 nm and a first absorbance peak with FWHM of less than 160 nm. In some embodiments, the detectable moieties having the heptamethine cyanine core have a peak absorbance wavelength of about 780+/−10 nm and a first absorbance peak with FWHM of less than 160 nm.

In some embodiments, the detectable moieties having the heptamethine cyanine core have a peak absorbance wavelength of about 950+/−10 nm and a first absorbance peak with FWHM of less than 130 nm. In some embodiments, the detectable moieties having the heptamethine cyanine core have a peak absorbance wavelength of about 945+/−10 nm and a first absorbance peak with FWHM of less than 130 nm. In some embodiments, the detectable moieties having the heptamethine cyanine core have a peak absorbance wavelength of about 940+/−10 nm and a first absorbance peak with FWHM of less than 130 nm. In some embodiments, the detectable moieties having the heptamethine cyanine core have a peak absorbance wavelength of about 935+/−10 nm and a first absorbance peak with FWHM of less than 130 nm. In some embodiments, the detectable moieties having the heptamethine cyanine core have a peak absorbance wavelength of about 930+/−10 nm and a first absorbance peak with FWHM of less than 130 nm. In some embodiments, the detectable moieties having the heptamethine cyanine core have a peak absorbance wavelength of about 925+/−10 nm and a first absorbance peak with FWHM of less than 130 nm. In some embodiments, the detectable moieties having the heptamethine cyanine core have a peak absorbance wavelength of about 920+/−10 nm and a first absorbance peak with FWHM of less than 130 nm. In some embodiments, the detectable moieties having the heptamethine cyanine core have a peak absorbance wavelength of about 915+/−10 nm and a first absorbance peak with FWHM of less than 130 nm. In some embodiments, the detectable moieties having the heptamethine cyanine core have a peak absorbance wavelength of about 910+/−10 nm and a first absorbance peak with FWHM of less than 130 nm. In some embodiments, the detectable moieties having the heptamethine cyanine core have a peak absorbance wavelength of about 905+/−10 nm and a first absorbance peak with FWHM of less than 130 nm. In some embodiments, the detectable moieties having the heptamethine cyanine core have a peak absorbance wavelength of about 900+/−10 nm and a first absorbance peak with FWHM of less than 130 nm. In some embodiments, the detectable moieties having the heptamethine cyanine core have a peak absorbance wavelength of about 895+/−10 nm and a first absorbance peak with FWHM of less than 130 nm. In some embodiments, the detectable moieties having the heptamethine cyanine core have a peak absorbance wavelength of about 890+/−10 nm and a first absorbance peak with FWHM of less than 130 nm. In some embodiments, the detectable moieties having the heptamethine cyanine core have a peak absorbance wavelength of about 885+/−10 nm and a first absorbance peak with FWHM of less than 130 nm. In some embodiments, the detectable moieties having the heptamethine cyanine core have a peak absorbance wavelength of about 880+/−10 nm and a first absorbance peak with FWHM of less than 130 nm. In some embodiments, the detectable moieties having the heptamethine cyanine core have a peak absorbance wavelength of about 870+/−10 nm and a first absorbance peak with FWHM of less than 130 nm. In some embodiments, the detectable moieties having the heptamethine cyanine core have a peak absorbance wavelength of about 865+/−10 nm and a first absorbance peak with FWHM of less than 130 nm. In some embodiments, the detectable moieties having the heptamethine cyanine core have a peak absorbance wavelength of about 860+/−10 nm and a first absorbance peak with FWHM of less than 130 nm. In some embodiments, the detectable moieties having the heptamethine cyanine core have a peak absorbance wavelength of about 855+/−10 nm and a first absorbance peak with FWHM of less than 130 nm. In some embodiments, the detectable moieties having the heptamethine cyanine core have a peak absorbance wavelength of about 850+/−10 nm and a first absorbance peak with FWHM of less than 130 nm. In some embodiments, the detectable moieties having the heptamethine cyanine core have a peak absorbance wavelength of about 845+/−10 nm and a first absorbance peak with FWHM of less than 130 nm. In some embodiments, the detectable moieties having the heptamethine cyanine core have a peak absorbance wavelength of about 840+/−10 nm and a first absorbance peak with FWHM of less than 130 nm. In some embodiments, the detectable moieties having the heptamethine cyanine core have a peak absorbance wavelength of about 835+/−10 nm and a first absorbance peak with FWHM of less than 130 nm. In some embodiments, the detectable moieties having the heptamethine cyanine core have a peak absorbance wavelength of about 830+/−10 nm and a first absorbance peak with FWHM of less than 130 nm. In some embodiments, the detectable moieties having the heptamethine cyanine core have a peak absorbance wavelength of about 825+/−10 nm and a first absorbance peak with FWHM of less than 130 nm. In some embodiments, the detectable moieties having the heptamethine cyanine core have a peak absorbance wavelength of about 820+/−10 nm and a first absorbance peak with FWHM of less than 130 nm. In some embodiments, the detectable moieties having the heptamethine cyanine core have a peak absorbance wavelength of about 815+/−10 nm and a first absorbance peak with FWHM of less than 130 nm. In some embodiments, the detectable moieties having the heptamethine cyanine core have a peak absorbance wavelength of about 800+/−10 nm and a first absorbance peak with FWHM of less than 130 nm. In some embodiments, the detectable moieties having the heptamethine cyanine core have a peak absorbance wavelength of about 795+/−10 nm and a first absorbance peak with FWHM of less than 130 nm. In some embodiments, the detectable moieties having the heptamethine cyanine core have a peak absorbance wavelength of about 790+/−10 nm and a first absorbance peak with FWHM of less than 130 nm. In some embodiments, the detectable moieties having the heptamethine cyanine core have a peak absorbance wavelength of about 785+/−10 nm and a first absorbance peak with FWHM of less than 130 nm. In some embodiments, the detectable moieties having the heptamethine cyanine core have a peak absorbance wavelength of about 780+/−10 nm and a first absorbance peak with FWHM of less than 130 nm.

In some embodiments, the detectable moieties having the heptamethine cyanine core have a peak absorbance wavelength of about 950+/−10 nm and a first absorbance peak with FWHM of less than 100 nm. In some embodiments, the detectable moieties having the heptamethine cyanine core have a peak absorbance wavelength of about 945+/−10 nm and a first absorbance peak with FWHM of less than 100 nm. In some embodiments, the detectable moieties having the heptamethine cyanine core have a peak absorbance wavelength of about 940+/−10 nm and a first absorbance peak with FWHM of less than 100 nm. In some embodiments, the detectable moieties having the heptamethine cyanine core have a peak absorbance wavelength of about 935+/−10 nm and a first absorbance peak with FWHM of less than 100 nm. In some embodiments, the detectable moieties having the heptamethine cyanine core have a peak absorbance wavelength of about 930+/−10 nm and a first absorbance peak with FWHM of less than 100 nm. In some embodiments, the detectable moieties having the heptamethine cyanine core have a peak absorbance wavelength of about 925+/−10 nm and a first absorbance peak with FWHM of less than 100 nm. In some embodiments, the detectable moieties having the heptamethine cyanine core have a peak absorbance wavelength of about 920+/−10 nm and a first absorbance peak with FWHM of less than 100 nm. In some embodiments, the detectable moieties having the heptamethine cyanine core have a peak absorbance wavelength of about 915+/−10 nm and a first absorbance peak with FWHM of less than 100 nm. In some embodiments, the detectable moieties having the heptamethine cyanine core have a peak absorbance wavelength of about 910+/−10 nm and a first absorbance peak with FWHM of less than 100 nm. In some embodiments, the detectable moieties having the heptamethine cyanine core have a peak absorbance wavelength of about 905+/−10 nm and a first absorbance peak with FWHM of less than 100 nm. In some embodiments, the detectable moieties having the heptamethine cyanine core have a peak absorbance wavelength of about 900+/−10 nm and a first absorbance peak with FWHM of less than 100 nm. In some embodiments, the detectable moieties having the heptamethine cyanine core have a peak absorbance wavelength of about 895+/−10 nm and a first absorbance peak with FWHM of less than 100 nm. In some embodiments, the detectable moieties having the heptamethine cyanine core have a peak absorbance wavelength of about 890+/−10 nm and a first absorbance peak with FWHM of less than 100 nm. In some embodiments, the detectable moieties having the heptamethine cyanine core have a peak absorbance wavelength of about 885+/−10 nm and a first absorbance peak with FWHM of less than 100 nm. In some embodiments, the detectable moieties having the heptamethine cyanine core have a peak absorbance wavelength of about 880+/−10 nm and a first absorbance peak with FWHM of less than 100 nm. In some embodiments, the detectable moieties having the heptamethine cyanine core have a peak absorbance wavelength of about 870+/−10 nm and a first absorbance peak with FWHM of less than 100 nm. In some embodiments, the detectable moieties having the heptamethine cyanine core have a peak absorbance wavelength of about 865+/−10 nm and a first absorbance peak with FWHM of less than 100 nm. In some embodiments, the detectable moieties having the heptamethine cyanine core have a peak absorbance wavelength of about 860+/−10 nm and a first absorbance peak with FWHM of less than 100 nm. In some embodiments, the detectable moieties having the heptamethine cyanine core have a peak absorbance wavelength of about 855+/−10 nm and a first absorbance peak with FWHM of less than 100 nm. In some embodiments, the detectable moieties having the heptamethine cyanine core have a peak absorbance wavelength of about 850+/−10 nm and a first absorbance peak with FWHM of less than 100 nm. In some embodiments, the detectable moieties having the heptamethine cyanine core have a peak absorbance wavelength of about 845+/−10 nm and a first absorbance peak with FWHM of less than 100 nm. In some embodiments, the detectable moieties having the heptamethine cyanine core have a peak absorbance wavelength of about 840+/−10 nm and a first absorbance peak with FWHM of less than 100 nm. In some embodiments, the detectable moieties having the heptamethine cyanine core have a peak absorbance wavelength of about 835+/−10 nm and a first absorbance peak with FWHM of less than 100 nm. In some embodiments, the detectable moieties having the heptamethine cyanine core have a peak absorbance wavelength of about 830+/−10 nm and a first absorbance peak with FWHM of less than 100 nm. In some embodiments, the detectable moieties having the heptamethine cyanine core have a peak absorbance wavelength of about 825+/−10 nm and a first absorbance peak with FWHM of less than 100 nm. In some embodiments, the detectable moieties having the heptamethine cyanine core have a peak absorbance wavelength of about 820+/−10 nm and a first absorbance peak with FWHM of less than 100 nm. In some embodiments, the detectable moieties having the heptamethine cyanine core have a peak absorbance wavelength of about 815+/−10 nm and a first absorbance peak with FWHM of less than 100 nm. In some embodiments, the detectable moieties having the heptamethine cyanine core have a peak absorbance wavelength of about 800+/−10 nm and a first absorbance peak with FWHM of less than 100 nm. In some embodiments, the detectable moieties having the heptamethine cyanine core have a peak absorbance wavelength of about 795+/−10 nm and a first absorbance peak with FWHM of less than 100 nm. In some embodiments, the detectable moieties having the heptamethine cyanine core have a peak absorbance wavelength of about 790+/−10 nm and a first absorbance peak with FWHM of less than 100 nm. In some embodiments, the detectable moieties having the heptamethine cyanine core have a peak absorbance wavelength of about 785+/−10 nm and a first absorbance peak with FWHM of less than 100 nm. In some embodiments, the detectable moieties having the heptamethine cyanine core have a peak absorbance wavelength of about 780+/−10 nm and a first absorbance peak with FWHM of less than 100 nm.

In some embodiments, the detectable moieties having the heptamethine cyanine core have a peak absorbance wavelength of about 950+/−10 nm and a first absorbance peak with FWHM of less than 60 nm. In some embodiments, the detectable moieties having the heptamethine cyanine core have a peak absorbance wavelength of about 945+/−10 nm and a first absorbance peak with FWHM of less than 60 nm. In some embodiments, the detectable moieties having the heptamethine cyanine core have a peak absorbance wavelength of about 940+/−10 nm and a first absorbance peak with FWHM of less than 60 nm. In some embodiments, the detectable moieties having the heptamethine cyanine core have a peak absorbance wavelength of about 935+/−10 nm and a first absorbance peak with FWHM of less than 60 nm. In some embodiments, the detectable moieties having the heptamethine cyanine core have a peak absorbance wavelength of about 930+/−10 nm and a first absorbance peak with FWHM of less than 60 nm. In some embodiments, the detectable moieties having the heptamethine cyanine core have a peak absorbance wavelength of about 925+/−10 nm and a first absorbance peak with FWHM of less than 60 nm. In some embodiments, the detectable moieties having the heptamethine cyanine core have a peak absorbance wavelength of about 920+/−10 nm and a first absorbance peak with FWHM of less than 60 nm. In some embodiments, the detectable moieties having the heptamethine cyanine core have a peak absorbance wavelength of about 915+/−10 nm and a first absorbance peak with FWHM of less than 60 nm. In some embodiments, the detectable moieties having the heptamethine cyanine core have a peak absorbance wavelength of about 910+/−10 nm and a first absorbance peak with FWHM of less than 60 nm. In some embodiments, the detectable moieties having the heptamethine cyanine core have a peak absorbance wavelength of about 905+/−10 nm and a first absorbance peak with FWHM of less than 60 nm. In some embodiments, the detectable moieties having the heptamethine cyanine core have a peak absorbance wavelength of about 900+/−10 nm and a first absorbance peak with FWHM of less than 60 nm. In some embodiments, the detectable moieties having the heptamethine cyanine core have a peak absorbance wavelength of about 895+/−10 nm and a first absorbance peak with FWHM of less than 60 nm.

In some embodiments, the detectable moieties having the heptamethine cyanine core have a peak absorbance wavelength of about 890+/−10 nm and a first absorbance peak with FWHM of less than 60 nm. In some embodiments, the detectable moieties having the heptamethine cyanine core have a peak absorbance wavelength of about 885+/−10 nm and a first absorbance peak with FWHM of less than 60 nm. In some embodiments, the detectable moieties having the heptamethine cyanine core have a peak absorbance wavelength of about 880+/−10 nm and a first absorbance peak with FWHM of less than 60 nm. In some embodiments, the detectable moieties having the heptamethine cyanine core have a peak absorbance wavelength of about 870+/−10 nm and a first absorbance peak with FWHM of less than 60 nm. In some embodiments, the detectable moieties having the heptamethine cyanine core have a peak absorbance wavelength of about 865+/−10 nm and a first absorbance peak with FWHM of less than 60 nm. In some embodiments, the detectable moieties having the heptamethine cyanine core have a peak absorbance wavelength of about 860+/−10 nm and a first absorbance peak with FWHM of less than 60 nm. In some embodiments, the detectable moieties having the heptamethine cyanine core have a peak absorbance wavelength of about 855+/−10 nm and a first absorbance peak with FWHM of less than 60 nm. In some embodiments, the detectable moieties having the heptamethine cyanine core have a peak absorbance wavelength of about 850+/−10 nm and a first absorbance peak with FWHM of less than 60 nm. In some embodiments, the detectable moieties having the heptamethine cyanine core have a peak absorbance wavelength of about 845+/−10 nm and a first absorbance peak with FWHM of less than 60 nm. In some embodiments, the detectable moieties having the heptamethine cyanine core have a peak absorbance wavelength of about 840+/−10 nm and a first absorbance peak with FWHM of less than 60 nm. In some embodiments, the detectable moieties having the heptamethine cyanine core have a peak absorbance wavelength of about 835+/−10 nm and a first absorbance peak with FWHM of less than 60 nm. In some embodiments, the detectable moieties having the heptamethine cyanine core have a peak absorbance wavelength of about 830+/−10 nm and a first absorbance peak with FWHM of less than 60 nm. In some embodiments, the detectable moieties having the heptamethine cyanine core have a peak absorbance wavelength of about 825+/−10 nm and a first absorbance peak with FWHM of less than 60 nm. In some embodiments, the detectable moieties having the heptamethine cyanine core have a peak absorbance wavelength of about 820+/−10 nm and a first absorbance peak with FWHM of less than 60 nm. In some embodiments, the detectable moieties having the heptamethine cyanine core have a peak absorbance wavelength of about 815+/−10 nm and a first absorbance peak with FWHM of less than 60 nm. In some embodiments, the detectable moieties having the heptamethine cyanine core have a peak absorbance wavelength of about 800+/−10 nm and a first absorbance peak with FWHM of less than 60 nm. In some embodiments, the detectable moieties having the heptamethine cyanine core have a peak absorbance wavelength of about 795+/−10 nm and a first absorbance peak with FWHM of less than 60 nm. In some embodiments, the detectable moieties having the heptamethine cyanine core have a peak absorbance wavelength of about 790+/−10 nm and a first absorbance peak with FWHM of less than 60 nm. In some embodiments, the detectable moieties having the heptamethine cyanine core have a peak absorbance wavelength of about 785+/−10 nm and a first absorbance peak with FWHM of less than 60 nm. In some embodiments, the detectable moieties having the heptamethine cyanine core have a peak absorbance wavelength of about 780+/−10 nm and a first absorbance peak with FWHM of less than 60 nm.

In some embodiments, the detectable moiety includes or is derived from a croconate core (i.e., the detectable moiety includes a croconate core). Non-limiting examples of detectable moieties having the croconate core have Formula (VIIA) as described herein.

In some embodiments, the croconate core (includes (or is modified to include) one or more electron withdrawing groups (where each electron withdrawing group may be the same or different). In some embodiments, the croconate core includes (or is modified to include) one electron withdrawing group. In some embodiments, the croconate core includes (or is modified to include) two electron withdrawing groups. In some embodiments, the croconate core includes (or is modifying to include) three electron withdrawing groups. In some embodiments, the croconate core includes (or is modifying to include) three different electron withdrawing groups. In some embodiments, the croconate core includes (or is modified to include) four electron withdrawing groups.

In some embodiments, the croconate core (includes (or is modified to include) one or more electron donating groups (where each electron withdrawing group may be the same or different). In some embodiments, the croconate core includes (or is modified to include) one electron donating group. In some embodiments, the croconate core includes (or is modified to include) two electron donating groups. In some embodiments, the croconate core includes (or is modifying to include) three electron donating groups. In some embodiments, the croconate core includes (or is modifying to include) three different electron donating groups. In some embodiments, the croconate core includes (or is modified to include) four electron donating groups.

In some embodiments, the detectable moieties having the croconate core have a wavelength ranging from about 780 nm to about 900 nm. In some embodiments, the detectable moieties having the croconate core have a wavelength ranging from about 800 nm to about 880 nm. In some embodiments, the detectable moieties having the croconate core have a wavelength ranging from about 820 nm to about 860 nm.

In some embodiments, the detectable moieties having the croconate core have a wavelength ranging from about 780 nm to about 900 nm and a first absorbance peak with FWHM of less than 160 nm. In some embodiments, the detectable moieties having the croconate core have a wavelength ranging from about 800 nm to about 880 nm and a first absorbance peak with FWHM of less than 160 nm. In some embodiments, the detectable moieties having the croconate core have a wavelength ranging from about 820 nm to about 860 nm and a first absorbance peak with FWHM of less than 160 nm.

In some embodiments, the detectable moieties having the croconate core have a wavelength ranging from about 780 nm to about 900 nm and a first absorbance peak with FWHM of less than 130 nm. In some embodiments, the detectable moieties having the croconate core have a wavelength ranging from about 800 nm to about 880 nm and a first absorbance peak with FWHM of less than 130 nm. In some embodiments, the detectable moieties having the croconate core have a wavelength ranging from about 820 nm to about 860 nm and a first absorbance peak with FWHM of less than 130 nm.

In some embodiments, the detectable moieties having the croconate core have a wavelength ranging from about 780 nm to about 900 nm and a first absorbance peak with FWHM of less than 100 nm. In some embodiments, the detectable moieties having the croconate core have a wavelength ranging from about 800 nm to about 880 nm and a first absorbance peak with FWHM of less than 100 nm. In some embodiments, the detectable moieties having the croconate core have a wavelength ranging from about 820 nm to about 860 nm and a first absorbance peak with FWHM of less than 100 nm.

In some embodiments, the detectable moieties having the croconate core have a wavelength ranging from about 780 nm to about 900 nm and a first absorbance peak with FWHM of less than 80 nm. In some embodiments, the detectable moieties having the croconate core have a wavelength ranging from about 800 nm to about 880 nm and a first absorbance peak with FWHM of less than 80 nm. In some embodiments, the detectable moieties having the croconate core have a wavelength ranging from about 820 nm to about 860 nm and a first absorbance peak with FWHM of less than 80 nm.

In some embodiments, the detectable moieties having the croconate core have a wavelength ranging from about 780 nm to about 900 nm and a first absorbance peak with FWHM of less than 60 nm. In some embodiments, the detectable moieties having the croconate core have a wavelength ranging from about 800 nm to about 880 nm and a first absorbance peak with FWHM of less than 60 nm. In some embodiments, the detectable moieties having the croconate core have a wavelength ranging from about 820 nm to about 860 nm and a first absorbance peak with FWHM of less than 60 nm.

In some embodiments, the detectable moieties having the croconate core have a peak absorbance wavelength of about 900+/−10 nm. In some embodiments, the detectable moieties having the croconate core have a peak absorbance wavelength of about 895+/−10 nm. In some embodiments, the detectable moieties having the croconate core have a peak absorbance wavelength of about 890+/−10 nm. In some embodiments, the detectable moieties having the croconate core have a peak absorbance wavelength of about 885+/−10 nm. In some embodiments, the detectable moieties having the croconate core have a peak absorbance wavelength of about 880+/−10 nm. In some embodiments, the detectable moieties having the croconate core have a peak absorbance wavelength of about 870+/−10 nm. In some embodiments, the detectable moieties having the croconate core have a peak absorbance wavelength of about 865+/−10 nm. In some embodiments, the detectable moieties having the croconate core have a peak absorbance wavelength of about 860+/−10 nm. In some embodiments, the detectable moieties having the croconate core have a peak absorbance wavelength of about 855+/−10 nm. In some embodiments, the detectable moieties having the croconate core have a peak absorbance wavelength of about 850+/−10 nm. In some embodiments, the detectable moieties having the croconate core have a peak absorbance wavelength of about 845+/−10 nm. In some embodiments, the detectable moieties having the croconate core have a peak absorbance wavelength of about 840+/−10 nm. In some embodiments, the detectable moieties having the croconate core have a peak absorbance wavelength of about 835+/−10 nm. In some embodiments, the detectable moieties having the croconate core have a peak absorbance wavelength of about 830+/−10 nm. In some embodiments, the detectable moieties having the croconate core have a peak absorbance wavelength of about 825+/−10 nm. In some embodiments, the detectable moieties having the croconate core have a peak absorbance wavelength of about 820+/−10 nm. In some embodiments, the detectable moieties having the croconate core have a peak absorbance wavelength of about 815+/−10 nm. In some embodiments, the detectable moieties having the croconate core have a peak absorbance wavelength of about 800+/−10 nm. In some embodiments, the detectable moieties having the croconate core have a peak absorbance wavelength of about 795+/−10 nm. In some embodiments, the detectable moieties having the croconate core have a peak absorbance wavelength of about 790+/−10 nm. In some embodiments, the detectable moieties having the croconate core have a peak absorbance wavelength of about 785+/−10 nm. In some embodiments, the detectable moieties having the croconate core have a peak absorbance wavelength of about 780+/−10 nm.

In some embodiments, the detectable moieties having the croconate core have a peak absorbance wavelength of about 900+/−10 nm and a first absorbance peak with FWHM of less than 160 nm. In some embodiments, the detectable moieties having the croconate core have a peak absorbance wavelength of about 895+/−10 nm and a first absorbance peak with FWHM of less than 160 nm. In some embodiments, the detectable moieties having the croconate core have a peak absorbance wavelength of about 890+/−10 nm and a first absorbance peak with FWHM of less than 160 nm. In some embodiments, the detectable moieties having the croconate core have a peak absorbance wavelength of about 885+/−10 nm and a first absorbance peak with FWHM of less than 160 nm. In some embodiments, the detectable moieties having the croconate core have a peak absorbance wavelength of about 880+/−10 nm and a first absorbance peak with FWHM of less than 160 nm. In some embodiments, the detectable moieties having the croconate core have a peak absorbance wavelength of about 870+/−10 nm and a first absorbance peak with FWHM of less than 160 nm. In some embodiments, the detectable moieties having the croconate core have a peak absorbance wavelength of about 865+/−10 nm and a first absorbance peak with FWHM of less than 160 nm. In some embodiments, the detectable moieties having the croconate core have a peak absorbance wavelength of about 860+/−10 nm and a first absorbance peak with FWHM of less than 160 nm. In some embodiments, the detectable moieties having the croconate core have a peak absorbance wavelength of about 855+/−10 nm and a first absorbance peak with FWHM of less than 160 nm. In some embodiments, the detectable moieties having the croconate core have a peak absorbance wavelength of about 850+/−10 nm and a first absorbance peak with FWHM of less than 160 nm. In some embodiments, the detectable moieties having the croconate core have a peak absorbance wavelength of about 845+/−10 nm and a first absorbance peak with FWHM of less than 160 nm. In some embodiments, the detectable moieties having the croconate core have a peak absorbance wavelength of about 840+/−10 nm and a first absorbance peak with FWHM of less than 160 nm. In some embodiments, the detectable moieties having the croconate core have a peak absorbance wavelength of about 835+/−10 nm and a first absorbance peak with FWHM of less than 160 nm. In some embodiments, the detectable moieties having the croconate core have a peak absorbance wavelength of about 830+/−10 nm and a first absorbance peak with FWHM of less than 160 nm. In some embodiments, the detectable moieties having the croconate core have a peak absorbance wavelength of about 825+/−10 nm and a first absorbance peak with FWHM of less than 160 nm. In some embodiments, the detectable moieties having the croconate core have a peak absorbance wavelength of about 820+/−10 nm and a first absorbance peak with FWHM of less than 160 nm. In some embodiments, the detectable moieties having the croconate core have a peak absorbance wavelength of about 815+/−10 nm and a first absorbance peak with FWHM of less than 160 nm. In some embodiments, the detectable moieties having the croconate core have a peak absorbance wavelength of about 800+/−10 nm and a first absorbance peak with FWHM of less than 160 nm. In some embodiments, the detectable moieties having the croconate core have a peak absorbance wavelength of about 795+/−10 nm and a first absorbance peak with FWHM of less than 160 nm. In some embodiments, the detectable moieties having the croconate core have a peak absorbance wavelength of about 790+/−10 nm and a first absorbance peak with FWHM of less than 160 nm. In some embodiments, the detectable moieties having the croconate core have a peak absorbance wavelength of about 785+/−10 nm and a first absorbance peak with FWHM of less than 160 nm. In some embodiments, the detectable moieties having the croconate core have a peak absorbance wavelength of about 780+/−10 nm and a first absorbance peak with FWHM of less than 160 nm.

In some embodiments, the detectable moieties having the croconate core have a peak absorbance wavelength of about 900+/−10 nm and a first absorbance peak with FWHM of less than 130 nm. In some embodiments, the detectable moieties having the croconate core have a peak absorbance wavelength of about 895+/−10 nm and a first absorbance peak with FWHM of less than 130 nm. In some embodiments, the detectable moieties having the croconate core have a peak absorbance wavelength of about 890+/−10 nm and a first absorbance peak with FWHM of less than 130 nm. In some embodiments, the detectable moieties having the croconate core have a peak absorbance wavelength of about 885+/−10 nm and a first absorbance peak with FWHM of less than 130 nm. In some embodiments, the detectable moieties having the croconate core have a peak absorbance wavelength of about 880+/−10 nm and a first absorbance peak with FWHM of less than 130 nm. In some embodiments, the detectable moieties having the croconate core have a peak absorbance wavelength of about 870+/−10 nm and a first absorbance peak with FWHM of less than 130 nm. In some embodiments, the detectable moieties having the croconate core have a peak absorbance wavelength of about 865+/−10 nm and a first absorbance peak with FWHM of less than 130 nm. In some embodiments, the detectable moieties having the croconate core have a peak absorbance wavelength of about 860+/−10 nm and a first absorbance peak with FWHM of less than 130 nm. In some embodiments, the detectable moieties having the croconate core have a peak absorbance wavelength of about 855+/−10 nm and a first absorbance peak with FWHM of less than 130 nm. In some embodiments, the detectable moieties having the croconate core have a peak absorbance wavelength of about 850+/−10 nm and a first absorbance peak with FWHM of less than 130 nm. In some embodiments, the detectable moieties having the croconate core have a peak absorbance wavelength of about 845+/−10 nm and a first absorbance peak with FWHM of less than 130 nm. In some embodiments, the detectable moieties having the croconate core have a peak absorbance wavelength of about 840+/−10 nm and a first absorbance peak with FWHM of less than 130 nm. In some embodiments, the detectable moieties having the croconate core have a peak absorbance wavelength of about 835+/−10 nm and a first absorbance peak with FWHM of less than 130 nm. In some embodiments, the detectable moieties having the croconate core have a peak absorbance wavelength of about 830+/−10 nm and a first absorbance peak with FWHM of less than 130 nm. In some embodiments, the detectable moieties having the croconate core have a peak absorbance wavelength of about 825+/−10 nm and a first absorbance peak with FWHM of less than 130 nm. In some embodiments, the detectable moieties having the croconate core have a peak absorbance wavelength of about 820+/−10 nm and a first absorbance peak with FWHM of less than 130 nm. In some embodiments, the detectable moieties having the croconate core have a peak absorbance wavelength of about 815+/−10 nm and a first absorbance peak with FWHM of less than 130 nm. In some embodiments, the detectable moieties having the croconate core have a peak absorbance wavelength of about 800+/−10 nm and a first absorbance peak with FWHM of less than 130 nm. In some embodiments, the detectable moieties having the croconate core have a peak absorbance wavelength of about 795+/−10 nm and a first absorbance peak with FWHM of less than 130 nm. In some embodiments, the detectable moieties having the croconate core have a peak absorbance wavelength of about 790+/−10 nm and a first absorbance peak with FWHM of less than 130 nm. In some embodiments, the detectable moieties having the croconate core have a peak absorbance wavelength of about 785+/−10 nm and a first absorbance peak with FWHM of less than 130 nm. In some embodiments, the detectable moieties having the croconate core have a peak absorbance wavelength of about 780+/−10 nm and a first absorbance peak with FWHM of less than 130 nm.

In some embodiments, the detectable moieties having the croconate core have a peak absorbance wavelength of about 900+/−10 nm and a first absorbance peak with FWHM of less than 100 nm. In some embodiments, the detectable moieties having the croconate core have a peak absorbance wavelength of about 895+/−10 nm and a first absorbance peak with FWHM of less than 100 nm. In some embodiments, the detectable moieties having the croconate core have a peak absorbance wavelength of about 890+/−10 nm and a first absorbance peak with FWHM of less than 100 nm. In some embodiments, the detectable moieties having the croconate core have a peak absorbance wavelength of about 885+/−10 nm and a first absorbance peak with FWHM of less than 100 nm. In some embodiments, the detectable moieties having the croconate core have a peak absorbance wavelength of about 880+/−10 nm and a first absorbance peak with FWHM of less than 100 nm. In some embodiments, the detectable moieties having the croconate core have a peak absorbance wavelength of about 870+/−10 nm and a first absorbance peak with FWHM of less than 100 nm. In some embodiments, the detectable moieties having the croconate core have a peak absorbance wavelength of about 865+/−10 nm and a first absorbance peak with FWHM of less than 100 nm. In some embodiments, the detectable moieties having the croconate core have a peak absorbance wavelength of about 860+/−10 nm and a first absorbance peak with FWHM of less than 100 nm. In some embodiments, the detectable moieties having the croconate core have a peak absorbance wavelength of about 855+/−10 nm and a first absorbance peak with FWHM of less than 100 nm. In some embodiments, the detectable moieties having the croconate core have a peak absorbance wavelength of about 850+/−10 nm and a first absorbance peak with FWHM of less than 100 nm. In some embodiments, the detectable moieties having the croconate core have a peak absorbance wavelength of about 845+/−10 nm and a first absorbance peak with FWHM of less than 100 nm. In some embodiments, the detectable moieties having the croconate core have a peak absorbance wavelength of about 840+/−10 nm and a first absorbance peak with FWHM of less than 100 nm. In some embodiments, the detectable moieties having the croconate core have a peak absorbance wavelength of about 835+/−10 nm and a first absorbance peak with FWHM of less than 100 nm. In some embodiments, the detectable moieties having the croconate core have a peak absorbance wavelength of about 830+/−10 nm and a first absorbance peak with FWHM of less than 100 nm. In some embodiments, the detectable moieties having the croconate core have a peak absorbance wavelength of about 825+/−10 nm and a first absorbance peak with FWHM of less than 100 nm. In some embodiments, the detectable moieties having the croconate core have a peak absorbance wavelength of about 820+/−10 nm and a first absorbance peak with FWHM of less than 100 nm. In some embodiments, the detectable moieties having the croconate core have a peak absorbance wavelength of about 815+/−10 nm and a first absorbance peak with FWHM of less than 100 nm. In some embodiments, the detectable moieties having the croconate core have a peak absorbance wavelength of about 800+/−10 nm and a first absorbance peak with FWHM of less than 100 nm. In some embodiments, the detectable moieties having the croconate core have a peak absorbance wavelength of about 795+/−10 nm and a first absorbance peak with FWHM of less than 100 nm. In some embodiments, the detectable moieties having the croconate core have a peak absorbance wavelength of about 790+/−10 nm and a first absorbance peak with FWHM of less than 100 nm. In some embodiments, the detectable moieties having the croconate core have a peak absorbance wavelength of about 785+/−10 nm and a first absorbance peak with FWHM of less than 100 nm. In some embodiments, the detectable moieties having the croconate core have a peak absorbance wavelength of about 780+/−10 nm and a first absorbance peak with FWHM of less than 100 nm.

In some embodiments, the detectable moieties having the croconate core have a peak absorbance wavelength of about 900+/−10 nm and a first absorbance peak with FWHM of less than 60 nm. In some embodiments, the detectable moieties having the croconate core have a peak absorbance wavelength of about 895+/−10 nm and a first absorbance peak with FWHM of less than 60 nm. In some embodiments, the detectable moieties having the croconate core have a peak absorbance wavelength of about 890+/−10 nm and a first absorbance peak with FWHM of less than 60 nm. In some embodiments, the detectable moieties having the croconate core have a peak absorbance wavelength of about 885+/−10 nm and a first absorbance peak with FWHM of less than 60 nm. In some embodiments, the detectable moieties having the croconate core have a peak absorbance wavelength of about 880+/−10 nm and a first absorbance peak with FWHM of less than 60 nm. In some embodiments, the detectable moieties having the croconate core have a peak absorbance wavelength of about 870+/−10 nm and a first absorbance peak with FWHM of less than 60 nm. In some embodiments, the detectable moieties having the croconate core have a peak absorbance wavelength of about 865+/−10 nm and a first absorbance peak with FWHM of less than 60 nm. In some embodiments, the detectable moieties having the croconate core have a peak absorbance wavelength of about 860+/−10 nm and a first absorbance peak with FWHM of less than 60 nm. In some embodiments, the detectable moieties having the croconate core have a peak absorbance wavelength of about 855+/−10 nm and a first absorbance peak with FWHM of less than 60 nm. In some embodiments, the detectable moieties having the croconate core have a peak absorbance wavelength of about 850+/−10 nm and a first absorbance peak with FWHM of less than 60 nm. In some embodiments, the detectable moieties having the croconate core have a peak absorbance wavelength of about 845+/−10 nm and a first absorbance peak with FWHM of less than 60 nm. In some embodiments, the detectable moieties having the croconate core have a peak absorbance wavelength of about 840+/−10 nm and a first absorbance peak with FWHM of less than 60 nm. In some embodiments, the detectable moieties having the croconate core have a peak absorbance wavelength of about 835+/−10 nm and a first absorbance peak with FWHM of less than 60 nm. In some embodiments, the detectable moieties having the croconate core have a peak absorbance wavelength of about 830+/−10 nm and a first absorbance peak with FWHM of less than 60 nm. In some embodiments, the detectable moieties having the croconate core have a peak absorbance wavelength of about 825+/−10 nm and a first absorbance peak with FWHM of less than 60 nm. In some embodiments, the detectable moieties having the croconate core have a peak absorbance wavelength of about 820+/−10 nm and a first absorbance peak with FWHM of less than 60 nm. In some embodiments, the detectable moieties having the croconate core have a peak absorbance wavelength of about 815+/−10 nm and a first absorbance peak with FWHM of less than 60 nm. In some embodiments, the detectable moieties having the croconate core have a peak absorbance wavelength of about 800+/−10 nm and a first absorbance peak with FWHM of less than 60 nm. In some embodiments, the detectable moieties having the croconate core have a peak absorbance wavelength of about 795+/−10 nm and a first absorbance peak with FWHM of less than 60 nm. In some embodiments, the detectable moieties having the croconate core have a peak absorbance wavelength of about 790+/−10 nm and a first absorbance peak with FWHM of less than 60 nm. In some embodiments, the detectable moieties having the croconate core have a peak absorbance wavelength of about 785+/−10 nm and a first absorbance peak with FWHM of less than 60 nm. In some embodiments, the detectable moieties having the croconate core have a peak absorbance wavelength of about 780+/−10 nm and a first absorbance peak with FWHM of less than 60 nm.

Chemical Structures of Suitable Detectable Moieties

In some embodiments, the "detectable moiety" has any one of Formulas (IIA), (IIB), (IIC), (IIIA), (IIIB), (IVA), (IVB), (IVC), (IVD), (IVE), (IVF), (IVG), (IVH), (VA), (VB), (VI), (VIIA), (VIIB), and (VIIC).

In some embodiments, W is a moiety having Formula (IIA):

(IIA)

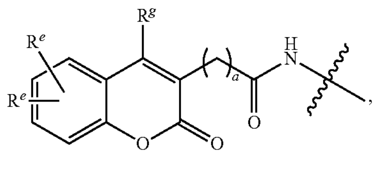

wherein each $R^e$ is independently —OH, —O-alkyl, or —$N(R^x)(R^y)$, where $R^x$ and $R^y$ are independently H or a branched or unbranched $C_1$-$C_4$ alkyl group optionally substituted with one or more halogen atoms, or where $R^x$ and $R^y$ together form a 3-, 4-, or 5-membered cyclic ring or heterocyclic ring which may be optionally substituted with one or more halogen atoms or one or more $C_1$-$C_2$ alkyl groups;

$R^g$ is —H, —$CH_3$ or —$CH_2$—$CH_3$; and a is 0 or an integer ranging from 1 to 4.

In some embodiments, the symbol “ ” refers to the site in which the moiety having Formula (IIA) is coupled to the group “Q” of Formula (I).

In some embodiments, when $R^e$ is —N($R^x$)($R^y$), then at least one of $R^x$ and $R^y$ comprise a $C_1$-$C_4$ alkyl group including a halogen, e.g., a fluorine atom.

In some embodiments, if $R^e$ is —N($R^x$)($R^y$) and each of $R^x$ and $R^y$ are —$CH_2$—$CH_2$—, then the compound of Formula (IIA) further includes either (i) a second $R^e$ group that is other than H; or (ii) a $R^g$ group that is other than H.

In some embodiments, when $R^e$ is —N($R^x$)($R^y$) and of $R^x$ and $R^y$ form a heterocyclic ring including nitrogen, then the heterocyclic ring further comprises a substitution, such as a halogen substitution. In some embodiments, when $R^e$ is —N($R^x$)($R^y$) and of $R^x$ and $R^y$ form a heterocyclic ring including nitrogen, then the compound of Formula (IIA) further includes either (i) a second $R^e$ group that is other than H; or (ii) a $R^g$ group that is other than H.

In some embodiments, $R^g$ is H and a is 0 or 1. In some embodiments, $R^e$ is H and a is 0.

In some embodiments, $R^e$ is —N(H)(Me). In some embodiments, $R^e$ is —N(H)(Et). In some embodiments, $R^e$ is —$NH_2$. In some embodiments, $R^e$ is —N(H)$CF_3$. In some embodiments, $R^e$ is —N(H)—$CH_2$—F. In some embodiments, $R^e$ is —N(H)—$CH_2$—$CH_2$—F. In some embodiments, $R^e$ is —N(H)—CH(F)(F). In some embodiments, $R^e$ is —N(Me)$CF_3$. In some embodiments, $R^e$ is —N(Et)$CF_3$. In some embodiments, $R^e$—N(H)(Ipr).

In some embodiments, $R^e$ is —N($R^x$)($R^y$), and where $R^x$ and $R^y$ together form a 4-membered cyclic ring which is unsubstituted. In some embodiments, $R^e$ is —N($R^x$)($R^y$), and where $R^x$ and $R^y$ together form a 5-membered cyclic ring which is unsubstituted. In some embodiments, $R^e$ is —N($R^x$)($R^y$), and where $R^x$ and $R_y$ together form a 4-membered cyclic ring which is substituted with one or more halogen atoms. In some embodiments, $R^e$ is —N($R^x$)($R^y$), and where $R^x$ and $R^y$ together form a 5-membered cyclic ring which is substituted with one or more halogen atoms.

In some embodiments, a is 0.

In some embodiments, W is a moiety having Formula (IIB):

(IIB)

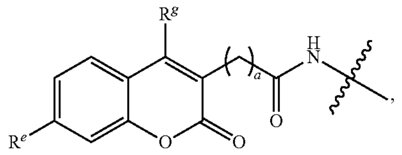

wherein $R^e$ is —OH, —O-alkyl, or —N($R^x$)($R^y$), where $R^x$ and $R^y$ are independently H or a branched or unbranched $C_1$-$C_4$ alkyl group optionally substituted with one or more halogen atoms, or where $R^x$ and $R^y$ together form a 3-, 4-, or 5-membered cyclic ring which may be optionally substituted with one or more halogen atoms or one or more $C_1$-$C_2$ alkyl groups;

$R^g$ is —H, —$CH_3$ or —$CH_2$—$CH_3$; and a is 0 or an integer ranging from 1 to 4.

In some embodiments, when $R^e$ is —N($R^x$)($R^y$), then at least one of $R^x$ and $R^y$ comprises a $C_1$-$C_4$ alkyl group including a halogen, e.g., a fluorine atom.

In some embodiments, if $R^e$ is —N($R^x$)($R^y$) and each of $R^x$ and $R^y$ are —$CH_2$—$CH_2$—, then $R^g$ group that is other than H.

In some embodiments, a is 0.

In some embodiments, $R^e$ is —N(H)(Me). In some embodiments, $R^e$ is —N(H)(Et). In some embodiments, $R^e$ is —$NH_2$. In some embodiments, $R^e$ is —N(H)$CF_3$. In some embodiments, $R^e$ is —N(H)—$CH_2$—F. In some embodiments, $R^e$ is —N(H)—$CH_2$—$CH_2$—F. In some embodiments, $R^e$ is —N(H)—CH(F)(F). In some embodiments, $R^e$ is —N(Me)$CF_3$. In some embodiments, $R^e$ is —N(Et)$CF_3$. In some embodiments, $R^e$—N(H)(Ipr). In some embodiments, a is 0.

In some embodiments, $R^e$ is —N($R^x$)($R^y$), and where $R^x$ and $R^y$ together form a 3-, 4-, or 5-membered cyclic ring which may be optionally substituted with one or more halogen atoms or one or more $C_1$-$C_2$ alkyl groups. In some embodiments, a is 0.

In some embodiments, $R^e$ is —N($R^x$)($R^y$), and where $R^x$ and $R^y$ together form a 4-membered cyclic ring which may be optionally substituted with one or more halogen atoms or one or more $C_1$-$C_2$ alkyl groups. In some embodiments, $R^e$ is —N($R^x$)($R^y$), and where $R^x$ and $R^y$ together form a 5-membered cyclic ring which may be optionally substituted with one or more halogen atoms or one or more $C_1$-$C_2$ alkyl groups. In some embodiments, a is 0.

In some embodiments, $R^e$ is —N($R^x$)($R^y$), and where $R^x$ and $R^y$ together form a 4-membered cyclic ring which is unsubstituted. In some embodiments, $R^e$ is —N($R^x$)($R^y$), and where $R^x$ and $R^y$ together form a 5-membered cyclic ring which is unsubstituted. In some embodiments, $R^e$ is —N($R^x$)($R^y$), and where $R^x$ and $R^y$ together form a 4-membered cyclic ring which is substituted with one or more halogen atoms. In some embodiments, $R^e$ is —N($R^x$)($R^y$), and where $R^x$ and $R^y$ together form a 5-membered cyclic ring which is substituted with one or more halogen atoms.

In some embodiments, a is 0, $R^e$ is —N(H)(Me). In some embodiments, a is 0, $R^e$ is —N(H)(Et). In some embodiments, a is 0, $R^e$ is —$NH_2$. In some embodiments, a is 0, $R^e$ is —N(H)$CF_3$. In some embodiments, a is 0, $R^e$ is —N(H)—$CH_2$—F. In some embodiments, a is 0, $R^e$ is —N(H)—$CH_2$—$CH_2$—F. In some embodiments, a is 0, $R^e$ is —N(H)—CH(F)(F). In some embodiments, a is 0, $R^e$ is —N(Me)$CF_3$. In some embodiments, a is 0, $R^e$ is —N(Et)$CF_3$. In some embodiments, $R^e$—N(H)(Ipr).

In some embodiments, a is 0, $R^e$ is —N($R^x$)($R^y$), and where $R^x$ and $R^y$ together form a 3-, 4-, or 5-membered cyclic ring which may be optionally substituted with one or more halogen atoms or one or more $C_1$-$C_2$ alkyl groups.

In some embodiments, a is 0, $R^e$ is —N($R^x$)($R^y$), and where $R^x$ and $R^y$ together form a 4-membered cyclic ring which may be optionally substituted with one or more halogen atoms or one or more $C_1$-$C_2$ alkyl groups. In some embodiments, a is 0, $R^e$ is —N($R^x$)($R^y$), and where $R^x$ and $R^y$ together form a 5-membered cyclic ring which may be optionally substituted with one or more halogen atoms or one or more $C_1$-$C_2$ alkyl groups.

In some embodiments, a is 0, $R^e$ is —N($R^x$)($R^y$), and where $R^x$ and $R^y$ together form a 4-membered cyclic ring which is unsubstituted. In some embodiments, a is 0, $R^e$ is —N($R^x$)($R^y$), and where $R^x$ and $R^y$ together form a 5-membered cyclic ring which is unsubstituted. In some embodiments, a is 0, $R^e$ is —N($R^x$)($R^y$), and where $R^x$ and $R^y$ together form a 4-membered cyclic ring which is substituted with one or more halogen atoms. In some embodiments, a is 0, $R^e$ is —$N(R^x)(R^y)$, and where $R^x$ and $R^y$ together form a 5-membered cyclic ring which is substituted with one or more halogen atoms.

In some embodiments, $R^e$ is —OH. In some embodiments, $R^e$ is —OH and $R^e$ is H. In some embodiments, a is 0, $R^e$ is —OH and $R^e$ is H.

In some embodiments, $R^e$ is —O-Me. In some embodiments, $R^e$ is —O-Et. In some embodiments, $R^e$ is —O-Ipr. In some embodiments, a is 0 and $R^e$ is —O-Me. In some embodiments, a is 0 and $R^e$ is —O-Et. In some embodiments, a is 0 and $R^e$ is —O-Ipr.

In some embodiments, W is a moiety having Formula (IIC):

(IIC)

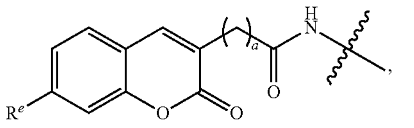

wherein $R^e$ is —OH, —O-alkyl, or —$N(R^x)(R^y)$, where $R^x$ and $R^y$ are independently H or a branched or unbranched $C_1$-$C_4$ alkyl group optionally substituted with one or more halogen atoms, or where $R^x$ and $R^y$ together form a 3-, 4-, or 5-membered cyclic ring which may be optionally substituted with one or more halogen atoms or one or more $C_1$-$C_2$ alkyl groups; and a is 0 or an integer ranging from 1 to 6.

In some embodiments, when $R^e$ is —$N(R^x)(R^y)$, then at least one of $R^x$ and $R^y$ comprises a $C_1$-$C_4$ alkyl group including at least one substituent. In some embodiments, when $R^e$ is —$N(R^x)(R^y)$, then at least one of $R^x$ and $R^y$ comprises a $C_1$-$C_4$ alkyl group including a halogen, e.g., a fluorine atom.

In some embodiments, a is 0. In some embodiments, a is 1. In some embodiments a is 2. In some embodiments a is 3. In some embodiments a is 4.

In some embodiments, $R^e$ is —N(H)(Me). In some embodiments, $R^e$ is —N(H)(Et). In some embodiments, $R^e$ is —$NH_2$. In some embodiments, $R^e$ is —$N(H)CF_3$. In some embodiments, $R^e$ is —N(H)—$CH_2$—F. In some embodiments, $R^e$ is —N(H)—$CH_2$—$CH_2$—F. In some embodiments, $R^e$ is —N(H)—CH(F)(F). In some embodiments, $R^e$ is —$N(Me)CF_3$. In some embodiments, $R^e$ is —$N(Et)CF_3$. In some embodiments, $R^e$—N(H)(Ipr). In some embodiments, a is 0.

In some embodiments, $R^e$ is —$N(R^x)(R^y)$, and where $R^x$ and $R^y$ together form a 3-, 4-, or 5-membered cyclic ring which may be optionally substituted with one or more halogen atoms or one or more $C_1$-$C_2$ alkyl groups. In some embodiments, a is 0.

In some embodiments, $R^e$ is —$N(R^x)(R^y)$, and where $R^x$ and $R^y$ together form a 4-membered cyclic ring which may be optionally substituted with one or more halogen atoms or one or more $C_1$-$C_2$ alkyl groups. In some embodiments, $R^e$ is —$N(R^x)(R^y)$, and where $R^x$ and $R^y$ together form a 5-membered cyclic ring which may be optionally substituted with one or more halogen atoms or one or more $C_1$-$C_2$ alkyl groups. In some embodiments, a is 0.

In some embodiments, $R^e$ is —$N(R^x)(R^y)$, and where $R^x$ and $R^y$ together form a 4-membered cyclic ring which is unsubstituted. In some embodiments, $R^e$ is —$N(R^x)(R^y)$, and where $R^x$ and $R^y$ together form a 5-membered cyclic ring which is unsubstituted. In some embodiments, $R^e$ is —$N(R^x)(R^y)$, and where $R^x$ and $R^y$ together form a 4-membered cyclic ring which is substituted with one or more halogen atoms. In some embodiments, $R^e$ is —$N(R^x)(R^y)$, and where $R^x$ and $R^y$ together form a 5-membered cyclic ring which is substituted with one or more halogen atoms.

Specific examples of detectable moieties of Formulas (IIA)-(IIC) include the following:

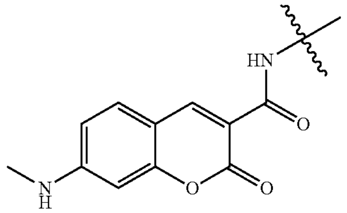
,

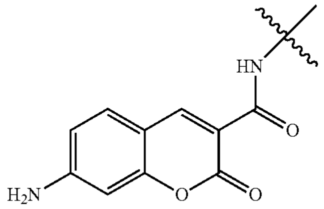
,

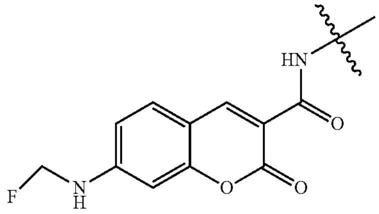
,

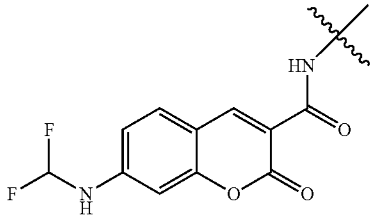
,

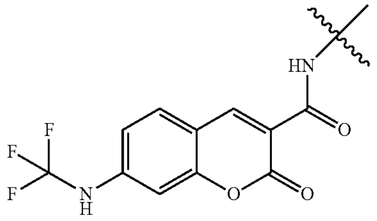
,

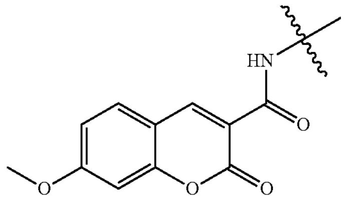
,

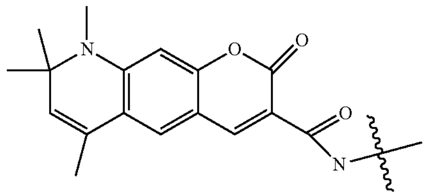
,

-continued

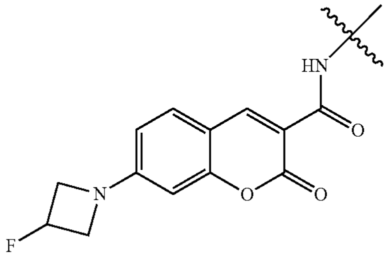
,

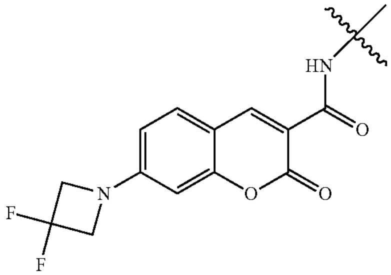
,

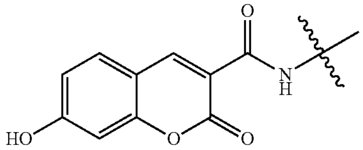
,

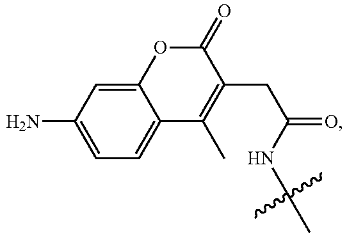
and

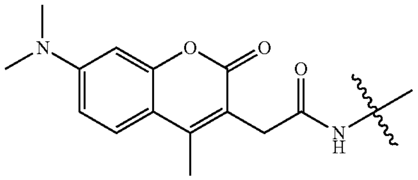
, where the symbol "" refers to the site in which the moiety having Formula (IIA) is coupled to the group "Q" of Formula (I).

In some embodiments, W is selected from Formula (IIIA):

(IIIA)

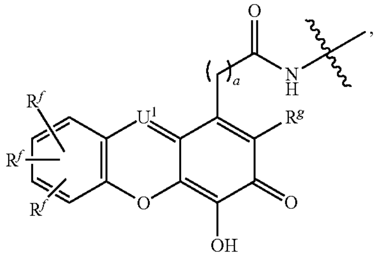

wherein each $R^f$ is independently —$N(R^x)(R^y)$, where $R^x$ and $R^y$ are independently H or a branched or unbranched $C_1$-$C_4$ alkyl group optionally substituted with one or more halogen atoms; or where any two $R^f$ groups may together form a substituted or unsubstituted, saturated or unsaturated ring which may be optionally substituted with one or more heteroatoms;

$R^g$ is —H, —$CH_3$ or —$CH_2$—$CH_3$;

$U^1$ is O, N, or S; and a is 0 or an integer ranging from 1 to 6.

In some embodiments, a is 0.

In some embodiments, $R^f$ is —N(H)(Me). In some embodiments, $R^f$ is —N(H)(Et). In some embodiments, $R^f$ is —$NH_2$. In some embodiments, $R^f$ is —N(H)$CF_3$. In some embodiments, $R^f$ is —N(H)—$CH_2$—F. In some embodiments, $R^f$ is —N(H)—$CH_2$—$CH_2$—F. In some embodiments, $R^f$ is —N(H)—CH(F)(F). In some embodiments, $R^f$ is —N(Me)$CF_3$. In some embodiments, $R^f$ is —N(Et)$CF_3$. In some embodiments, $R^f$—N(H)(Ipr). In some embodiments, a is 0.

In some embodiments, a is 0 and $R^f$ is —N(H)(Me). In some embodiments, a is 0 and $R^f$ is —N(H)(Et). In some embodiments, a is 0 and $R^f$ is —$NH_2$. In some embodiments, a is 0 and $R^f$ is —N(H)$CF_3$. In some embodiments, a is 0 and $R^f$ is —N(H)—$CH_2$—F. In some embodiments, $R^f$ is —N(H)—$CH_2$—$CH_2$—F. In some embodiments, a is 0 and $R^f$ is —N(H)—CH(F)(F). In some embodiments, a is 0 and $R^f$ is —N(Me)$CF_3$. In some embodiments, $R^f$ is —N(Et)$CF_3$. In some embodiments, a is 0 and $R^f$—N(H)(Ipr). In some embodiments, a is 0.

In some embodiments, $U^1$ is N; and $R^f$ is —N(H)(Me). In some embodiments, $U^1$ is N; and $R^f$ is —N(H)(Et). In some embodiments, $U^1$ is N; and $R^f$ is —$NH_2$. In some embodiments, $U^1$ is N; and $R^f$ is —N(H)$CF_3$. In some embodiments, $U^1$ is N; and $R^f$ is —N(H)—$CH_2$—F. In some embodiments, $U^1$ is N; and $R^f$ is —N(H)—$CH_2$—$CH_2$—F. In some embodiments, $U^1$ is N; and $R^f$ is —N(H)—CH(F)(F). In some embodiments, $U^1$ is N; and $R^f$ is —N(Me)$CF_3$. In some embodiments, $U^1$ is N; and $R^f$ is —N(Et)$CF_3$. In some embodiments, $U^1$ is N; and $R^f$—N(H)(Ipr). In some embodiments, a is 0.

In some embodiments, a is 0; $U^1$ is N; and $R^f$ is —N(H)(Me). In some embodiments, a is 0; $U^1$ is N; and $R^f$ is —N(H)(Et). In some embodiments, a is 0; $U^1$ is N; and $R^f$ is —$NH_2$. In some embodiments, a is 0; a is 0; $U^1$ is N; and $R^f$ is —N(H)$CF_3$. In some embodiments, a is 0; $U^1$ is N; and $R^f$ is —N(H)—$CH_2$—F. In some embodiments, a is 0; $U^1$ is N; and $R^f$ is —N(H)—$CH_2$—$CH_2$—F. In some embodiments, a is 0; $U^1$ is N; and $R^f$ is —N(H)—CH(F)(F). In some embodiments, a is 0; $U^1$ is N; and $R^f$ is —N(Me)$CF_3$. In some embodiments, a is 0; $U^1$ is N; and $R^f$ is —N(Et)$CF_3$. In some embodiments, a is 0; $U^1$ is N; and $R^f$—N(H)(Ipr). In some embodiments, a is 0.

In some embodiments, W is selected from Formula (IIIB):

(IIIB)

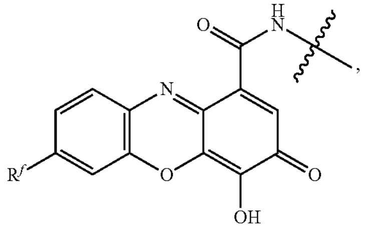

wherein $R^f$ is —$N(R^x)(R^y)$, where $R^x$ and $R^y$ are independently H or a branched or unbranched $C_1$-$C_4$ alkyl group optionally substituted with one or more halogen atoms;

$R^g$ is —H, —$CH_3$ or —$CH_2$—$CH_3$;

$U^1$ is O, N, or S; and a is 0 or an integer ranging from 1 to 6.

In some embodiments, a is 0.

In some embodiments, $R^f$ is —N(H)(Me). In some embodiments, $R^f$ is —N(H)(Et). In some embodiments, $R^f$ is —$NH_2$. In some embodiments, $R^f$ is —N(H)$CF_3$. In some embodiments, $R^f$ is —N(H)—$CH_2$—F. In some embodiments, $R^f$ is —N(H)—$CH_2$—$CH_2$—F. In some embodiments, $R^f$ is —N(H)—CH(F)(F). In some embodiments, $R^f$ is —N(Me)$CF_3$. In some embodiments, $R^f$ is —N(Et)$CF_3$. In some embodiments, $R^f$—N(H)(Ipr). In some embodiments, a is 0.

In some embodiments, a is 0 and $R^f$ is —N(H)(Me). In some embodiments, a is 0 and $R^f$ is —N(H)(Et). In some embodiments, a is 0 and $R^f$ is —$NH_2$. In some embodiments, a is 0 and $R^f$ is —N(H)$CF_3$. In some embodiments, a is 0 and $R^f$ is —N(H)—$CH_2$—F. In some embodiments, $R^f$ is —N(H)—$CH_2$—$CH_2$—F. In some embodiments, a is 0 and $R^f$ is —N(H)—CH(F)(F). In some embodiments, a is 0 and $R^f$ is —N(Me)$CF_3$. In some embodiments, $R^f$ is —N(Et)$CF_3$. In some embodiments, a is 0 and $R^f$—N(H)(Ipr). In some embodiments, a is 0.

One example of a moiety having any one of Formulas (IIIA) or (IIIB) is provided below:

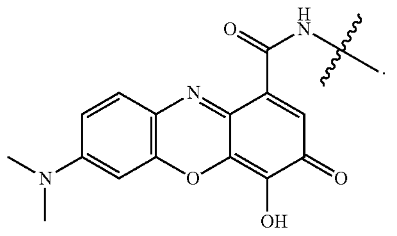 [SMILES: *NC(=O)c1cc(=O)c(O)c2oc3cc(N(C)C)ccc3nc1-2]

In some embodiments, W is selected from Formula (IVA):

(IVA)

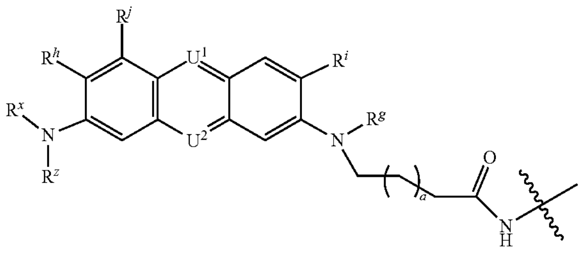

wherein $U^1$ is O, N, or S;

$U^2$ is O or S;

$R^g$ is —$CH_3$ or —$CH_2$—$CH_3$;

$R^i$ is H or a branched or unbranched $C_1$-$C_6$ alkyl group;

or where $R^g$ and $R^i$ together form a 5-, 6-, or 7-membered cyclic or aromatic ring which may be optionally substituted with a halogen, a $C_1$-$C_4$ alkyl group;

$R^h$ is H or a branched or unbranched $C_1$-$C_4$ alkyl group;

$R^x$ is H or a branched or unbranched $C_1$-$C_4$ alkyl group optionally substituted with one or more halogen atoms;

$R^z$ is H, or a branched or unbranched $C_1$-$C_4$ alkyl group optionally substituted with one or more halogen atoms or with a —S(O)(O)—$O^-$ group;

or where $R^x$ and $R^z$ together form a 3-, 4-, or 5-membered ring which may optionally be substituted;

or where $R^h$ and one of $R^x$ or $R^z$ together form a 5-, 6-, or 7-membered cyclic or aromatic ring which may be optionally substituted with one or more halogen atoms or one or more $C_1$-$C_2$ alkyl groups;

$R^j$ is H or a branched or unbranched $C_1$-$C_6$ alkyl group;

or where $R^j$ and $R^h$ form a 5- or 6-membered ring, optionally substituted with one or more $C_1$-$C_4$ alkyl groups; and a is 0 or an integer ranging from 1 to 6.

In some embodiments, a is 0.

In some embodiments, $R^x$ is a $C_1$-$C_2$ alkyl group. In some embodiments, $R^x$ is a methyl group. In some embodiments, $R^x$ is a $C_1$-$C_2$ alkyl group and $R^z$ is an unbranched $C_1$-$C_4$ alkyl group which is unsubstituted. In some embodiments, both $R^x$ and $R^z$ are methyl or ethyl. In some embodiments, $U^2$ is O, and $R^x$ is a $C_1$-$C_2$ alkyl group. In some embodiments, $U^2$ is O and both $R^x$ and $R^z$ are methyl or ethyl. In some embodiments, a is 0.

In some embodiments, $U^2$ is S and $R^x$ is a $C_1$-$C_2$ alkyl group. In some embodiments, $U^2$ is S and both $R^x$ and $R^z$ are methyl or ethyl. In some embodiments, $U^1$ is N, $U^2$ is O, and $R^x$ is a $C_1$-$C_2$ alkyl group. In some embodiments, $U^1$ is N, $U^2$ is O, and both $R^x$ and $R^z$ are methyl or ethyl. In some embodiments, $U^1$ is N, $U^2$ is S and $R^x$ is a $C_1$-$C_2$ alkyl group. In some embodiments, $U^1$ is N, $U^2$ is S, and both $R^x$ and $R^z$ are methyl or ethyl.

In some embodiments, $R^z$ is an unbranched $C_1$-$C_4$ alkyl group substituted with a —S(O)(O)—$O^-$ group. In some embodiments, $R^x$ is a $C_1$-$C_2$ alkyl group and $R^z$ is an unbranched $C_1$-$C_4$ alkyl group substituted with a —S(O)(O)—$O^-$ group. In some embodiments, a is 0.

In some embodiments, $U^2$ is O and $R^z$ is an unbranched $C_1$-$C_4$ alkyl group substituted with a —S(O)(O)—$O^-$ group. In some embodiments, $U^2$ is S and $R^z$ is an unbranched $C_1$-$C_4$ alkyl group substituted with a —S(O)(O)—$O^-$ group. In some embodiments, $U^2$ is O, $R^x$ is a $C_1$-$C_2$ alkyl group, and $R^z$ is an unbranched $C_1$-$C_4$ alkyl group substituted with a —S(O)(O)—$O^-$ group. In some embodiments, $U^2$ is S, $R^x$ is a $C_1$-$C_2$ alkyl group, and $R^z$ is an unbranched $C_1$-$C_4$ alkyl group substituted with a —S(O)(O)—$O^-$ group. In some embodiments, a is 0.

In some embodiments, $U^1$ is N, $U^2$ is O and $R^z$ is an unbranched $C_1$-$C_4$ alkyl group substituted with a —S(O)(O)—$O^-$ group. In some embodiments, $U^1$ is N, $U^2$ is O, $R^x$ is a $C_1$-$C_2$ alkyl group, and $R^z$ is an unbranched $C_1$-$C_4$ alkyl group substituted with a —S(O)(O)—$O^-$ group. In some embodiments, $U^1$ is N, $U^2$ is S and $R^z$ is an unbranched $C_1$-$C_4$ alkyl group substituted with a —S(O)(O)—$O^-$ group. In some embodiments, $U^1$ is N, $U^2$ is O, $R^x$ is a $C_1$-$C_2$ alkyl group, and $R^z$ is an unbranched $C_1$-$C_4$ alkyl group substituted with a —S(O)(O)—$O^-$ group. In some embodiments, a is 0.

In some embodiments, $R^z$ is an unbranched $C_1$-$C_4$ alkyl group substituted with one or more halogen atoms. In some embodiments, $R^x$ is a $C_1$-$C_2$ alkyl group and W is an unbranched $C_1$-$C_4$ alkyl group substituted with one or more halogen atoms. In some embodiments, $U^2$ is O and $R^z$ is an unbranched $C_1$-$C_4$ alkyl group substituted with one or more halogen atoms. In some embodiments, $U^2$ is O, $R^x$ is a $C_1$-$C_2$ alkyl group, and $R^z$ is an unbranched $C_1$-$C_4$ alkyl group substituted with one or more halogen atoms. In some embodiments, a is 0.

In some embodiments, $U^2$ is S and $R^z$ is an unbranched $C_1$-$C_4$ alkyl group substituted with one or more halogen atoms. In some embodiments, $U^2$ is S, $R^x$ is a $C_1$-$C_2$ alkyl group, and $R^z$ is an unbranched $C_1$-$C_4$ alkyl group substituted with one or more halogen atoms. In some embodiments, a is 0.

In some embodiments, $U^1$ is N, $U^2$ is O and $R^z$ is an unbranched $C_1$-$C_4$ alkyl group substituted with one or more halogen atoms. In some embodiments, $U^1$ is N, $U^2$ is O, $R^x$ is a $C_1$-$C_2$ alkyl group, and $R^z$ is an unbranched $C_1$-$C_4$ alkyl group substituted with one or more halogen atoms. In some embodiments, a is 0.

In some embodiments, $U^1$ is N, $U^2$ is S and $R^z$ is an unbranched $C_1$-$C_4$ alkyl group substituted with one or more halogen atoms. In some embodiments, $U^1$ is N, $U^2$ is S, $R^x$ is a $C_1$-$C_2$ alkyl group, and $R^z$ is an unbranched $C_1$-$C_4$ alkyl group substituted with one or more halogen atoms. In some embodiments, a is 0.

In some embodiments, $R^x$ and $R^z$ together form a 4-membered ring which is substituted with one or more halogen atoms. In some embodiments, $U^2$ is O and $R^x$ and $R^z$ together form a 4-membered ring which is substituted with one or more halogen atoms. In some embodiments, $U^2$ is S and $R^x$ and $R^z$ together form a 4-membered ring which is substituted with one or more halogen atoms. In some embodiments, $U^1$ is N, $U^2$ is O, and $R^x$ and $R^z$ together form a 4-membered ring which is substituted with one or more halogen atoms. In some embodiments, $U^1$ is N, $U^2$ is S and $R^x$ and $R^z$ together form a 4-membered ring which is substituted with one or more halogen atoms. In some embodiments, a is 0.

In some embodiments, W is selected from Formula (IVB):

(IVB)

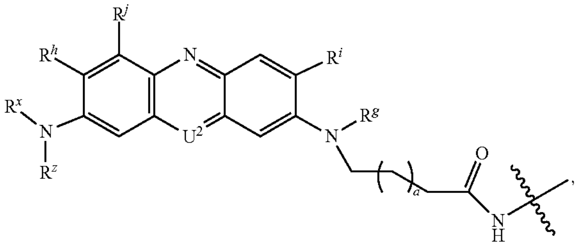

wherein $U^2$ is O or S;

$R^g$ is —$CH_3$ or —$CH_2$—$CH_3$;

$R^i$ is H or a branched or unbranched $C_1$-$C_6$ alkyl group;

or where $R^g$ and $R^i$ together form a 5-, 6-, or 7-membered ring which may be optionally substituted with a halogen, a $C_1$-$C_4$ alkyl group;

$R^h$ is H or a branched or unbranched $C_1$-$C_4$ alkyl group;

$R^x$ is H or a branched or unbranched $C_1$-$C_4$ alkyl group optionally substituted with one or more halogen atoms;

$R^z$ is H, or a branched or unbranched $C_1$-$C_4$ alkyl group optionally substituted with one or more halogen atoms or with a —S(O)(O)—$O^-$ group;

or where $R^h$ and one of $R^x$ or $R^z$ together form a 5-, 6-, or 7-membered cyclic or aromatic ring which may be optionally substituted with one or more halogen atoms or one or more $C_1$-$C_2$ alkyl groups;

$R^j$ is H or a branched or unbranched $C_1$-$C_6$ alkyl group;

or where $R^j$ and $R^h$ form a 5- or 6-membered ring, optionally substituted with one or more $C_1$-$C_4$ alkyl groups; and a is 0 or an integer ranging from 1 to 6.

In some embodiments, a is 0.

In some embodiments, $R^x$ is a $C_1$-$C_2$ alkyl group. In some embodiments, $R^x$ is a methyl group. In some embodiments, $R^x$ is a $C_1$-$C_2$ alkyl group and $R^z$ is an unbranched $C_1$-$C_4$ alkyl group which is unsubstituted. In some embodiments, both $R^x$ and $R^z$ are methyl or ethyl. In some embodiments, $U^2$ is O, and $R^x$ is a $C_1$-$C_2$ alkyl group. In some embodiments, $U^2$ is O and both $R^x$ and $R^z$ are methyl or ethyl. In some embodiments, $U^2$ is S and $R^x$ is a $C_1$-$C_2$ alkyl group. In some embodiments, $U^2$ is S and both $R^x$ and $R^z$ are methyl or ethyl.

In some embodiments, $R^z$ is an unbranched $C_1$-$C_4$ alkyl group substituted with a —S(O)(O)—$O^-$ group. In some embodiments, $R^x$ is a $C_1$-$C_2$ alkyl group and $R^z$ is an unbranched $C_1$-$C_4$ alkyl group substituted with a —S(O)(O)—$O^-$ group. In some embodiments, $U^2$ is O and $R^z$ is an unbranched $C_1$-$C_4$ alkyl group substituted with a —S(O)(O)—$O^-$ group. In some embodiments, $U^2$ is S and $R^z$ is an unbranched $C_1$-$C_4$ alkyl group substituted with a —S(O)(O)—$O^-$ group. In some embodiments, $U^2$ is O, $R^x$ is a $C_1$-$C_2$ alkyl group, and $R^z$ is an unbranched $C_1$-$C_4$ alkyl group substituted with a —S(O)(O)—$O^-$ group. In some embodiments, $U^2$ is S, $R^x$ is a $C_1$-$C_2$ alkyl group, and $R^z$ is an unbranched $C_1$-$C_4$ alkyl group substituted with a —S(O)(O)—$O^-$ group.

In some embodiments, $R^z$ is an unbranched $C_1$-$C_4$ alkyl group substituted with one or more halogen atoms. In some embodiments, $R^x$ is a $C_1$-$C_2$ alkyl group and $R^z$ is an unbranched $C_1$-$C_4$ alkyl group substituted with one or more halogen atoms. In some embodiments, $U^2$ is O and $R^z$ is an unbranched $C_1$-$C_4$ alkyl group substituted with one or more halogen atoms. In some embodiments, $U^2$ is O, $R^x$ is a $C_1$-$C_2$ alkyl group, and $R^z$ is an unbranched $C_1$-$C_4$ alkyl group substituted with one or more halogen atoms. In some embodiments, $U^2$ is S and $R^z$ is an unbranched $C_1$-$C_4$ alkyl group substituted with one or more halogen atoms. In some embodiments, $U^2$ is S, $R^x$ is a $C_1$-$C_2$ alkyl group, and $R^z$ is an unbranched $C_1$-$C_4$ alkyl group substituted with one or more halogen atoms.

In some embodiments, $R^x$ and $R^z$ together form a 4-membered ring which is substituted with one or more halogen atoms. In some embodiments, $U^2$ is O and $R^x$ and $R^z$ together form a 4-membered ring which is substituted with one or more halogen atoms. In some embodiments, $U^2$ is S and $R^x$ and $R^z$ together form a 4-membered ring which is substituted with one or more halogen atoms.

In some embodiments, W is selected from any one of Formulas (IVC) and (IVD):

(IVC)

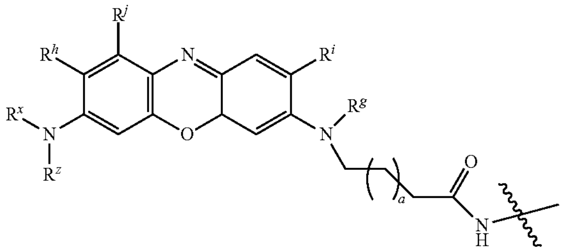

,

-continued (IVD)

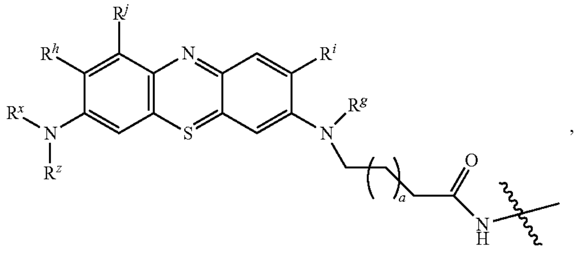

wherein $R^g$ is —$CH_3$ or —$CH_2$—$CH_3$;

$R^i$ is H or a branched or unbranched $C_1$-$C_6$ alkyl group;

or where $R^g$ and $R^i$ together form a 5-, 6-, or 7-membered ring which may be optionally substituted with a halogen, a $C_1$-$C_4$ alkyl group;

$R^h$ is H or a branched or unbranched $C_1$-$C_4$ alkyl group;

$R^x$ is H or a branched or unbranched $C_1$-$C_4$ alkyl group optionally substituted with one or more halogen atoms;

$R^z$ is H, or a branched or unbranched $C_1$-$C_4$ alkyl group optionally substituted with one or more halogen atoms or with a —S(O)(O)—$O^-$ group;

or where $R^h$ and one of $R^x$ or $R^z$ together form a 5-, 6-, or 7-membered cyclic or aromatic ring which may be optionally substituted with one or more halogen atoms or one or more $C_1$-$C_2$ alkyl groups;

$R^j$ is H or a branched or unbranched $C_1$-$C_6$ alkyl group;

or where $R^j$ and $R^h$ form a 5- or 6-membered ring, optionally substituted with one or more $C_1$-$C_4$ alkyl groups; and a is 0 or an integer ranging from 1 to 6.

In some embodiments, a is 0.

In some embodiments, $R^x$ is a $C_1$-$C_2$ alkyl group. In some embodiments, $R^x$ is a methyl group. In some embodiments, $R^x$ is a $C_1$-$C_2$ alkyl group and $R^z$ is an unbranched $C_1$-$C_4$ alkyl group which is unsubstituted. In some embodiments, both $R^x$ and $R^z$ are methyl or ethyl.

In some embodiments, $R^z$ is an unbranched $C_1$-$C_4$ alkyl group substituted with a —S(O)(O)—$O^-$ group. In some embodiments, $R^x$ is a $C_1$-$C_2$ alkyl group and $R^z$ is an unbranched $C_1$-$C_4$ alkyl group substituted with a —S(O)(O)—$O^-$ group.

In some embodiments, $R^z$ is an unbranched $C_1$-$C_4$ alkyl group substituted with one or more halogen atoms. In some embodiments, $R^x$ is a $C_1$-$C_2$ alkyl group and $R^z$ is an unbranched $C_1$-$C_4$ alkyl group substituted with one or more halogen atoms.

In some embodiments, $R^x$ and $R^z$ together form a 4-membered ring which is substituted with one or more halogen atoms.

In some embodiments, W is selected from Formula (IVE):

(IVE)

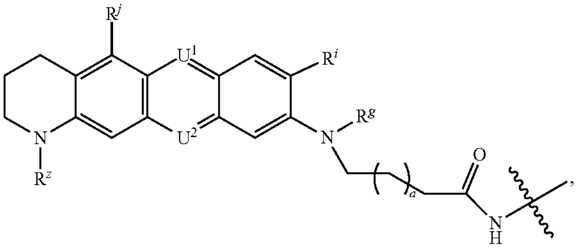

wherein $U^1$ is O, N, or S;

$U^2$ is O or S;

$R^g$ is —$CH_3$ or —$CH_2$—$CH_3$;

$R^i$ is H or a branched or unbranched $C_1$-$C_6$ alkyl group;

or where $R^g$ and $R^i$ together form a 5-, 6-, or 7-membered ring which may be optionally substituted with a halogen, a $C_1$-$C_4$ alkyl group;

$R^z$ is H, or a branched or unbranched $C_1$-$C_4$ alkyl group optionally substituted with one or more halogen atoms or with a —S(O)(O)—$O^-$ group;

$R^j$ is H or a branched or unbranched $C_1$-$C_6$ alkyl group;

a is 0 or an integer ranging from 1 to 6.

In some embodiments, a is 0.

In some embodiments, $R^z$ is a $C_1$-$C_4$ alkyl group. In some embodiments, $R^z$ is an unbranched $C_1$-$C_4$ alkyl group. In some embodiments, $R^z$ is an unbranched $C_1$-$C_4$ alkyl group substituted with a —S(O)(O)—$O^-$ group. In some embodiments, $R^z$ is an unbranched $C_1$-$C_3$ alkyl group substituted with a —S(O)(O)—$O^-$ group.

In some embodiments, $U^1$ is N, and $R^z$ is a $C_1$-$C_4$ alkyl group. In some embodiments, $U^1$ is N, and $R^z$ is an unbranched $C_1$-$C_4$ alkyl group. In some embodiments, $U^1$ is N, and $R^z$ is an unbranched $C_1$-$C_4$ alkyl group substituted with a —S(O)(O)—$O^-$ group. In some embodiments, $U^1$ is N, and $R^z$ is an unbranched $C_1$-$C_3$ alkyl group substituted with a —S(O)(O)—$O^-$ group.

In some embodiments, $U^2$ is O, and $R^z$ is a $C_1$-$C_4$ alkyl group. In some embodiments, $U^2$ is O, and $R^z$ is an unbranched $C_1$-$C_4$ alkyl group. In some embodiments, $U^2$ is O, and $R^z$ is an unbranched $C_1$-$C_4$ alkyl group substituted with a —S(O)(O)—$O^-$ group. In some embodiments, $U^2$ is O, and $R^z$ is an unbranched $C_1$-$C_3$ alkyl group substituted with a —S(O)(O)—$O^-$ group.

In some embodiments, $U^2$ is S, and $R^z$ is a $C_1$-$C_4$ alkyl group. In some embodiments, $U^2$ is S, and $R^z$ is an unbranched $C_1$-$C_4$ alkyl group. In some embodiments, $U^2$ is S, and $R^z$ is an unbranched $C_1$-$C_4$ alkyl group substituted with a —S(O)(O)—$O^-$ group. In some embodiments, $U^2$ is S, and $R^z$ is an unbranched $C_1$-$C_3$ alkyl group substituted with a —S(O)(O)—$O^-$ group.

In some embodiments, $R^i$ and $R^g$ are each independently a $C_1$-$C_2$ alkyl group and $R^z$ is a $C_1$-$C_4$ alkyl group. In some embodiments, $R^i$ and $R^g$ are each independently a $C_1$-$C_2$ alkyl group, and $R^z$ is an unbranched $C_1$-$C_4$ alkyl group substituted with a —S(O)(O)—$O^-$ group. In some embodiments, $R^i$ and $R^g$ are each independently a $C_1$-$C_2$ alkyl group, and $R^z$ is an unbranched $C_1$-$C_3$ alkyl group substituted with a —S(O)(O)—$O^-$ group.

In some embodiments, $U^2$ is S, $R^i$ and $R^g$ are each independently a $C_1$-$C_2$ alkyl group, and $R^z$ is a $C_1$-$C_4$ alkyl group. In some embodiments, $R^i$ and $R^g$ are each independently a $C_1$-$C_2$ alkyl group, $U^2$ is S, and $R^z$ is an unbranched $C_1$-$C_4$ alkyl group substituted with a —S(O)(O)—$O^-$ group.

In some embodiments, $R^i$ and $R^g$ are each independently a $C_1$-$C_2$ alkyl group, $U^2$ is S, and $R^z$ is an unbranched $C_1$-$C_3$ alkyl group substituted with a —S(O)(O)—$O^-$ group.

In some embodiments, $U^2$ is O, $R^i$ and $R^g$ are each independently a $C_1$-$C_2$ alkyl group, and $R^z$ is a $C_1$-$C_4$ alkyl group. In some embodiments, $R^i$ and $R^g$ are each independently a $C_1$-$C_2$ alkyl group, $U^2$ is O, and $R^z$ is an unbranched $C_1$-$C_4$ alkyl group substituted with a —S(O)(O)—$O^-$ group. In some embodiments, $R^i$ and $R^g$ are each independently a $C_1$-$C_2$ alkyl group, $U^2$ is O, and $R^z$ is an unbranched $C_1$-$C_3$ alkyl group substituted with a —S(O)(O)—$O^-$ group.

In some embodiments, $R^i$ and $R^g$ together form a 6-membered cyclic ring and $R^z$ is a $C_1$-$C_4$ alkyl group. In some embodiments, $R^i$ and $R^g$ together form a 6-membered cyclic ring and $R^z$ is an unbranched $C_1$-$C_4$ alkyl group substituted with a —S(O)(O)—$O^-$ group. In some embodiments, $R^i$ and $R^g$ together form a 6-membered cyclic ring, and $R^z$ is an unbranched $C_1$-$C_3$ alkyl group substituted with a —S(O)(O)—$O^-$ group.

In some embodiments, $U^2$ is S, $R^i$ and $R^g$ together form a 6-membered cyclic ring, and $R^z$ is a $C_1$-$C_4$ alkyl group. In some embodiments, $R^i$ and $R^g$ together form a 6-membered cyclic ring $U^2$ is S, and $R^z$ is an unbranched $C_1$-$C_4$ alkyl group substituted with a —S(O)(O)—$O^-$ group. In some embodiments, $R^i$ and $R^g$ together form a 6-membered cyclic ring, $U^2$ is S, and $R^z$ is an unbranched $C_1$-$C_3$ alkyl group substituted with a —S(O)(O)—$O^-$ group.

In some embodiments, $U^2$ is O, $R^i$ and $R^g$ together form a 6-membered cyclic ring and $R^z$ is a $C_1$-$C_4$ alkyl group. In some embodiments, $R^i$ and $R^g$ together form a 6-membered cyclic ring, $U^2$ is O, and $R^z$ is an unbranched $C_1$-$C_4$ alkyl group substituted with a —S(O)(O)—$O^-$ group. In some embodiments, $R^i$ and $R^g$ together form a 6-membered cyclic ring, $U^2$ is O, and $R^z$ is an unbranched $C_1$-$C_3$ alkyl group substituted with a —S(O)(O)—$O^-$ group.

In some embodiments, W is selected from Formula (IVF):

(IVF)

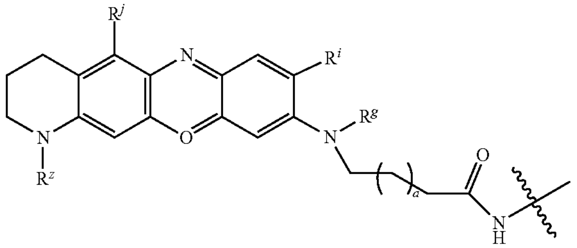

wherein $R^g$ is-$CH_3$ or —$CH_2$—$CH_3$;

$R^i$ is H or a branched or unbranched $C_1$-$C_6$ alkyl group; or where $R^g$ and $R^i$ together form a 5-, 6-, or 7-membered ring which may be optionally substituted with a halogen, a $C_1$-$C_4$ alkyl group;

$R^z$ is H, or a branched or unbranched $C_1$-$C_4$ alkyl group optionally substituted with one or more halogen atoms or with a —S(O)(O)—$O^-$ group;

$R^j$ is H or a branched or unbranched $C_1$-$C_6$ alkyl group;

a is 0 or an integer ranging from 1 to 6.

In some embodiments, a is 0.

In some embodiments, $R^z$ is a $C_1$-$C_4$ alkyl group. In some embodiments, $R^z$ is an unbranched $C_1$-$C_4$ alkyl group. In some embodiments, $R^z$ is an unbranched $C_1$-$C_4$ alkyl group substituted with a —S(O)(O)—$O^-$ group. In some embodiments, $R^z$ is an unbranched $C_1$-$C_3$ alkyl group substituted with a —S(O)(O)—$O^-$ group.

In some embodiments, $R^i$ and $R^g$ are each independently a $C_1$-$C_2$ alkyl group and $R^z$ is a $C_1$-$C_4$ alkyl group. In some embodiments, $R^i$ and $R^g$ are each independently a $C_1$-$C_2$ alkyl group, and $R^z$ is an unbranched $C_1$-$C_4$ alkyl group substituted with a —S(O)(O)—$O^-$ group. In some embodiments, $R^i$ and $R^g$ are each independently a $C_1$-$C_2$ alkyl group, and $R^z$ is an unbranched $C_1$-$C_3$ alkyl group substituted with a —S(O)(O)—$O^-$ group.

In some embodiments, $R^i$ and $R^g$ together form a 6-membered cyclic ring and $R^z$ is a $C_1$-$C_4$ alkyl group. In some embodiments, $R^i$ and $R^g$ together form a 6-membered cyclic ring and $R^z$ is an unbranched $C_1$-$C_4$ alkyl group substituted with a —S(O)(O)—$O^-$ group. In some embodiments, $R^i$ and $R^g$ together form a 6-membered cyclic ring, and $R^z$ is an unbranched $C_1$-$C_3$ alkyl group substituted with a —S(O)(O)—$O^-$ group.

In some embodiments, W is selected from any one of Formulas (IVG) or (IVH):

(IVG)

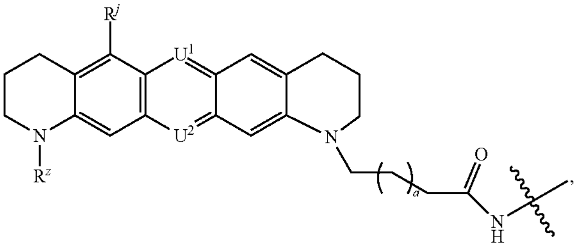

(IVH)

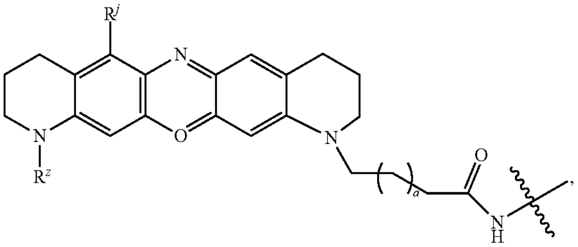

wherein $U^1$ is O, N, or S;

$U^2$ is O or S;

$R^z$ is H, or a branched or unbranched $C_1$-$C_4$ alkyl group optionally substituted with one or more halogen atoms or with a —S(O)(O)—$O^-$ group;

$R^j$ is H or a branched or unbranched $C_1$-$C_6$ alkyl group;

a is 0 or an integer ranging from 1 to 6.

In some embodiments, a is 0.

In some embodiments, $R^z$ is a $C_1$-$C_4$ alkyl group. In some embodiments, $R^z$ is an unbranched $C_1$-$C_4$ alkyl group. In some embodiments, $R^z$ is an unbranched $C_1$-$C_4$ alkyl group substituted with a —S(O)(O)—$O^-$ group. In some embodiments, $R^z$ is an unbranched $C_1$-$C_3$ alkyl group substituted with a —S(O)(O)—$O^-$ group.

Non-liming examples of detectable moieties of Formulas (IVA) to (IVH) include the following:

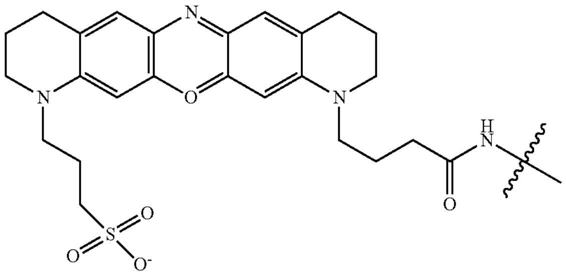
,

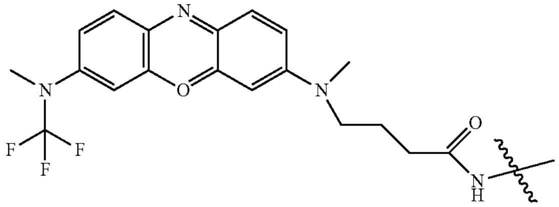
,

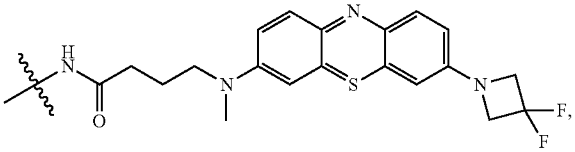

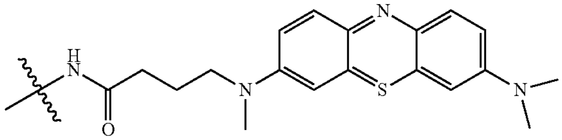
,

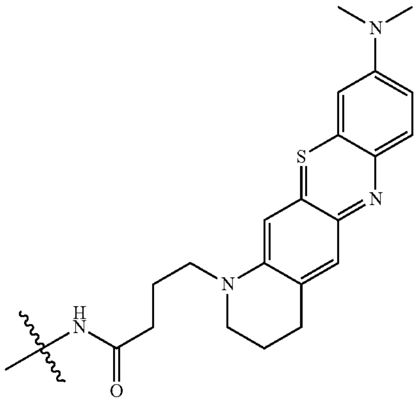
,

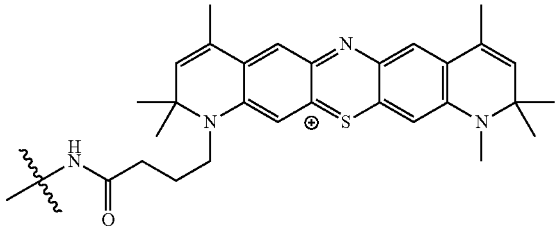
,

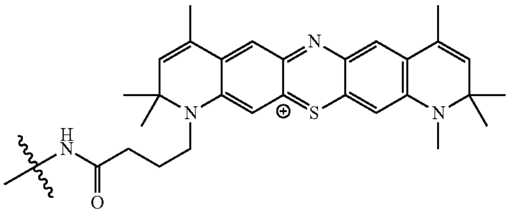
, and

-continued

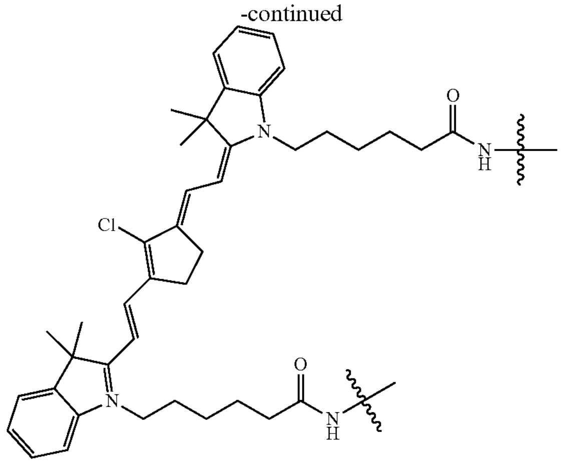
.

In some embodiments, W is selected from any one of Formulas (VA) or (VB):

(VA)

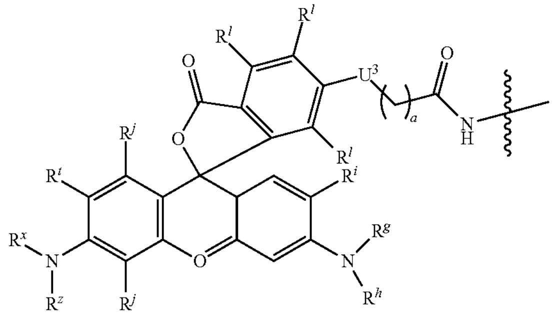
, (VB)

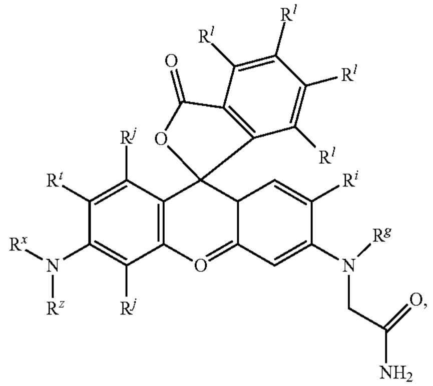

wherein $R^g$ is —$CH_3$ or —$CH_2$—$CH_3$;

$R^i$ is H or a branched or unbranched $C_1$-$C_6$ alkyl group;

or where $R^g$ and $R^i$ together form a 5-, 6-, or 7-membered ring which may be optionally substituted with a halogen, a $C_1$-$C_4$ alkyl group;

$R^h$ is H or a branched or unbranched $C_1$-$C_4$ alkyl group;

$R^x$ is H or a branched or unbranched $C_1$-$C_4$ alkyl group optionally substituted with one or more halogen atoms;

$R^z$ is H, or a $C_1$-$C_4$ alkyl group optionally substituted with one or more halogen atoms or with a —S(O)(O)—$O^-$ group;

$R^t$ is H or a branched or unbranched $C_1$-$C_4$ alkyl group;

or where $R^t$ and one of $R^x$ or $R^z$ together form a 5-, 6-, or 7-membered cyclic or aromatic ring which may be optionally substituted with one or more halogen atoms or one or more $C_1$-$C_2$ alkyl groups;

each $R^j$ is independently H or a branched or unbranched $C_1$-$C_6$ alkyl group;

or where $R^j$ and $R^t$ form a 5- or 6-membered ring, optionally substituted with one or one or more $C_1$-$C_2$ alkyl groups; or where $R^j$ and one of $R^x$ or $R^z$ form a 5- or 6-membered ring, optionally substituted with one or more $C_1$-$C_2$ alkyl groups; or where $R^x$, $R^t$, and $R^j$ together form a bicyclic ring which may be saturated or unsaturated and which may be optionally substituted with one or more halogen atoms or one or more $C_1$-$C_2$ alkyl groups;

each $R^l$ is independently H or a halogen atom; and a is 0 or an integer ranging from 1 to 6.

In some embodiments, a is 0.

In some embodiments, $R^t$ and $R^x$ together form a 6-membered ring. In some embodiments, R and $R^x$ together form a 6-membered substituted ring. In some embodiments, $R^t$ and $R^x$ together form a 6-membered ring substituted with one or more methyl or ethyl groups, one or more $-CH_2-S(O)(O)(OH)$ groups, one or more $-CH_2-CH_2-S(O)(O)(OH)$ groups, $-CH_2-CH_2-CH_2-S(O)(O)(OH)$ groups, or $-CH_2-CH_2-CH_2-CH_2-S(O)(O)(OH)$ groups.

In some embodiments, $R^i$ and $R^g$ together form a 6-membered ring. In some embodiments, $R^i$ and $R^g$ together form a 6-membered substituted ring. In some embodiments, $R^i$ and $R^g$ together form a 6-membered ring substituted with one or more methyl or ethyl groups, one or more $-CH_2-S(O)(O)(OH)$ groups, one or more $-CH_2-CH_2-S(O)(O)(OH)$ groups, $-CH_2-CH_2-CH_2-S(O)(O)(OH)$ groups, or $-CH_2-CH_2-CH_2-CH_2-S(O)(O)(OH)$ groups.

In some embodiments, $R^t$ and $R^x$ together form a 6-membered ring, and $R^i$ and $R^g$ together form a 6-membered ring. In some embodiments, $R^t$ and $R^x$ together form a 6-membered ring, $R^i$ and $R^g$ together form a 6-membered ring, and each $R^l$ is a halogen. In some embodiments, $R^t$ and $R^x$ together form a 6-membered ring, $R^i$ and $R^g$ together form a 6-membered ring, and each $R^l$ is chlorine.

In some embodiments, $R^x$, $R^t$, and $R^j$ together form a bicyclic ring. In some embodiments, $R^x$, $R^t$, and $R^j$ together form a bicyclic ring, and $R^i$ and $R^g$ together form a 6-membered ring. In some embodiments, $R^x$, $R^t$, and $R^j$ together form a substituted bicyclic ring. In some embodiments, $R^x$, $R^t$, and $R^j$ together form a substituted bicyclic ring, and $R^i$ and $R^g$ together form a substituted or unsubstituted 6-membered ring. In some embodiments, $R^x$, $R^t$, and $R^j$ together form a substituted bicyclic ring, and $R^i$ and $R^g$ together form a substituted 6-membered ring.

Non-liming examples of detectable moieties of Formulas (VA) to (VB) include the following:

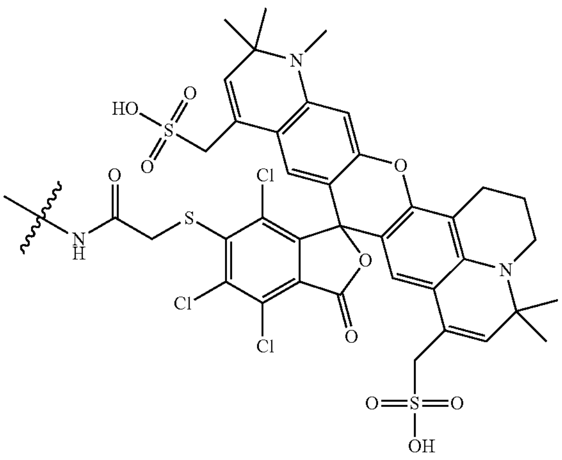
,

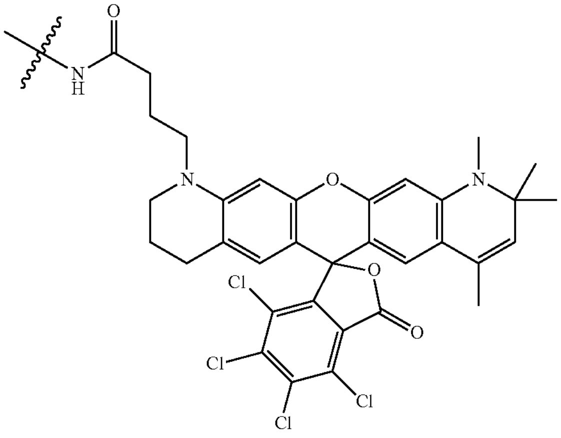
,

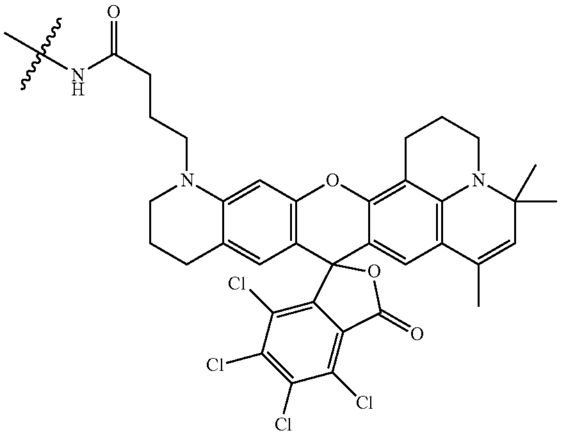
,

-continued

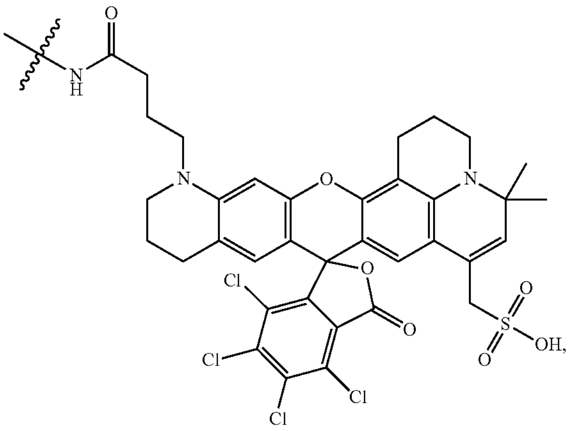

,

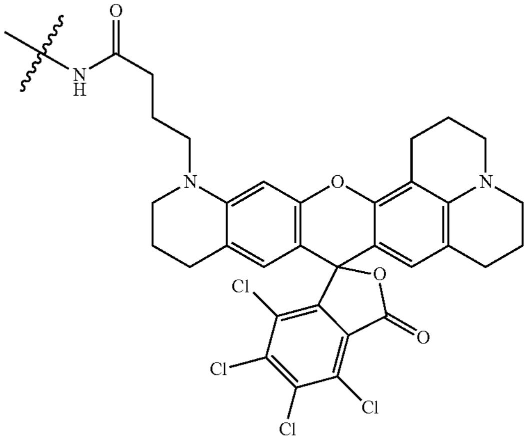

,

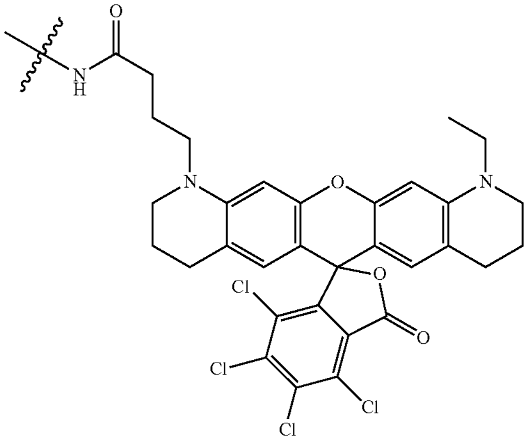

,

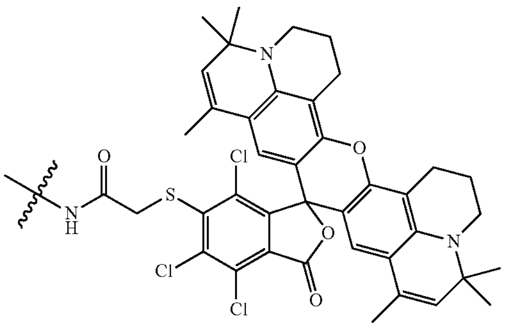

, and

-continued

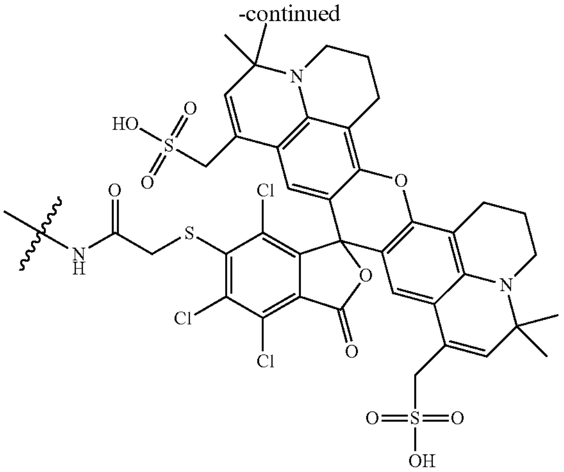

.

In some embodiments, W is selected from Formula (VI):

(VI)

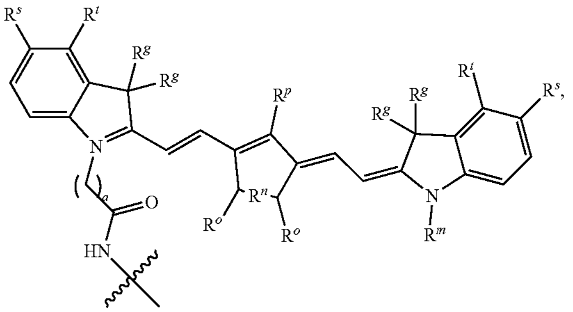

wherein a is 0 or an integer ranging from 1 to 6;

$R^p$ is a halogen atom;

$R^n$ is a bond or —$CH_2$—;

each $R^o$ is independently a branched or unbranched $C_1$-$C_4$ alkyl group, or when $R^n$ is —$CH_2$-then both $R^o$ groups together may form a 6-member cyclic or aromatic ring, optionally substituted with one or more halogen groups or one or more $C_1$-$C_2$ alkyl groups;

each $R^g$ is independently-$CH_3$ or —$CH_2$—$CH_3$;

$R^m$ is H, a branched or unbranched $C_1$-$C_4$ alkyl group which is optionally substituted with one or more halogen atoms and or one or more —S(O)(O)(OH) groups, or a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction;

each $R^s$ or $R^t$ group is independently selected from a branched or unbranched $C_1$-$C_6$ alkyl group or a —S(O)(O)(OH) group;

or wherein any two adjacent $R^s$ and $R^t$ groups and/or any two adjacent $R_g$ and $R^t$ groups may together form a 5- or 6-membered cyclic or aromatic group, optionally substituted with one or more $C_1$-$C_2$ alkyl groups or with one or more —S(O)(O)(OH) groups.

In some embodiments, at least one $R^s$ or $R^t$ moiety comprises a —S(O)(O)(OH) group. In other embodiments, at least two $R^s$ or $R^t$ moieties comprises a —S(O)(O)(OH) group. In yet other embodiments, at least three $R^s$ or $R^t$ moieties comprises a —S(O)(O)(OH) group. In further embodiments, at least four $R^s$ or $R^t$ moieties comprises a —S(O)(O)(OH) group.

In some embodiments, $R''$ is a bond and wherein at least one $R^g$ is methyl. In some embodiments, $R''$ is a bond and wherein at least two $R^g$ groups are both methyl.

In some embodiments, $R''$ is —$CH_2$—. In some embodiments, $R''$ is —$CH_2$— and each $R^o$ together forms a 6-membered ring. In some embodiments, $R''$ is —$CH_2$— and each $R^o$ together forms a 6-membered aromatic ring. In some embodiments, $R''$ is —$CH_2$— and each $R^o$ together forms a 6-membered substituted aromatic ring.

In some embodiments, one set of adjacent $R^t$ and $R^s$ groups forms a 6-membered ring. In some embodiments, both sets of adjacent $R^t$ and $R^s$ groups form a 6-membered ring. In some embodiments, one set of adjacent $R^t$ and $R^s$ groups forms a 6-membered ring, and where $R''$ is —$CH_2$— and each $R^o$ together forms a 6-membered ring. In some embodiments, both sets of adjacent $R^t$ and $R^s$ groups form a 6-membered ring, and where $R''$ is —$CH_2$— and each $R^o$ together forms a 6-membered ring.

In some embodiments, one set of adjacent $R^t$, $R^s$, and $R^g$ groups forms a bicyclic ring. In some embodiments, one set of adjacent $R^t$, $R^s$, and $R^g$ groups forms a bicyclic ring, and another set of adjacent $R^t$ and $R^s$ groups forms a 6-membered ring. In some embodiments, one set of adjacent $R^t$, $R^s$, and $R^g$ groups forms a bicyclic ring, and where $R''$ is —$CH_2$— and each $R^o$ together forms a 6-membered ring. In some embodiments, one set of adjacent $R^t$, $R^s$, and $R^g$ groups forms a bicyclic ring, and another set of adjacent $R^t$ and $R^s$ groups forms a 6-membered ring, and where $R''$ is —$CH_2$— and each $R^o$ together forms a 6-membered ring.

In some embodiments, $R''$ is a bond, at least one $R^g$ is methyl, and wherein $R'''$ is a branched or unbranched $C_1$-$C_4$ alkyl group which is optionally substituted with one or more halogen atoms and or one or more —S(O)(O)(OH) groups. In some embodiments, $R''$ is a bond, at least two $R^g$ groups are both methyl, and wherein $R'''$ is a branched or unbranched $C_1$-$C_4$ alkyl group which is optionally substituted with one or more halogen atoms and or one or more —S(O)(O)(OH) groups.

In some embodiments, $R''$ is —$CH_2$—, and wherein $R'''$ is a branched or unbranched $C_1$-$C_4$ alkyl group which is optionally substituted with one or more halogen atoms and or one or more —S(O)(O)(OH) groups. In some embodiments, $R''$ is —$CH_2$—, each $R^o$ together forms a 6-membered ring, and wherein $R'''$ is a branched or unbranched $C_1$-$C_4$ alkyl group which is optionally substituted with one or more halogen atoms and or one or more —S(O)(O)(OH) groups. In some embodiments, $R''$ is —$CH_2$—, each $R^o$ together forms a 6-membered aromatic ring, and wherein $R''$ is a branched or unbranched $C_1$-$C_4$ alkyl group which is optionally substituted with one or more halogen atoms and or one or more —S(O)(O)(OH) groups. In some embodiments, $R''$ is —$CH_2$—, each $R^o$ together forms a 6-membered substituted aromatic ring, and wherein $R'''$ is a branched or unbranched $C_1$-$C_4$ alkyl group which is optionally substituted with one or more halogen atoms and or one or more —S(O)(O)(OH) groups.

In some embodiments, one set of adjacent $R^t$ and $R^s$ groups forms a 6-membered ring, and wherein $R'''$ is a branched or unbranched $C_1$-$C_4$ alkyl group which is optionally substituted with one or more halogen atoms and or one or more —S(O)(O)(OH) groups. In some embodiments, both sets of adjacent $R^t$ and $R^s$ groups form a 6-membered ring, and wherein $R'''$ is a branched or unbranched $C_1$-$C_4$ alkyl group which is optionally substituted with one or more halogen atoms and or one or more —S(O)(O)(OH) groups. In some embodiments, one set of adjacent $R^t$ and $R^s$ groups forms a 6-membered ring, $R''$ is —$CH_2$— and each $R^o$ together forms a 6-membered ring, and wherein $R'''$ is a branched or unbranched $C_1$-$C_4$ alkyl group which is optionally substituted with one or more halogen atoms and or one or more —S(O)(O)(OH) groups. In some embodiments, both sets of adjacent $R^t$ and $R^s$ groups form a 6-membered ring, $R''$ is —$CH_2$— and each $R^o$ together forms a 6-membered ring, and wherein $R'''$ is a branched or unbranched $C_1$-$C_4$ alkyl group which is optionally substituted with one or more halogen atoms and or one or more —S(O)(O)(OH) groups.

In some embodiments, one set of adjacent $R^t$, $R^s$, and $R^g$ groups forms a bicyclic ring, and wherein $R'''$ is a branched or unbranched $C_1$-$C_4$ alkyl group which is optionally substituted with one or more halogen atoms and or one or more —S(O)(O)(OH) groups. In some embodiments, one set of adjacent $R^t$, $R^s$, and $R^g$ groups forms a bicyclic ring, another set of adjacent $R^t$ and $R^s$ groups forms a 6-membered ring, and wherein $R'''$ is a branched or unbranched $C_1$-$C_4$ alkyl group which is optionally substituted with one or more halogen atoms and or one or more —S(O)(O)(OH) groups. In some embodiments, one set of adjacent $R^t$, $R^s$, and $R^g$ groups forms a bicyclic ring, $R'''$ is —$CH_2$—, each $R^o$ together forms a 6-membered ring, and wherein $R'''$ is a branched or unbranched $C_1$-$C_4$ alkyl group which is optionally substituted with one or more halogen atoms and or one or more —S(O)(O)(OH) groups. In some embodiments, one set of adjacent $R^t$, $R^s$, and $R^g$ groups forms a bicyclic ring, another set of adjacent $R^t$ and $R^s$ groups forms a 6-membered ring, $R''$ is —$CH_2$—, each $R^o$ together forms a 6-membered ring, and wherein $R'''$ is a branched or unbranched $C_1$-$C_4$ alkyl group which is optionally substituted with one or more halogen atoms and or one or more —S(O)(O)(OH) groups.

In some embodiments, $R''$ is a bond, at least one $R^g$ is methyl, and wherein $R'''$ is a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction. In some embodiments, $R''$ is a bond, at least two $R^g$ groups are both methyl, and wherein $R'''$ is a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction.

In some embodiments, $R''$ is —$CH_2$—, and wherein $R'''$ is a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction. In some embodiments, $R''$ is —$CH_2$—, each $R^o$ together forms a 6-membered ring, and wherein $R'''$ is a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction. In some embodiments, $R''$ is —$CH_2$—, each $R^o$ together forms a 6-membered aromatic ring, and wherein $R'''$ is a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction. In some embodiments, R″ is —$CH_2$—, each $R^o$ together forms a 6-membered substituted aromatic ring, and wherein R‴ is a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction.

In some embodiments, one set of adjacent $R^t$ and $R^s$ groups forms a 6-membered ring, and wherein R‴ is a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction. In some embodiments, both sets of adjacent Rand $R^s$ groups form a 6-membered ring, and wherein R‴ is a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction. In some embodiments, one set of adjacent $R^t$ and $R^s$ groups forms a 6-membered ring, R″ is —$CH_2$— and each $R^o$ together forms a 6-membered ring, and wherein R‴ is a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction. In some embodiments, both sets of adjacent $R^t$ and $R^s$ groups form a 6-membered ring, R″ is —$CH_2$— and each $R^o$ together forms a 6-membered ring, and wherein R‴ is a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction.

In some embodiments, one set of adjacent $R^t$, $R^s$, and $R^g$ groups forms a bicyclic ring, and wherein R‴ is a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction. In some embodiments, one set of adjacent $R^t$, $R^s$, and $R^g$ groups forms a bicyclic ring, another set of adjacent $R^t$ and $R^s$ groups forms a 6-membered ring, and wherein R‴ is a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction. In some embodiments, one set of adjacent $R^t$, $R^s$, and $R^g$ groups forms a bicyclic ring, R″ is —$CH_2$—, each $R^o$ together forms a 6-membered ring, and wherein R‴ is a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction. In some embodiments, one set of adjacent $R^t$, $R^s$, and $R^g$ groups forms a bicyclic ring, another set of adjacent $R^t$ and $R^s$ groups forms a 6-membered ring, R″ is —$CH_2$—, each $R^o$ together forms a 6-membered ring, and wherein R‴ is a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction.

Non-liming examples of detectable moieties of Formula (VI) include the following:

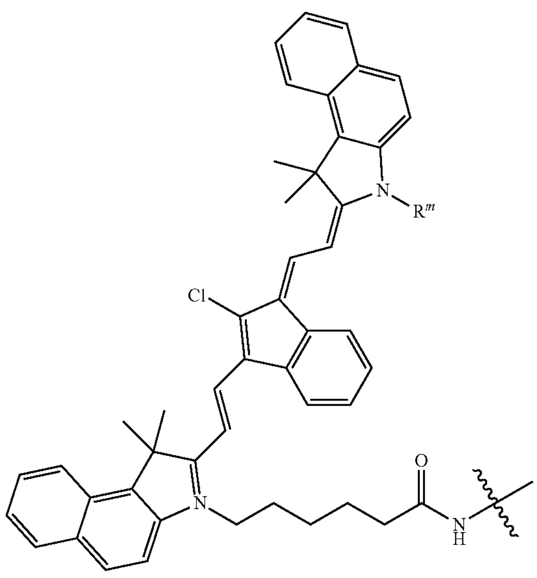
,

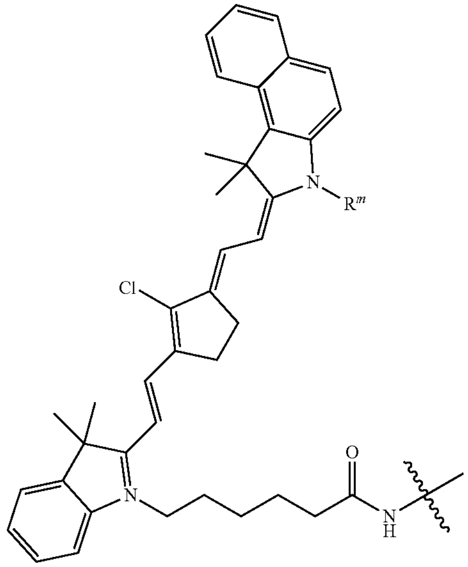
,

-continued

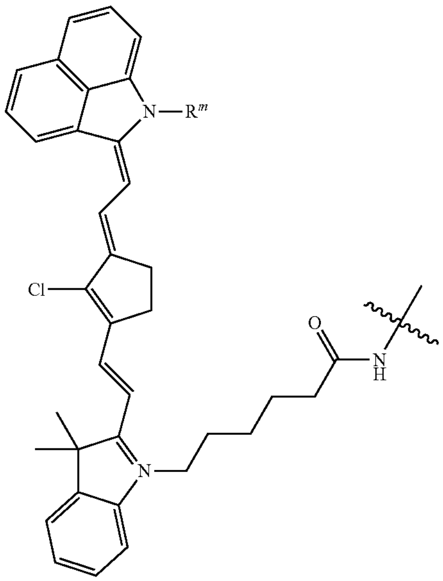

,

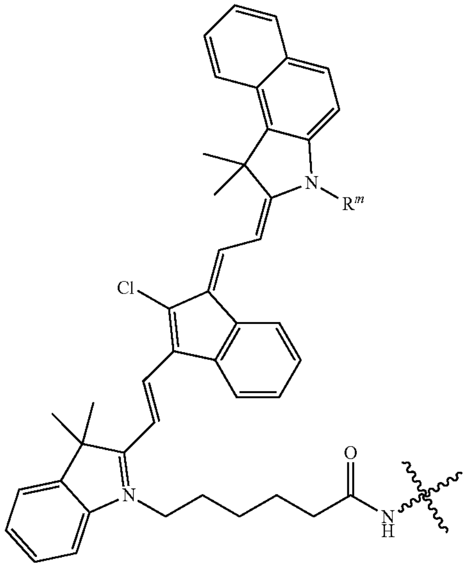

,

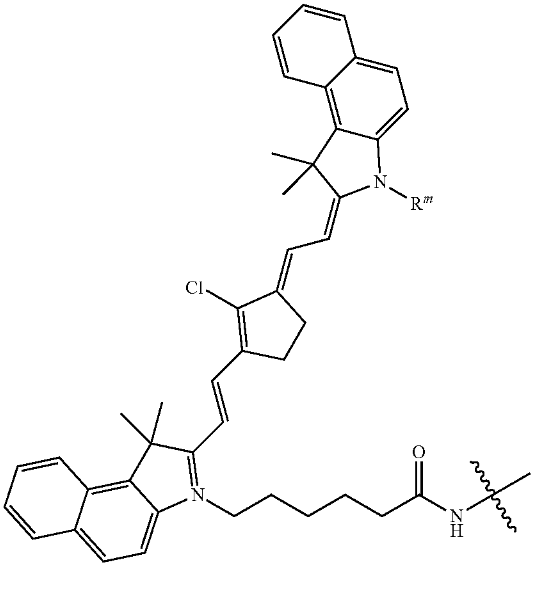

,

-continued

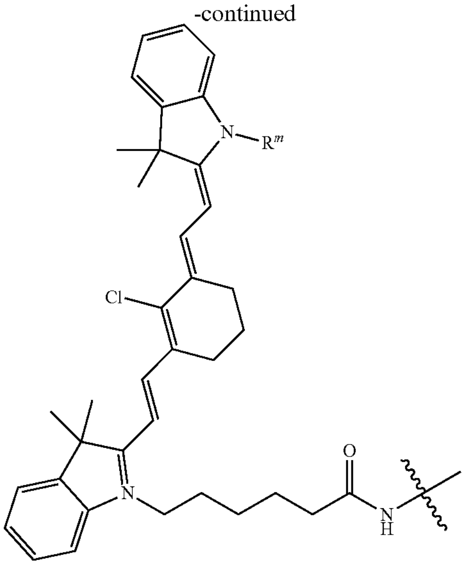

, and

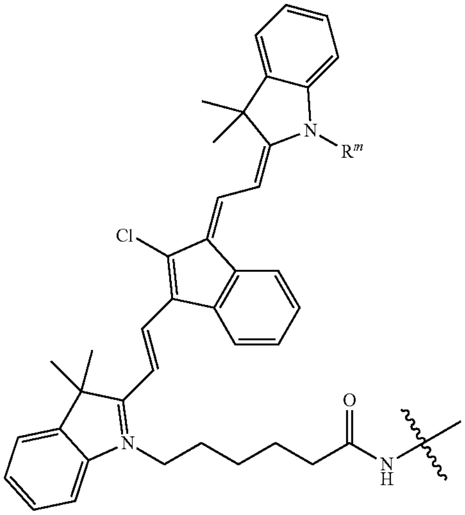

.

In some embodiments, W is selected from Formula (VIIA):

(VIIA)

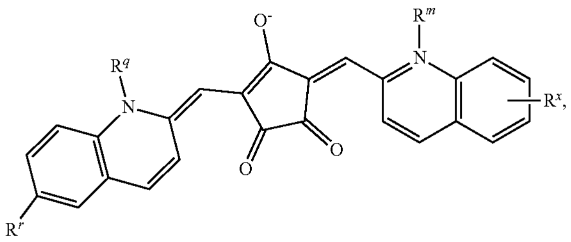

wherein $R^x$ is H or a branched or unbranched $C_1$-$C_4$ alkyl group optionally substituted with one or more halogen atoms;

$R^m$ is H, a branched or unbranched $C_1$-$C_4$ alkyl group which is optionally substituted with one or more halogen atoms and or one or more —S(O)(O)(OH) group, or a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction;

$R^q$ and $R^r$ are each independently H, a branched or unbranched $C_1$-$C_4$ alkyl group optionally substituted with one or more halogen atoms, or a group $R^s$, where $R^s$ is a saturated or unsaturated $C_1$-$C_{20}$ alkyl group comprising at least one amide group, and which is optionally substituted with one or more heteroatoms, provided that the group $R^s$ terminates in a moiety capable of participating in a click chemistry reaction, provided that at least one of $R^q$ or $R^r$ comprises a group $R^s$, and further provided that $R^q$ and $R^r$ are both not $R^s$.

In some embodiments, $R^f$ and $R^x$ are both H. In some embodiments, $R'''$ is a branched or unbranched $C_1$-$C_4$ alkyl group which is optionally substituted with one or more halogen atoms and or one or more —S(O)(O)(OH) group. In some embodiments, $R'''$ is an unbranched $C_1$-$C_4$ alkyl group which is optionally substituted with one or more halogen atoms and or one or more —S(O)(O)(OH) group.

In some embodiments, one of $R^f$ or $R'''$ is a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction. In some embodiments, both of $R^f$ and $R'''$ are a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction. In some embodiments, one of $R^f$ or $R'''$ is an unbranched $C_1$-$C_{10}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction. In some embodiments, both of $R^f$ and $R'''$ are an unbranched $C_1$-$C_{10}$ alkyl group optionally including one or more heteroatoms selected from O or N, and optionally including one or more carbonyl groups, provided that the $C_1$-$C_{10}$ alkyl group terminates in a moiety capable of participating in a click chemistry reaction.

In some embodiments, one of $R^f$ or $R'''$ is a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction, and the other of $R^f$ or $R'''$ is a branched or unbranched $C_1$-$C_4$ alkyl group which is optionally substituted with one or more halogen atoms and or one or more —S(O)(O)(OH) group. In some embodiments, one of $R^f$ or $R'''$ is a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction, and the other of $R^f$ or $R'''$ is an unbranched $C_1$-$C_4$ alkyl group which is optionally substituted with one or more halogen atoms and or one or more —S(O)(O)(OH) group.

In some embodiments, one of $R^f$ or $R'''$ is a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction; the other of $R^f$ or $R'''$ is a branched or unbranched $C_1$-$C_4$ alkyl group which is optionally substituted with one or more halogen atoms and or one or more —S(O)(O)(OH) group; and $R^q$ is a methyl group. In some embodiments, one of $R^f$ or $R'''$ is a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction; the other of $R^f$ or $R'''$ is an unbranched $C_1$-$C_4$ alkyl group which is optionally substituted with one or more halogen atoms and or one or more —S(O)(O)(OH) group; and $R^q$ is a methyl group.

In some embodiments, W is selected from any one of Formulas (VIIB) and (VIIC):

(VIIB)

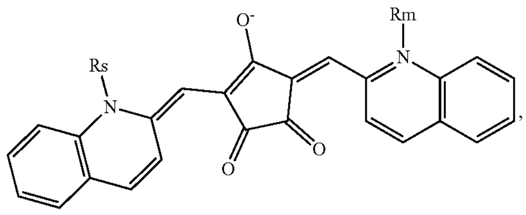

(VIIC)

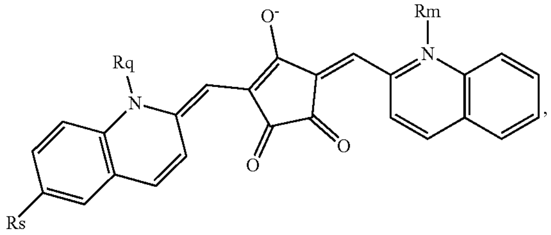

wherein $R^x$ is H or a branched or unbranched $C_1$-$C_4$ alkyl group optionally substituted with one or more halogen atoms;

$R'''$ is H, a branched or unbranched $C_1$-$C_4$ alkyl group which is optionally substituted with one or more halogen atoms and or one or more —S(O)(O)(OH) group, or a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction;

$R^q$ is H or a branched or unbranched $C_1$-$C_4$ alkyl group optionally substituted with one or more halogen atoms;

$R^s$ is a saturated or unsaturated $C_1$-$C_{20}$ alkyl group comprising at least one amide group, and which is optionally substituted with one or more heteroatoms, provided that the group $R^s$ terminates in a moiety capable of participating in a click chemistry reaction.

Non-limiting examples of the moieties of Formula (VIIA) include:

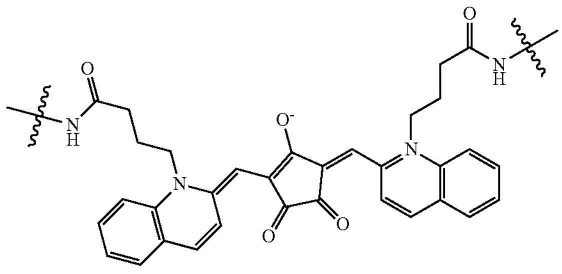

,

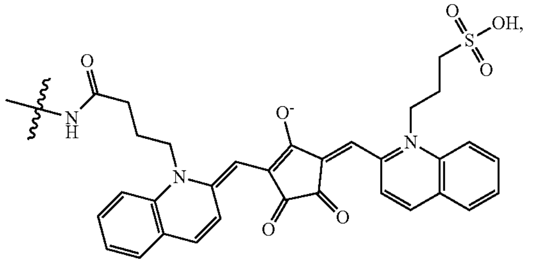

and

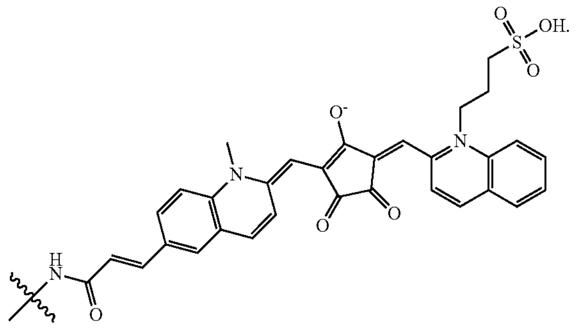

Tissue Reactive Moieties

As used herein, the term “tissue reactive moiety” refers to a moiety that is capable of reacting with an enzyme. As such, when a conjugate comprising a tissue reactive moiety is reacted with an appropriate enzyme, the tissue reactive moiety portion of the conjugate undergoes a structural, conformational, and/or electronic change, thereby providing a tissue reactive species (an intermediate) suitable for bonding directly or indirectly onto (or, to the extent possible, within) a biological sample.

For example, where the tissue reactive moiety is a tyramide or derivative thereof, when the tyramide reacts with an appropriate enzyme (e.g., an HRP), a tyramide radical species is formed. This highly reactive tyramide radical species is capable of bonding to tyrosine residues in biological samples. In a similar manner, where the tissue reactive moiety is a quinone methide precursor or derivative thereof, upon reaction with an appropriate enzyme (e.g., AP), the quinone methide precursor is converted to a quinone methide (or respective derivative thereof), which is believed to be highly reactive with nucleophiles in a biological sample. The role of the tissue reactive moiety portion of any conjugate, its interaction with a suitable enzyme, and the formation of an immobilized tissue-conjugate complex suitable for detection is described further herein.

In some embodiments, the tissue reactive moiety is a quinone methide precursor or a derivative thereof. In some embodiments, a quinone methide precursor moiety has the structure provided by Formula (IXA)):

(IXA)

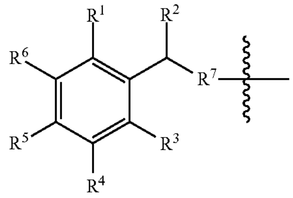

, $R^1$ is a group selected from phosphate, amide, nitro, urea, sulfate, methyl, ester, beta-lactam, or a sugar;

$R^2$ is a halide;

$R^3$, $R^4$, $R^5$, and $R^6$ are independently selected from hydrogen or an aliphatic group having between 1 and 4 carbon atoms; and $R^7$ is $-(CH_2)_wNH-$, $-O(CH_2)_wNH-$, $-N(H)C(O)(CH_2)_wNH-$, $-C(O)N(H)(CH_2)_wNH-$, $-(CH_2)_wO-$, $-O(CH_2)_wO-$, $-O(CH_2CH_2O)_w-$, $-N(H)C(O)(CH_2)_wO-$, $-C(O)N(H)(CH_2)_wO-$, $-C(o)N(H)(CH_2CH_2O)_w-$, $-(CH_2)_wS-$, $-O(CH_2)_wS-$, $-N(H)C(O)(CH_2)_wS-$, $-C(O)N(H)(CH_2)_wS-$, $-(CH_2)_wNH-$, $-C(O)N(H)(CH_2CH_2O)_wCH_2CH_2NH$, $-C(O)(CH_2CH_2O)_wCH_2CH_2NH-$, $-C(O)N(H)(CH_2)NHC(O)CH(CH_3)(CH_2)_wNH-$, or $-N(H)(CH_2)_wNH-$, where w is an integer ranging from 1 to 12.

In other embodiments, the quinone methide precursor moiety has the structure provided by Formula (IXB):

(IXC)

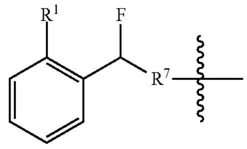

,

In other embodiments, the quinone methide precursor moiety has the structure provided by Formula (IXD):

(IXD)

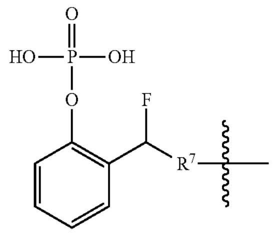

, where $R^7-(CH_2)_wNH-$, $-O(CH_2)_wNH-$, $-N(H)C(O)(CH_2)_wNH-$, $C(O)N(H)(CH_2)_wNH-$, $-(CH_2)_wO-$, $-O(CH_2)_wO-$, $-O(CH_2CH_2O)_w-$, $-N(H)C(O)(CH_2)_wO-$, $-C(O)N(H)(CH_2)_wO-$, $-C(o)N(H)(CH_2CH_2O)_w-$, $-(CH_2)_wS-$, $-O(CH_2)_wS-$, $-N(H)C(O)(CH_2)_wS-$, $-C(O)N(H)(CH_2)_wS-$, $-(CH_2)_wNH-$, $-C(O)N(H)(CH_2CH_2O)_wCH_2CH_2NH$, $-C(O)(CH_2CH_2O)_wCH_2CH_2NH-$, $-C(O)N(H)(CH_2)NHC(O)CH(CH_3)(CH_2)_wNH-$, or $-N(H)(CH_2)_wNH-$, where w is independently an integer ranging from 1 to 12. In some embodiments, $R^7$ is $C(O)N(H)(CH_2)_wNH$ and w is as defined above. In other embodiments, $R^7$ is $C(O)N(H)(CH_2)_wNH$ and w ranges from 2 to 6.

In other embodiments, the quinone methide precursor moiety has the structure provided by Formula (IXE):

(IXE)

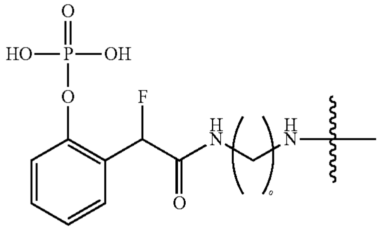

, where w ranges from 1 to 12. In some embodiments w ranges from 1 to 8. In other embodiments, w ranges from 2 to 8. In yet other embodiments, w ranges from 2 to 6. In further embodiments, w is 6.

In some embodiments, the quinone methide precursor moiety portion of any conjugate is derived from one of the derivatives which follow.

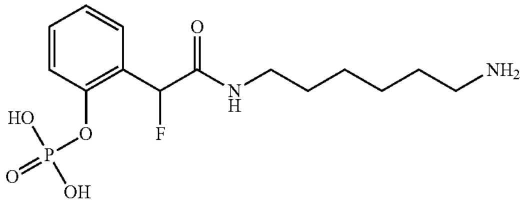

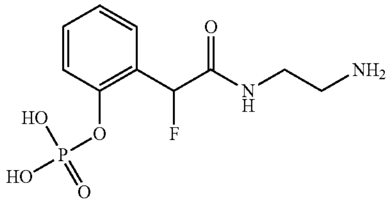

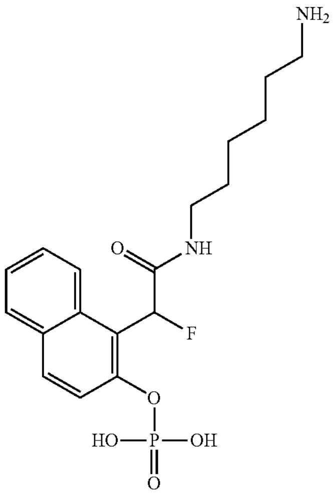

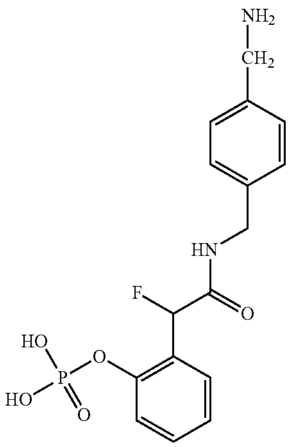

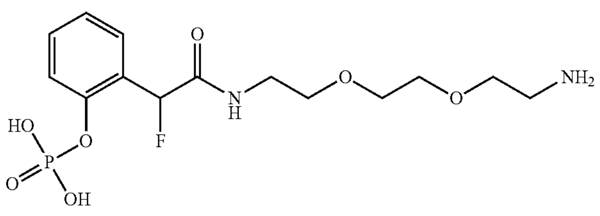

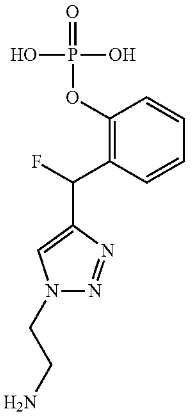

-continued

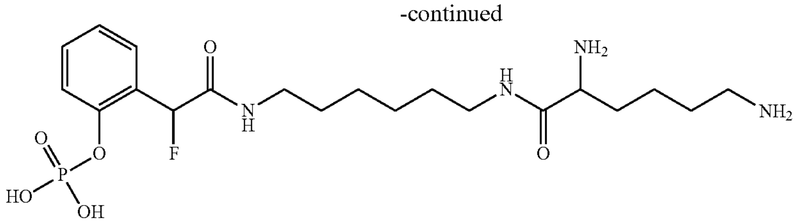

In some embodiments, the tissue reactive moiety is a tyramide or a derivative thereof. In some embodiments, the tyramide has the structure provided by Formula (XA):

(XA)

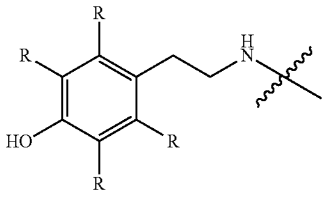

wherein each R group is independently selected from hydrogen or lower alkyl group having between 1 and 4 carbon atoms.

In other embodiments, the tyramide moiety has the structure provided by Formula (XB):

(XB)

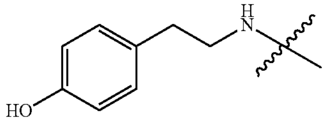

As noted herein, Q may be a branched or unbranched, linear or cyclic, substituted or unsubstituted group having between 2 and 40 carbon atoms, and optionally having one or more heteroatoms selected from O, N, or S. In some embodiments, Q may comprise carbonyl, amine, ester, ether, amide, imine, thione or thiol groups. In some embodiments, Q is a branched or unbranched linear group having between 2 and 20 carbon atoms, optionally having one or more heteroatoms selected from O, N, or S, and one or more terminal groups selected from an amine, a carbonyl, ester, ether, amide, imine, thione, or thiol. In other embodiments, Q is a branched or unbranched linear group having between 2 and 20 carbon atoms, optionally having one or more oxygen heteroatoms. In yet other embodiments, the group Q comprises components intended to increase the water-solubility of the molecule.

Functional Groups or Moieties Including Functional Groups Capable of Participating in a Click Chemistry Reaction "Click chemistry" is a chemical philosophy, independently defined by the groups of Sharpless and Meldal, that describes chemistry tailored to generate substances quickly and reliably by joining small units together. "Click chemistry" has been applied to a collection of reliable and self-directed organic reactions (Kolb, H. C.; Finn, M. G.; Sharpless, K. B. Angew). Chem. Int. Ed. 2001, 40, 2004-2021). For example, the identification of the copper catalyzed azide-alkyne [3+2] cycloaddition as a highly reliable molecular connection in water (Rostovtsev, V. V.; et al. Angew. Chem. Int. Ed. 2002, 41, 2596-2599) has been used to augment several types of investigations of biomolecular interactions (Wang, Q.; et al. J. Am. Chem. Soc. 2003, 125, 3192-3193; Speers, A. E.; et al. J. Am. Chem. Soc. 2003, 125, 4686-4687; Link, A. J.; Tirrell, D. A. J. Am. Chem. Soc. 2003, 125, 11164-11165; Deiters, A.; et al. J. Am. Chem. Soc. 2003, 125, 11782-11783). In addition, applications to organic synthesis (Lee, L. V.; et al. J. Am. Chem. Soc. 2003, 125, 9588-9589), drug discovery (Kolb, H. C.; Sharpless, K. B. Drug Disc. Today 2003, 8, 1128-1137; Lewis, W. G.; et al. Angew. Chem. Int. Ed. 2002, 41, 1053-1057), and the functionalization of surfaces (Meng, J.-C.; et al. Angew. Chem. Int. Ed. 2004, 43, 1255-1260; Fazio, F.; et al. J. Am. Chem. Soc. 2002, 124, 14397-14402; Collman, J. P.; et al. Langmuir 2004, ASAP, in press; Lummerstorfer, T.; Hoffmann, H. J. Phys. Chem. B 2004, in press) have also appeared.

In some embodiments, when Z is a functional group or a moiety including a functional group capable of participating in a click chemistry reaction, then Z is a dibenzocyclooctyne, a trans-cyclooctene, an alkyne, an alkene, an azide, a tetrazine, a maleimide, a N-hydroxysuccinimide, a thiol, a 1,3-nitrone, an aldehyde, a ketone, a hydrazine, a hydroxylamine, an amino group. Other suitable functional groups are described herein.

Linkers

In some embodiments, the group Q is designed to act as a "spacer." In other embodiments, the group Q is designed to increase the water solubility of the conjugates.

In some embodiments, Q has the structure depicted in Formula (XIA):

(XIA)

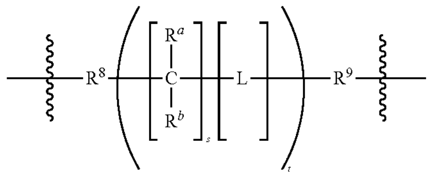

wherein f is 0, 1, or 2;

L is a bond, O, S, or $N(R^c)(R^d)$;

$R^a$ and $R^b$ are independently H, a $C_1$-$C_4$ alkyl group, F, Cl, or —$N(R^c)(R^d)$;

$R^c$ and $R^d$ are independently selected from $CH_3$ or H;

$R^8$ and $R^9$ are independently a bond, or a group selected from carbonyl, amide, imide, ester, ether, amine, thione, thiol; and j is an integer ranging from 1 to 8.

In some embodiments, at least one of $R^a$ or $R^b$ is H. In some embodiments, at least one of $R^a$ or $R^b$ is H and f is 1. In some embodiments, at least one of $R^a$ or $R^b$ is H, f is 1 and s is at least 2.

In some embodiments, Q has the structure depicted in Formula (XIB):

(XIB)

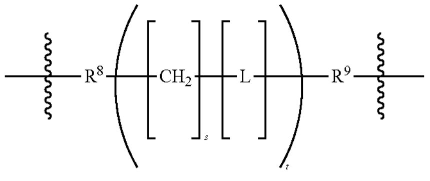

, wherein f is 0, 1, or 2;

L is a bond, O, S, or $N(R^c)(R^d)$;

$R^c$ and $R^d$ are independently $CH_3$ or H;

$R^8$ and $R^9$ are independently a bond, or a group selected from carbonyl, amide, imide, ester, ether, amine, or thiol; and j is an integer ranging from 1 to 8.

In some embodiments, f is 1 and s is at least 2. In some embodiments, $R^8$ is a bond; f is 1; s is 2 to 10; and $R^9$ and $R^{10}$ are as defined above. In other embodiments, $R^8$ is a bond; f is 1; s is 2 to 6; and $R^9$ and $R^{10}$ are as defined above. In other embodiments, $R^8$ is a bond; f is 1; s is 2 to 4; and $R^9$ and $R^{10}$ are both amines.

In some embodiments, Q has the structure depicted in Formula (XIC):

(XIC)

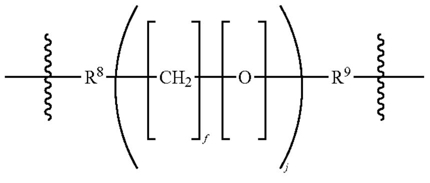

, wherein f is 0, 1, or 2; and j is an integer ranging from 1 to 8.

In some embodiments, f is 1; $R^9$ and $R^{10}$ are independently a bond, or a group selected from carbonyl, amide, imide, ester, ether, amine, or thiol; and s is at least 2. In some embodiments, f is 1 and s is 2. In some embodiments, f is 1 and s is 3. In some embodiments, f is 1 and s is 4.

The alkylene oxide-based L groups of Formulas (XIA), (XIB), and (XIC) are represented herein by reference to glycols, such as ethylene glycols. In some embodiments, the incorporation of such alkylene oxide linkers is believed to increase the hydrophilicity of the conjugate. A person of ordinary skill in the art will appreciate that, as the number alkylene oxide repeat units in the linker increases, the hydrophilicity of the conjugate also may increase. Additional heterobifunctional polyalkyleneglycol spacers useful for practicing certain disclosed embodiments of the present disclosure are described in assignee's co-pending applications, including "Nanoparticle Conjugates," U.S. patent application Ser. No. 11/413,778, filed Apr. 28, 2006; "Antibody Conjugates," U.S. application Ser. No. 11/413,415, filed Apr. 27, 2006; and "Molecular Conjugate," U.S. Provisional Patent Application No. 60/739,794, filed Nov. 23, 2005; all of which applications are incorporated herein by reference.

Compounds Having Formula (VIII)

In some embodiments of the present disclosure is a compound having Formula (XII):

$$[X]\text{-}[Q]_m\text{-}[W] \qquad \text{(VIII)},$$

where Q is a branched or unbranched, linear or cyclic, substituted or unsubstituted group having between 2 and 40 carbon atoms, and optionally having one or more heteroatoms selected from O, N, or S; m is 0, 1, or 2; W is a detectable moiety; and X is a "tissue reactive moiety."

In some embodiments, W is moiety having any one of Formulas (IIA), (IIB), (IIC), (IIIA), (IIIB), (IVA), (IVB), (IVC), (IVD), (IVE), (IVF), (IVG), (IVH), (VA), (VB), (VI), (VIIA), (VIIB), and (VIIC). In some embodiments, X is selected from any one of Formulas (IXA) through (IXE), (XA), and (XB), as described herein.

In some embodiments, the present disclosure provides a compound having Formula VIIIA):

(VIIIA)

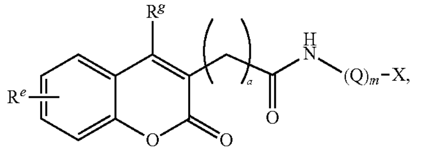

wherein $R^e$ is —OH, —O-alkyl, or —$N(R^x)(R^y)$, where $R^x$ and $R^y$ are independently H or a branched or unbranched $C_1$-$C_4$ alkyl group optionally substituted with one or more halogen atoms, or where $R^x$ and $R^y$ together form a 3-, 4-, or 5-membered cyclic ring which may be optionally substituted with one or more halogen atoms or one or more $C_1$-$C_2$ alkyl groups;

$R^g$ is —H, —$CH_3$ or —$CH_2$—$CH_3$;

a is 0 or an integer ranging from 1 to 4;

Q is a branched or unbranched, linear or cyclic, substituted or unsubstituted group having between 2 and 40 carbon atoms, and optionally having one or more heteroatoms selected from O, N, or S;

m is 0, 1, or 2; and

X is a "tissue reactive moiety."

In some embodiments, X is selected from any one of Formulas (IXA) through (IXE), (XA), and (XB), as described herein.

In some embodiments, the present disclosure provides a compound having Formula VIIIB):

(VIIIB)

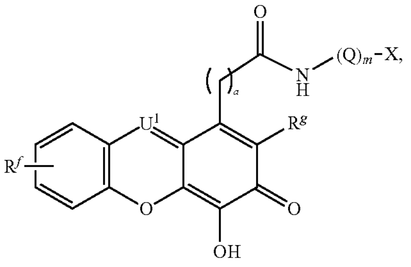

wherein $R^f$ is —$N(R^x)(R^y)$, where $R^x$ and $R^y$ are independently H or a branched or unbranched $C_1$-$C_4$ alkyl group optionally substituted with one or more halogen atoms;

$R^g$ is —H, —$CH_3$ or —$CH_2$—$CH_3$;

$U^1$ is O, N, or S;

a is 0 or an integer ranging from 1 to 6.

Q is a branched or unbranched, linear or cyclic, substituted or unsubstituted group having between 2 and 40 carbon atoms, and optionally having one or more heteroatoms selected from O, N, or S;

m is 0, 1, or 2;

and X is a "tissue reactive moiety."

In some embodiments, X is selected from any one of Formulas (IXA) through (IXE), (XA), and (XB), as described herein.

In some embodiments, the present disclosure provides a compound having Formula (VIIIC):

(VIIIC)

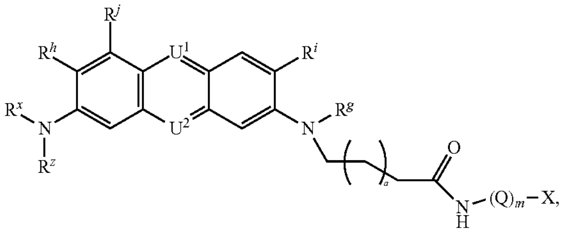

wherein $U^1$ is O, N, or S;

$U^2$ is O or S;

$R^g$ is —$CH_3$ or —$CH_2$—$CH_3$;

$R^i$ is H or a branched or unbranched $C_1$-$C_6$ alkyl group;

or where $R^g$ and $R^i$ together form a 5-, 6-, or 7-membered cyclic or aromatic ring which may be optionally substituted with a halogen, a $C_1$-$C_4$ alkyl group;

$R^h$ is H or a branched or unbranched $C_1$-$C_4$ alkyl group;

$R^x$ is H or a branched or unbranched $C_1$-$C_4$ alkyl group optionally substituted with one or more halogen atoms;

$R^z$ is H, or a branched or unbranched $C_1$-$C_4$ alkyl group optionally substituted with one or more halogen atoms or with a —S(O)(O)—$O^-$ group;

or where $R^x$ and $R^z$ together form a 3-, 4-, or 5-membered ring which may optionally be substituted;

or where $R^h$ and one of $R^x$ or $R^z$ together form a 5-, 6-, or 7-membered cyclic or aromatic ring which may be optionally substituted with one or more halogen atoms or one or more $C_1$-$C_2$ alkyl groups;

$R^j$ is H or a branched or unbranched $C_1$-$C_6$ alkyl group;

or where $R^j$ and $R^h$ form a 5- or 6-membered ring, optionally substituted with one or more $C_1$-$C_4$ alkyl groups;

a is 0 or an integer ranging from 1 to 6;

Q is a branched or unbranched, linear or cyclic, substituted or unsubstituted group having between 2 and 40 carbon atoms, and optionally having one or more heteroatoms selected from O, N, or S;

m is 0, 1, or 2; and

X is a "tissue reactive moiety."

In some embodiments, X is selected from any one of Formulas (IXA) through (IXE), (XA), and (XB), as described herein.

In some embodiments, the present disclosure provides a compound having Formula (VIIID) or (VIIIE):

(VIIID)

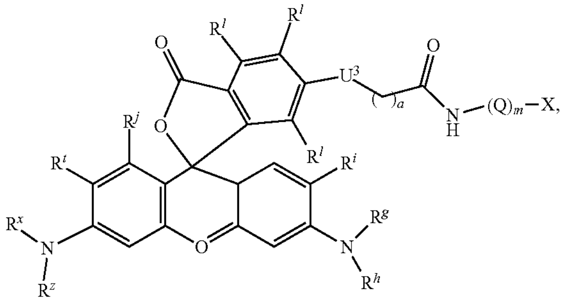

(VIIIE)

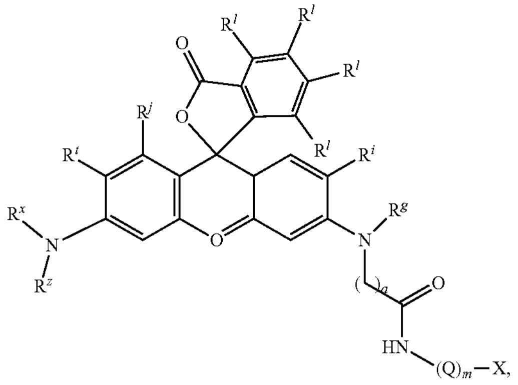

wherein $R^g$ is —$CH_3$ or —$CH_2$—$CH_3$;

$R^i$ is H or a branched or unbranched $C_1$-$C_6$ alkyl group;

or where $R^g$ and $R^i$ together form a 5-, 6-, or 7-membered ring which may be optionally substituted with a halogen, a $C_1$-$C_4$ alkyl group;

$R^h$ is H or a branched or unbranched $C_1$-$C_4$ alkyl group;

$R^x$ is H or a branched or unbranched $C_1$-$C_4$ alkyl group optionally substituted with one or more halogen atoms;

$R^z$ is H, or a $C_1$-$C_4$ alkyl group optionally substituted with one or more halogen atoms or with a —S(O)(O)—$O^-$ group;

$R^t$ is H or a branched or unbranched $C_1$-$C_4$ alkyl group;

or where $R^t$ and one of $R^x$ or $R^z$ together form a 5-, 6-, or 7-membered cyclic or aromatic ring which may be optionally substituted with one or more halogen atoms or one or more $C_1$-$C_2$ alkyl groups;

$R^j$ is H or a branched or unbranched $C_1$-$C_6$ alkyl group;

or where $R^j$ and $R^t$ form a 5- or 6-membered ring, optionally substituted with one or one or more $C_1$-$C_2$ alkyl groups; or where $R^x$, $R^t$, and $R^j$ together form a bicyclic ring which may be saturated or unsaturated and which may be optionally substituted with one or more halogen atoms or one or more $C_1$-$C_2$ alkyl groups;

each $R^l$ is independently H or a halogen atom;

a is 0 or an integer ranging from 1 to 6;

Q is a branched or unbranched, linear or cyclic, substituted or unsubstituted group having between 2 and 40 carbon atoms, and optionally having one or more heteroatoms selected from O, N, or S;

m is 0, 1, or 2; and

X is a "tissue reactive moiety."

In some embodiments, X is selected from any one of Formulas (IXA) through (IXE), (XA), and (XB), as described herein.

In some embodiments, the present disclosure provides a compound having Formula (VIIIF):

(VIIIF)

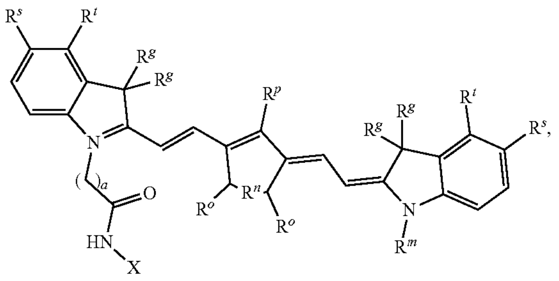

wherein a is 0 or an integer ranging from 1 to 6;

$R^p$ is a halogen atom;

$R^n$ is a bond or —$CH_2$—;

each $R^o$ is independently a branched or unbranched $C_1$-$C_4$ alkyl group, or when $R^n$ is —$CH_2$-then both $R^o$ groups together may form a 6-member cyclic or aromatic ring, optionally substituted with one or more halogen groups or one or more $C_1$-$C_2$ alkyl groups;

each $R^g$ is independently-$CH_3$ or —$CH_2$—$CH_3$;

$R^m$ is H, a branched or unbranched $C_1$-$C_4$ alkyl group which is optionally substituted with one or more halogen atoms and or one or more —S(O)(O)(OH) groups, or a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction;

each $R^s$ or $R^t$ group is independently selected from a branched or unbranched $C_1$-$C_6$ alkyl group;

or wherein any two adjacent $R^s$ and $R^t$ groups and/or any two adjacent $R_g$ and $R^t$ groups may together form a 5- or 6-membered cyclic or aromatic group, optionally substituted with one or more $C_1$-$C_2$ alkyl groups;

Q is a branched or unbranched, linear or cyclic, substituted or unsubstituted group having between 2 and 40 carbon atoms, and optionally having one or more heteroatoms selected from O, N, or S;

m is 0, 1, or 2;

and X is a "tissue reactive moiety."

In some embodiments, X is selected from any one of Formulas (IXA) through (IXE), (XA), and (XB), as described herein.

Non-limiting examples of the compounds of Formula (I) and Formulas (VIIIA) to (VIIIF) are set forth below, along with on slide absorbance spectra.

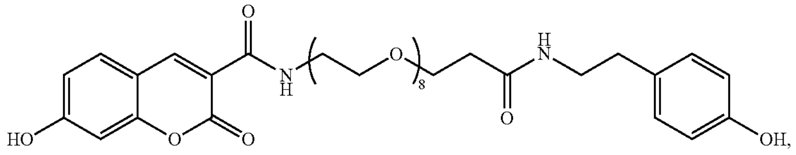

(wavelength max = 345)

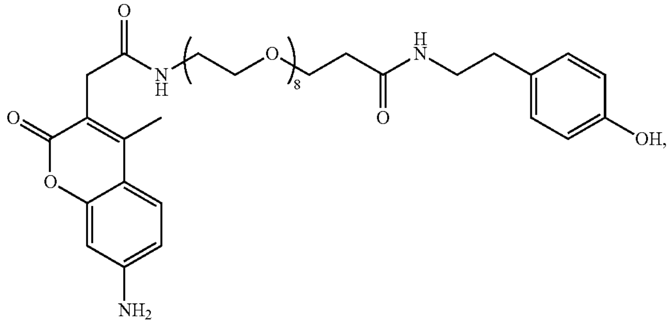

(wavelength max = 345)

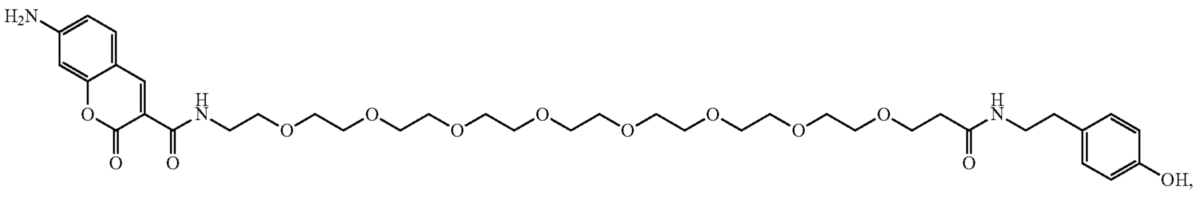

(wavelength max = 380-390)

-continued
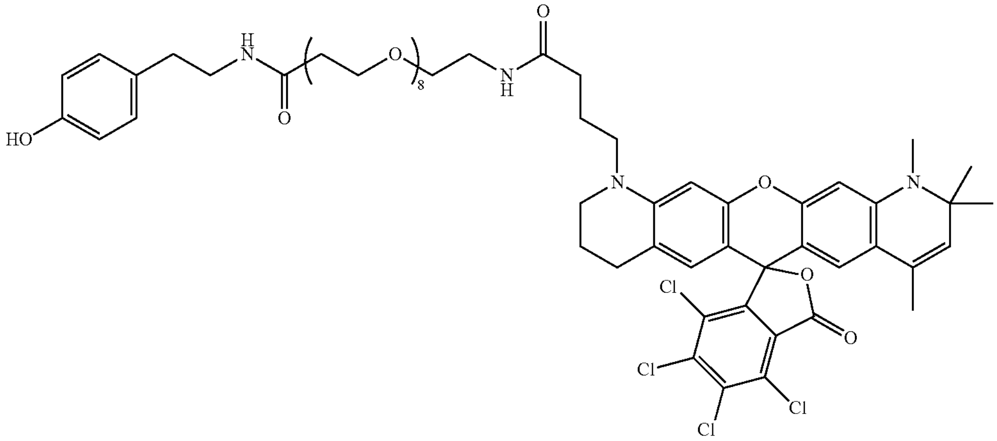
,
(wavelength max = 604)
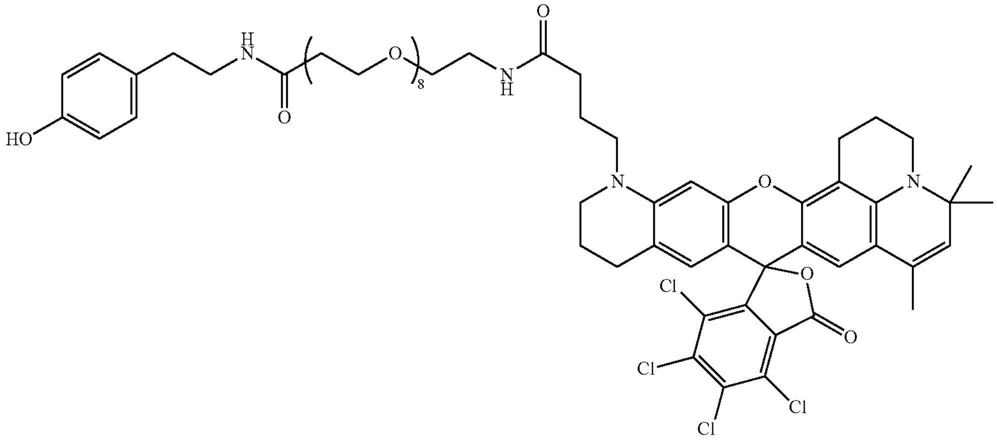
,
(wavelength max = 614)
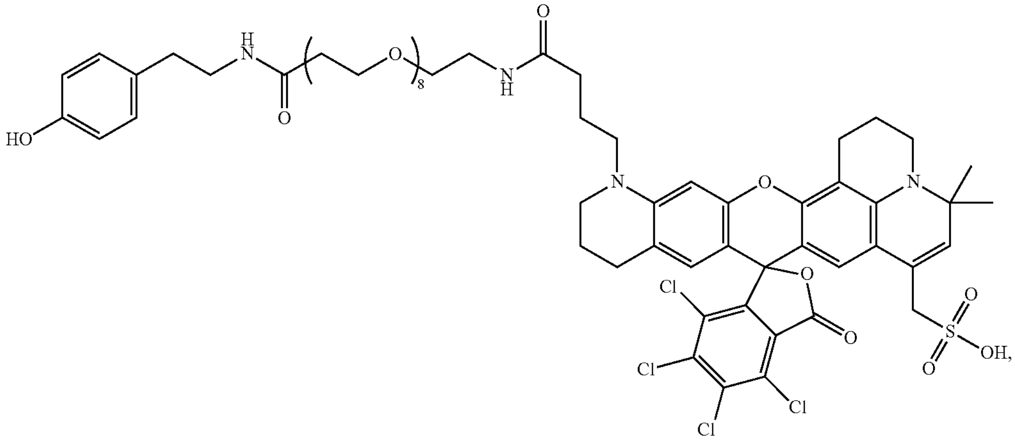
(wavelength max = 614)

-continued
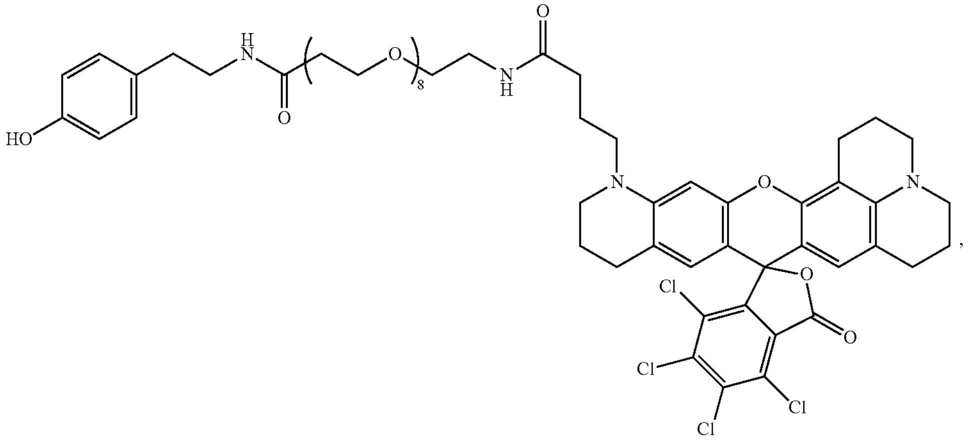
(wavelength max = 598)
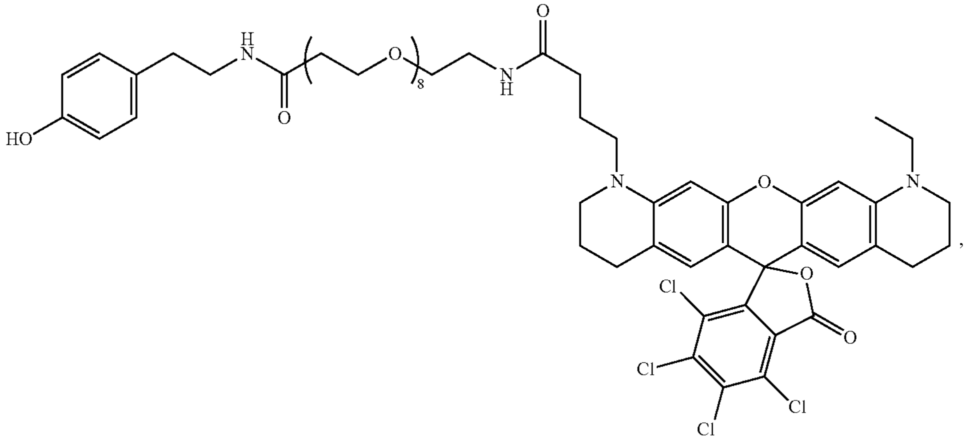
(wavelength max = 588)
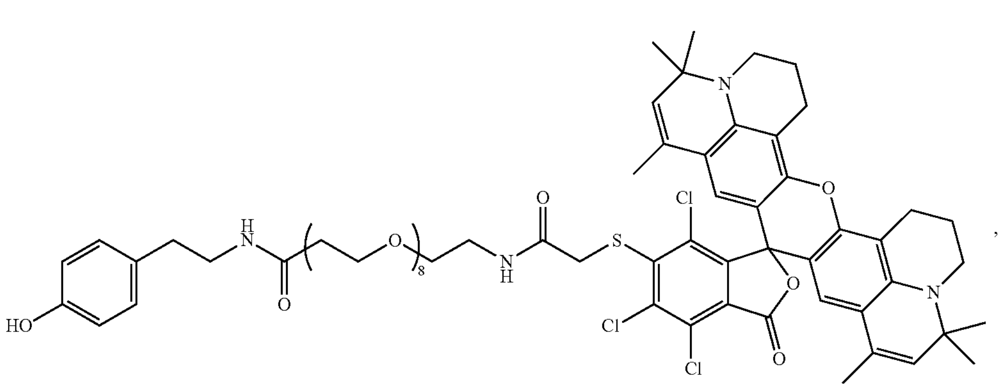
(wavelength max = 634)

-continued
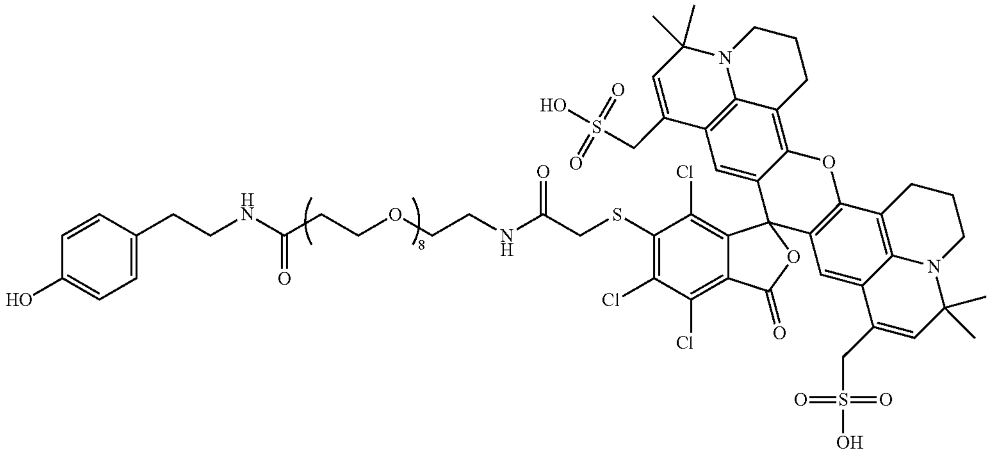
,
(wavelength max = 634)
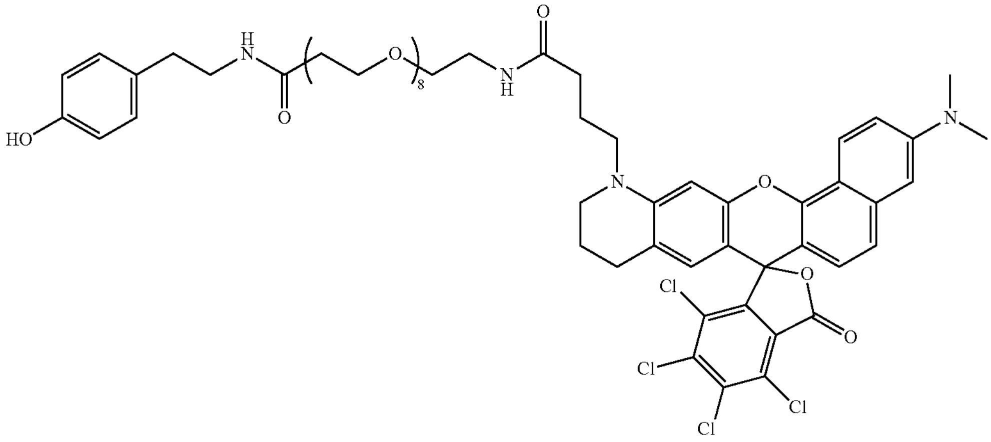
,
(wavelength max = 631)
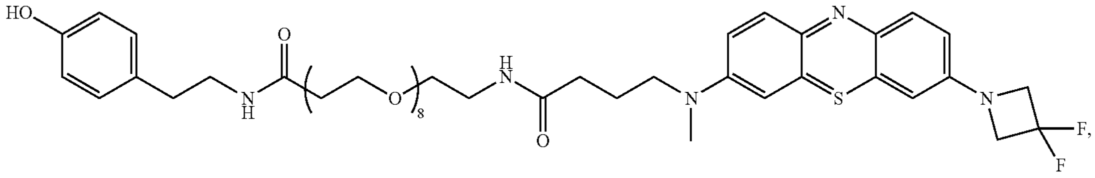
(wavelength max = 649)
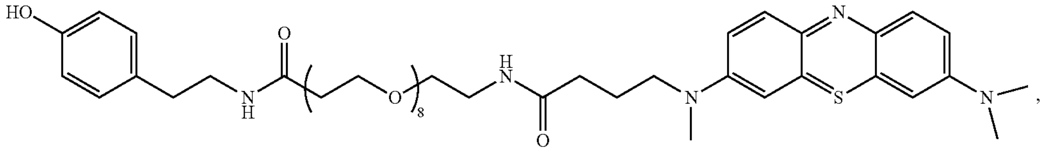
(wavelength max = 665)

-continued
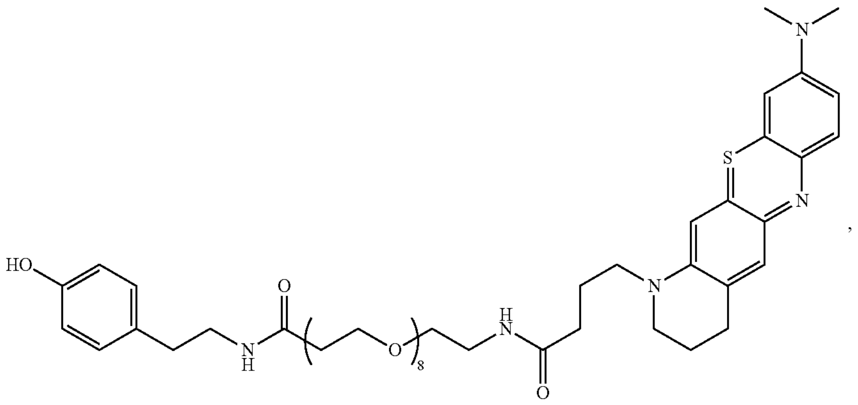
(wavelength max = 675)
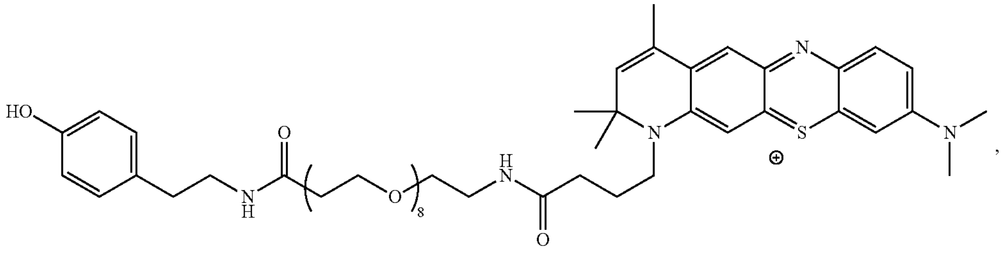
(wavelength max = 694)
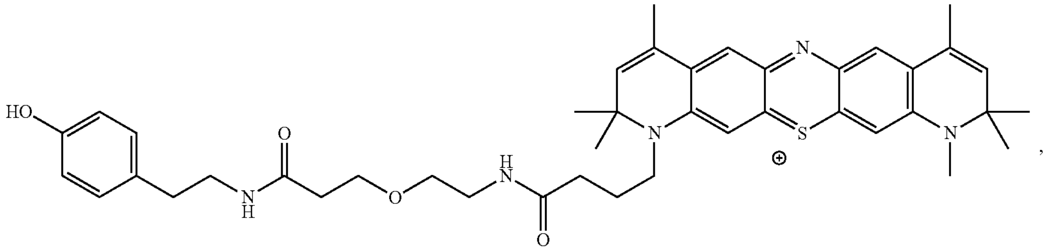
(wavelength max = 710)
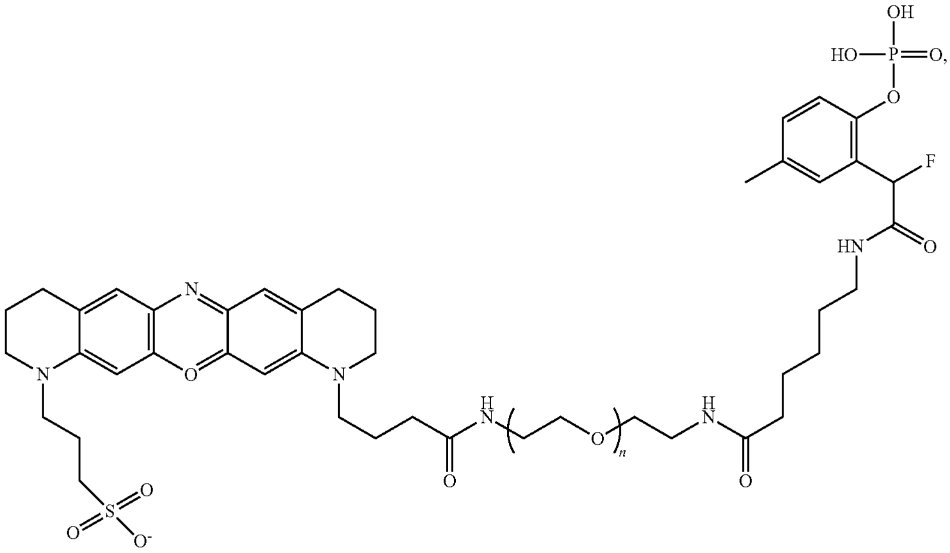
(wavelength max = 665)

-continued
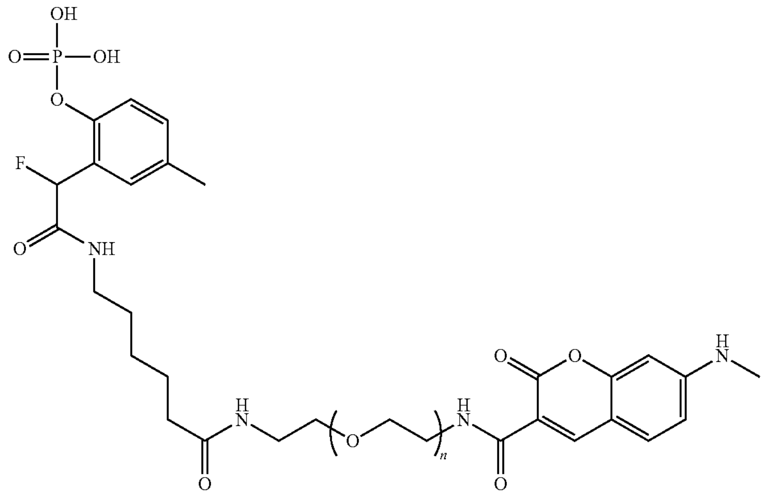
,
(wavelength max = 410)
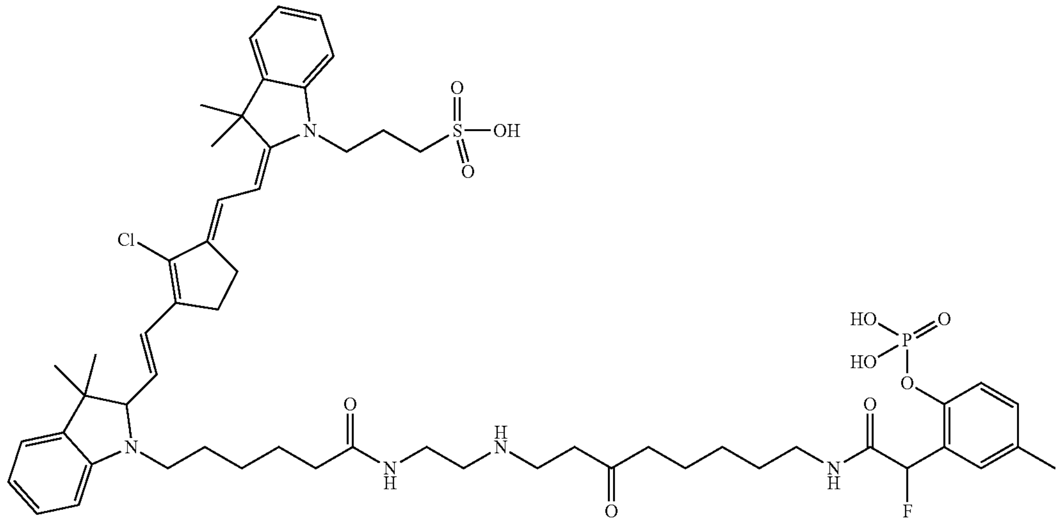
,
(wavelength max = 825)
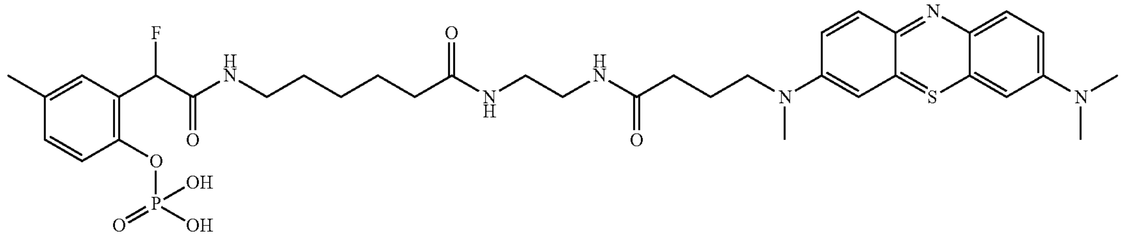
,
(wavelength max = 665)

-continued
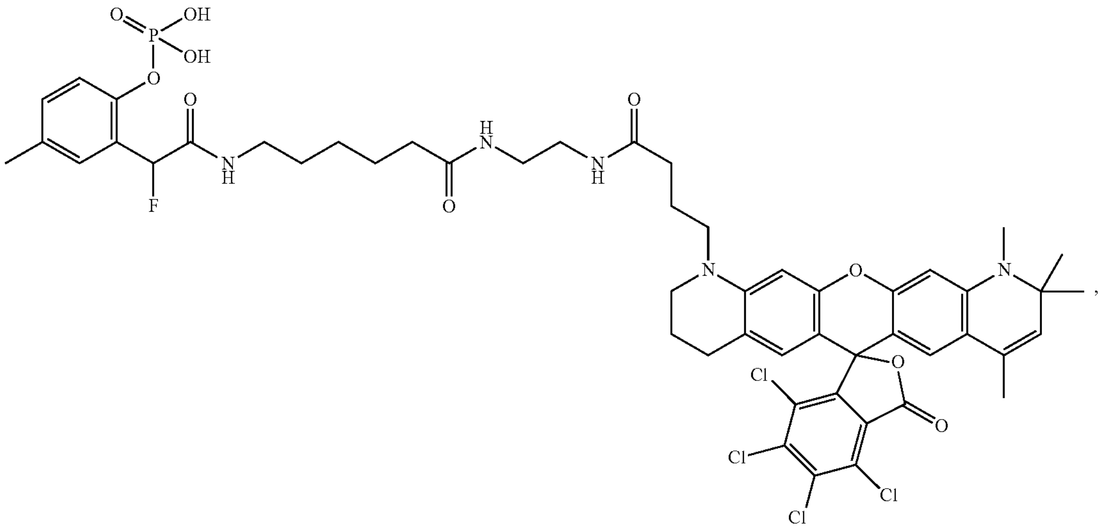
(wavelength max = 604)
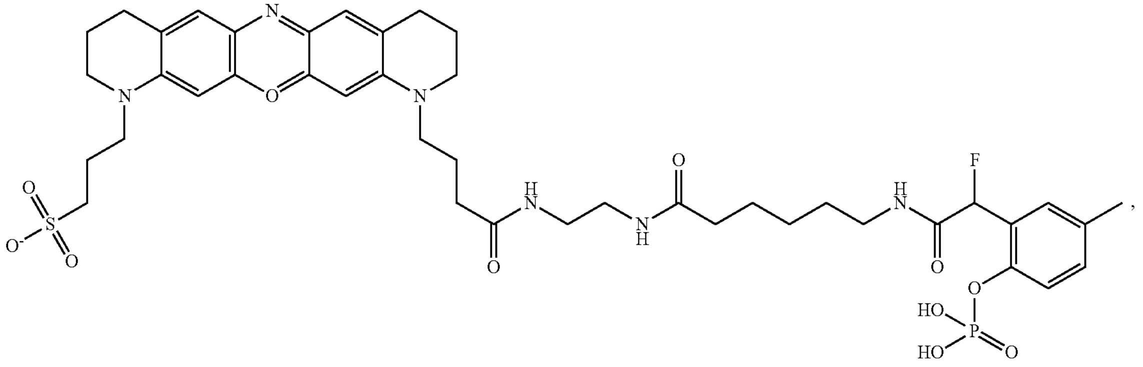
(wavelength max = 665)
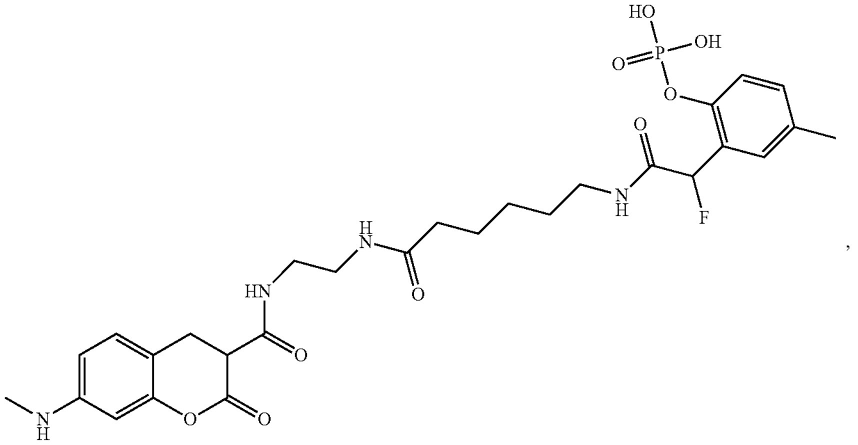
(wavelength max = 410)
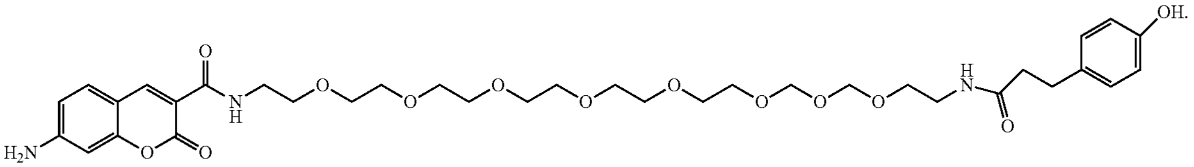 [SMILES: Nc1ccc2cc(C(=O)NCCOCCOCCOCCOCCOCCOCOCOCCNC(=O)CCc3ccc(O)cc3)c(=O)oc2c1]

Compounds Having Formula (XII)

In some embodiments of the present disclosure is a compound having Formula (XII):

$[Y]-[Q]_m-[W]$ (XII), where Q is a branched or unbranched, linear or cyclic, substituted or unsubstituted group having between 2 and 40 carbon atoms, and optionally having one or more heteroatoms selected from O, N, or S; m is 0, 1, or 2; W is a detectable moiety; and Y is a functional group or a moiety including a functional group capable of participating in a "click chemistry" reaction.

In some embodiments, W is moiety having any one of Formulas (IIA), (IIB), (IIC), (IIIA), (IIIB), (IVA), (IVB), (IVC), (IVD), (IVE), (IVF), (IVG), (IVH), (VA), (VB), (VI), (VIIA), (VIIB), and (VIIC). In some embodiments, Y is a functional group or a moiety including a functional group capable of participating in a "click chemistry" reaction. In some embodiments, Y is selected from a dibenzocyclooctyne, a trans-cyclooctene, an alkyne, an alkene, an azide, a tetrazine, a maleimide, a N-hydroxysuccinimide, a thiol, a 1,3-nitrone, an aldehyde, a ketone, a hydrazine, a hydroxylamine, an amino group.

In some embodiments, the present disclosure provides a compound having Formula XIIA):

(XIIA)

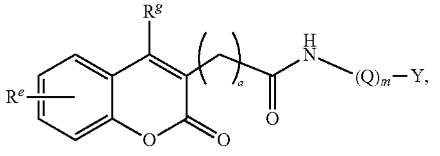

wherein $R^e$ is —OH, —O-alkyl, or —$N(R^x)(R^y)$, where $R^x$ and $R^y$ are independently H or a branched or unbranched $C_1$-$C_4$ alkyl group optionally substituted with one or more halogen atoms, or where $R^x$ and $R^y$ together form a 3-, 4-, or 5-membered cyclic ring which may be optionally substituted with one or more halogen atoms or one or more $C_1$-$C_2$ alkyl groups;

$R^g$ is —H, —$CH_3$ or —$CH_2$—$CH_3$;

a is 0 or an integer ranging from 1 to 4;

Q is a branched or unbranched, linear or cyclic, substituted or unsubstituted group having between 2 and 40 carbon atoms, and optionally having one or more heteroatoms selected from O, N, or S;

m is 0, 1, or 2;

and X is a "tissue reactive moiety."

In some embodiments, Y is selected from a dibenzocyclooctyne, a trans-cyclooctene, an alkyne, an alkene, an azide, a tetrazine, a maleimide, a N-hydroxysuccinimide, a thiol, a 1,3-nitrone, an aldehyde, a ketone, a hydrazine, a hydroxylamine, an amino group.

In some embodiments, the present disclosure provides a compound having Formula XIIB):

(XIIB)

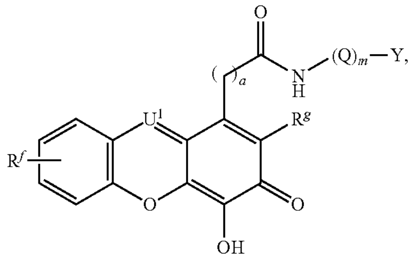

wherein $R^f$ is —$N(R^x)(R^y)$, where $R^x$ and $R^y$ are independently H or a branched or unbranched $C_1$-$C_4$ alkyl group optionally substituted with one or more halogen atoms;

$R^g$ is —H, —$CH_3$ or —$CH_2$—$CH_3$;

$U^1$ is O, N, or S;

a is 0 or an integer ranging from 1 to 6.

Q is a branched or unbranched, linear or cyclic, substituted or unsubstituted group having between 2 and 40 carbon atoms, and optionally having one or more heteroatoms selected from O, N, or S;

m is 0, 1, or 2;

and X is a "tissue reactive moiety."

In some embodiments, Y is selected from a dibenzocyclooctyne, a trans-cyclooctene, an alkyne, an alkene, an azide, a tetrazine, a maleimide, a N-hydroxysuccinimide, a thiol, a 1,3-nitrone, an aldehyde, a ketone, a hydrazine, a hydroxylamine, an amino group.

In some embodiments, the present disclosure provides a compound having Formula (XIIC):

(XIIC)

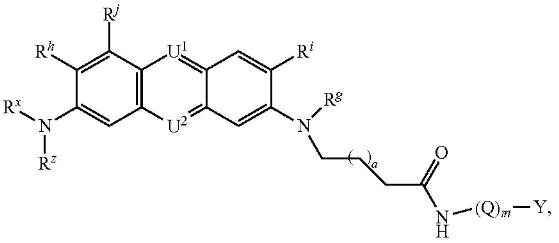

wherein $U^1$ is O, N, or S;

$U^2$ is O or S;

$R^g$ is —$CH_3$ or —$CH_2$—$CH_3$;

$R^i$ is H or a branched or unbranched $C_1$-$C_6$ alkyl group;

or where $R^g$ and $R^i$ together form a 5-, 6-, or 7-membered cyclic or aromatic ring which may be optionally substituted with a halogen, a $C_1$-$C_4$ alkyl group;

$R^h$ is H or a branched or unbranched $C_1$-$C_4$ alkyl group;

$R^x$ is H or a branched or unbranched $C_1$-$C_4$ alkyl group optionally substituted with one or more halogen atoms;

$R^z$ is H, or a branched or unbranched $C_1$-$C_4$ alkyl group optionally substituted with one or more halogen atoms or with a —S(O)(O)—$O^-$ group;

or where $R^x$ and $R^z$ together form a 3-, 4-, or 5-membered ring which may optionally be substituted;

or where $R^h$ and one of $R^x$ or $R^z$ together form a 5-, 6-, or 7-membered cyclic or aromatic ring which may be optionally substituted with one or more halogen atoms or one or more $C_1$-$C_2$ alkyl groups;

$R^j$ is H or a branched or unbranched $C_1$-$C_6$ alkyl group;

or where $R^j$ and $R^h$ form a 5- or 6-membered ring, optionally substituted with one or more $C_1$-$C_4$ alkyl groups;

a is 0 or an integer ranging from 1 to 6;

Q is a branched or unbranched, linear or cyclic, substituted or unsubstituted group having between 2 and 40 carbon atoms, and optionally having one or more heteroatoms selected from O, N, or S;

m is 0, 1, or 2;

and X is a "tissue reactive moiety."

In some embodiments, Y is selected from a dibenzocyclooctyne, a trans-cyclooctene, an alkyne, an alkene, an azide, a tetrazine, a maleimide, a N-hydroxysuccinimide, a thiol, a 1,3-nitrone, an aldehyde, a ketone, a hydrazine, a hydroxylamine, an amino group.

In some embodiments, the present disclosure provides a compound having Formula (XIID) or (XIIE):

(XIID)

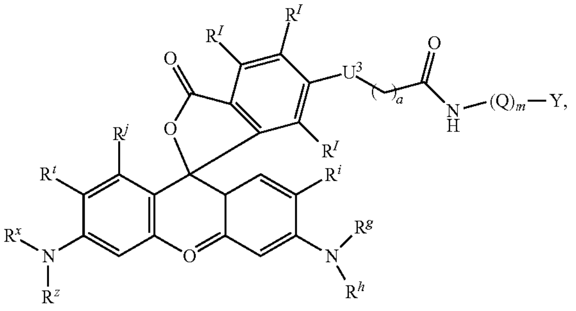

(XIIE)

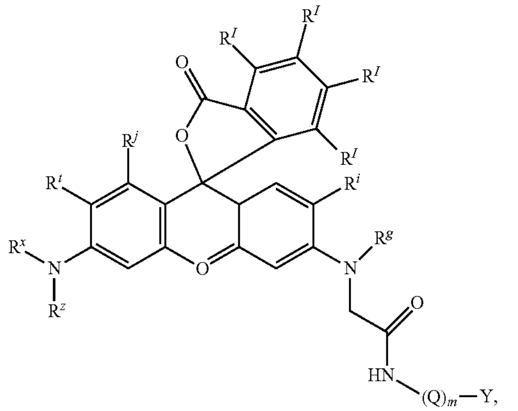

wherein $R^g$ is —$CH_3$ or —$CH_2$—$CH_3$;

$R^i$ is H or a branched or unbranched $C_1$-$C_6$ alkyl group;

or where $R^g$ and $R^i$ together form a 5-, 6-, or 7-membered ring which may be optionally substituted with a halogen, a $C_1$-$C_4$ alkyl group;

$R^h$ is H or a branched or unbranched $C_1$-$C_4$ alkyl group;

$R^x$ is H or a branched or unbranched $C_1$-$C_4$ alkyl group optionally substituted with one or more halogen atoms;

$R^z$ is H, or a $C_1$-$C_4$ alkyl group optionally substituted with one or more halogen atoms or with a —S(O)(O)—$O^-$ group;

$R^t$ is H or a branched or unbranched $C_1$-$C_4$ alkyl group;

or where $R^t$ and one of $R^x$ or $R^z$ together form a 5-, 6-, or 7-membered cyclic or aromatic ring which may be optionally substituted with one or more halogen atoms or one or more $C_1$-$C_2$ alkyl groups;

$R^j$ is H or a branched or unbranched $C_1$-$C_6$ alkyl group;

or where $R^j$ and $R^t$ form a 5- or 6-membered ring, optionally substituted with one or one or more $C_1$-$C_2$ alkyl groups; or where $R^x$, $R^t$, and $R^j$ together form a bicyclic ring which may be saturated or unsaturated and which may be optionally substituted with one or more halogen atoms or one or more $C_1$-$C_2$ alkyl groups;

each $R^l$ is independently H or a halogen atom;

a is 0 or an integer ranging from 1 to 6;

Q is a branched or unbranched, linear or cyclic, substituted or unsubstituted group having between 2 and 40 carbon atoms, and optionally having one or more heteroatoms selected from O, N, or S;

m is 0, 1, or 2;

and Y is a "tissue reactive moiety."

In some embodiments, Y is selected from a dibenzocyclooctyne, a trans-cyclooctene, an alkyne, an alkene, an azide, a tetrazine, a maleimide, a N-hydroxysuccinimide, a thiol, a 1,3-nitrone, an aldehyde, a ketone, a hydrazine, a hydroxylamine, an amino group.

In some embodiments, the present disclosure provides a compound having Formula (XIIF):

(XIIF)

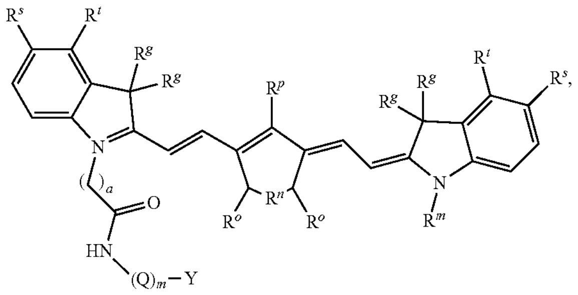

wherein a is 0 or an integer ranging from 1 to 6;

$R^p$ is a halogen atom;

$R^n$ is a bond or —$CH_2$—;

each $R^o$ is independently a branched or unbranched $C_1$-$C_4$ alkyl group, or when $R^n$ is —$CH_2$-then both $R^o$ groups together may form a 6-member cyclic or aromatic ring, optionally substituted with one or more halogen groups or one or more $C_1$-$C_2$ alkyl groups;

each $R^g$ is independently-$CH_3$ or —$CH_2$—$CH_3$;

$R^m$ is H, a branched or unbranched $C_1$-$C_4$ alkyl group which is optionally substituted with one or more halogen atoms and or one or more —S(O)(O)(OH) groups, or a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction;

each $R^s$ or $R^t$ group is independently selected from a branched or unbranched $C_1$-$C_6$ alkyl group;

or wherein any two adjacent $R^s$ and $R^t$ groups and/or any two adjacent $R_g$ and $R^t$ groups may together form a 5- or 6-membered cyclic or aromatic group, optionally substituted with one or more $C_1$-$C_2$ alkyl groups;

Q is a branched or unbranched, linear or cyclic, substituted or unsubstituted group having between 2 and 40 carbon atoms, and optionally having one or more heteroatoms selected from O, N, or S;

m is 0, 1, or 2;

and Y is a "tissue reactive moiety."

In some embodiments, Y is selected from a dibenzocyclooctyne, a trans-cyclooctene, an alkyne, an alkene, an azide, a tetrazine, a maleimide, a N-hydroxysuccinimide, a thiol, a 1,3-nitrone, an aldehyde, a ketone, a hydrazine, a hydroxylamine, an amino group.

Non-limiting examples of compounds having Formula (I) and Formulas (XIIA) through (XIIF) are set forth below, along with on slide absorbance spectra.

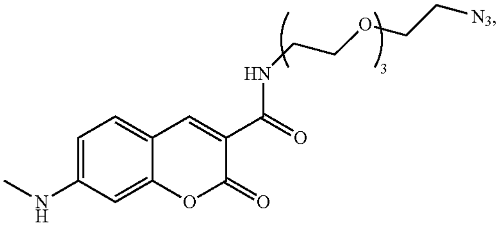

wavelength max = 410

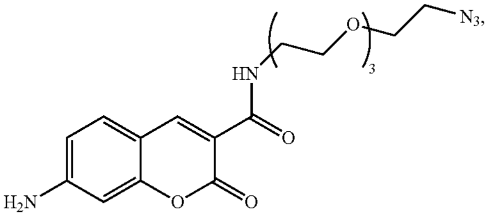

wavelength max = 390

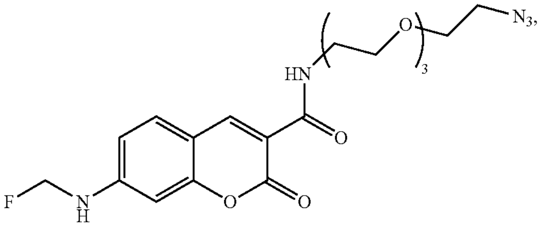

wavelength max = 390

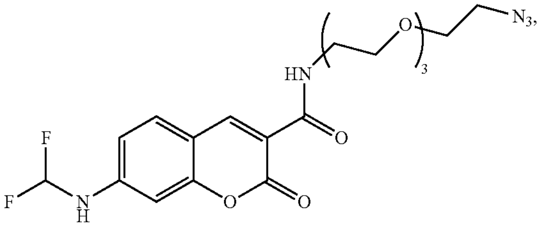

wavelength max = 375

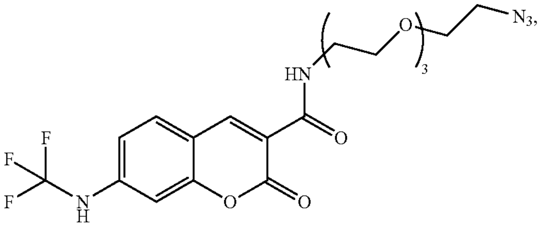

wavelength max = 365

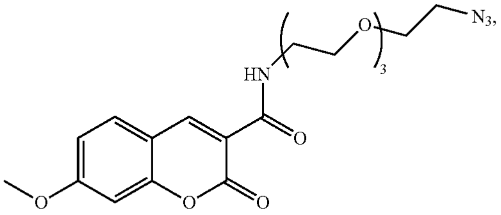

wavelength max = 330

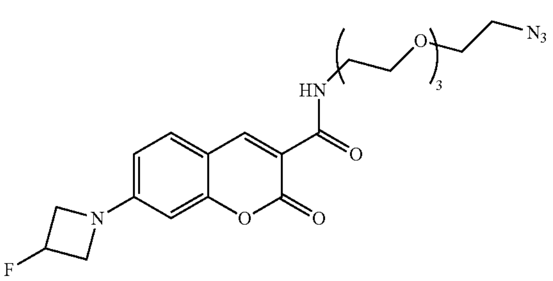

wavelength max = 375 ,

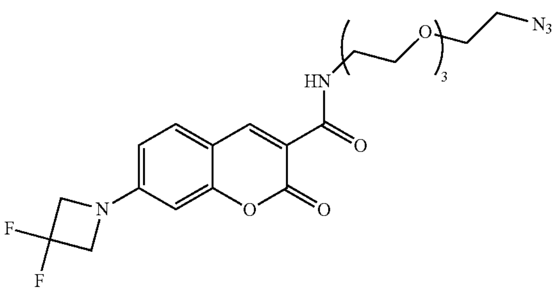

wavelength max = 365 ,

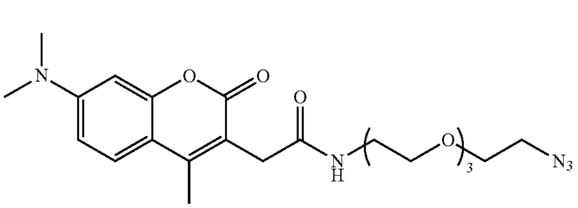

wavelength max = 410 ,

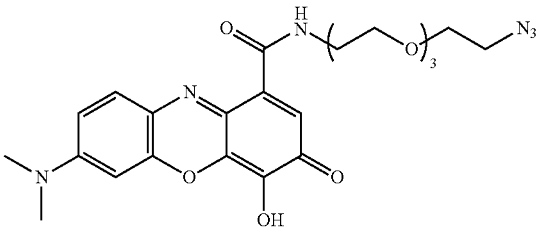

wavelength max = 630 ,

-continued
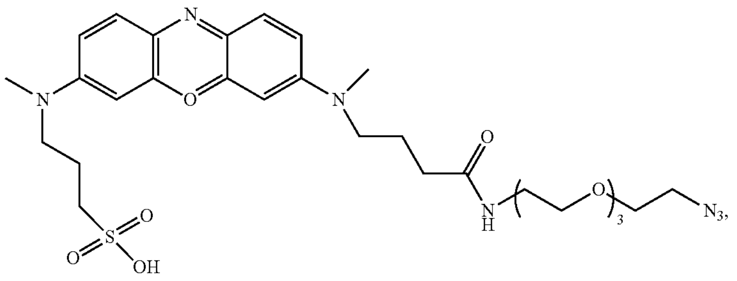
wavelength, max = 620
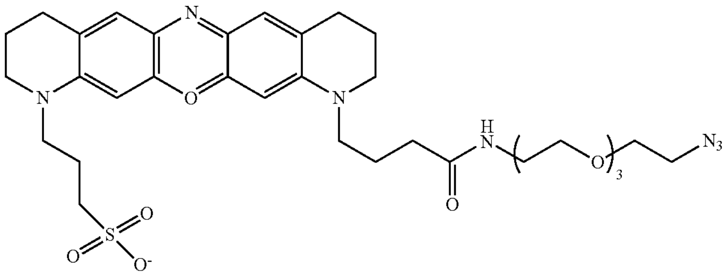
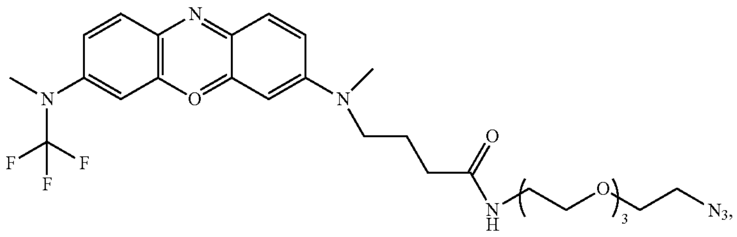
wavelength max = 825
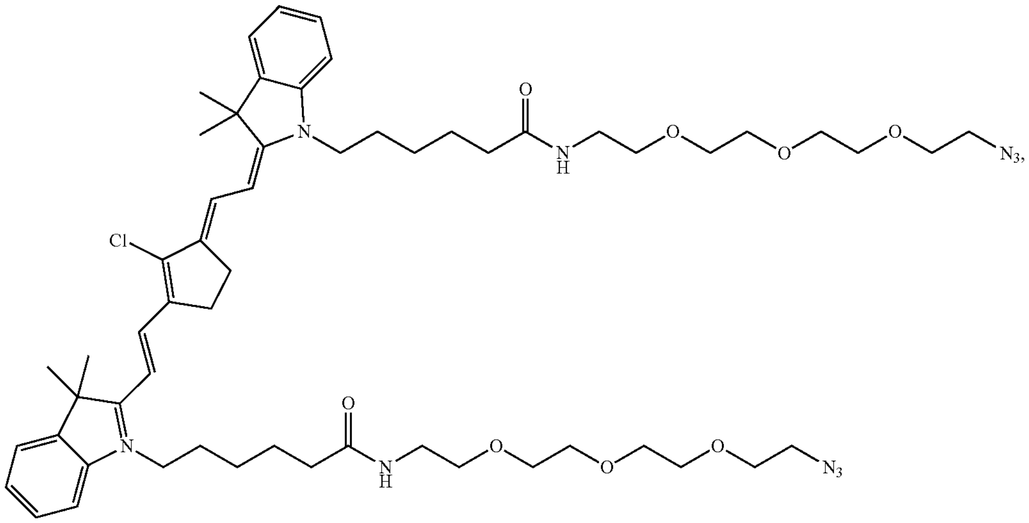
wavelength max = 825

-continued
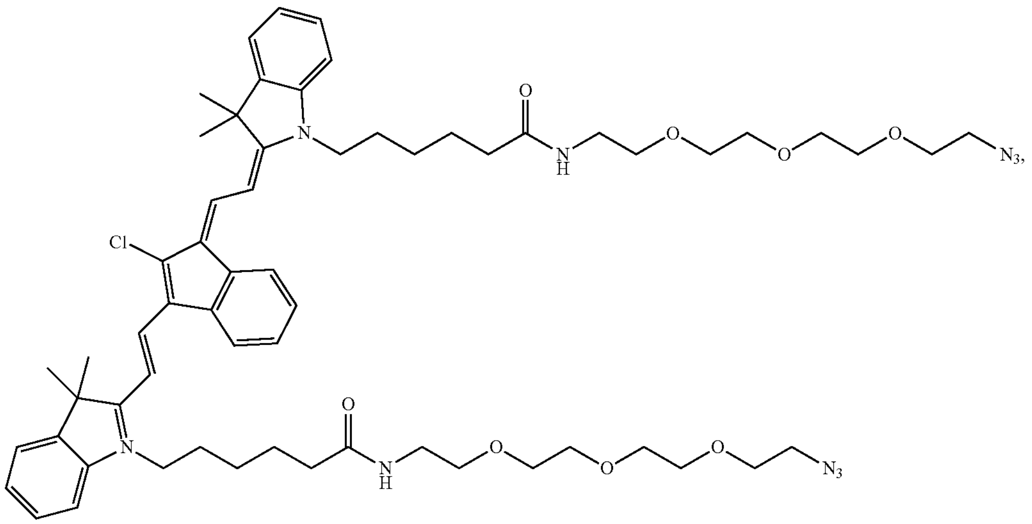
wavelength max = 835
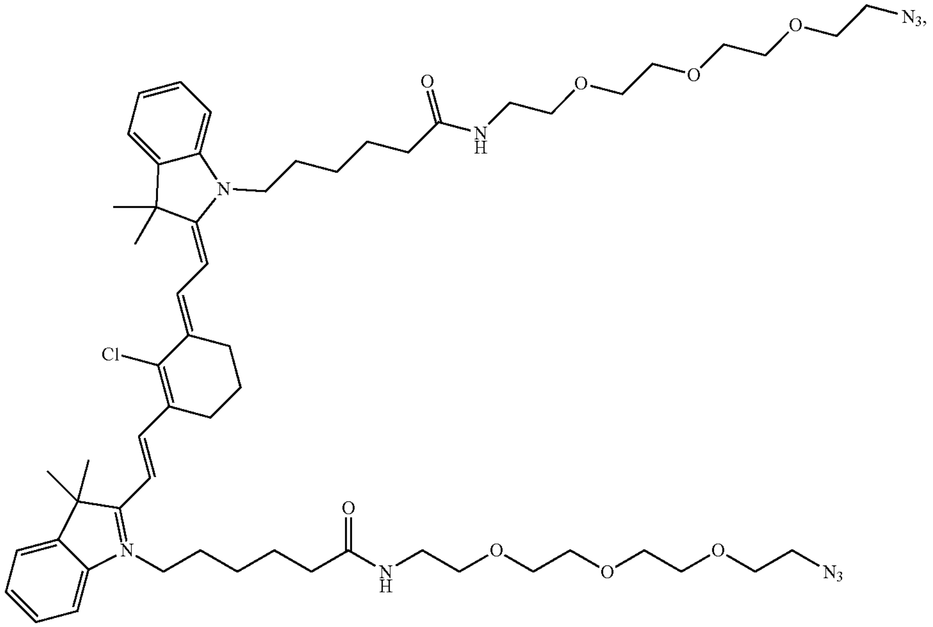
wavelength max = 815

-continued
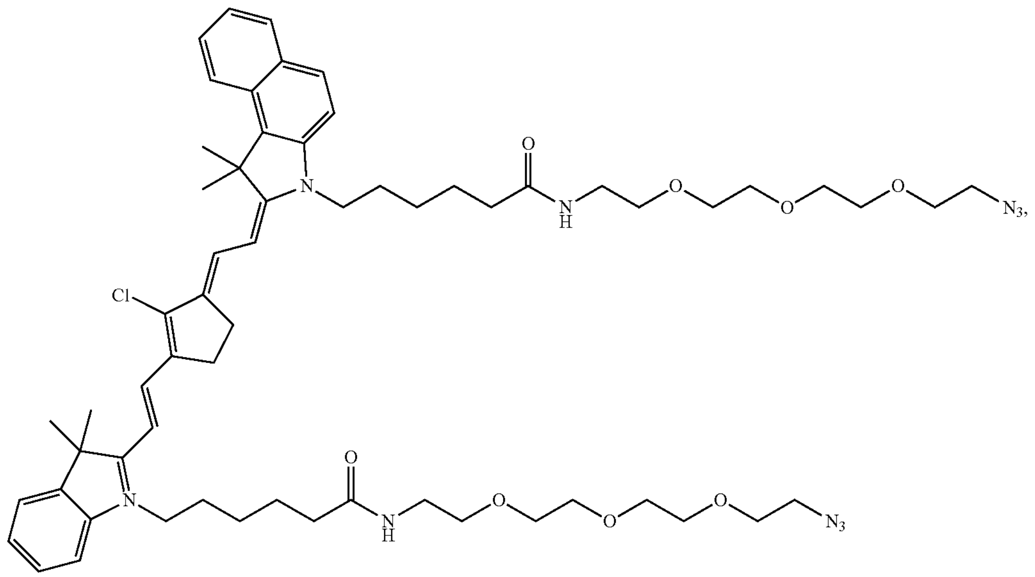
wavelength max = 870
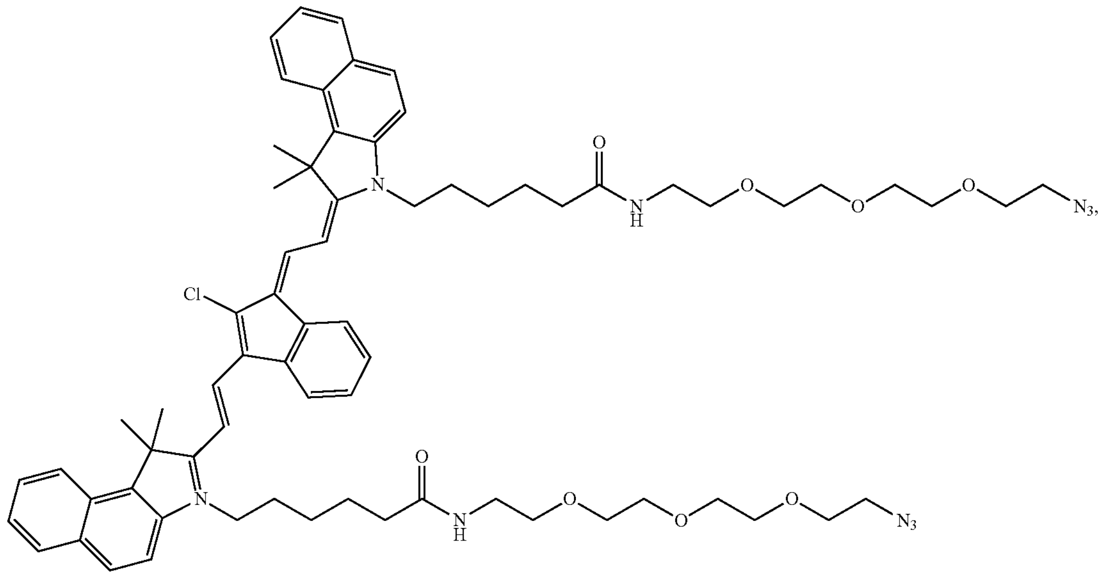
wavelength max = 880

-continued
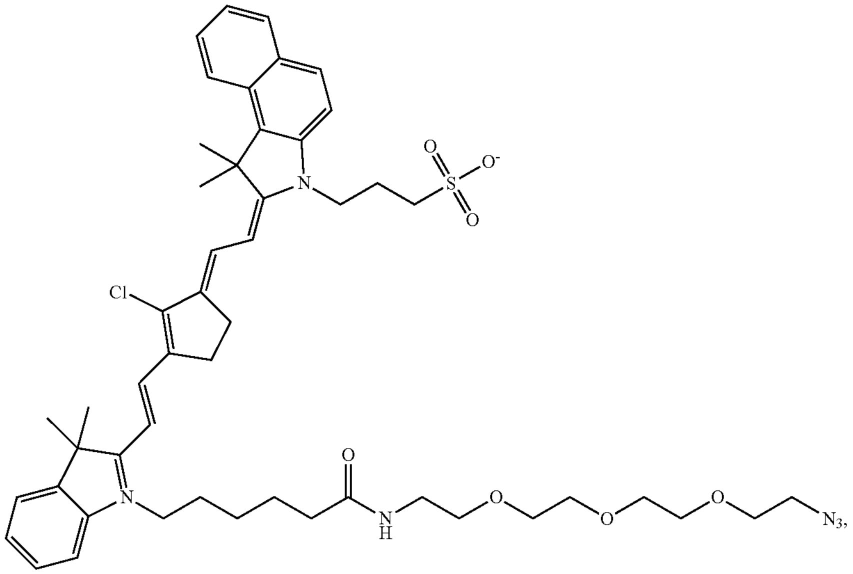
wavelength max = 850
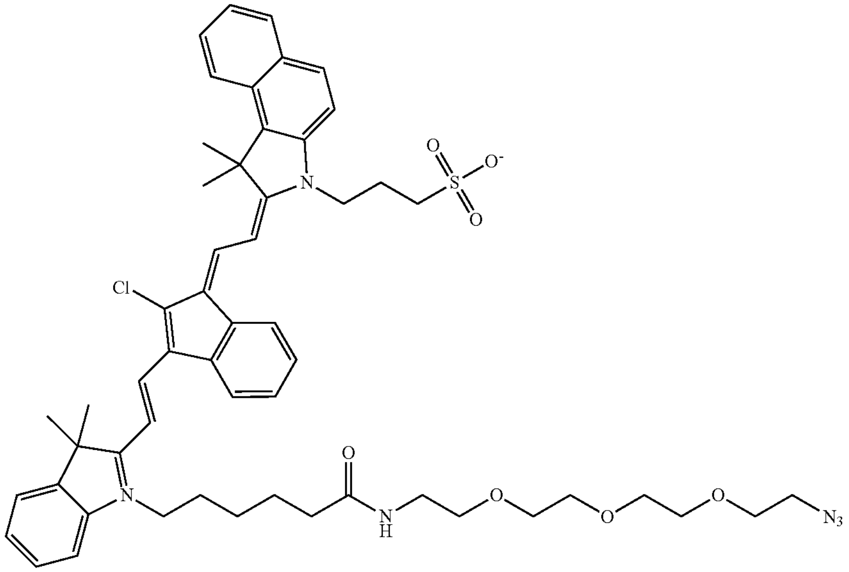
wavelength max = 860

-continued
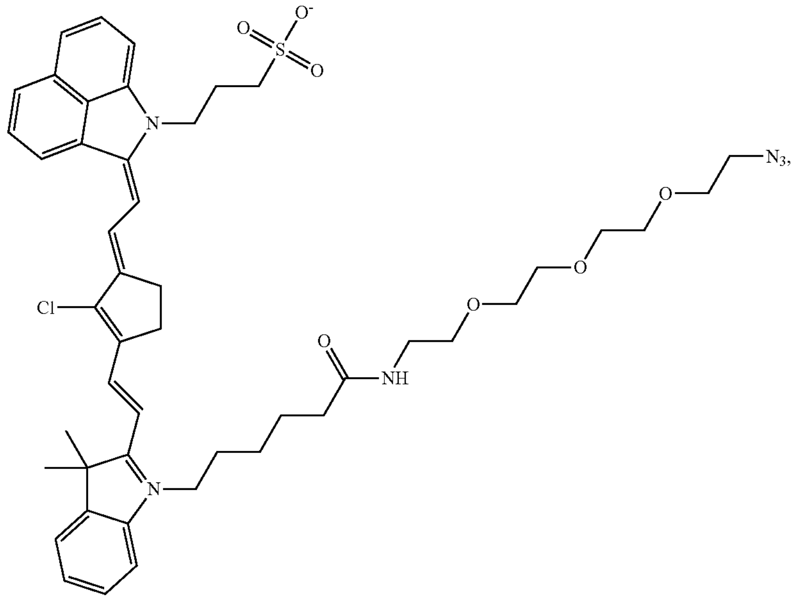
wavelength max = 880
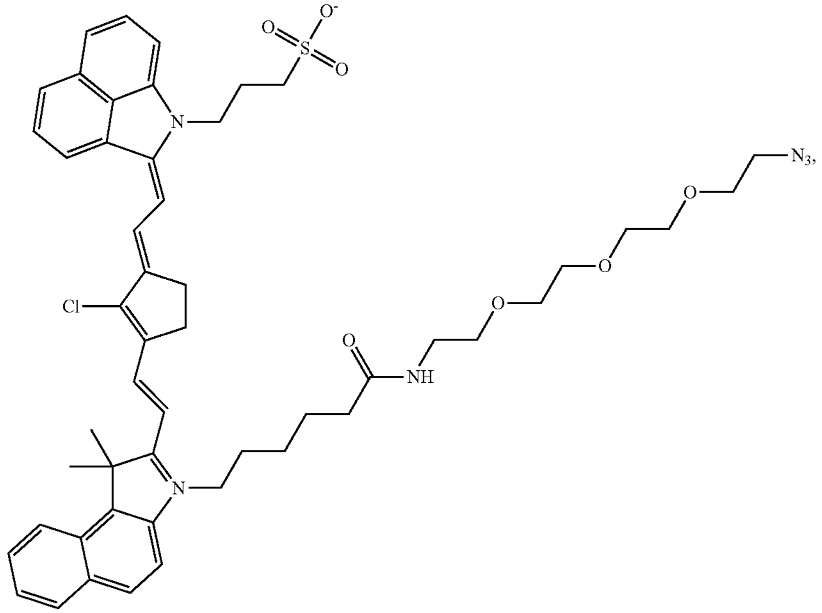
wavelength max = 905

-continued
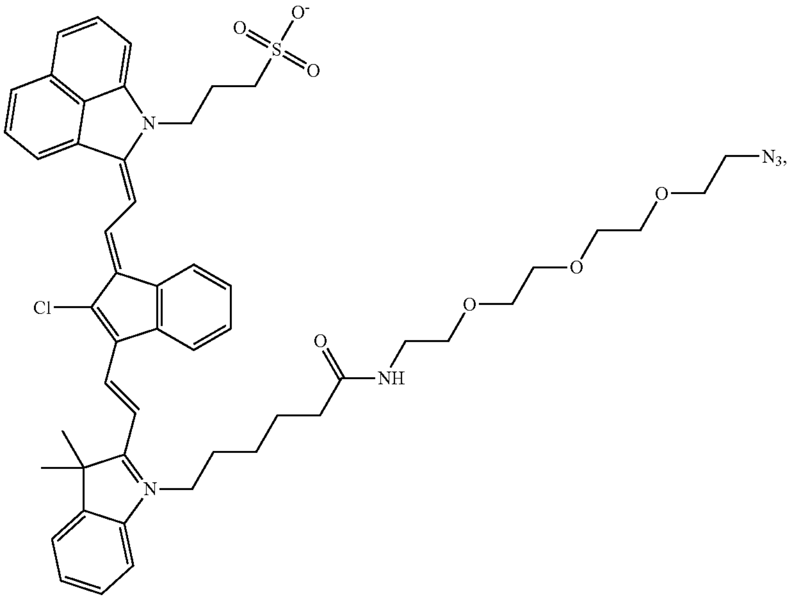
wavelength max = 905
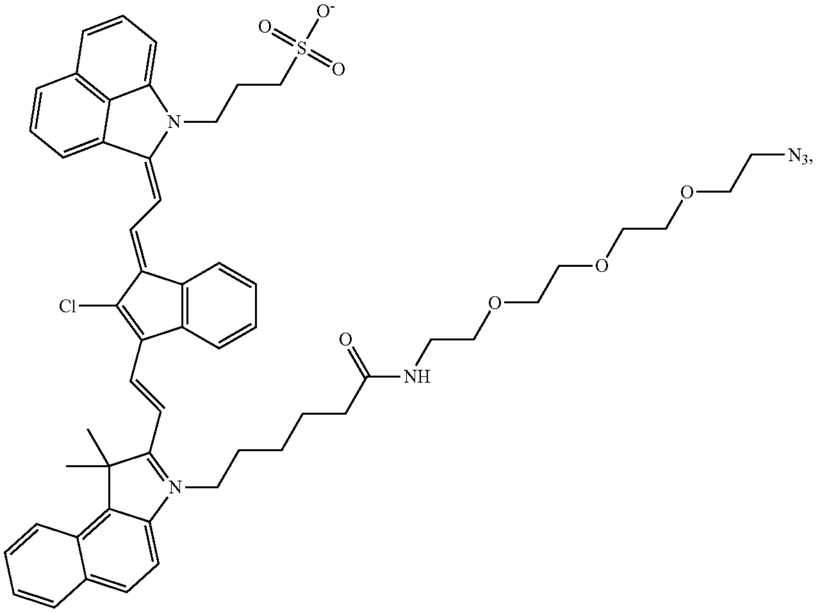
wavelength max = 915
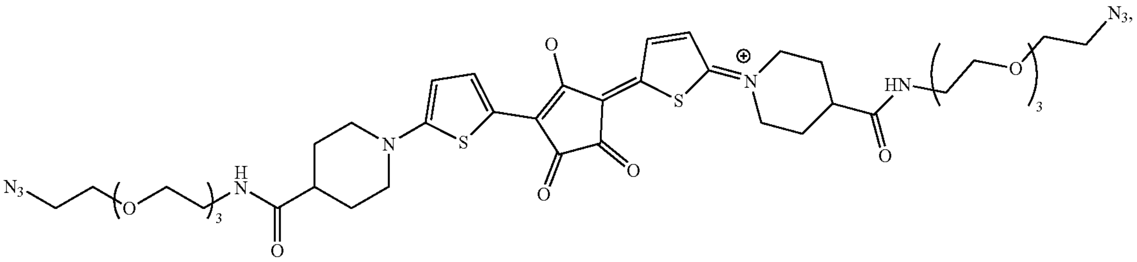
wavelength max = 804

-continued
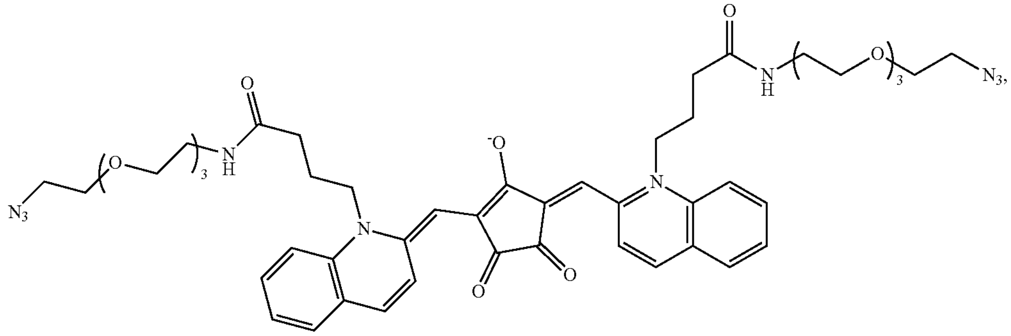
wavelength max = 850
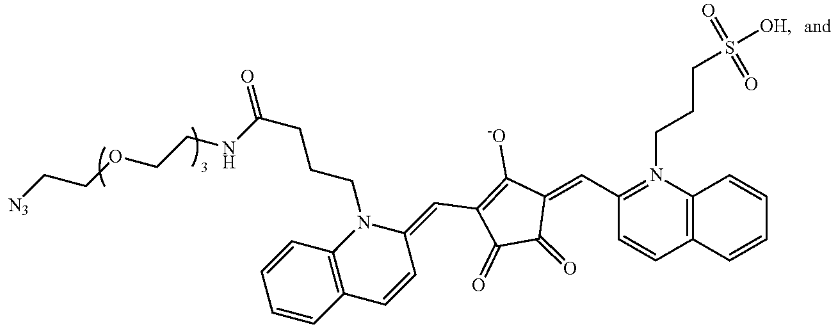
and
wavelength max = 850
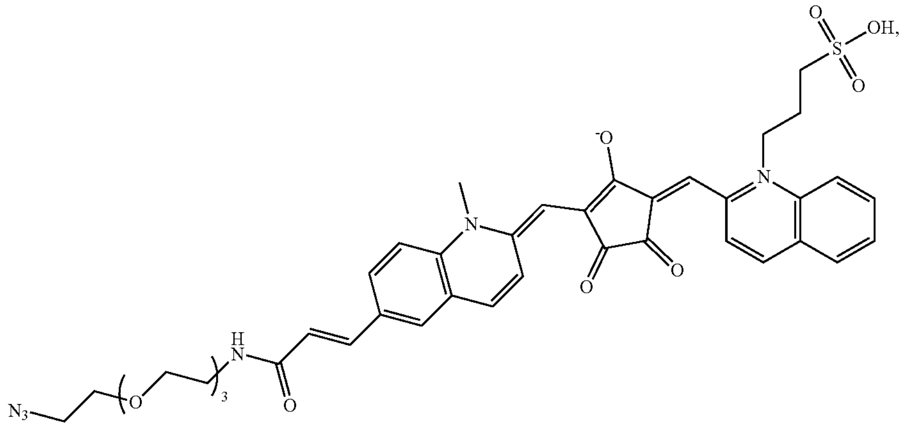
wavelength max = 860

-continued

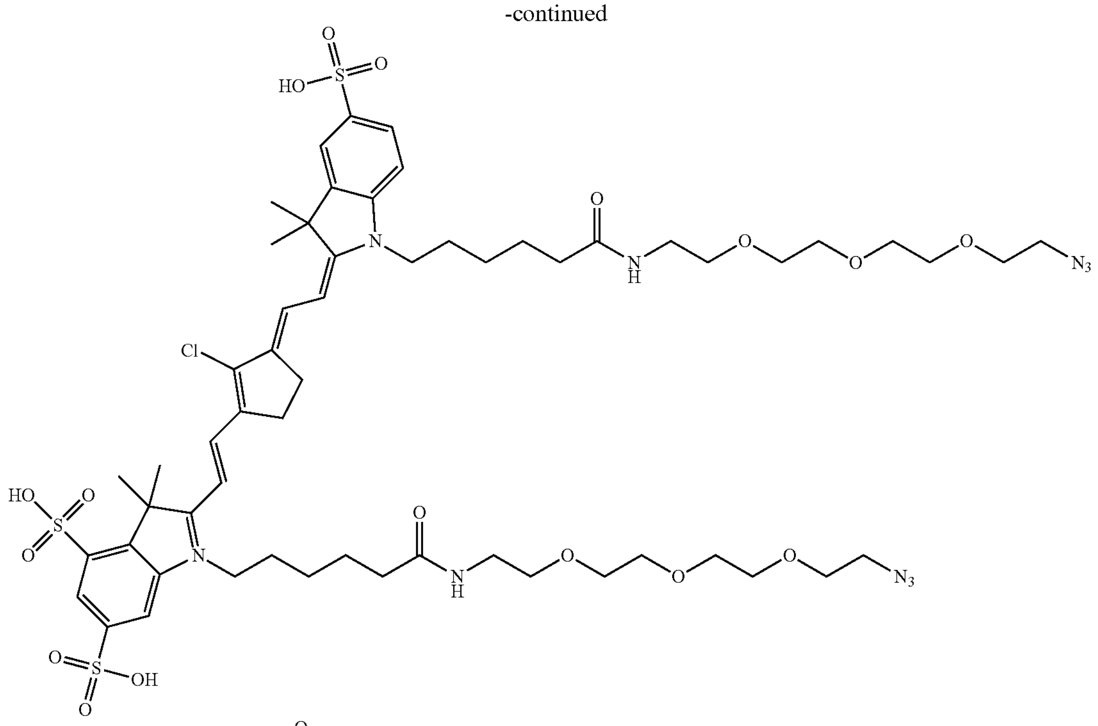

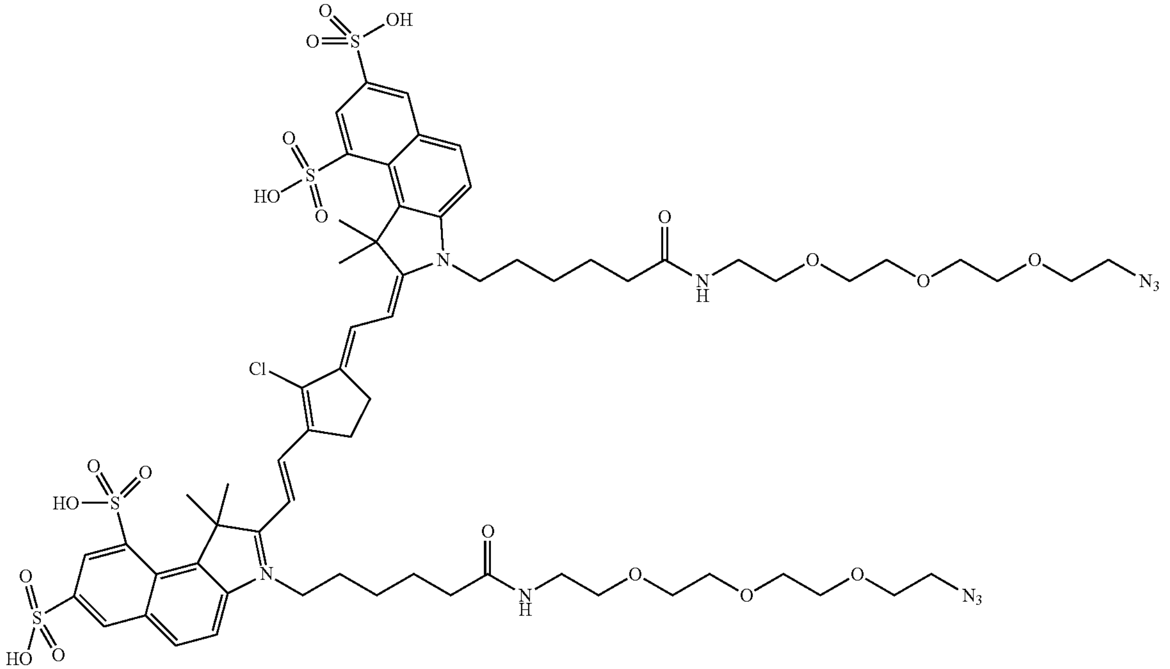

The skilled artisan will appreciate that while each of the exemplified compounds includes an azide group (i.e., $N_3$), that another functional group capable of participating in a "click chemistry" reaction may be substituted for the azide group, including any of the click functional groups described herein (see, for instance, Table 1).

Kits

The present disclosure provides kits comprising two subsets of click conjugates. A first subset of click conjugates comprises a tissue reactive moiety coupled to a reactive functional group through an optional linker. In some embodiments, this first subset of click conjugates is used as first members of pairs of click conjugates. A second subset of click conjugates comprises one or more detectable moieties coupled to a reactive functional group through an optional linker. In some embodiments, this second subset of click conjugates are used as second members of pairs of click conjugates (see the "Methods" described herein). It will be appreciated that the different subsets of click conjugates disclosed herein may serve as modular "building blocks" such that when any two conjugates having appropriate reactive function groups are combined (a "pair of click conjugates"), they may undergo a reaction and form a covalent bond, thereby coupling the two conjugates to form a "click adduct" having the desired structure or component parts.

In some embodiments, the "click adducts" formed may serve as species suitable for detecting targets in a biological assay. Without wishing to be bound by any particular theory, it is believed that the click conjugates disclosed herein are stable in aqueous media, and thus suitable for use in certain biological assays, including in IHC and ISH.

In some embodiments, a kit comprises (a) a compound having Formula (XIII) (a "detectable conjugate"):

$$[Y^1]\text{-}[Q]_m\text{-}[W] \quad \text{(XIII)},$$

where Q is a branched or unbranched, linear or cyclic, substituted or unsubstituted group having between 2 and 40 carbon atoms, and optionally having one or more heteroatoms selected from O, N, or S;

m is 0, 1, or 2;

W is a detectable moiety, including any of those described herein; and $Y^1$ comprises a moiety including a first member of a pair of reactive functional groups capable of participating in a click chemistry reaction; and (b) a compound having Formula (XIV) (a "tissue reactive conjugate"):

$$[X]\text{-}[M]_n\text{-}[Y^2] \quad \text{(XIV)},$$

wherein X is a "tissue reactive moiety;"

n is 0, 1, or 2;

M is a substituted or unsubstituted, linear or cyclic, aliphatic group having between 1 and 12 carbon atoms, and optionally substituted one or more heteroatoms selected from O, N, or S, and optionally including one or more carbonyl groups; and $Y^2$ comprises a moiety including a second member of the pair of reactive functional groups capable of participating in a click chemistry reaction.

In some embodiments, $Y^1$ and $Y^2$ are selected from a dibenzocyclooctyne, a trans-cyclooctene, an alkyne, an alkene, an azide, a tetrazine, a maleimide, a N-hydroxysuccinimide, a thiol, a 1,3-nitrone, an aldehyde, a ketone, a hydrazine, a hydroxylamine, an amino group, with the proviso that $Y^1$ and $Y^2$ are different and capable of reacting with one another. The skilled artisan will recognize that the click conjugates disclosed herein are suitable for coupling to each other to form "click adducts." The skilled artisan will also recognize that for one member of a pair of click conjugates to react with another member of the pair of click conjugates, and thus form a covalent bond, the two members of the pair of click conjugates must have reactive functional groups capable of reacting with each other. The table which follows exemplifies different pairs of reactive functional groups that will react with each other to form a covalent bond. Examples of suitable $Y^1$ and $Y^2$ are set forth in Table 1.

In some embodiments, the click conjugates are coupled via "strain-promoted azide-alkyne cycloaddition" (SPAAC), or "TCO-tetrazine ligation" (TTL). SPAAC involves the reaction between azides and strained alkynes, whose high energy allows the 1,3-dipolar cycloaddition to occur in the absence of a Cu(I) catalyst (required for traditional azide-alkyne "click" chemistry). In some embodiments, dibenzocyclooctynes are utilized as the strained cyclooctyne due to their commercial availability and literature precedent. TTL utilizes the reaction between trans-cyclooctene and tetrazine to form a dihydropyridazine bond. These reagents are also commercially available and have been shown to react orthogonally to the SPAAC system.

TABLE 1

First and second members of reactive functional group pairs.

| Reactive Functional Group on a First Member of a Pair of Click Conjugates | Reactive Functional Group on a Second Member of a Pair of Click Conjugates |
|---|---|
| Alkyne | Azide |
| Azide | Alkyne |
| diarylcyclooctyne ("DBCO") | Azide |
| Alkene | Tetrazine |
| Trans-cyclooctene ("TCO") | Tetrazine |
| Maleimide | Thiol |
| DBCO | 1,3-Nitrone |
| Aldehyde or ketone | Hydrazine |
| Aldehyde or ketone | Hydroxylamine |
| Azide | DBCO |
| Tetrazine | TCO |
| Thiol | Maleimide |
| 1,3-Nitrone | DBCO |
| Hydrazine | Aldehyde or ketone |
| Hydroxylamine | Aldehyde or ketone |
| Tetrazine | Alkene |

In some embodiments, W is moiety having any one of Formulas (IIA), (IIB), (IIC), (IIIA), (IIIB), (IVA), (IVB), (IVC), (IVD), (IVE), (IVF), (IVG), (IVH), (VA), (VB), (VI), (VIIA), (VIIB), and (VIIC), such as described herein.

Non-limiting examples of the compounds having Formula (XIII) include:

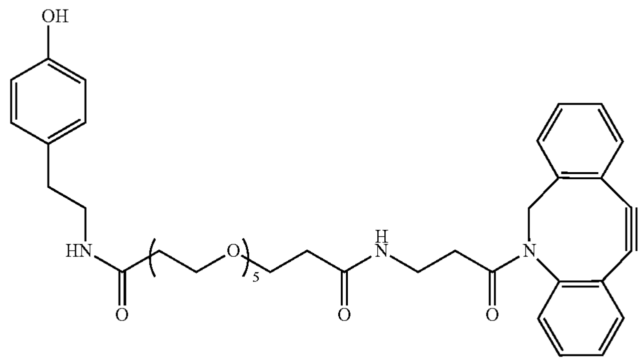

Tyramide-DBCO

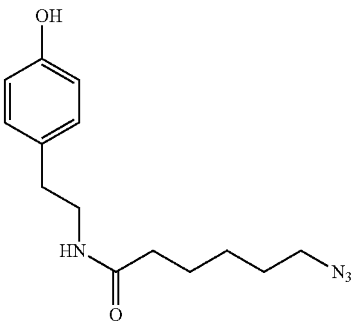

Tyramide-Azide

-continued
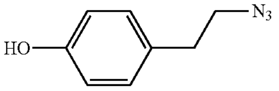
Tyrazide
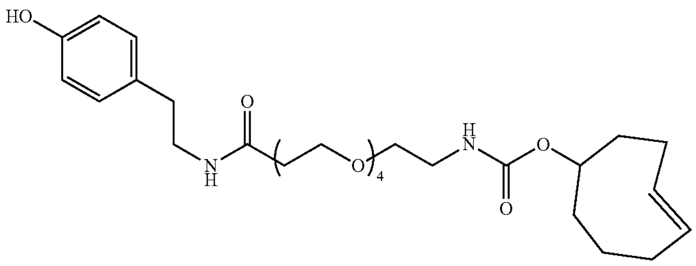
Tyramide-TCO
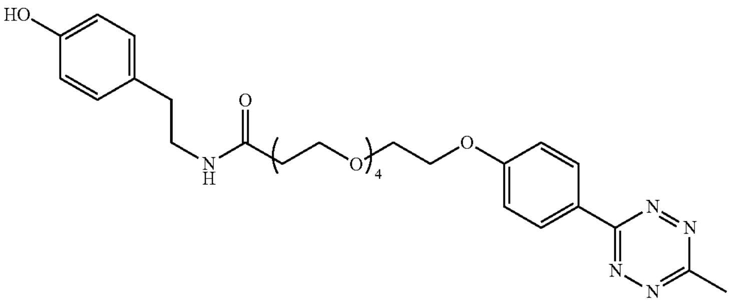
Tyramide-tetrazine
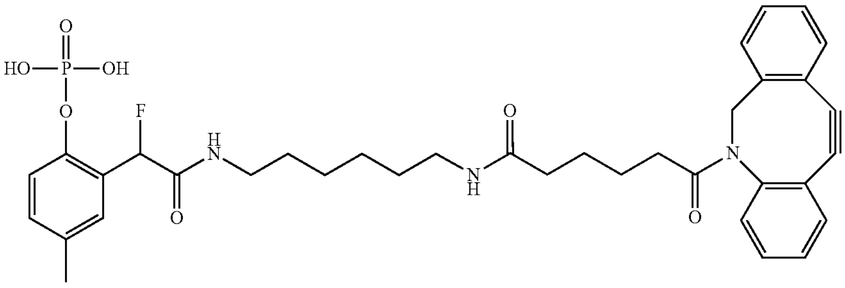
Quinone Methide-DBCO
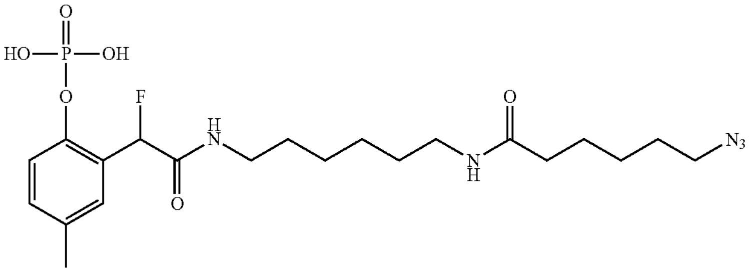
Quinone Methide-Azide
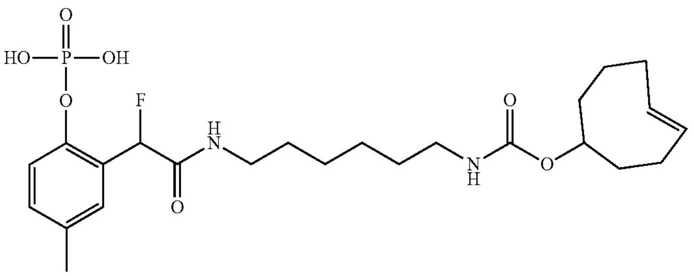
Quinone Methide-TCO -continued

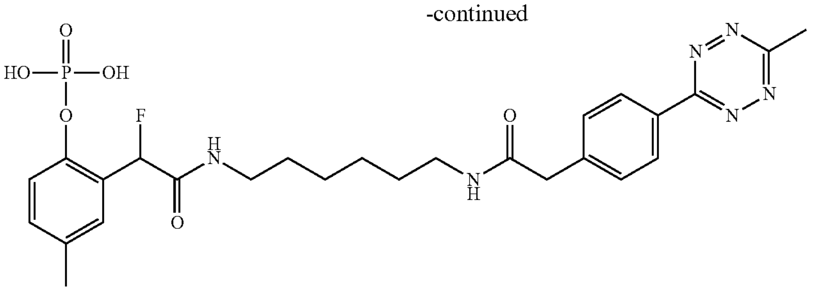

Quinone Methide-Tetrazine

Synthesis (1)

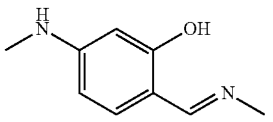

5-(methylamino)-2-((methylimino)methyl)phenol (1). 350 mg (1.0 eq. 1.74 mmol) of 4-bromo-2-hydroxybenzaldehydel was dissolved in 10 ml of 40% aq. methyl amine in a 50 ml pressure vessel. 11 mg (0.1 eq., 0.174 mmol) of Cu dust was added, the vessel sealed under air and heated on an oil bath at 100 C.° for 16 hours. The reaction was diluted with 50 ml of DCM and washed 2× with D.I. water and 2× with brine. The organic layer filtered through a plug of magnesium sulfate then concentrated under vacuum to give 279 mg (98% yield) of the imine as a brown powder. The product was used without further purification.

(2)

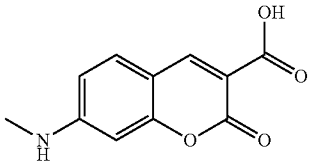

7-(methylamino)-2-oxo-2H-chromene-3-carboxylic acid (2). 200 mg (1.0 eq. 1.4 mmol) of 2-(ethylideneamino)-5-(methylamino)phenol was dissolved in 20 ml of ethanol in a 100 ml round bottom flask. 252 mg (1.25 eq., 1.75 mmol) of Meldrum's acid and 358 mg (3.0 eq., 4.2 mmol) of piperidine were added and the reaction refluxed for 16 hours. The reaction was cooled on an ice bath and the product collected by filtration. The yellow solid was washed 2× with 5 ml cold ethanol and dried under vacuum to give 151 mg of product (49% yield)

(3)

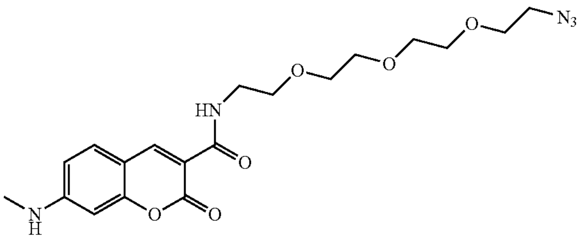

N-(2-(2-(2-(2-azidoethoxy)ethoxy)ethoxy)ethyl)-7-(methylamino)-2-oxo-2H-chromene-3-carboxamide (Nm-ethyl coumarin) (3). A 50 ml round bottom flask was charged with 66 mg (1.0 eq., 0.30 mmol) 7-(methylamino)-2-oxo-2H-chromene-3-carboxylic acid in 5 ml of dry DMF. 95 mg (1.2 eq., 0.36 mmol) of DSC and 55 mg (1.5 eq., 0.45 mmol) of DMAP then added. The reaction blanketed with nitrogen and stirred at room temperature until ester formation was complete as determined by HPLC. After 30 minutes the reaction was complete, and 131 mg (2.0 eq., 0.60 mmol) of 2-(2-(2-(2-azidoethoxy)ethoxy)ethoxy)ethan-1-amine was added and the reaction stirred at room temperature for 16 hours. The reaction was diluted with 50 ml of DCM and washed 2× with D.I. water and 2× with brine. The organic layer filtered through a plug of magnesium sulfate then concentrated under vacuum. Flash chromatography (3-15% MeOH/DCM) afforded 95 mg of the product as a waxy yellow solid (75% yield).

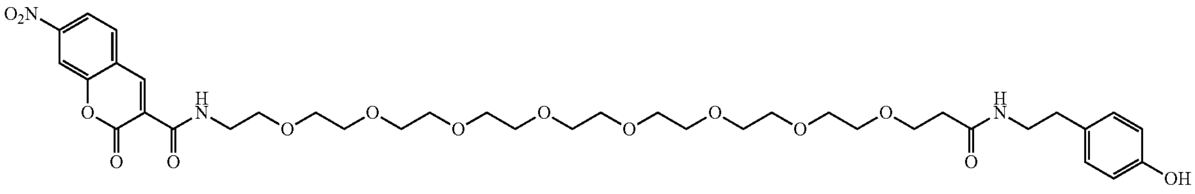 [SMILES: O=C(CCOCCOCCOCCOCCOCCOCCOCCOCCNC(=O)c1cc2ccc([N+](=O)[O-])cc2oc1=O)NCCc1ccc(O)cc1]

N-(30-(4-hydroxyphenyl)-27-oxo-3,6,9,12,15,18,21,24-octaoxa-28-azatriacontyl)-7-nitro-2-oxo-2H-chromene-3-carboxamide. In a 25 ml round bottom flask was taken 139 mg 7-nitro-coumarin-3-carboxylic acid (1.0, 0.59 mmol) in 15 ml of anhydrous DCM then added 0.71 ml 1.0 M DCC in DCM (1.4 eq, 0.77 mmol) followed by 88 mg NHS (1.4 eq, 0.77 mmol). The reaction stirred at room temperature under nitrogen until ester formation was complete as indicated by HPLC (60 minutes). Then added 480 mg 1-amino-N-(4-hydroxyphenethyl)-3,6,9,12,15,18,21,24-octaoxaheptacosan-27-amide trifluoroacetate salt (1.2 eq, 0.71 mmol) followed by 247 µl triethyl amine (3.0 eq, 1.77 mmol). The reaction stirred at room temperature under nitrogen until amide formation was complete as indicated by HPLC (16 hours). The reaction was dried under vacuum and the residue taken in minimal methanol. Preparative HPLC followed by lyophilization afforded 385 mg (84% yield) of the pure coumarin as a waxy solid.

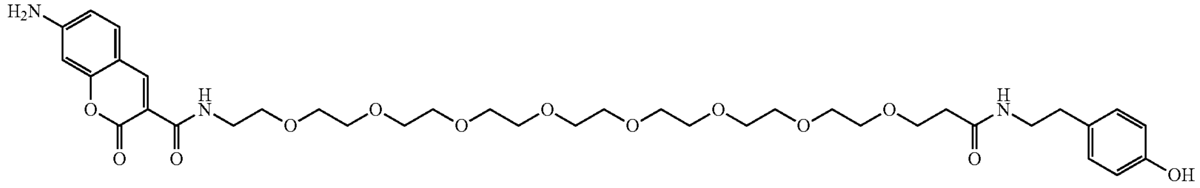

7-amino-N-(30-(4-hydroxyphenyl)-27-oxo-3,6,9,12,15,18,21,24-octaoxa-28-azatriacontyl)-2-oxo-2H-chromene-3-carboxamide. In a 25 ml round bottom flask was taken 385 mg N-(30-(4-hydroxyphenyl)-27-oxo-3,6,9,12,15,18,21,24-octaoxa-28-azatriacontyl)-7-nitro-2-oxo-2H-chromene-3-carboxamide (1.0 eq, 0.50 mmol) in 15 ml of anhydrous ethanol then added 376 mg stannous chloride (4.0 eq, 0.77 mmol). The reaction stirred at reflux until reduction was complete as indicated by HPLC (60 minutes). The reaction was dried under vacuum and the residue taken in minimal methanol. Preparative HPLC followed by lyophilization afforded 341 mg (92% yield) of the pure coumarin (lambda max 385) as a waxy solid.

(4)

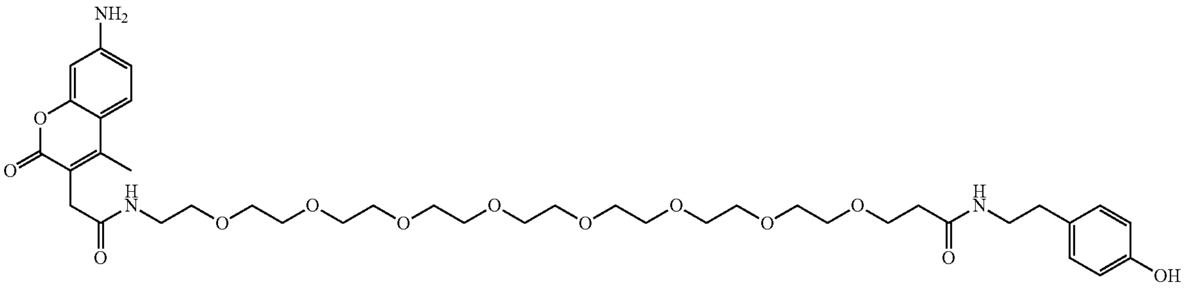

2-(7-amino-4-methyl-2-oxo-2H-chromen-3-yl)-N-(2-(2-(2-(2-azidoethoxy)ethoxy)ethoxy)ethyl)acetamide (4). In a 25 ml round bottom flask was taken 250 mg 7-Amino-4-methyl-3-coumarinylacetic acid (1.0, 1.1 mmol) in 10 ml of anhydrous DMF then added 328 mg DSC (1.2 eq, 1.3 mmol) followed by 196 mg DMAP (1.5 eq, 1.6 mmol). The reaction stirred at room temperature under nitrogen until ester formation was complete as indicated by HPLC (30 minutes). Then added 1.44 g 1-amino-N-(4-hydroxyphenethyl)-3,6,9,12,15,18,21,24-octaoxaheptacosan-27-amide trifluoroacetate salt (2.0 eq, 2.1 mmol) followed by 597 µL triethyl amine (4.0 eq, 4.28 mmol). The reaction stirred at room temperature under nitrogen until amide formation was complete as indicated by HPLC (16 hours). Preparative HPLC followed by lyophilization afforded 559 mg (72% yield) of the pure coumarin as a waxy solid.

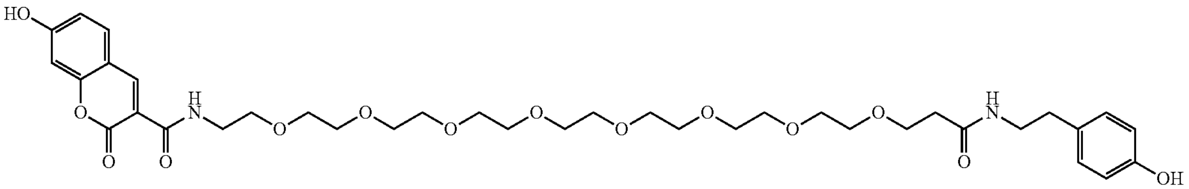 [SMILES: O=C(CCOCCOCCOCCOCCOCCOCCOCCOCCNC(=O)c1cc2ccc(O)cc2oc1=O)NCCc1ccc(O)cc1]

(5)

7-hydroxy-N-(30-(4-hydroxyphenyl)-27-oxo-3,6,9,12,15,18,21,24-octaoxa-28-azatriacontyl)-2-oxo-2H-chromene-3-carboxamide (5). In a 25 ml round bottom flask was taken 250 mg 7-Hydroxycoumarin-3-carboxylic acid (1.0, 1.2 mmol) in 15 ml of anhydrous DMF then added 373 mg DSC (1.2 eq, 1.5 mmol) followed by 221 mg DMAP (1.5 eq, 1.8 mmol). The reaction stirred at room temperature under nitrogen until ester formation was complete as indicated by HPLC (20 minutes). Then added 980 mg 1-amino-N-(4-hydroxyphenethyl)-3,6,9,12,15,18,21,24-octaoxaheptacosan-27-amide trifluoroacetate salt (1.2 eq, 1.5 mmol) followed by 506 μL triethyl amine (3.0 eq, 3.6 mmol). The reaction stirred at room temperature under nitrogen until amide formation was complete as indicated by HPLC (16 hours). Preparative HPLC followed by lyophilization afforded 716 mg (79% yield) of the pure coumarin as a waxy solid.

The synthesis of blue chromogens with a wavelength max abs between 580-700 nm was accomplished by the appropriate tuning of rhodamine, thioninium and phenoxazine core structures.

(6)

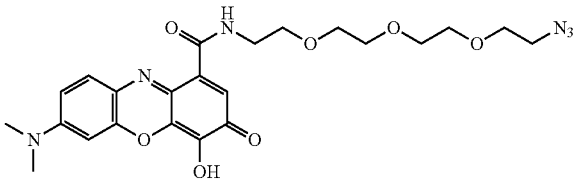

N-(2-(2-(2-(2-azidoethoxy)ethoxy)ethoxy)ethyl)-7-(dimethylamino)-4-hydroxy-3-oxo-3H-phenoxazine-1-carboxamide (6). In a 50 ml round bottom was taken 350 mg (1.0 eq., 1.1 mmol) gallocyanine in 15 ml of dry DMF. 362 mg (1.2 eq., 1.4 mmol) of DSC and 198 mg (1.5 eq., 1.62 mmol) of DMAP then added. The reaction blanketed with nitrogen and stirred at room temperature until ester formation was complete as determined by HPLC. After 20 minutes the reaction was complete, and 471 mg (2.0 eq., 2.16 mmol) of 2-(2-(2-(2-azidoethoxy)ethoxy)ethoxy)ethan-1-amine was added and the reaction stirred at room temperature for 16 hours. The reaction was diluted with 50 ml of DCM and washed 2× with D.I. water and 2× with brine. The organic layer filtered through a plug of magnesium sulfate then concentrated under vacuum. Flash chromatography (5-15% MeOH/DCM) afforded 368 mg of the product as a waxy blue solid (68% yield).

(21)

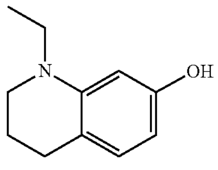

1-ethyl-1,2,3,4-tetrahydroquinolin-7-ol (21). To a solution of 2.45 g 1,2,3,4-tetrahydroquinolin-7-ol 1.02 g (1.0 eq., 6.83 mmol) in 10 ml of anhydrous DMF was added 1.6 g ethyl iodide(1.5 eq., 10.25 mmol) and 2.05 g potassium bicarbonate (3.0 eq., 20.5 mmol). The reaction heated on an oil bath at 60 C.° for 24 hours, then diluted with 40 ml of DCM and washed 2× with D.I. water and 2× with brine. The organic layer filtered through a plug of magnesium sulfate then concentrated under vacuum. Flash chromatography (0-10% MeOH/DCM) afforded 1.1 g of the product as a tan solid (91% yield).

(8)

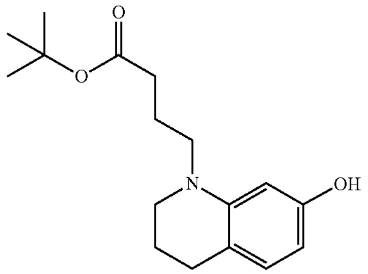

tert-butyl 4-(7-hydroxy-3,4-dihydroquinolin-1(2H)-yl) butanoate (8). To a solution of 2.45 g 1,2,3,4-tetrahydroquinolin-7-ol (1.0 eq., 16.34 mmol) in 20 ml of anhydrous DMF was added 4.0 g tert-butyl 4-bromobutanoate (1.1 eq., 18.0 mmol) and 4.9 g potassium bicarbonate (3.0 eq., 49.0 mmol). The reaction heated on an oil bath at 60 C.° for 24 hours, then diluted with 50 ml of DCM and washed 2× with D.I. water and 2× with brine. The organic layer filtered through a plug of magnesium sulfate then concentrated under vacuum. Flash chromatography (0-10% MeOH/DCM) afforded 3.38 g of the product as a tan solid (71% yield).

(7)

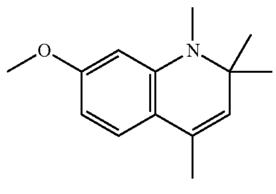

7-methoxy-1,2,2,4-tetramethyl-1,2-dihydroquinoline (7). To a solution of 1.5 g 7-methoxy-2,2,4-trimethyl-1,2-dihydroquinoline (1.0 eq., 7.38 mmol) in 25 ml of anhydrous DMF was added 1.57 g methyl iodide (1.5 eq., 11.06 mmol) and 2.2 g potassium bicarbonate (3.0 eq., 22.14 mmol). The reaction heated on an oil bath at 60 C.° for 24 hours, then diluted with 50 ml of DCM and washed 3× with D.I. water and 2× with brine. The organic layer filtered through a plug of magnesium sulfate then concentrated under vacuum. Flash chromatography (0-10% MeOH/DCM) afforded 1.59 g of the product as a tan solid (99% yield).

(10)

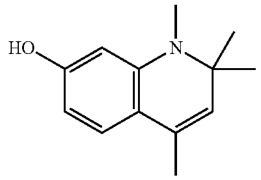

1,2,2,4-tetramethyl-1,2-dihydroquinolin-7-ol (10). In a 250 ml round bottom flask was taken 1.51 g 7-methoxy-2,2,4-trimethyl-1,2-dihydroquinoline (1.0 eq., 7.3 mmol) in 40 ml of DCM. To the flask was added 21.9 ml of 1.0 M $BBr_3$ in DCM (3.0 eq., 21.9 mmol) and the reaction stirred at room temperature 16 hours. The reaction was diluted with 50 ml of DCM, cooled on an ice bath and carefully quenched with the addition of saturated sodium bicarbonate. The organic layer washed 2× with D.I. water, 2× with brine and concentrated under vacuum. Flash chromatography (2-15% Me OH/DCM) afforded 1.14 g (77% yield) of the product as a white solid.

(13)

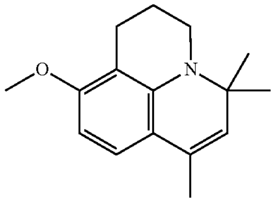

10-methoxy-5,5,7-trimethyl-2,3-dihydro-1H,5H-pyrido [3,2,1-ij]quinolone (13). To a solution of 2.54 g 7-methoxy-2,2,4-trimethyl-1,2-dihydroquinoline (1.0 eq., 13.0 mmol) and 5.77 g 1-bromo-3-iodopropane (4.0 eq., 53 mmol) in 40 ml of anhydrous ACN was added 1.5 g potassium bicarbonate (2.0 eq., 26.0 mmol) and 12 g potassium iodide (0.8 eq., 10.4 mmol). The reaction refluxed on an oil bath for 24 hours, then diluted with 50 ml of DCM and washed 2× with D.I. water and 2× with brine. The organic layer filtered through a plug of magnesium sulfate then concentrated under vacuum. Flash chromatography (50% hexane/DCM-DCM) afforded 2.8 g of the product as slightly yellow solid (88% yield). To a solution of 2.54 g 7-methoxy-2,2,4-trimethyl-1,2-dihydroquinoline (1.0 eq., 13.0 mmol) and 5.77 g 1-bromo-3-iodopropane (4.0 eq., 53 mmol) in 40 ml of anhydrous ACN was added 1.5 g potassium bicarbonate (2.0 eq., 26.0 mmol) and 12 g potassium iodide (0.8 eq., 10.4 mmol). The reaction refluxed on an oil bath for 24 hours, then diluted with 50 ml of DCM and washed 2× with D.I. water and 2× with brine. The organic layer filtered through a plug of magnesium sulfate then concentrated under vacuum. Flash chromatography (50% hexane/DCM-DCM) afforded 2.8 g of the product as slightly yellow solid (88% yield).

(14)

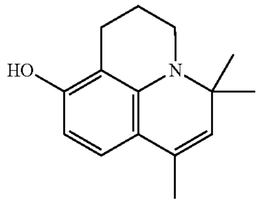

5,5,7-trimethyl-2,3-dihydro-1H,5H-pyrido[3,2,1-ij]quinolin-10-ol (14). In a 250 ml round bottom flask was taken 3.16 g 10-methoxy-5,5,7-trimethyl-2,3-dihydro-1H,5H-pyrido[3,2,1-ij]quinolone (1.0 eq., 13.0 mmol) in 25 ml of DCM. To the flask was added 52 ml of 1.0 M $BBr_3$ in DCM (4.0 eq., 52 mmol) and the reaction stirred at room temperature 16 hours. The reaction diluted with 50 ml of DCM, cooled on an ice bath and quenched with the careful addition of saturated sodium bicarbonate. The organic layer washed 2× with D.I. water, 2× with brine and concentrated under vacuum. Flash chromatography (0-5% MeOH/DCM) afforded 1.7 g (74% yield) of the deprotected product as a white solid.

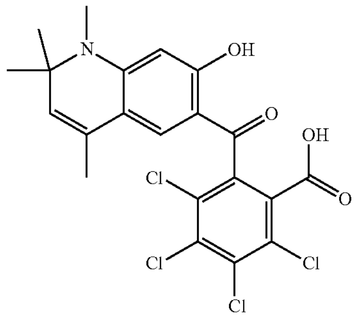 [SMILES: CC1=CC(C)(C)N(C)c2cc(O)c(C(=O)c3c(Cl)c(Cl)c(Cl)c(Cl)c3C(=O)O)cc21]

2,3,4,5-tetrachloro-6-(7-hydroxy-1,2,2,4-tetramethyl-1,2-dihydroquinoline-6-carbonyl)benzoic acid. In a 50 ml round bottom flask was taken 325 mg 5,5,7-trimethyl-2,3-dihydro-1H,5H-pyrido[3,2,1-ij]quinolin-10-ol (1.0 eq., 1.4 mmol) and 405 mg 4,5,6,7-tetrachloroisobenzofuran-1,3-dione (1.0 eq., 1.4 mmol) in 20 ml of toluene. The flask was fitted with a Dean Stark tap and a reflux condenser, and the reaction refluxed for 16 hours. The reaction cooled on an ice bath and the product collected by filtration. Washing 2× with toluene and drying under high vacuum afforded 679 mg (3.52 mmol, 93% yield) of the product as a green solid.

(9)

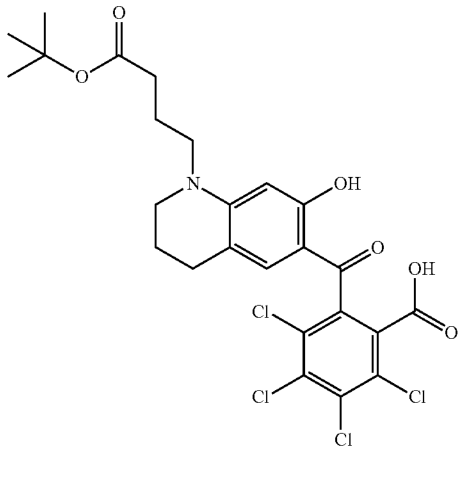

2-(1-(4-(tert-butoxy)-4-oxobutyl)-7-hydroxy-1,2,3,4-tetrahydroquinoline-6-carbonyl)-3,4,5,6-tetrachlorobenzoic acid (9). In a 100 ml round bottom flask was taken 1.39 g tert-butyl 4-(7-hydroxy-3,4-dihydroquinolin-1(2H)-yl)butanoate (1.0 eq., 4.75 mmol) and 1.36 g 4,5,6,7-tetrachloroisobenzofuran-1,3-dione (1.0 eq., 4.75 mmol) in 40 ml of toluene. The flask was fitted with a Dean Stark tap and a reflux condenser, and the reaction refluxed for 16 hours. The reaction cooled on an ice bath and the product collected by filtration. Washing 2× with toluene and drying under high vacuum afforded 2.25 g (82% yield) of the product as a green solid.

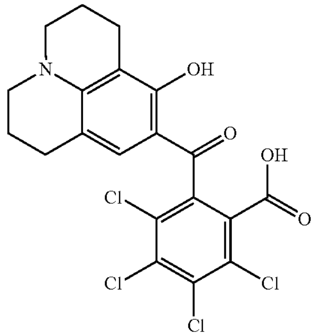 [SMILES: O=C(O)c1c(Cl)c(Cl)c(Cl)c(Cl)c1C(=O)c1cc2c3c(c1O)CCCN3CCC2]

2,3,4,5-tetrachloro-6-(8-hydroxy-2,3,6,7-tetrahydro-1H,5H-pyrido[3,2,1-ij]quinoline-9-carbonyl)benzoic acid. In a 50 ml round bottom flask was taken 700 mg 2,3,6,7-tetrahydro-1H,5H-pyrido[3,2,1-ij]quinolin-8-ol (1.0 eq., 3.7 mmol) and 1.06 g 4,5,6,7-tetrachloroisobenzofuran-1,3-dione (1.0 eq., 3.7 mmol) in 20 ml of toluene. The flask was fitted with a Dean Stark tap and a reflux condenser, and the reaction refluxed for 16 hours. The reaction cooled on an ice bath and the product collected by filtration. Washing 2× with toluene and drying under high vacuum afforded 1.6 g (3.52 mmol, 95% yield) of the product as a green solid

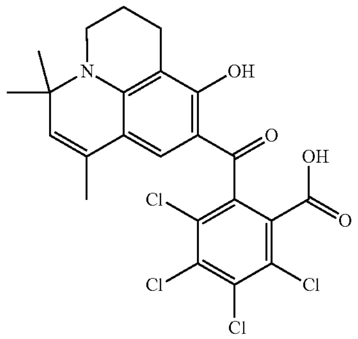 [SMILES: CC1=CC(C)(C)N2CCCc3c(O)c(C(=O)c4c(Cl)c(Cl)c(Cl)c(Cl)c4C(=O)O)cc1c32]

2,3,4,5-tetrachloro-6-(10-hydroxy-5,5,7-trimethyl-2,3-dihydro-1H,5H-pyrido[3,2,1-ij]quinoline-9-carbonyl)benzoic acid. In a 50 ml round bottom flask was taken 325 mg 5,5,7-trimethyl-2,3-dihydro-1H,5H-pyrido[3,2,1-ij]quinolin-10-ol (1.0 eq., 1.4 mmol) and 405 mg 4,5,6,7-tetrachloroisobenzofuran-1,3-dione (1.0 eq., 1.4 mmol) in 20 ml of toluene. The flask was fitted with a Dean Stark tap and a reflux condenser, and the reaction refluxed for 16 hours. The reaction cooled on an ice bath and the product collected by filtration. Washing 2× with toluene and drying under high vacuum afforded 679 mg (3.52 mmol, 93% yield) of the product as a green solid.

(11)

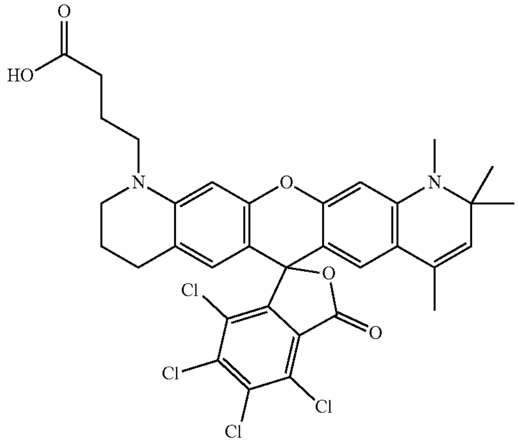

Xanthene (11). In a 25 ml round bottom flask was taken 210 mg 2,3,4,5-tetrachloro-6-(7-hydroxy-1,2,2,4-tetramethyl-1,2-dihydroquinoline-6-carbonyl)benzoic acid (1.0 eq., 0.45 mmol) and 143 mg tert-butyl 4-(7-hydroxy-3,4-dihydroquinolin-1(2H)-yl)butanoate (1.1 eq., 0.49 mmol) in 4 ml of anhydrous DMF. To the flask added 1 ml TMS polyphosphoric acid and the reaction heated on an oil bath at 80 C.° for 4 hours. Preparative HPLC of the crude reaction followed by lyophilization of the purified fractions afforded 239 mg (0.35 mmol, 78% yield) of the pure xanthene as a blue solid (wavelength max abs 604 nm).

(24)

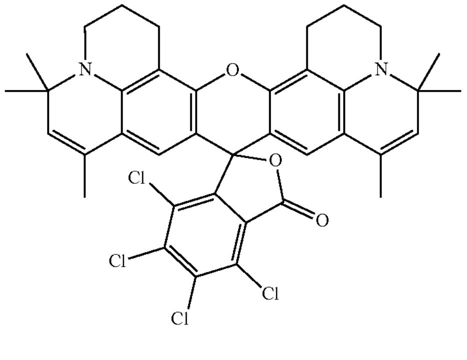

Xanthene (24). In a 25 ml round bottom flask was taken 199 mg 2,3,4,5-tetrachloro-6-(10-hydroxy-5,5,7-trimethyl-2,3-dihydro-1H,5H-pyrido[3,2,1-ij]quinoline-9-carbonyl) benzoic acid (1.0 eq., 0.42 mmol) and 122 mg 5,5,7-trimethyl-2,3-dihydro-1H,5H-pyrido[3,2,1-ij]quinolin-10-ol (1.0 eq., 0.42 mmol) in 4 ml of anhydrous DMF. To the flask added 1 ml TMS polyphosphoric acid and the reaction heated on an oil bath at 80 C.° for 4 hours. Preparative HPLC of the crude reaction followed by lyophilization of the purified fractions afforded 218 mg (77% yield) of the pure xanthene as a blue solid.

(25)

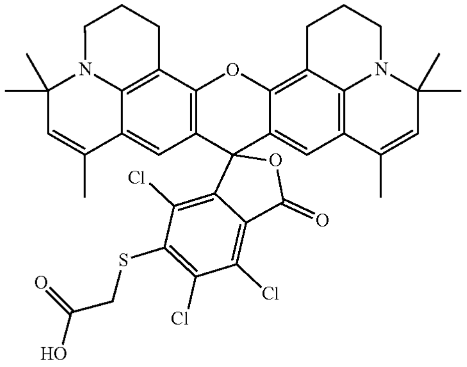

Xanthene (25). In a 25 ml round bottom flask was taken 380 mg xanthene 2 (1.0 eq., 0.54 mmol), 280 μL Huenig's base (3.0 eq., 1.6 mmol) and 75 μL2-(16-sulfanyl)acetic acid (2.0 eq., 1.1 mmol) in 5 ml of anhydrous DMF. The reaction stirred at room temperature for 16 hours, then diluted with 50 ml of DCM and washed 2× with D.I. water and 2× with brine. The organic filtered through a plug of magnesium sulfate then concentrated under vacuum. Preparative HPLC of the crude reaction followed by lyophilization of the purified fractions afforded 372 mg (90% yield) of the pure xanthene as a blue solid.

(27)

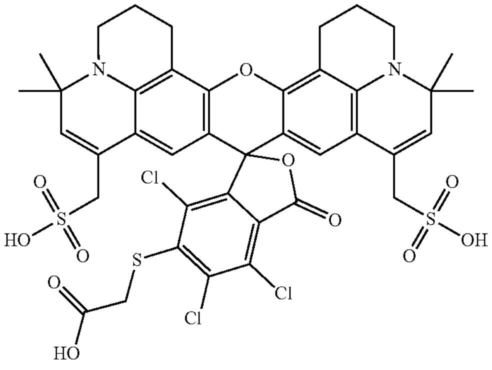

Xanthene (27). Xanthene 3 (150 mg, 0.20 mmol) was dissolved in 1 ml of conc. $H_2SO_4$ and stirred at room temperature under nitrogen for 3 days. The reaction cooled on an ice bath then carefully quenched with saturated sodium bicarbonate. Preparative HPLC followed by lyophilization afforded 156 mg (86% yield) of the pure xanthene.

(22)

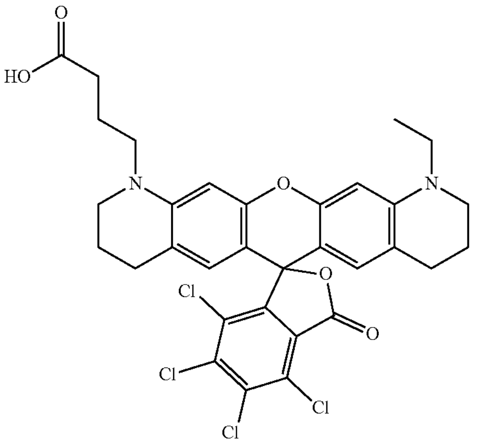

Xanthene (22). In a 25 ml round bottom flask was taken 215 2-(1-(4-(tert-butoxy)-4-oxobutyl)-7-hydroxy-1,2,3,4-tetrahydroquinoline-6-carbonyl)-3,4,5,6-tetrachlorobenzoic acid (1.0 eq., 0.37 mmol) and 66 mg 1-ethyl-1,2,3,4-tetrahydroquinolin-7-ol (1.0 eq., 0.37 mmol) in 4 ml of anhydrous DMF. To the flask added 1 ml TMS polyphosphoric acid and the reaction heated on an oil bath at 80 C.° for 4 hours. Preparative HPLC of the crude reaction followed by lyophilization of the purified fractions afforded 193 mg (79% yield) of the pure xanthene as a blue solid (wavelength max abs 588 nm).

(15)

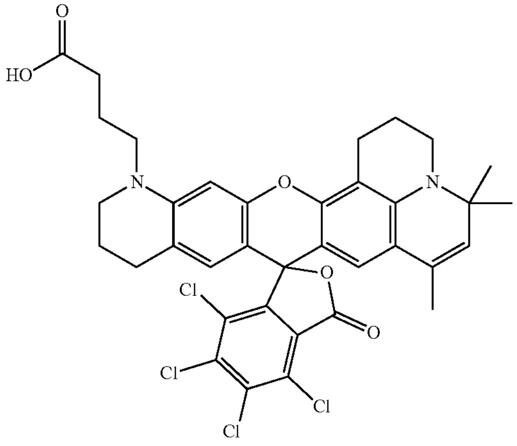

Xanthene (15). In a 25 ml round bottom flask was taken 433 mg 2-(1-(4-(tert-butoxy)-4-oxobutyl)-7-hydroxy-1,2,3,4-tetrahydroquinoline-6-carbonyl)-3,4,5,6-tetrachlorobenzoic acid (1.0 eq., 0.75 mmol) and 172 mg (1.0 eq., 0.75 mmol) 5,5,7-trimethyl-2,3-dihydro-1H,5H-pyrido[3,2,1-ij]quinolin-10-ol in 4 ml of anhydrous DMF. To the flask added 1 ml TMS polyphosphoric acid and the reaction heated on an oil bath at 90 C.° for 2 hours. Preparative HPLC of the crude reaction followed by lyophilization of the purified fractions afforded 391 mg (73% yield) of the pure xanthene as a blue solid.

(29)

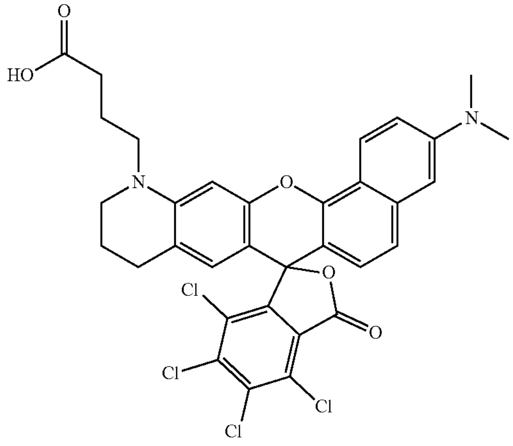

4-(4',5',6',7'-tetrachloro-3-(dimethylamino)-3'-oxo-10,11-dihydro-3'H-spiro[benzo[7,8]chromeno[3,2-g]quinoline-7,1'-isobenzofuran]-12(9H)-yl)butanoic acid (29). In a 25 ml round bottom flask was taken 410 mg 2-(1-(4-(tert-butoxy)-4-oxobutyl)-7-hydroxy-1,2,3,4-tetrahydroquinoline-6-carbonyl)-3,4,5,6-tetrachlorobenzoic acid (1.0 eq., 0.71 mmol) and 133 mg 6-(dimethylamino)naphthalen-1-ol (1.0 eq., 0.71 mmol) in 4 ml of anhydrous DMF. To the flask added 1 ml TMS polyphosphoric acid and the reaction heated on an oil bath at 80 C.° for 2 hours. Preparative HPLC of the crude reaction followed by lyophilization of the purified fractions afforded 335 mg (70% yield) of the pure xanthene as a blue solid (wavelength max abs 631 nm).

(12)

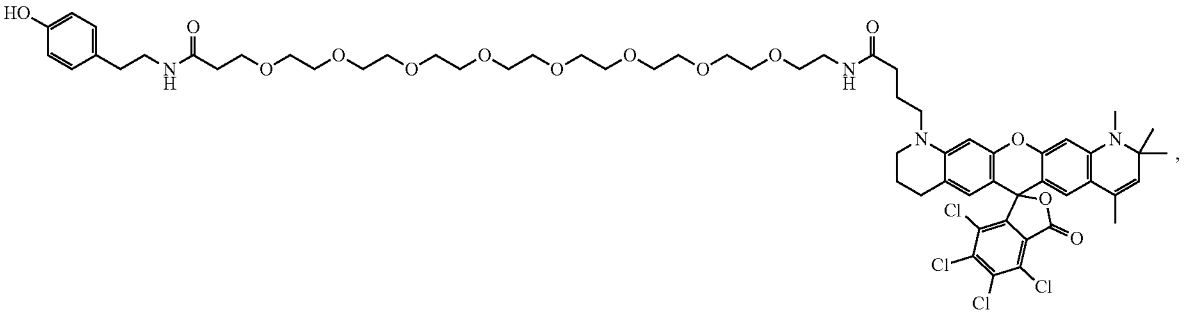

Xanthene (12). In a 50 ml round bottom flask was taken 252 mg Xanthene 11 (1.0, 0.36 mmol) in 4 ml of anhydrous DMF then added 112 mg DSC (1.2 eq, 0.44 mmol) followed by 106 mg DMAP (2.4 eq, 0.87 mmol). The reaction stirred at room temperature under nitrogen until ester formation was complete as indicated by HPLC (30 minutes). Then added 490 mg 1-amino-N-(4-hydroxyphenethyl)-3,6,9,12,15,18,21,24-octaoxaheptacosan-27-amide trifluoroacetate salt (2.0 eq, 0.73 mmol) followed by 202 μL triethyl amine (4.0 eq, 01.09 mmol). The reaction stirred at room temperature under nitrogen until amide formation was complete as indicated by HPLC (16 hours). Preparative HPLC followed by lyophilization afforded 306 mg (69% yield) of the pure xanthene as a blue solid.

Xanthene (12). In a 50 ml round bottom flask was taken 252 mg Xanthene 11 (1.0, 0.36 mmol) in 4 ml of anhydrous DMF then added 112 mg DSC (1.2 eq, 0.44 mmol) followed by 106 mg DMAP (2.4 eq, 0.87 mmol). The reaction stirred at room temperature under nitrogen until ester formation was complete as indicated by HPLC (30 minutes). Then added 490 mg 1-amino-N-(4-hydroxyphenethyl)-3,6,9,12,15,18,21,24-octaoxaheptacosan-27-amide trifluoroacetate salt (2.0 eq, 0.73 mmol) followed by 202 μL triethyl amine (4.0 eq, 01.09 mmol). The reaction stirred at room temperature under nitrogen until amide formation was complete as indicated by HPLC (16 hours). Preparative HPLC followed by lyophilization afforded 306 mg (69% yield) of the pure xanthene as a blue solid.

(16)

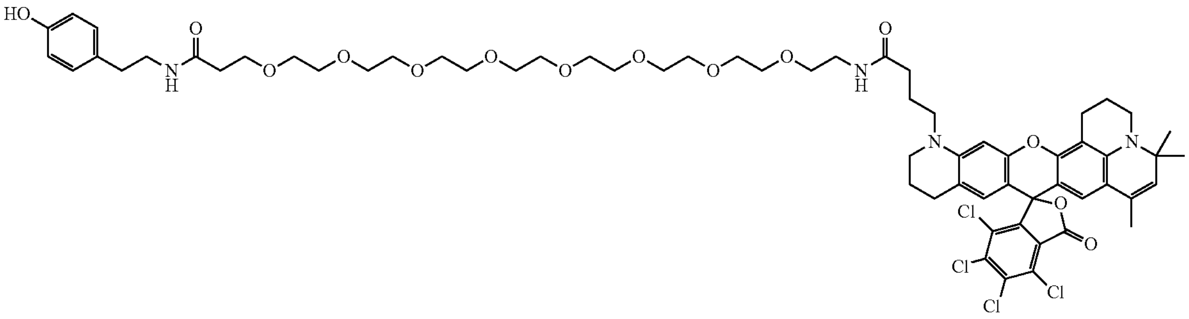

Xanthene (16). Xanthene 15 (35 mg, 0.049 mmol) was dissolved in 3 ml of DCM then added 49 μL1.0 M DCC (1.0 eq, 0.049 mmol) followed by 5.6 mg NHS (1.0 eq, 0.049 mmol). The reaction stirred at room temperature under nitrogen until ester formation was complete as indicated by HPLC (6 hours). The urea was removed by filtration then added 66 mg 1-amino-N-(4-hydroxyphenethyl)-3,6,9,12,15,18,21,24-octaoxaheptacosan-27-amide trifluoroacetate salt (2.0 eq, 0.098 mmol) followed by 16 μL triethyl amine (3.0 eq, 0.147 mmol). The reaction stirred at room temperature under nitrogen until amide formation was complete as indicated by HPLC (12 hours). Preparative HPLC followed by lyophilization afforded 44 mg (71% yield) of the pure xanthene.

(17)

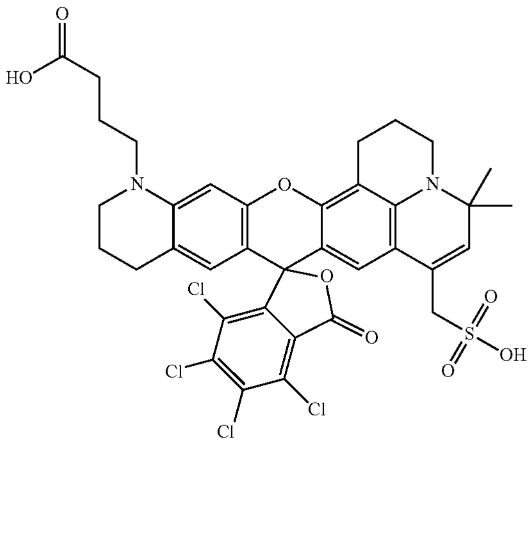

Xanthene (17). Xanthene 15 (50 mg, 0.07 mmol) was dissolved in 1 ml of conc. $H_2SO_4$ and stirred at room temperature under nitrogen for 3 days. The reaction cooled on an ice bath then carefully quenched with saturated sodium bicarbonate. Preparative HPLC followed by lyophilization afforded 44 mg (80% yield) of the pure xanthene (wavelength max abs 614 nm).

(18)

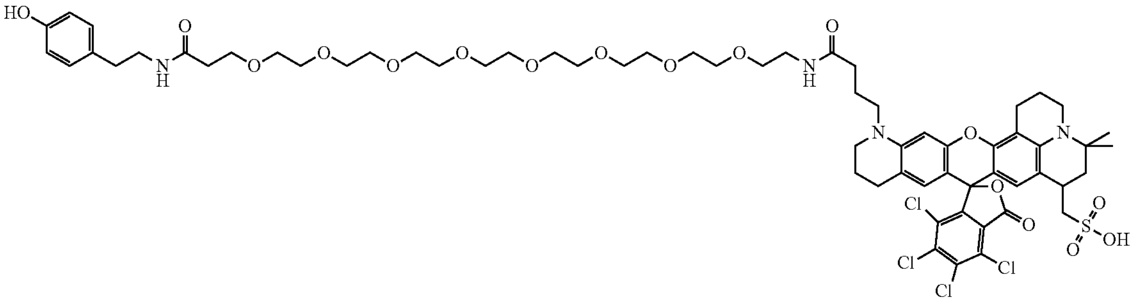

Xanthene (18). 30 mg of Xanthene 17 (1.0 eq, 0.038 mmol) was dissolved in 3 ml of anhydrous DMF then added 9.7 mg DSC (1.2 eq, 0.046 mmol) followed by 7.5 mg DMAP (1.5 eq, 057 mmol). The reaction stirred at room temperature under nitrogen until ester formation was complete as indicated by HPLC (1 hour). Then added 51 mg 1-amino-N-(4-hydroxyphenethyl)-3,6,9,12,15,18,21,24-octaoxaheptacosan-27-amide trifluoroacetate salt (2.0 eq, 0.076 mmol) followed by 20 μL triethyl amine (3.0 eq, 0.114 mmol). The reaction stirred at room temperature under nitrogen until amide formation was complete as indicated by HPLC (12 hours). Preparative HPLC followed by lyophilization afforded 35 mg (69% yield) of the pure xanthene as a blue solid.

(19)

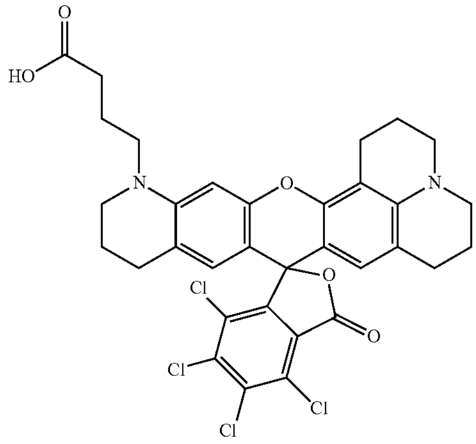

Xanthene (19). In a 25 ml round bottom flask was taken 430 mg 2-(1-(4-(tert-butoxy)-4-oxobutyl)-7-hydroxy-1,2,3,4-tetrahydroquinoline-6-carbonyl)-3,4,5,6-tetrachlorobenzoic acid (1.0 eq., 0.75 mmol) and 142 mg (1.0 eq., 0.75 mmol) 2,3,6,7-tetrahydro-1H,5H-pyrido[3,2,1-ij]quinolin-8-ol in 4 ml of anhydrous DMF. To the flask added 1 ml TMS polyphosphoric acid and the reaction heated on an oil bath at 90 C.° for 2 hours. Preparative HPLC of the crude reaction followed by lyophilization of the purified fractions afforded 465 mg (69% yield) of the pure xanthene as a blue solid (wavelength max abs 598 nm).

(20)

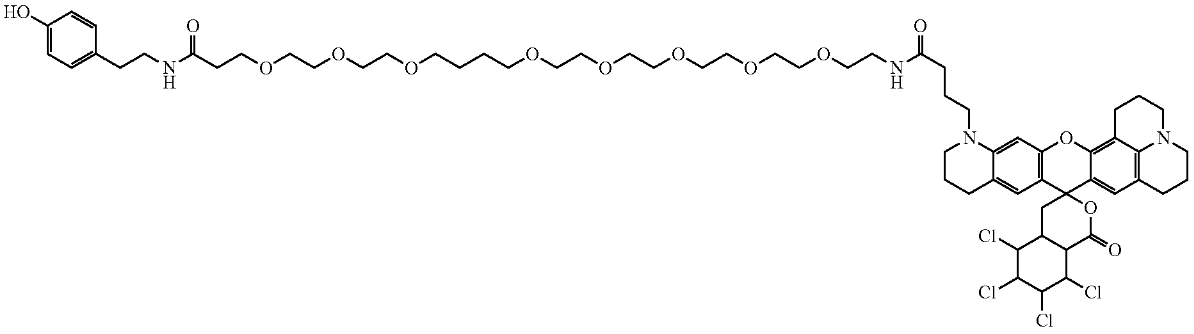

Xanthene (20). To a solution of 142 mg xanthene 19 (1.0 eq., 0.21 mmol) in 5 ml of anhydrous DMF was added 65 mg of DSC (1.2 eq., 0.25 mmol) and 39 mg of DMAP (1.5 eq., 0.32 mmol) the reaction blanketed with nitrogen and stirred at room temperature until ester formation was complete as determined by HPLC (30 minutes). 257 mg 1-amino-N-(4-hydroxyphenethyl)-3,6,9,12,15,18,21,24-octaoxaheptacosan-27-amide trifluoroacetate salt (1.5 eq, 0.38 mmol) followed by 20 μL triethyl amine (3.0 eq, 0.114 mmol) were then added. The reaction stirred at room temperature under nitrogen until amide formation was complete as indicated by HPLC (12 hours). Preparative HPLC followed by lyophilization afforded 219 mg (0.18 mmol, 72% yield) of the pure xanthene as a blue solid.

(22)

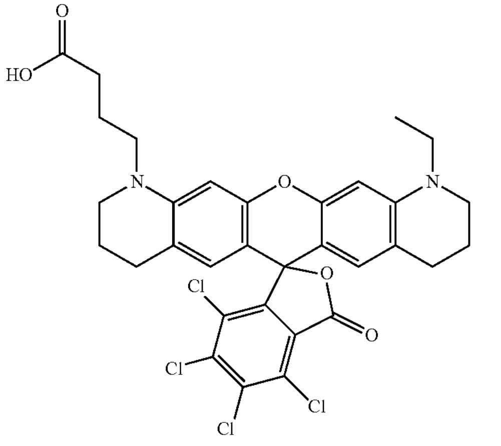

Xanthene (22). In a 25 ml round bottom flask was taken 215 mg 2-(1-(4-(tert-butoxy)-4-oxobutyl)-7-hydroxy-1,2,3,4-tetrahydroquinoline-6-carbonyl)-3,4,5,6-tetrachlorobenzoic acid (1.0 eq., 0.37 mmol) and 66 mg (1.0 eq., 0.37 mmol) 1-ethyl-1,2,3,4-tetrahydroquinolin-7-ol in 4 ml of anhydrous DMF. To the flask added 1 ml TMS polyphosphoric acid and the reaction heated on an oil bath at 80 C.° for 3 hours. Preparative HPLC of the crude reaction followed by lyophilization of the purified fractions afforded 192 mg (0.29 mmol, 78% yield) of the pure xanthene as a blue solid (wavelength max abs 588 nm).

(23)

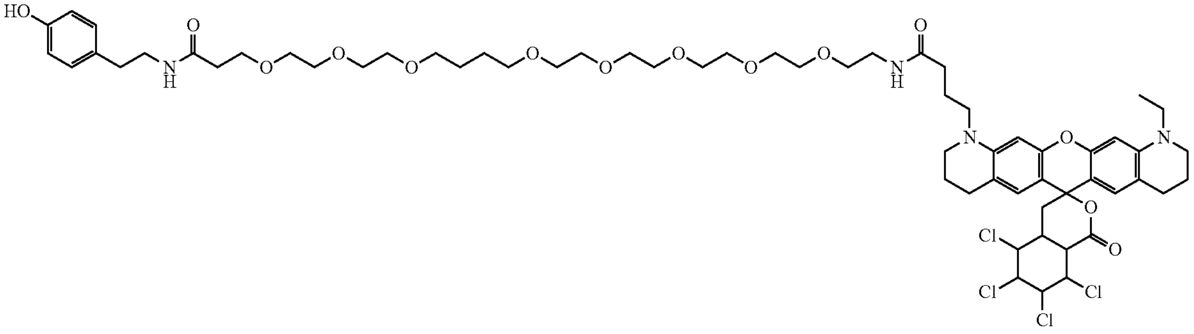

Xanthene (23). To a solution of 67 mg xanthene 22 (1.0 eq., 0.10 mmol) in 3 ml of anhydrous DMF was added 28 mg of DSC (1.1 eq., 0.25 mmol) and 18 mg of DMAP (1.5 eq., 0.15 mmol) the reaction blanketed with nitrogen and stirred at room temperature until ester formation was complete as determined by HPLC (30 minutes). 102 mg 1-amino-N-(4-hydroxyphenethyl)-3,6,9,12,15,18,21,24-octaoxaheptacosan-27-amide trifluoroacetate salt (1.5 eq, 0.15 mmol) followed by 42 μL triethyl amine (3.0 eq, 0.30 mmol) were then added. The reaction stirred at room temperature under nitrogen for 16 hours (amide formation complete as indicated by HPLC). Preparative HPLC followed by lyophilization afforded 96 mg (0.18 mmol, 79% yield) of the pure xanthene as a blue solid.

(28)

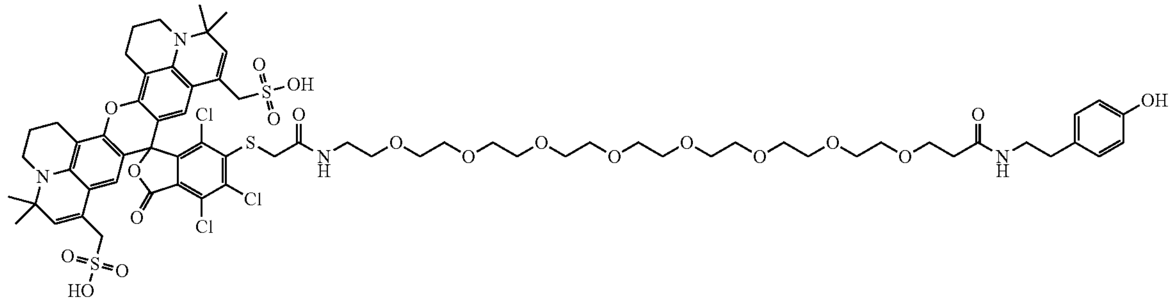

Xanthene (28). To a solution of 78 mg xanthene 27 (1.0 eq., 0.085 mmol) in 3 ml of DCM was added 101 μL 1.0 M DCC (1.2 eq, 0.10 mmol) followed by 12 mg NHS (1.2 eq, 0.049 mmol). The reaction stirred at room temperature under nitrogen until ester formation was complete as indicated by HPLC (5 hours). The urea was removed by filtration then added 114 mg 1-amino-N-(4-hydroxyphenethyl)-3,6,9,12,15,18,21,24-octaoxaheptacosan-27-amide trifluoroacetate salt (2.0 eq, 0.17 mmol) followed by 55 μL triethyl amine (3.0 eq, 0.147 mmol). The reaction stirred at room temperature under nitrogen until amide formation was complete as indicated by HPLC (16 hours). Preparative HPLC followed by lyophilization afforded 97 mg (0.06 mmol, 78% yield) of the pure xanthene.

(26)

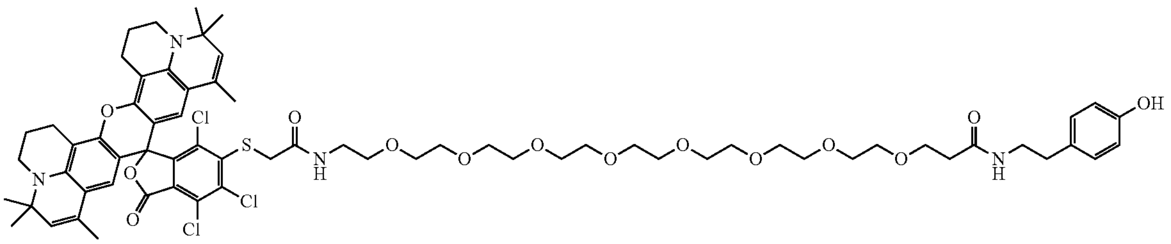

Xanthene (26). To a solution of 85 mg xanthene 24 (1.0 eq., 0.11 mmol) in 3 ml of anhydrous DMF was added 32 mg of DSC (1.1 eq., 0.12 mmol) and 20 mg of DMAP (1.5 eq., 0.17 mmol). The reaction blanketed with nitrogen and stirred at room temperature until ester formation was complete as determined by HPLC (40 minutes). 148 mg 1-amino-N-(4-hydroxyphenethyl)-3,6,9,12,15,18,21,24-octaoxaheptacosan-27-amide trifluoroacetate salt (2.0 eq, 0.22 mmol) followed by 46 μL triethyl amine (3.0 eq, 0.33 mmol) were then added. The reaction stirred at room temperature under nitrogen for 16 hours (amide formation complete as indicated by HPLC). Preparative HPLC followed by lyophilization afforded 114 mg (79% yield) of the pure xanthene as a blue solid.

(30)

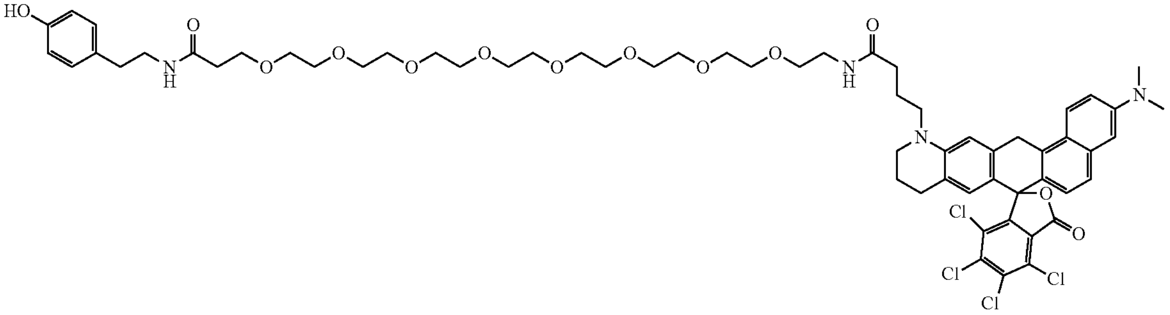

,

Xanthene (30). To a solution of 40 mg 4-(4',5',6',7'-tetrachloro-3-(dimethylamino)-3'-oxo-10,11-dihydro-3'H-spiro[benzo[7,8]chromeno[3,2-g]quinoline-7,1'-isobenzofuran]-12(9H)-yl)butanoic acid (1.0 eq., 0.06 mmol) in 3 ml of anhydrous DMF was added 18 mg of DSC (1.2 eq., 0.072 mmol) and 12 mg of DMAP (1.6 eq., 0.095 mmol) the reaction blanketed with nitrogen and stirred at room temperature until ester formation was complete as determined by HPLC (15 minutes). 80 mg 1-amino-N-(4-hydroxyphenethyl)-3,6,9,12,15,18,21,24-octaoxaheptacosan-27-amide trifluoroacetate salt (2.0 eq, 0.12 mmol) followed by 42 μL triethyl amine (4.0 eq, 0.24 mmol) were then added. The reaction stirred at room temperature under nitrogen for 2 hours (amide formation complete as indicated by HPLC). Preparative HPLC followed by lyophilization afforded 54 mg (0.087 mmol, 75% yield) of the pure xanthene as a blue solid.

(40)

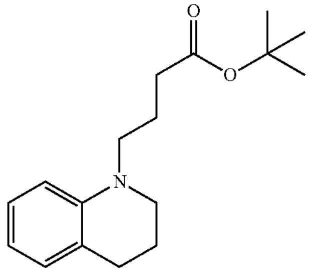

tert-butyl 4-(3,4-dihydroquinolin-1(2H)-yl)butanoate (40). To a solution of 1.14 g 1,2,3,4-tetrahydroquinoline (1.0 eq., 8.55 mmol) in 15 ml of anhydrous DMF was added 3.82 g tert-butyl 4-bromobutanoate (2.0 eq., 17.1 mmol) and 2.57 g potassium bicarbonate (3.0 eq., 25.65 mmol). The reaction heated on an oil bath at 60 C.° for 24 hours, then diluted with 50 ml of DCM and washed 2× with D.I. water and 2× with brine. The organic layer filtered through a plug of magnesium sulfate then concentrated under vacuum. Flash chromatography (0-10% MeOH/DCM) afforded 2.02 g of the product as a tan solid (86% yield).

(33)

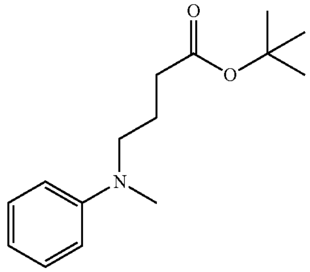

tert-butyl 4-(methyl(phenyl)amino)butanoate (33). To a solution of N-methylaniline 2.0 g (1.0 eq., 18.66 mmol) in 15 ml of anhydrous DMF was added 5.0 g tert-butyl 4-bromobutanoate (1.2 eq., 22.4 mmol) and 2.57 g potassium bicarbonate (3.0 eq., 55.98 mmol). The reaction heated on an oil bath at 60 C.° for 18 hours, then diluted with 70 ml of DCM and washed 2× with D.I. water and 2× with brine. The organic layer filtered through a plug of magnesium sulfate then concentrated under vacuum. Flash chromatography (0-10% MeOH/DCM) afforded 3.86 g of the product as a tan solid (83% yield).

(31)

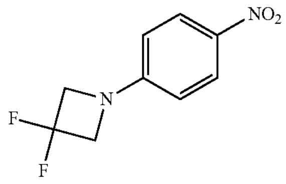

3,3-difluoro-1-(4-nitrophenyl)azetidine (31)

(32)

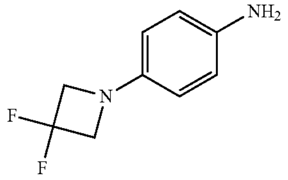

4-(3,3-difluoroazetidin-1-yl)aniline (32). In a 150 ml RB flask was taken 660 mg 3,3-difluoro-1-(4-nitrophenyl)azetidine in 40 ml of 1:1 MeOH/THF and added 25 mg of 10% Pd on carbon. The reaction blanketed with a continuous flow of hydrogen and stirred at room temperature for 3 hours (reaction complete by HPLC). The reaction filtered through celite, and the solvent removed under vacuum. Azeotroping with toluene 3× and drying under vacuum afforded the aniline as a yellow solid. The product was used without purification.

(34)

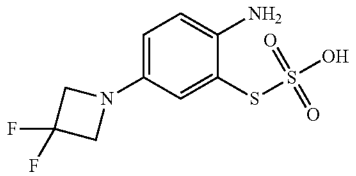

S-(2-amino-5-(3,3-difluoroazetidin-1-yl)phenyl) O-hydrogen sulfurothioate (34). To a solution of 412 mg 4-(3,3-difluoroazetidin-1-yl)aniline (1.0 eq., 2.24 mmol) in 10 ml of D.I. water was added all at once 407 mg sodium thiosulfate pentahydrate (1.1 eq., 2.58 mmol) in 2 ml D.I. water. The solution cooled to 5 C.° on and ice bath and added 533 mg sodium persulfate (1.0 eq., 2.24 mmol) in 5 ml D.I. water dropwise over fifteen minutes. The reaction was stirred at 5 C.° for three hours then allowed to come to room temperature and stirred for 1 hour. The black solid precipitate was collected via filtration and washed with water (10 ml) then dried under vacuum. The crude diamine-5-thiosulfonic acid was taken in a round bottom flask and ethyl acetate (20 ml) was added. The slurry was heated to reflux for one hour and then cooled to room temperature. Once the slurry had cooled, the purple solid was collected via filtration washed with ethyl acetate (50 ml) and dried under vacuum to give 478 mg of product as a purple solid (72% yield).

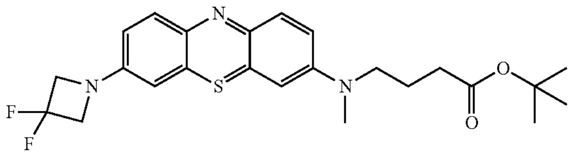

tert-butyl 4-((7-(3,3-difluoroazetidin-1-yl)-5l3-phenothiazin-3-yl)(methyl)amino)butanoate. To a solution of 107 mg S-(2-amino-5-(3,3-difluoroazetidin-1-yl)phenyl) O-hydrogen sulfurothioate (1.0 eq., 0.36 mmol) in 20 ml of MeOH/D.I. water (2:1) was added all at once 90 mg tert-butyl 4-(methyl(phenyl)amino)butanoate (1.0 eq., 0.36 mmol) and 360 mg $AgCO_3$ on celite (50 weight %). The reaction refluxed for 2 hours then cooled to room temperature and filtered. Preparative HPLC followed by lyophilization afforded 124 mg (75% yield) of the pure thioninium as a blue solid.

(35)

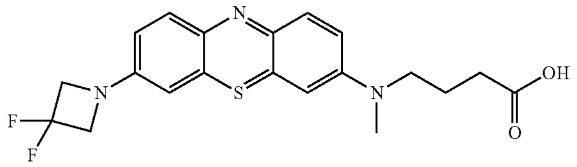

4-((7-(3,3-difluoroazetidin-1-yl)-5l3-phenothiazin-3-yl)(methyl)amino)butanoic acid (35). 124 mg tert-butyl 4-((7-(3,3-difluoroazetidin-1-yl)-5l3-phenothiazin-3-yl)(methyl)amino)butanoate was taken in 15 ml of 30% trifluoracetic acid/DCM and stirred at room temperature for 1.5 hours. The solvent removed under vacuum and the residue azeotroped with toluene 3×. The blue residue was dried under vacuum and used without purification.

(36)

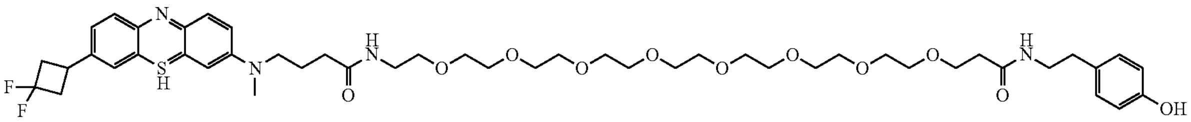

1-(4-((7-(3,3-difluoroazetidin-1-yl)-5l3-phenothiazin-3-yl)(methyl)amino)butanamido)-N-(4-hydroxyphenethyl)-3,6,9,12,15,18,21,24-octaoxaheptacosan-27-amide (36). 33.5 mg 4-((7-(3,3-difluoroazetidin-1-yl)-5l3-phenothiazin-3-yl)(methyl)amino)butanoic acid (1.0 eq, 0.083 mmol) was dissolved in 4 ml of DCM then added 100 μL 1.0 M DCC (1.2 eq, 0.10 mmol) followed by 11.5 mg NHS (1.2 eq, 0.10 mmol). The reaction stirred at room temperature under nitrogen until ester formation was complete as indicated by HPLC (5 hours). The urea was removed by filtration then added 62 mg 1-amino-N-(4-hydroxyphenethyl)-3,6,9,12,15,18,21,24-octaoxaheptacosan-27-amide trifluoroacetate salt (1.1 eq, 0.411 mmol) followed by 41 μL triethyl amine (3.0 eq, 0.25 mmol). The reaction stirred at room temperature under nitrogen until amide formation was complete as indicated by HPLC (14 hours). Preparative HPLC followed by lyophilization afforded 56 mg (71% yield) of the pure thioninium.

(37)

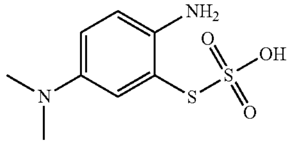

S-(2-amino-5-(dimethylamino)phenyl) O-hydrogen sulfurothioate (37). To a solution of 5.0 g N1,N1-dimethylbenzene-1,4-diamine (1.0 eq., 36.0 mmol) in 100 ml of D.I. water was added all at once 10.03 g sodium thiosulfate pentahydrate (1.1 eq., 40 mmol) in 20 ml D.I. water. The solution cooled to 5 C.° on and ice bath and added 8.57 g sodium persulfate (1.0 eq., 36 mmol) in 40 m D.I. water dropwise over fifteen minutes. The reaction stirred at 5 C.° for three hours then allowed to come to room temperature and stirred for 1 hour. The black solid precipitate collected via filtration and washed with water (50 ml) then dried under vacuum. The N',N'-dimethyl-p-phenylene diamine-5-thiosulfonic acid was added to a round bottom flask and ethyl acetate (100 ml) was added. The slurry heated to reflux for one hour and then cooled to room temperature. Once the slurry had cooled the purple solid was collected via filtration washed with ethyl acetate (50 ml) and dried under vacuum to give 6.6 g of product as a purple solid (74% yield).

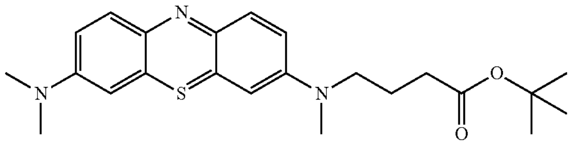

tert-butyl 4-((7-(dimethylamino)-5l3-phenothiazin-3-yl)(methyl)amino)butanoate. To a solution of 500 mg S-(2-amino-5-(dimethylamino)phenyl) O-hydrogen sulfurothioate (1.0 eq., 2.0 mmol) in 30 ml of MeOH/D.I. water (2:1) was added all at once 500 mg tert-butyl 4-(methyl(phenyl)amino)butanoate (1.0 eq., 2.0 mmol) and 2.0 g $AgCO_3$ on celite (50 weight %). The reaction refluxed for 2 hours, cooled to room temperature and filtered. Preparative HPLC followed by lyophilization afforded 586 mg (71% yield) of the pure thioninium as a blue solid.

(38)

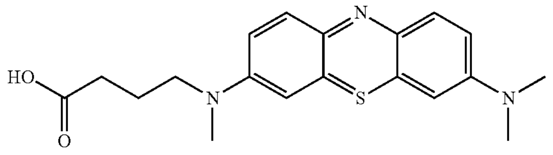

4-((7-(dimethylamino)-5l3-phenothiazin-3-yl)(methyl)amino)butanoic acid (38). 500 mg tert-butyl 4-((7-(dimethylamino)-5l3-phenothiazin-3-yl)(methyl)amino)butanoate was taken in 20 ml of 30% trifluoracetic acid/DCM and stirred at room temperature for 3 hours. The solvent removed under vacuum and the residue azeotroped with toluene 3×. The blue residue dried under vacuum and used without purification.

(41)

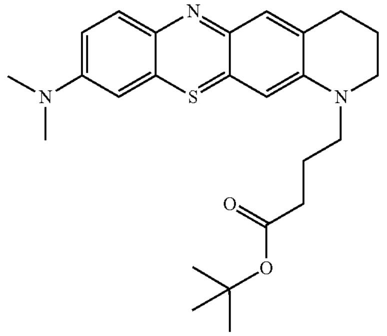

tert-butyl 4-(9-(dimethylamino)-3,4-dihydro-1l13-pyrido[3,2-b]phenothiazin-1(2H)-yl)butanoate (41). To a solution of 211 mg S-(2-amino-5-(dimethylamino)phenyl) O-hydrogen sulfurothioate (1.0 eq., 0.85 mmol) in 30 ml of MeOH/D.I. water (2:1) was added all at once 237 mg tert-butyl 4-(3,4-dihydroquinolin-1(2H)-yl)butanoate (1.0 eq., 2.85 mmol) and 1.0 g $AgCO_3$ on celite (50 weight %). The reaction refluxed for 2 hours cooled to room temperature and filtered. Preparative HPLC followed by lyophilization afforded 288 mg (77% yield) of the pure thioninium as a blue solid.

(42)

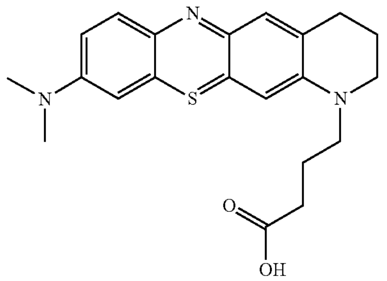

4-(9-(dimethylamino)-3,4-dihydro-1l13-pyrido[3,2-b]phenothiazin-1(2H)-yl)butanoic acid (42). 288 mg tert-butyl 4-(9-(dimethylamino)-3,4-dihydro-1l13-pyrido[3,2-b]phenothiazin-1(2H)-yl)butanoate was taken in 20 ml of 30% trifluoracetic acid/DCM and stirred at room temperature for 3 hours. The solvent removed under vacuum and the residue azeotroped with toluene 3×. The blue residue dried under vacuum and used without purification.

(39)

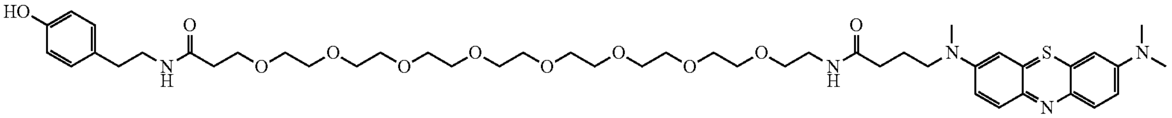

1-(4-((7-(dimethylamino)-5l3-phenothiazin-3-yl)(methyl)amino)butanamido)-N-(4-hydroxyphenethyl)-3,6,9,12,15,18,21,24-octaoxaheptacosan-27-amide (39). 133 mg 4-(9-(dimethylamino)-3,4-dihydro-1l13-pyrido[3,2-b]phenothiazin-1(2H)-yl)butanoic acid (1.0 eq, 0.374 mmol) was dissolved in 5 ml of DCM then added 448 μL 1.0 M DCC (1.2 eq, 0.448 mmol) followed by 52 mg NHS (1.2 eq, 0.448 mmol). The reaction stirred at room temperature under nitrogen until ester formation was complete as indicated by HPLC (6 hours). The urea was removed by filtration then added 278 mg 1-amino-N-(4-hydroxyphenethyl)-3,6,9,12,15,18,21,24-octaoxaheptacosan-27-amide trifluoroacetate salt (1.1 eq, 0.411 mmol) followed by 156 μL triethyl amine (3.0 eq, 1.12 mmol). The reaction stirred at room temperature under nitrogen until amide formation was complete as indicated by HPLC (14 hours). Preparative HPLC followed by lyophilization afforded 29 mg (77% yield) of the pure thioninium.

(43)

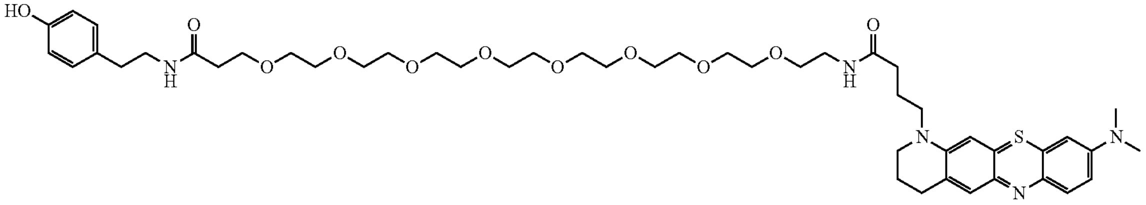

1-(4-(9-(dimethylamino)-3,4-dihydro-1113-pyrido[3,2-b]phenothiazin-1(2H)-yl)butanamido)-N-(4-hydroxyphenethyl)-3,6,9,12,15,18,21,24-octaoxaheptacosan-27-amide (43). 4-(9-(dimethylamino)-3,4-dihydro-1113-pyrido[3,2-b]phenothiazin-1(2H)-yl)butanoic acid (15 mg, 0.049 mmol) was dissolved in 3 ml of DCM then added 84 µL 1.0 M DCC (2.0 eq, 0.084 mmol) followed by 9.7 mg NHS (2.0 eq, 0.084 mmol). The reaction stirred at room temperature under nitrogen until ester formation was complete as indicated by HPLC (6 hours). The urea was removed by filtration then added 85 mg 1-amino-N-(4-hydroxyphenethyl)-3,6,9,12,15,18,21,24-octaoxaheptacosan-27-amide trifluoroacetate salt (3.0 eq, 0.126 mmol) followed by 30 µL triethyl amine (5.0 eq, 0.21 mmol). The reaction stirred at room temperature under nitrogen until amide formation was complete as indicated by HPLC (14 hours). Preparative HPLC followed by lyophilization afforded 29 mg (77% yield) of the pure thioninium.

(46)

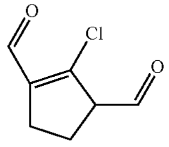

2-chlorocyclopentane-1,3-dicarbaldehyde (46). To a 100 ml RB flask was added 16 ml anhydrous DMF and 16 ml DCM and the flask placed on an ice bath with stirring. To the flask then added 14.5 ml $POCl_3$ in 14 ml DCM and the reaction stirred for 1 hr. The reaction was allowed to come to room temperature and 3.43 g of cyclopentanone in 10 ml of DMF was added over 5 minutes. The reaction was placed on an oil bath at 65 C.° for 3 hr. After cooling, the reaction was poured onto 80 g of ice and made basic with the careful addition of 10 M NaOH. The dialdehyde precipitate was collected by filtration and washed 3× with cold water. Drying under vacuum afforded 5.1 g (77% yield) of the pure dialdehyde.

(47)

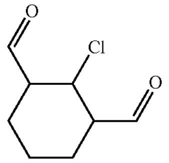

2-chlorocyclohexane-1,3-dicarbaldehyde (47). To a 100 ml RB flask was added 16 ml anhydrous DMF and 16 ml DCM and the flask placed on an ice bath with stirring. To the flask was then added 14.5 ml $POCl_3$ in 14 ml DCM and the reaction stirred for 1 hr. The reaction was allowed to come to room temperature and 4.0 g of cyclohexanone in 10 ml of DMF was added over 5 minutes. The reaction then heated on an oil bath at 65 C.° for 3 hr. After cooling, the reaction was poured onto 80 g of ice and made basic with the careful addition of 10 M NaOH. The dialdehyde precipitate was collected by filtration and washed 3× with cold water. Drying under vacuum afforded 4.9 g (69% yield) of the pure dialdehyde.

(44)

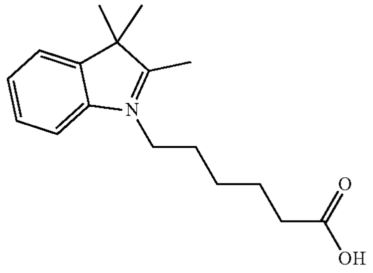

6-(2,3,3-trimethyl-3H-114-indol-1-yl)hexanoic acid (44). To a 100 ml RB pressure vessel was added 35 ml dichlorobenzene, 5.0 g 2,3,3-trimethyl-3H-indole (1.0 eq. 31.4 mmol) and 7.5 g 6-bromohexanoic acid (1.5 eq. 47.1 mmol). The flask was placed on an oil bath at 110 C.° for 16 hours. After cooling to room temperature, the product was collected by filtration then washed 2× with dichlorobenzene and 2× with ether. The product dried under vacuum to give 6.1 g (71% yield) of the pure acid as pale white crystals.

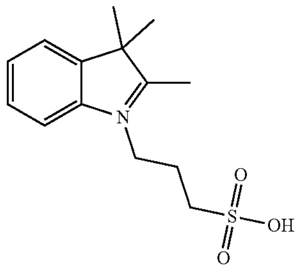

3-(2,3,3-trimethyl-3H-114-indol-1-yl)propane-1-sulfonic acid. To a 100 ml RB pressure vessel was added 35 ml dichlorobenzene, 5.0 g 2,3,3-trimethyl-3H-indole (1.0 eq. 31.4 mmol) and 5.75 g 1,2-oxathiolane 2,2-dioxide (1.5 eq. 47.1 mmol). The flask was placed on an oil bath at 110 C.° for 16 hours. After cooling to room temperature, the product was collected by filtration then washed 2× with dichlorobenzene and 2× with ether. The product dried under vacuum to give 6.9 g (78% yield) of the sulfonic acid as a crystalline solid.

(50)

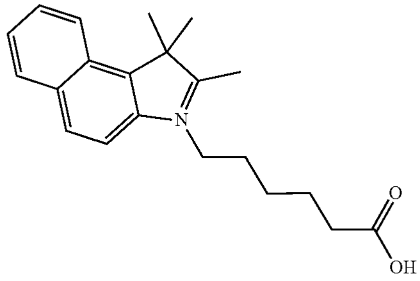

6-(1,1,2-trimethyl-1H-314-benzo[e]indol-3-yl)hexanoic acid (50). To a 100 ml RB pressure vessel was added 35 dichlorobenzene, 5.0 g 1,1,2-trimethyl-1H-benzo[e]indole (1.0 eq. 23.9 mmol) and 7.0 g 6-bromohexanoic acid (1.5 eq. 35.8 mmol). The flask was placed on an oil bath at 110 C.° for 16 hours. After cooling to room temperature, the product was collected by filtration then washed 2× with dichlorobenzene and 2× with ether. The product dried under vacuum to give 3.56 g (46% yield) of the acid as gray crystals.

(53)

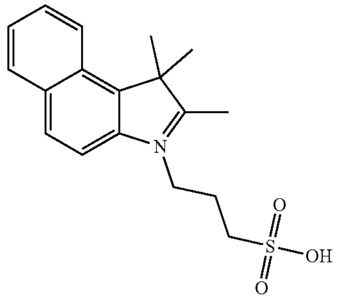

3-(1,1,2-trimethyl-1H-314-benzo[e]indol-3-yl)propane-1-sulfonic acid (53). To a 100 ml RB pressure vessel was added 35 ml dichlorobenzene, 5.0 g 1,1,2-trimethyl-1H-benzo[e]indole (1.0 eq. 23.9 mmol) and 4.37 g 2-oxathiolane 2,2-dioxide (1.5 eq. 35.8 mmol). The flask was placed on an oil bath at 110 C.° for 16 hours. After cooling to room temperature, the product was collected by filtration then washed 2× with dichlorobenzene and 2× with ether. Drying under vacuum gave 5.8 g (73% yield) of the crystalline sulfonic acid.

(45)

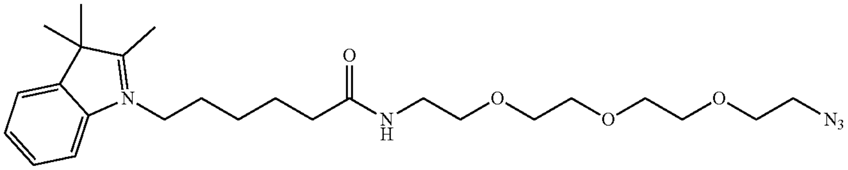

N-(2-(2-(2-(2-azidoethoxy)ethoxy)ethoxy)ethyl)-6-(2,3,3-trimethyl-3H-114-indol-1-yl)hexanamide (45). To a solution of 2.5 g 6-(2,3,3-trimethyl-3H-114-indol-1-yl)hexanoic acid (1.0 eq., 9.12 mmol) in 25 ml of anhydrous DMF was added 2.8 g of DSC (1.2 eq., 10.95 mmol) and 1.67 g of DMAP (1.5 eq., 1.37 mmol) the reaction blanketed with nitrogen and stirred at room temperature until ester formation was complete as determined by HPLC (30 minutes). 2.99 g of 2-(2-(2-(2-azidoethoxy)ethoxy)ethoxy)ethan-1-amine (1.5 eq, 0.15 mmol) was then added. The reaction stirred at room temperature under nitrogen for 16 hours (amide formation complete as indicated by HPLC). Preparative HPLC followed by lyophilization afforded 2.64 g (61% yield) of the pure azide.

(51)

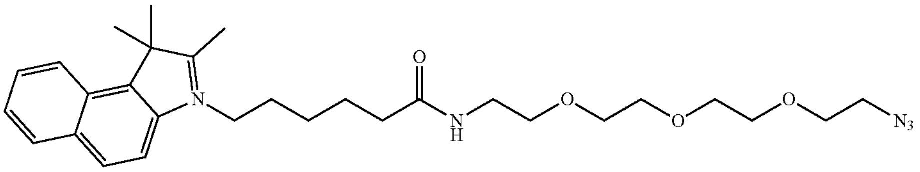

N-(2-(2-(2-(2-azidoethoxy)ethoxy)ethoxy)ethyl)-6-(1,1,2-trimethyl-1H-314-benzo[e]indol-3-yl)hexanamide (51). To a solution of 1.0 g 6-(1,1,2-trimethyl-1H-314-benzo[e]indol-3-yl)hexanoic acid (1.0 eq., 3.22 mmol) in 20 ml of anhydrous DMF was added 990 mg of DSC (1.2 eq., 3.67 mmol) and 560 mg of DMAP (1.5 eq., 4.83 mmol) the reaction blanketed with nitrogen and stirred at room temperature until ester formation was complete as determined by HPLC (20 minutes). 915 g of 2-(2-(2-(2-azidoethoxy)ethoxy)ethoxy)ethan-1-amine (1.3 eq, 4.19 mmol) was then added and the reaction stirred at room temperature under nitrogen for 18 hours. Preparative HPLC followed by lyophilization afforded 1.13 g (67% yield) of the pure azide.

(48)

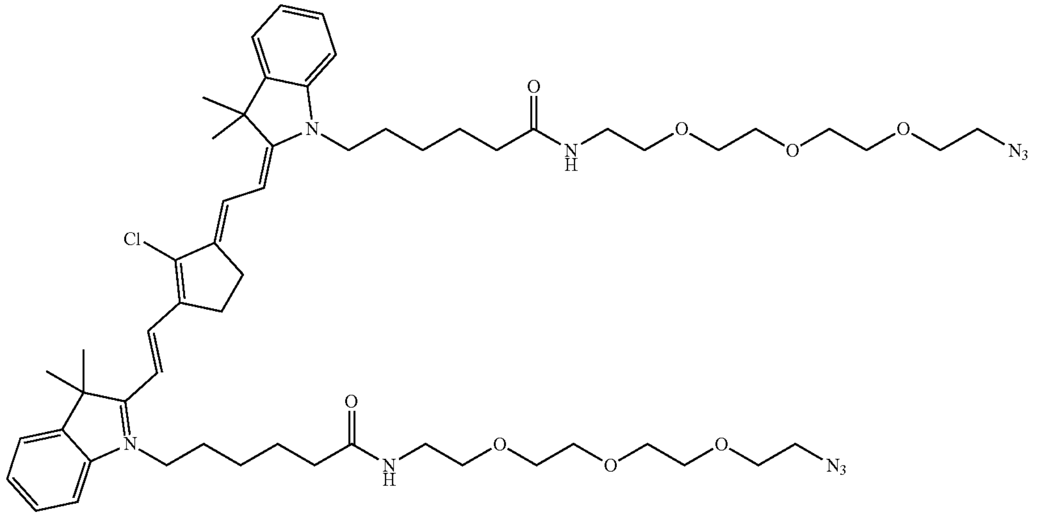

-

6-((E)-2-((E)-2-(3-((E)-2-(1-(1-azido-13-oxo-3,6,9-trioxa-12-azaoctadecan-18-yl)-3,3-dimethyl-3H-114-indol-2-yl)vinyl)-2-chlorocyclopent-2-en-1-ylidene)ethylidene)-3,3-dimethylindolin-1-yl)-N-(2-(2-(2-(2-azidoethoxy)ethoxy)ethoxy)ethyl)hexanamide (48). In a 20 ml amber vial was taken 216 mg N-(2-(2-(2-(2-azidoethoxy)ethoxy)ethoxy)ethyl)-6-(2,3,3-trimethyl-3H-4-indol-1-yl)hexanamide (2.0 eq., 0.45 mmol), 36 mg 2-chlorocyclopentane-1,3-dicarbaldehyde (1.0 eq., 0.23 mmol) and 56 mg of anhydrous sodium acetate (3.0 eq., 0.68) in 9 ml of absolute ethanol. The vial was blanketed with nitrogen sealed and placed on an oil bath at 70 C.° for 90 minutes. Preparative HPLC followed by lyophilization afforded 140 mg (57% yield) of the pure cyanine heptamethine dye.

(49)

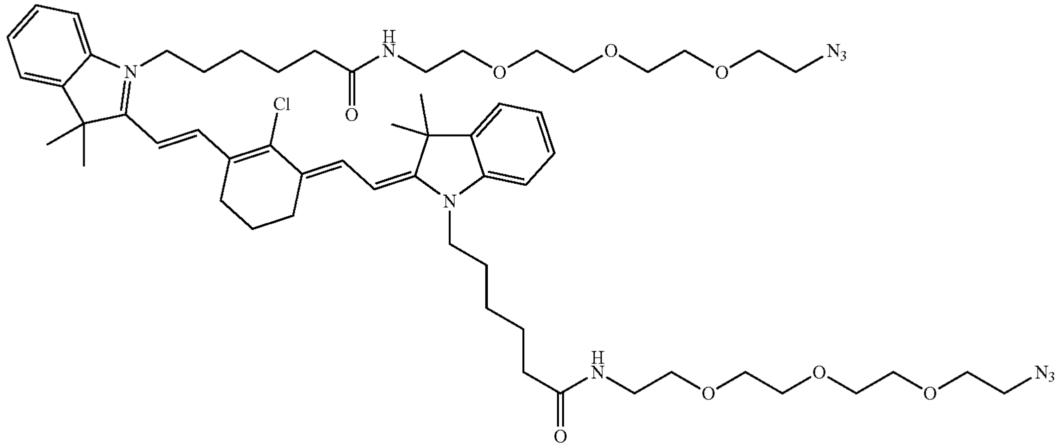

6-((E)-2-((E)-2-(3-((E)-2-(1-(1-azido-13-oxo-3,6,9-trioxa-12-azaoctadecan-18-yl)-3,3-dimethyl-3H-114-indol-2-yl)vinyl)-2-chlorocyclohex-2-en-1-ylidene)ethylidene)-3,3-dimethylindolin-1-yl)-N-(2-(2-(2-(2-azidoethoxy)ethoxy)ethoxy)ethyl)hexanamide (49). In a 20 ml amber vial was taken 182 mg N-(2-(2-(2-(2-azidoethoxy)ethoxy)ethoxy)ethyl)-6-(2,3,3-trimethyl-3H-114-indol-1-yl)hexanamide (2.0 eq., 0.38 mmol), 26 mg 2-chlorocyclohexane-1,3-dicarbaldehyde (1.0 eq., 0.19 mmol) and 47 mg of anhydrous sodium acetate (3.0 eq., 0.57) in 8 ml of absolute ethanol. The vial was flushed with nitrogen, sealed and placed on an oil bath at 70 C.° for 90 minutes. Preparative HPLC followed by lyophilization provided 109 mg (53% yield) of the pure cyanine heptamethine dye.

6-(2-((E)-2-((E)-3-((E)-2-(3-(1-azido-13-oxo-3,6,9-trioxa-12-azaoctadecan-18-yl)-1,1-dimethyl-1,3-dihydro-2H- benzo[e]indol-2-ylidene)ethylidene)-2-chlorocyclopent-1-en-1-yl)vinyl)-1,1-dimethyl-1H-314-benzo[e]indol-3-yl)-N-(2-(2-(2-(2-azidoethoxy)ethoxy)ethoxy)ethyl)hexanamide. In a 20 ml amber vial was taken 80 mg N-(2-(2-(2-(2-azidoethoxy)ethoxy)ethoxy)ethyl)-6-(1,1,2-trimethyl-1H-314-benzo[e]indol-3-yl)hexanamide (2.0 eq., 0.15 mmol), 12 mg 2-chlorocyclopentane-1,3-dicarbaldehyde (1.0 eq., 0.076 mmol) and 19 mg of anhydrous sodium acetate (3.0 eq., 0.23) in 7 ml of absolute ethanol. The vial was purged with nitrogen, sealed and placed on an oil bath at 70 C.° for 90 minutes. Preparative HPLC followed by lyophilization afforded 44 mg (49% yield) of the pure cyanine heptamethine dye.

(54)

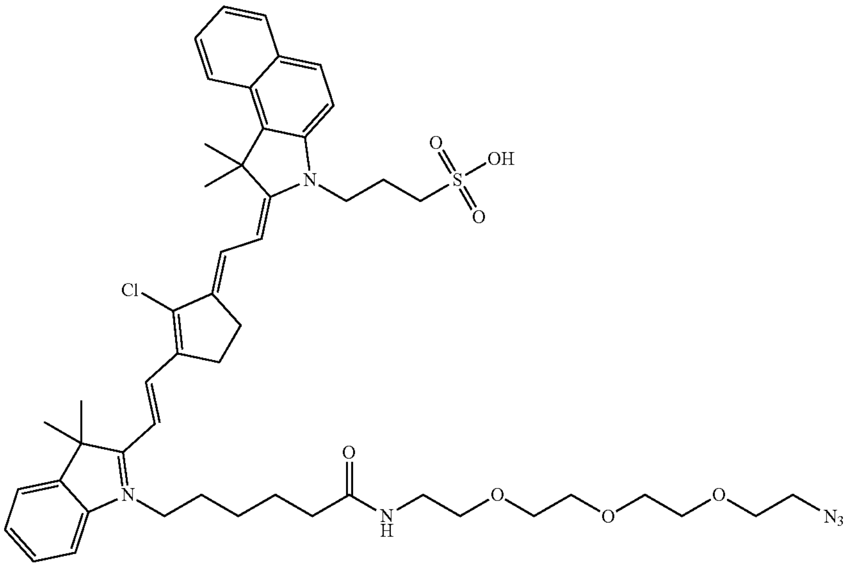

-

3-((E)-2-((E)-2-(3-((E)-2-(1-(1-azido-13-oxo-3,6,9-trioxa-12-azaoctadecan-18-yl)-3,3-dimethyl-3H-114-indol-2-yl)vinyl)-2-chlorocyclopent-2-en-1-ylidene)ethylidene)-1,1-dimethyl-1,2-dihydro-3H-benzo[e]indol-3-yl)propane-1-sulfonic acid (54). In a 20 ml amber vial was taken 100 mg N-(2-(2-(2-(2-azidoethoxy)ethoxy)ethoxy)ethyl)-6-(2,3,3-trimethyl-3H-114-indol-1-yl)hexanamide (1.0 eq., 0.21), 70 mg 3-(1,1,2-trimethyl-1H-314-benzo[e]indol-3-yl)propane-1-sulfonic acid (1.0 eq., 0.21), 33 mg 2-chlorocyclopentane-1,3-dicarbaldehyde (1.0 eq., 0.21 mmol) and 52 mg of anhydrous sodium acetate (3.0 eq., 0.63) in 12 ml of absolute ethanol. The vial was flushed with nitrogen, sealed and placed on an oil bath at 70 C.° for 90 minutes. Preparative HPLC followed by lyophilization afforded 76 mg (39% yield) of the pure nonsymmetric cyanine heptamethine dye.

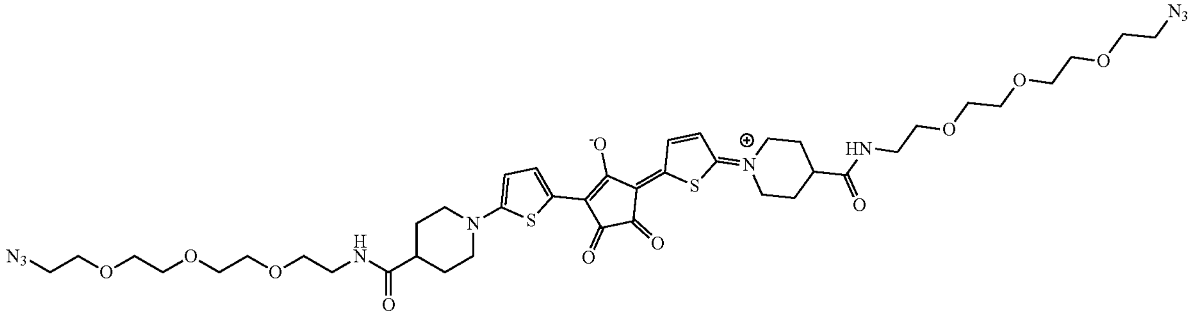

(Z)—N-(2-(2-(2-(2-azidoethoxy)ethoxy)ethoxy)ethyl)-1-(5-(3-(5-(4-((2-(2-(2-(2-azidoethoxy)ethoxy)ethoxy)ethyl) carbamoyl)-114-piperidin-1-ylidene)thiophen-2(5H)-ylidene)-2-hydroxy-4,5-dioxocyclopent-1-en-1-yl) thiophen-2-yl)piperidine-4-carboxamide. To a solution of 500 mg (Z)-5-(5-(4-carboxy-114-piperidin-1-ylidene)thiophen-2(5H)-ylidene)-2-(5-(4-carboxypiperidin-1-yl)thiophen-2-yl)-3,4-dioxocyclopent-1-en-1-olate (1.0 eq., 0.95 mmol) in 30 ml of anhydrous DMF was added 301 mg of DSC (1.2 eq., 1.14 mmol) and 174 mg of DMAP (1.5 eq., 1.43 mmol) the reaction blanketed with nitrogen and stirred at room temperature until ester formation was complete as determined by HPLC (15 minutes). 249 mg of 2-(2-(2-(2-azidoethoxy)ethoxy)ethoxy)ethan-1-amine (1.2 eq, 1.14 mmol) was then added and the reaction stirred at room temperature under nitrogen for 18 hours. Preparative HPLC followed by lyophilization afforded 652 mg (74% yield) of the pure azide.

In some embodiments, the click conjugates of Formula (XIV) may be synthesized according to any method as known to those of ordinary skill in the art. In some embodiments, a reagent comprising the desired reactive functional group and linker are merely coupled with a tyramide or derivative or analog thereof as illustrated in the reaction schemes below. For example, a tyramide (having a terminal amine group) may be coupled to a compound comprising an amine reactive group (e.g., active esters such as N-Hydroxysuccinimide (NHS) or sulfo-NHS, isothiocyanates, isocyanates, acyl azides, sulfonyl chlorides, aldehydes, glyoxals, epoxides, oxiranes, carbonates, aryl halides, imidoesters, anhydrides and the like).

In some of the specific examples below, a Click partner having an NHS-ester group is coupled with a tyramide. In some embodiments, the reaction takes place in DMSO and is allowed to react for 60 minutes. The reaction is then diluted with methanol and directly purified by preparative HPLC.

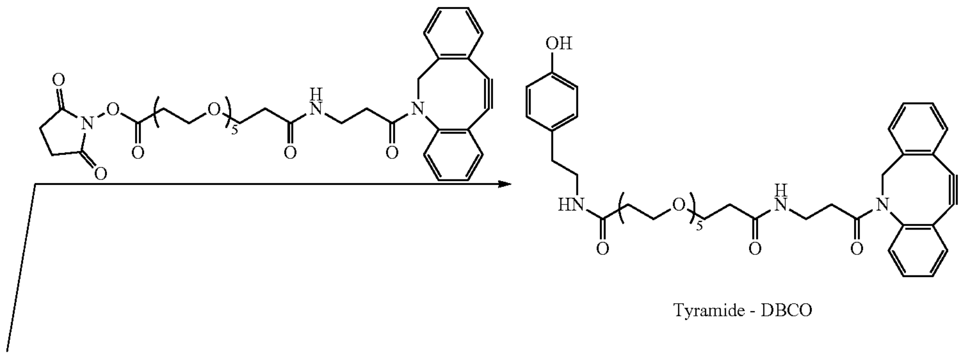

Tyramide - DBCO

-continued

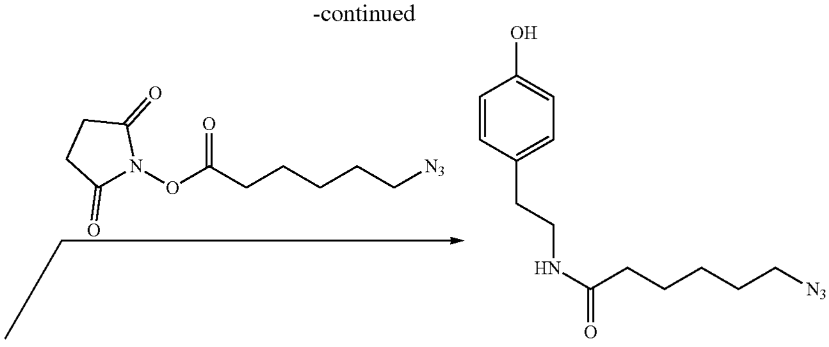

Tyramide - Azide

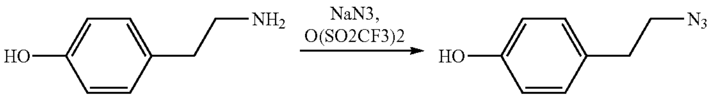

Tyrazide

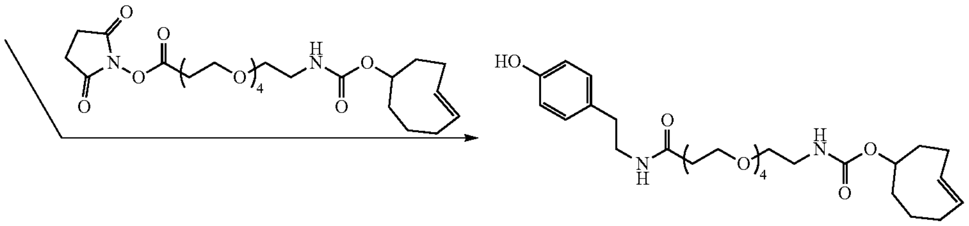

Tyramide - TCO

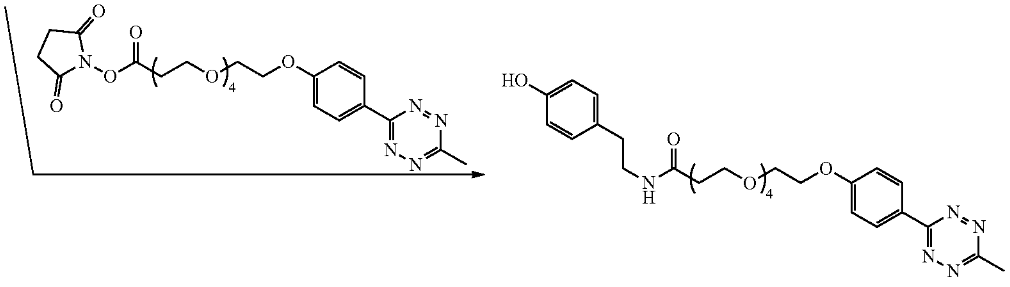

Tyramide - Tetrazine

In other embodiments, click conjugates of Formula (XIV) may be synthesized according to any method as known to those of ordinary skill in the art. In some embodiments, a reagent comprising the desired reactive functional group and linker are merely coupled with a quinone methide precursor or derivative or analog thereof as illustrated in the reaction schemes which follow. For example, a quinone methide precursor having a terminal amine group may be coupled to a compound comprising an amine reactive group (e.g., active esters such as N-Hydroxysuccinimide (NHS) or sulfo-NHS, isothiocyanates, isocyanates, acyl azides, sulfonyl chlorides, aldehydes, glyoxals, epoxides, oxiranes, carbonates, aryl halides, imidoesters, anhydrides and the like).

In some of the specific examples below, a Click partner having an NHS-ester group is coupled with a quinone methide precursor having a terminal amine. In some embodiments, the reaction takes place in DMSO and is allowed to react for 60 minutes. The reaction is then diluted with methanol and directly purified by preparative HPLC.

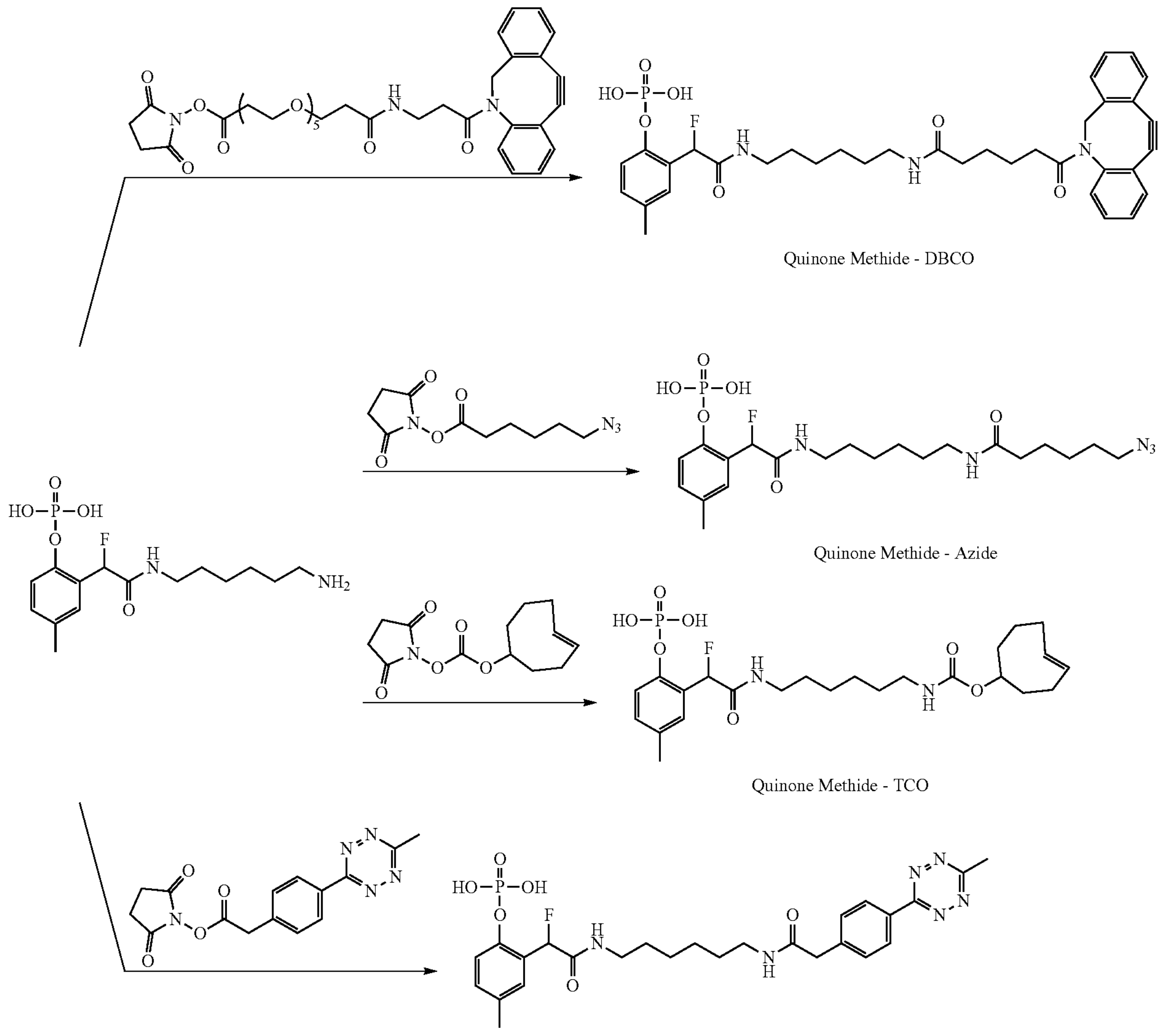

Quinone Methide - DBCO

Quinone Methide - Azide

Quinone Methide - TCO

Quinone Methide - Tetrazine

Methods

The present disclosure also provides a method of detecting a target (e.g., a protein target or a nucleic acid target) within a biological sample using any of the conjugates described herein. In some embodiments, the present disclosure provides methods of detecting two or more targets within a biological sample using any of the conjugates described herein.

In some embodiments, the conjugate (including the detectable moieties) is covalently deposited onto the biological sample. In some embodiments, covalent deposition of a conjugate including a detectable moiety is accomplished using Tyramide Signal Amplification (TSA), which has also been referred to as catalyzed reporter deposition (CARD). U.S. Pat. No. 5,583,001 discloses a method for detecting and/or quantitating an analyte using an analyte-dependent enzyme activation system that relies on catalyzed reporter deposition to amplify the detectable label signal. Catalysis of an enzyme in a CARD or TSA method is enhanced by reacting a labeled phenol molecule with an enzyme. Modern methods utilizing TSA effectively increase the signals obtained from IHC and ISH assays while not producing significant background signal amplification (see, for example, U.S. application publication No. 2012/0171668 which is hereby incorporated by reference in its entirety for disclosure related to tyramide amplification reagents). Reagents for these amplification approaches are being applied to clinically important targets to provide robust diagnostic capabilities previously unattainable (VENTANA OptiView Amplification Kit, Ventana Medical Systems, Tucson Ariz., Catalog No. 760-099).

TSA takes advantage of a reaction catalyzed by horseradish peroxidase (HRP) acting on tyramide. In the presence of $H_2O_2$, tyramide is converted to a highly reactive and short-lived radical intermediate that reacts preferentially with electron-rich amino acid residues on proteins. Covalently bound conjugates or conjugates including a detectable moiety can then be detected by variety of chromogenic visualization techniques and/or by fluorescence microscopy. In IHC and ISH, where spatial and morphological context is highly valued, the short lifetime of the radical intermediate results in covalent binding of the tyramide to on the tissue in close proximity to the site of generation, thereby giving discrete and specific signals at the locations of proteins and nucleic acid targets.

In other embodiments, covalent deposition of a conjugate including a detectable moiety is performed using quinone methide chemistry. U.S. Pat. No. 10,168,336, entitled "Quinone Methide Analog Signal Amplification," granted on Jan. 1, 2019, describes a technique ("QMSA") that, like TSA, may be used to increase signal amplification without significantly increasing background signals. In particular, U.S. Pat. No. 10,168,336 describes novel quinone methide analog precursors and methods of using the quinone methide analog precursors to detect one or more targets in a biological sample. In a particular embodiment, the method of detection includes contacting the sample with a detection antibody or probe, then contacting the sample with a labeling conjugate that comprises an alkaline phosphatase (AP) enzyme and a binding moiety, where the binding moiety recognizes the antibody or probe (for example, by binding to a hapten or a species-specific antibody epitope, or a combination thereof). The alkaline phosphatase enzyme of the labeling conjugate interacts with a quinone methide analog precursor comprising the detectable moiety, thereby forming a reactive quinone methide analog, which binds covalently to the biological sample proximally to or directly on the target. The detectable label is then detected, such as visually or through imaging techniques. U.S. Pat. No. 10,168,336 is incorporated by reference herein in its entirety.

Another technique for depositing a conjugate including a detectable moiety employs "click" chemistry to form a covalent bond between a detectable moiety and a biomarker in a sample. "Click chemistry" is a chemical philosophy, independently defined by the groups of Sharpless and Meldal, that describes chemistry tailored to generate substances quickly and reliably by joining small units together. "Click chemistry" has been applied to a collection of reliable and self-directed organic reactions (Kolb, H. C.; Finn, M. G.; Sharpless, K. B. Angew. Chem. Int. Ed. 2001, 40, 2004-2021). In the context of covalently depositing detectable labels onto a biological sample, a click chemistry technique is described in US2019/0204330, which incorporated by reference herein. In this technique, either tyramide deposition as described above or quinone methide deposition also described above, is used to covalently anchor a first reactive group capable of participating in a click chemistry reaction to the biological sample. A second component of the detection system having a corresponding second reactive group capable of participating in a click chemistry reaction is then reacted with the first reactive group to covalently bind the second component to the biological sample. In a particular embodiment, the technique described includes contacting the biological sample with a first detection probe specific to a first target. The first detection probe may be a primary antibody or a nucleic acid probe. Subsequently, the sample is contacted with a first labeling conjugate, the first labeling conjugate comprising a first enzyme. In some embodiments, the first labeling conjugate is a secondary antibody specific for either the primary antibody (such as the species from which the antibody was obtained) or to a label (such as a hapten) conjugated to the nucleic acid probe. Next, the biological sample is contacted with a first member of a pair of click conjugates. The first enzyme cleaves the first member of the pair of click conjugates having a tyramide or quinone methide precursor, thereby converting the first member into a reactive intermediate which covalently binds to the biological sample proximally to or directly on the first target. Next, a second member of the pair of click conjugates is contacted with the biological sample, the second member of the pair of click conjugates comprising a first reporter moiety (e.g., a chromophore) and a second reactive functional group, where the second reactive functional group of the second member of the first pair of click conjugates is capable of reacting with the first reactive functional group of the first member of the pair of click conjugates. Finally, signals from the first reporter moiety are detected, In some embodiments of the present disclosure, two methods of detecting a target in a biological sample are described herein. The first method utilizes detectable moieties (including any of those described herein) conjugated to a tyramide or quinone methide precursor moiety (either directly or indirectly through one or more linkers). The second method utilizes detectable moieties (including any of those described herein) conjugated (either directly or indirectly through one or more linkers) to a reactive functional group capable of participating in a click chemistry reaction. Methods and reagents for detecting targets in biological samples using tyramide chemistry, quinone methide chemistry, and click chemistry are described in U.S. Pat. No. 10,041,950, and in U.S. Publication Nos. 2019/0204330, 2017/0089911, and 2019/0187130, the disclosures of which are hereby incorporated by reference herein in their entireties.

In both methods, the target in the biological sample is first labeled with an enzyme. Said another way, a first step in either method is forming a target-enzyme complex. In some embodiments, target-enzyme complex serves as an intermediate for further reaction in either of the two methods described herein. Suitable enzymes for labeling the target-enzyme complex include, but are not limited to, horseradish peroxidase (HRP), alkaline phosphatase (AP), acid phosphatase, glucose oxidase, p-galactosidase, β-glucuronidase or β-lactamase. In some embodiments, the target-enzyme complex is labeled with horseradish peroxidase or alkaline phosphatase.

Figure 1B:
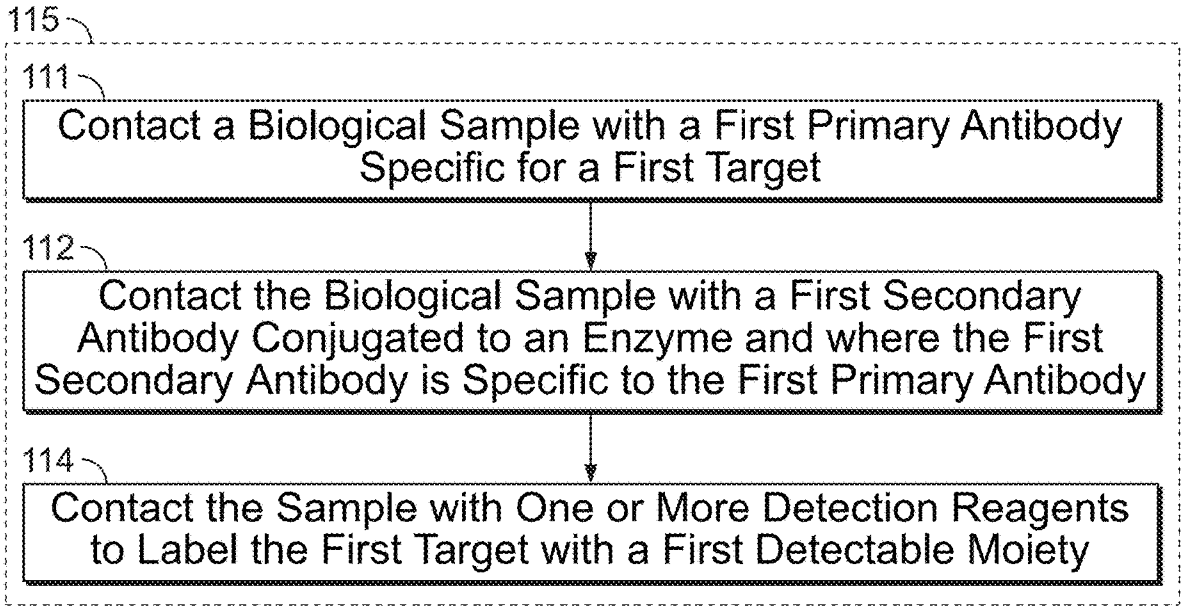
FIG. 1B illustrates methods of labeling a target with a detectable moiety in accordance with one embodiment of the present disclosure.

To facilitate the labeling of the target with an enzyme, in some embodiments, a specific binding entity specific to the target is introduced to the biological sample. With reference to FIGS. 1A and 1B, in some embodiments the one or more specific binding entities specific to the target is a primary antibody (step 101, 111). Following introduction of the primary antibody, a secondary antibody conjugated to a label (directly or indirectly through a linker) may be introduced, where the secondary antibody is specific to the primary antibody (e.g., the secondary antibody is an anti-primary antibody antibody) (steps 102, 112). In some embodiments, the label of the secondary antibody is an enzyme, including any of those described above (see step 112 of FIG. 1B).

In other embodiments, the label of the secondary antibody is a hapten (see step 102 of FIG. 1A). Non-limiting examples of haptens include an oxazole, a pyrazole, a thiazole, a benzofurazan, a triterpene, a urea, a thiourea other than a rhodamine thiourea, a nitroaryl other than dinitrophenyl or trinitrophenyl, a rotenoid, a cyclolignan, a heterobiaryl, an azoaryl, a benzodiazepine, 2,3,6,7-tetrahydro-11-oxo-1H, 5H,11H-[1]benzopyrano[6,7,8-ij]quinolizine-10-carboxylic acid, or 7-diethylamino-3-carboxycoumarin. Other suitable haptens are disclosed in U.S. Pat. No. 8,846,320, the disclosure of which is hereby incorporated by reference herein in its entirety. In those embodiments where the secondary antibody is conjugated to a hapten, an anti-hapten antibody conjugated to an enzyme (including any of those described above) may be introduced to the biological sample to label the target with one or more enzymes (step 103). Subsequently, suitable detection reagents may be introduced to the biological sample to facilitate the labeling of the target (now coupled indirectly to an enzyme) with a detectable moiety (including any of the detectable moieties described herein) (steps 104, 114). The steps in FIGS. 1A and 1B may be repeated any number of times (see steps 105 and 115).

In some embodiments, the specific binding entity is a primary antibody conjugate or a nucleic acid probe conjugate. In some embodiments, the specific binding entity is a primary antibody conjugate coupled to an enzyme. In some embodiments, the primary antibody conjugate is conjugated to horseradish peroxidase or alkaline phosphatase. In other embodiments, the specific binding entity is a nucleic acid probe conjugated to an enzyme, e.g., horseradish peroxidase or alkaline phosphatase. Introduction of the specific binding entity conjugated to an enzyme facilitates the formation of a target-enzyme complex.

In some embodiments, the specific binding entity is a primary antibody conjugate coupled to a hapten or a nucleic acid probe conjugated to a hapten (including any of those haptens described in U.S. Pat. No. 8,846,320, the disclosure of which is hereby incorporated by reference herein in its entirety). In these embodiments, the introduction of a specific binding entity conjugated to hapten facilitates for the formation of a hapten-labeled target. In these embodiments, an anti-hapten antibody-enzyme conjugate specific to the hapten of the hapten-labeled target is introduced to the biological sample so as to label the hapten-labeled target with an enzyme to provide a target-enzyme complex. The primary antibody conjugate, secondary antibody, and/or nucleic acid probe may be introduced to a sample according to procedures known to those of ordinary skill in the art to effect labeling of the target in the biological sample with an enzyme and as illustrated herein.

Methods of Detecting a Target in a Sample Using Tyramide or Quinone Methide Precursor Conjugates In some embodiments, the present disclosure provides methods of labeling one or more targets using a detectable conjugate comprising (i) a tyramide and/or quinone methide precursor moiety, and (ii) a detectable moiety, including any of the detectable moieties described herein. In some embodiments, two or more targets within a sample may be labeled with two or more detectable conjugates including any of the detectable moieties described herein. In some embodiments, three or more targets within a sample may be labeled with two or more detectable conjugates including any of the detectable moieties described herein. In some embodiments, four or more targets within a sample may be labeled with two or more detectable conjugates including any of the detectable moieties described herein. In some embodiments, five or more targets within a sample may be labeled with two or more detectable conjugates including any of the detectable moieties described herein. In some embodiments, six or more targets within a sample may be labeled with two or more detectable conjugates including any of the detectable moieties described herein. In some embodiments, seven or more targets within a sample may be labeled with two or more detectable conjugates including any of the detectable moieties described herein. In some embodiments, eight or more targets within a sample may be labeled with two or more detectable conjugates including any of the detectable moieties described herein. In some embodiments, nine or more targets within a sample may be labeled with two or more detectable conjugates including any of the detectable moieties described herein. In some embodiments, ten or more targets within a sample may be labeled with two or more detectable conjugates including any of the detectable moieties described herein. In some embodiments, the detectable conjugates have Formula (VIII).

Figure 2:
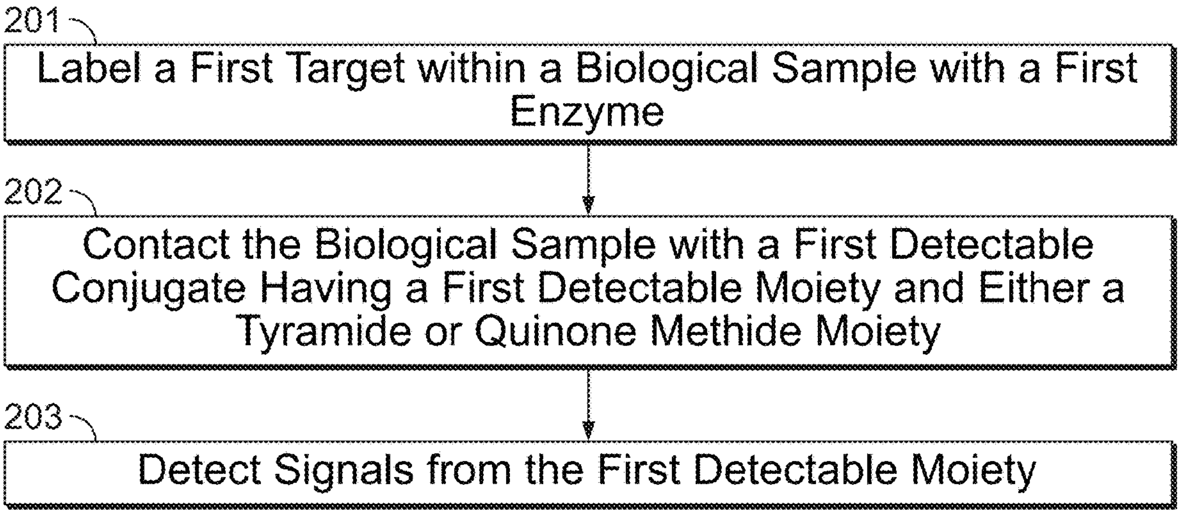
FIG. 2 illustrates a method of detecting signals corresponding to a target in a biological sample, where the method utilizes detectable conjugates including (i) a detectable moiety, and (ii) a tyramide moiety, a derivative of a tyramide moiety, a quinone methide precursor moiety, or a derivative of a quinone methide precursor moiety, in accordance with one embodiment of the present disclosure.

In some embodiments, and with reference to FIG. 2, a biological sample having a first target is labeled with a first enzyme (step 201) to form a first target-enzyme complex. Methods of labeling a first target with a first enzyme are described above and also illustrated in FIGS. 1A and 1B. The biological sample is then contacted with a first detectable conjugate (step 202), the first detectable conjugate comprising a first detectable moiety (including any of those described herein) and either a tyramide, a quinone methide precursor, or a derivative or analog thereof. Examples of detectable conjugates including a tyramide moiety, a quinone methide precursor moiety, or a derivative or analog thereof are described herein (see, e.g., Formulas (VIII) and (VIIIA)-(VIIIF)) Upon interaction of the first enzyme of the first target-enzyme complex with the tyramide or the quinone methide precursor portion of the first detectable conjugate, at least the first detectable moiety of the detectable conjugate is deposited proximal to or onto the first target (see also FIGS. 3 and 4 which illustrate the deposition of a detectable moiety proximal to or onto a target molecule within a biological sample). Finally, signals from the first detectable moiety are detected (e.g., such as using brightfield microscopy) (step 203). Methods of detecting one or more signals from one or more detectable moieties are described in PCT Application No. WO/2014/143155, the disclosure of which is hereby incorporated by reference herein in its entirety.

Figure 3:
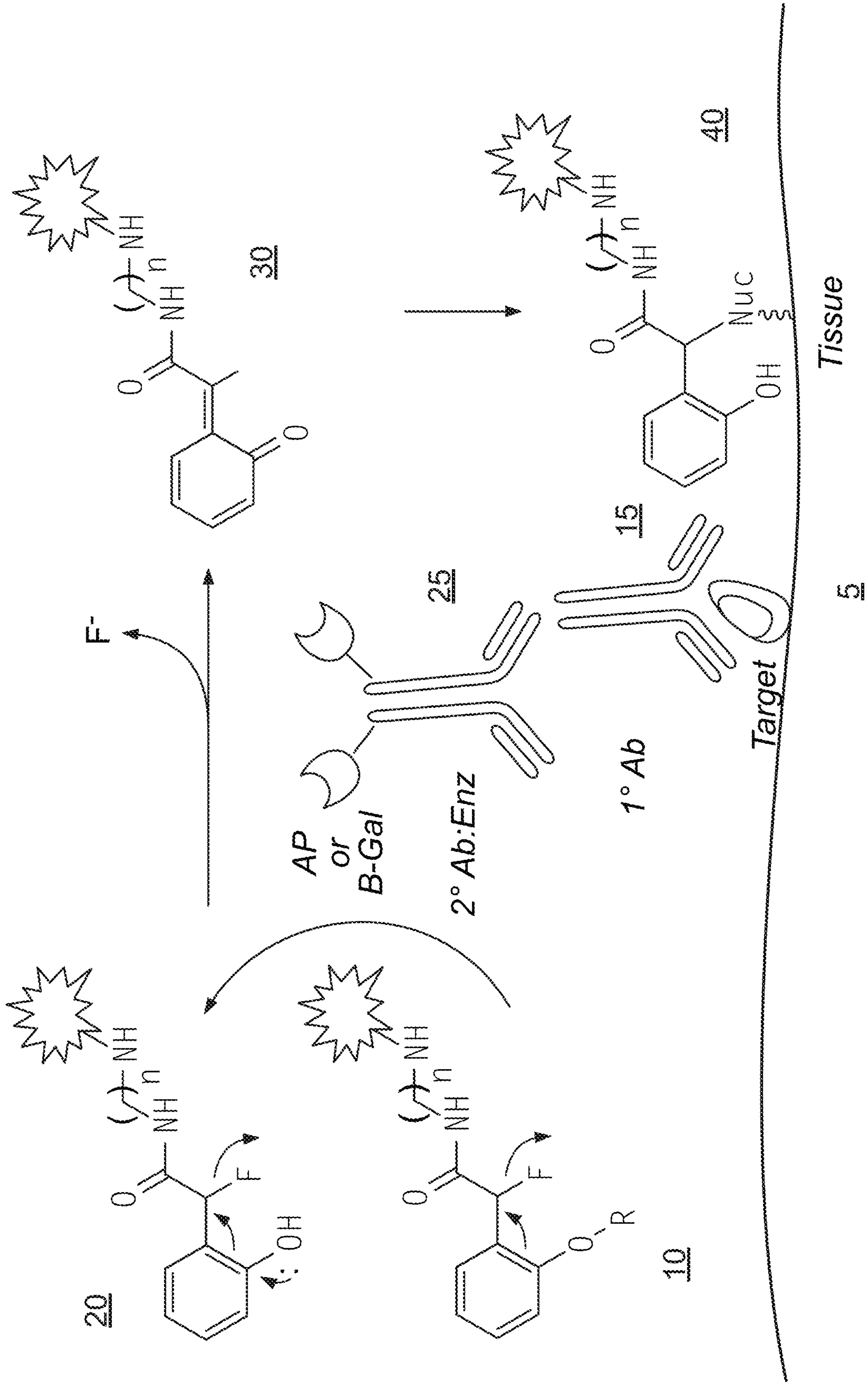
FIG. 3 illustrates the deposition of a conjugate including a quinone methide precursor moiety in accordance with one embodiment of the present disclosure.
Figure 4:
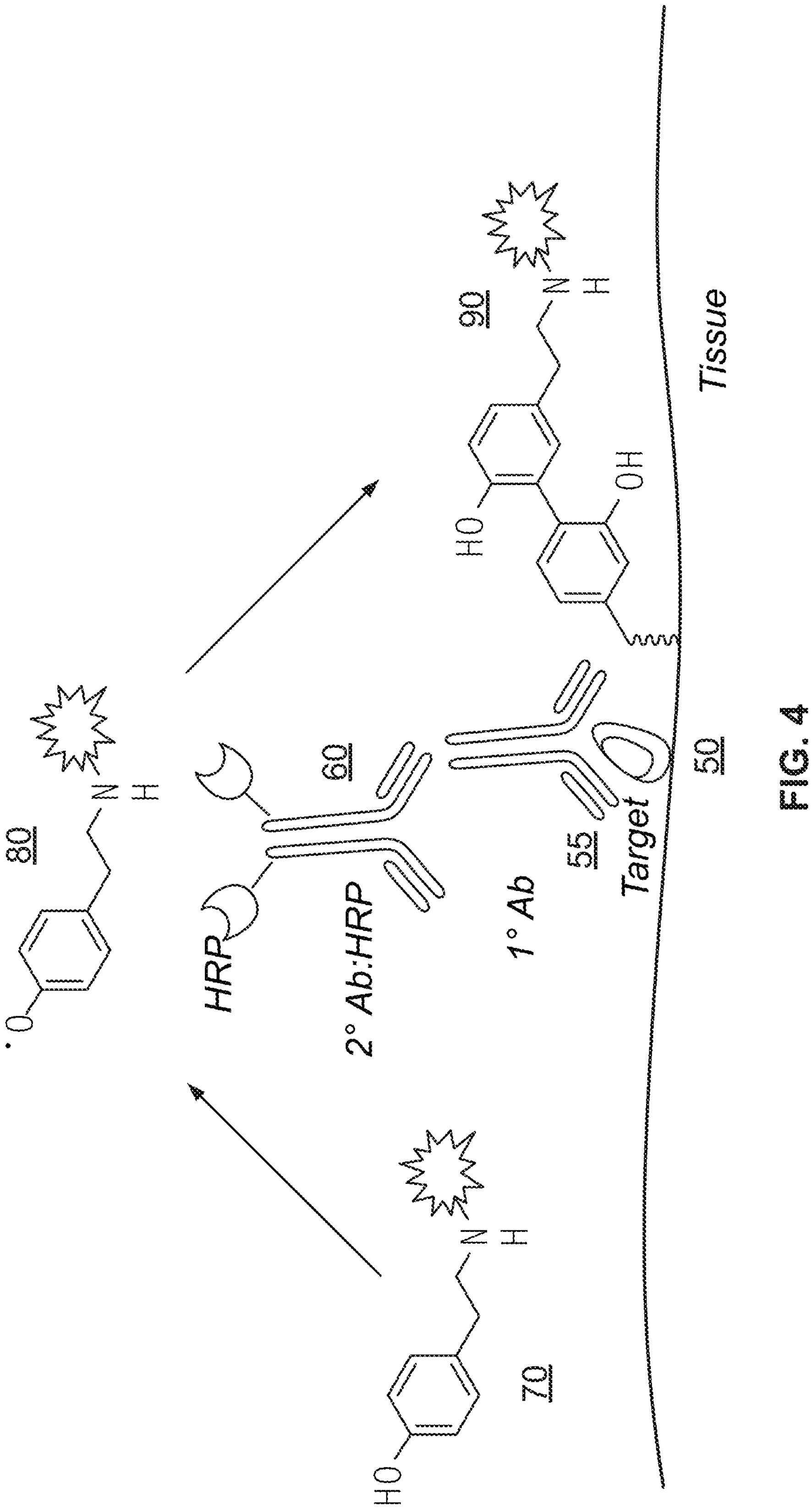
FIG. 4 illustrates the deposition of a conjugate including a tyramide moiety in accordance with one embodiment of the present disclosure.

FIGS. 3 and 4 further illustrate the reactions that take place between the various components introduced to the biological sample. With reference to FIG. 4, a specific binding entity 15 is first introduced to a biological sample having a target 5 to form a target-detection probe complex. In some embodiments, the specific binding entity 15 is a primary antibody. Subsequently, a labeling conjugate 25 is introduced to the biological sample, the labeling conjugate 25 comprising at least one enzyme conjugated thereto. In the embodiment depicted, the labeling conjugate 25 is a secondary antibody, where the secondary antibody is an anti-species antibody conjugated to an enzyme. Next, a detectable conjugate 10 is introduced, such as a detectable conjugate including any of the detectable moieties described herein coupled directly or indirectly to a quinone methide precursor moiety or a derivative or analog thereof. Upon interaction of the enzyme (e.g., AP or beta-Gal) with the detectable conjugate 10, the detectable conjugate 10 undergoes a structural, conformational, or electronic change 20 to form a tissue reactive intermediate 30. In this particular embodiment, the detectable conjugate comprises a quinone methide precursor moiety that, upon interaction with the alkaline phosphatase enzyme (of the labeling conjugate 25), causes a fluorine leaving group to be ejected, resulting in the respective quinone methide intermediate 30. The quinone methide intermediate 30 then forms a covalent bond with the tissue proximal or directly on the tissue to form a detectable moiety complex 40. Signals from the detectable moiety complex 40 may then be detected according to methods known to those of ordinary skill in the art, such as those described in U.S. Pat. No. 10,041,950, and in U.S. Publication Nos. 2019/0204330, 2017/0089911, and 2019/0187130 and in PCT Publication No. WO/2014/143155, the disclosures of which are hereby incorporated by reference herein in its entirety.

With reference to FIG. 4, a specific binding entity 55 is first introduced to a biological sample having a target 50 to form a target-detection probe complex. In some embodiments, the specific binding entity 55 is a primary antibody. Subsequently, a labeling conjugate 60 is introduced to the biological sample, the labeling conjugate 60 comprising at least one enzyme conjugated thereto. In the embodiment depicted, the labeling conjugate is a secondary antibody, where the secondary antibody is an anti-species antibody conjugated to an enzyme. Next, a detectable conjugate 70 is introduced, such as a detectable conjugate including any of the detectable moieties described herein coupled directly or indirectly to a tyramide moiety or a derivative or analog thereof. Upon interaction of the enzyme with the detectable conjugate 70, a tissue reactive intermediate 80 is formed. In this particular embodiment, the detectable conjugate 70 comprises a tyramide moiety that, upon interaction with horseradish peroxidase enzyme, causes formation of the radical species 80. The radical intermediate 80 then forms a covalent bond with the tissue proximal or directly on the tissue to form a detectable moiety complex 90. Signals from the detectable moiety complex 90 may then be detected according to methods known to those of ordinary skill in the art, such as those described in U.S. Pat. No. 10,041,950, and in U.S. Publication Nos. 2019/0204330, 2017/0089911, and 2019/0187130 and in PCT Publication No. WO/2014/143155, the disclosures of which are hereby incorporated by reference herein in its entirety.

In some embodiments, the biological samples are pre-treated with an enzyme inactivation composition to substantially or completely inactivate endogenous peroxidase activity. For example, some cells or tissues contain endogenous peroxidase. Using an HRP conjugated antibody may result in high, non-specific background staining. This non-specific background can be reduced by pre-treatment of the sample with an enzyme inactivation composition as disclosed herein. In some embodiments, the samples are pre-treated with hydrogen peroxide only (about 1% to about 3% by weight of an appropriate pre-treatment solution) to reduce endogenous peroxidase activity. Once the endogenous peroxidase activity has been reduced or inactivated, detection kits may be added, followed by inactivation of the enzymes present in the detection kits, as provided above. The disclosed enzyme inactivation composition and methods can also be used as a method to inactivate endogenous enzyme peroxidase activity. Additional inactivation compositions are described in U.S. Publication No. 2018/0120202, the disclosure of which is hereby incorporated by reference herein in its entirety.

In some embodiments if the specimen is a sample embedded in paraffin, the sample can be deparaffinized using appropriate deparaffinizing fluid(s). After a waste remover removes the deparaffinizing fluid(s), any number of substances can be successively applied to the specimen. The substances can be for pretreatment (e.g., protein-crosslinking, expose nucleic acids, etc.), denaturation, hybridization, washing (e.g., stringency wash), detection (e.g., link a visual or marker molecule to a probe), amplifying (e.g., amplifying proteins, genes, etc.), counterstaining, coverslipping, or the like.

In embodiments where more than one target is detected (i.e., where the steps of the above method are repeated to detect more than one target in a sample), detectable conjugates are selected which include different detectable moieties (including any of those described herein or any having any of the absorbance and/or FWHM properties described herein). For example, in some embodiments, the first and second detectable moieties of the first and second detectable conjugates are selected such that the first and second detectable moieties have different peak absorbance wavelengths and which do not substantially overlap (e.g. the different peak absorbance wavelengths different by at least about 20 nm, by at least about 25 nm, by at least about 30 nm, by at least about 40 nm, by at least about 50 nm, by at least about 60 nm, by at least about 70 nm, by at least about 80 nm, by at least about 90 nm, by at least about 100 nm, by at least about 110 nm, by at least about 120 nm, by at least about 130 nm, by at least about 140 nm, by at least about 150 nm, by at least about 170 nm, by at least about 190 nm, by at least about 210 nm, by at least about 230 nm, by at least about 250 nm, by at least about 270 nm, by at least about 290 nm, by at least about 310 nm, etc.).

In some embodiments, the first and second detectable moieties of the first and second detectable conjugates have different peak absorbance wavelengths, wherein the different peak absorbance wavelengths of the first and second detectable moieties are separated by at least 20 nm, and wherein each of the first and second detectable moieties have FWHM of less than 200 nm. In some embodiments, the first and second detectable moieties of the first and second detectable conjugates have different peak absorbance wavelengths, wherein the different peak absorbance wavelengths of the first and second detectable moieties are separated by at least 30 nm, and wherein each of the first and second detectable moieties have FWHM of less than 200 nm. In some embodiments, the first and second detectable moieties of the first and second detectable conjugates have different peak absorbance wavelengths, wherein the different peak absorbance wavelengths of the first and second detectable moieties are separated by at least 40 nm, and wherein each of the first and second detectable moieties have FWHM of less than 200 nm. In some embodiments, the first and second detectable moieties of the first and second detectable conjugates have different peak absorbance wavelengths, wherein the different peak absorbance wavelengths of the first and second detectable moieties are separated by at least 50 nm, and wherein each of the first and second detectable moieties have FWHM of less than 200 nm. In some embodiments, the first and second detectable moieties of the first and second detectable conjugates have different peak absorbance wavelengths, wherein the different peak absorbance wavelengths of the first and second detectable moieties are separated by at least 70 nm, and wherein each of the first and second detectable moieties have FWHM of less than 200 nm.

In some embodiments, the first and second detectable moieties of the first and second detectable conjugates have different peak absorbance wavelengths, wherein the different peak absorbance wavelengths of the first and second detectable moieties are separated by at least 20 nm, and wherein each of the first and second detectable moieties have FWHM of less than 130 nm. In some embodiments, the first and second detectable moieties of the first and second detectable conjugates have different peak absorbance wavelengths, wherein the different peak absorbance wavelengths of the first and second detectable moieties are separated by at least 30 nm, and wherein each of the first and second detectable moieties have FWHM of less than 130 nm. In some embodiments, the first and second detectable moieties of the first and second detectable conjugates have different peak absorbance wavelengths, wherein the different peak absorbance wavelengths of the first and second detectable moieties are separated by at least 40 nm, and wherein each of the first and second detectable moieties have FWHM of less than 130 nm. In some embodiments, the first and second detectable moieties of the first and second detectable conjugates have different peak absorbance wavelengths, wherein the different peak absorbance wavelengths of the first and second detectable moieties are separated by at least 50 nm, and wherein each of the first and second detectable moieties have FWHM of less than 130 nm. In some embodiments, the first and second detectable moieties of the first and second detectable conjugates have different peak absorbance wavelengths, wherein the different peak absorbance wavelengths of the first and second detectable moieties are separated by at least 70 nm, and wherein each of the first and second detectable moieties have FWHM of less than 130 nm.

In some embodiments, the first and second detectable moieties of the first and second detectable conjugates have different peak absorbance wavelengths, wherein the different peak absorbance wavelengths of the first and second detectable moieties are separated by at least 20 nm, and wherein each of the first and second detectable moieties have FWHM of less than 100 nm. In some embodiments, the first and second detectable moieties of the first and second detectable conjugates have different peak absorbance wavelengths, wherein the different peak absorbance wavelengths of the first and second detectable moieties are separated by at least 30 nm, and wherein each of the first and second detectable moieties have FWHM of less than 100 nm. In some embodiments, the first and second detectable moieties of the first and second detectable conjugates have different peak absorbance wavelengths, wherein the different peak absorbance wavelengths of the first and second detectable moieties are separated by at least 40 nm, and wherein each of the first and second detectable moieties have FWHM of less than 100 nm. In some embodiments, the first and second detectable moieties of the first and second detectable conjugates have different peak absorbance wavelengths, wherein the different peak absorbance wavelengths of the first and second detectable moieties are separated by at least 50 nm, and wherein each of the first and second detectable moieties have FWHM of less than 100 nm. In some embodiments, the first and second detectable moieties of the first and second detectable conjugates have different peak absorbance wavelengths, wherein the different peak absorbance wavelengths of the first and second detectable moieties are separated by at least 70 nm, and wherein each of the first and second detectable moieties have FWHM of less than 100 nm.

In some embodiments, the first and second detectable moieties of the first and second detectable conjugates have different peak absorbance wavelengths, wherein the different peak absorbance wavelengths of the first and second detectable moieties are separated by at least 20 nm, and wherein each of the first and second detectable moieties have FWHM of less than 80 nm. In some embodiments, the first and second detectable moieties of the first and second detectable conjugates have different peak absorbance wavelengths, wherein the different peak absorbance wavelengths of the first and second detectable moieties are separated by at least 30 nm, and wherein each of the first and second detectable moieties have FWHM of less than 80 nm. In some embodiments, the first and second detectable moieties of the first and second detectable conjugates have different peak absorbance wavelengths, wherein the different peak absorbance wavelengths of the first and second detectable moieties are separated by at least 40 nm, and wherein each of the first and second detectable moieties have FWHM of less than 80 nm. In some embodiments, the first and second detectable moieties of the first and second detectable conjugates have different peak absorbance wavelengths, wherein the different peak absorbance wavelengths of the first and second detectable moieties are separated by at least 50 nm, and wherein each of the first and second detectable moieties have FWHM of less than 80 nm. In some embodiments, the first and second detectable moieties of the first and second detectable conjugates have different peak absorbance wavelengths, wherein the different peak absorbance wavelengths of the first and second detectable moieties are separated by at least 70 nm, and wherein each of the first and second detectable moieties have FWHM of less than 80 nm.

In some embodiments, the first and second detectable moieties of the first and second detectable conjugates have different peak absorbance wavelengths, wherein the different peak absorbance wavelengths of the first and second detectable moieties are separated by at least 20 nm, and wherein each of the first and second detectable moieties have FWHM of less than 60 nm. In some embodiments, the first and second detectable moieties of the first and second detectable conjugates have different peak absorbance wavelengths, wherein the different peak absorbance wavelengths of the first and second detectable moieties are separated by at least 30 nm, and wherein each of the first and second detectable moieties have FWHM of less than 60 nm. In some embodiments, the first and second detectable moieties of the first and second detectable conjugates have different peak absorbance wavelengths, wherein the different peak absorbance wavelengths of the first and second detectable moieties are separated by at least 40 nm, and wherein each of the first and second detectable moieties have FWHM of less than 60 nm. In some embodiments, the first and second detectable moieties of the first and second detectable conjugates have different peak absorbance wavelengths, wherein the different peak absorbance wavelengths of the first and second detectable moieties are separated by at least 50 nm, and wherein each of the first and second detectable moieties have FWHM of less than 60 nm. In some embodiments, the first and second detectable moieties of the first and second detectable conjugates have different peak absorbance wavelengths, wherein the different peak absorbance wavelengths of the first and second detectable moieties are separated by at least 70 nm, and wherein each of the first and second detectable moieties have FWHM of less than 60 nm.

In some embodiments, the first detectable moiety comprises a coumarin core. In some embodiments, the second detectable moiety is within the visible spectrum or within the infrared spectrum. In some embodiments, the second detectable moiety is within the ultraviolet spectrum. In some embodiments, the first and second detectable moieties of the first and second detectable conjugates have absorbance maximums (λmax) that are separated by at least 20 nm.

In some embodiments, the first detectable moiety comprises a phenoxazinone core, a 4-Hydroxy-3-phenoxazinone core, a 7-amino-4-Hydroxy-3-phenoxazinone core, a thioninium core, a phenoxazine core, a phenoxathiin-3-one core, or a xanthene core. In some embodiments, the second detectable moiety is within the ultraviolet spectrum or within the infrared spectrum. In some embodiments, the second detectable moiety is within the visible spectrum. In some embodiments, wherein the first and second detectable moieties of the first and second detectable conjugates have absorbance maximums (λmax) that are separated by at least 20 nm.

In some embodiments, the first detectable moiety comprises a heptamethine cyanine core or a croconate core. In some embodiments, the second detectable moiety is within the visible spectrum or within the ultraviolet spectrum. In some embodiments, the second detectable moiety is within the infrared spectrum. In some embodiments, the first and second detectable moieties of the first and second detectable conjugates have absorbance maximums (λmax) that are separated by at least 20 nm.

Methods of Detecting a Target in a Sample Using a Pair of Click Conjugates

The present disclosure also provides methods of detecting one or more targets (e.g., two or more targets, three or more targets, four or more targets, five or more targets, six or more targets, seven or more targets, eight or more targets, nine or more targets, ten or more targets, etc.) within a biological sample using pairs of click conjugates, where one member of the pair of click conjugates is a compound having Formula (XII).

In some embodiments, any of the kits including pairs of click conjugates described herein may be utilized in facilitating the presently disclosed methods. While certain disclosed embodiments herein may refer to the use of the click conjugates in conjunction in an IHC assay, the skilled artisan will appreciate that the click conjugates may also be used in situ hybridization (ISH) assays, or any combination of IHC and ISH assays.

In these assays, one member of a pair of click conjugates comprises a detectable conjugate comprising: (i) a first functional group capable of participating in a click chemistry reaction, and (ii) a detectable moiety, including any of the detectable moieties described herein. Non-limiting examples of suitable detectable conjugates are described herein. Another member of the pair of click conjugates (hereinafter referred to as "tissue reactive conjugates") comprises a conjugate comprising: (i) a tyramide moiety, a quinone methide precursor moiety, or a derivative or analog of a tyramide moiety or a quinone methide precursor moiety; and (ii) a second functional group capable of reacting the first functional group of the detectable conjugate. Suitable first and second functional groups coupled to the detectable conjugate and the tissue reactive conjugate are described in Table 1 herein. Non-limiting examples of suitable tissue reactive conjugates are described herein (see Formula XIV). Other suitable "tissue reactive conjugates" are described in U.S. Publication Nos. 2019/0204330, 2017/0089911, and 2019/0187130, the disclosures of which are hereby incorporated by reference herein their entireties.

In general, as a first step of labeling a target with a detectable moiety (such as any of those described herein) comprises covalently depositing a tissue reactive conjugate onto tissue using quinone methide signal amplification ("QMSA") and/or tyramide signal amplification ("TSA"). The introduction of the tissue reactive conjugate introduces a first member of a pair of reactive functional groups to the target within the biological sample. These amplification procedures are described in U.S. Publication Nos. 2019/0204330, 2017/0089911, and 2019/0187130, the disclosures of which are each hereby incorporated by reference in their entireties. Then, a detectable conjugate is introduced to the tissue. The "click" reaction between the two "click" conjugates (i.e., the tissue reactive conjugate and the detectable conjugate including the functional groups capable of reacting with each other) occurs rapidly, covalently binding the detectable moieties to tissue in the locations dictated by the QMSA or TSA chemistries. Each of these steps are described in greater detail herein.

Figure 5:
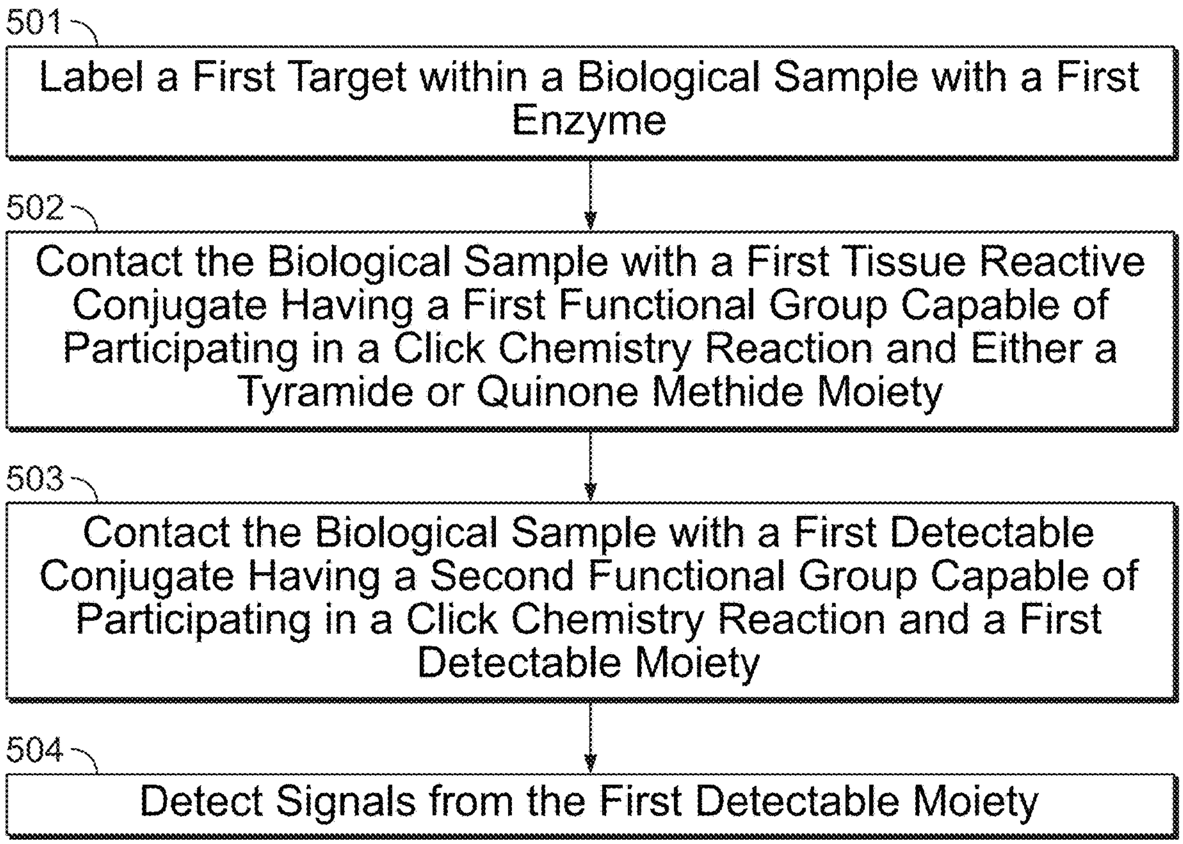
FIG. 5 illustrates a method of detecting signals corresponding to a target in a biological sample, where the method utilizes detectable conjugates including (i) a detectable moiety, and (ii) reactive functional groups capable of participating in a click chemistry reaction, in accordance with one embodiment of the present disclosure.

In some embodiments, and with reference to FIG. 5, a biological sample having a first target is labeled with a first enzyme (step 501) to form a first target-enzyme complex. Methods of labeling a first target marker with a first enzyme are described above and also illustrated in FIGS. 1A and 1B. The biological sample is then contacted with a first tissue reactive conjugate (step 502), the first tissue reactive conjugate comprising a first functional group capable of participating in a click chemistry reaction (including any of those described in Table 1 herein) and either a tyramide, a quinone methide precursor, or a derivative or analog thereof (see, e.g., the compounds of Formula (XIV)). Upon interaction of the first enzyme of the first target marker-enzyme complex with the tyramide or the quinone methide precursor portion of the first tissue reactive conjugate, at least a first immobilized tissue-click conjugate complex is deposited proximal to or onto the first target (see also FIGS. 6 and 7 which further illustrate the "click chemistry" reactions that may take place and the formation of the resulting "first immobilized tissue-click conjugate complex" and "first immobilized tissue-click adduct complex"). Following the formation of the first immobilized tissue-click conjugate complex, the biological sample is then contacted with a first detectable conjugate comprising: (i) a second functional group capable of reacting with the first reactive functional group of the first immobilized tissue-click conjugate complex, and (ii) a first detectable moiety (step 503). The reaction product of first immobilized tissue-click conjugate complex and first detectable conjugate produces a first immobilized tissue-click adduct complex which may be detected. Finally, signals from the first detectable moiety are detected (e.g., such as using brightfield microscopy) (step 504). Methods of detecting one or more signals from one or more detectable moieties are described in U.S. Pat. No. 10,778,913, the disclosure of which is hereby incorporated by reference herein in its entirety.

Figure 6:
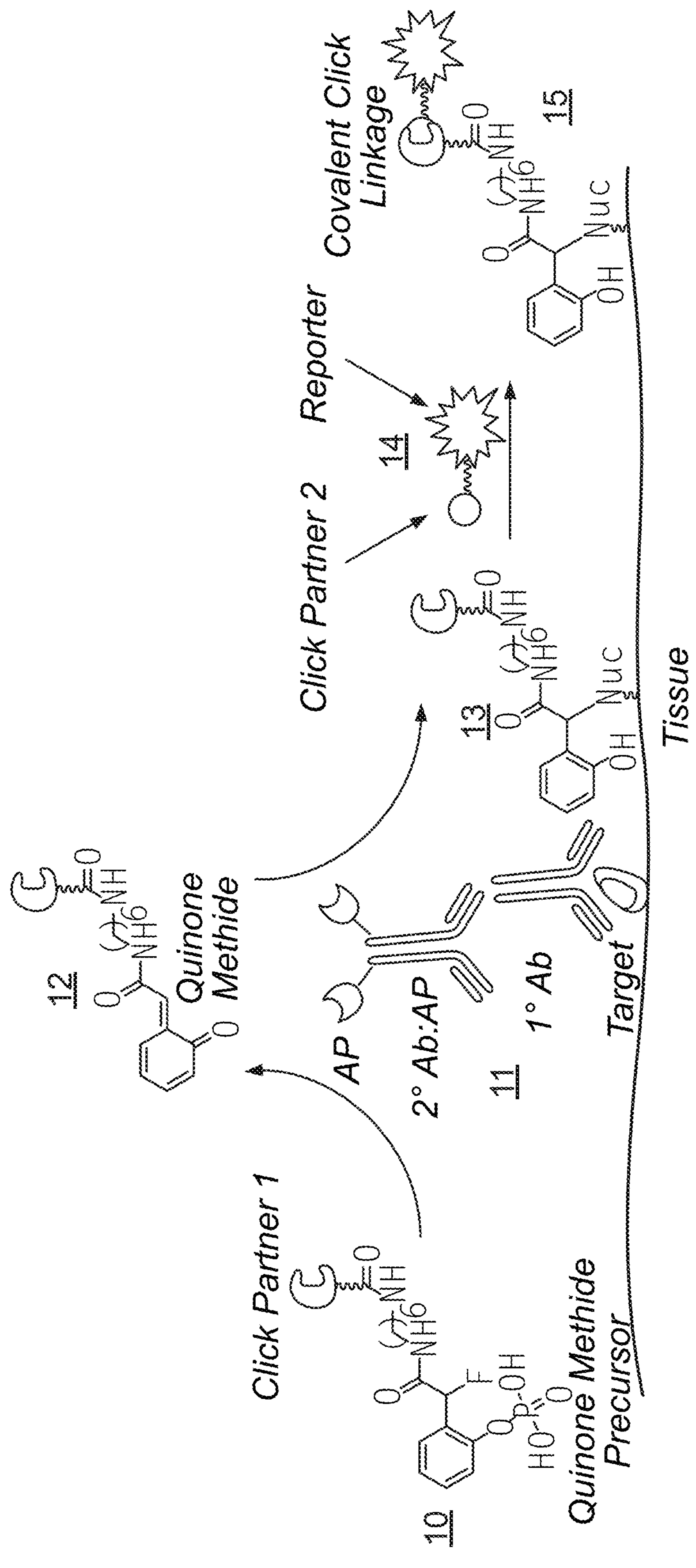
FIG. 6 illustrates the deposition of a conjugate including a quinone methide precursor moiety in accordance with one embodiment of the present disclosure.
Figure 7:
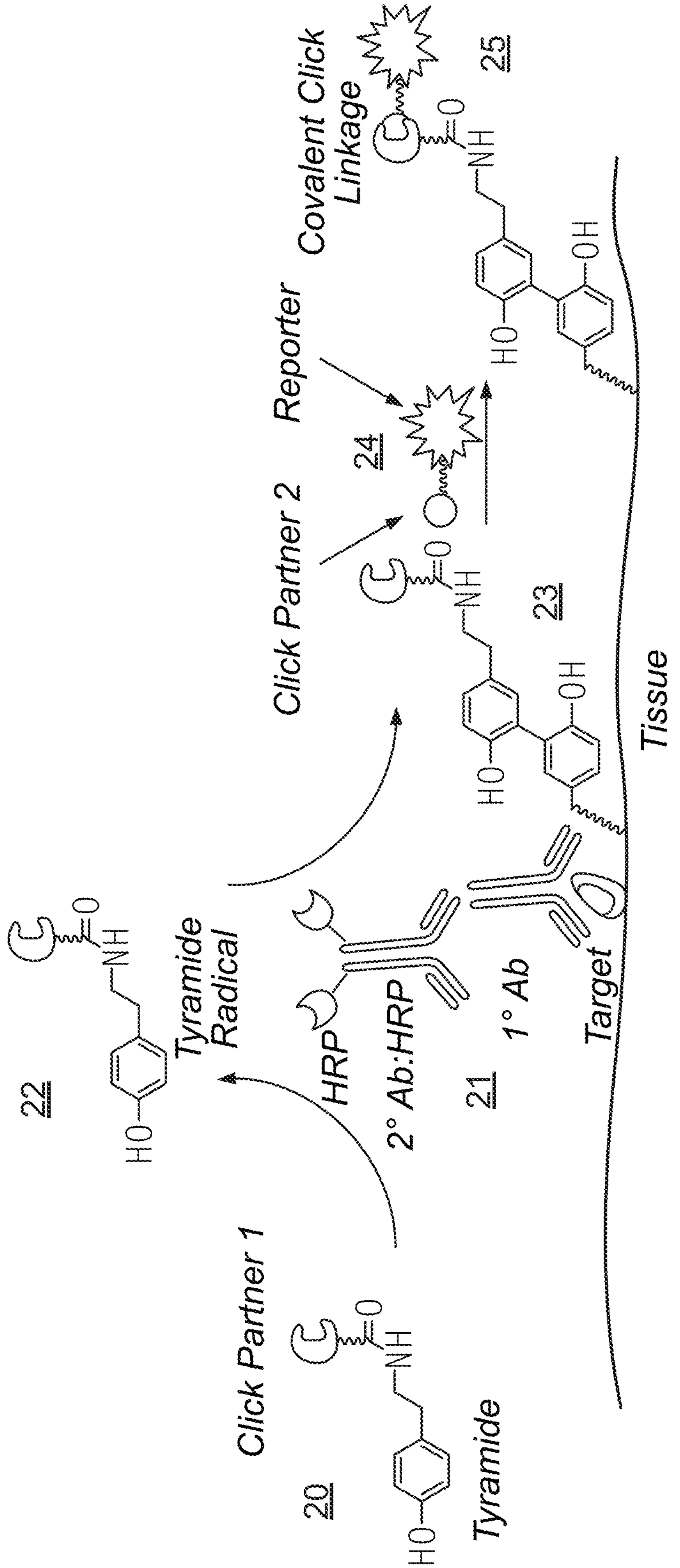
FIG. 7 illustrates the deposition of a conjugate including a tyramide moiety in accordance with one embodiment of the present disclosure.
Figure 8:
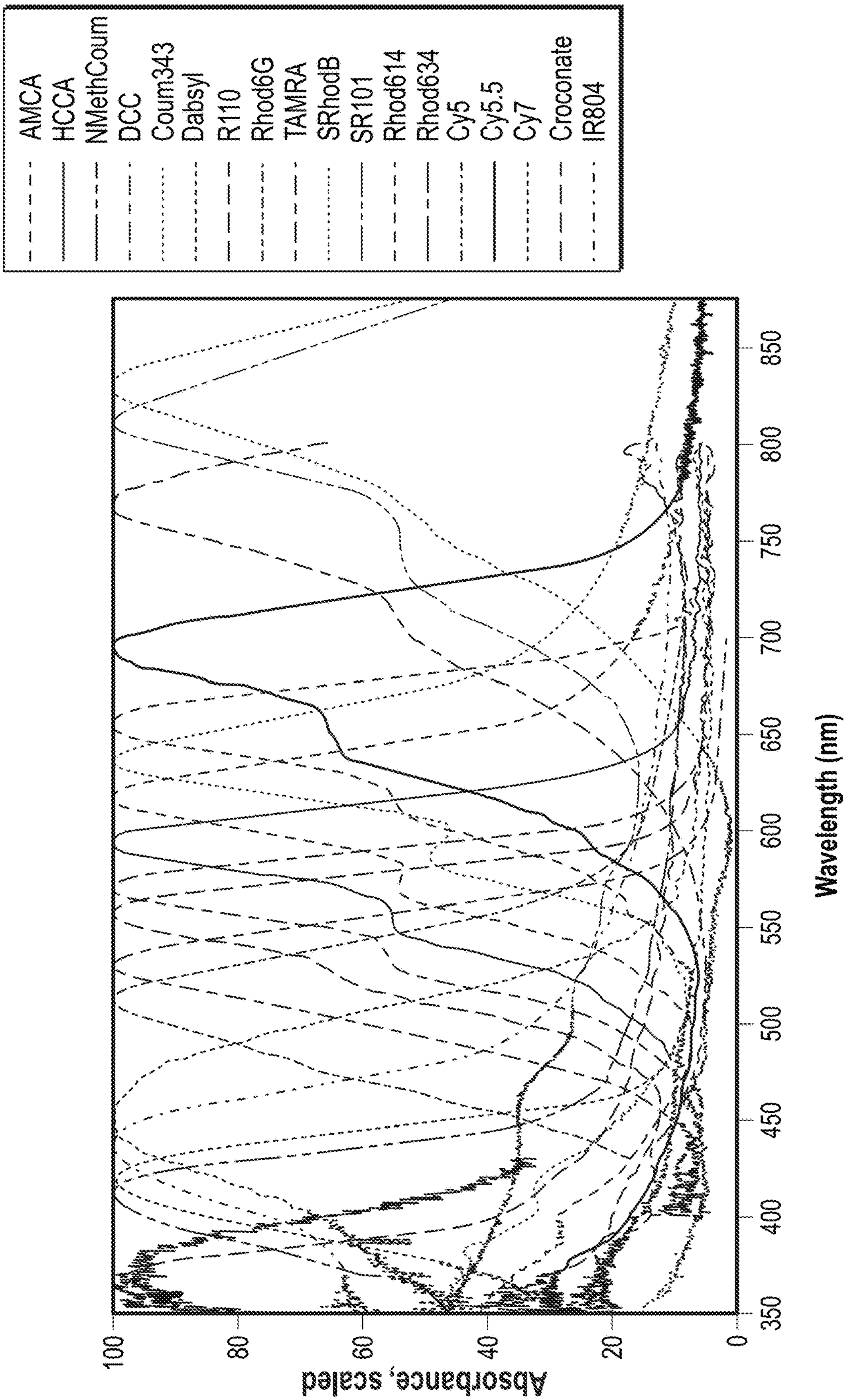
FIG. 8 illustrates the absorbance spectra of several detectable moieties and, in particular, illustrates the differing absorbance maxima of the different detectable moieties.

FIGS. 6 and 7 further illustrate the reaction between a first member of a pair of click conjugates having a tissue reactive moiety (10, 20) and a target-bound enzyme (11, 21) to form an immobilized tissue-click conjugate complex (13, 23). This first part of the amplification process is similar to that used in QMSA and TSA amplification processes. FIGS. 7 and 8 illustrate the subsequent reaction between the immobilized tissue-click conjugate (13, 23) complex and a second member of the pair of click conjugates (14, 24), to provide an immobilized tissue-click adduct complex (15, 25) comprising a detectable reporter moiety.

With reference to FIG. 6 a tissue reactive conjugate comprising a reactive functional group (10) is brought into contact with a target-bound enzyme (11) to produce a reactive intermediate (12). In this example, the reactive intermediate, a quinone methide precursor, forms a covalent bond to a nucleophile on or within a biological sample, thus providing an immobilized tissue-click conjugate complex (13). The immobilized tissue-click conjugate complex may then react with a detectable conjugate having any of the detectable moieties described herein (14), provided that the tissue reactive conjugate 10 and the detectable conjugate 14 possess reactive functional groups that may react with each other to form a covalent bond. The reaction product of immobilized tissue-click conjugate complex 13 and click conjugate 14 produces the immobilized tissue-click adduct complex 15. The tissue-click adduct complex 15 may be detected by virtue of signals transmitted from the linked detectable moiety.

Similarly, and with reference to FIG. 7, a tissue reactive conjugate comprising a reactive functional group (20) is brought into contact with a target-bound enzyme (21), to produce a reactive intermediate (22), namely a tyramide radical species (or derivative thereof). The tyramide radical intermediate may then form a covalent bond to a biological sample, thus providing an immobilized tissue-click conjugate complex (23). The immobilized tissue-click conjugate complex may then react with a detectable conjugate including any of the detectable moieties described herein (24), provided that tissue reactive conjugate and the detectable conjugate 20 and 24, respectively, possess reactive functional groups that may react with each other to form a covalent bond. The reaction product of immobilized tissue-click conjugate complex 23 and click conjugate 24 produces the tissue-click adduct complex 25.

In embodiments where more than one target is detected (i.e., where the steps of the above method are repeated to detect more than one target in a sample), detectable conjugates are selected which include different detectable moieties (including any of those described herein or any having any of the absorbance and/or FWHM properties described herein). For example, in some embodiments, the first and second detectable moieties of the first and second detectable conjugates are selected such that the first and second detectable moieties have different peak absorbance wavelengths and which do not substantially overlap (e.g. the different peak absorbance wavelengths different by at least about 20 nm, by at least about 25 nm, by at least about 30 nm, by at least about 40 nm, by at least about 50 nm, by at least about 60 nm, by at least about 70 nm, by at least about 80 nm, by at least about 90 nm, by at least about 100 nm, by at least about 110 nm, by at least about 120 nm, by at least about 130 nm, by at least about 140 nm, by at least about 150 nm, by at least about 170 nm, by at least about 190 nm, by at least about 210 nm, by at least about 230 nm, by at least about 250 nm, by at least about 270 nm, by at least about 290 nm, by at least about 310 nm, etc.).

In some embodiments, the first and second detectable moieties of the first and second detectable conjugates have different peak absorbance wavelengths, wherein the different peak absorbance wavelengths of the first and second detectable moieties are separated by at least 20 nm, and wherein each of the first and second detectable moieties have FWHM of less than 200 nm. In some embodiments, the first and second detectable moieties of the first and second detectable conjugates have different peak absorbance wavelengths, wherein the different peak absorbance wavelengths of the first and second detectable moieties are separated by at least 30 nm, and wherein each of the first and second detectable moieties have FWHM of less than 200 nm. In some embodiments, the first and second detectable moieties of the first and second detectable conjugates have different peak absorbance wavelengths, wherein the different peak absorbance wavelengths of the first and second detectable moieties are separated by at least 40 nm, and wherein each of the first and second detectable moieties have FWHM of less than 200 nm. In some embodiments, the first and second detectable moieties of the first and second detectable conjugates have different peak absorbance wavelengths, wherein the different peak absorbance wavelengths of the first and second detectable moieties are separated by at least 50 nm, and wherein each of the first and second detectable moieties have FWHM of less than 200 nm. In some embodiments, the first and second detectable moieties of the first and second detectable conjugates have different peak absorbance wavelengths, wherein the different peak absorbance wavelengths of the first and second detectable moieties are separated by at least 70 nm, and wherein each of the first and second detectable moieties have FWHM of less than 200 nm.

In some embodiments, the first and second detectable moieties of the first and second detectable conjugates have different peak absorbance wavelengths, wherein the different peak absorbance wavelengths of the first and second detectable moieties are separated by at least 20 nm, and wherein each of the first and second detectable moieties have FWHM of less than 130 nm. In some embodiments, the first and second detectable moieties of the first and second detectable conjugates have different peak absorbance wavelengths, wherein the different peak absorbance wavelengths of the first and second detectable moieties are separated by at least 30 nm, and wherein each of the first and second detectable moieties have FWHM of less than 130 nm. In some embodiments, the first and second detectable moieties of the first and second detectable conjugates have different peak absorbance wavelengths, wherein the different peak absorbance wavelengths of the first and second detectable moieties are separated by at least 40 nm, and wherein each of the first and second detectable moieties have FWHM of less than 130 nm. In some embodiments, the first and second detectable moieties of the first and second detectable conjugates have different peak absorbance wavelengths, wherein the different peak absorbance wavelengths of the first and second detectable moieties are separated by at least 50 nm, and wherein each of the first and second detectable moieties have FWHM of less than 130 nm. In some embodiments, the first and second detectable moieties of the first and second detectable conjugates have different peak absorbance wavelengths, wherein the different peak absorbance wavelengths of the first and second detectable moieties are separated by at least 70 nm, and wherein each of the first and second detectable moieties have FWHM of less than 130 nm.

In some embodiments, the first and second detectable moieties of the first and second detectable conjugates have different peak absorbance wavelengths, wherein the different peak absorbance wavelengths of the first and second detectable moieties are separated by at least 20 nm, and wherein each of the first and second detectable moieties have FWHM of less than 100 nm. In some embodiments, the first and second detectable moieties of the first and second detectable conjugates have different peak absorbance wavelengths, wherein the different peak absorbance wavelengths of the first and second detectable moieties are separated by at least 30 nm, and wherein each of the first and second detectable moieties have FWHM of less than 100 nm. In some embodiments, the first and second detectable moieties of the first and second detectable conjugates have different peak absorbance wavelengths, wherein the different peak absorbance wavelengths of the first and second detectable moieties are separated by at least 40 nm, and wherein each of the first and second detectable moieties have FWHM of less than 100 nm. In some embodiments, the first and second detectable moieties of the first and second detectable conjugates have different peak absorbance wavelengths, wherein the different peak absorbance wavelengths of the first and second detectable moieties are separated by at least 50 nm, and wherein each of the first and second detectable moieties have FWHM of less than 100 nm. In some embodiments, the first and second detectable moieties of the first and second detectable conjugates have different peak absorbance wavelengths, wherein the different peak absorbance wavelengths of the first and second detectable moieties are separated by at least 70 nm, and wherein each of the first and second detectable moieties have FWHM of less than 100 nm.

In some embodiments, the first and second detectable moieties of the first and second detectable conjugates have different peak absorbance wavelengths, wherein the different peak absorbance wavelengths of the first and second detectable moieties are separated by at least 20 nm, and wherein each of the first and second detectable moieties have FWHM of less than 80 nm. In some embodiments, the first and second detectable moieties of the first and second detectable conjugates have different peak absorbance wavelengths, wherein the different peak absorbance wavelengths of the first and second detectable moieties are separated by at least 30 nm, and wherein each of the first and second detectable moieties have FWHM of less than 80 nm. In some embodiments, the first and second detectable moieties of the first and second detectable conjugates have different peak absorbance wavelengths, wherein the different peak absorbance wavelengths of the first and second detectable moieties are separated by at least 40 nm, and wherein each of the first and second detectable moieties have FWHM of less than 80 nm. In some embodiments, the first and second detectable moieties of the first and second detectable conjugates have different peak absorbance wavelengths, wherein the different peak absorbance wavelengths of the first and second detectable moieties are separated by at least 50 nm, and wherein each of the first and second detectable moieties have FWHM of less than 80 nm. In some embodiments, the first and second detectable moieties of the first and second detectable conjugates have different peak absorbance wavelengths, wherein the different peak absorbance wavelengths of the first and second detectable moieties are separated by at least 70 nm, and wherein each of the first and second detectable moieties have FWHM of less than 80 nm.

In some embodiments, the first and second detectable moieties of the first and second detectable conjugates have different peak absorbance wavelengths, wherein the different peak absorbance wavelengths of the first and second detectable moieties are separated by at least 20 nm, and wherein each of the first and second detectable moieties have FWHM of less than 60 nm. In some embodiments, the first and second detectable moieties of the first and second detectable conjugates have different peak absorbance wavelengths, wherein the different peak absorbance wavelengths of the first and second detectable moieties are separated by at least 30 nm, and wherein each of the first and second detectable moieties have FWHM of less than 60 nm. In some embodiments, the first and second detectable moieties of the first and second detectable conjugates have different peak absorbance wavelengths, wherein the different peak absorbance wavelengths of the first and second detectable moieties are separated by at least 40 nm, and wherein each of the first and second detectable moieties have FWHM of less than 60 nm. In some embodiments, the first and second detectable moieties of the first and second detectable conjugates have different peak absorbance wavelengths, wherein the different peak absorbance wavelengths of the first and second detectable moieties are separated by at least 50 nm, and wherein each of the first and second detectable moieties have FWHM of less than 60 nm. In some embodiments, the first and second detectable moieties of the first and second detectable conjugates have different peak absorbance wavelengths, wherein the different peak absorbance wavelengths of the first and second detectable moieties are separated by at least 70 nm, and wherein each of the first and second detectable moieties have FWHM of less than 60 nm.

In some embodiments, the first detectable moiety comprises a coumarin core. In some embodiments, the second detectable moiety is within the visible spectrum or within the infrared spectrum. In some embodiments, the second detectable moiety is within the ultraviolet spectrum. In some embodiments, the first and second detectable moieties of the first and second detectable conjugates have absorbance maximums ($\lambda$max) that are separated by at least 20 nm.

In some embodiments, the first detectable moiety comprises a phenoxazinone core, a 4-Hydroxy-3-phenoxazinone core, a 7-amino-4-Hydroxy-3-phenoxazinone core, a thioninium core, a phenoxazine core, a phenoxathiin-3-one core, or a xanthene core. In some embodiments, the second detectable moiety is within the ultraviolet spectrum or within the infrared spectrum. In some embodiments, the second detectable moiety is within the visible spectrum. In some embodiments, wherein the first and second detectable moieties of the first and second detectable conjugates have absorbance maximums ($\lambda$max) that are separated by at least 20 nm.

In some embodiments, the first detectable moiety comprises a heptamethine cyanine core or a croconate core. In some embodiments, the second detectable moiety is within the visible spectrum or within the ultraviolet spectrum. In some embodiments, the second detectable moiety is within the infrared spectrum. In some embodiments, the first and second detectable moieties of the first and second detectable conjugates have absorbance maximums ($\lambda$max) that are separated by at least 20 nm.

Automation

The assays and methods of the present disclosure may be automated and may be combined with a specimen processing apparatus. The specimen processing apparatus can be an automated apparatus, such as the BENCHMARK XT instrument and DISCOVERY XT instrument sold by Ventana Medical Systems, Inc. Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. Published Patent Application Nos. 20030211630 and 20040052685, each of which is incorporated herein by reference in its entirety. Alternatively, specimens can be manually processed.

The specimen processing apparatus can apply fixatives to the specimen. Fixatives can include cross-linking agents (such as aldehydes, e.g., formaldehyde, paraformaldehyde, and glutaraldehyde, as well as non-aldehyde cross-linking agents), oxidizing agents (e.g., metallic ions and complexes, such as osmium tetroxide and chromic acid), protein-denaturing agents (e.g., acetic acid, methanol, and ethanol), fixatives of unknown mechanism (e.g., mercuric chloride, acetone, and picric acid), combination reagents (e.g., Camoy's fixative, methacam, Bouin's fluid, B5 fixative, Rossman's fluid, and Gendre's fluid), microwaves, and miscellaneous fixatives (e.g., excluded volume fixation and vapor fixation).

If the specimen is a sample embedded in paraffin, the sample can be deparaffinized with the specimen processing apparatus using appropriate deparaffinizing fluid(s). After the waste remover removes the deparaffinizing fluid(s), any number of substances can be successively applied to the specimen. The substances can be for pretreatment (e.g., protein-crosslinking, expose nucleic acids, etc.), denaturation, hybridization, washing (e.g., stringency wash), detection (e.g., link a visual or marker molecule to a probe), amplifying (e.g., amplifying proteins, genes, etc.), counterstaining, coverslipping, or the like.

The specimen processing apparatus can apply a wide range of substances to the specimen. The substances include, without limitation, stains, probes, reagents, rinses, and/or conditioners. The substances can be fluids (e.g., gases, liquids, or gas/liquid mixtures), or the like. The fluids can be solvents (e.g., polar solvents, non-polar solvents, etc.), solutions (e.g., aqueous solutions or other types of solutions), or the like. Reagents can include, without limitation, stains, wetting agents, antibodies (e.g., monoclonal antibodies, polyclonal antibodies, etc.), antigen recovering fluids (e.g., aqueous- or non-aqueous-based antigen retrieval solutions, antigen recovering buffers, etc.), or the like. Probes can be an isolated nucleic acid or an isolated synthetic oligonucleotide, attached to a detectable label. Labels can include radioactive isotopes, enzyme substrates, co-factors, ligands, chemiluminescent or fluorescent agents, haptens, and enzymes.

After the specimens are processed, a user can transport specimen-bearing slides to the imaging apparatus. The imaging apparatus used here is a brightfield imager slide scanner. One brightfield imager is the iScan Coreo™ brightfield scanner sold by Ventana Medical Systems, Inc. In automated embodiments, the imaging apparatus is a digital pathology device as disclosed in International Patent Application No.: PCT/US2010/002772 (Patent Publication No.: WO/2011/049608) entitled IMAGING SYSTEM AND TECHNIQUES or disclosed in U.S. Patent Application Publication No. 2014/0178169, filed on Feb. 3, 2014, entitled IMAGING SYSTEMS, CASSETTES, AND METHODS OF USING THE SAME. International Patent Application No. PCT/US2010/002772 and U.S. Patent Application Publication No. 2014/0178169 are incorporated by reference in their entities. In other embodiments, the imaging apparatus includes a digital camera coupled to a microscope.

Counterstaining

Counterstaining is a method of post-treating the samples after they have already been stained with agents to detect one or more targets, such that their structures can be more readily visualized under a microscope. For example, a counterstain is optionally used prior to coverslipping to render the immunohistochemical stain more distinct. Counterstains differ in color from a primary stain. Numerous counterstains are well known, such as hematoxylin, eosin, methyl green, methylene blue, Giemsa, Alcian blue, and Nuclear Fast Red. DAPI (4',6-diamidino-2-phenylindole) is a fluorescent stain that may be used.

In some examples, more than one stain can be mixed together to produce the counterstain. This provides flexibility and the ability to choose stains. For example, a first stain, can be selected for the mixture that has a particular attribute, but yet does not have a different desired attribute. A second stain can be added to the mixture that displays the missing desired attribute. For example, toluidine blue, DAPI, and pontamine sky blue can be mixed together to form a counterstain.

Detection and/or Imaging

Certain aspects, or all, of the disclosed embodiments can be automated, and facilitated by computer analysis and/or image analysis system. In some applications, precise color or fluorescence ratios are measured. In some embodiments, light microscopy is utilized for image analysis. Certain disclosed embodiments involve acquiring digital images. This can be done by coupling a digital camera to a microscope. Digital images obtained of stained samples are analyzed using image analysis software. Color or fluorescence can be measured in several different ways. For example, color can be measured as red, blue, and green values; hue, saturation, and intensity values; and/or by measuring a specific wavelength or range of wavelengths using a spectral imaging camera. The samples also can be evaluated qualitatively and semi-quantitatively. Qualitative assessment includes assessing the staining intensity, identifying the positively staining cells and the intracellular compartments involved in staining, and evaluating the overall sample or slide quality. Separate evaluations are performed on the test samples and this analysis can include a comparison to known average values to determine if the samples represent an abnormal state.

Suitable detection methods are described in in PCT Application No. WO/2014/143155 and U.S. Pat. No. 10,778,913, the disclosures of which are hereby incorporated by reference herein in their entireties. In some embodiments, a suitable detection system comprises an imaging apparatus, one or more lenses, and a display in communication with the imaging apparatus. The imaging apparatus includes means for sequentially emitting energy and means for capturing an image/video. In some embodiments, the means for capturing is positioned to capture specimen images, each corresponding to the specimen being exposed to energy. In some embodiments, the means for capturing can include one or more cameras positioned on a front side and/or a backside of the microscope slide carrying the biological sample. The display means, in some embodiments, includes a monitor or a screen. In some embodiments, the means for sequentially emitting energy includes multiple energy emitters. Each energy emitter can include one or more IR energy emitters, UV energy emitters, LED light emitters, combinations thereof, or other types of energy emitting devices. The imaging system can further include means for producing contrast enhanced color image data based on the specimen images captured by the means for capturing. The displaying means displays the specimen based on the contrast enhanced color image data.

Samples and Targets

Samples include biological components and generally are suspected of including one or more target molecules of interest. Target molecules can be on the surface of cells and the cells can be in a suspension, or in a tissue section. Target molecules can also be intracellular and detected upon cell lysis or penetration of the cell by a probe. One of ordinary skill in the art will appreciate that the method of detecting target molecules in a sample will vary depending upon the type of sample and probe being used. Methods of collecting and preparing samples are known in the art.

Samples for use in the embodiments of the method and with the composition disclosed herein, such as a tissue or other biological sample, can be prepared using any method known in the art by of one of ordinary skill. The samples can be obtained from a subject for routine screening or from a subject that is suspected of having a disorder, such as a genetic abnormality, infection, or a neoplasia. The described embodiments of the disclosed method can also be applied to samples that do not have genetic abnormalities, diseases, disorders, etc., referred to as "normal" samples. Such normal samples are useful, among other things, as controls for comparison to other samples. The samples can be analyzed for many different purposes. For example, the samples can be used in a scientific study or for the diagnosis of a suspected malady, or as prognostic indicators for treatment success, survival, etc.

Samples can include multiple targets that can be specifically bound by a probe or reporter molecule. The targets can be nucleic acid sequences or proteins. Throughout this disclosure when reference is made to a target protein it is understood that the nucleic acid sequences associated with that protein can also be used as a target. In some examples, the target is a protein or nucleic acid molecule from a pathogen, such as a virus, bacteria, or intracellular parasite, such as from a viral genome. For example, a target protein may be produced from a target nucleic acid sequence associated with (e.g., correlated with, causally implicated in, etc.) a disease.

A target nucleic acid sequence can vary substantially in size. Without limitation, the nucleic acid sequence can have a variable number of nucleic acid residues. For example, a target nucleic acid sequence can have at least about 10 nucleic acid residues, or at least about 20, 30, 50, 100, 150, 500, 1000 residues. Similarly, a target polypeptide can vary substantially in size. Without limitation, the target polypeptide will include at least one epitope that binds to a peptide specific antibody, or fragment thereof. In some embodiments that polypeptide can include at least two epitopes that bind to a peptide specific antibody, or fragment thereof.

In specific, non-limiting examples, a target protein is produced by a target nucleic acid sequence (e.g., genomic target nucleic acid sequence) associated with a neoplasm (for example, a cancer). Numerous chromosome abnormalities (including translocations and other rearrangements, amplification or deletion) have been identified in neoplastic cells, especially in cancer cells, such as B cell and T cell leukemias, lymphomas, breast cancer, colon cancer, neurological cancers and the like. Therefore, in some examples, at least a portion of the target molecule is produced by a nucleic acid sequence (e.g., genomic target nucleic acid sequence) amplified or deleted in at least a subset of cells in a sample.

Oncogenes are known to be responsible for several human malignancies. For example, chromosomal rearrangements involving the SYT gene located in the breakpoint region of chromosome 18q11.2 are common among synovial sarcoma soft tissue tumors. The t(18q11.2) translocation can be identified, for example, using probes with different labels: the first probe includes FPC nucleic acid molecules generated from a target nucleic acid sequence that extends distally from the SYT gene, and the second probe includes FPC nucleic acid generated from a target nucleic acid sequence that extends 3' or proximal to the SYT gene. When probes corresponding to these target nucleic acid sequences (e.g., genomic target nucleic acid sequences) are used in an in-situ hybridization procedure, normal cells, which lack a t(18q11.2) in the SYT gene region, exhibit two fusions (generated by the two labels in close proximity) signals, reflecting the two intact copies of SYT. Abnormal cells with a t(18q11.2) exhibit a single fusion signal.

In other examples, a target protein produced from a nucleic acid sequence (e.g., genomic target nucleic acid sequence) is selected that is a tumor suppressor gene that is deleted (lost) in malignant cells. For example, the p16 region (including D9S1749, D9S1747, p16(INK4A), p14(ARF), D9S1748, p15(INK4B), and D9S1752) located on chromosome 9p21 is deleted in certain bladder cancers. Chromosomal deletions involving the distal region of the short arm of chromosome 1 (that encompasses, for example, SHGC57243, TP73, EGFL3, ABL2, ANGPTL1, and SHGC-1322), and the pericentromeric region (e.g., 19p13-19q13) of chromosome 19 (that encompasses, for example, MAN2B1, ZNF443, ZNF44, CRX, GLTSCR2, and GLTSCR1) are characteristic molecular features of certain types of solid tumors of the central nervous system.

The aforementioned examples are provided solely for purpose of illustration and are not intended to be limiting. Numerous other cytogenetic abnormalities that correlate with neoplastic transformation and/or growth are known to those of ordinary skill in the art. Target proteins that are produced by nucleic acid sequences (e.g., genomic target nucleic acid sequences), which have been correlated with neoplastic transformation and which are useful in the disclosed methods, also include the EGFR gene (7p12; e.g., GENBANK™ Accession No. NC-000007, nucleotides 55054219-55242525), the C-MYC gene (8q24.21; e.g., GENBANK™ Accession No. NC-000008, nucleotides 128817498-128822856), D5S271 (5p15.2), lipoprotein lipase (LPL) gene (8p22; e.g., GENBANK™ Accession No. NC-000008, nucleotides 19841058-19869049), RB1 (13q14; e.g., GENBANK™ Accession No. NC-000013, nucleotides 47775912-47954023), p53 (17p13.1; e.g., GENBANK™ Accession No. NC-000017, complement, nucleotides 7512464-7531642)), N-MYC (2p24; e.g., GENBANK™ Accession No. NC-000002, complement, nucleotides 151835231-151854620), CHOP (12q13; e.g., GENBANK™ Accession No. NC-000012, complement, nucleotides 56196638-56200567), FUS (16p11.2; e.g., GENBANK™ Accession No. NC-000016, nucleotides 31098954-31110601), FKHR (13p14; e.g., GENBANK™ Accession No. NC-000013, complement, nucleotides 40027817-40138734), as well as, for example: ALK (2p23; e.g., GENBANK™ Accession No. NC-000002, complement, nucleotides 29269144-29997936), Ig heavy chain, CCND1 (11q13; e.g., GENBANK™ Accession No. NC-000011, nucleotides 69165054.69178423), BCL2 (18q21.3; e.g., GENBANK™ Accession No. NC-000018, complement, nucleotides 58941559-59137593), BCL6 (3q27; e.g., GENBANK™ Accession No. NC-000003, complement, nucleotides 188921859-188946169), MALF1, AP1 (lp32-p31; e.g., GENBANK™ Accession No. NC-000001, complement, nucleotides 59019051-59022373), TOP2A (17q21-q22; e.g., GENBANK™ Accession No. NC-000017, complement, nucleotides 35798321-35827695), TMPRSS (21q22.3; e.g., GENBANK™ Accession No. NC-000021, complement, nucleotides 41758351-41801948), ERG (21q22.3; e.g., GENBANK™ Accession No. NC-000021, complement, nucleotides 38675671-38955488); ETV1 (7p21.3; e.g., GENBANK™ Accession No. NC-000007, complement, nucleotides 13897379-13995289), EWS (22q12.2; e.g., GENBANK™ Accession No. NC-000022, nucleotides 27994271-28026505); FLI1 (11q24.1-q24.3; e.g., GENBANK™ Accession No. NC-000011, nucleotides 128069199-128187521), PAX3 (2q35-q37; e.g., GENBANK™ Accession No. NC-000002, complement, nucleotides 222772851-222871944), PAX7 (lp36.2-p36.12; e.g., GENBANK™ Accession No. NC-000001, nucleotides 18830087-18935219), PTEN (10q23.3; e.g., GENBANK™ Accession No. NC-000010, nucleotides 89613175-89716382), AKT2 (19q13.1-q13.2; e.g., GENBANK™ Accession No. NC-000019, complement, nucleotides 45431556-45483036), MYCL1 (lp34.2; e.g., GENBANK™ Accession No. NC-000001, complement, nucleotides 40133685-40140274), REL (2p13-p12; e.g., GENBANK™ Accession No. NC-000002, nucleotides 60962256-61003682) and CSF1R (5q33-q35; e.g., GENBANK™ Accession No. NC-000005, complement, nucleotides 149413051-149473128).

In other examples, a target protein is selected from a virus or other microorganism associated with a disease or condition. Detection of the virus- or microorganism-derived target nucleic acid sequence (e.g., genomic target nucleic acid sequence) in a cell or tissue sample is indicative of the presence of the organism. For example, the target peptide, polypeptide or protein can be selected from the genome of an oncogenic or pathogenic virus, a bacterium or an intracellular parasite (such as *Plasmodium falciparum* and other *Plasmodium* species, *Leishmania* (sp.), *Cryptosporidium*

*parvum*, *Entamoeba histolytica*, and *Giardia lamblia*, as well as *Toxoplasma*, *Eimeria*, *Theileria*, and *Babesia* species).

In some examples, the target protein is produced from a nucleic acid sequence (e.g., genomic target nucleic acid sequence) from a viral genome. Exemplary viruses and corresponding genomic sequences (GENBANK™ RefSeq Accession No. in parentheses) include human adenovirus A (NC-001460), human adenovirus B (NC-004001), human adenovirus C(NC-001405), human adenovirus D (NC-002067), human adenovirus E (NC-003266), human adenovirus F (NC-001454), human astrovirus (NC-001943), human BKpolyomavirus (V01109; GI:60851) human bocavirus (NC-007455), human coronavirus 229E (NC-002645), human coronavirus HKU1 (NC-006577), human coronavirus NL63 (NC-005831), human coronavirus OC43 (NC-005147), human enterovirus A (NC-001612), human enterovirus B (NC-001472), human enterovirus C(NC-001428), human enterovirus D (NC-001430), human erythrovirus V9 (NC-004295), human foamy virus (NC-001736), human herpesvirus 1 (Herpes simplex virus type 1) (NC-001806), human herpesvirus 2 (Herpes simplex virus type 2) (NC-001798), human herpesvirus 3 (Varicella zoster virus) (NC-001348), human herpesvirus 4 type 1 (Epstein-Barr virus type 1) (NC-007605), human herpesvirus 4 type 2 (Epstein-Barr virus type 2) (NC-009334), human herpesvirus 5 strain AD 169 (NC-001347), human herpesvirus 5 strain Merlin Strain (NC-006273), human herpesvirus 6A (NC-001664), human herpesvirus 6B (NC-000898), human herpesvirus 7 (NC-001716), human herpesvirus 8 type M (NC-003409), human herpesvirus 8 type P (NC-009333), human immunodeficiency virus 1 (NC-001802), human immunodeficiency virus 2 (NC-001722), human metapneumovirus (NC-004148), human papillomavirus-1 (NC-001356), human papillomavirus-18 (NC-001357), human papillomavirus-2 (NC-001352), human papillomavirus-54 (NC-001676), human papillomavirus-61 (NC-001694), human papillomavirus-cand90 (NC-004104), human papillomavirus RTRX7 (NC-004761), human papillomavirus type 10 (NC-001576), human papillomavirus type 101 (NC-008189), human papillomavirus type 103 (NC-008188), human papillomavirus type 107 (NC-009239), human papillomavirus type 16 (NC-001526), human papillomavirus type 24 (NC-001683), human papillomavirus type 26 (NC-001583), human papillomavirus type 32 (NC-001586), human papillomavirus type 34 (NC-001587), human papillomavirus type 4 (NC-001457), human papillomavirus type 41 (NC-001354), human papillomavirus type 48 (NC-001690), human papillomavirus type 49 (NC-001591), human papillomavirus type 5 (NC-001531), human papillomavirus type 50 (NC-001691), human papillomavirus type 53 (NC-001593), human papillomavirus type 60 (NC-001693), human papillomavirus type 63 (NC-001458), human papillomavirus type 6b (NC-001355), human papillomavirus type 7 (NC-001595), human papillomavirus type 71 (NC-002644), human papillomavirus type 9 (NC-001596), human papillomavirus type 92 (NC-004500), human papillomavirus type 96 (NC-005134), human parainfluenza virus 1 (NC-003461), human parainfluenza virus 2 (NC-003443), human parainfluenza virus 3 (NC-001796), human parechovirus (NC-001897), human parvovirus 4 (NC-007018), human parvovirus B19 (NC-000883), human respiratory syncytial virus (NC-001781), human rhinovirus A (NC-001617), human rhinovirus B (NC-001490), human spumaretrovirus (NC-001795), human T-lymphotropic virus 1 (NC-001436), human T-lymphotropic virus 2 (NC-001488).

In certain examples, the target protein is produced from a nucleic acid sequence (e.g., genomic target nucleic acid sequence) from an oncogenic virus, such as Epstein-Barr Virus (EBV) or a Human Papilloma Virus (HPV, e.g., HPV16, HPV18). In other examples, the target protein produced from a nucleic acid sequence (e.g., genomic target nucleic acid sequence) is from a pathogenic virus, such as a Respiratory Syncytial Virus, a Hepatitis Virus (e.g., Hepatitis C Virus), a Coronavirus (e.g., SARS virus), an Adenovirus, a Polyomavirus, a Cytomegalovirus (CMV), or a Herpes Simplex Virus (HSV).

EXAMPLES

On-Slide Absorbance Spectra

Absorbance spectra of deposited chromogens and conventional stains were recorded on slide-mounted specimens placed on the stage of an Olympus BX-63 microscope under tungsten illumination. Transmitted light was measured between 350 and 800 nm in approximately 0.5 nm increments using a Pryor Scientific Inc. (Rockland, MA) Lumaspec 800 power meter. The power meter was upgraded with an Ocean HDX UV to NIR spectrometer that permitted spectral measurements between 200 and 1100 nm. The spectrum of light transmitted through a stained region of the slide was divided by the spectrum transmitted through on an unstained region to provide the transmission (T) spectrum, which was converted to the chromogen absorbance (A) spectrum using the relationship $A=\log 10(1/T)$.

Immunohistochemistry

In order to obtain on slide absorbance spectra of individual chromogens, Ki67 on tonsil was stained by IHC. The Discovery Universal Procedure was used to create protocols for the IHC. IHC was performed at 37° C. as follows. A slide-mounted paraffin section was de-paraffinized by warming the slide to 70° C. for 3 cycles each 8 mins long. Antigen retrieval performed by applying Cell Conditioning 1 (VMSI Cat #950-124), warming up the slide to 94° C. for 64 mins. Staining of Ki67 was performed in sequential steps that included incubation with primary antibody targeting that biomarker, washing in reaction buffer to remove unbound antibody, incubation with anti-species antibody (goat anti-rabbit) conjugated to HRP targeting the primary antibody, washing with reaction buffer, incubation with tyramide or tyramide DBCO, washing with reaction buffer, incubation with chromogen azide if applicable and washing with reaction buffer. Slides were then manually dehydrated through an ethanol series (2×80% ethanol, 1 min each, 2×90% ethanol, 1 min each, 3×100% ethanol, 3× xylene, 1 min each), at ambient temperature, and cover slipped utilizing a Sukura automated coverslipper.

Example—Detectable Moities and their Use in Multiplex Brightfield Immunohistochemistry INTRODUCTION. Immunohistochemical analysis is believed to be a valuable tool in pathology for diagnosis and prognosis of disease, and prediction of patient response to therapy. Routine clinical immunohistochemical analysis typically targets a biomarker per assay and is performed by immunohistochemistry (IHC) using colored stains, called chromogens that are evaluated by visual inspection using brightfield microscopy. Multiplexing in IHC is believed to be a valuable because it conserves specimen by combining assays for several biomarkers into a single assay, and it enables analysis of multiple cell types and tumor heterogeneity. Multiplexing in brightfield IHC is problematic in that conventional chromogens have broad absorbance spectra that limit the number of chromogens that can be used simultaneously and still permit visual distinction. There exists a need for greater multiplexing capacity which exceeds the ability to add more visually distinguishable chromogens within a visible portion of a light spectrum.

METHODS. 7-amino-4-methylcoumarin-3-acetate was attached to tyramine via a PEG8 linker forming a UV absorbing chromogenic substrate (AMCA-tyr) with absorbance maximum=345 nm (TRIS/EDTA pH 8), stored at −20° C. in DMSO). 7-hydroxycoumarin-3-carboxylate was attached to tyramine via a PEG8 linker a far blue absorbing chromogenic substrate (HCCA-tyr) with absorbance maximum=403 nm (TRIS/EDTA pH 8), stored at −20° C. in DMSO. Cy7 was attached to a quinone methide precursor forming a far red/near IR absorbing chromogen (Cy7-QM), with absorbance maximum=747.

Fully automated multiplexed IHC was performed on a Ventana Discovery Ultra system (Ventana Medical Systems, Inc.). Single marker DAB staining was accomplished using a Benchmark XT or Benchmark Ultra system and the ultraView Universal DAB Detection Kit (Cat. No. 760-500), according to the manufacturer's recommendations (Ventana Medical Systems, Inc.). Single IHC was performed using each of the 3 detectable moieties individually. AMC-tyr and HC-tyr were used to stain HER2 on Calu-3 xenografts using anti-HER2 primary antibody and peroxidase-anti-rabbit IgG secondary antibody. Each chromogen was used at 1 mM in 10% DMSO (Bill Day notebook). IHC was performed with Cy7-QM to detect Ki67 in tonsil tissue (Julia Ashworth-Sharpe notebook) at several different concentrations (200 μg, 400 μg, and 800 μg) and pH values (pH 8 and 10). The stained slides were viewed under unfiltered tungsten illumination (typical brightfield viewing) and with bandpass filters transmitting light in the region of each chromogen's absorbance. The filters used for AMC-tyr, HC-tyr, and $C_7$-QM were 376 nm (30 nm), 405 nm (30 nm), and 725 nm (48 nm), respectively, where the first number is the center wavelength of the transmission band and the number in parenthesis is the full width of the band at half the maximum transmission (FWHM). The filters were held in a Sutter Lambda 10-3 10-position filter wheel (Sutter Instruments, Novato, CA) located between the lamp and an Olympus BX-51 microscope (Olympus, Waltham, MA) illumination port. A Photometrics EZ2 CoolSnap monochrome CCD camera was used to record digital images (Teledyne Photometrics, Tucson, AZ). Micromanager software was used to control acquisition of images of individual microscope fields and ImageJ was used for image processing.

The Discovery Universal Procedure was used to create a protocol for the multiplex IHC plus hematoxylin. In general, multiplex IHC was performed at 37° C., unless otherwise noted, as follows. A slide-mounted paraffin section was de-paraffinized by warming the slide to 70° C. for 3 cycles each 8 mins long. Antigen retrieval performed by applying Cell Conditioning 1 (VMSI Cat #950-124), warming up the slide to 94° C. for 64 mins. Staining of each biomarker was performed in sequential steps that included incubation with primary antibody targeting that biomarker, washing in reaction buffer to remove unbound antibody, incubation with anti-species antibody targeting the primary antibody (either anti-mouse or anti-rabbit) conjugated to either peroxidase or alkaline phosphatase, depending on whether the chromogen is a tyramide or quinone methide derivative, respectively, washing with reaction buffer, incubation with tyramide or quinone methide precursor chromogenic reagent, and washing with reaction buffer. Before the application of the next biomarker in sequence, the slide was incubated with Cell Conditioning 2 (VMSI Cat #950-123) at 100° C. for 8 min., followed by washing in reaction buffer. Slides were then counterstained with diluted Hematoxylin II (VMSI Cat #790-2208) and Bluing (VMSI Cat #760-2037) for 4 min and washed with reaction buffer. Slides were then manually dehydrated through an ethanol series (2×80% ethanol, 1 min each, 2×90% ethanol, 1 min each, 3×100% ethanol, 3× xylene, 1 min each), at ambient temperature, and mounted in Cytoseal xyl (ThermoFisher Scientific, Waltham, MA). Multiplex IHC was evaluated using the following filters to image each of 7 chromogens plus hematoxylin (single bandpass filter center wavelength and FWHM in parenthesis): AMCA 376 nm (30 nm), Dabsyl 438 nm (29.5), Rhod110 510 (15), TAMRA 549 (17.6), SRhod110 580 (21.2), HTX 620 (19.3), Cy5 676 (39.9), and Cy7 725 (48). Unmixing of images to correct for spectral overlaps (8, 9) and color composite formation were performed using macros written for ImageJ.

Figure 9:
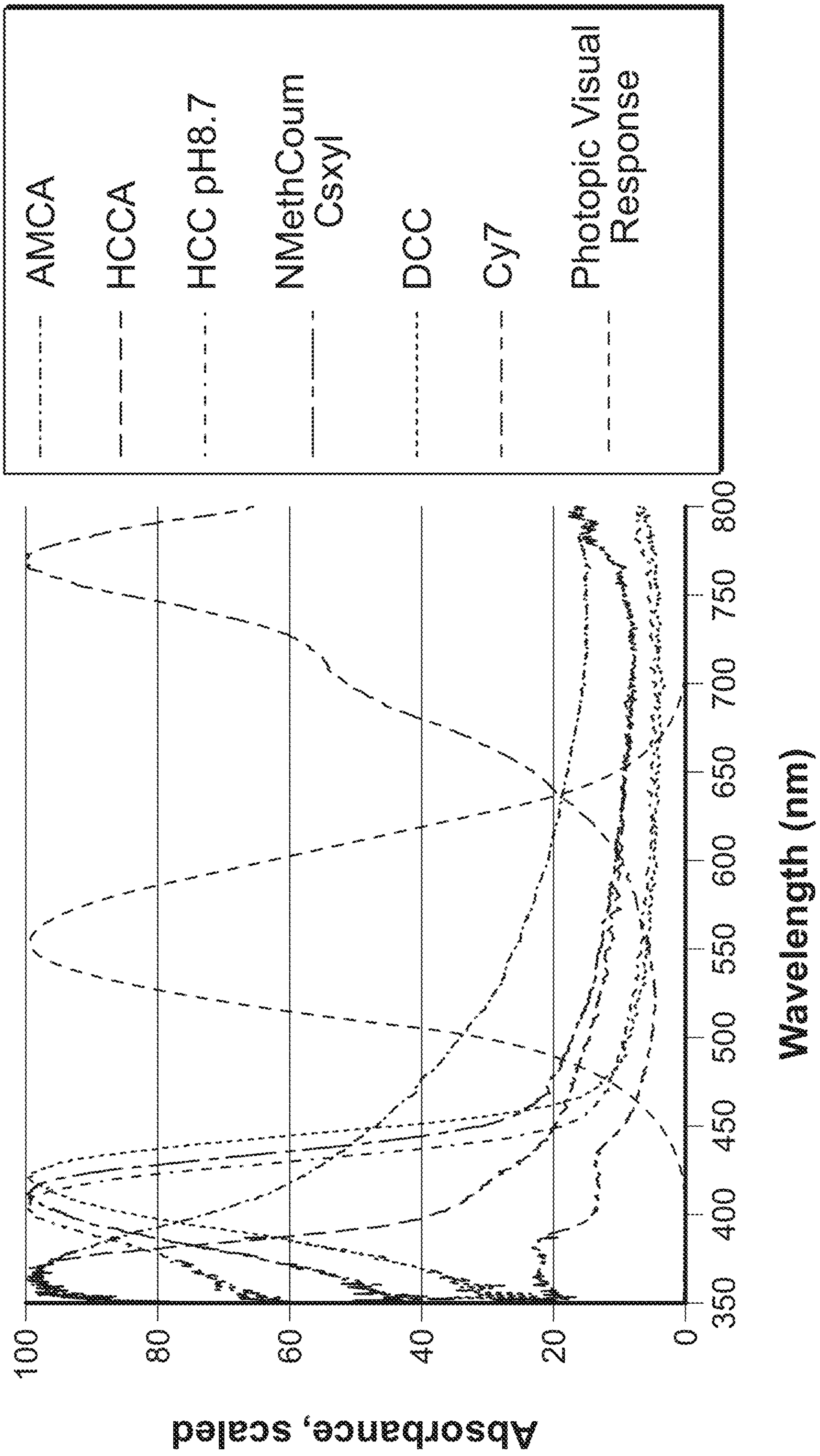
FIG. 9 illustrates detectable moiety absorbance spectra and relative visual response.
Figure 10A:
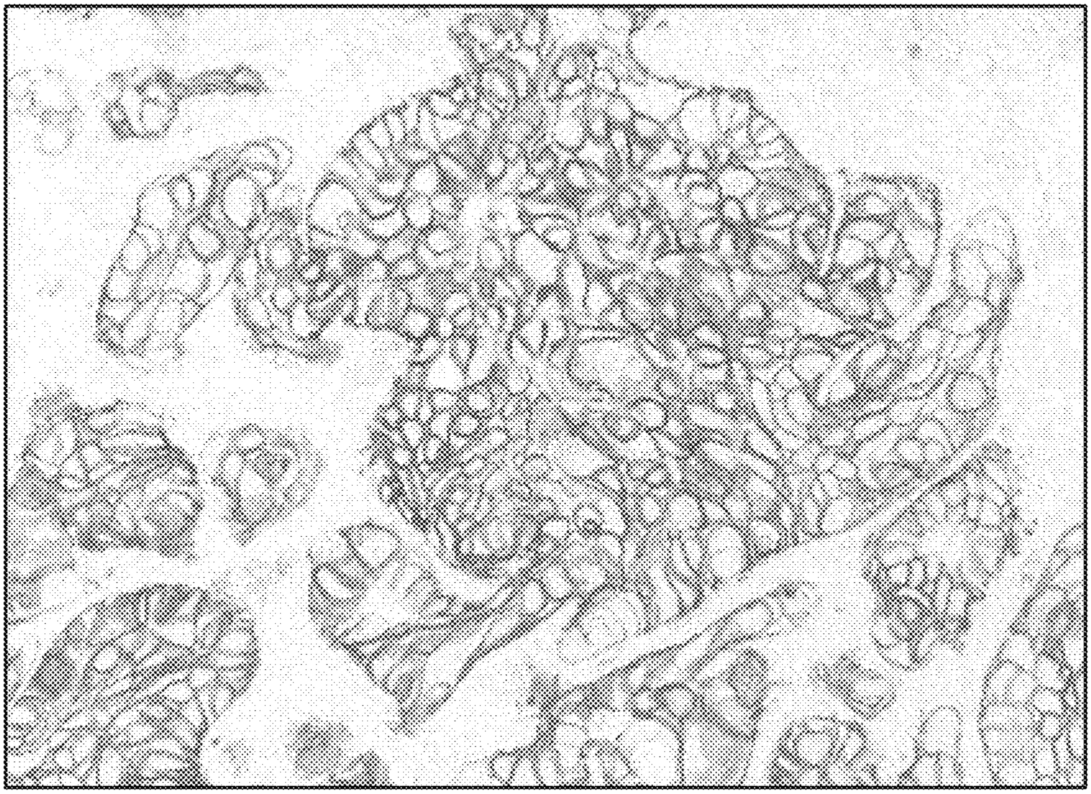
FIG. 10A depicts Hydroxycoumarin-tyramide staining HER2 on Calu-3 xenograft viewed through 405 nm (30 nm FWHM) filter.
Figure 10B:
FIG. 10B depicts Hydroxycoumarin-tyramide staining HER2 on Calu-3 xenograft viewed with no filter (white light from tungsten lamp).
Figure 11A:
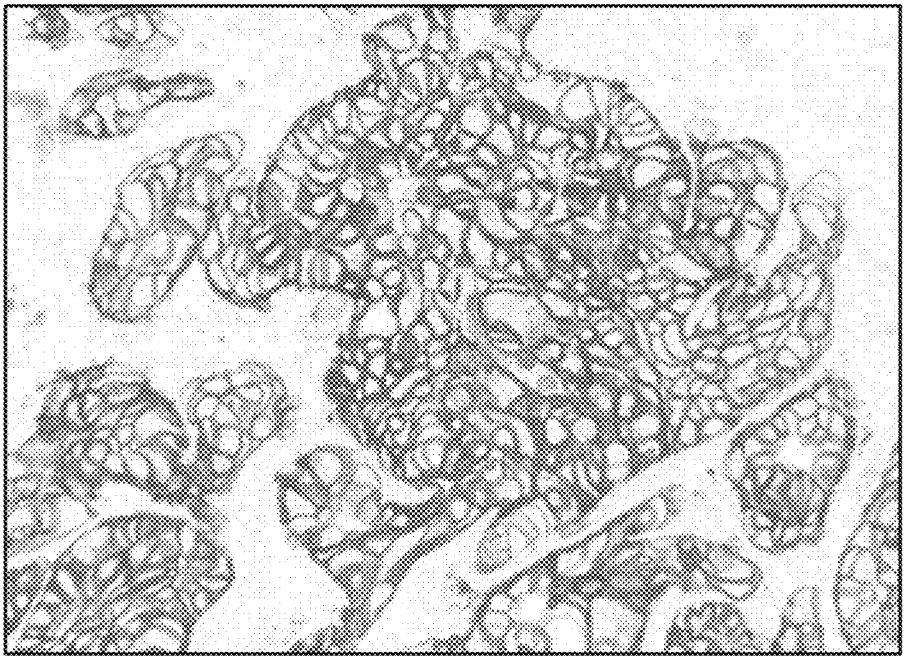
FIG. 11A depicts Aminomethylcoumarin-tyramide staining HER2 on Calu-3 xenograft viewed through 376 nm (30 nm FWHM) filter.
Figure 11B:
FIG. 11B depicts Aminomethylcoumarin-tyramide staining HER2 on Calu-3 xenograft viewed with no filter (white light from tungsten lamp).
Figure 12A:
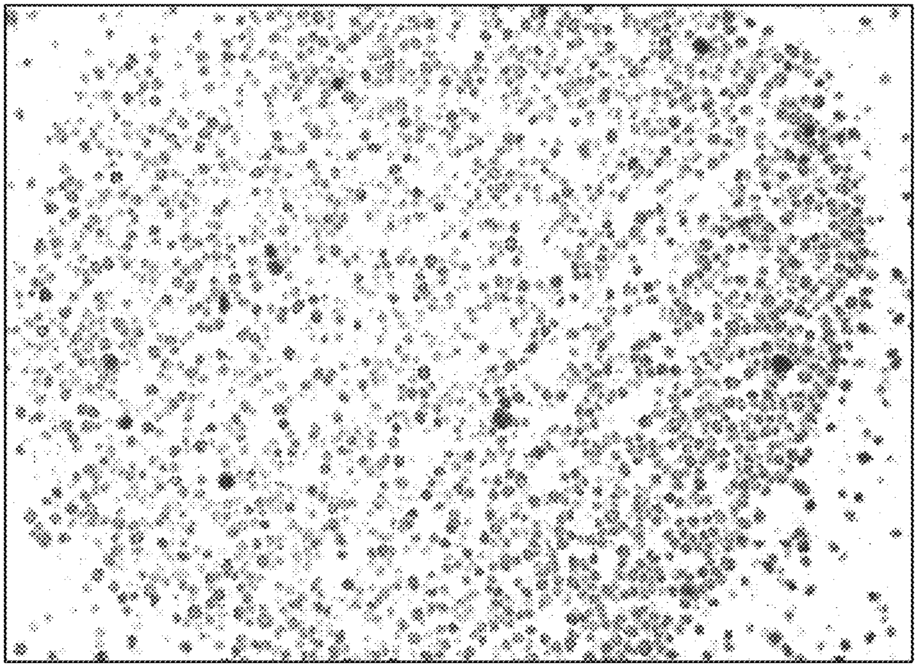
FIG. 12A depicts Cy7-quinone methide staining Ki67 on tonsil tissue viewed through 725 nm (48 nm FWHM) filter.
Figure 12B:
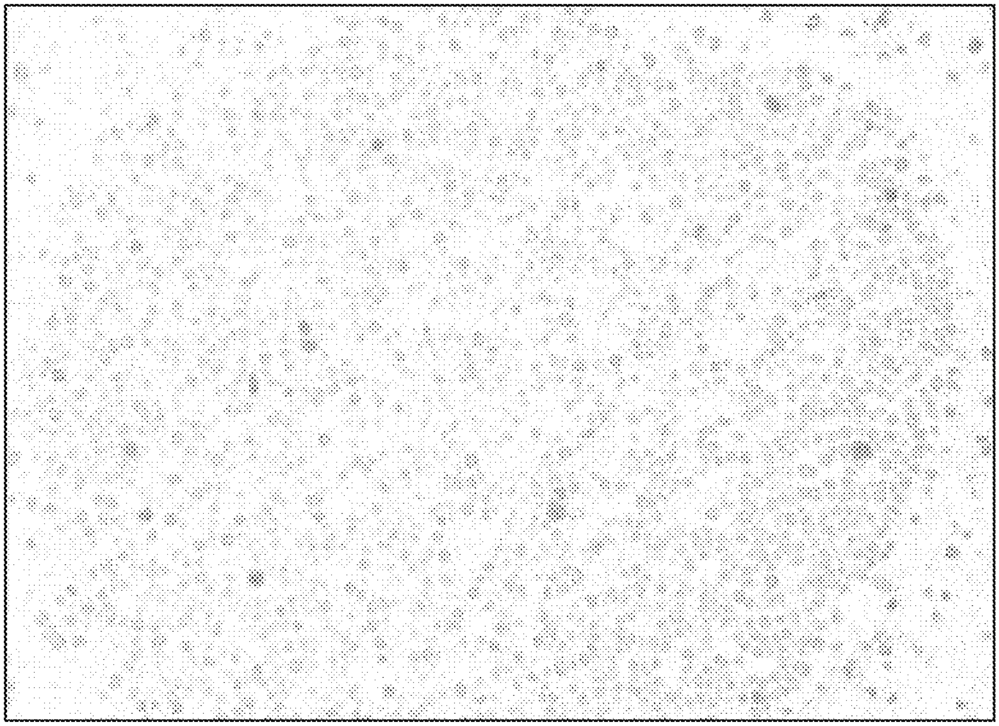
FIG. 12B depicts Cy7-quinone methide staining Ki67 on tonsil tissue viewed with no filter (white light from tungsten lamp).
Figure 13A:
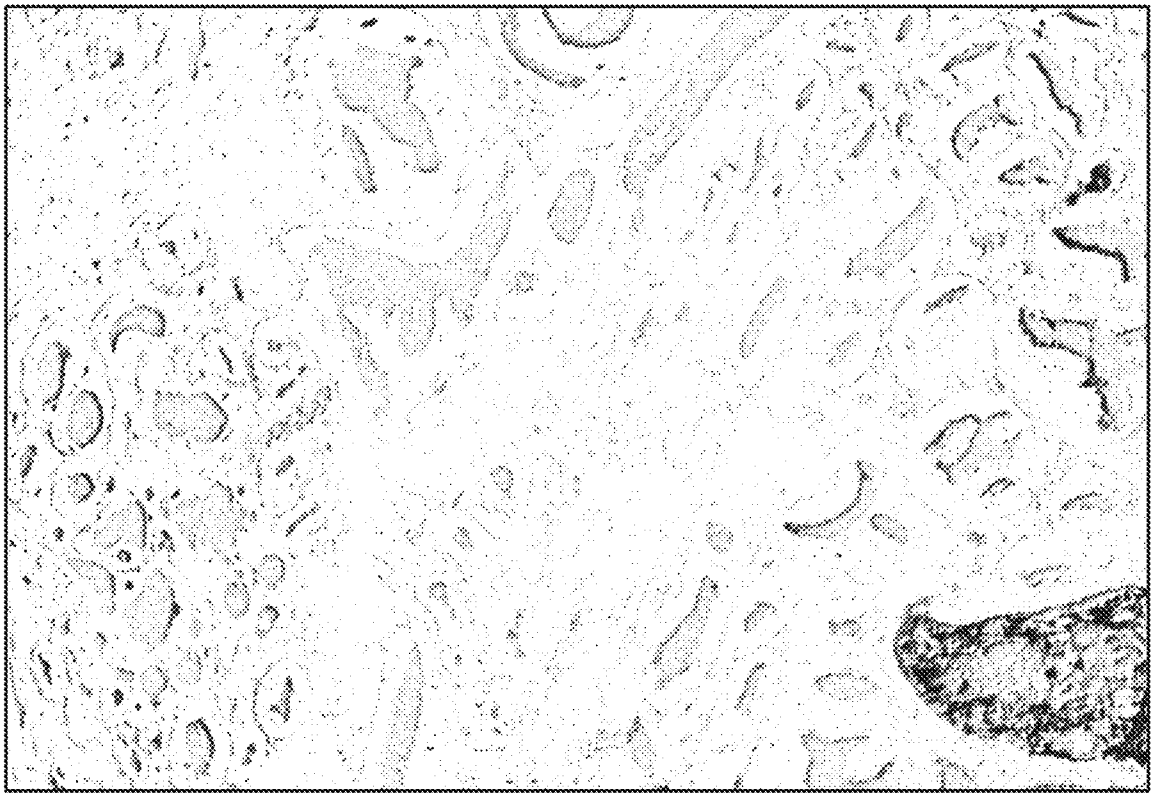
FIG. 13A depicts multiplex IHC sample imaged with illumination through 376 nm filter-unmixed.
Figure 13B:
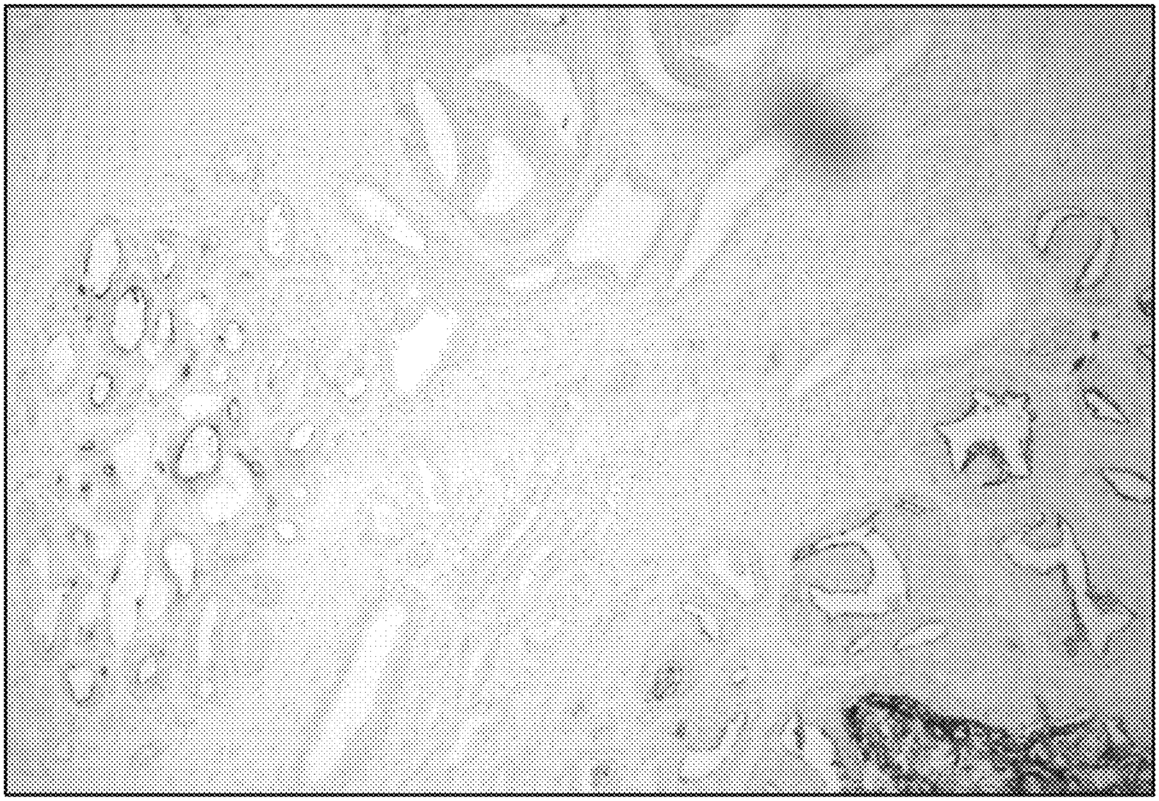
FIG. 13B depicts a serial section, PSMA stained with DAB.
Figure 14A:
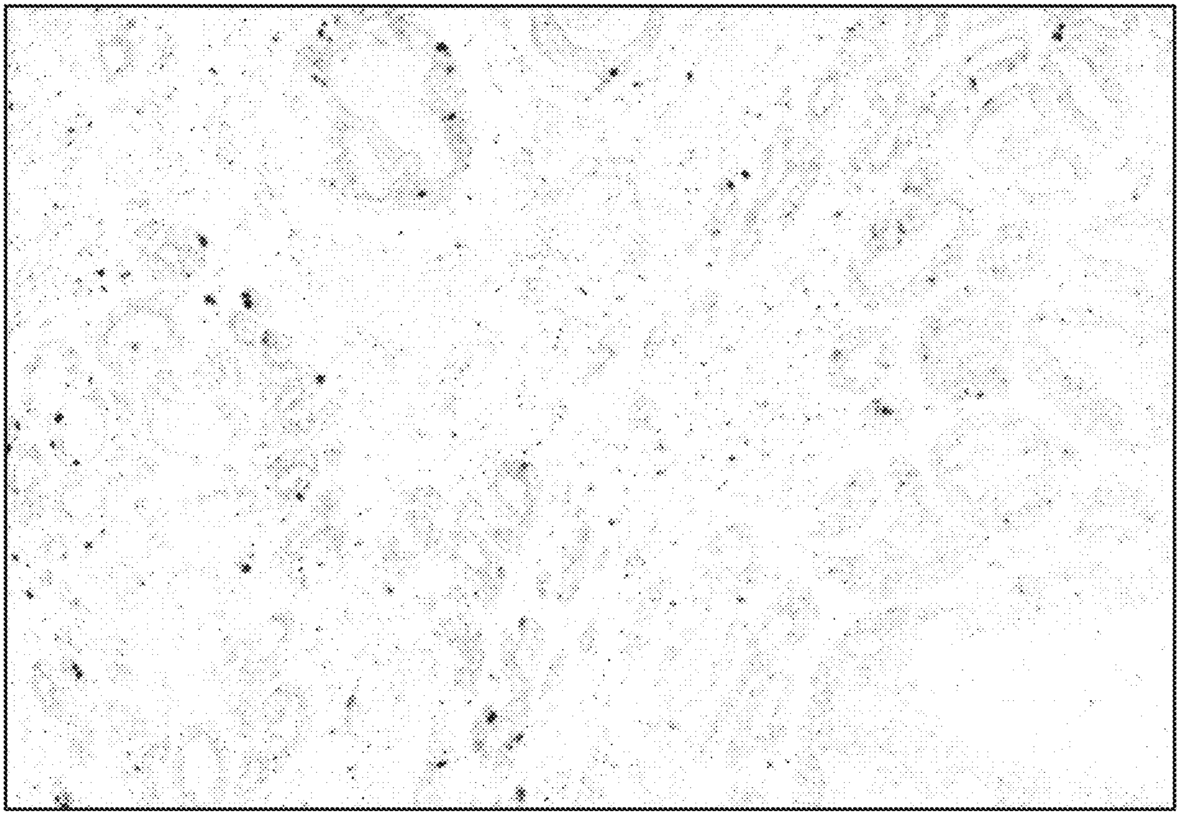
FIG. 14A depicts a multiplex IHC sample imaged with illumination through 438 nm filter-unmixed.
Figure 14B:
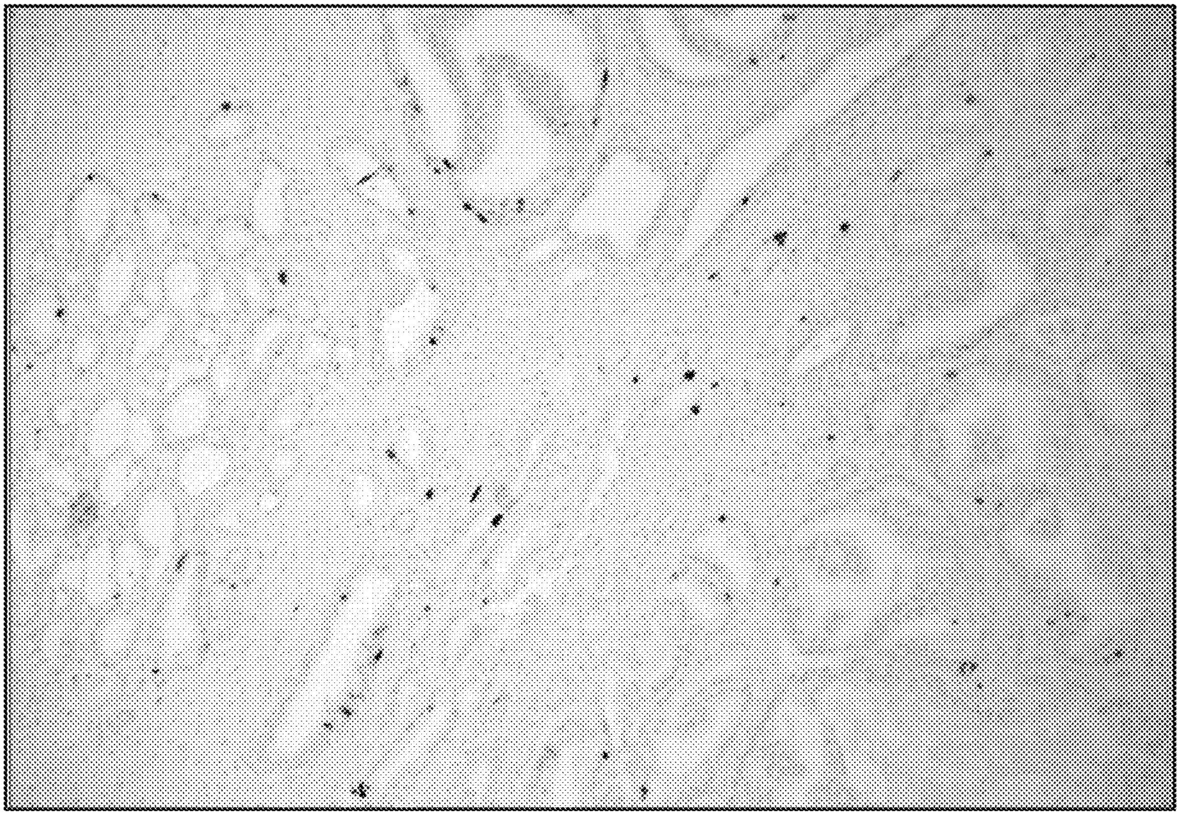
FIG. 14B depicts a serial section, Ki67 stained with DAB.
Figure 15A:
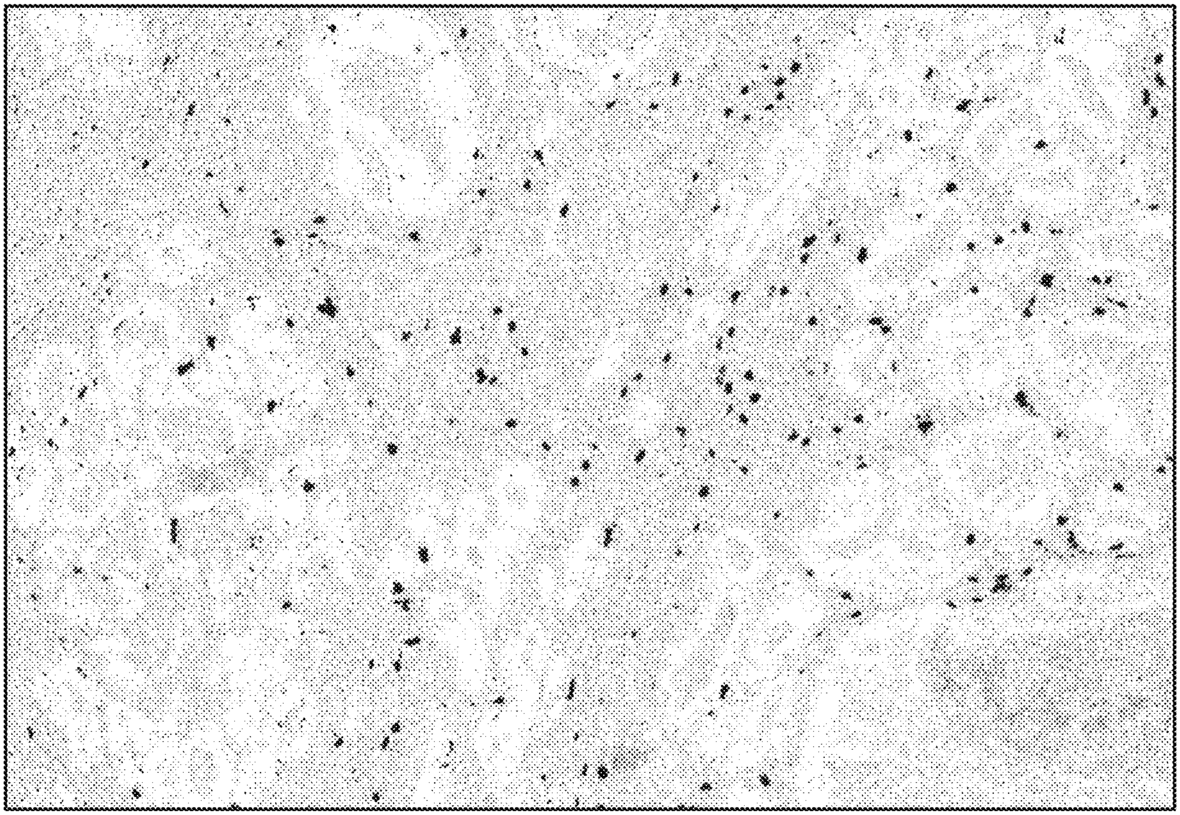
FIG. 15A depicts a multiple IHC sample imaged with illumination through 510 nm filter-unmixed.
Figure 15B:
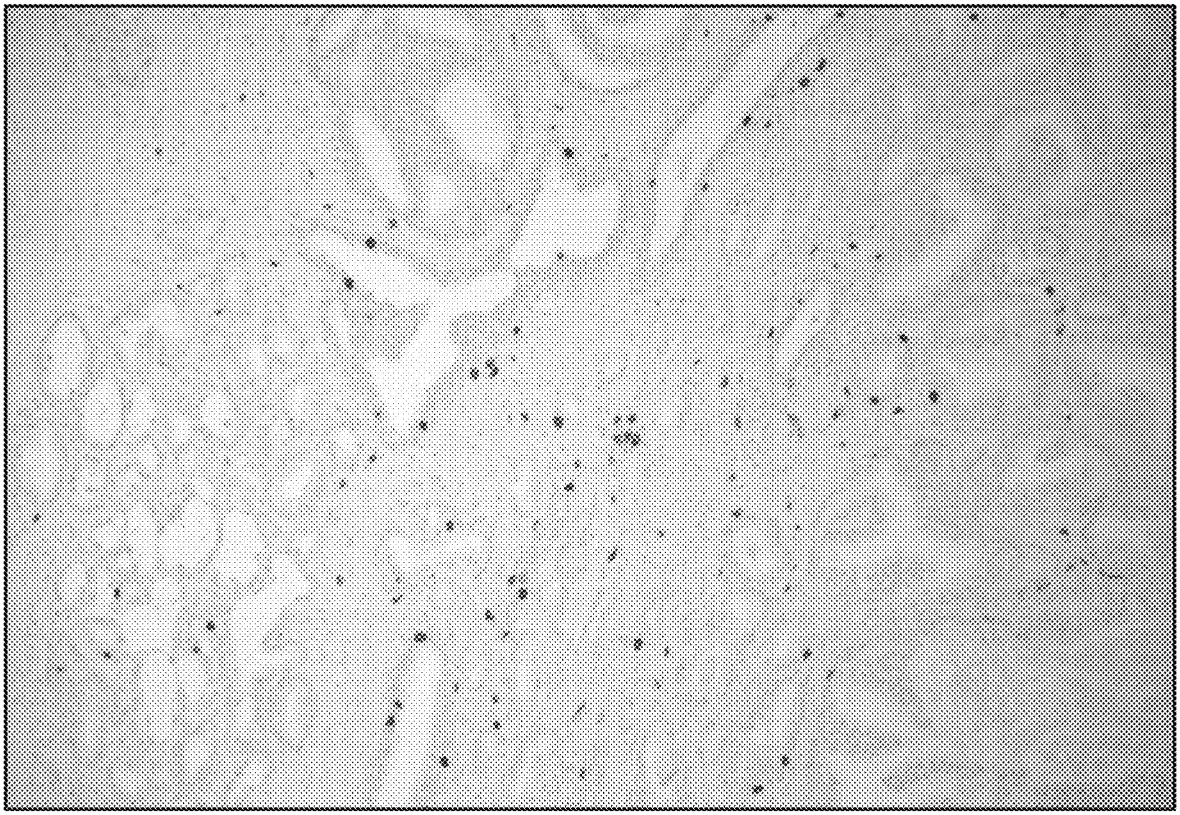
FIG. 15B depicts a serial section, CD8 stained with DAB.
Figure 16A:
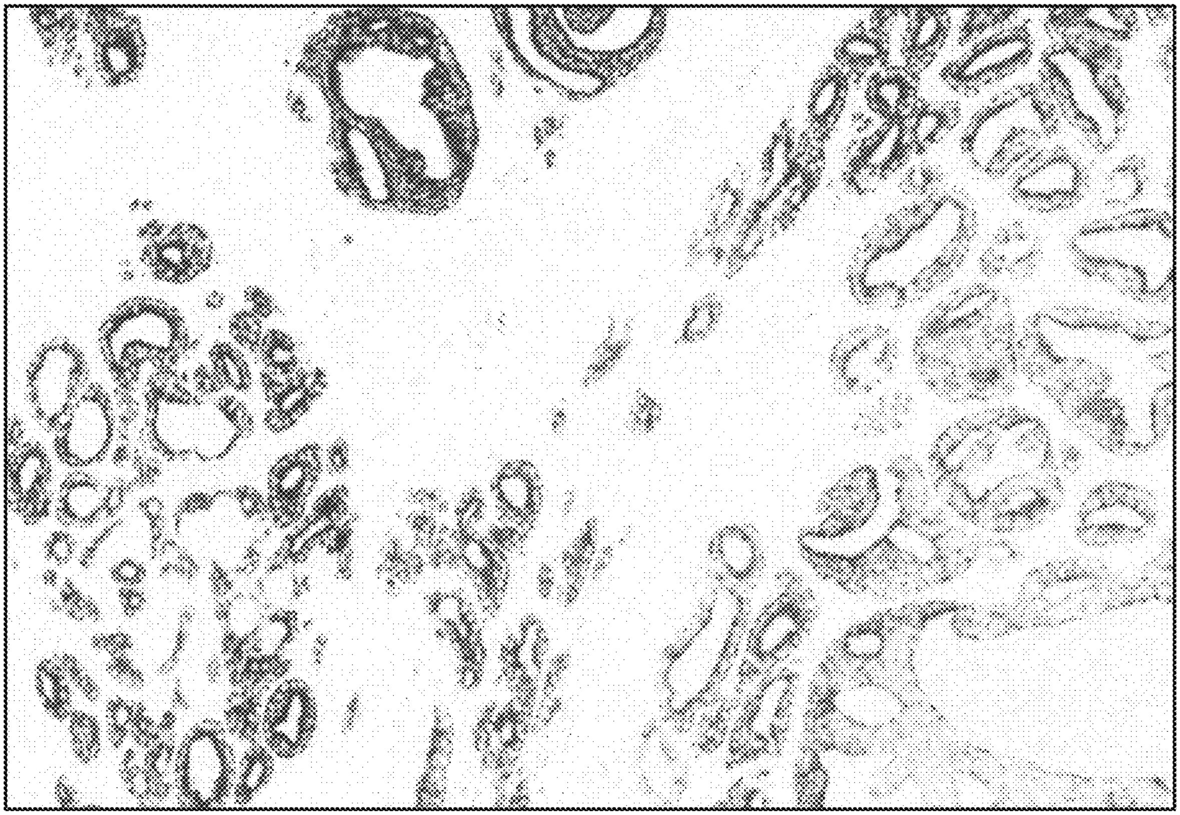
FIG. 16A depicts a multiplex IHC sample imaged with illumination through 549 nm filter-unmixed.
Figure 16B:
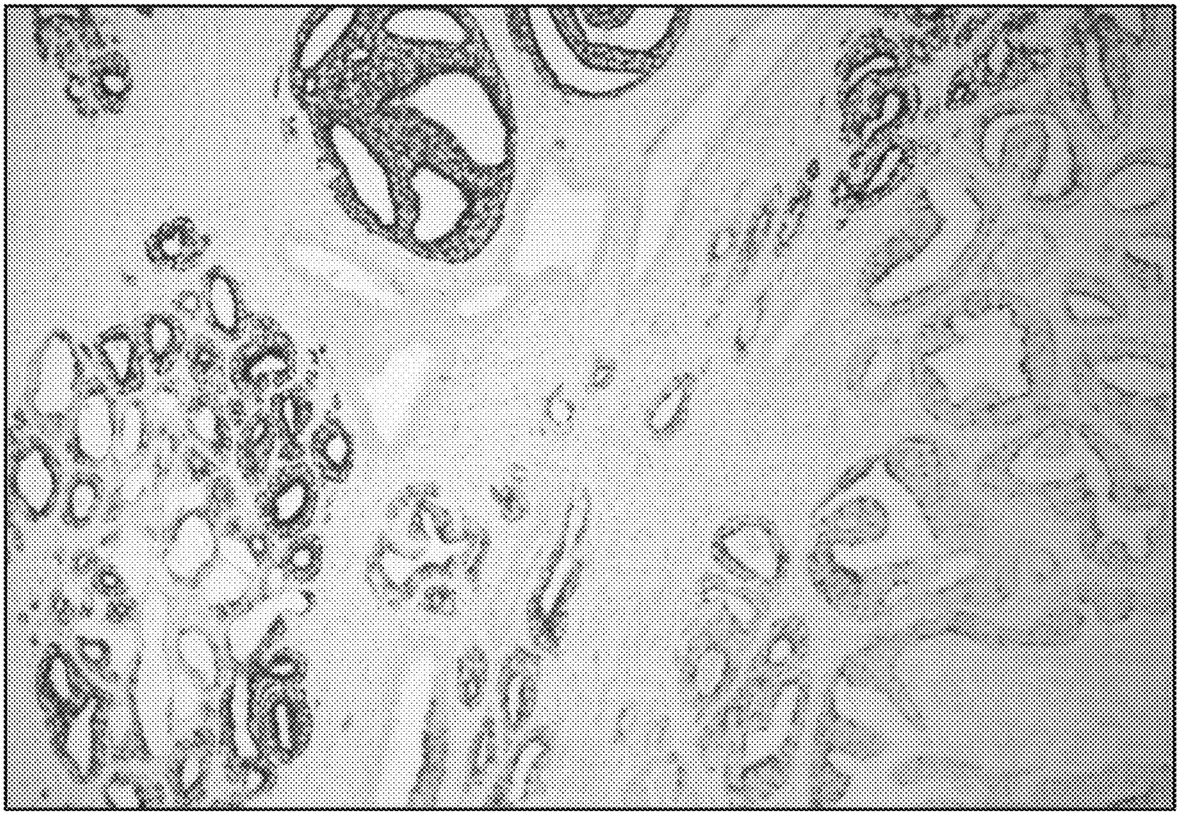
FIG. 16B depicts a serial section, P504x (AMACR) stained with DAB.
Figure 17A:
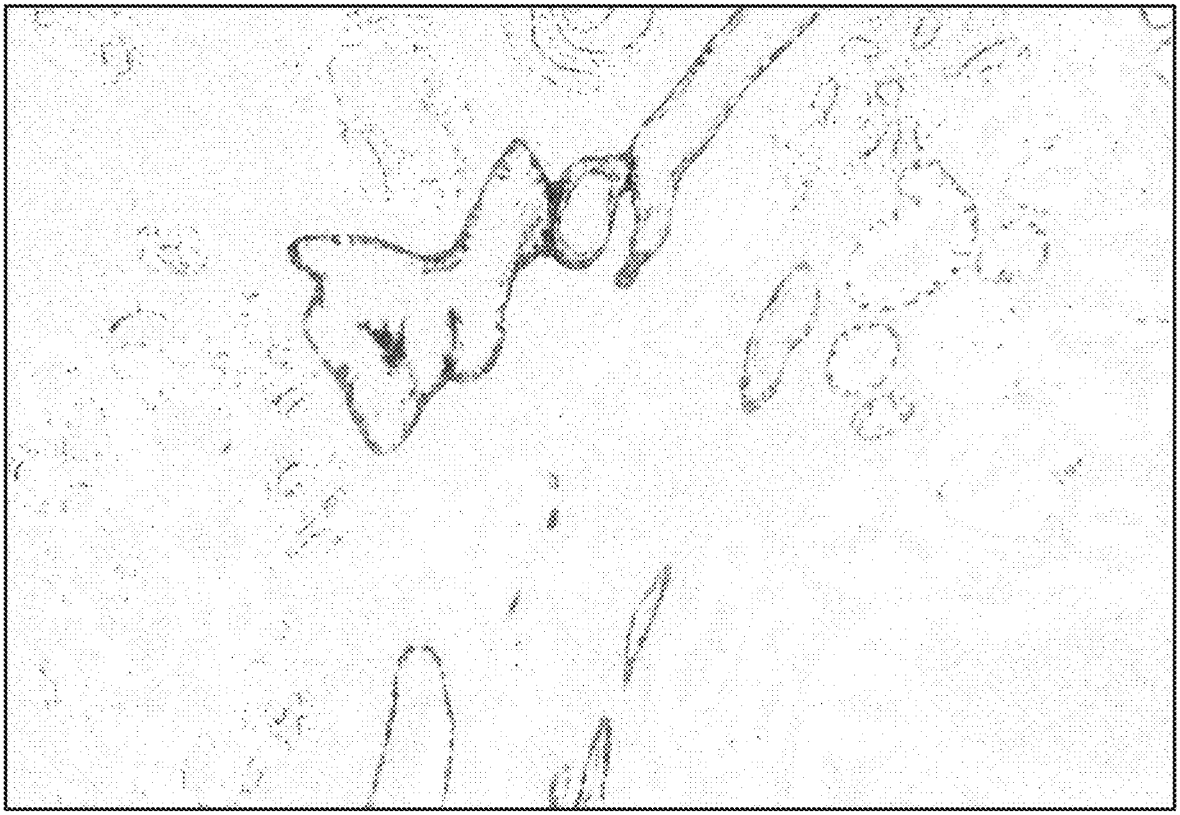
FIG. 17A depicts a multiplex IHC sample imaged with illumination through 580 nm filter-unmixed.
Figure 17B:
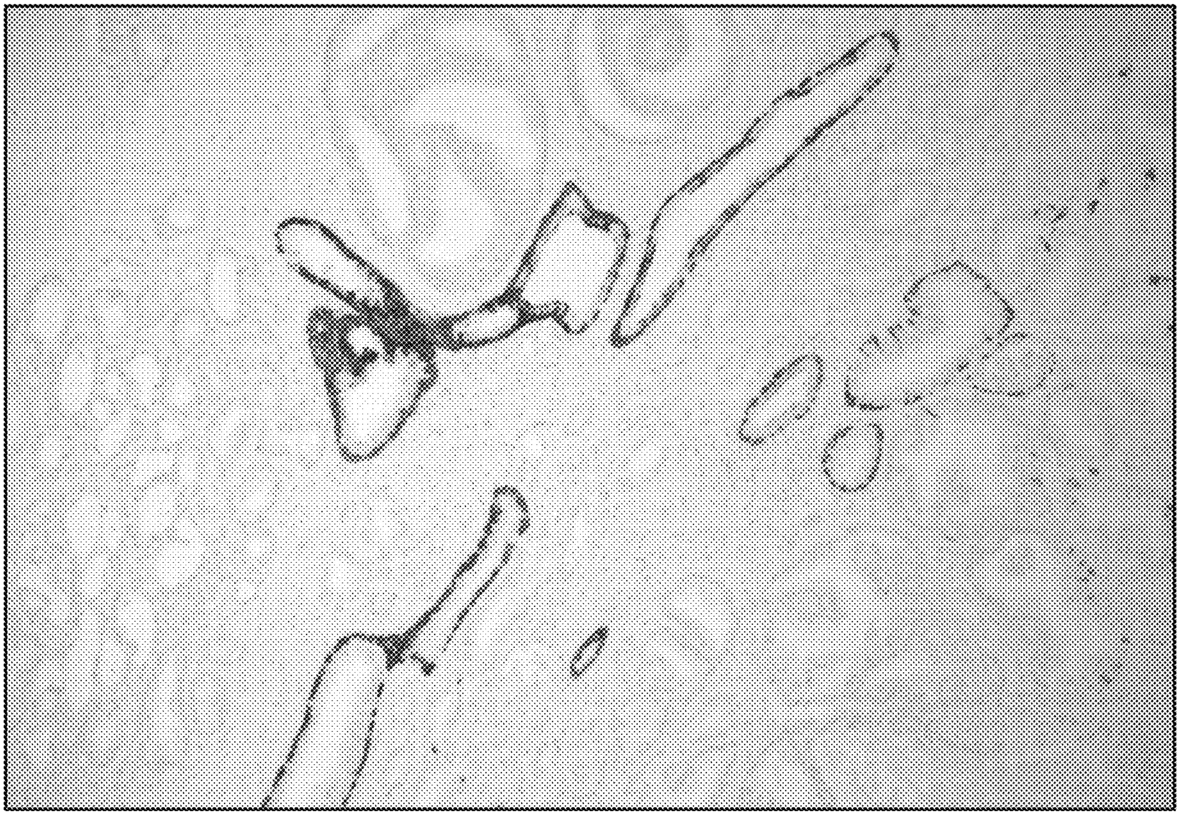
FIG. 17B depicts a serial section, basal cells stained with DAB.
Figure 18:
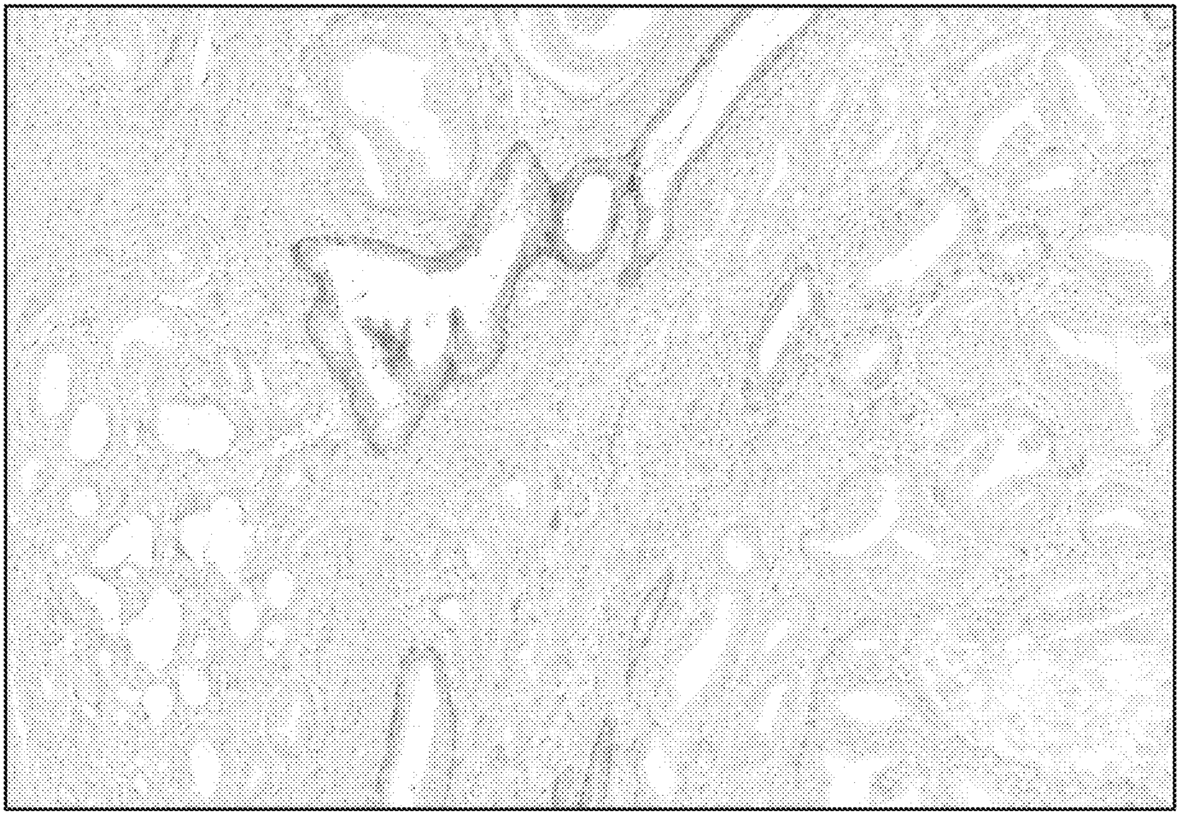
FIG. 18 depicts a multiplex IHC sample imaged with illumination through 620 nm filter-unmixed. No part B is provided since this is the absorbance of the hematoxylin nuclear stain (no DAB IHC equivalent).
Figure 19A:
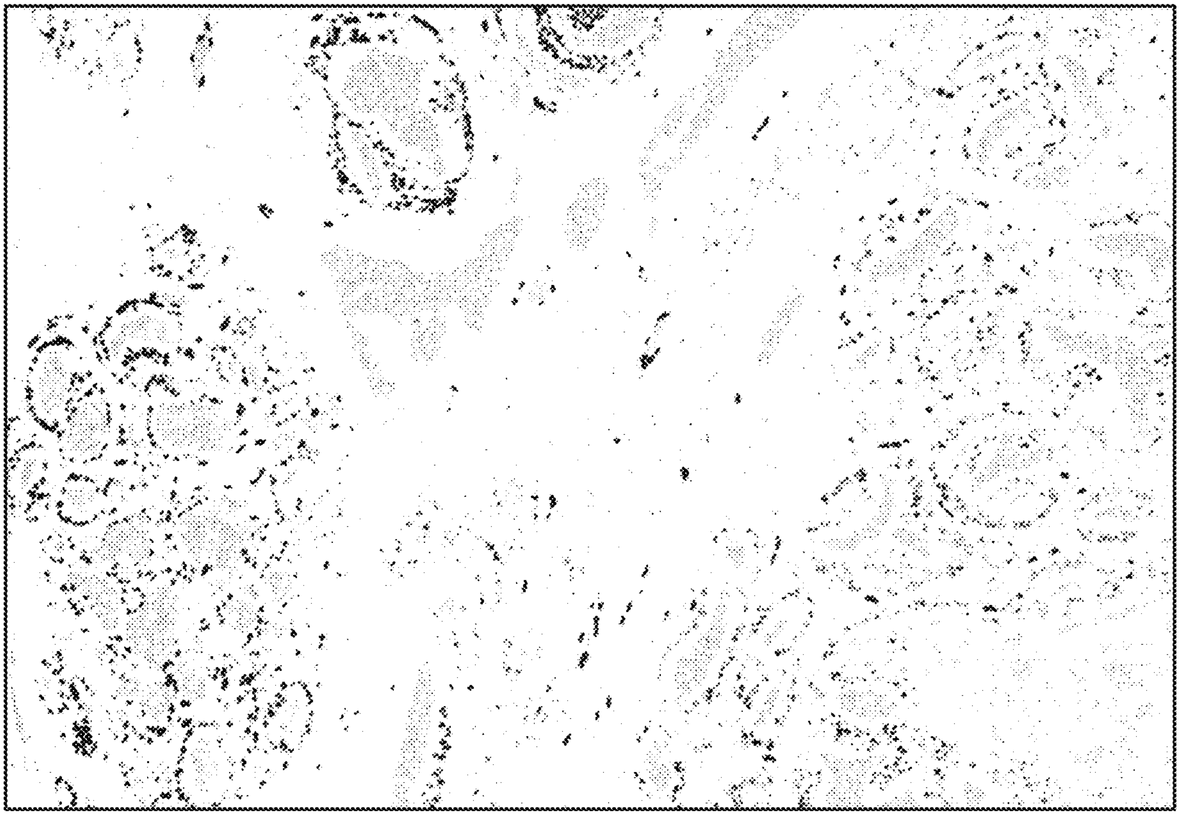
FIG. 19A depicts a multiplex IHC sample imaged with illumination through 676 nm filter-unmixed.
Figure 19B:
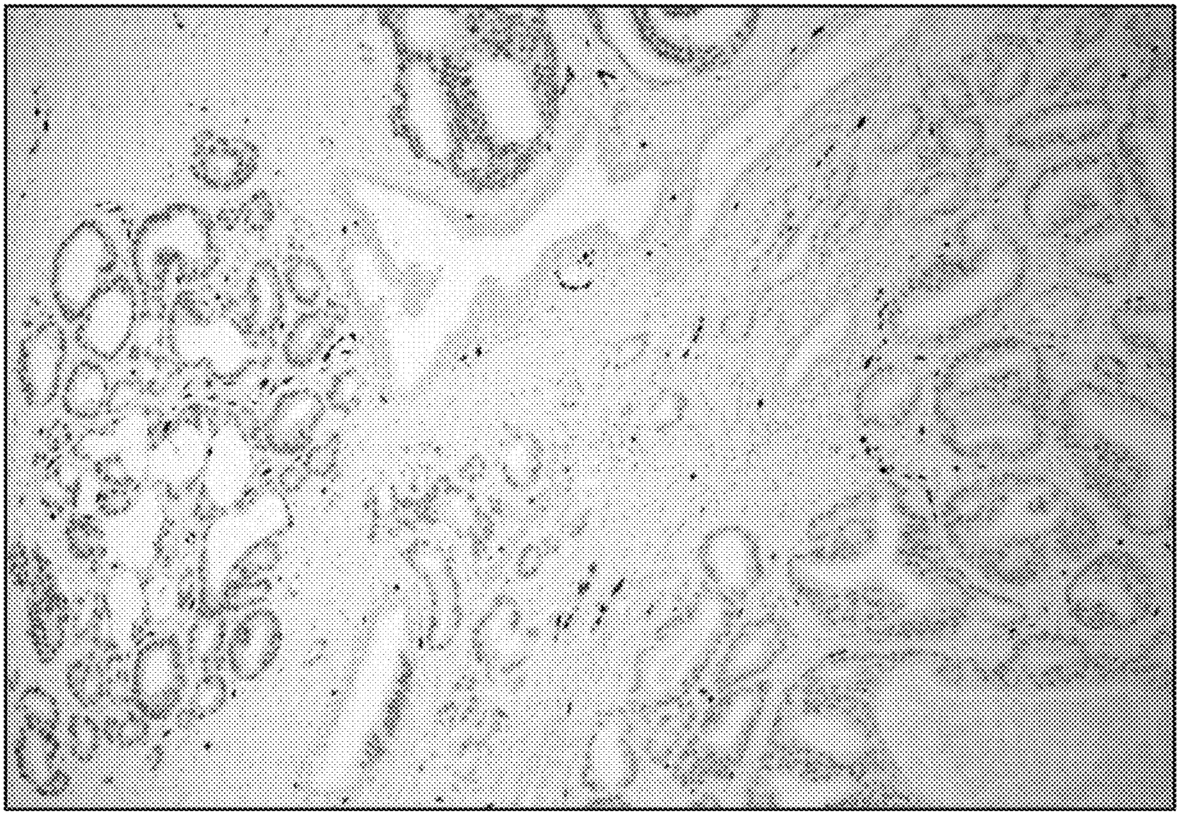
FIG. 19B depicts a serial section, ERG stained with DAB.
Figure 20A:
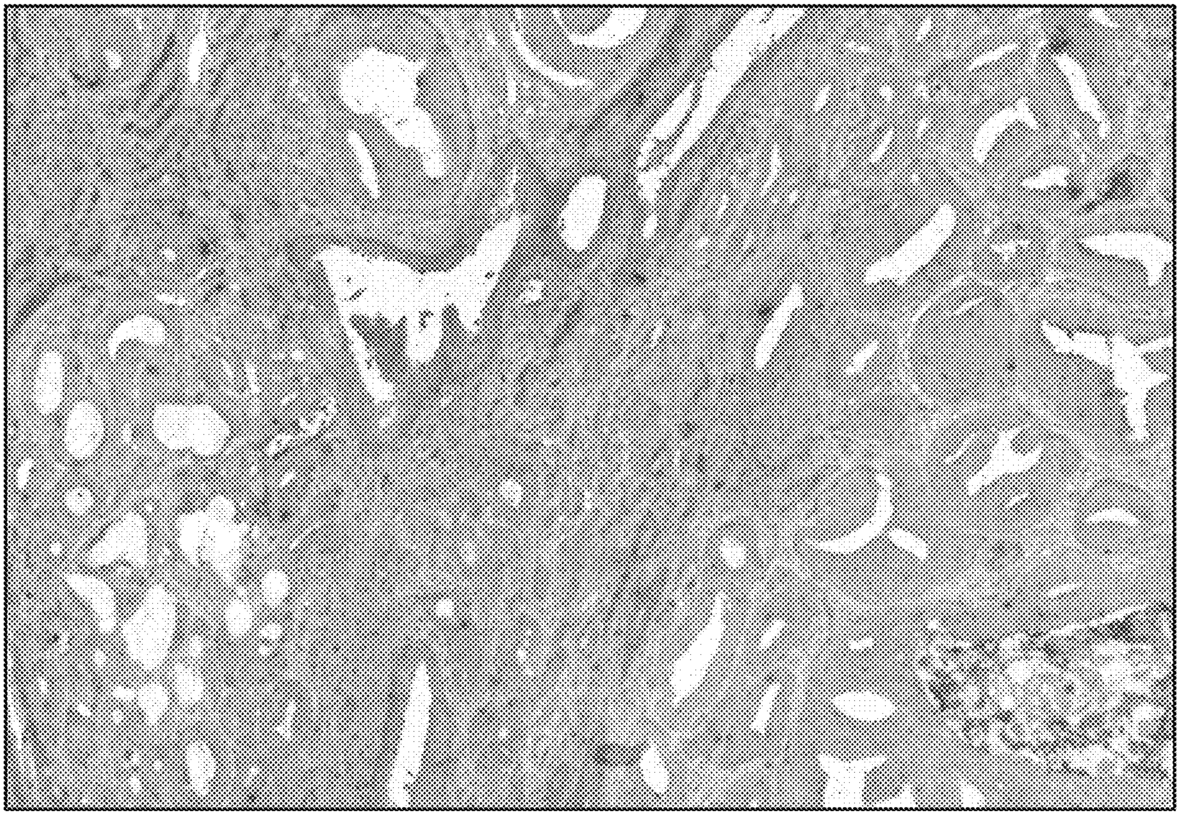
FIG. 20A depicts a multiplex IHC sample imaged with illumination through 725 nm filter-unmixed.
Figure 20B:
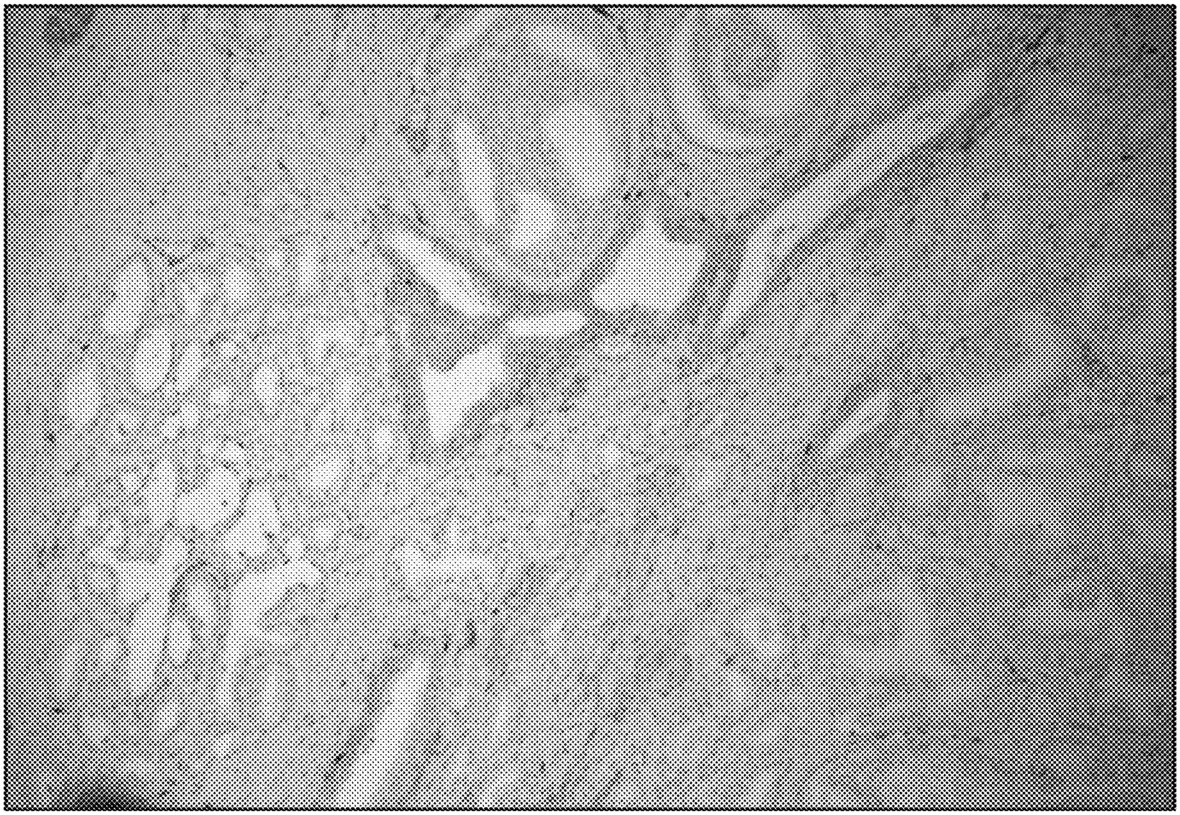
FIG. 20B depicts a serial section, PTEN stained with DAB.

RESULTS. FIG. 9 shows the absorbance spectra of several chromogens deposited by IHC targeting the Ki-67 protein, together with a plot of the human visual response that defines the visible portion the electromagnetic spectrum. Note that the visual response was very low at the wavelength of maximum absorption for each of the detectable moieties described here, and the IHC performed with each chromogen showed only very weak staining by eye under unfiltered tungsten illumination. The weakly visible pattern was believed to be partly or entirely (in the case of the UV dye AMCA-tyramide) due to effects other than chromogen light absorption, such as refraction and/or scattering of the illumination light. It was believed that portions of the HCCA-tyr and the Cy7-QM absorbance spectra trailed into spectral regions where the eye could detect light if the intensity was greatly increased. In fact, these two chromogens could be easily distinguished using the 405 nm and 725 nm filters, respectively, when the tungsten lamp intensity was increased well above a level of comfortable viewing without the filters. Through the filters, staining of HCCA-tyr was visualized as distinct dark regions on a deep blue background (405 nm filter) and staining of Cy7-QM was visualized as distinct dark regions on a deep red background (725 nm filter). Light through the 376 nm filter was very difficult to distinguish, even at the highest lamp intensity. Staining of each of the 3 chromogens could be distinctly detected in images recorded with a monochrome CCD camera (see FIGS. 10A, 11A, and 12A). The images in FIGS. 10A and 11A only required 2 ms exposures while the image in FIG. 12A required 2 s exposure due to weak tungsten lamp output at 376 nm and reduced sensitivity of the CCD camera at 376 nm. The glass used in the microscope optics was believed to transmit less efficiently at short wavelengths, indicating that chromogens absorbing wavelengths shorter than AMCA-tyr will likely not be useful in brightfield microscopy with the common glass optics. Images recorded in unfiltered illumination are shown in FIGS. 10B, 11B, and 12B to provide an idea of how poorly these detectable moieties were discerned under normal brightfield conditions. The Cy7-QM could be deposited more heavily at pH8 at higher chromogen concentration, as was more visible by eye, but spectral cross talk would be high with the neighboring Cy5 dye, used as a cyan or blue visible chromogen in multiplex IHC. Taking advantage of the strong far red peak absorbance, lower deposition could be used to reduce cross talk to acceptable levels, and the Cy7 could be detected with a filter and electronic imaging as a detectable moiety.

Figure 21:
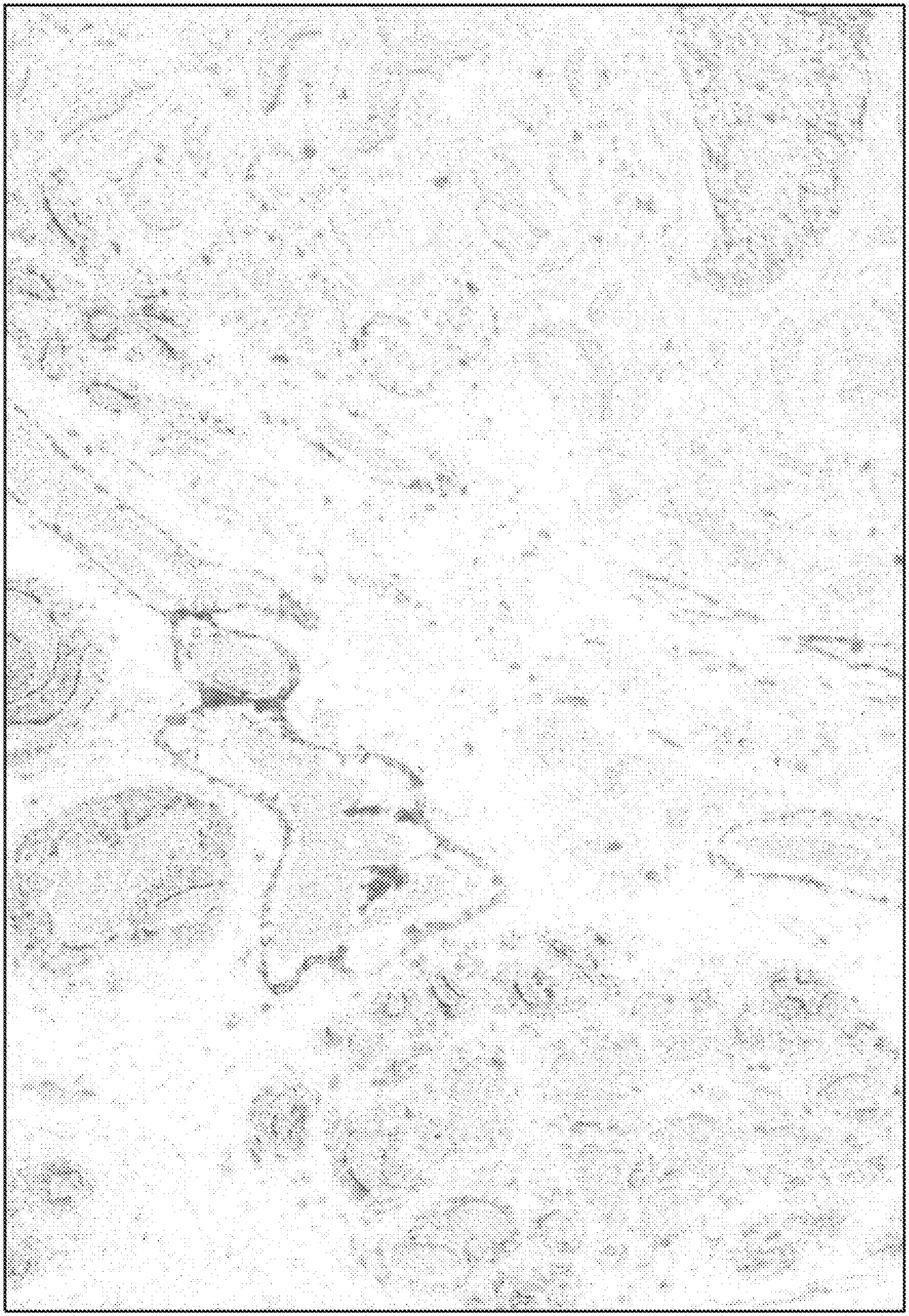
FIG. 21 depicts a color composite image using pseudo-coloring parameters (see Table 2, herein).

AMCA-tyr and Cy7-QM were used in a multiplex IHC on prostate tissue together with 5 visible tyramide and QM chromogens and a hematoxylin nuclear counterstain. The multiplex IHC consisted of primary antibodies to a basal cell biomarker, P504s (AMACR), Ki67, CD8, ERG, PSMA, and PTEN, and peroxidase and alkaline phosphatase conjugated anti-species antibodies. The biomarkers were detected respectively with 5 visible covalently deposited chromogens sulforhodamine 101-tyramide, TAMRA-tyramide, dabsyl-quinone methide, rhodamine 110-tyramide, Cy5-quinone methide and the 2 detectable moieties AMCA-tyramide and Cy7-quinone methide. The multiplex IHC was treated with hematoxylin for staining of cell nuclei. Several microscope fields were imaged using tungsten illumination and 8 different single bandpass filters to highlight each of the 7 different chromogens and the hematoxylin counterstain, and the images were spectrally unmixed (see FIGS. 13A-20A). Seven different serial sections of the prostate tumor specimen were each stained with one of the biomarkers separately and detected with DAB. Images of the corresponding region of the multiplex images are shown in FIGS. 13B-20B. FIG. 21 shows a color composite image constructed from the 8 unmixed chromogen images of the multiplex IHC. The chromogens used to detect each biomarker, the center wavelength of the bandpass filters use to image each chromogen, and the pseudocolor assignments and weighting factors (gain) for each of the unmixed chromogen images are listed in Table 2.

CONCLUSION. Multiplexing provides a valuable extension to immunohistochemical analysis providing the ability to evaluate multiple biomarkers in a single assay. Although brightfield IHC dominates clinical immunohistochemical analysis, multiplexing is typically performed using immunofluorescence (IF), evaluated by fluorescence microscopy. A large reason for this is the relatively low number and broad spectral absorbance of available chromogens, relative to fluorescent dyes, leading to greater multiplexing capacity in IF. However, clinical adoption of multiplexed IF has been low, with one factor being the preference of pathologists for brightfield microscopy. Recently we developed a new type of chromogen for brightfield microscopy that simplifies design and preparation of chromogens with desired spectral characteristics, such as wavelength of peak absorbance and narrow absorbance bands, which rivals the spectral characteristics of fluorescent dyes. This new approach to chromogens has allowed us to prepare chromogens that absorb light at the edges of the visible spectrum or completely outside the visible spectrum in the deep-blue/UV or far-red/near-IR spectral regions. As shown in FIGS. 10-12, these detectable moieties are only very weakly visible or invisible by visual analysis through the microscope. In the presence of nuclear counterstain and visible chromogens, evenly the weakly visible chromogens would not be detected by visual examination under the microscope under appropriate staining levels. The AMCA and Cy7 chromogens were used successfully in combination with five visible chromogens and hematoxylin nuclear stain to identify locations of seven biomarkers plus all nuclei, as shown in FIGS. 13-20. Comparisons of the unmixed images of each chromogen (FIGS. 12A-20A) to staining with DAB for each biomarker individually on serial sections (FIGS. 12B-20B) show that the gold standard DAB staining pattern of each biomarker is faithfully reproduced by the multiplexed chromogens. This level of multiplexing exceeds that of current commercial IF assays is competitive with or exceeds that of published research IF assays.

TABLE 2

Multiplex IHC biomarker, chromogen, filter, and pseudocoloring scheme for FIGS. 5-13.

| Chromogen # and biomarker | Chromogen name | Filter center WL near dye peak | Pseudo-color | R | G | B | M (gain) |
|---|---|---|---|---|---|---|---|
| 8 - PTEN | CY7 | 725 | yellow | 255 | 255 | 0 | .3 |
| 5 - basal | SRH101 | 580 | Blue-magenta | 192 | 0 | 255 | 3.5 |
| 3 - CD8 | RH110 | 510 | Red-magenta | 255 | 0 | 127 | 1 |
| 4 - P504s (AMACR) | TAMRA | 549 | Red | 255 | 0 | 0 | 0.7 |
| 2 - Ki67 | DABSYL | 438 | Green | 0 | 255 | 0 | .9 |
| 7 - ERG | Cy5 | 676 | blue | 0 | 0 | 255 | 1.5 |
| 6 - nuclear CS | HTX | 620 | cyan | 0 | 255 | 255 | 1.2 |
| 1 - PSMA | AMC | 376 | Orange | 255 | 100 | 0 | 3.5 |

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary, to employ concepts of the various patents, applications and publications to provide yet further embodiments.

Although the disclosure herein has been described with reference to particular embodiments, it is to be understood that these embodiments are merely illustrative of the principles and applications of the present disclosure. It is therefore understood that numerous modifications may be made to the illustrative embodiments and that other arrangements may be devised without departing from the spirit and scope of the present disclosure as defined by the appended claims.

Additional Embodiments

Additional Embodiment 1. A compound having Formula (I):

$$[Z]\text{-}[Q]_m\text{-}[W] \quad \text{(I)},$$

wherein

Z is (i) a "tissue reactive moiety," or (ii) a functional group or a moiety including a functional group capable of participating in a "click chemistry" reaction;

Q is a branched or unbranched, linear or cyclic, substituted or unsubstituted group having between 2 and 40 carbon atoms, and optionally having one or more heteroatoms selected from O, N, or S;

m is 0, 1, or 2; and

W has Formula (IIA):

(IIA)

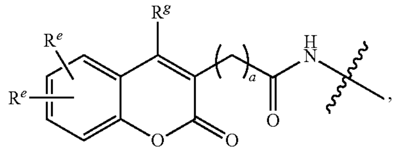

wherein each $R^e$ is independently —OH, —O-alkyl, or —$N(R^x)(R^y)$, where $R^x$ and $R^y$ are independently H or a branched or unbranched $C_1$-$C_4$ alkyl group optionally substituted with one or more halogen atoms, or where $R^x$ and $R^y$ together form a 3-, 4-, or 5-membered cyclic ring which may be optionally substituted with one or more halogen atoms or one or more $C_1$-$C_2$ alkyl groups;

$R^g$ is —H, —$CH_3$ or —$CH_2$—$CH_3$; and a is 0 or an integer ranging from 1 to 4.

Additional Embodiment 2. The compound of additional embodiment 1, wherein W has Formula (IIB):

(IIB)

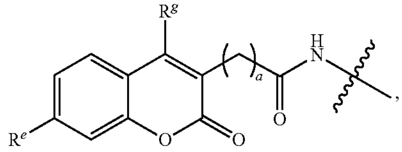

wherein $R^e$ is —OH, —O-alkyl, or —$N(R^x)(R^y)$, where $R^x$ and $R^y$ are independently H or a branched or unbranched $C_1$-$C_4$ alkyl group optionally substituted with one or more halogen atoms, or where $R^x$ and $R^y$ together form a 3-, 4-, or 5-membered cyclic ring which may be optionally substituted with one or more halogen atoms or one or more $C_1$-$C_2$ alkyl groups;

$R^g$ is —H, —$CH_3$ or —$CH_2$—$CH_3$; and a is 0 or an integer ranging from 1 to 4.

Additional Embodiment 3. The compound of additional embodiment 2, wherein $R^e$ is —N(H)(Me).

Additional Embodiment 4. The compound of additional embodiment 2, wherein $R^e$ is —$N(H)CF_3$.

Additional Embodiment 5. The compound of additional embodiment 2, wherein $R^e$ is —$N(R^x)(R^y)$, and where $R^x$ and $R^y$ together form a 3-, 4-, or 5-membered cyclic ring which may be optionally substituted with one or more halogen atoms or one or more $C_1$-$C_2$ alkyl groups.

Additional Embodiment 6. The compound of additional embodiment 2, wherein $R^e$ is —$N(R^x)(R^y)$, and where $R^x$ and $R^y$ together form a 4-membered cyclic ring which is unsubstituted.

Additional Embodiment 7. The compound of additional embodiment 2, wherein $R^e$ is —$N(R^x)(R^y)$, and where $R^x$ and $R^y$ together form a 4-membered cyclic ring which is substituted with a halogen.

Additional Embodiment 8. The compound of additional embodiment 1, wherein W has Formula (IIC).

(IIC)

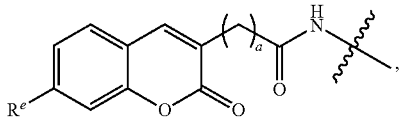

wherein $R^e$ is —OH, —O-alkyl, or —$N(R^x)(R^y)$, where $R^x$ and $R^y$ are independently H or a branched or unbranched $C_1$-$C_4$ alkyl group optionally substituted with one or more halogen atoms, or where $R^x$ and $R^y$ together form a 3-, 4-, or 5-membered cyclic ring which may be optionally substituted with one or more halogen atoms or one or more $C_1$-$C_2$ alkyl groups; and a is 0 or an integer ranging from 1 to 6.

Additional Embodiment 9. The compound of additional embodiment 1, wherein a is 0.

Additional Embodiment 10. The compound of additional embodiment 1, wherein W is selected from the group consisting of:

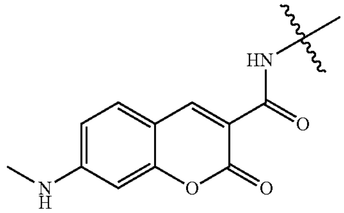

,

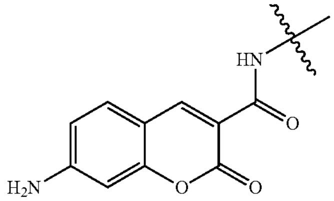

,

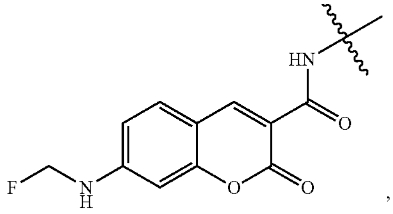

,

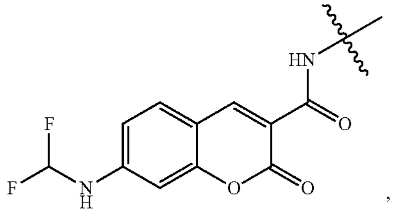

,

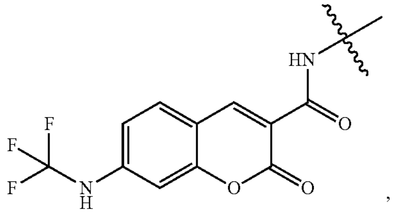

,

-continued

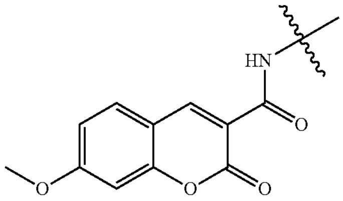

,

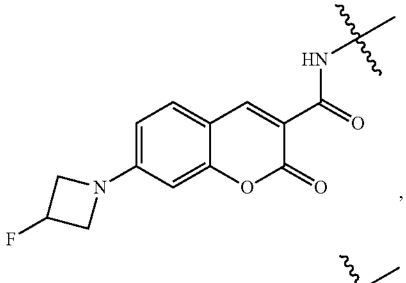

,

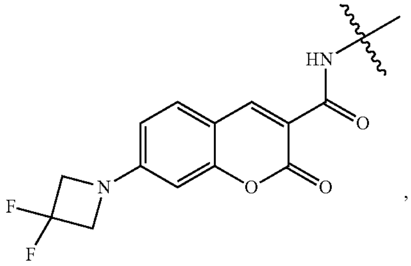

,

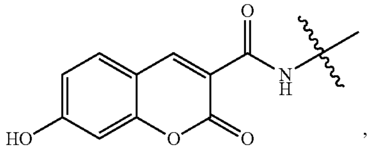

,

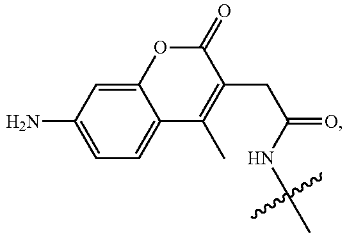

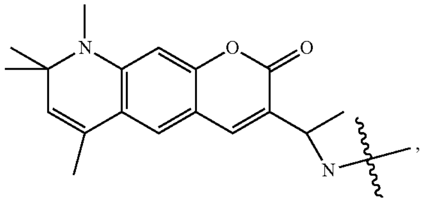

, and

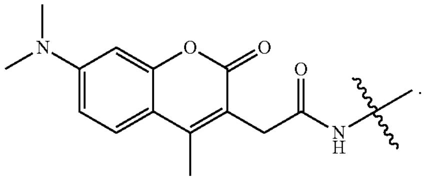

.

Additional Embodiment 11. A compound having Formula (I):

[Z]-[Q]$_m$-[W] (I), wherein

Z is (i) a "tissue reactive moiety," or (ii) a functional group or a moiety including a functional group capable of participating in a "click chemistry" reaction;

Q is a branched or unbranched, linear or cyclic, substituted or unsubstituted group having between 2 and 40 carbon atoms, and optionally having one or more heteroatoms selected from O, N, or S;

m is 0, 1, or 2; and

W has Formula (IIIA):

(IIIA)

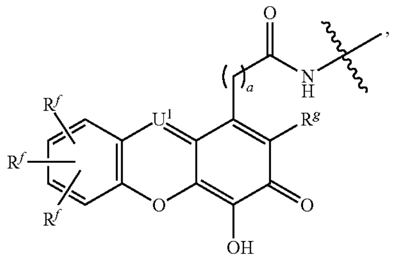

wherein each $R^f$ is independently $N(R^x)(R^y)$, where $R^x$ and $R^y$ are independently H or a branched or unbranched $C_1$-$C_4$ alkyl group optionally substituted with one or more halogen atoms; or where any two $R^f$ groups may together form a substituted or unsubstituted, saturated or unsaturated ring;

$R^g$ is —H, —$CH_3$ or —$CH_2$—$CH_3$;

$U^1$ is O, N, or S; and a is 0 or an integer ranging from 1 to 6.

Additional Embodiment 12. The compound of additional embodiment 11, wherein $R^e$ is —N(H)(Me).

Additional Embodiment 13. The compound of additional embodiment 11, wherein $R^e$ is —N(H)$CF_3$.

Additional Embodiment 14. The compound of additional embodiment 11, wherein $U^1$ is N; and $R^f$ is —N(H)(Me), —$NH_2$, —N(H)$CF_3$, —N(H)—$CH_2$—F, —N(H)—$CH_2$—$CH_2$—F, —N(H)—CH(F)(F), —N(Me)$CF_3$, —N(Et)$CF_3$, or —N(H)(Ipr).

Additional Embodiment 15. The compound of additional embodiment 14, wherein a is 0.

Additional Embodiment 16. The compound of additional embodiment 11, wherein $U^1$ is N.

Additional Embodiment 17. The compound of additional embodiment 11, wherein W has Formula (IIIB):

(IIIB)

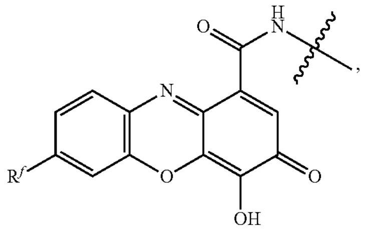

wherein $R^f$ is $N(R^x)(R^y)$, where $R^x$ and $R^y$ are independently H or a branched or unbranched $C_1$-$C_4$ alkyl group optionally substituted with one or more halogen atoms;

$R^g$ is —H, —$CH_3$ or —$CH_2$—$CH_3$;

$U^1$ is O, N, or S; and a is 0 or an integer ranging from 1 to 6.

Additional Embodiment 18. The compound of additional embodiment 17, wherein at least one of $R^x$ and $R^y$ is H.

Additional Embodiment 19. The compound of additional embodiment 17, wherein a is 0.

Additional Embodiment 20. The compound of additional embodiment 11, wherein W is:

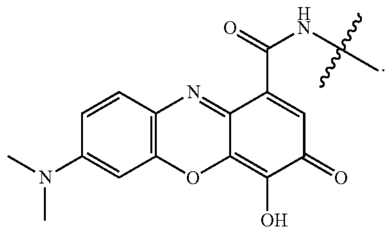 [SMILES: *NC(=O)c1cc(=O)c(O)c2oc3cc(N(C)C)ccc3nc1-2]

Additional Embodiment 21. A compound having Formula (I):

$$[Z]\text{-}[Q]_m\text{-}[W] \qquad (I),$$

wherein

Z is (i) a "tissue reactive moiety," or (ii) a functional group or a moiety including a functional group capable of participating in a "click chemistry" reaction;

Q is a branched or unbranched, linear or cyclic, substituted or unsubstituted group having between 2 and 40 carbon atoms, and optionally having one or more heteroatoms selected from O, N, or S;

m is 0, 1, or 2; and

W has Formula (IVA):

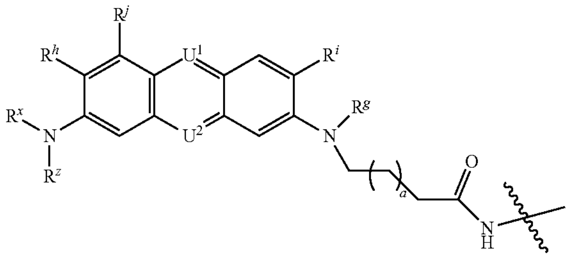

wherein $U^1$ is O, N, or S;

$U^2$ is O or S;

$R^g$ is-$CH_3$ or —$CH_2$—$CH_3$;

$R^i$ is H or a branched or unbranched $C_1$-$C_6$ alkyl group;

or where $R^g$ and $R^i$ together form a 5-, 6-, or 7-membered cyclic or aromatic ring which may be optionally substituted with a halogen, a $C_1$-$C_4$ alkyl group;

$R^h$ is H or a branched or unbranched $C_1$-$C_4$ alkyl group;

$R^x$ is H or a branched or unbranched $C_1$-$C_4$ alkyl group optionally substituted with one or more halogen atoms;

$R^z$ is H, or a branched or unbranched $C_1$-$C_4$ alkyl group optionally substituted with one or more halogen atoms or with a —S(O)(O)—$O^-$ group;

or where $R^x$ and $R^z$ together form a 3-, 4-, or 5-membered ring which may be optionally be substituted;

or where $R^h$ and one of $R^x$ or $R^z$ together form a 5-, 6-, or 7-membered cyclic or aromatic ring which may be optionally substituted with one or more halogen atoms or one or more $C_1$-$C_2$ alkyl groups;

$R^j$ is H or a branched or unbranched $C_1$-$C_6$ alkyl group;

or where $R^j$ and $R^h$ form a 5- or 6-membered ring, optionally substituted with one or more $C_1$-$C_4$ alkyl groups; and a is 0 or an integer ranging from 1 to 6.

Additional Embodiment 22. The compound of additional embodiment 21, wherein a is 0.

Additional Embodiment 23. The compound of additional embodiment 21, wherein $R^x$ is a $C_1$-$C_2$ alkyl group.

Additional Embodiment 24. The compound of additional embodiment 21, wherein $U^2$ is S.

Additional Embodiment 25. The compound of additional embodiment 21, wherein $U^1$ is N.

Additional Embodiment 26. The compound of additional embodiment 21, $U^2$ is O and $R^z$ is an unbranched $C_1$-$C_4$ alkyl group substituted with a —S(O)(O)—$O^-$ group.

Additional Embodiment 27. The compound of additional embodiment 21, $U^1$ is N, $U^2$ is O and $R^z$ is an unbranched $C_1$-$C_4$ alkyl group substituted with a —S(O)(O)—$O^-$ group.

Additional Embodiment 28. The compound of additional embodiment 21, wherein $U^2$ is S and $R^z$ is an unbranched $C_1$-$C_4$ alkyl group substituted with one or more halogen atoms.

Additional Embodiment 29. The compound of additional embodiment 21, wherein $U^1$ is N, $U^2$ is O and $R^z$ is an unbranched $C_1$-$C_4$ alkyl group substituted with one or more halogen atoms.

Additional Embodiment 30. The compound of additional embodiment 21, wherein $U^1$ is N, $U^2$ is S and $R^z$ is an unbranched $C_1$-$C_4$ alkyl group substituted with one or more halogen atoms.

Additional Embodiment 31. The compound of additional embodiment 21, wherein W has any one of Formulas (IVC) or (IVD):

(IVC)

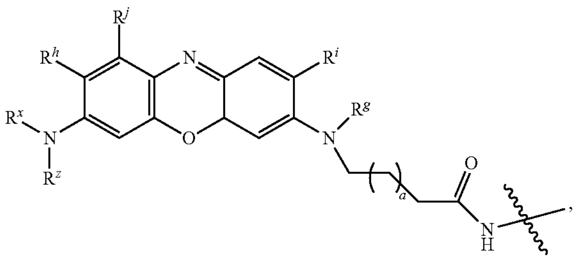

(IVD)

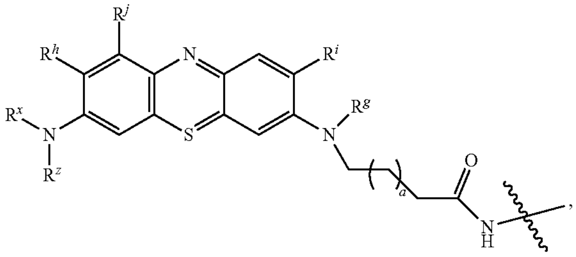

$R^g$ is-$CH_3$ or —$CH_2$—$CH_3$;

$R^i$ is H or a branched or unbranched $C_1$-$C_6$ alkyl group;

or where $R^g$ and $R^i$ together form a 5-, 6-, or 7-membered ring which may be optionally substituted with a halogen, a $C_1$-$C_4$ alkyl group;

$R^h$ is H or a branched or unbranched $C_1$-$C_4$ alkyl group;

$R^x$ is H or a branched or unbranched $C_1$-$C_4$ alkyl group optionally substituted with one or more halogen atoms;

$R^z$ is H, or a branched or unbranched $C_1$-$C_4$ alkyl group optionally substituted with one or more halogen atoms or with a —S(O)(O)—$O^-$ group;

or where $R^h$ and one of $R^x$ or $R^z$ together form a 5-, 6-, or 7-membered cyclic or aromatic ring which may be optionally substituted with one or more halogen atoms or one or more $C_1$-$C_2$ alkyl groups;

$R^j$ is H or a branched or unbranched $C_1$-$C_6$ alkyl group;

or where $R^j$ and $R^h$ form a 5- or 6-membered ring, optionally substituted with one or more $C_1$-$C_4$ alkyl groups; and a is 0 or an integer ranging from 1 to 6.

Additional Embodiment 32. The compound of additional embodiment 21, wherein W has Formula (IVE):

(IVE)

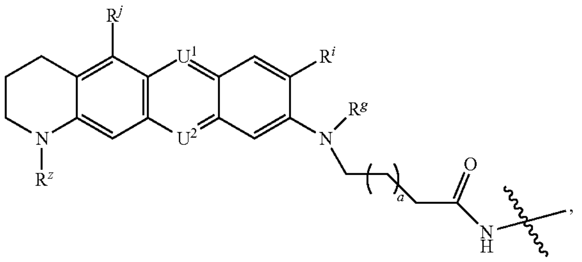

wherein $U^1$ is O, N, or S;

$U^2$ is O or S;

$R^g$ is-$CH_3$ or —$CH_2$—$CH_3$;

$R^i$ is H or a branched or unbranched $C_1$-$C_6$ alkyl group; or where $R^g$ and $R^i$ together form a 5-, 6-, or 7-membered ring which may be optionally substituted with a halogen, a $C_1$-$C_4$ alkyl group;

$R^z$ is H, or a branched or unbranched $C_1$-$C_4$ alkyl group optionally substituted with one or more halogen atoms or with a —S(O)(O)—$O^-$ group;

$R^j$ is H or a branched or unbranched $C_1$-$C_6$ alkyl group;

a is 0 or an integer ranging from 1 to 6.

Additional Embodiment 33. The compound of additional embodiment 32, wherein $R^i$ and $R^g$ together form a 6-membered cyclic ring and $R^z$ is a $C_1$-$C_4$ alkyl group.

Additional Embodiment 34. The compound of additional embodiment 32, wherein $U^2$ is O, $R^i$ and $R^g$ together form a 6-membered cyclic ring and $R^z$ is a $C_1$-$C_4$ alkyl group.

Additional Embodiment 35. The compound of additional embodiment 32, wherein $U^2$ is S, $R^i$ and $R^g$ together form a 6-membered cyclic ring, and $R^z$ is a $C_1$-$C_4$ alkyl group.

Additional Embodiment 36. The compound of additional embodiment 32, wherein $R^i$ and $R^g$ together form a 6-membered cyclic ring, $U^2$ is O, and $R^z$ is an unbranched $C_1$-$C_4$ alkyl group substituted with a —S(O)(O)—$O^-$ group.

Additional Embodiment 37. The compound of additional embodiment 21, wherein W has any one of Formulas (IVG) and (IVH):

(IVG)

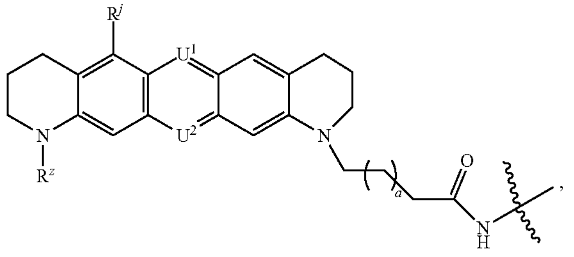

-continued (IVH)

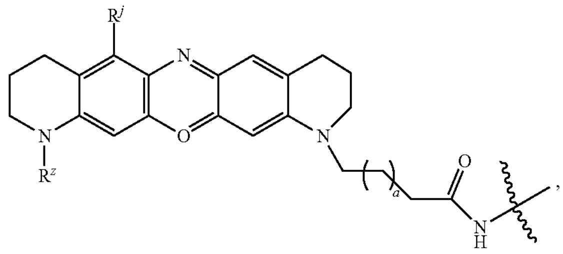

wherein $U^1$ is O, N, or S;

$U^2$ is O or S;

$R^z$ is H, or a branched or unbranched $C_1$-$C_4$ alkyl group optionally substituted with one or more halogen atoms or with a —S(O)(O)—$O^-$ group;

$R^j$ is H or a branched or unbranched $C_1$-$C_6$ alkyl group;

a is 0 or an integer ranging from 1 to 6.

Additional Embodiment 38. The compound of additional embodiment 37, wherein $R^z$ is a $C_1$-$C_4$ alkyl group.

Additional Embodiment 39. The compound of additional embodiment 37, wherein $R^z$ is an unbranched $C_1$-$C_4$ alkyl group.

Additional Embodiment 40. The compound of additional embodiment 37, wherein $R^z$ is an unbranched $C_1$-$C_3$ alkyl group substituted with a —S(O)(O)—$O^-$ group.

Additional Embodiment 41. The compound of additional embodiment 21, wherein W is selected from the group consisting of:

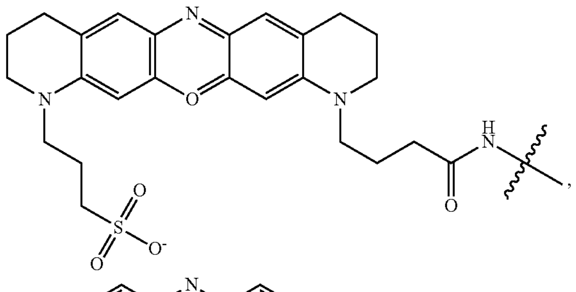

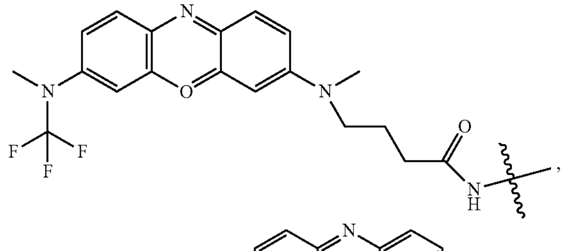

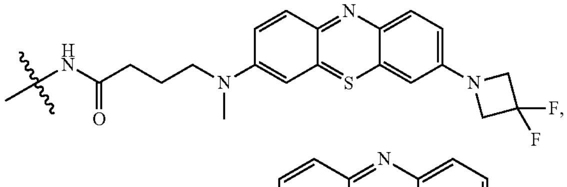

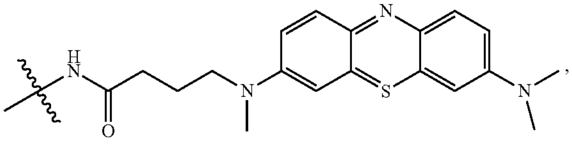

-continued

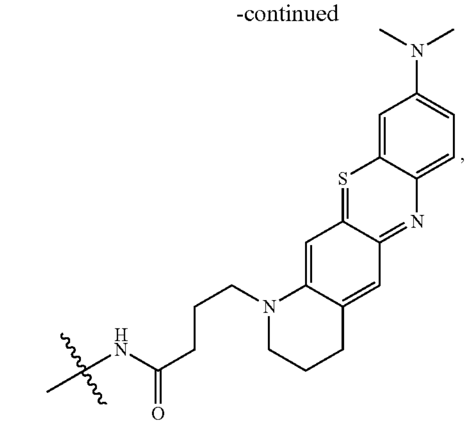

,

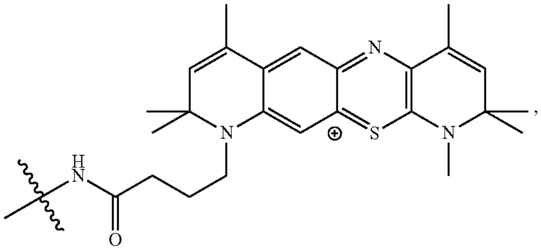

,

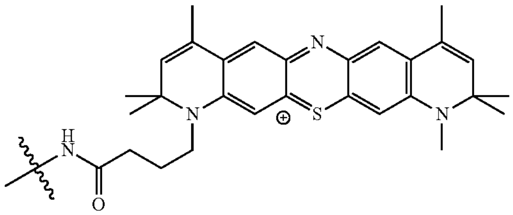

, and

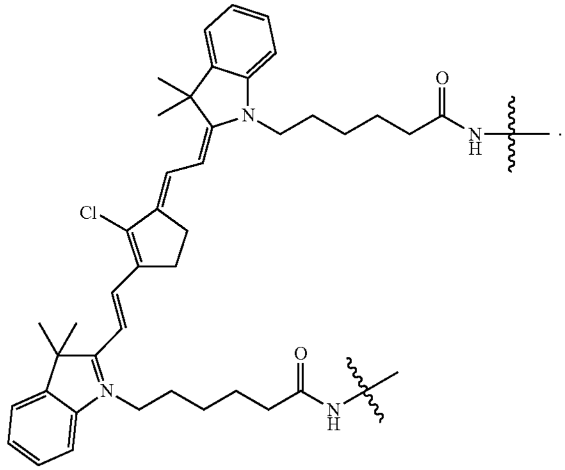

.

Additional Embodiment 42. A compound having Formula (I):

$$[Z]\text{-}[Q]_m\text{-}[W] \quad (I),$$

wherein

Z is (i) a "tissue reactive moiety," or (ii) a functional group or a moiety including a functional group capable of participating in a "click chemistry" reaction;

Q is a branched or unbranched, linear or cyclic, substituted or unsubstituted group having between 2 and 40 carbon atoms, and optionally having one or more heteroatoms selected from O, N, or S;

m is 0, 1, or 2; and

W has any one of Formulas (VA) and (VB):

(VA)

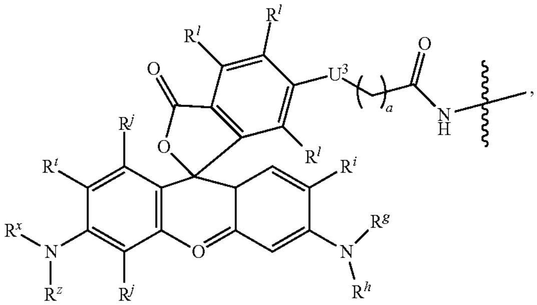

, (VB)

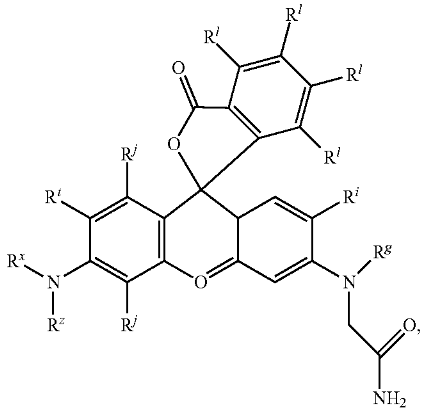

, wherein $R^g$ is-$CH_3$ or —$CH_2$—$CH_3$;

$R^i$ is H or a branched or unbranched $C_1$-$C_6$ alkyl group; or where $R^g$ and $R^i$ together form a 5-, 6-, or 7-membered ring which may be optionally substituted with a halogen, a $C_1$-$C_4$ alkyl group;

$R^h$ is H or a branched or unbranched $C_1$-$C_4$ alkyl group;

$R^x$ is H or a branched or unbranched $C_1$-$C_4$ alkyl group optionally substituted with one or more halogen atoms;

$R^z$ is H, or a $C_1$-$C_4$ alkyl group optionally substituted with one or more halogen atoms or with a —S(O)(O)—$O^-$ group;

$R^t$ is H or a branched or unbranched $C_1$-$C_4$ alkyl group; or where $R^t$ and one of $R^x$ or $R^z$ together form a 5-, 6-, or 7-membered cyclic or aromatic ring which may be optionally substituted with one or more halogen atoms or one or more $C_1$-$C_2$ alkyl groups;

each $R^j$ is independently H or a branched or unbranched $C_1$-$C_6$ alkyl group;

or where $R^j$ and $R^t$ form a 5- or 6-membered ring, optionally substituted with one or one or more $C_1$-$C_2$ alkyl groups; or where $R^j$ and one of $R^x$ or $R^z$ form a 5- or 6-membered ring, optionally substituted with one or more $C_1$-$C_2$ alkyl groups; or where $R^x$, $R^t$, and $R^j$ together form a bicyclic ring which may be saturated or unsaturated and which may be optionally substituted with one or more halogen atoms or one or more $C_1$-$C_2$ alkyl groups;

each $R^l$ is independently H or a halogen atom; and a is 0 or an integer ranging from 1 to 6.

Additional Embodiment 43. The compound of additional embodiment 42, wherein $R^t$ and $R^x$ together form a 6-membered ring.

Additional Embodiment 44. The compound of additional embodiment 42, wherein $R^t$ and $R^x$ together form a 6-membered ring substituted with one or more methyl or ethyl groups, one or more —$CH_2$—S(O)(O)(OH) groups, one or more —$CH_2$—$CH_2$—S(O)(O)(OH) groups, —$CH_2$—$CH_2$—$CH_2$—S(O)(O)(OH) groups, or —$CH_2$—$CH_2$—$CH_2$—$CH_2$—S(O)(O)(OH) groups.

Additional Embodiment 45. The compound of additional embodiment 42, wherein $R^i$ and $R^g$ together form a 6-membered substituted ring.

Additional Embodiment 46. The compound of additional embodiment 42, wherein $R^t$ and $R^x$ together form a 6-membered ring, and $R^i$ and $R^g$ together form a 6-membered ring.

Additional Embodiment 47. The compound of additional embodiment 42, wherein $R^x$, $R^t$, and $R^j$ together form a bicyclic ring.

Additional Embodiment 48. The compound of additional embodiment 42, wherein $R^x$, $R^t$, and $R^j$ together form a bicyclic ring, and $R^i$ and $R^g$ together form a 6-membered ring.

Additional Embodiment 49. The compound of additional embodiment 42, wherein $R^i$ and $R^g$ together form a 6-membered ring substituted with one or more methyl or ethyl groups, one or more —$CH_2$—S(O)(O)(OH) groups, one or more —$CH_2$—$CH_2$—S(O)(O)(OH) groups, —$CH_2$—$CH_2$—$CH_2$—S(O)(O)(OH) groups, or —$CH_2$—$CH_2$—$CH_2$—$CH_2$—S(O)(O)(OH) groups.

Additional Embodiment 50. The compound of additional embodiment 42, wherein a is 0.

Additional Embodiment 51. The compound of additional embodiment 42, wherein W is selected from the group consisting of:

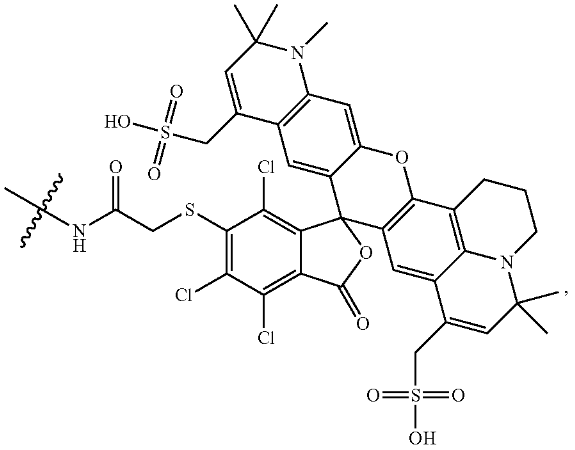

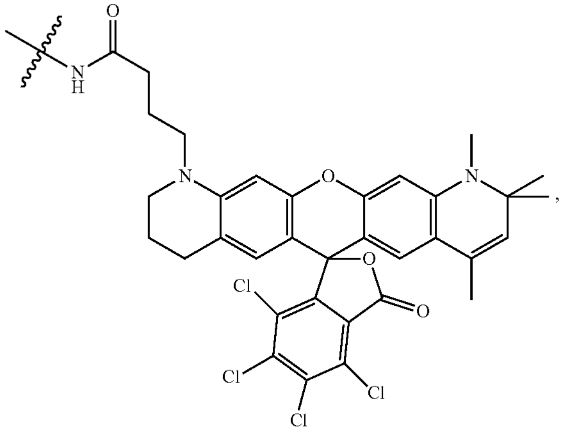

-continued

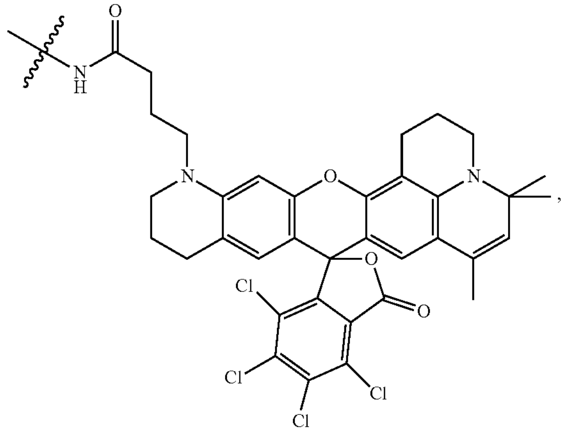

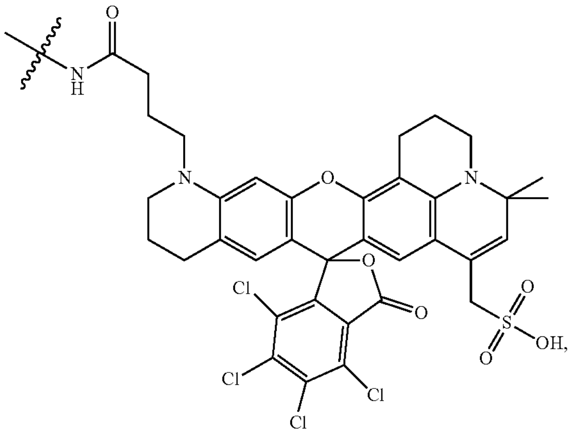

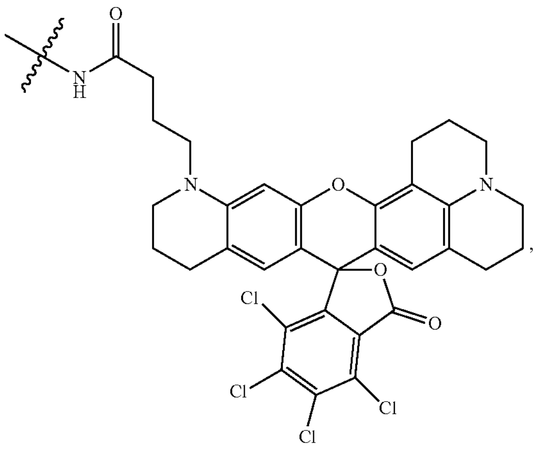

-continued

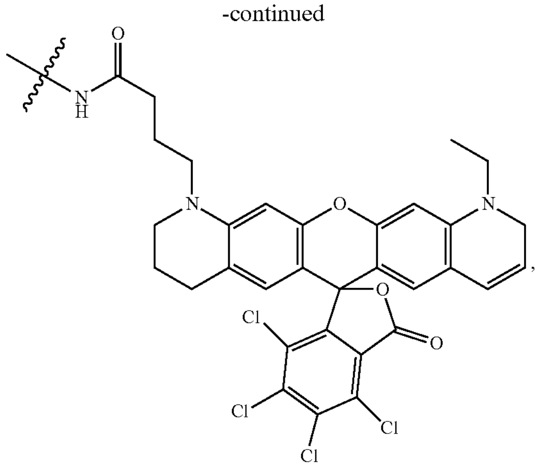

,

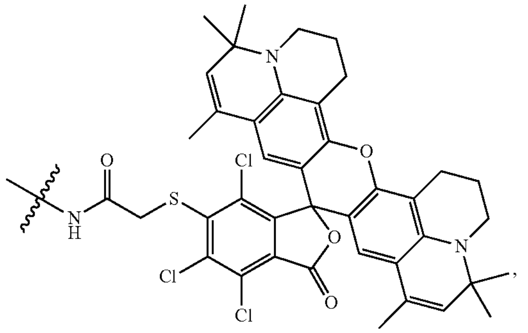

, and

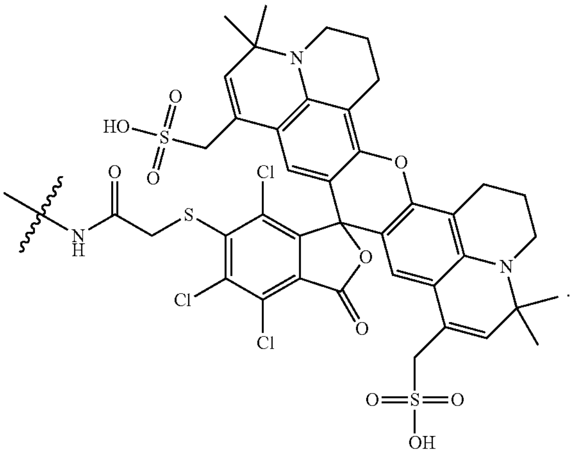

.

Additional Embodiment 52. A compound having Formula (I):

[Z]-[Q]$_m$-[W] (I), wherein

Z is (i) a "tissue reactive moiety," or (ii) a functional group or a moiety including a functional group capable of participating in a "click chemistry" reaction;

Q is a branched or unbranched, linear or cyclic, substituted or unsubstituted group having between 2 and 40 carbon atoms, and optionally having one or more heteroatoms selected from O, N, or S;

m is 0, 1, or 2; and

W has Formula (VI):

(VI)

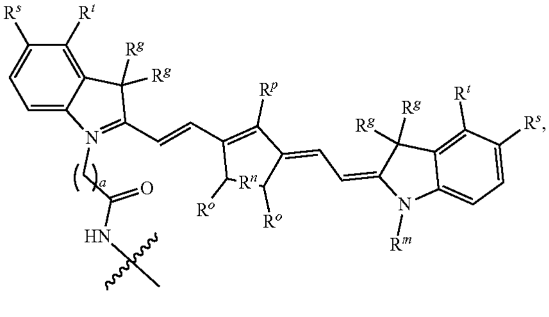

wherein a is 0 or an integer ranging from 1 to 6;

$R^p$ is a halogen atom;

$R^n$ is a bond or —$CH_2$—;

each $R^o$ is independently a branched or unbranched $C_1$-$C_4$ alkyl group, or when $R^n$ is —$CH_2$— then both $R^o$ groups together may form a 6-member cyclic or aromatic ring, optionally substituted with one or more halogen groups or one or more $C_1$-$C_2$ alkyl groups;

each $R^g$ is independently-$CH_3$ or —$CH_2$—$CH_3$;

$R^m$ is H, a branched or unbranched $C_1$-$C_4$ alkyl group which is optionally substituted with one or more halogen atoms and or one or more —S(O)(O)(OH) groups, or a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction;

each $R^s$ or $R^t$ group is independently selected from a branched or unbranched $C_1$-$C_6$ alkyl group;

or wherein any two adjacent $R^s$ and $R^t$ groups and/or any two adjacent $R_g$ and $R^t$ groups may together form a 5- or 6-membered cyclic or aromatic group, optionally substituted with one or more $C_1$-$C_2$ alkyl groups.

Additional Embodiment 53. The compound of additional embodiment 52, wherein $R^n$ is —$CH_2$—.

Additional Embodiment 54. The compound of additional embodiment 52, wherein $R^n$ is a bond and wherein at least one $R^g$ is methyl.

Additional Embodiment 55. The compound of additional embodiment 52, wherein $R^n$ is —$CH_2$— and each $R^o$ together forms a 6-membered ring.

Additional Embodiment 56. The compound of additional embodiment 52, wherein one set of adjacent $R^t$ and $R^s$ groups forms a 6-membered ring.

Additional Embodiment 57. The compound of additional embodiment 52, wherein both sets of adjacent $R^t$ and $R^s$ groups form a 6-membered ring.

Additional Embodiment 58. The compound of additional embodiment 52, wherein one set of adjacent $R^t$ and $R^s$ groups forms a 6-membered ring, and where $R^m$ is —$CH_2$— and each $R^o$ together forms a 6-membered ring.

Additional Embodiment 59. The compound of additional embodiment 52, wherein at least one set of adjacent $R^t$, $R^s$, and $R^g$ groups forms a bicyclic ring.

Additional Embodiment 60. The compound of additional embodiment 52, wherein $R^n$ is —$CH_2$—, and wherein $R^m$ is a branched or unbranched $C_1$-$C_4$ alkyl group which is optionally substituted with one or more halogen atoms and or one or more —S(O)(O)(OH) groups.

Additional Embodiment 61. The compound of additional embodiment 52, wherein one set of adjacent $R^t$ and $R^s$ groups forms a 6-membered ring, and wherein $R^m$ is a branched or unbranched $C_1$-$C_4$ alkyl group which is optionally substituted with one or more halogen atoms and or one or more —S(O)(O)(OH) groups.

Additional Embodiment 62. The compound of additional embodiment 52, wherein one set of adjacent $R^t$, $R^s$, and $R^g$ groups forms a bicyclic ring, another set of adjacent $R^t$ and $R^s$ groups forms a 6-membered ring, and wherein $R^m$ is a branched or unbranched $C_1$-$C_4$ alkyl group which is optionally substituted with one or more halogen atoms and or one or more —S(O)(O)(OH) groups.

Additional Embodiment 63. The compound of additional embodiment 52, wherein $R^n$ is a bond, at least one $R^g$ is methyl, and wherein $R^m$ is a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction.

Additional Embodiment 64. The compound of additional embodiment 52, wherein $R^n$ is —$CH_2$—, and wherein $R^m$ is a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction.

Additional Embodiment 65. The compound of additional embodiment 52, wherein one set of adjacent $R^t$, $R^s$, and $R^g$ groups forms a bicyclic ring, and wherein $R^m$ is a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction.

Additional Embodiment 66. The compound of additional embodiment 52, wherein W is selected from the group consisting of:

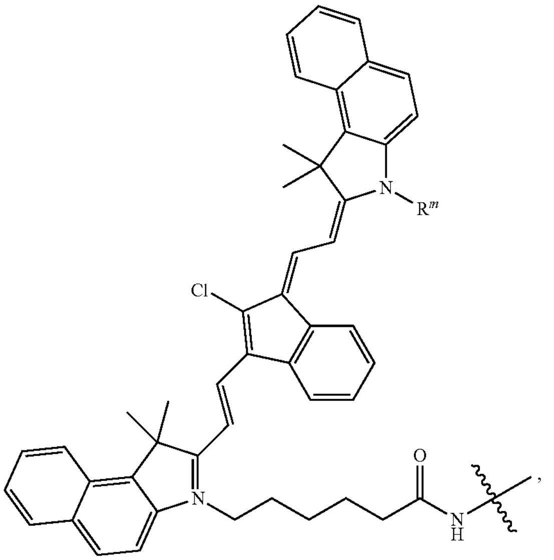

-continued

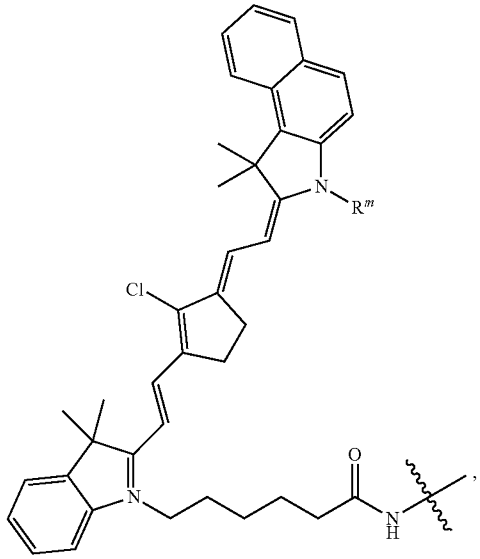

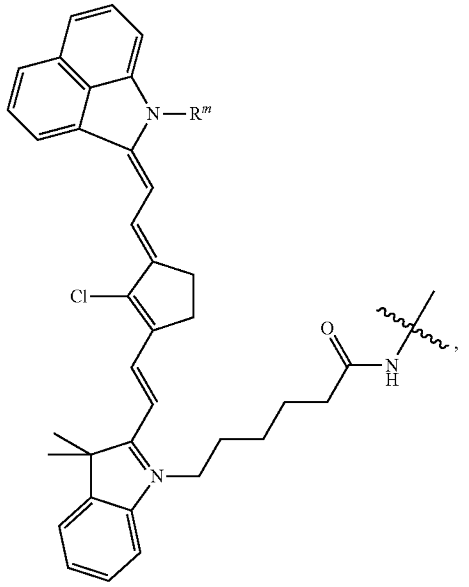

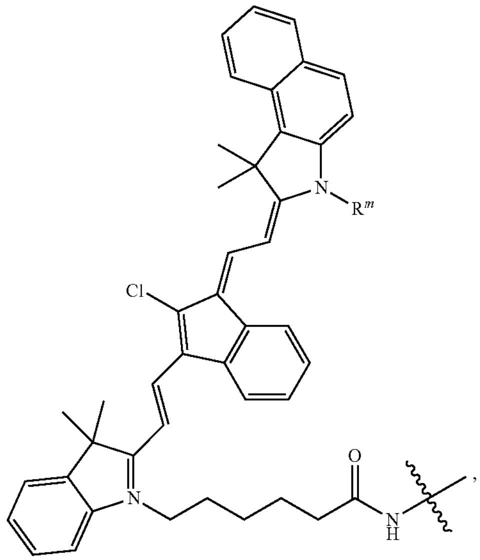

-continued

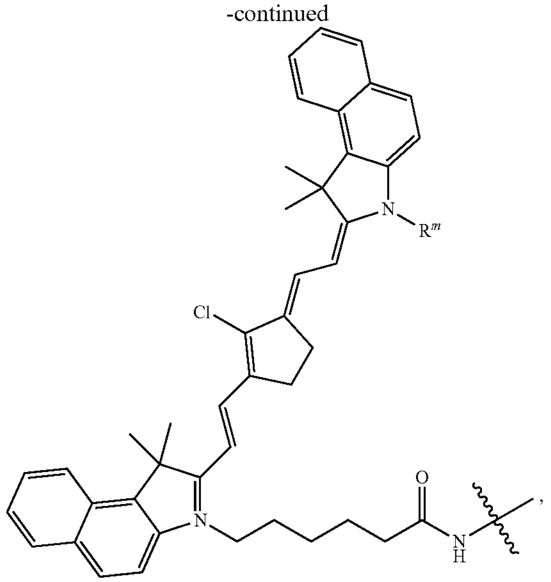

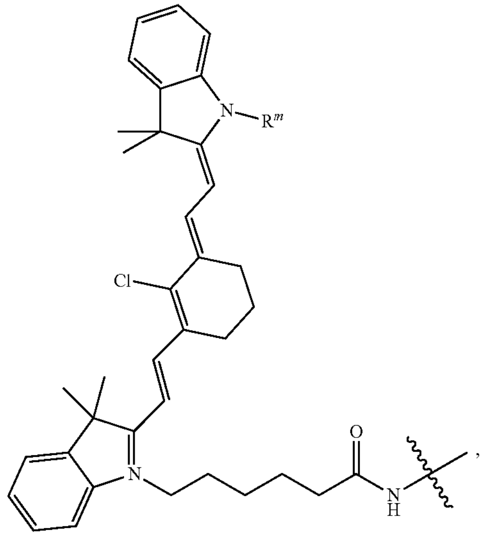

and

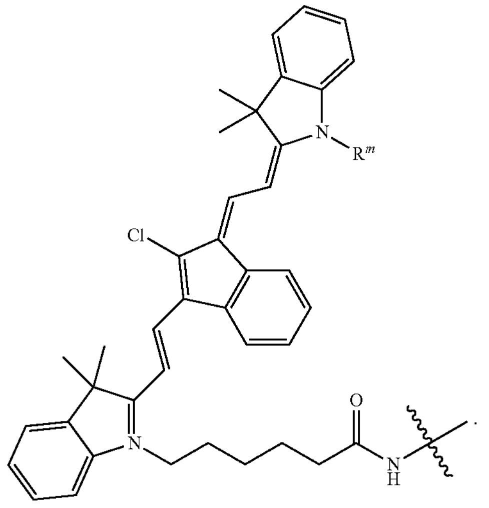

Additional Embodiment 67. A compound having Formula (I):

$$[Z]\text{-}[Q]_m\text{-}[W] \quad (I),$$

wherein

Z is (i) a "tissue reactive moiety," or (ii) a functional group or a moiety including a functional group capable of participating in a "click chemistry" reaction;

Q is a branched or unbranched, linear or cyclic, substituted or unsubstituted group having between 2 and 40 carbon atoms, and optionally having one or more heteroatoms selected from O, N, or S;

m is 0, 1, or 2; and

W has Formula (VIIA):

(VIIA)

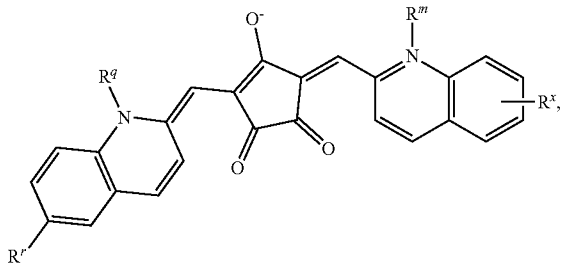

wherein $R^x$ is H or a branched or unbranched $C_1$-$C_4$ alkyl group optionally substituted with one or more halogen atoms;

$R^m$ is H, a branched or unbranched $C_1$-$C_4$ alkyl group which is optionally substituted with one or more halogen atoms and or one or more —S(O)(O)(OH) group, or a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction;

$R^q$ and $R^r$ are each independently H, a branched or unbranched $C_1$-$C_4$ alkyl group optionally substituted with one or more halogen atoms, or a group $R^s$, where $R^s$ is a saturated or unsaturated $C_1$-$C_{20}$ alkyl group comprising at least one amide group, and which is optionally substituted with one or more heteroatoms, provided that the group $R^s$ terminates in a moiety capable of participating in a click chemistry reaction, provided that at least one of $R^q$ or $R^r$ comprises a group $R^s$, and further provided that $R^q$ and $R^r$ are both not $R^s$.

Additional Embodiment 68. The compound of additional embodiment 67, wherein $R^f$ and $R^x$ are both H.

Additional Embodiment 69. The compound of additional embodiment 67, wherein $R^m$ is a branched or unbranched $C_1$-$C_4$ alkyl group which is optionally substituted with one or more halogen atoms and or one or more —S(O)(O)(OH) group.

Additional Embodiment 70. The compound of additional embodiment 67, wherein one of $R^f$ or $R^m$ is a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction.

Additional Embodiment 71. The compound of additional embodiment 67, wherein W has any one of Formulas (VIIB) and (VIIC):

(VIIB)

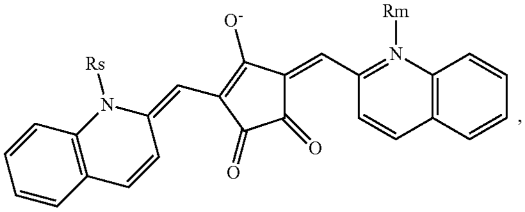

(VIIC)

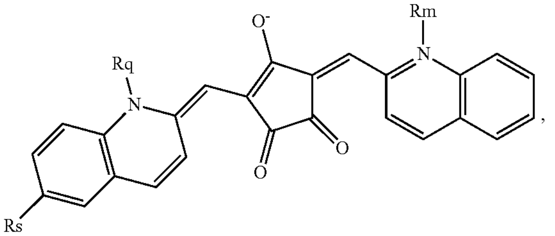

wherein $R^x$ is H or a branched or unbranched $C_1$-$C_4$ alkyl group optionally substituted with one or more halogen atoms;

$R^m$ is H, a branched or unbranched $C_1$-$C_4$ alkyl group which is optionally substituted with one or more halogen atoms and or one or more —S(O)(O)(OH) group, or a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction;

$R^q$ is H or a branched or unbranched $C_1$-$C_4$ alkyl group optionally substituted with one or more halogen atoms; and $R^s$ is a saturated or unsaturated $C_1$-$C_{20}$ alkyl group comprising at least one amide group, and which is optionally substituted with one or more heteroatoms, provided that the group $R^s$ terminates in a moiety capable of participating in a click chemistry reaction.

Additional Embodiment 72. The compound of additional embodiment 67, wherein W is selected from the group consisting of:

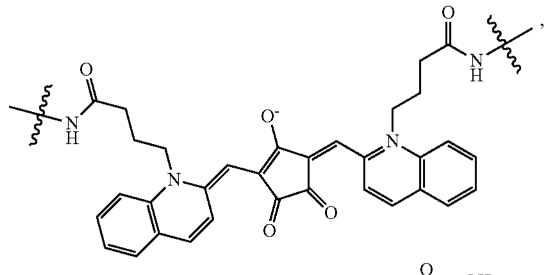

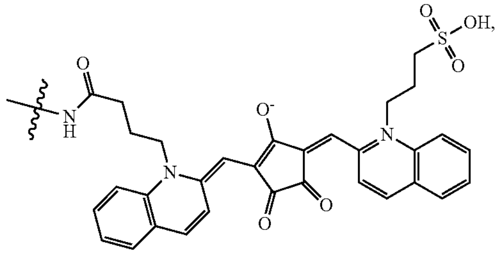

and

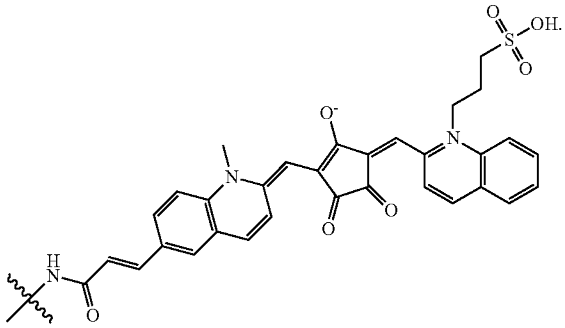

Additional Embodiment 73. A conjugate selected from the group consisting of:

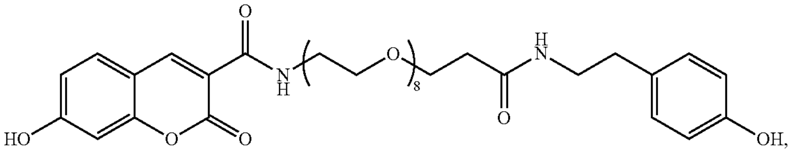

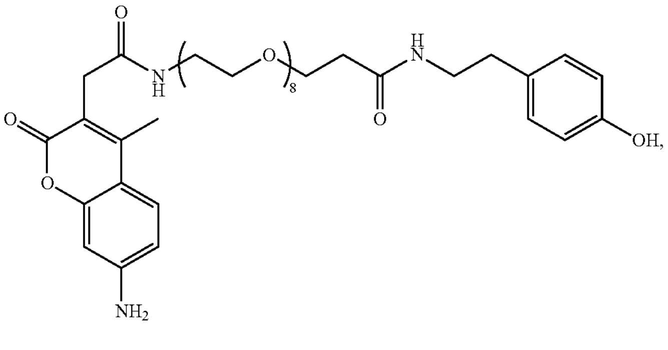

-continued
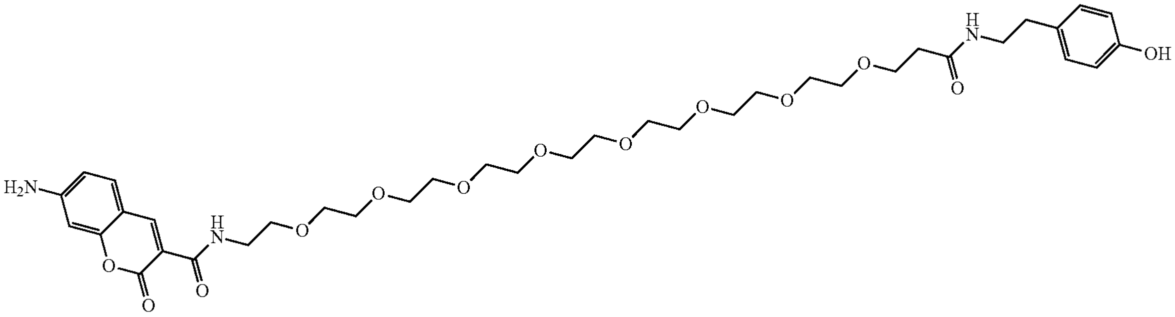
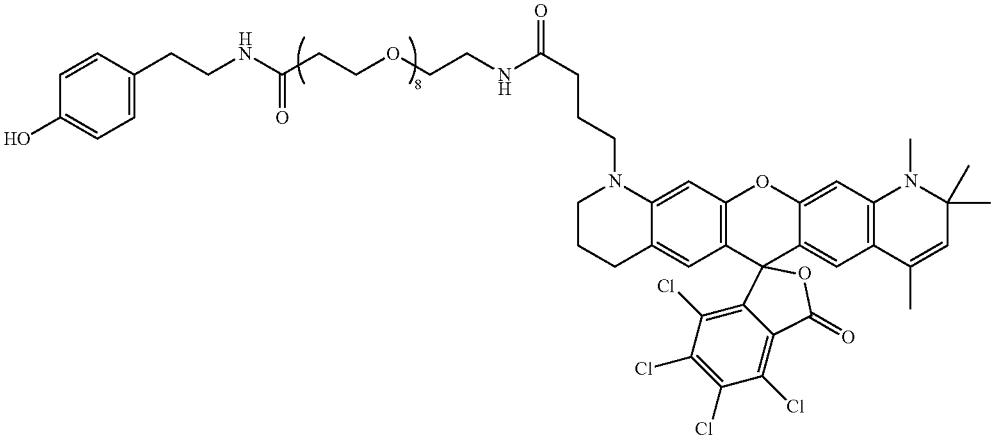
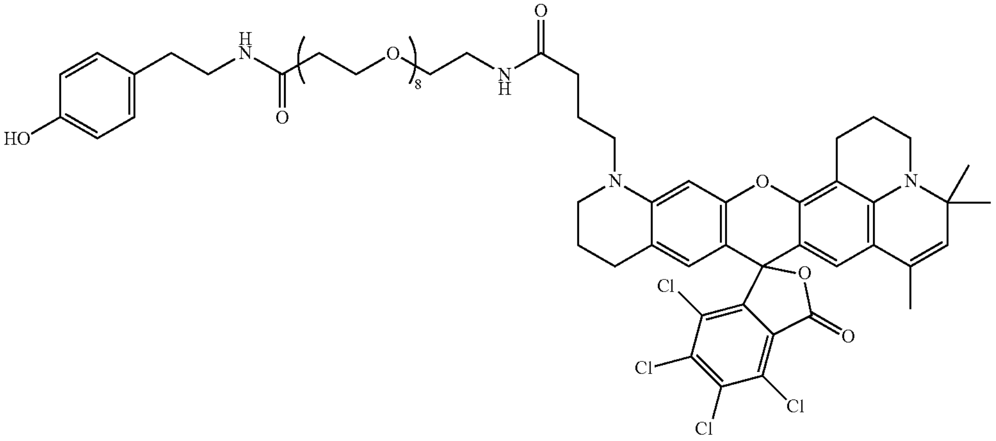
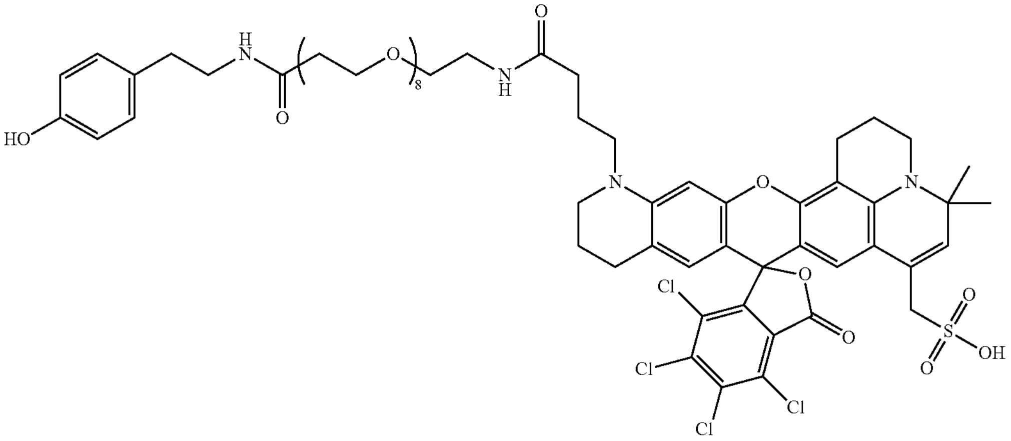

-continued
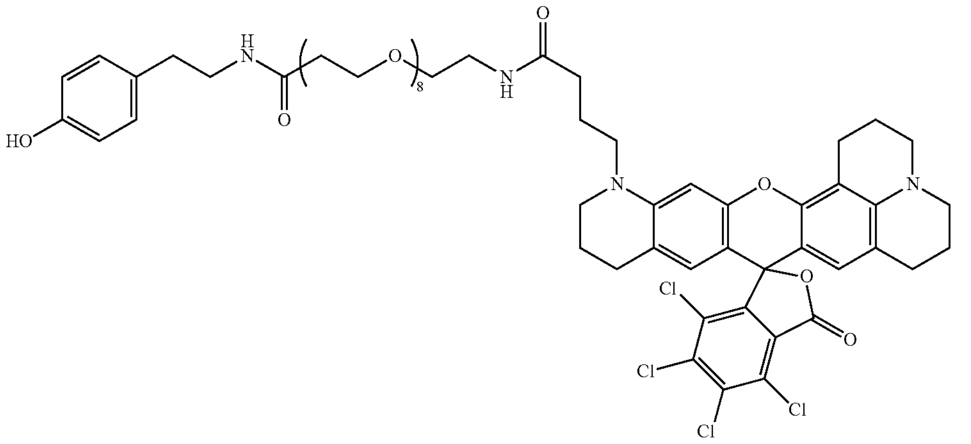
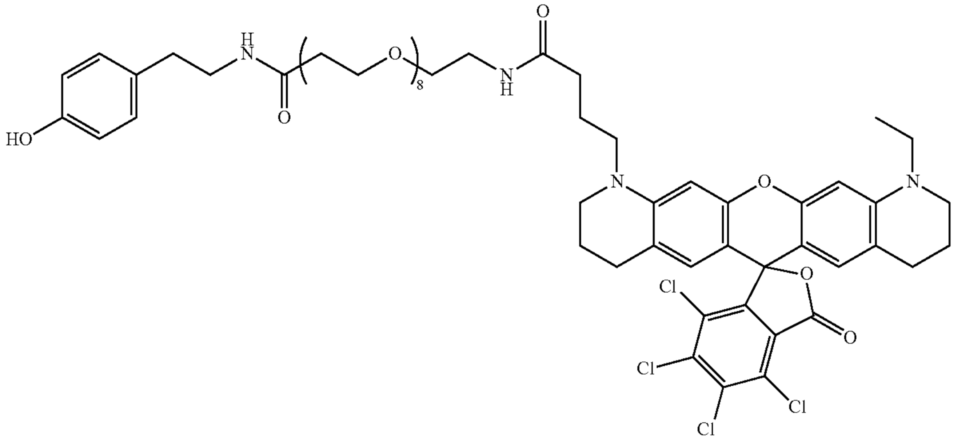
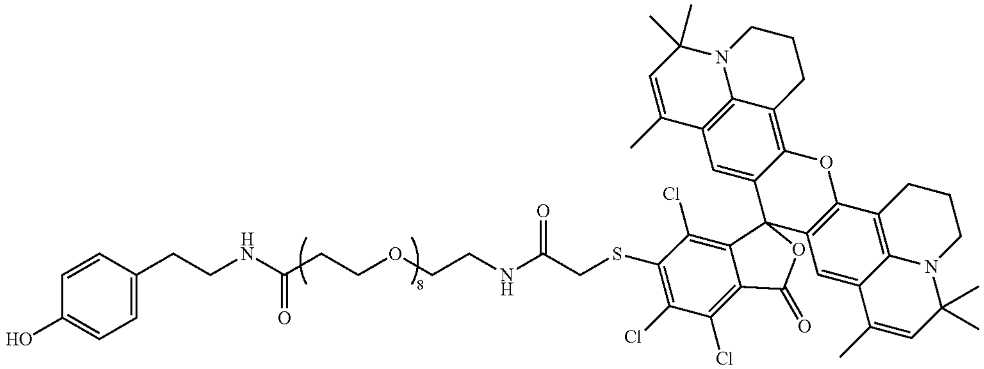
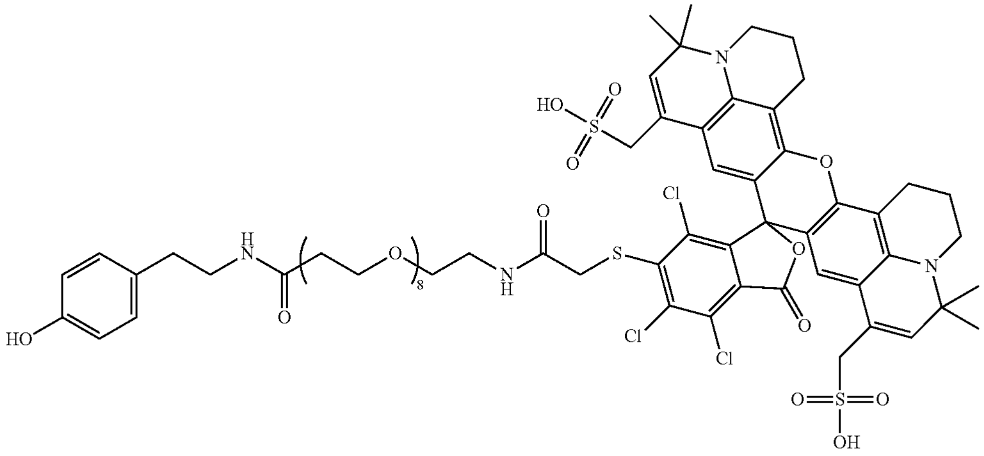

-continued
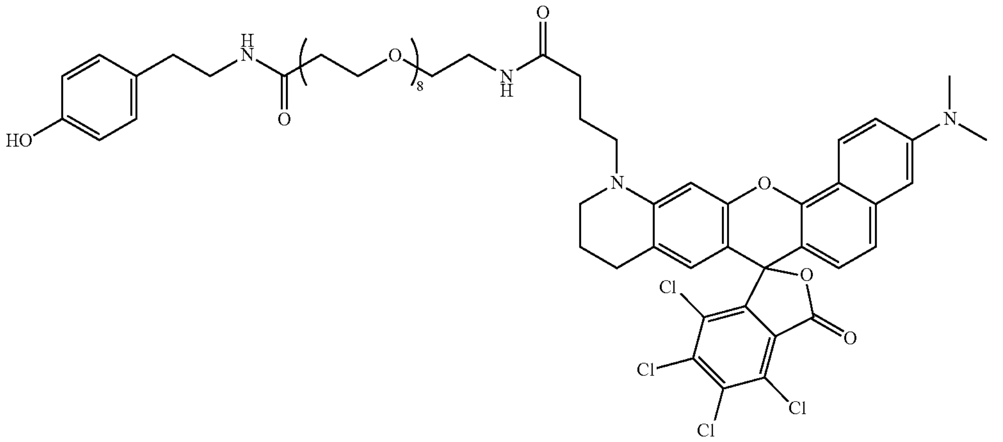
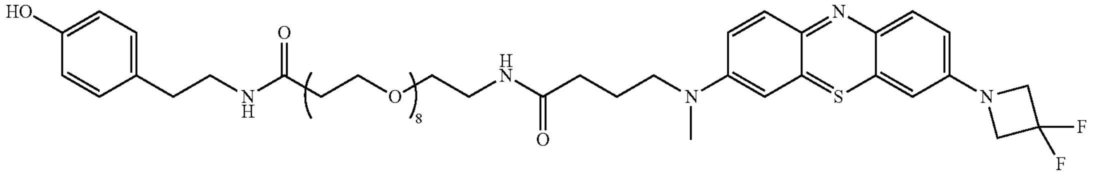
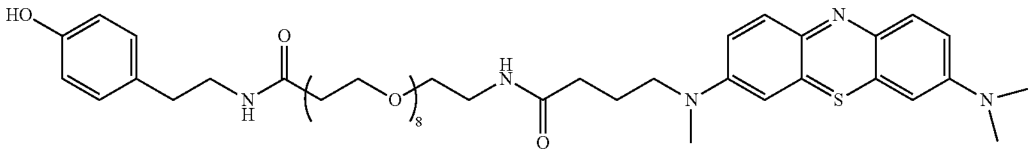
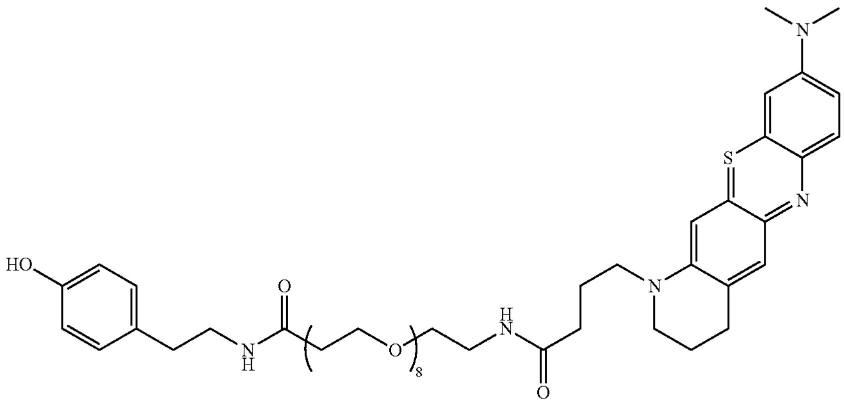
,
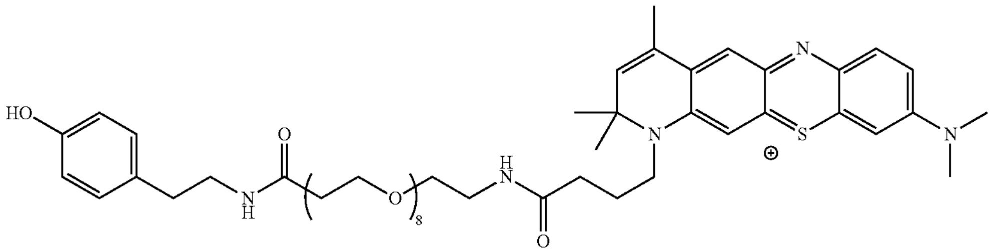
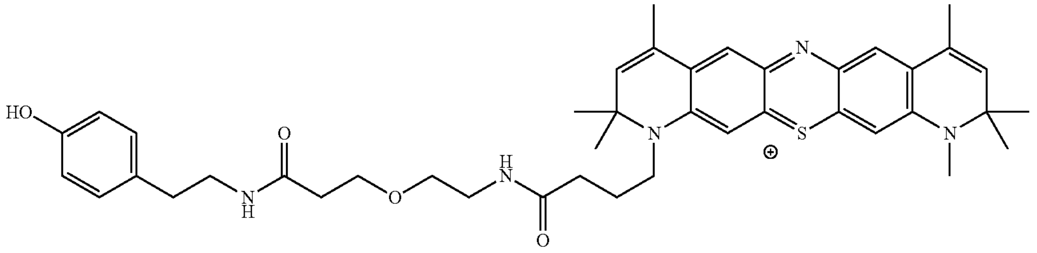
, -continued
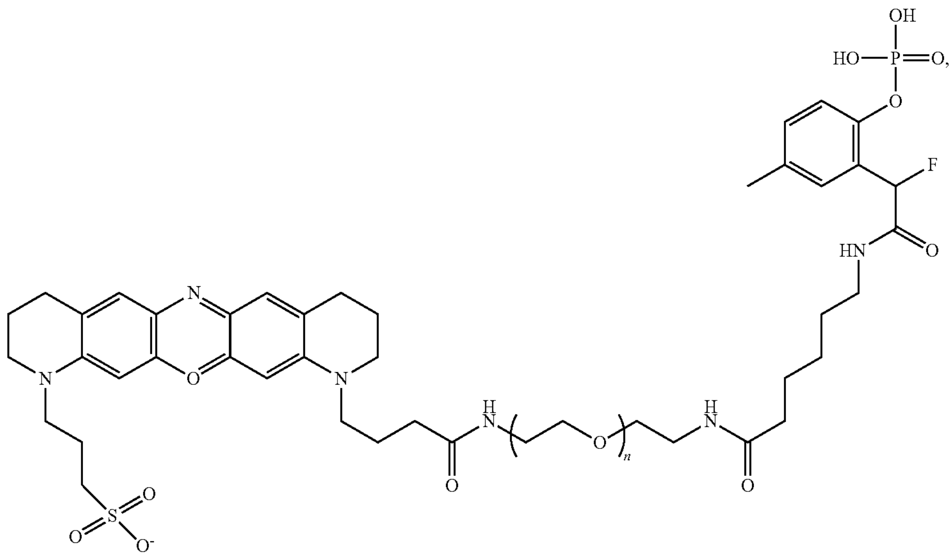
,
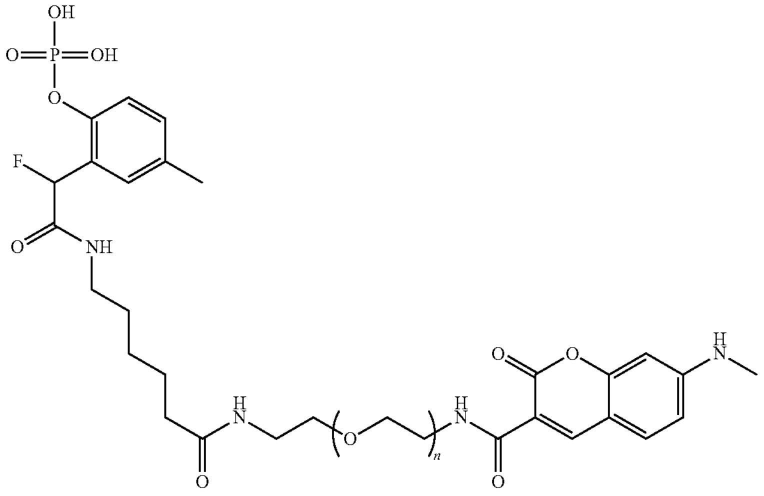
,
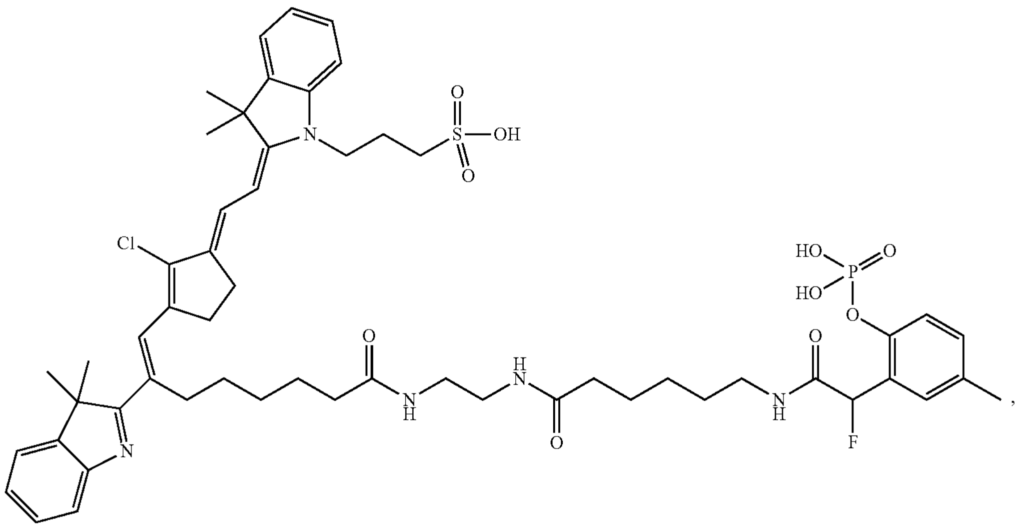
, -continued
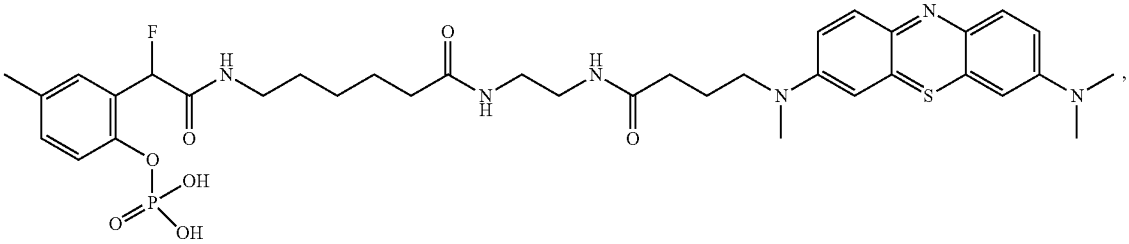
,
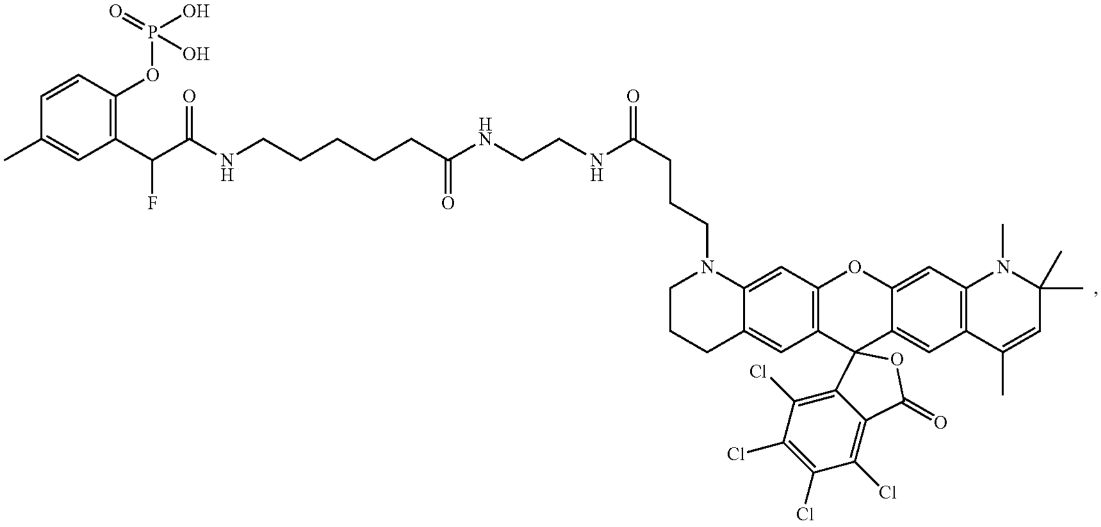
,
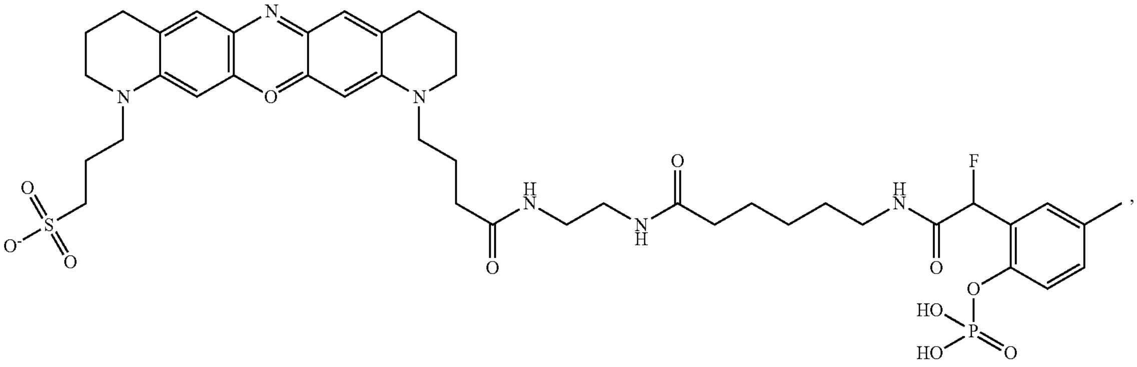
, and
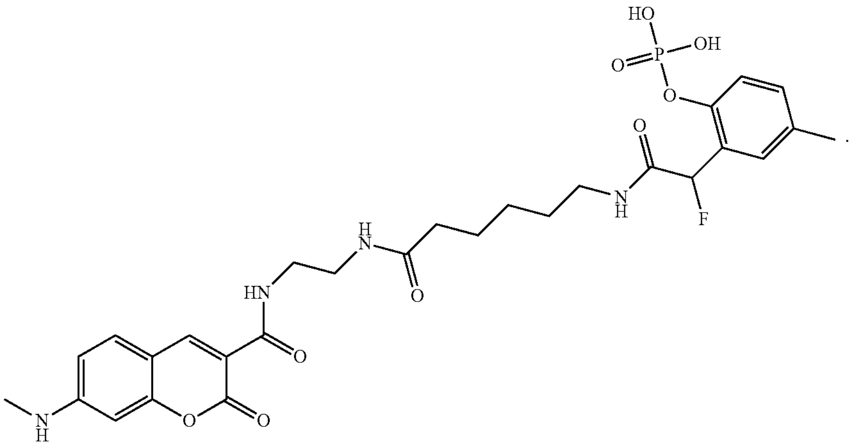
.

Additional Embodiment 74. A kit comprising any two of the conjugates of additional embodiment 73.

Additional Embodiment 75. A kit comprising any three of the conjugates of additional embodiment 73.

Additional Embodiment 76. A kit comprising any four of the conjugates of additional embodiment 73.

Additional Embodiment 77. A biological sample comprising at least one stained target, wherein the target is stained in an immunohistochemical assay which utilizes at least one of the conjugates of additional embodiment 73.

Additional Embodiment 78. A conjugate selected from the group consisting of:

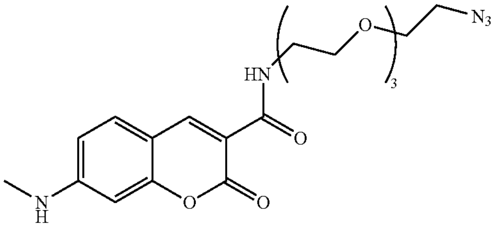

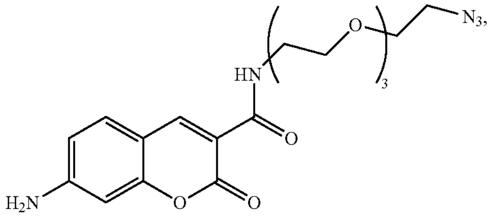

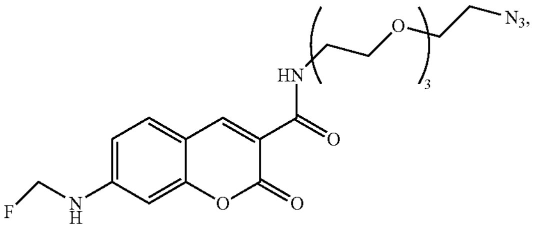

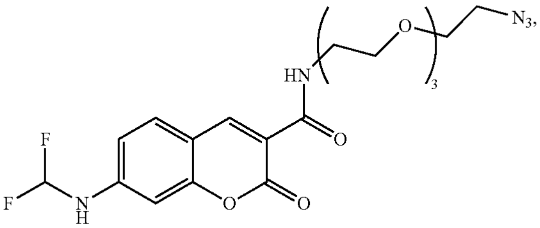

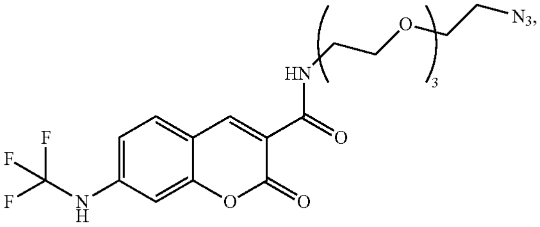

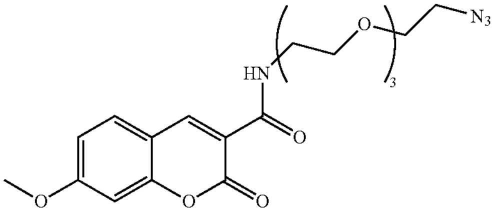

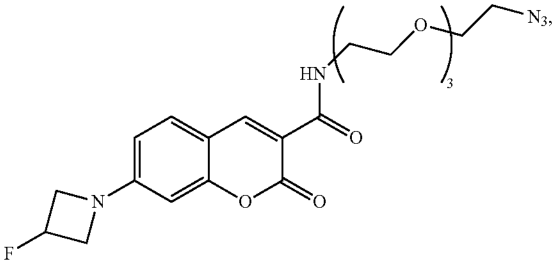

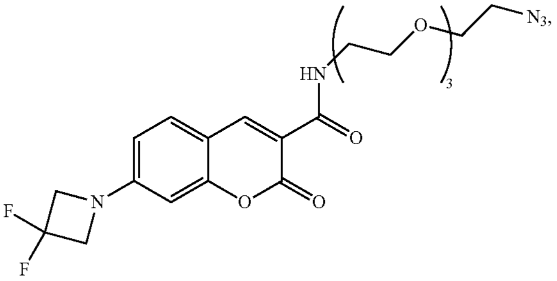

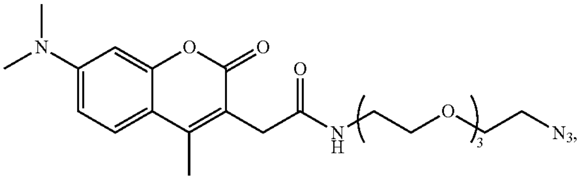

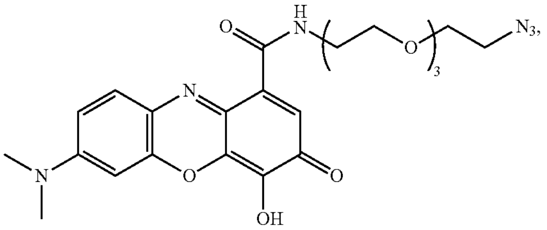

-continued
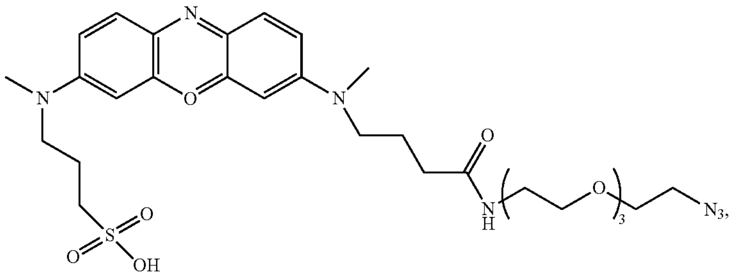
,
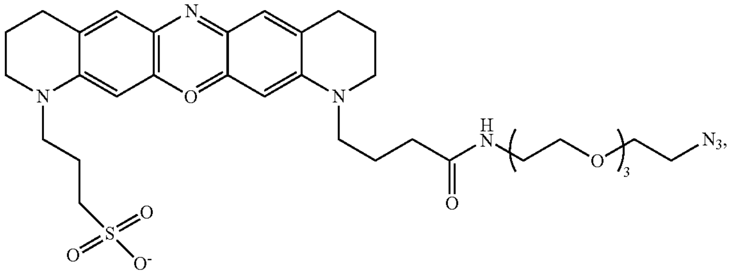
,
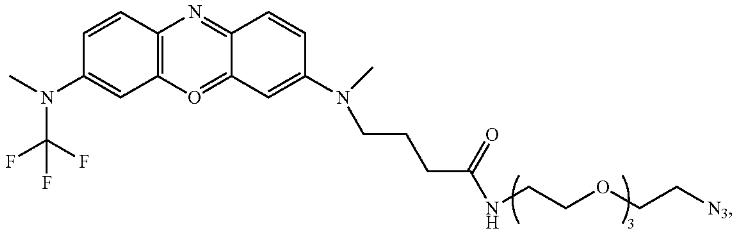
,
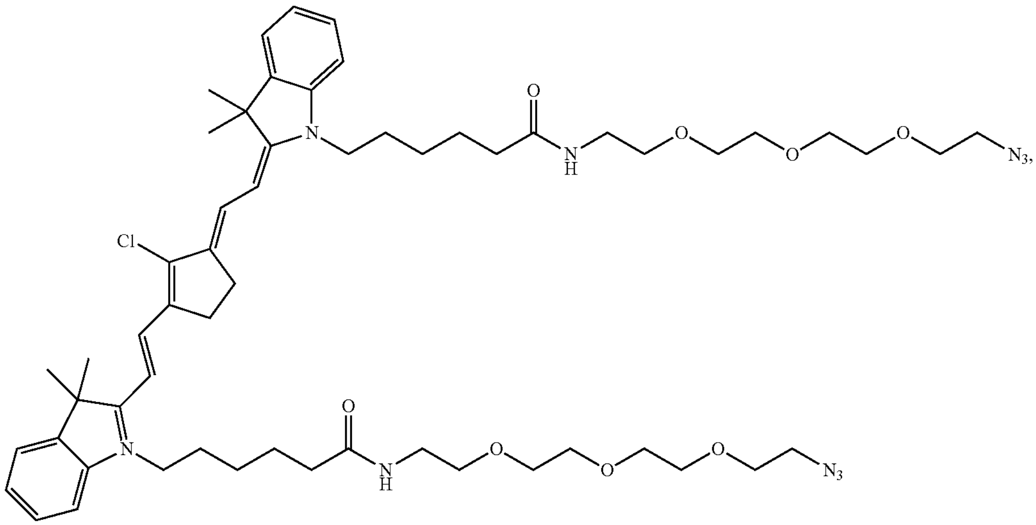
,

-continued
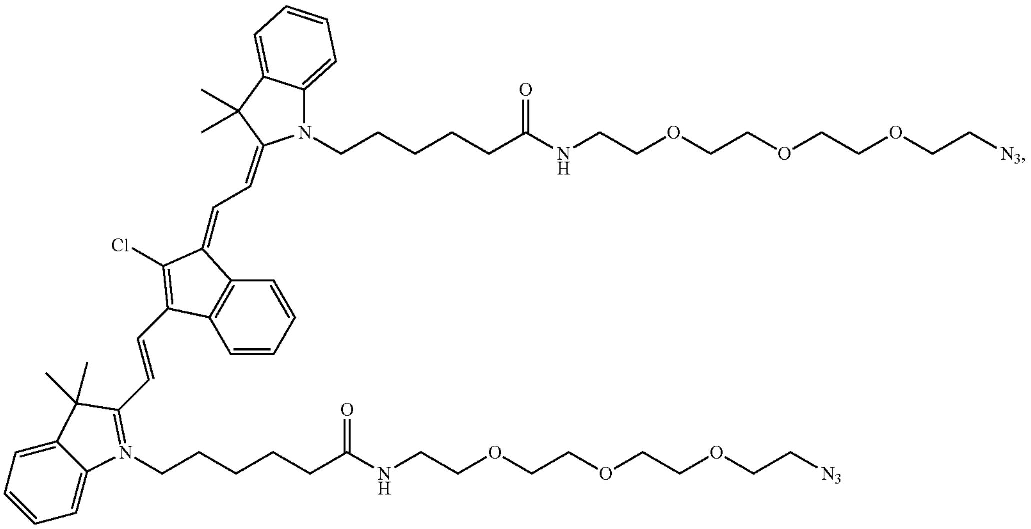
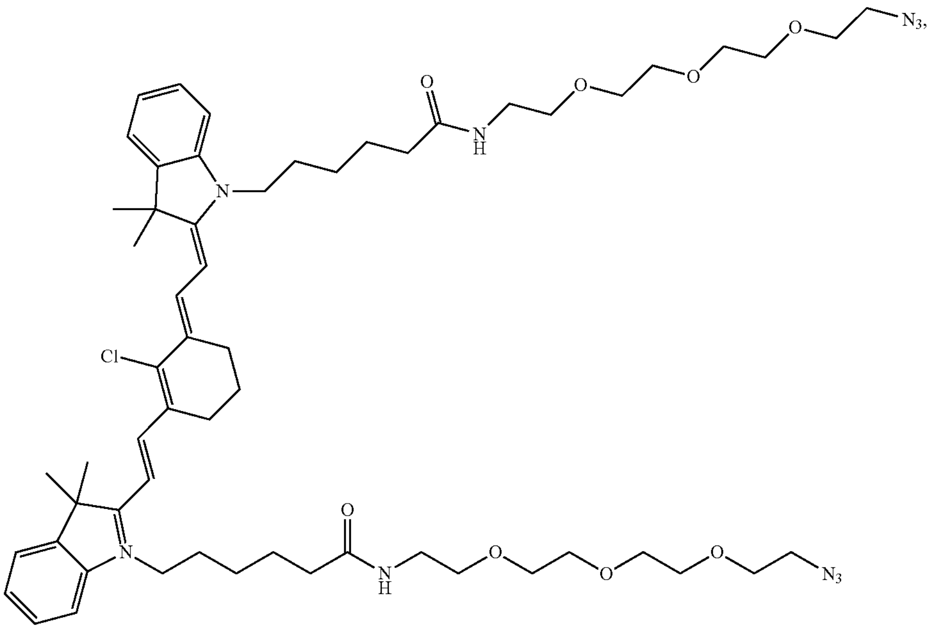

-continued
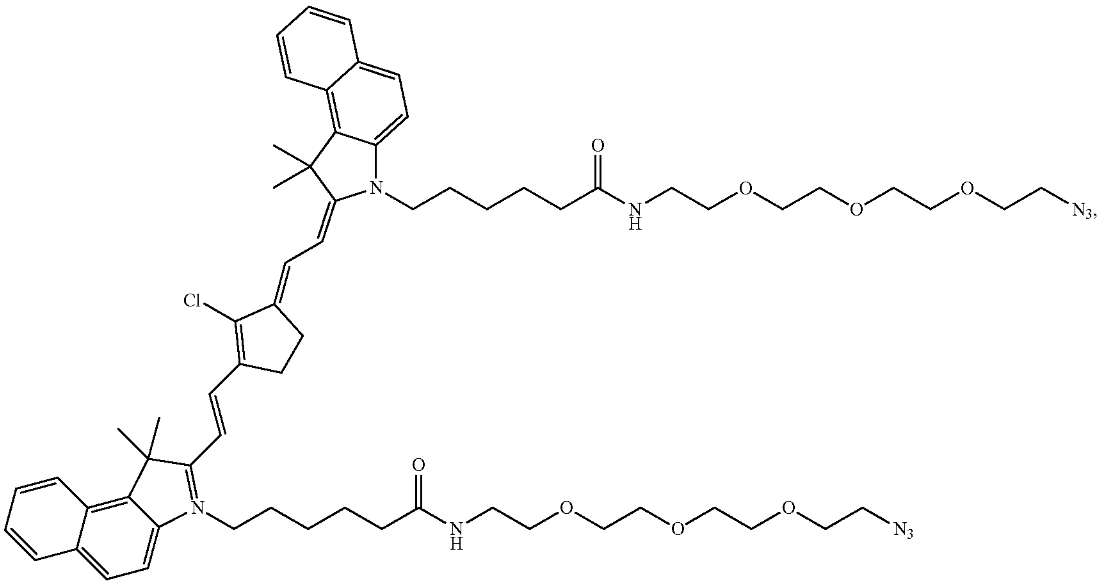
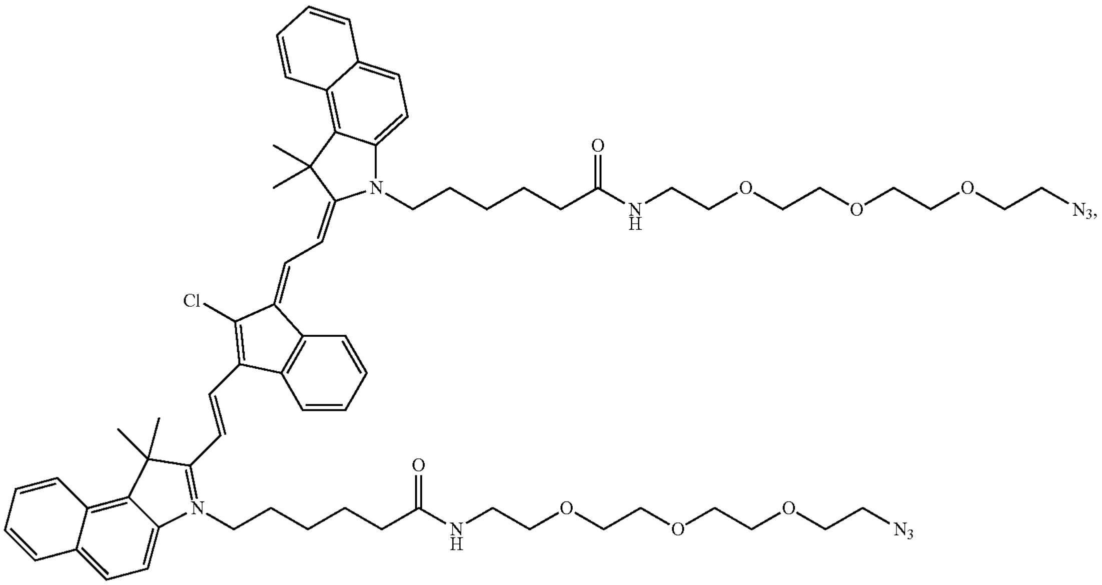

-continued
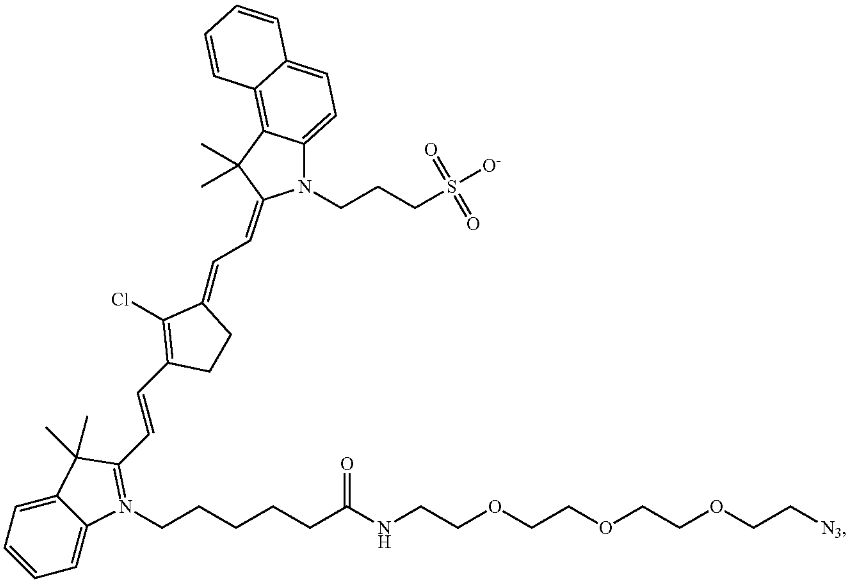
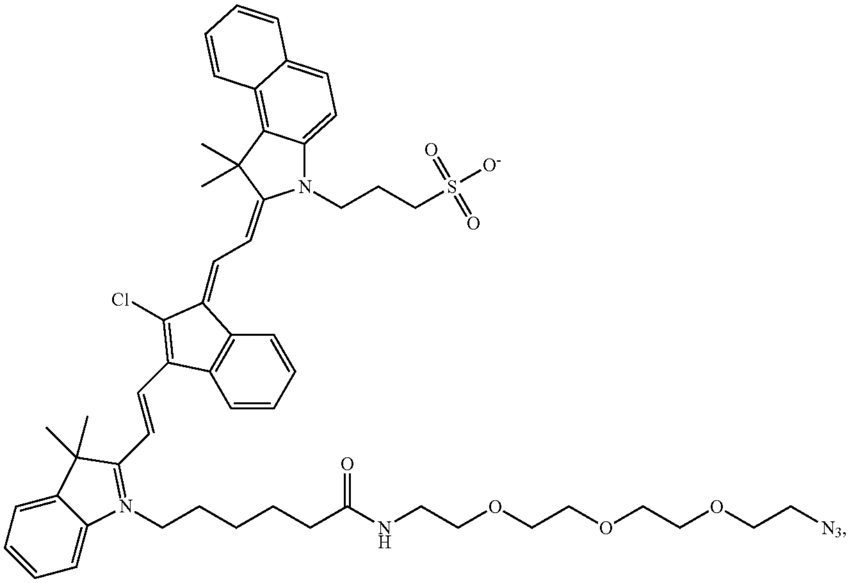

-continued
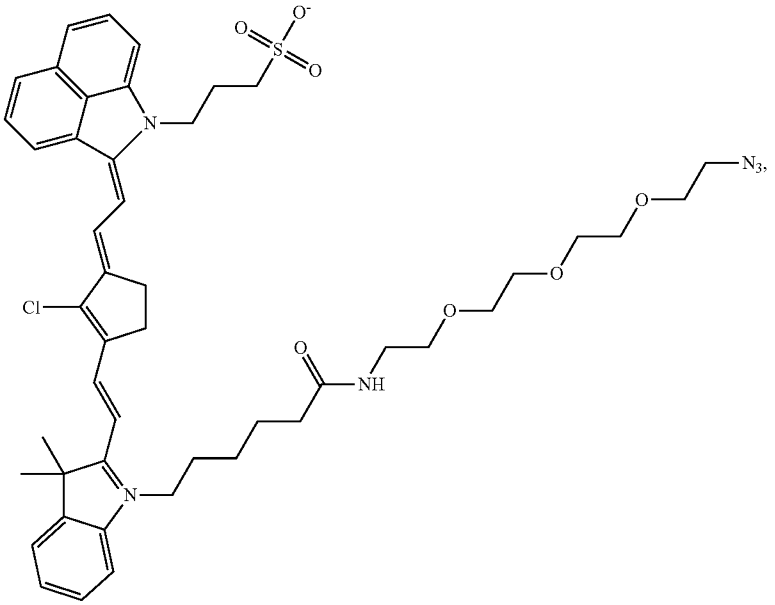
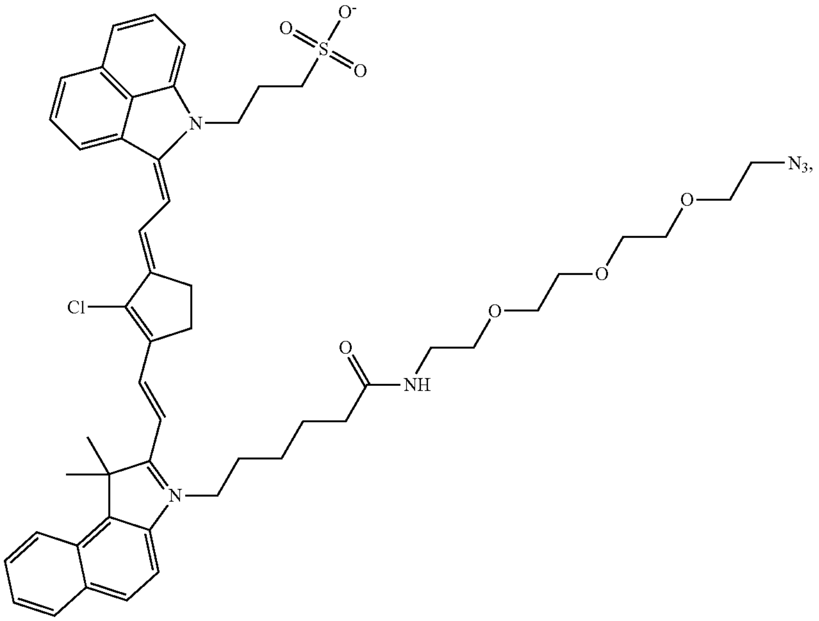

-continued
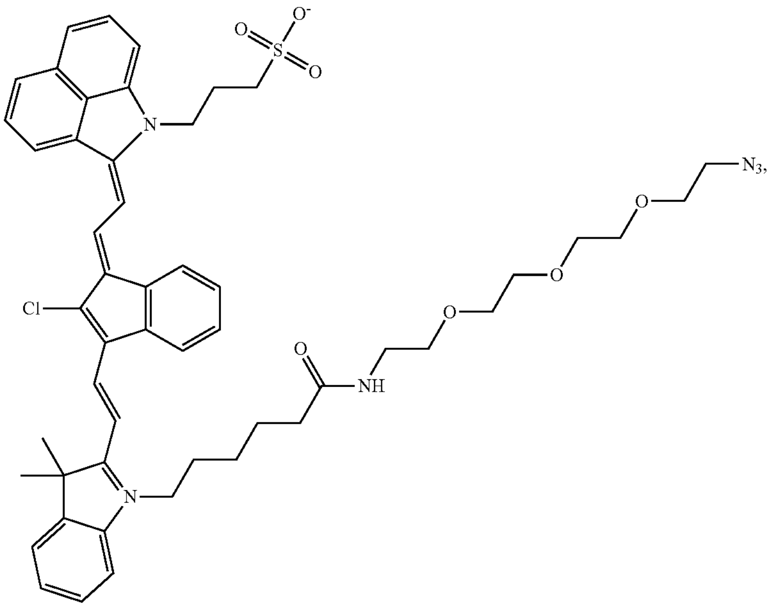
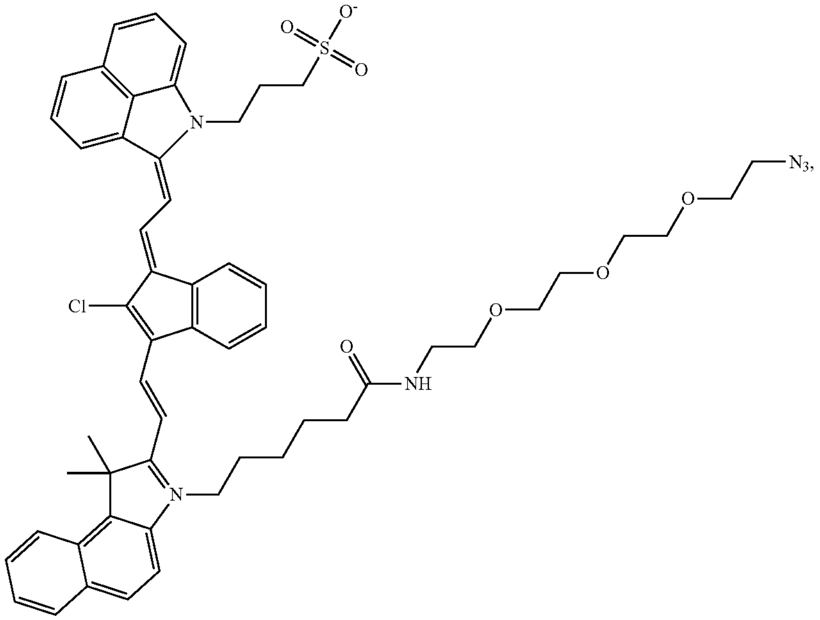
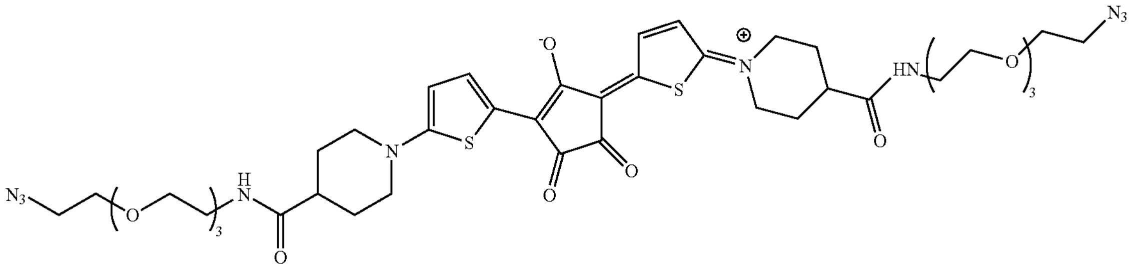

-continued

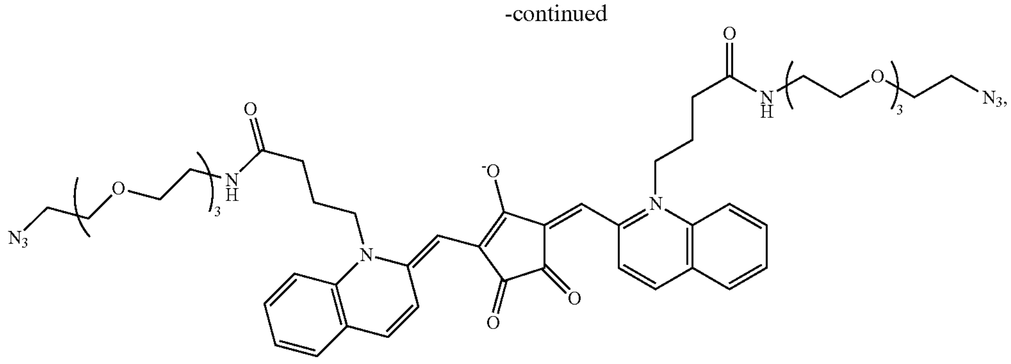

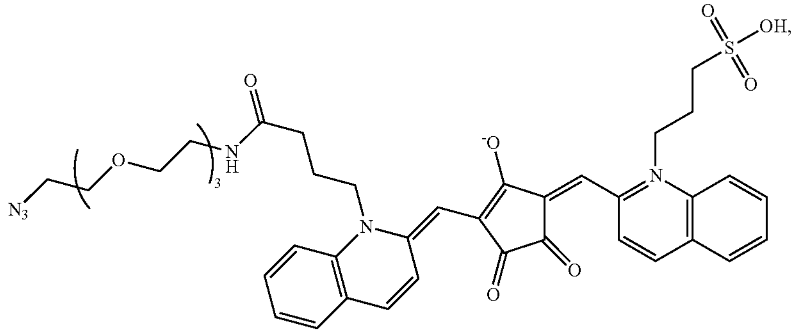

and

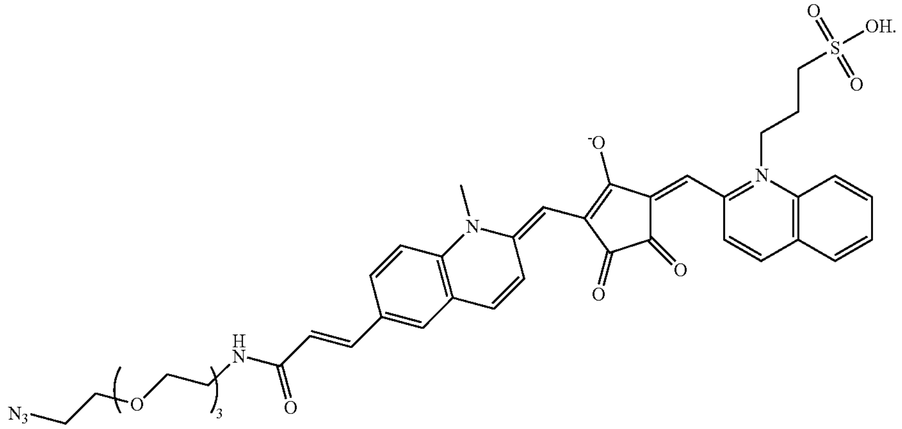

Additional Embodiment 79. A kit comprising any two of the conjugates of additional embodiment 78.

Additional Embodiment 80. A kit comprising any three of the conjugates of additional embodiment 78.

Additional Embodiment 81. A kit comprising any four of the conjugates of additional embodiment 78.

Additional Embodiment 82. A biological sample comprising at least one stained target, wherein the at least one stained target is stained in an immunohistochemical assay which utilizes at least one of the conjugates of additional embodiment 78.

Additional Embodiment 83. A kit comprising any two of the conjugates of additional embodiments 1-73.

Additional Embodiment 84. A kit comprising any three of the conjugates of additional embodiments 1-73.

Additional Embodiment 85. A biological sample comprising at least one stained target, wherein the at least one stained target is stained in an immunohistochemical assay which utilizes at least one of the conjugates of additional embodiments 1-73.

Additional Embodiment 86. A biological sample comprising at least two stained targets, wherein the at least two stained targets are stained in an immunohistochemical assay which utilizes at least one of the conjugates of additional embodiments 1-73.

Additional Embodiment 87. Use of any one of the conjugates of additional embodiments 1-73 for staining one or more targets within a biological sample.

The invention claimed is:

1. A compound having Formula (I):

$$[Z]\text{-}[Q]_m\text{-}[W] \quad \text{(I)},$$

wherein

Z is (i) a tissue reactive moiety selected from a tyramide, a tyramide derivative, or a quinone methide precursor, or (ii) a functional group or a moiety including a functional group capable of participating in a click chemistry reaction, wherein the functional group or the moiety including the functional group capable of participating in the click chemistry reaction is a dibenzocyclooctyne, a trans-cyclooctene, an alkyne, an alkene, an azide, a tetrazine, a maleimide, a N-hydroxysuccinimide, a thiol, a 1,3-nitrone, an aldehyde, a ketone, a hydrazine, a hydroxylamine, an amino group;

Q is a branched or unbranched, linear or cyclic, substituted or unsubstituted group having between 2 and 40 carbon atoms, and optionally having one or more heteroatoms selected from O, N, or S;

m is 0, 1, or 2; and

W has Formula (VIIA):

(VIIA)

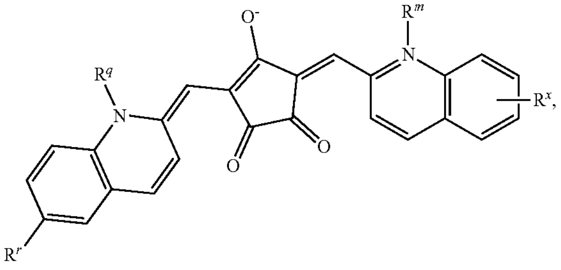

wherein $R^x$ is H or a branched or unbranched $C_1$-$C_4$ alkyl group optionally substituted with one or more halogen atoms;

$R^m$ is H, a branched or unbranched $C_1$-$C_4$ alkyl group which is optionally substituted with one or more halogen atoms and or one or more —S(O)(O)(OH) groups, or a branched or unbranched $C_1$-$C_{20}$ alkyl group optionally including one or more heteroatoms selected from O or N, and optionally including one or more carbonyl groups, provided that the $C_1$-$C_{20}$ alkyl group terminates in a moiety capable of participating in a click chemistry reaction, wherein the moiety capable of participating in the click chemistry reaction is a dibenzocyclooctyne, a trans-cyclooctene, an alkyne, an alkene, an azide, a tetrazine, a maleimide, a N-hydroxysuccinimide, a thiol, a 1,3-nitrone, an aldehyde, a ketone, a hydrazine, a hydroxylamine, an amino group;

$R^q$ and $R^r$ are each independently H, a branched or unbranched $C_1$-$C_4$ alkyl group optionally substituted with one or more halogen atoms, or a group $R^s$, where $R^s$ is a saturated or unsaturated $C_1$-$C_{20}$ alkyl group comprising at least one amide group, and which is optionally substituted with one or more heteroatoms, provided that the group $R^s$ terminates in a moiety capable of participating in a click chemistry reaction, wherein the moiety capable of participating in the click chemistry reaction is a dibenzocyclooctyne, a trans-cyclooctene, an alkyne, an alkene, an azide, a tetrazine, a maleimide, a N-hydroxysuccinimide, a thiol, a 1,3-nitrone, an aldehyde, a ketone, a hydrazine, a hydroxylamine, an amino group, provided that at least one of $R^q$ or $R^r$ comprises a group $R^s$, and further provided that $R^q$ and $R^r$ are both not $R^s$.

2. The compound of claim 1, wherein $R^m$ is the branched or unbranched $C_1$-$C_4$ alkyl group which is optionally substituted with the one or more halogen atoms and or the one or more —S(O)(O)(OH) groups.

3. The compound of claim 1, wherein $R^m$ is the branched or unbranched $C_1$-$C_{20}$ alkyl group optionally including the one or more heteroatoms selected from O or N, and optionally including the one or more carbonyl groups, provided that the $C_1$-$C_{20}$ alkyl group terminates in the moiety capable of participating in the click chemistry reaction.

4. The compound of claim 1, wherein W has any one of Formulas (VIIB) and (VIIC):

(VIIB)

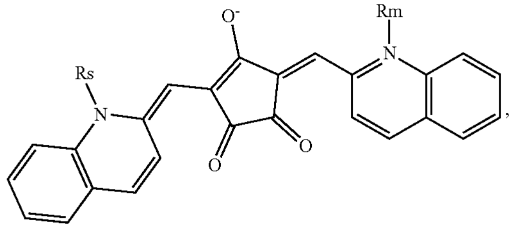

, (VIIC)

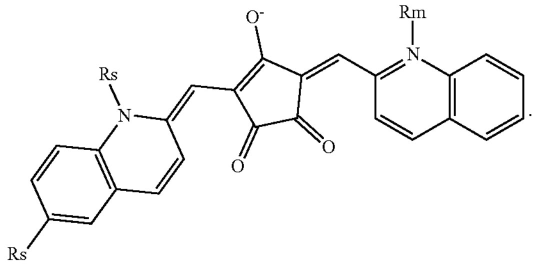

.

5. The compound of claim 1, wherein W is selected from the group consisting of:

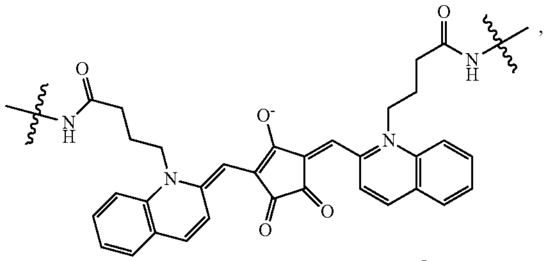

,

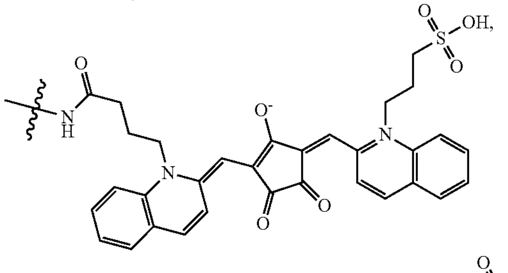

and

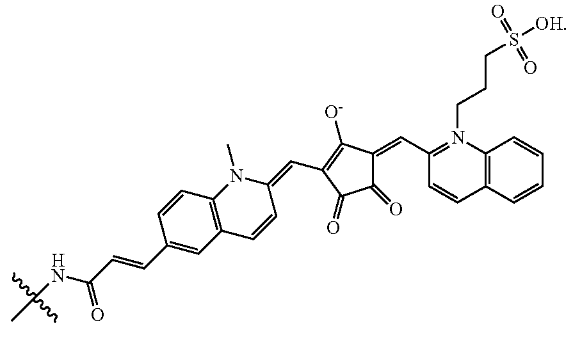

6. The compound of claim 1, wherein Z is the tissue reactive moiety.

7. The compound of claim 6, wherein the tissue reactive moiety is the quinone methide precursor.

8. The compound of claim 6, wherein the tissue reactive moiety is the tyramide or a tyramide derivative.

9. The compound of claim 1, wherein Z is the functional group or the A moiety including the functional group capable of participating in the click chemistry reaction.

10. The compound of claim 9, wherein the functional group or the moiety A including the functional group capable of participating in the click chemistry reaction is selected from the group consisting of azide, diarylcyclooctyne, alkyne, and Trans-cyclooctene.

11. The compound of claim 2, wherein $R^m$ is an unsubstituted branched or unbranched $C_1$-$C_4$ alkyl group.

12. The compound of claim 2, wherein $R^m$ is an unbranched $C_1$-$C_4$ alkyl group including one —S(O)(O)(OH) group.

13. The compound of claim 1, wherein $R^q$ and $R^m$ both include a group $R^s$.

14. The compound of claim 13, wherein $R^s$ includes a $C_3$ or $C_4$ alkyl group and includes one amide group.

15. The compound of claim 1, wherein $R^m$ is the branched or unbranched $C_1$-$C_{20}$ alkyl group optionally including the one or more heteroatoms selected from O or N, and optionally including the one or more carbonyl groups, provided that the $C_1$-$C_{20}$ alkyl group terminates in the moiety capable of participating in the click chemistry reaction; and $R^q$ is a methyl group.

16. The compound of claim 15, wherein the moiety capable of A participating in a click chemistry reaction is selected from the group consisting of azide, diarylcyclooctyne, alkyne, and Trans-cyclooctene.

17. The compound of claim 1, wherein $R^q$ is H.

18. The compound of claim 1, wherein the tyramide or the tyramide derivative has the structure of any one of Formulas (XA) or (XB):

(XA)

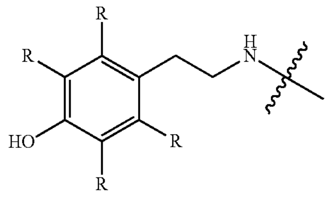

or (XB)

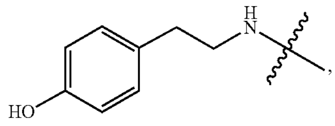

, wherein each R group is independently selected from hydrogen or lower alkyl group having between 1 and 4 carbon atoms.

19. The compound of claim 1, wherein the quinone methide has the structure of any one of Formulas (IXA) or (IXE):

(IXA)

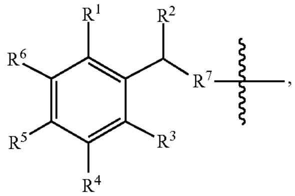

, (IXE)

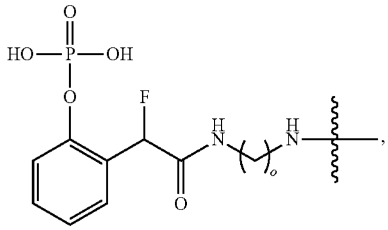

, where $R^1$ is selected from the group consisting of phosphate, amide, nitro, urea, sulfate, methyl, ester, beta-lactam, and a sugar; $R^2$ is a halide; $R^3$, $R^4$, $R^5$, and $R^6$ are independently selected from hydrogen or an aliphatic group having between 1 and 4 carbon atoms; and $R^7$ is $-(CH_2)_wNH-$, $-O(CH_2)_wNH-$, $-N(H)C(O)(CH_2)_wNH-$, $-C(O)N(H)(CH_2)_wNH-$, $-(CH_2)_wO-$, $-O(CH_2)_wO-$, $-O(CH_2CH_2O)_w-$, $-N(H)C(O)(CH_2)_wO-$, $-C(O)N(H)(CH_2)_wO-$, $-C(O)N(H)(CH_2CH_2O)_w-$, $-(CH_2)_wS-$, $-O(CH_2)_wS-$, $-N(H)C(O)(CH_2)_wS-$, $-C(O)N(H)(CH_2)_wS-$, $-(CH_2)_wNH-$, $-C(O)N(H)(CH_2CH_2O)_wCH_2CH_2NH$, $-C(O)(CH_2CH_2O)_wCH_2CH_2NH-$, $-C(O)N(H)(CH_2)NHC(O)CH(CH_3)(CH_2)_wNH-$, or $-N(H)(CH_2)_wNH-$, where w is an integer ranging from 1 to 12.

* * * * *